US012595270B2

(12) United States Patent
Zhang et al.

(10) Patent No.: US 12,595,270 B2
(45) Date of Patent: Apr. 7, 2026

(54) BENZO NITROGEN-CONTAINING HETEROAROMATIC RING DERIVATIVE AND USE THEREOF IN MEDICINE

(71) Applicant: Xizang Haisco Pharmaceutical Co., Ltd., Tibet (CN)

(72) Inventors: Chen Zhang, Chengdu (CN); Yuting Liao, Chengdu (CN); Guozhi Zhu, Chengdu (CN); Dachao Tang, Chengdu (CN); Yan Yu, Chengdu (CN); Pingming Tang, Chengdu (CN); Xinfan Cheng, Chengdu (CN); Yao Li, Chengdu (CN); Jia Ni, Chengdu (CN); Pangke Yan, Chengdu (CN)

(73) Assignee: Xizang Haisco Pharmaceutical Co., Ltd., Lhoka (CN)

( * ) Notice: Subject to any disclaimer, the term of this patent is extended or adjusted under 35 U.S.C. 154(b) by 0 days.

(21) Appl. No.: 19/352,045

(22) Filed: Oct. 7, 2025

(65) Prior Publication Data

US 2026/0035385 A1 Feb. 5, 2026

Related U.S. Application Data

(63) Continuation of application No. 18/684,549, filed as application No. PCT/CN2022/113216 on Aug. 18, 2022.

(30) Foreign Application Priority Data

| | | |
|---|---|---|
| Aug. 18, 2021 | (CN) | 202110940107.4 |
| Sep. 8, 2021 | (CN) | 202111048416.7 |
| Dec. 16, 2021 | (CN) | 202111532328.4 |
| Mar. 22, 2022 | (CN) | 202210255370.4 |
| May 12, 2022 | (CN) | 202210496109.3 |
| May 25, 2022 | (CN) | 202210558720.4 |
| Jul. 29, 2022 | (CN) | 202210903696.3 |

(51) Int. Cl.

| | |
|---|---|
| ***C07D 498/10*** | (2006.01) |
| ***A61K 31/407*** | (2006.01) |
| ***A61K 31/438*** | (2006.01) |
| ***A61K 31/454*** | (2006.01) |
| ***A61K 31/4545*** | (2006.01) |
| ***A61K 31/496*** | (2006.01) |
| ***A61K 31/5386*** | (2006.01) |
| ***C07D 401/06*** | (2006.01) |
| ***C07D 401/14*** | (2006.01) |

(Continued)

(52) U.S. Cl.

CPC .......... *C07D 498/10* (2013.01); *A61K 31/407* (2013.01); *A61K 31/438* (2013.01); *A61K 31/454* (2013.01); *A61K 31/4545* (2013.01); *A61K 31/496* (2013.01); *A61K 31/5386* (2013.01); *C07D 401/06* (2013.01); *C07D 401/14* (2013.01); *C07D 403/06* (2013.01); *C07D 405/14* (2013.01); *C07D 471/10* (2013.01); *C07D 491/08* (2013.01); *C07D 491/107* (2013.01); *C07D 495/10* (2013.01)

(58) Field of Classification Search

CPC .. C07D 498/10; C07D 495/10; C07D 401/06; C07D 401/14; C07D 403/06; C07D 405/14; C07D 471/10; C07D 491/08; C07D 491/107; A61K 31/438; A61K 31/454; A61K 31/4545; A61K 31/496; A61K 31/5386; A61K 31/407

See application file for complete search history.

(56) References Cited

U.S. PATENT DOCUMENTS 9,682,968 B2 6/2017 Adams et al.
12,076,319 B2 * 9/2024 Huang .................. C07K 16/18

(Continued)

FOREIGN PATENT DOCUMENTS

CN 105579444 A 5/2016
CN 109414441 A 3/2019

(Continued)

OTHER PUBLICATIONS

Office Action dated Aug. 29, 2024 issued in Eurasian Patent Application No. 202490196. (7 pages).

(Continued)

*Primary Examiner* — D Margaret M Seaman
(74) *Attorney, Agent, or Firm* — Rothwell, Figg, Ernst & Manbeck, P.C.

(57) ABSTRACT

Provided are a compound as shown in general formula (I), or a stereoisomer, deuterate, solvate, prodrug, metabolite, pharmaceutically acceptable salt or co-crystal thereof, an intermediate thereof, a preparation method therefor, and the use thereof in the preparation of a drug for treating a disease associated with the activity or expression quantity of complement factor B.

(I)

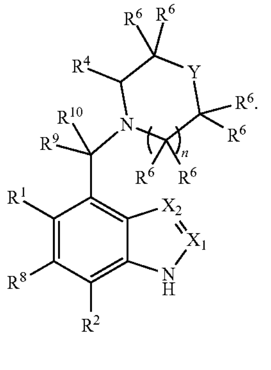

8 Claims, No Drawings

(51) Int. Cl.

| | |
|---|---|
| ***C07D 403/06*** | (2006.01) |
| ***C07D 405/14*** | (2006.01) |
| ***C07D 471/10*** | (2006.01) |
| ***C07D 491/08*** | (2006.01) |
| ***C07D 491/107*** | (2006.01) |
| ***C07D 495/10*** | (2006.01) |

(56) References Cited

U.S. PATENT DOCUMENTS

| | | | |
|---|---|---|---|
| 2016/0152605 | A1 | 6/2016 | Adams et al. |
| 2019/0135825 | A1 | 5/2019 | Wiles et al. |
| 2020/0338059 | A1 | 10/2020 | Eder et al. |
| 2022/0169630 | A1 | 6/2022 | Fu et al. |
| 2023/0286947 | A1 | 9/2023 | Luan et al. |
| 2023/0331710 | A1 | 10/2023 | Luan et al. |

FOREIGN PATENT DOCUMENTS

| | | | |
|---|---|---|---|
| CN | 111032042 | A | 4/2020 |
| CN | 114057758 | A | 2/2022 |
| EA | 202390060 | A1 | 6/2023 |
| EP | 4273137 | A1 | 11/2023 |
| WO | 2015009616 | A1 | 1/2015 |
| WO | 2020016749 | A2 | 1/2020 |
| WO | 2022028507 | A1 | 2/2022 |
| WO | 2022143940 | A1 | 7/2022 |
| WO | 2022/256586 | A2 | 12/2022 |
| WO | 2023/278698 | A1 | 1/2023 |
| WO | 2023072197 | A1 | 5/2023 |

OTHER PUBLICATIONS

International Search Report for International Application No. PCT/CN2022/113216 mailed Nov. 21, 2022, with English Translation (4 pages).

European Search Report dated Jul. 30, 2025 issued in European Patent Application No. 22857877.9. (17 pages).

Extended European Search Report issued on Dec. 15, 2025 for counterpart European patent application No. 22857877.9.

* cited by examiner

BENZO NITROGEN-CONTAINING HETEROAROMATIC RING DERIVATIVE AND USE THEREOF IN MEDICINE

CROSS-REFERENCE TO RELATED APPLICATIONS

This application is a continuation of U.S. patent application Ser. No. 18/684,549, filed on Feb. 16, 2024, which is a 371 National Stage of International Application No. PCT/CN2022/113216, filed on Aug. 18, 2022. The International Application claims priority to Chinese Patent Application No. 202110940107.4, filed on Aug. 18, 2021, Chinese Patent Application No. 202111048416.7, filed on Sep. 8, 2021, Chinese Patent Application No. 202111532328.4, filed on Dec. 16, 2021, Chinese Patent Application No. 202210255370.4, filed on Mar. 22, 2022, Chinese Patent Application No. 202210496109.3, filed on May 12, 2022, Chinese Patent Application No. 202210558720.4, filed on May 25, 2022 and Chinese Patent Application No. 202210903696.3, filed on Jul. 29, 2022. The aforementioned patent applications are hereby incorporated by reference in their entireties.

TECHNICAL FIELD

The present disclosure relates to a compound as shown in general formula (I), or a stereoisomer, deuterate, solvate, prodrug, metabolite, pharmaceutically acceptable salt or co-crystal thereof, an intermediate thereof, a preparation method therefor, and the use thereof in the preparation of a drug for treating a disease associated with the activity or expression quantity of complement factor B.

BACKGROUND ART

Complement factor B is a component of the complement alternative pathway and participates in the body's specific and non-specific immune mechanisms. It contains a serine protease (SP) domain. When activated, it will provide catalytic activity of C3 and C5 convertases of the alternative pathway. Complement factor B circulates as an inactive proenzyme (i.e., zymogen) and is activated only after being cleaved by protein factor D. However, protein factor D can only cleave complement factor B when bound to C3:C3 ($H_2O$) and C3b in the activated form. Complement factor B is produced as a single-chain protein and is cleaved by factor D to produce two peptide fragments (Ba and Bb). The Bb region (containing the SP domain) remains bound to C3 ($H_2O$) and C3b, forming the alternative pathway convertase [C3($H_2O$)Bb and C3bBb]. The SP domain of Bb, as part of the C3 convertase, has special catalytic activity for the cleavage of C3 molecules. Adding another C3b molecule to C3 convertase of the alternative pathway can produces C5 convertase (C3bBbC3b). As part of the C5 convertase of the alternative pathway, the SP domain of Bb cleaves the C5 molecule, allowing C5-C9 to assemble and ultimately form the membrane attack complex (MAC), which participates in mediating various kidney diseases through cell lysis, promoting the release of cytokines and inflammatory mediators, cooperating with cytokines and promoting collagen IV synthesis. Therefore, complement factor B is a key enzyme in the activation process of the complement alternative pathway and can be used as a suitable target to inhibit the complement activation pathway.

SUMMARY OF THE DISCLOSURE

The objective of the present disclosure is to provide a compound or a stereoisomer, deuterate, solvate, prodrug, metabolite, pharmaceutically acceptable salt or co-crystal thereof capable of inhibiting complement factor B, an intermediate thereof, a preparation method therefor, and the use thereof in the preparation of a drug for treating a disease associated with the activity or expression quantity of complement factor B.

The compound of the present disclosure has good inhibitory activity on complement factor B, and has good inhibition rate of C3a level in vivo, bioavailability and safety.

The present disclosure provides a compound of general formula (I) or a stereoisomer, deuterate, solvate, prodrug, metabolite, pharmaceutically acceptable salt or co-crystal thereof, wherein (I)

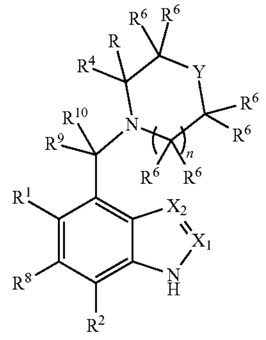

in some embodiments, the compound of general formula (I) is selected from a compound represented by general formula (Ia), (Ib), (Ic), (Id), (Ie) or (If), (Ia)

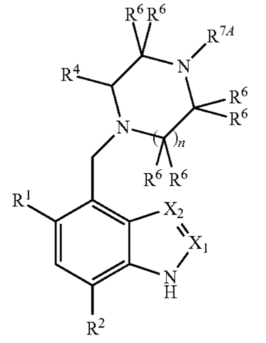

(Ib)

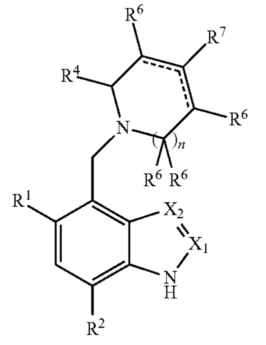

-continued (Ic)

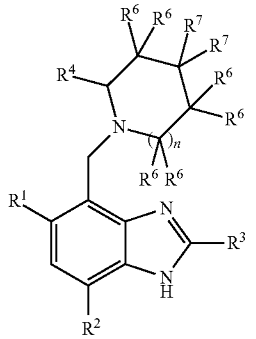

(Id)

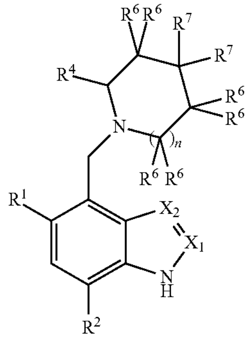

(Ie)

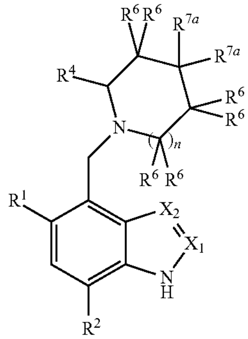

(If)

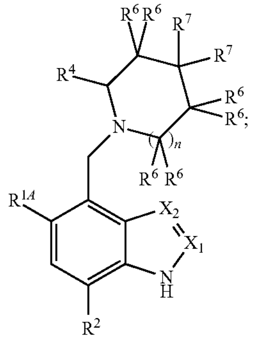

in some embodiments, the compound of general formula (I) is selected from the compound represented by general formula (Id-1) or general formula (Id-2)

(Id-1)

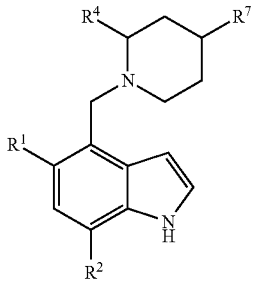

(Id-2)

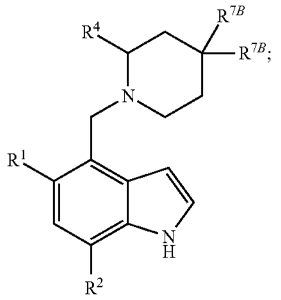

in some embodiments, the compound of general formula (I) is selected from the compound represented by general formula (Id-3) and general formula (Id-4), (Id-3)

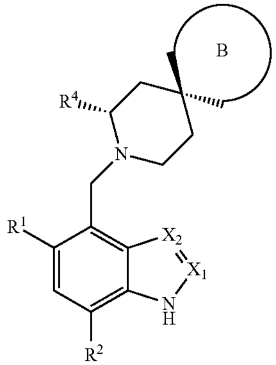

(Id-4)

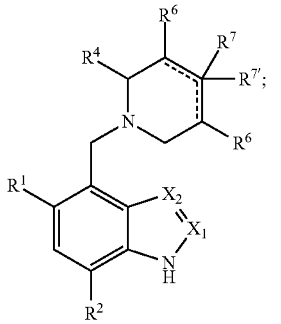

in some embodiments, the compound of general formula (I) is selected from the compound represented by general formula (Id-5), general formula (Id-6), general formula (Id-7), and general formula (Id-8), (Id-5)

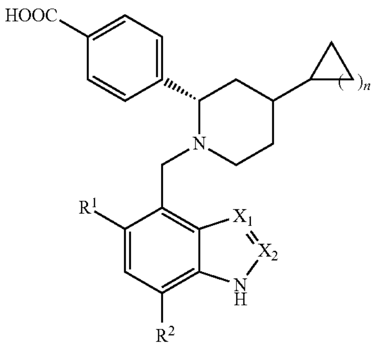

(Id-6)

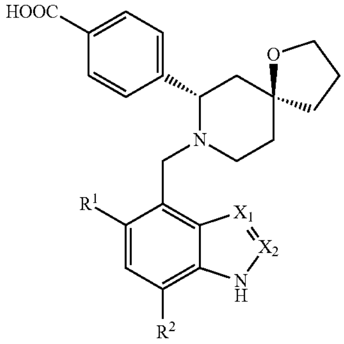

(Id-7)

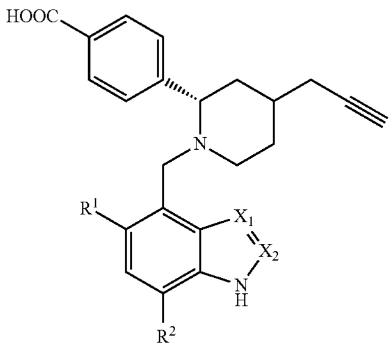

(Id-8)

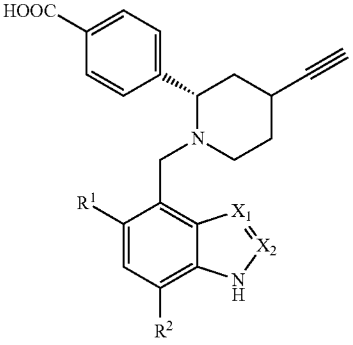

;

-continued (Id-8-a)

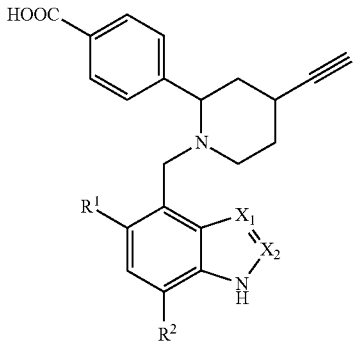

in some embodiments, $R^1$ is selected from H, halogen, OH, cyano, $NH_2$, $C_{1-6}$ alkyl, $C_{2-6}$ alkenyl, $C_{2-6}$ alkynyl, $C_{1-6}$ alkoxy, —C(═O)$C_{1-6}$ alkyl, —S(═O)$_p$$C_{1-6}$ alkyl, —W—$R^{1d}$, —$CH_2$NHC(O)$C_{1-4}$ alkyl, —$CH_2$C(═O)$R^{1e}$, —O$CH_2$C(═O)$R^{1e}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-6}$ alkyl, $C_{2-6}$ alkynyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, $R^1$ is selected from H, halogen, OH, cyano, $NH_2$, $C_{1-4}$ alkyl, $C_{2-4}$ alkenyl, $C_{2-4}$ alkynyl, $C_{1-4}$ alkoxy, —C(═O)$C_{1-4}$ alkyl, —S(═O)$_p$$C_{1-4}$ alkyl, —W—$R^{1d}$, —$CH_2$NHC(O)$C_{1-4}$ alkyl, —$CH_2$C(═O)$R^{1c}$, —O$CH_2$C(═O)$R^{1c}$, $C_{3-6}$ carbocyclyl or 4- to 8-membered heterocyclyl, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, $R^1$ is selected from H, halogen, OH, cyano, $NH_2$, $C_{1-4}$ alkyl, $C_{2-4}$ alkenyl, $C_{2-4}$ alkynyl, $C_{1-4}$ alkoxy, $C_{1-4}$ alkylthio, —W—$R^{1d}$, $C_{3-6}$ carbocyclyl or 4- to 8-membered heterocyclyl, wherein the alkyl, alkenyl, alkynyl, alkoxy, alkylthio, carbocyclyl or heterocyclyl is optionally further substituted with 0 to 4 substituents selected from H, D, halogen, OH, ═O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, $R^1$ is selected from $R^{1A}$.

in some embodiments, each $R^1$ is independently selected from H, F, Cl, Br, I, OH, cyano, $NH_2$, methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl or —W—$R^{1d}$, wherein the methyl, ethyl, propyl, isopropyl, tert-butyl, methoxy, ethoxy, isopropoxy, vinyl, ethynyl, propynyl, propargyl, methylthio, ethylthio, cyclopropyl, or cyclobutyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^1$ is independently selected from H, F, Cl, Br, I, OH, cyano, $NH_2$, methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl, —O-cyclopropyl, —O-cyclobutyl, —O-cyclopentyl, wherein the methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl, —O-cyclopropyl, —O-cyclobutyl, or —O-cyclopentyl is optionally further substituted with 0 to 4 substituents selected from H, D, F, Cl, Br, I, OH, =O, cyano, $NH_2$, methyl, ethyl, ethynyl, methoxy, ethoxy, $CF_3$, —$CH_2F$, —$CH_2OH$, cyclopropyl, cyclobutyl, azacyclobutyl or pyrrolidinyl;

in some embodiments, each $R^1$ is independently selected from H, F, Cl, Br, I, OH, cyano, $NH_2$, —$OCD_3$, $CD_3$, methyl, ethyl, propyl, isopropyl, tert-butyl, methoxy, ethoxy, isopropoxy, cyclopropyl, ethynyl, —$CH_2$-cyclopropyl or —O-cyclopropyl;

in some embodiments, each $R^1$ is independently selected from —$OCH_2F$, —$OCHF_2$, —$OCF_3$,

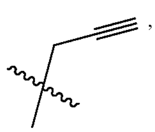
, or
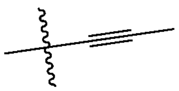
;

in some embodiments, $R^1$ is selected from H, F, Cl, Br, I, —$OCD_3$, $CD_3$, methyl, ethyl, propyl, methoxy, ethoxy, isopropoxy, cyclopropyl, —$CH_2$-cyclopropyl or —O—cyclopropyl;

in some embodiments, $R^1$ is selected from —$OCH_3$ or —$OCD_3$;

in some embodiments, $R^{1A}$ is selected from ethynyl, propynyl, propargyl, —$CH_2$— cyclopropyl, —$CH_2$-cyclobutyl, —$CH_2$-cyclopentyl, —$CH_2$-oxacyclobutyl, —$CH_2$— azacyclobutyl, —$CH_2$-pyrrolidinyl, —O-cyclopropyl, —O-cyclobutyl, —O-cyclopentyl, the ethynyl, propynyl, propargyl, —O-cyclopropyl, —O-cyclobutyl, —O-cyclopentyl or —$CH_2$— is optionally further substituted with 0 to 2 substituents selected from H, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, $R^{1A}$ is selected from ethynyl, propynyl, propargyl, —$CH_2$— cyclopropyl, —$CH_2$-cyclobutyl, —$CH_2$-cyclopentyl, —$CH_2$-oxacyclobutyl, —$CH_2$— azacyclobutyl, —$CH_2$-pyrrolidinyl, —O-cyclopropyl, —O-cyclobutyl, —O-cyclopentyl, the ethynyl, propynyl, propargyl, —O-cyclopropyl, —O-cyclobutyl, —O-cyclopentyl or —$CH_2$— is optionally further substituted with 0 to 2 substituents selected from H, F, Cl, Br, I, OH, =O, cyano, $NH_2$, methyl, ethyl, ethynyl, methoxy, ethoxy, $CF_3$, —$CH_2F$, —$CH_2OH$, cyclopropyl, cyclobutyl, azacyclobutyl or pyrrolidinyl;

in some embodiments, W is selected from O or S;

in some embodiments, n is selected from 0, 1, or 2;

in some embodiments, p is selected from 0, 1, or 2;

in some embodiments, $X_1$ and $X_2$ are each independently selected from N or $CR^3$;

in some embodiments, $X_1$ is selected from $CR^3$, and $X_2$ is selected from $CR^3$;

in some embodiments, $X_1$ is selected from N, and $X_2$ is selected from $CR^3$;

in some embodiments, $X_1$ is selected from $CR^3$ and $X_2$ is selected from N;

in some embodiments, $X_1$ is selected from N or CH, $X_2$ is selected from N or CH, wherein the CH is optionally substituted with 1 methyl or ethyl;

in some embodiments, $X_1$ and $X_2$ are each independently selected from N;

in some embodiments, Y is selected from $NR^7$ or $C(R^7)_2$;

in some embodiments, Y is selected from $CR^7R^{7'}$;

in some embodiments, Y is selected from $NR^{7A}$;

in some embodiments, Y is selected from $C(R^{7a})_2$;

in some embodiments, Y is selected from $C(R^{7B})_2$;

in some embodiments, Y is selected from

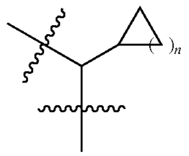

and n is selected from 1, 2 or 3;

in some embodiments,

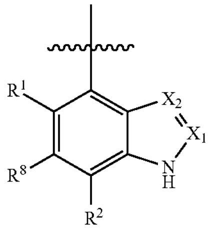

is selected from

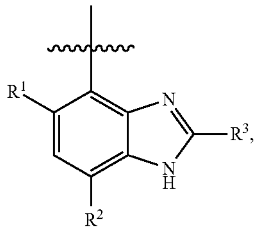
,
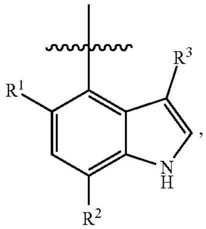
, or

-continued

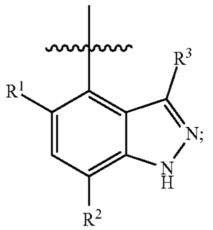

in some embodiments,

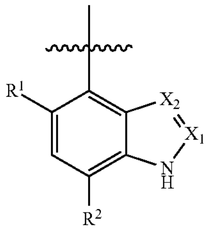

is selected from

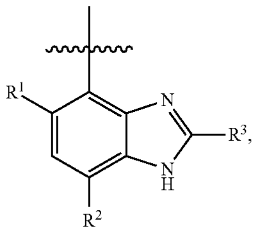

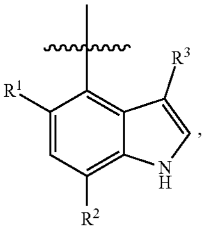

, or

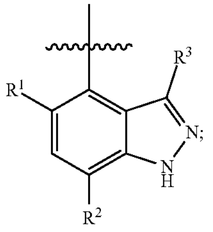

in some embodiments,

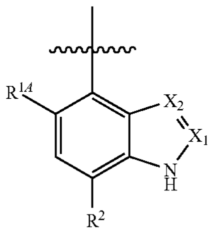

is selected from

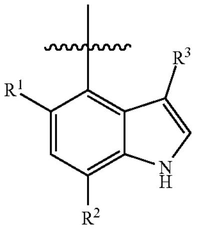

or

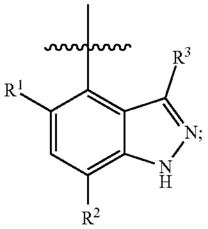

in some embodiments,

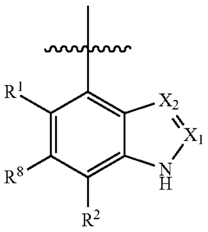

is selected from

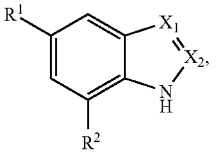

and

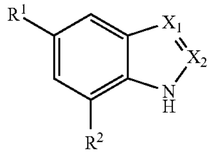

is selected from

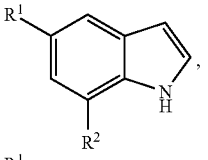

,

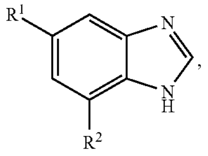

, or

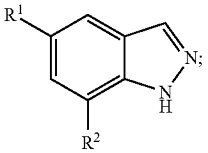

in some embodiments, each $R^3$ is independently selected from H, halogen, cyano, $C_{1-6}$ alkyl, $C_{1-6}$ alkoxy, $C_{2-6}$ alkenyl, $C_{2-6}$ alkynyl, $-CH_2C(=O)R^{1c}$, $-S(=O)_p$ $C_{1-6}$ alkyl, $-CH_2NHC(O)C_{1-4}$ alkyl, $-OCH_2C(=O)R^{1c}$, $C_{3-6}$ carbocyclyl or 5- to 6-membered heteroaryl, wherein the alkyl, $C_{1-6}$ alkoxy, $C_{2-6}$ alkenyl, $C_{2-6}$ alkynyl, carbocyclyl or heteroaryl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N;

in some embodiments, each $R^3$ is independently selected from H, halogen, cyano, $C_{1-4}$ alkyl, $C_{1-4}$ alkoxy, $C_{2-4}$ alkenyl, $C_{2-4}$ alkynyl, $—CH_2C(=O)R^{1c}$, $—S(=O)_p$ $C_{1-4}$ alkyl, $—CH_2NHC(O)C_{1-4}$ alkyl, $—OCH_2C(=O)R^{1c}$, $C_{3-6}$ carbocyclyl or 5- to 6-membered heteroaryl, wherein the alkyl, $C_{1-4}$ alkoxy, $C_{2-4}$ alkenyl, $C_{2-4}$ alkynyl, carbocyclyl or heteroaryl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heteroaryl contains 1 to 4 heteroatoms selected from O, S or N;

in some embodiments, each $R^3$ is independently selected from H, F, Cl, Br, I, cyano, methyl, ethyl, propyl, isopropyl, $—CH_2C(=O)OH$, or $—CH_2C(=O)NH_2$, wherein the methyl, ethyl, propyl or isopropyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, each $R^3$ is independently selected from H, F, Cl, Br, I, cyano, methyl, ethyl, propyl, isopropyl, $—CH_2C(=O)OH$, or $—CH_2C(=O)NH_2$, wherein the methyl, ethyl, propyl or isopropyl is optionally further substituted with 0 to 4 substituents selected from H, F, Cl, Br, I, OH, or cyano;

in some embodiments, each $R^3$ is independently selected from H, methyl, or ethyl;

in some embodiments, $R^2$ is selected from halogen, $C_{1-6}$ alkyl or $C_{1-6}$ alkoxy, wherein the alkyl or alkoxy is optionally further substituted with 0 to 4 substituents selected from H, D, halogen, OH, cyano or $NH_2$;

in some embodiments, $R^2$ is selected from halogen, $C_{1-4}$ alkyl or $C_{1-4}$ alkoxy, wherein the alkyl or alkoxy is optionally further substituted with 0 to 4 substituents selected from H, D, halogen, OH, cyano or $NH_2$;

in some embodiments, $R^2$ is selected from F, Cl, Br, I, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, D, F, Cl, Br, I, OH, cyano or $NH_2$;

in some embodiments, $R^2$ is selected from F, Cl, Br, I, methyl, ethyl, propyl, isopropyl, tert-butyl, methoxy, ethoxy, or isopropoxy;

in some embodiments, each $R^2$ is independently selected from F, Cl, Br, I, methyl, ethyl, propyl, or isopropyl;

in some embodiments, $R^2$ is selected from F, Cl, Br, I, methyl, ethyl, propyl, or isopropyl;

in some embodiments, each $R^2$ is independently selected from $CD_3$, $CHD_2$, or $CH_2D$;

in some embodiments, each $R^2$ is independently selected from $—CH_3$, or $—CD_3$;

in some embodiments, each $R^6$ is independently selected from H, halogen, OH, $—NR^{1a}R^{1b}$, $C_{1-6}$ alkyl or $C_{1-6}$ alkoxy, wherein the alkyl, and alkoxy are optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^6$ is independently selected from H, halogen, OH, $—NR^{1a}R^{1b}$, $C_{1-4}$ alkyl or $C_{1-4}$ alkoxy, wherein the alkyl, and alkoxy are optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^6$ is independently selected from H, F, Cl, Br, I, OH, $NH_2$, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, each $R^6$ is independently selected from H, F, Cl, Br, I, OH, $NH_2$, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, F, Cl, Br, I, OH, =O, cyano, $NH_2$, methyl, ethyl, methoxy, ethoxy, $CF_3$, $—CH_2F$ or $—CH_2OH$;

in some embodiments, each $R^6$ is independently selected from H, F, Cl, Br, I, OH, $NH_2$, methyl, ethyl, propyl, isopropyl, tert-butyl, methoxy, ethoxy or isopropoxy;

in some embodiments, each $R^6$ is independently selected from H, F, Cl, Br, I, OH, $NH_2$, methyl, ethyl, propyl, or isopropyl;

in some embodiments, R is selected from H, or $C_{1-6}$ alkyl, wherein the alkyl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl;

in some embodiments, R is selected from H, or $C_{1-4}$ alkyl, wherein the alkyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, R is selected from H, methyl, ethyl, propyl or isopropyl, wherein the methyl, ethyl, propyl or isopropyl is optionally further substituted with 0 to 4 substituents selected from H, F, Cl, Br, I, OH, =O, cyano, $NH_2$, methyl, ethyl or $CF_3$;

in some embodiments, R is selected from H;

in some embodiments, each $R^7$ is independently selected from H, halogen, OH, $—NR^{1a}R^{1b}$, $C_{1-6}$ alkyl, $C_{1-6}$ alkoxy, $C_{2-6}$ alkenyl, $C_{2-6}$ alkynyl, $—C(=O)R^{1d}$, $—S(=O)_2R^{1d}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-6}$ alkyl, $C_{1-6}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^7$ is independently selected from H, halogen, OH, —$NR^{1a}R^{1b}$, $C_{1-4}$ alkyl, $C_{1-4}$ alkoxy, $C_{2-4}$ alkenyl, $C_{2-4}$ alkynyl, —C(=O)$R^{1d}$, —S(=O)$_2R^{1d}$, $C_{3-6}$ carbocyclyl or 3- to 8-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl is contains 1 to 4 heteroatoms selected from O, S or N;

in some embodiments, each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, —C(=O)$R^{1d}$, —S(=O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, —C(=O)$R^{1d}$, —S(=O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, ethynyl, propynyl, methoxy, ethoxy, $CF_3$, —$CH_2F$, —$CH_2OH$, cyclopropyl, cyclobutyl, azacyclobutyl or pyrrolidinyl;

in some embodiments, each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, —$CH_2$-propynyl, —$CH_2$-cyclopropyl, —$CH_2$-cyclobutyl, —$CH_2$-azacyclobutyl, —$CH_2OCH_3$, —$OCH_2CH_2OCH_3$, —$CH_2CH_2OCH_3$, —$CH_2CF_3$, —$OCH_2$— cyclopropyl, —C(=O)$CH_3$, —C(=O)-cyclopropyl, —C(=O)-phenyl, —S(=O)$_2CH_3$, —S(=O)$_2$ $CH_2CH_3$, —S(=O)$_2$-cyclopropyl, —S(=O)$_2$—$CH_2$-cyclopropyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, ethynyl, propynyl, methoxy, ethoxy, $CF_3$, —$CH_2F$, —$CH_2OH$, cyclopropyl, cyclobutyl, azacyclobutyl or pyrrolidinyl;

in some embodiments, $R^7$ is selected from methoxymethyl, methoxyethyl, cyclopropyl, cyclobutyl, cyclopentyl, cyclohexyl, azacyclobutyl, azacyclopentyl, azacyclohexyl, oxacyclobutyl, oxacyclopentyl, oxacyclohexyl, ethynyl, propynyl or propargyl, wherein the cyclopropyl, cyclobutyl, cyclopentyl, cyclohexyl, azacyclobutyl, azacyclopentyl, azacyclohexyl, oxacyclobutyl, oxacyclopentyl, oxacyclohexyl, ethynyl, propynyl or propargyl is optionally further substituted with 0 to 4 substituents selected from H, D, F, Cl, Br, $CF_3$, OH, =O, cyano, $NH_2$, methyl, or methoxy;

in some embodiments, $R^7$ is selected from ethynyl, propynyl or propargyl, wherein the ethynyl, propynyl or propargyl is optionally further substituted with 0 to 4 substituents selected from H, D, F, Cl, Br, $CF_3$, OH, =O, cyano, $NH_2$, methyl, or methoxy.

in some embodiments, two $R^{7B}$ together with the carbon to which they are attached form the following ring:

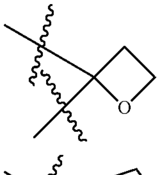
,
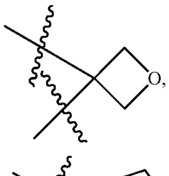
,
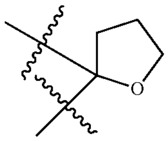
,
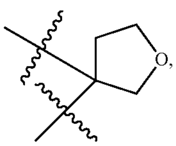
,
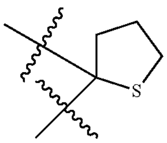
,
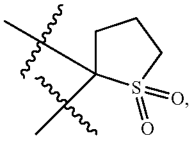
, or
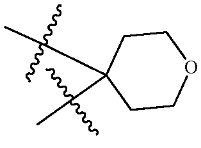
;

in some embodiments, $R^{7'}$ is selected from $R^7$;

in some embodiments, $R^{7'}$ is selected from H, F, OH, $NH_2$, methyl, ethyl, methoxy, or ethoxy, wherein the methyl, ethyl, methoxy, and ethoxy are optionally further substituted with 0 to 4 substituents selected from H, D, F, Cl, Br, $CF_3$, OH, methyl, ethyl, methoxy or ethoxy;

in some embodiments,

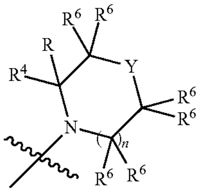

is selected from

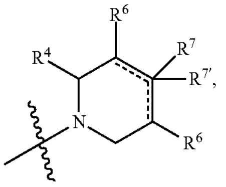

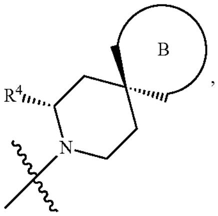

, or

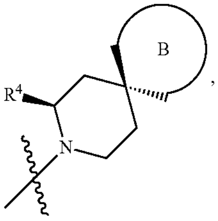

,

 is selected from a single bond or a double bond, when it is selected from a double bond, $R^{7'}$ does not exist, and at most 1  in

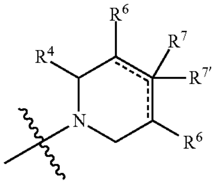

is selected from a double bond;

in some embodiments, ring B is selected from 3- to 6-membered heterocyclyl, wherein the heterocyclyl is optionally further substituted with 0 to 4 substituents selected from H, halogen, OH, =O, cyano, —C(=O)$R^{1d}$, —S(=O)$_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, ring B is selected from 3- to 6-membered heterocycloalkyl, wherein the heterocycloalkyl is optionally further substituted with 0 to 4 substituents selected from H, halogen, OH, =O, cyano, $NH_2$, —C(=O)$C_{1-4}$ alkyl, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heterocycloalkyl contains 1 to 4 heteroatoms selected from O, S or N;

in some embodiments, ring B is selected from oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, halogen, OH, =O, cyano, $NH_2$, —C(=O)$C_{1-4}$ alkyl, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, ring B is selected from oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, F, Cl, Br, $CF_3$, OH, =O, cyano, $NH_2$, —C(=O)$CH_3$, methyl, ethyl, methoxy or ethoxy;

in some embodiments, each $R^6$ in

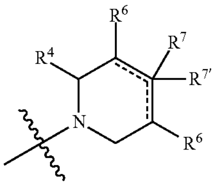

is independently selected from H, halogen, OH, $NH_2$, $C_{1-4}$ alkyl or $C_{1-4}$ alkoxy, wherein the alkyl or alkoxy is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, each $R^6$ in

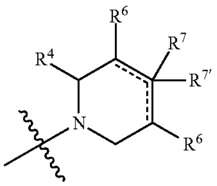

is independently selected from H, F, Cl, Br, $CF_3$, methyl or ethyl;

in some embodiments, in

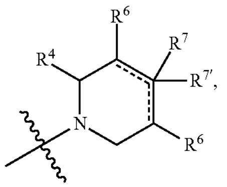

$R^7$ is selected from $C_{2-4}$ alkynyl, $C_{3-6}$ carbocyclyl, or 3- to 8-membered heterocyclyl, $R^{7'}$ is selected from H, halogen, OH, —$NR^{1a}R^{1b}$, $C_{1-4}$ alkyl, $C_{1-4}$ alkoxy, $C_{2-4}$ alkenyl, $C_{2-4}$ alkynyl, —C(═O)$R^{1d}$, —S(═O)$_2R^{1d}$, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl is contains 1 to 4 heteroatoms selected from O, S or N;

in some embodiments, in

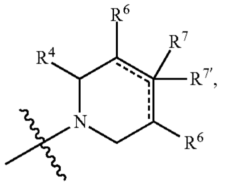

$R^7$ is selected from $C_{2-4}$ alkynyl, phenyl, $C_{3-6}$ cycloalkyl, 3- to 8-membered heterocycloalkyl or 5- to 6-membered heteroaryl, $R^{7'}$ is selected from H, halogen, OH, —$NH_2$, $C_{1-4}$ alkyl, $C_{1-4}$ alkoxy, $C_{2-4}$ alkenyl, $C_{2-4}$ alkynyl, —C(═O)$C_{1-4}$ alkyl, —S(═O)$_2C_{1-4}$ alkyl, wherein the alkyl, alkenyl, alkynyl, alkoxy, phenyl, cycloalkyl, heteroaryl, or heterocycloalkyl is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocycloalkyl, heterocyclyl or heteroaryl contains 1 to 4 heteroatoms selected from O, S or N;

in some embodiments, in

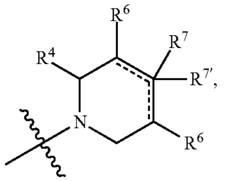

$R^7$ is selected from one of the following substituted or unsubstituted groups: ethynyl, propynyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, $R^{7'}$ is selected from H, F, OH, or $NH_2$, or one of the following substituted or unsubstituted groups: methyl, ethyl, propyl, isopropyl, tert-butyl, methoxy, ethoxy, isopropoxy, vinyl, ethynyl, propynyl or propargyl, $R^7$ or $R^{7'}$, when substituted, is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, in

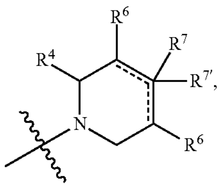

$R^7$ is selected from one of the following substituted or unsubstituted groups: ethynyl, propynyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, $R^{7'}$ is selected from H, F, OH, or $NH_2$, or one of the following substituted or unsubstituted groups: methyl, ethyl, propyl, isopropyl, tert-butyl, methoxy, ethoxy, isopropoxy, vinyl, ethynyl, propynyl or propargyl, $R^7$ or $R^{7'}$, when substituted, is optionally further substituted with 0 to 4 substituents selected from H, D, F, Cl, Br, $CF_3$, OH, ═O, cyano, $NH_2$, methyl, ethyl, methoxy, ethoxy, ethynyl, propynyl, propargyl, cyclopropyl, cyclobutyl, cyclopentyl, azacyclobutyl, pyrrolidinyl, piperidinyl, morpholinyl or piperazinyl;

in some embodiments, in

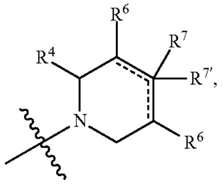

$R^7$ is selected from ethynyl, propynyl, propargyl, cyclopropyl, cyclobutyl, cyclopentyl, wherein the propynyl, propargyl, cyclopropyl, cyclobutyl, or cyclopentyl is optionally further substituted with 0 to 4 substituents selected from H, D, F, Cl, Br, $CF_3$, OH, methyl, ethyl, methoxy, ethoxy, or cyclopropyl, $R^{7'}$ is selected from H, F, OH, $NH_2$, methyl, ethyl, methoxy, or ethoxy, wherein the methyl, ethyl, methoxy, and ethoxy are optionally further substituted with 0 to 4 substituents selected from H, D, F, Cl, Br, $CF_3$, OH, methyl, ethyl, methoxy or ethoxy;

in some embodiments,

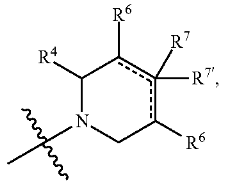

is selected from one of the following structures:

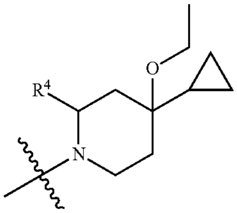

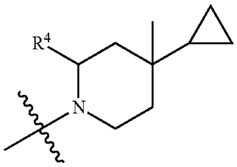

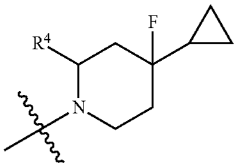

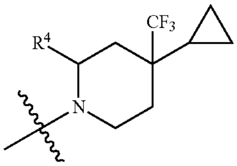

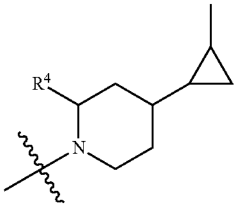

-continued

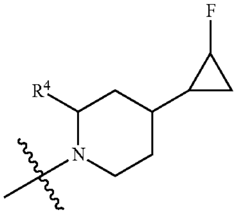

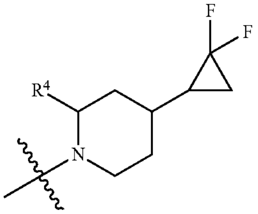

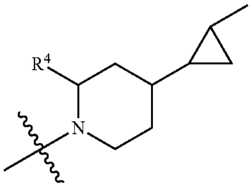

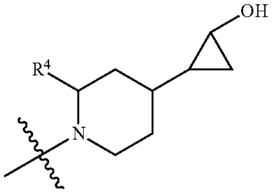

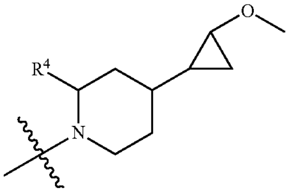

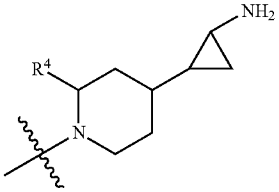

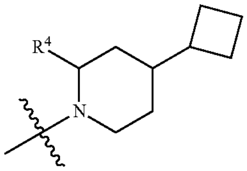

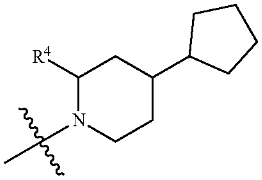

-continued
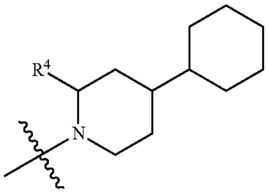
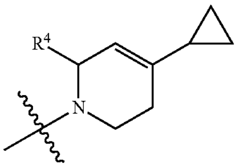
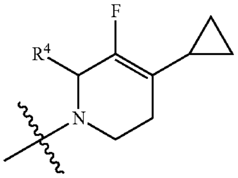
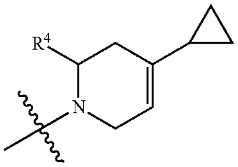
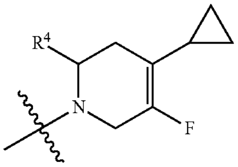
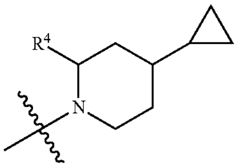
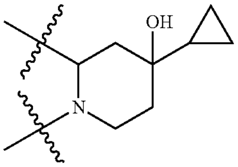
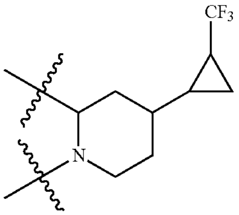 [SMILES: *C1CC(C2CC2C(F)(F)F)CCN1*]
-continued
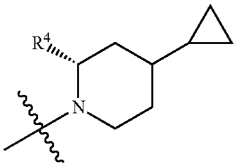
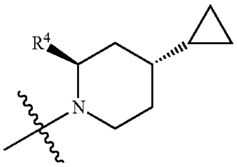
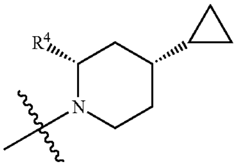
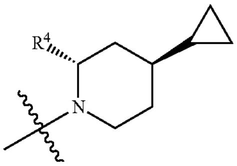
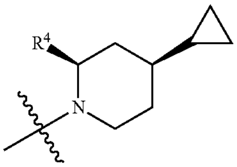
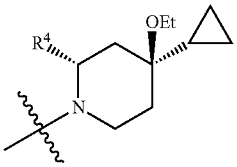
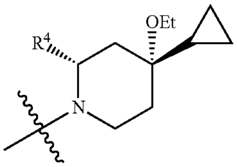
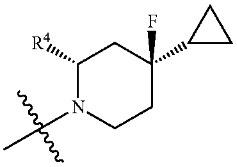
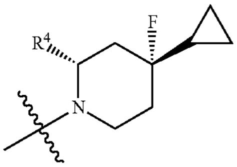

-continued
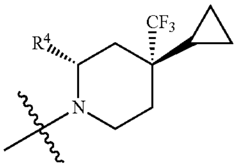
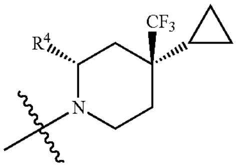
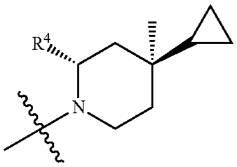
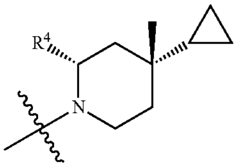
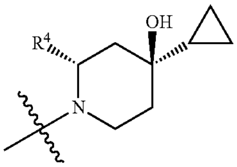
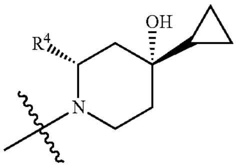
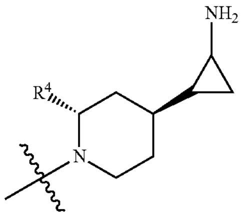
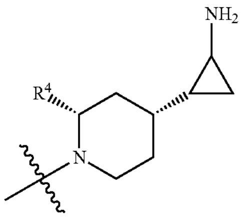
-continued
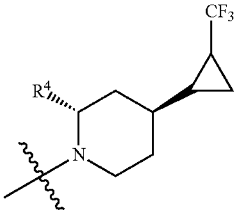
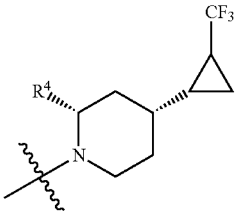
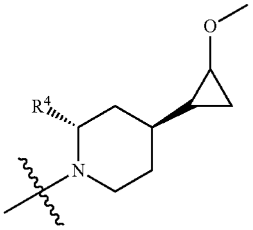
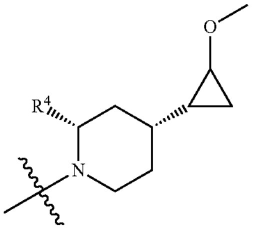
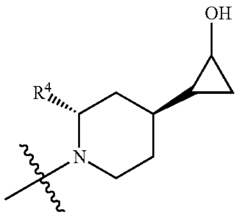
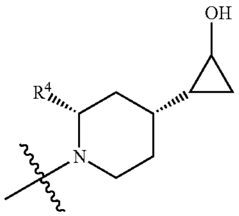
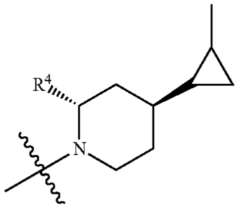

-continued
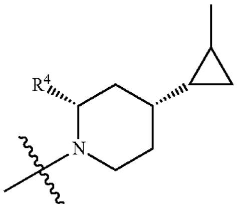
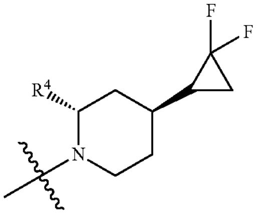
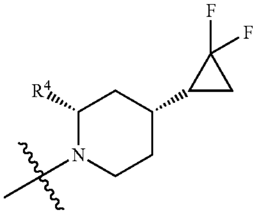
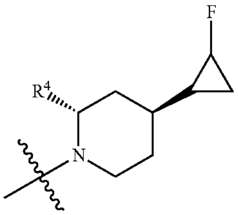
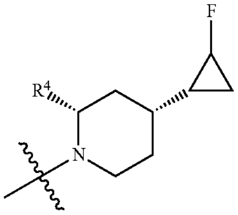
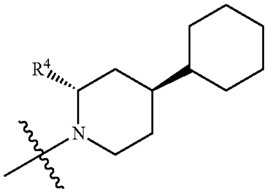
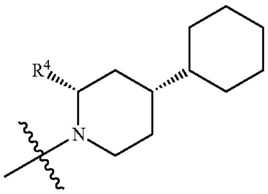
-continued
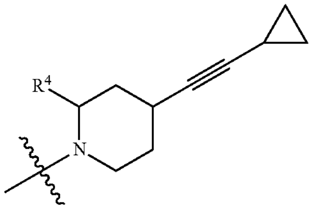
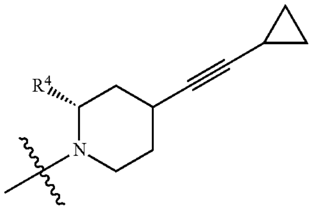
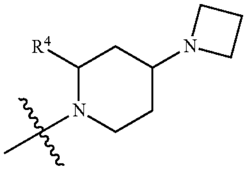
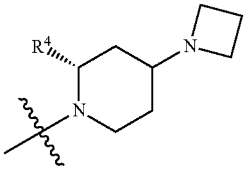
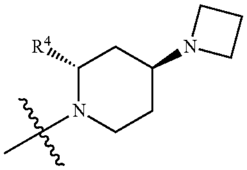
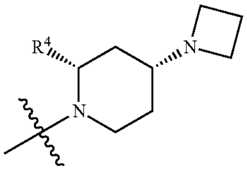
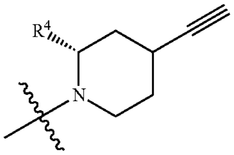
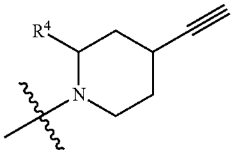

-continued
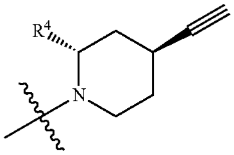
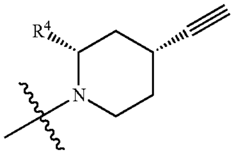
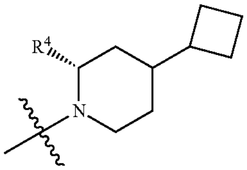
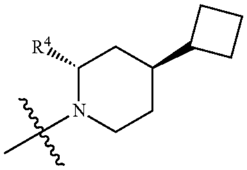
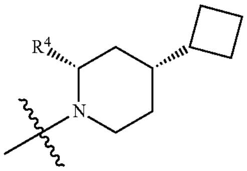
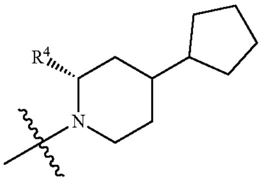
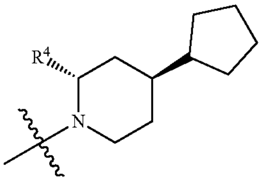
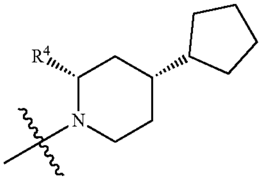
-continued
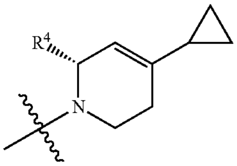
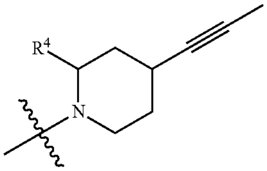
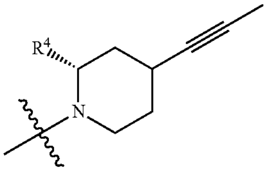
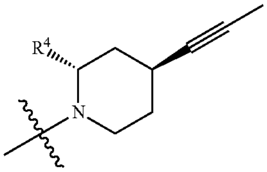
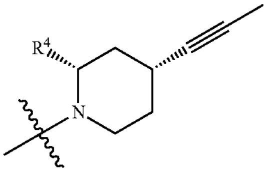
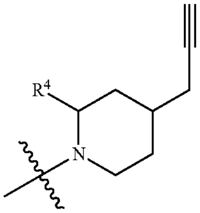
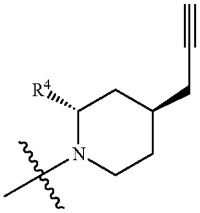
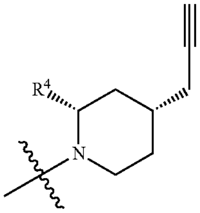

-continued

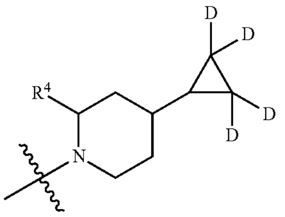

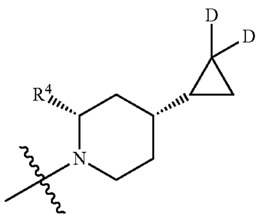

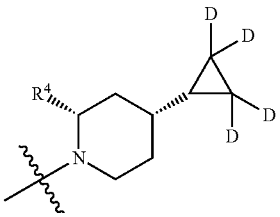

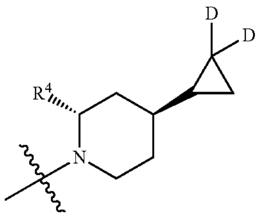

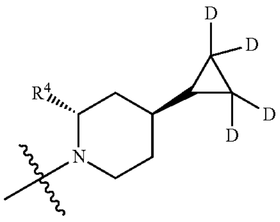

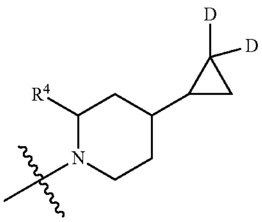

in some embodiments, $R^7$ is selected from $R^{7B}$, and two $R^{7B}$ together with the carbon to which they are attached form the following ring:

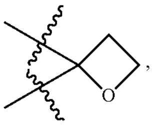
,
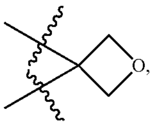

-continued

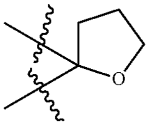
,
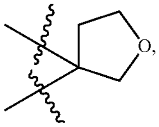

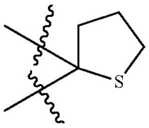
,
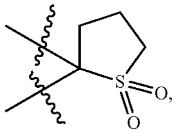
or
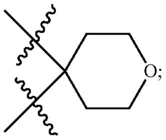

in some embodiments, $R^7$ is selected from $R^{7A}$ or $R^{7a}$;

in some embodiments, $R^{7A}$ is selected from H, F, Cl, Br, I, methyl, ethyl, propyl, isopropyl, tert-butyl, methoxy, ethoxy, isopropoxy, —C(=O)$R^{1d}$, —S(=O)$_2R^{1d}$, cyclopropyl, cyclobutyl, cyclopentyl, cyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, cyclopropyl, cyclobutyl, cyclopentyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, $R^{7A}$ is selected from H, F, Cl, Br, I, methyl, ethyl, propyl, isopropyl, tert-butyl, methoxy, ethoxy, isopropoxy, —C(=O)$R^{1d}$, —S(=O)$_2R^{1d}$, cyclopropyl, cyclobutyl, cyclopentyl, cyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, cyclopropyl, cyclobutyl, cyclopentyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, methoxy, ethoxy, $CF_3$, —$CH_2F$, —$CH_2OH$, cyclopropyl or cyclobutyl;

in some embodiments, $R^{7A}$ is selected from F, Cl, Br, I, methyl, ethyl, propyl, isopropyl, tert-butyl, —$CH_2$-cyclopropyl, —$CH_2$-cyclobutyl, —$CH_2$-azacyclobutyl, —$CH_2OCH_3$, —$CH_2CH_2OCH_3$, —$CH_2CF_3$, —C(=O)$CH_3$, —C(=O)-cyclopropyl, —C(=O)-phenyl, —S(=O)$_2CH_3$, —S(=O)$_2$-cyclopropyl, —S(=O)$_2$—$CH_2$-cyclopropyl, cyclopropyl, cyclobutyl, cyclopentyl or imidazolyl;

in some embodiments, each $R^7$ is independently selected from $R^d$, F, Cl, Br, I, vinyl, ethynyl, propynyl, propargyl, —C(=O)$R^{1d}$, —S(=O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, =O, cyano, $NH_2$, $C_{1-4}$ alkyl, C24 alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^7$ is independently selected from $R^d$, F, Cl, Br, I, vinyl, ethynyl, propynyl, propargyl, —C(=O)$R^{1d}$, —S(=O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, ethynyl, methoxy, ethoxy, $CF_3$, —$CH_2$F, —$CH_2$OH, cyclopropyl, cyclobutyl, azacyclobutyl or pyrrolidinyl;

in some embodiments, $R^{7a}$ is selected from F, Cl, Br, I, $CF_3$, —$CH_2$F, vinyl, ethynyl, propynyl, propargyl, —$CH_2$-propynyl, —$CH_2$-cyclopropyl, —$CH_2$-cyclobutyl, —$CH_2$— azacyclobutyl, —$CH_2OCH_3$, —$OCH_2CH_2OCH_3$, —$CH_2CH_2OCH_3$, —$CH_2CF_3$, —$OCH_2$— cyclopropyl, —C(=O)$CH_3$, —C(=O)-cyclopropyl, —C(=O)-phenyl, —S(=O)$_2CH_3$, —S(=O)$_2CH_2CH_3$, —S(=O)$_2$-cyclopropyl, —S(=O)$_2$—$CH_2$-cyclopropyl, cyclopropyl, cyclobutyl, cyclopentyl, azacyclobutyl, pyrrolidinyl, piperidinyl, morpholinyl, piperazinyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl;

in some embodiments, each $R^d$ is independently selected from methyl, ethyl, propyl, isopropyl, tert-butyl, methoxy, ethoxy, or isopropoxy, the methyl, ethyl, propyl, isopropyl, tert-butyl, methoxy, ethoxy, and isopropoxy is further substituted with 1 to 3 substituents selected from halogen, ethynyl, $C_{2-4}$ alkynyl, $C_{1-4}$ alkoxy, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl;

in some embodiments, each $R^d$ is independently selected from methyl, ethyl, propyl, isopropyl, tert-butyl, methoxy, ethoxy, or isopropoxy, the methyl, ethyl, propyl, isopropyl, tert-butyl, methoxy, ethoxy, and isopropoxy is further substituted with 1 to 3 substituents selected from F, Cl, Br, I, ethynyl, methoxy, ethoxy, $CF_3$, —$CH_2$F, cyclopropyl, cyclobutyl, azacyclobutyl or pyrrolidinyl;

in some embodiments, two $R^7$ together with the carbon atom to which they are attached form a 3- to 6-membered heterocyclyl, wherein the heterocyclyl is optionally further substituted with 0 to 4 substituents selected from H, halogen, OH, =O, cyano, —C(=O)$R^{1d}$, —S(=O)$_2R^{1d}$, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, two $R^7$ together with the carbon atom to which they are attached form a 3- to 6-membered heterocyclyl, wherein the heterocyclyl is optionally further substituted with 0 to 4 substituents selected from H, halogen, OH, =O, cyano, —C(=O)$R^{1d}$, —S(=O)$_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, two $R^7$ together with the carbon atom to which they are attached form oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, halogen, OH, =O, cyano, —C(=O) $R^{1d}$, —S(=O)$_2R^{1d}$ $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, $R^6$ and $R^7$ at adjacent positions can form a double bond;

in some embodiments, two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl, wherein the heterocyclyl contains 1 to 4 heteroatoms selected from O, S or N;

in some embodiments, two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heterocyclyl contains 1 to 4 heteroatoms selected from O, S or N;

in some embodiments, two $R^6$ together with the atom to which they are attached form cyclobutyl, cyclopentyl, cyclohexyl, oxacyclobutyl, oxacyclopentyl, oxacyclohexyl, thiocyclopentyl, azacyclobutyl, pyrrolidinyl, piperidinyl, morpholinyl or piperazinyl;

in some embodiments,
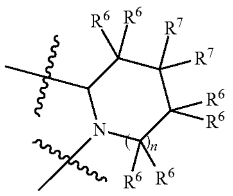
is selected from
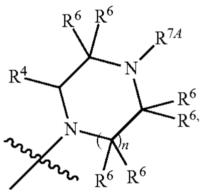
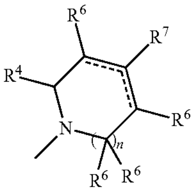
or
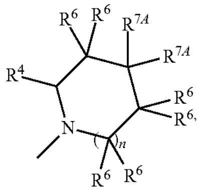
represents a single bond or a double bond, and wherein only one double bond is contained;
in some embodiments,
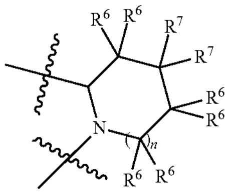
is selected from
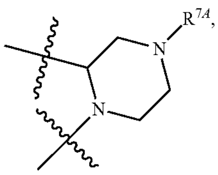
,
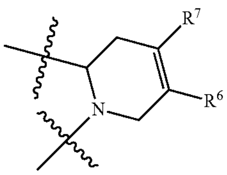
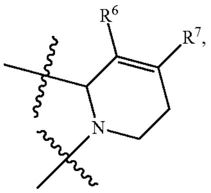
or
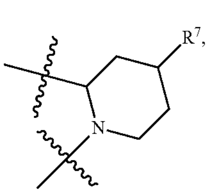
-continued
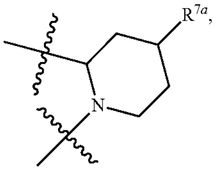
which is connected to $R^4$ at the upper part;
in some embodiments
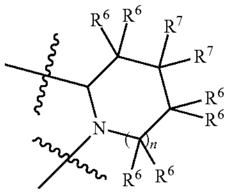
is selected from the fragments in the following table which are connected to $R^4$ at the upper part
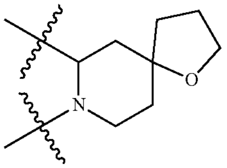
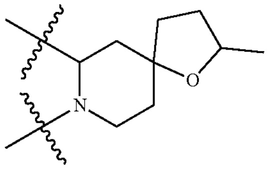
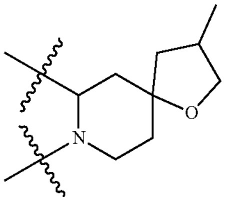
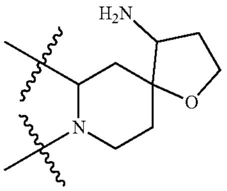
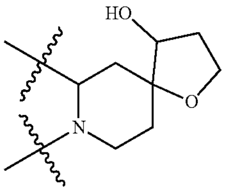

-continued
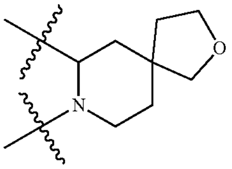
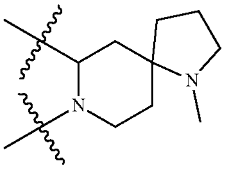
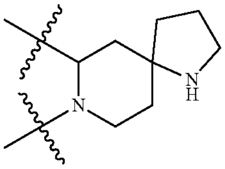
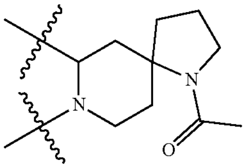
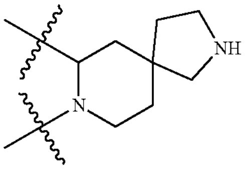
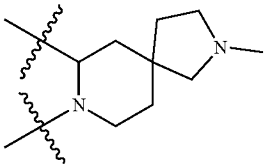
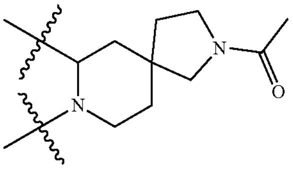
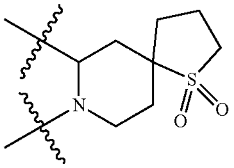
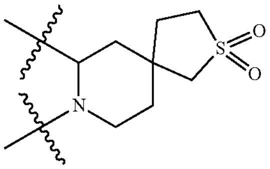
-continued
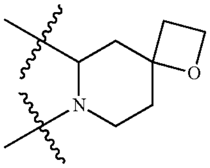
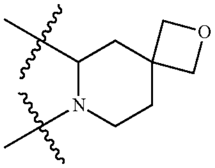
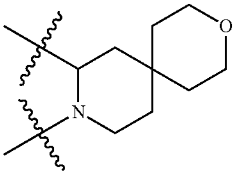
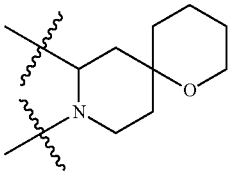
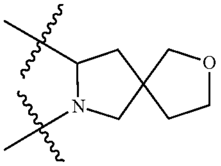 [SMILES: *C1CC2(CCOC2)CN1*]
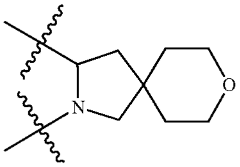 [SMILES: *C1CC2(CCOCC2)CN1*]
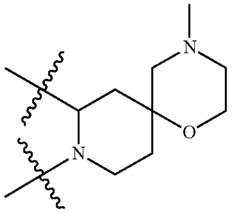 [SMILES: *C1CC2(CCN1*)CN(C)CCO2]
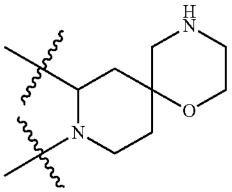 [SMILES: *C1CC2(CCN1*)CNCCO2]

-continued
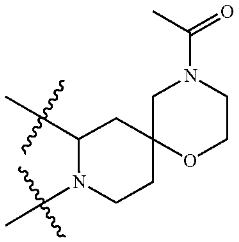 [SMILES: *C1CC2(CCN1*)CN(C(C)=O)CCO2]
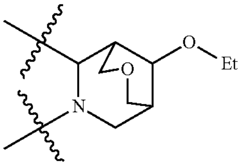 [SMILES: *C1C2COCC(CN1*)C2OCC]
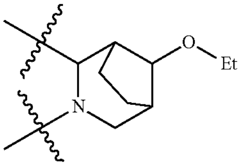 [SMILES: *C1C2CCC(CN1*)C2OCC]
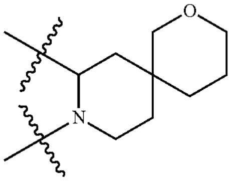
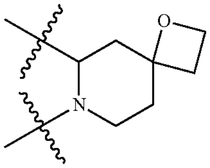
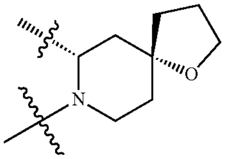
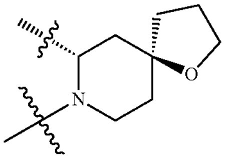
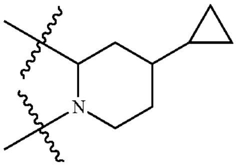 [SMILES: *C1CC(C2CC2)CCN1*]
-continued
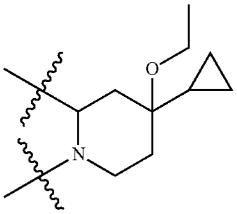 [SMILES: *C1CC(OCC)(C2CC2)CCN1*]
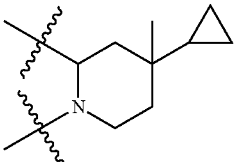 [SMILES: *C1CC(C)(C2CC2)CCN1*]
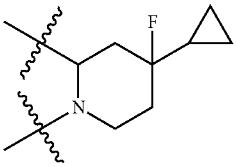 [SMILES: *C1CC(F)(C2CC2)CCN1*]
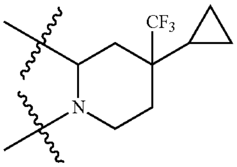 [SMILES: *C1CC(C2CC2)(C(F)(F)F)CCN1*]
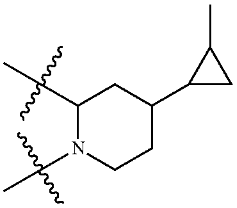 [SMILES: *C1CC(C2CC2C)CCN1*]
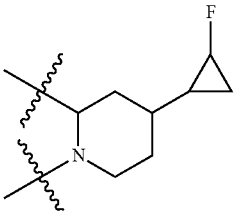 [SMILES: *C1CC(C2CC2F)CCN1*]
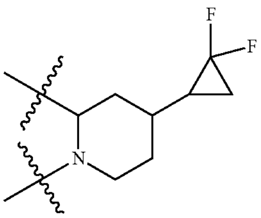 [SMILES: *C1CC(C2CC2(F)F)CCN1*]
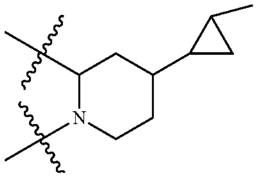 [SMILES: *C1CC(C2CC2C)CCN1*]

-continued
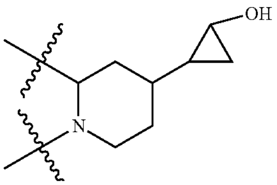 [SMILES: *C1CC(C2CC2O)CCN1*]
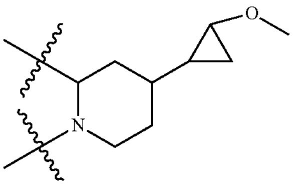 [SMILES: *C1CC(C2CC2OC)CCN1*]
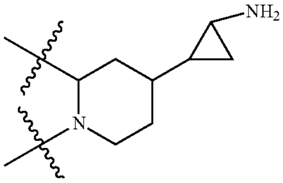 [SMILES: *C1CC(C2CC2N)CCN1*]
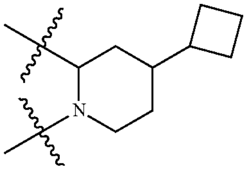 [SMILES: *C1CC(C2CCC2)CCN1*]
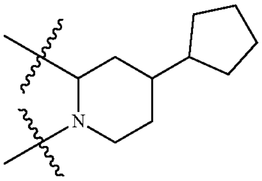 [SMILES: *C1CC(C2CCCC2)CCN1*]
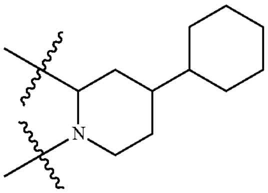 [SMILES: *C1CC(C2CCCCC2)CCN1*]
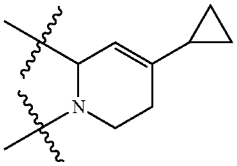 [SMILES: *C1C=C(C2CC2)CCN1*]
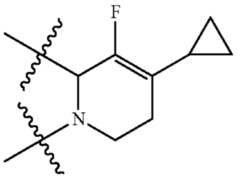 [SMILES: *C1C(F)=C(C2CC2)CCN1*]
-continued
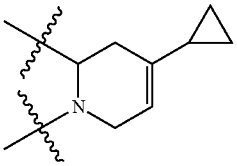 [SMILES: *C1CC(C2CC2)=CCN1*]
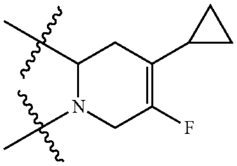 [SMILES: *C1CC(C2CC2)=C(F)CN1*]
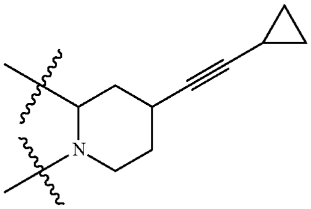 [SMILES: *C1CC(C#CC2CC2)CCN1*]
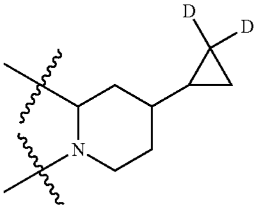 [SMILES: *C1CC(C2CC2([2H])[2H])CCN1*]
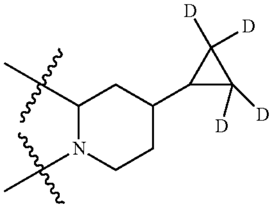 [SMILES: *C1CC(C2C([2H])([2H])C2([2H])[2H])CCN1*]
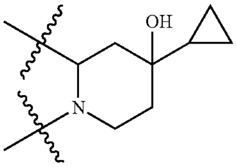 [SMILES: *C1CC(O)(C2CC2)CCN1*]
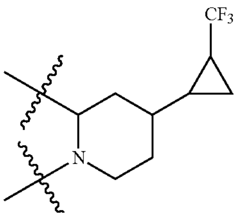
in some embodiments, $R^4$ is selected from $C_{5-12}$ carbocyclyl, 5- to 12-membered heterocyclyl, $C_{6-12}$ aryl or 5- to 12-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N;

in some embodiments, $R^4$ is selected from $C_{5-7}$ monocyclic carbocyclyl, $C_{5-12}$ fused carbocyclyl, $C_{5-12}$ spiro carbocyclyl, $C_{5-12}$ bridged carbocyclyl, 5- to 7-membered monocyclic heterocyclyl, 5- to 12-membered fused heterocyclyl, 5- to 12-membered spiro heterocyclyl or 5- to 12-membered bridged heterocyclyl, $C_{6-10}$ aryl or 5- to 10-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N;

in some embodiments, $R^4$ is selected from $C_{5-6}$ monocyclic carbocyclyl, $C_{5-10}$ fused carbocyclyl, $C_{5-11}$ spiro carbocyclyl, $C_{5-12}$ bridged carbocyclyl, 5- to 6-membered monocyclic heterocyclyl, 5- to 10-membered fused heterocyclyl, 5- to 11-membered spiro heterocyclyl, 5- to 12-membered bridged heterocyclyl, $C_{6-10}$ aryl or 5- to 10-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N;

in some embodiments, each $R^4$ is independently selected from cyclopentyl, cyclohexyl, benzocyclohexyl, benzocyclopentyl, phenyl, naphthyl, pyridyl, pyrazolyl, pyrimidinyl or naphthyridinyl, the cyclopentyl, cyclohexyl, benzocyclohexyl, benzocyclopentyl, phenyl, naphthyl, pyridyl, pyrazolyl, pyrimidinyl or naphthyridinyl is optionally further substituted with 0 to 4 $R^5$;

in some embodiments, each $R^4$ is independently selected from

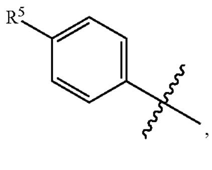
,
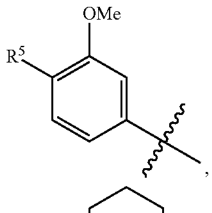
,
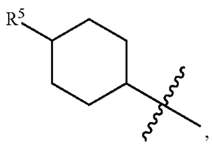
,
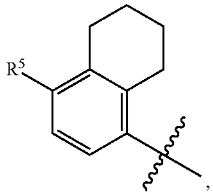
,
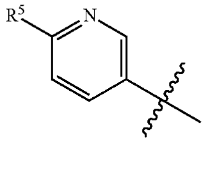
or
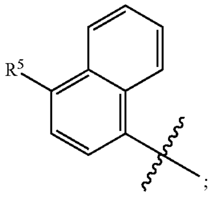
;

in some embodiments, $R^4$ is selected from

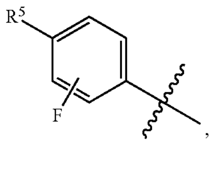
,
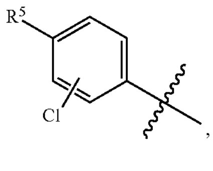
, or

-continued

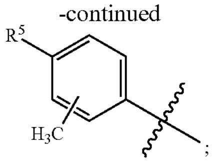
;

in some embodiments, $R^4$ is selected from

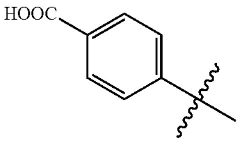
, or
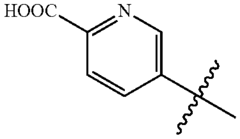
, wherein the $R^4$ is optionally substituted with 1, 2 or 3 substituents selected from F, Cl, Br, I, OH, cyano, methyl, ethyl, methoxy or ethoxy;

in some embodiments, $R^4$ is selected from

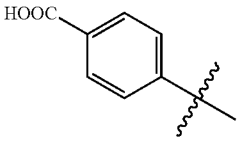
, wherein the $R^4$ is optionally further substituted with 0, 1, 2 or 3 substituents selected from F, Cl, Br, I, OH, cyano, methyl, ethyl, methoxy or ethoxy;

in some embodiments, each $R^5$ is independently selected from H, halogen, OH, cyano, $-C(=O)R^{4e}$, $-S(=O)_2R^{4e}$, $-CH_2C(=O)R^{4e}$, $-C(=O)NHS(=O)_2R^{4e}$, $-C(=O)NR^{4e}R^{4f}$, $-S(=O)_2NHC(=O)R^{4e}$, $-S(=O)_2NR^{4e}R^{4f}$, $-P(O)R^{4c}R^{4d}$,

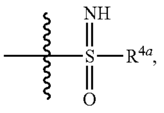
,
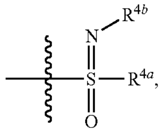
, $C_{1-6}$ alkyl, $C_{1-6}$ alkoxy, $C_{2-6}$ alkenyl, $C_{2-6}$ alkynyl, $C_{3-10}$ cycloalkyl or 4- to 12-membered heterocyclyl, wherein the alkyl, alkoxy, alkenyl, alkynyl, cycloalkyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl or $C_{3-6}$ cycloalkyl, wherein the heterocyclyl contains 1 to 5 heteroatoms selected from O, S or N;

in some embodiments, each $R^5$ is independently selected from H, halogen, OH, cyano, $-C(=O)R^{4e}$, $-S(=O)_2R^{4e}$, $-CH_2C(=O)R^{4e}$, $-C(=O)NHS(=O)_2R^{4e}$, $-C(=O)NR^{4e}R^{4f}$, $-S(=O)_2NHC(=O)R^{4e}$, $-S(=O)_2NR^{4e}R^{4f}$, $-P(O)R^{4c}R^{4d}$,

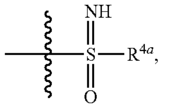
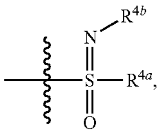

$C_{1-4}$ alkyl, $C_{1-4}$ alkoxy, $C_{2-4}$ alkenyl, $C_{2-4}$ alkynyl, $C_{3-8}$ cycloalkyl or 4 to 10-membered heterocyclyl, wherein the alkyl, alkoxy, alkenyl, alkynyl, cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl or $C_{3-6}$ cycloalkyl, wherein the heterocyclyl contains 1 to 5 heteroatoms selected from O, S or N;

in some embodiments, each $R^5$ is independently selected from H, halogen, OH, cyano, —C(=O)$R^{4e}$, —S(=O)$_2$$R^{4e}$, —CH$_2$C(=O)$R^{4e}$, —C(=O)NHS(=O)$_2$$R^{4e}$, —C(=O)N$R^{4e}R^{4f}$, —S(=O)$_2$NHC(=O)$R^{4e}$, —S(=O)$_2$N$R^{4e}R^{4f}$, —P(O)$R^{4e}R^{4d}$,

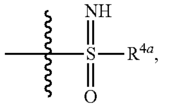
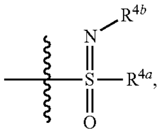

$C_{1-4}$ alkyl, $C_{1-4}$ alkoxy, $C_{2-4}$ alkenyl, $C_{2-4}$ alkynyl, $C_{3-6}$ cycloalkyl or 4 to 6-membered heterocyclyl, wherein the alkyl, alkoxy, alkenyl, alkynyl, cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl or $C_{3-6}$ cycloalkyl, wherein the heterocyclyl contains 1 to 5 heteroatoms selected from O, S or N;

in some embodiments, each $R^5$ is independently selected from H, F, Cl, Br, I, OH, cyano, methyl, ethyl, propyl, isopropyl, methoxy, ethoxy, propoxy, isopropoxy, —COOH, —CH$_2$OH, —S(=O)$_2$NH$_2$, —S(=O)$_2$NHCH$_3$, —S(=O)$_2$OH,

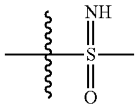 , 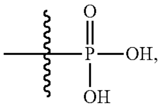 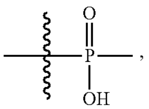 ,

—C(=O)NH$_2$, —C(=O)NHOH, —S(=O)$_2$NHC(=O)CH$_3$, —C(=O)NHS(=O)$_2$CH$_3$, pyrazolyl, tetrazolyl, wherein the methyl, ethyl, propyl, isopropyl, methoxy, ethoxy, propoxy, isopropoxy, pyrazolyl, or tetrazolyl is optionally further substituted with 0 to 4 substituents selected from H, F, Cl, Br, I, OH, =O, cyano, $NH_2$, methyl, ethyl, methoxy, ethoxy, $CF_3$, —CH$_2$F, —CH$_2$OH, cyclopropyl or cyclobutyl;

in some embodiments, $R^{1c}$ is selected from OH, $NH_2$, $C_{1-6}$ alkoxy, NHC$_{1-4}$ alkyl or N(C$_{1-4}$ alkyl)$_2$;

in some embodiments, $R^{1e}$ is selected from OH, $NH_2$, $C_{1-4}$ alkoxy, NHC$_{1-4}$ alkyl or N(C$_{1-4}$ alkyl)$_2$;

in some embodiments, $R^{1e}$ is selected from OH, $NH_2$, methoxy, ethoxy, NHCH$_3$, or N(CH$_3$)$_2$;

in some embodiments, $R^{4a}$ and $R^{4b}$ are each independently selected from H, OH, cyano, —N$R^{1a}R^{1b}$, $C_{1-6}$ alkyl, $C_{1-6}$ alkoxy, $C_{3-8}$ carbocyclyl, 4- to 10-membered heterocyclyl, $C_{6-10}$ aryl or 5 to 10 membered heteroaryl, wherein the alkyl, carbocyclyl, heterocyclyl, aryl or heteroaryl is optionally substituted with 0 to 4 substituents selected from H, halogen, OH, =O, cyano, $NH_2$, $C_{1-6}$ alkyl, $C_{1-6}$ alkoxy, halogen-substituted C1-6 alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or the heteroaryl contains 1 to 4 heteroatoms selected from O, S or N;

in some embodiments, $R^{4a}$ and $R^{4b}$ are each independently selected from H, OH, cyano, $NH_2$, $C_{1-4}$ alkyl, $C_{1-4}$ alkoxy, $C_{3-6}$ carbocyclyl, 4- to 8-membered heterocyclyl, $C_{6-10}$ aryl or 5 to 6 membered heteroaryl, wherein the alkyl, carbocyclyl, heterocyclyl, aryl or heteroaryl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heteroaryl contains 1 to 4 heteroatoms selected from O, S or N;

in some embodiments, $R^{4c}$ and $R^{4d}$ are each independently selected from H, OH, $C_{1-6}$ alkyl, $C_{1-6}$ alkoxy, —N$R^{1a}R^{1b}$, —O$R^{1d}$, —$C_{3-8}$ carbocyclyl, 4- to 10-membered heterocyclyl, $C_{6-10}$ aryl or 5 to 10 membered heteroaryl, wherein the alkyl, alkoxy, carbocyclyl, heterocyclyl, aryl or heteroaryl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N;

in some embodiments, $R^{4c}$ and $R^{4d}$ are each independently selected from H, OH, $C_{1-4}$ alkyl, $C_{1-4}$ alkoxy, —N$R^{1a}R^{1b}$, —O$R^{1d}$, $C_{3-6}$ carbocyclyl, 4- to 8-membered heterocyclyl, $C_{6-10}$ aryl or 5 to 10 membered heteroaryl, wherein the alkyl, alkoxy, carbocyclyl, heterocyclyl, aryl or heteroaryl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heteroaryl contains 1 to 4 heteroatoms selected from O, S or N;

in some embodiments, $R^{4e}$ and $R^{4f}$ are each independently selected from H, OH, —N$R^{1a}R^{1b}$, $C_{1-6}$ alkyl, $C_{1-6}$ alkoxy, $C_{3-8}$ cycloalkyl, or 5- to 12-membered heterocyclyl, wherein the heterocyclyl contains 1 to 4 heteroatoms selected from O, S or N;

in some embodiments, $R^{4e}$ and $R^{4f}$ are each independently selected from H, OH, —N$R^{1a}R^{1b}$, $C_{1-4}$ alkyl, $C_{1-4}$ alkoxy, $C_{3-6}$ cycloalkyl, or 5- to 10-membered heterocyclyl, wherein the heterocyclyl contains 1 to 4 heteroatoms selected from O, S or N;

in some embodiments, $R^{4a}$, $R^{4b}$, $R^{4c}$ and $R^{4d}$ are each independently selected from H, OH, $NH_2$, methyl, ethyl, propyl, isopropyl, methoxy, ethoxy, cyclopropyl or cyclobutyl, wherein the methyl, ethyl, propyl, isopropyl, methoxy, ethoxy, cyclopropyl or cyclobutyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, $R^{4a}$, $R^{4b}$, $R^{4c}$ and $R^{4d}$ are each independently selected from H, OH, $NH_2$, methyl, ethyl, propyl, isopropyl, methoxy, ethoxy, cyclopropyl or cyclobutyl, wherein the methyl, ethyl, propyl, isopropyl, methoxy, ethoxy, cyclopropyl or cyclobutyl is optionally further substituted with 0 to 4 substituents selected from H, F, Cl, Br, I, OH, =O, cyano, $NH_2$, methyl, ethyl or $CF_3$;

in some embodiments, $R^{4e}$ and $R^{4f}$ are each independently selected from H, OH, $NH_2$, methyl, ethyl, propyl, isopropyl, methoxy, ethoxy, cyclopropyl or cyclobutyl;

in some embodiments, each $R^{1d}$ is independently selected from H, $C_{1-6}$ alkyl, $C_{3-8}$ carbocyclyl or 4- to 10-membered heterocyclyl, wherein the alkyl, carbocyclyl or heterocyclyl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^{1d}$ is independently selected from H, $C_{1-4}$ alkyl, $C_{3-6}$ carbocyclyl or 4- to 8-membered heterocyclyl, wherein the alkyl, carbocyclyl or heterocyclyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^{1d}$ is independently selected from H, methyl, ethyl, propyl, isopropyl, cyclopropyl, cyclobutyl, cyclopentyl, oxacyclobutyl, azacyclobutyl, pyrrolidinyl or phenyl, wherein the methyl, ethyl, propyl, isopropyl, cyclopropyl, cyclobutyl, cyclopentyl, oxacyclobutyl, azacyclobutyl, pyrrolidinyl or phenyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^{1d}$ is independently selected from H, methyl, ethyl, propyl, isopropyl, cyclopropyl, cyclobutyl, cyclopentyl, oxacyclobutyl, azacyclobutyl, pyrrolidinyl or phenyl, wherein the methyl, ethyl, propyl, isopropyl, cyclopropyl, cyclobutyl, cyclopentyl, oxacyclobutyl, azacyclobutyl, pyrrolidinyl or phenyl is optionally substituted with 0 to 4 substituents selected from H, F, Cl, Br, I, OH, =O, cyano, $NH_2$, methyl, ethyl, methoxy, ethoxy, $CF_3$, $-CH_2F$, $-CH_2OH$, cyclopropyl, cyclobutyl, azacyclobutyl or pyrrolidinyl;

in some embodiments, each $R^{1d}$ is independently selected from methyl, ethyl, propyl, isopropyl, cyclopropyl, cyclobutyl, cyclopentyl, oxacyclobutyl, azacyclobutyl, pyrrolidinyl, phenyl, $-CH_2$-cyclopropyl or $-CH_2$-cyclobutyl;

in some embodiments, $R^8$ is selected from H, halogen, OH, cyano, $NH_2$, $C_{1-6}$ alkyl, $C_{2-6}$ alkenyl, $C_{2-6}$ alkynyl, $C_{1-6}$ alkoxy, $-S(=O)_pC_{1-6}$ alkyl, $-CH_2NHC(O)C_{1-4}$ alkyl, $-OCH_2C(=O)R^{1c}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^9$ or $R^{10}$ is independently selected from H, halogen, OH, cyano, $NH_2$, $C_{1-6}$ alkyl, $C_{2-6}$ alkenyl, $C_{2-6}$ alkynyl, $C_{1-6}$ alkoxy, $C_{1-6}$ alkylthio, $C_{3-8}$ carbocyclyl or 3- to 10-membered heterocyclyl, wherein the alkyl, alkenyl, alkynyl, alkoxy, alkylthio, carbocyclyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, each $R^8$, $R^9$ or $R^{10}$ is independently selected from H, halogen, OH, cyano, $NH_2$, $C_{1-4}$ alkyl, $C_{2-4}$ alkenyl, $C_{2-4}$ alkynyl, $C_{1-4}$ alkoxy, or $C_{1-4}$ alkylthio, wherein the alkyl, alkenyl, alkynyl, alkoxy, and alkylthio are optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, each $R^8$, $R^9$ or $R^{10}$ is independently selected from H, F, Cl, Br, I, OH, cyano, $CF_3$, $NH_2$, methyl, or ethyl;

in some embodiments, $R^{1a}$ and $R^{1b}$ are each independently selected from H, or $C_{1-6}$ alkyl, wherein the alkyl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

in some embodiments, $R^{1a}$ and $R^{1b}$ are each independently selected from H, or $C_{1-4}$ alkyl, wherein the alkyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, $R^{1a}$ and $R^{1b}$ are each independently selected from H, methyl, ethyl, propyl or isopropyl, wherein the methyl, ethyl, propyl or isopropyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

in some embodiments, $R^{1a}$ and $R^{1b}$ are each independently selected from H, methyl, ethyl, propyl or isopropyl, wherein the methyl, ethyl, propyl or isopropyl is optionally further substituted with 0 to 4 substituents selected from H, F, Cl, Br, I, OH, =O, cyano, $NH_2$, methyl, ethyl, methoxy, ethoxy, $CF_3$, —$CH_2F$, or —$CH_2OH$;

in some embodiments, when Y is selected from $C(R^7)_2$, $R^7$ is selected from H, OH, —$NR^{1a}R^{1b}$, unsubstituted $C_{1-6}$ alkyl, hydroxy $C_{1-6}$ alkyl, cyano $C_{1-6}$ alkyl or unsubstituted $C_{1-6}$ alkoxy, and the two $R^7$ and the carbon atom to which they are attached do not form 3- to 6-membered heterocyclyl together, one of the following conditions must be met:

1) $R^1$ is selected from $C_{2-6}$ alkynyl, $C_{3-6}$ cycloalkyl substituted $C_{1-6}$ alkyl, 3 to 8 membered heterocyclyl substituted $C_{1-6}$ alkyl, —W—$C_{3-8}$ carbocyclyl or —W-4- to 10-membered heterocyclyl, wherein the alkynyl, alkyl, carbocyclyl, or heterocyclyl is optionally further substituted with 0 to 4 substituents selected from H, D, halogen, OH, =O, cyano, $NH_2$, $C_{1-6}$ alkyl, $C_{2-6}$ alkynyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

2) $R^6$ and $R^7$ at adjacent positions form a double bond;

3) two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl, wherein the heterocyclyl contains 1 to 4 heteroatoms selected from O, S or N;

4) $X_2$ is selected from N;

in some embodiments, when Y is selected from $C(R^7)_2$, $R^7$ is selected from H, OH, —$NR^{1a}R^{1b}$, unsubstituted $C_{1-4}$ alkyl, hydroxy $C_{1-4}$ alkyl, cyano $C_{1-4}$ alkyl or unsubstituted $C_{1-4}$ alkoxy, and the two $R^7$ and the carbon atom to which they are attached do not form 3- to 6-membered heterocyclyl together, one of the following conditions must be met:

1) $R^1$ is selected from $C_{2-4}$ alkynyl, $C_{3-6}$ cycloalkyl substituted $C_{1-4}$ alkyl, 3 to 8 membered heterocyclyl substituted $C_{1-4}$ alkyl, —W—$C_{3-6}$ carbocyclyl or —W-4- to 8-membered heterocyclyl, wherein the alkynyl, alkyl, carbocyclyl, or heterocyclyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

2) $R^6$ and $R^7$ at adjacent positions form a double bond;

3) two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heterocyclyl contains 1 to 4 heteroatoms selected from O, S or N;

4) $X_2$ is selected from N;

in some embodiments, the compound of general formula (I) is not the racemate represented by the following compound:

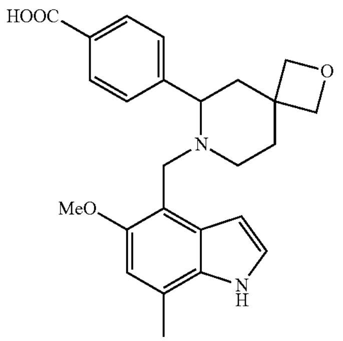

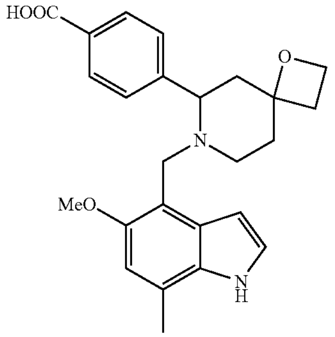

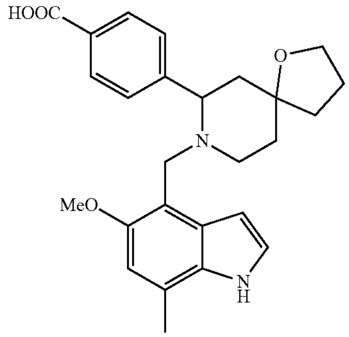

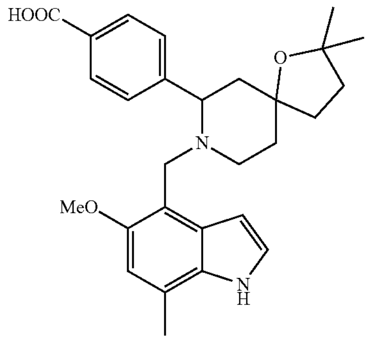

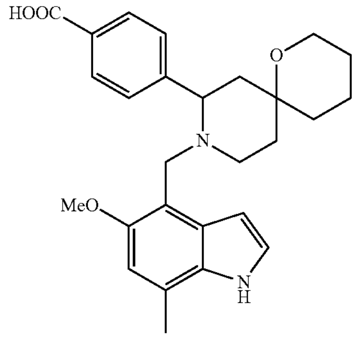

-continued
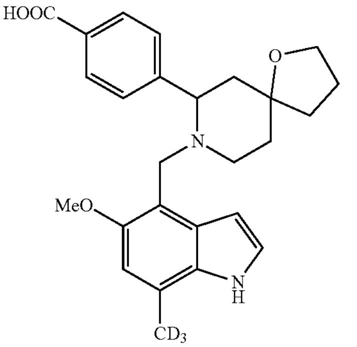
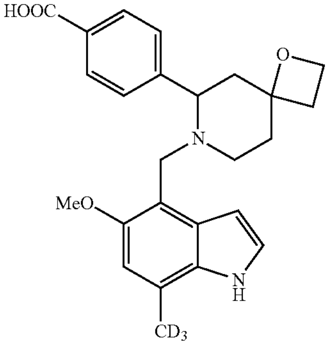
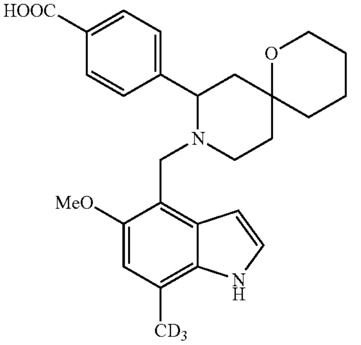
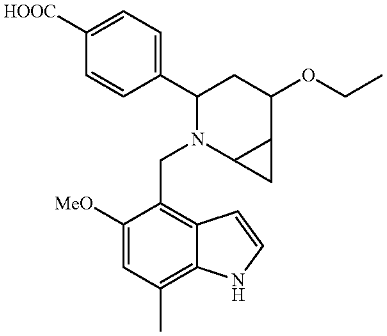
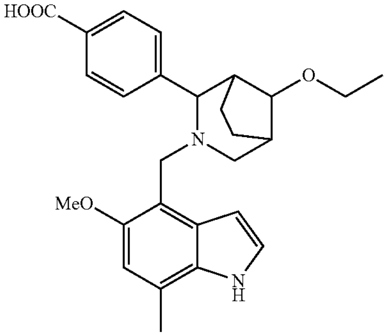
-continued
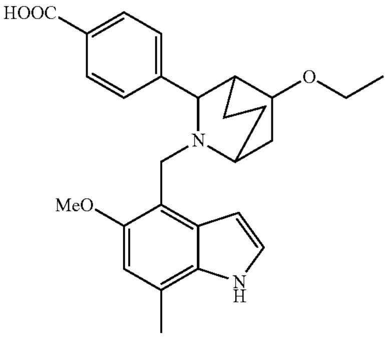
or
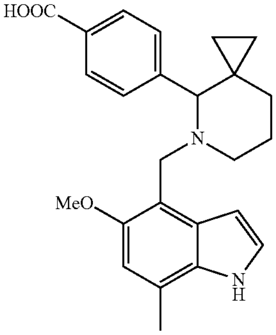
,
and the compound of general formula (I) is not the stereoisomer represented by the following compound:
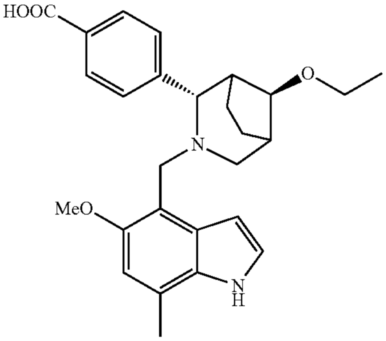
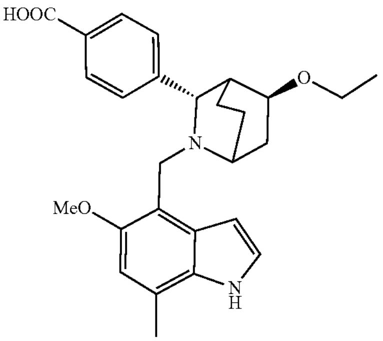
or -continued

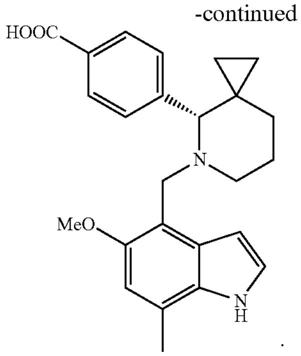

As a first embodiment of the present disclosure, the compound represented by the aforementioned general formula (I) or a stereoisomer, a deuterate, a solvate, a prodrug, a metabolite, a pharmaceutically acceptable salt or a co-crystal thereof is provided, (I)

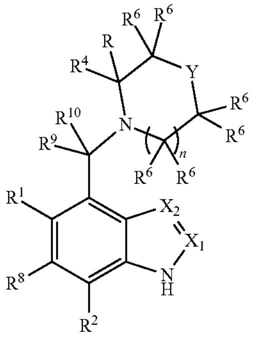

$R^1$ is selected from H, halogen, OH, cyano, $NH_2$, $C_{1-6}$ alkyl, $C_{2-6}$ alkenyl, $C_{2-6}$ alkynyl, $C_{1-6}$ alkoxy, $—C(═O)C_{1-6}$ alkyl, $—S(═O)_pC_{1-6}$ alkyl, $—W—R^{1d}$, $—CH_2NHC(O)C_{1-4}$ alkyl, $—CH_2C(═O)R^{1c}$, $—OCH_2C(═O)R^{1c}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-6}$ alkyl, $C_{2-6}$ alkynyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

p is selected from 0, 1 or 2;

n is selected from 0, 1 or 2;

W is selected from O or S;

$R^2$ is selected from halogen, $C_{1-6}$ alkyl or $C_{1-6}$ alkoxy, wherein the alkyl or alkoxy is optionally further substituted with 0 to 4 substituents selected from H, halogen, OH, cyano or $NH_2$;

$X_1$ and $X_2$ are each independently selected from N or $CR^3$;

Y is selected from $NR^7$ or $C(R^7)_2$;

each $R^6$ is independently selected from H, halogen, OH, $—NR^{1a}R^{1b}$, $C_{1-6}$ alkyl or $C_{1-6}$ alkoxy, wherein the alkyl, and alkoxy are optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

each $R^7$ is independently selected from H, halogen, OH, $—NR^{1a}R^{1b}$, $C_{1-6}$ alkyl, $C_{1-6}$ alkoxy, $C_{2-6}$ alkenyl, $C_{2-6}$ alkynyl, $—C(═O)R^{1d}$, $—S(═O)_2R^{1d}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-6}$ alkyl, $C_{1-6}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

alternatively, two $R^7$ together with the carbon atom to which they are attached form a 3- to 6-membered heterocyclyl, wherein the heterocyclyl is optionally further substituted with 0 to 4 substituents selected from H, halogen, OH, ═O, cyano, $—C(═O)R^{1d}$, $—S(═O)_2R^{1d}$, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

alternatively, $R^6$ and $R^7$ at adjacent positions can form a double bond;

Alternatively, two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl, wherein the heterocyclyl contains 1 to 4 heteroatoms selected from O, S or N;

each $R^3$ is independently selected from H, halogen, cyano, $C_{1-6}$ alkyl, $C_{1-6}$ alkoxy, $C_{2-6}$ alkenyl, $C_{2-6}$ alkynyl, $—CH_2C(═O)R^{1e}$, $—S(═O)_pC_{1-6}$ alkyl, $—CH_2NHC(O)C_{1-4}$ alkyl, $—OCH_2C(═O)R^{1e}$, $C_{3-6}$ carbocyclyl or 5- to 6-membered heteroaryl, wherein the alkyl, $C_{1-6}$ alkoxy, $C_{2-6}$ alkenyl, $C_{2-6}$ alkynyl, carbocyclyl or heteroaryl is optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N;

$R^{1c}$ is selected from OH, $NH_2$, $C_{1-6}$ alkoxy, $NHC_{1-4}$ alkyl or $N(C_{1-4}\ alkyl)_2$;

R is selected from H, or $C_{1-6}$ alkyl, wherein the alkyl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl;

$R^4$ is selected from $C_{5-12}$ carbocyclyl, 5- to 12-membered heterocyclyl, $C_{6-12}$ aryl or 5- to 12-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N;

each $R^5$ is independently selected from H, halogen, OH, cyano, $—C(═O)R^{4e}$, $—S(═O)_2R^{4e}$, $—CH_2C(═O)$ $R^{4e}$, —C(═O)NHS(═O)$_2R^{4e}$, —C(═O)NR$^{4e}R^{4f}$, —S(═O)$_2$NHC(═O)R$^{4e}$, —S(═O)$_2$NR$^{4e}R^{4f}$, —P(O)R$^{4c}R^{4d}$,

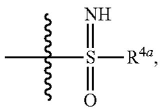,

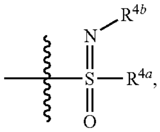, $C_{1-6}$ alkyl, $C_{1-6}$ alkoxy, $C_{2-6}$ alkenyl, $C_{2-6}$ alkynyl, $C_{3-10}$ cycloalkyl or 4- to 12-membered heterocyclyl, wherein the alkyl, alkoxy, alkenyl, alkynyl, cycloalkyl or heterocyclyl is optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl or $C_{3-6}$ cycloalkyl, wherein the heterocyclyl contains 1 to 5 heteroatoms selected from O, S or N;

$R^{4a}$ and $R^{4b}$ are each independently selected from H, OH, cyano, —NR$^{1a}R^{1b}$, $C_{1-6}$ alkyl, $C_{1-6}$ alkoxy, $C_{3-8}$ carbocyclyl, 4- to 10-membered heterocyclyl, $C_{6-10}$ aryl or 5 to 10 membered heteroaryl, wherein the alkyl, carbocyclyl, heterocyclyl, aryl or heteroaryl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N;

$R^{4c}$ and $R^{4d}$ are each independently selected from H, OH, $C_{1-6}$ alkyl, $C_{1-6}$ alkoxy, —NR$^{1a}R^{1b}$, —OR$^{1d}$, —$C_{3-8}$ carbocyclyl, 4- to 10-membered heterocyclyl, $C_{6-10}$ aryl or 5 to 10 membered heteroaryl, wherein the alkyl, alkoxy, carbocyclyl, heterocyclyl, aryl or heteroaryl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N;

$R^{4e}$ and $R^{4f}$ are each independently selected from H, OH, —NR$^{1a}R^{1b}$, $C_{1-6}$ alkyl, $C_{1-6}$ alkoxy, $C_{3-8}$ cycloalkyl, or 5- to 12-membered heterocyclyl, wherein the heterocyclyl contains 1 to 4 heteroatoms selected from O, S or N;

$R^{1a}$ and $R^{1b}$ are each independently selected from H, or $C_{1-6}$ alkyl, wherein the alkyl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

each $R^{1d}$ is independently selected from H, $C_{1-6}$ alkyl, $C_{3-8}$ carbocyclyl or 4- to 10-membered heterocyclyl, wherein the alkyl, carbocyclyl or heterocyclyl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

$R^8$ is selected from H, halogen, OH, cyano, $NH_2$, $C_{1-6}$ alkyl, $C_{2-6}$ alkenyl, $C_{2-6}$ alkynyl, $C_{1-6}$ alkoxy, —S(═O)$_p$C$_{1-6}$ alkyl, —CH$_2$NHC(O)C$_{1-4}$ alkyl, —OCH$_2$C(═O)R$^{1c}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

each $R^9$ or $R^{10}$ is independently selected from H, halogen, OH, cyano, $NH_2$, $C_{1-6}$ alkyl, $C_{2-6}$ alkenyl, $C_{2-6}$ alkynyl, $C_{1-6}$ alkoxy, $C_{1-6}$ alkylthio, $C_{3-8}$ carbocyclyl or 3- to 10-membered heterocyclyl, wherein the alkyl, alkenyl, alkynyl, alkoxy, alkylthio, carbocyclyl or heterocyclyl is optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

when Y is selected from $C(R^7)_2$, $R^7$ is selected from H, OH, —NR$^{1a}R^{1b}$, unsubstituted $C_{1-6}$ alkyl, hydroxy $C_{1-6}$ alkyl, cyano $C_{1-6}$ alkyl or unsubstituted $C_{1-6}$ alkoxy, and the two $R^7$ and the carbon atom to which they are attached do not form 3- to 6-membered heterocyclyl together, one of the following conditions must be met:

1) $R^1$ is selected from $C_{2-6}$ alkynyl, $C_{3-6}$ cycloalkyl substituted $C_{1-6}$ alkyl, 3 to 8 membered heterocyclyl substituted $C_{1-6}$ alkyl, —W—$C_{3-8}$ carbocyclyl or —W-4- to 10-membered heterocyclyl, wherein the alkynyl, alkyl, carbocyclyl, or heterocyclyl is optionally further substituted with 0 to 4 substituents selected from H, D, halogen, OH, ═O, cyano, $NH_2$, $C_{1-6}$ alkyl, $C_{2-6}$ alkynyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;

2) $R^6$ and $R^7$ at adjacent positions form a double bond;

3) two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl, wherein the heterocyclyl contains 1 to 4 heteroatoms selected from O, S or N;

4) $X_2$ is selected from N.

As a second embodiment of the present disclosure, the compound represented by the aforementioned general formula (I) or a stereoisomer, a deuterate, a solvate, a prodrug, a metabolite, a pharmaceutically acceptable salt or a co-crystal thereof is provided, $R^1$ is selected from H, halogen, OH, cyano, $NH_2$, $C_{1-4}$ alkyl, $C_{2-4}$ alkenyl, $C_{2-4}$ alkynyl, $C_{1-4}$ alkoxy, —C(═O)C$_{1-4}$ alkyl, —S(═O)$_p$C$_{1-4}$ alkyl, —W—R$^{1d}$, —CH$_2$NHC(O)C$_{1-4}$ alkyl, —CH$_2$C(═O)R$^{1c}$, —$OCH_2C(=O)R^{1c}$, $C_{3-6}$ carbocyclyl or 4- to 8-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

$R^2$ is selected from halogen, $C_{1-4}$ alkyl or $C_{1-4}$ alkoxy, wherein the alkyl or alkoxy is optionally further substituted with 0 to 4 substituents selected from H, D, halogen, OH, cyano or $NH_2$;

$X_1$ and $X_2$ are each independently selected from N or $CR^3$;

each $R^6$ is independently selected from H, halogen, OH, —$NR^{1a}R^{1b}$, $C_{1-4}$ alkyl or $C_{1-4}$ alkoxy, wherein the alkyl, and alkoxy are optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^7$ is independently selected from H, halogen, OH, —$NR^{1a}R^{1b}$, $C_{1-4}$ alkyl, $C_{1-4}$ alkoxy, $C_{2-4}$ alkenyl, $C_{2-4}$ alkynyl, —$C(=O)R^{1d}$, —$S(=O)_2R^{1d}$, $C_{3-6}$ carbocyclyl or 3- to 8-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

alternatively, two $R^7$ together with the carbon atom to which they are attached form a 3- to 6-membered heterocyclyl, wherein the heterocyclyl is optionally further substituted with 0 to 4 substituents selected from H, halogen, OH, =O, cyano, —C(=O)Rid. —$S(=O)_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

alternatively, $R^6$ and $R^7$ at adjacent positions can form a double bond;

alternatively, two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heterocyclyl contains 1 to 4 heteroatoms selected from O, S or N;

each $R^3$ is independently selected from H, halogen, cyano, $C_{1-4}$ alkyl, $C_{1-4}$ alkoxy, $C_{2-4}$ alkenyl, $C_{2-4}$ alkynyl, —$CH_2C(=O)R^{1e}$, —$S(=O)_pC_{1-4}$ alkyl, —$CH_2NHC(O)C_{1-4}$ alkyl, —$OCH_2C(=O)R^{1e}$, $C_{3-6}$ carbocyclyl or 5- to 6-membered heteroaryl, wherein the alkyl, $C_{1-4}$ alkoxy, $C_{2-4}$ alkenyl, $C_{2-4}$ alkynyl, carbocyclyl or heteroaryl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heteroaryl contains 1 to 4 heteroatoms selected from O, S or N;

$R^{1c}$ is selected from OH, $NH_2$, $C_{1-4}$ alkoxy, $NHC_{1-4}$ alkyl or $N(C_{1-4}$ alkyl$)_2$;

R is selected from H, or $C_{1-4}$ alkyl, wherein the alkyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

$R^4$ is selected from $C_{5-7}$ monocyclic carbocyclyl, $C_{5-12}$ fused carbocyclyl, $C_{5-12}$ spiro carbocyclyl, $C_{5-12}$ bridged carbocyclyl, 5- to 7-membered monocyclic heterocyclyl, 5- to 12-membered fused heterocyclyl, 5- to 12-membered spiro heterocyclyl or 5- to 12-membered bridged heterocyclyl, $C_{6-10}$ aryl or 5- to 10-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from 0, S or N;

each $R^5$ is independently selected from H, halogen, OH, cyano, —$C(=O)R^{4e}$, —$S(=O)_2R^{4e}$, —$CH_2C(=O)R^{4e}$, —$C(=O)NHS(=O)_2R^{4e}$, —$C(=O)NR^{4e}R^{4f}$, —$S(=O)_2NHC(=O)R^{4e}$, —$S(=O)_2NR^{4e}R^{4f}$, —$P(O)R^{4c}R^{4d}$,

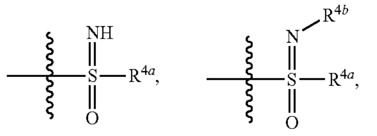

$C_{1-4}$ alkyl, $C_{1-4}$ alkoxy, $C_{2-4}$ alkenyl, $C_{2-4}$ alkynyl, $C_{3-8}$ cycloalkyl or 4- to 10-membered heterocyclyl, wherein the alkyl, alkoxy, alkenyl, alkynyl, cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl or $C_{3-6}$ cycloalkyl, wherein the heterocyclyl contains 1 to 5 heteroatoms selected from O, S or N;

$R^{4a}$ and $R^{4b}$ are each independently selected from H, OH, cyano, $NH_2$, $C_{1-4}$ alkyl, $C_{1-4}$ alkoxy, $C_{3-6}$ carbocyclyl, 4- to 8-membered heterocyclyl, C6.10 aryl or 5 to 6 membered heteroaryl, wherein the alkyl, carbocyclyl, heterocyclyl, aryl or heteroaryl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heteroaryl contains 1 to 4 heteroatoms selected from O, S or N;

$R^{4c}$ and $R^{4d}$ are each independently selected from H, OH, $C_{1-4}$ alkyl, $C_{1-4}$ alkoxy, —$NR^{1a}R^{1b}$, —$OR^{1d}$, $C_{3-6}$ carbocyclyl, 4- to 8-membered heterocyclyl, $C_{6-10}$ aryl or 5 to 10 membered heteroaryl, wherein the alkyl, alkoxy, carbocyclyl, heterocyclyl, aryl or heteroaryl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heteroaryl contains 1 to 4 heteroatoms selected from O, S or N;

$R^{4e}$ and $R^{4f}$ are each independently selected from H, OH, —$NR^{1a}R^{1b}$, $C_{1-4}$ alkyl, $C_{1-4}$ alkoxy, $C_{3-6}$ cycloalkyl, or 5- to 10-membered heterocyclyl, wherein the heterocyclyl contains 1 to 4 heteroatoms selected from O, S or N;

$R^{1a}$ and $R^{1b}$ are each independently selected from H, or $C_{1-4}$ alkyl, wherein the alkyl is optionally substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

each $R^{1d}$ is independently selected from H, $C_{1-4}$ alkyl, $C_{3-6}$ carbocyclyl or 4- to 8-membered heterocyclyl, wherein the alkyl, carbocyclyl or heterocyclyl is optionally substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^1$, $R^9$ or $R^{10}$ is independently selected from H, halogen, OH, cyano, $NH_2$, $C_{1-4}$ alkyl, $C_{2-4}$ alkenyl, $C_{2-4}$ alkynyl, $C_{1-4}$ alkoxy, or $C_{1-4}$ alkylthio, wherein the alkyl, alkenyl, alkynyl, alkoxy, and alkylthio are optionally further substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

when Y is selected from $C(R^7)_2$, $R^7$ is selected from H, OH, —$NR^{1a}R^{1b}$, unsubstituted $C_{1-4}$ alkyl, hydroxy $C_{1-4}$ alkyl, cyano $C_{1-4}$ alkyl or unsubstituted $C_{1-4}$ alkoxy, and the two $R^7$ and the carbon atom to which they are attached do not form 3- to 6-membered heterocyclyl together, one of the following conditions must be met:

1) $R^1$ is selected from $C_{2-4}$ alkynyl, $C_{3-6}$ cycloalkyl substituted $C_{1-4}$ alkyl, 3 to 8 membered heterocyclyl substituted $C_{1-4}$ alkyl, —W—$C_{3-6}$ carbocyclyl or —W-4- to 8-membered heterocyclyl, wherein the alkynyl, alkyl, carbocyclyl, or heterocyclyl is optionally further substituted with 0 to 4 substituents selected from H, D, halogen, OH, ═O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

2) $R^6$ and $R^7$ at adjacent positions form a double bond;

3) two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heterocyclyl contains 1 to 4 heteroatoms selected from O, S or N;

4) $X_2$ is selected from N.

The definitions of the remaining substituents are consistent with the first embodiment of the present disclosure.

As a third embodiment of the present disclosure, the compound represented by the aforementioned general formula (I) or a stereoisomer, a deuterate, a solvate, a prodrug, a metabolite, a pharmaceutically acceptable salt or a co-crystal thereof is provided, $R^1$ is selected from H, halogen, OH, cyano, $NH_2$, $C_{1-4}$ alkyl, $C_{2-4}$ alkenyl, $C_{2-4}$ alkynyl, $C_{1-4}$ alkoxy, $C_{1-4}$ alkylthio, —W—$R^{1d}$, $C_{3-6}$ carbocyclyl or 4- to 8-membered heterocyclyl, wherein the alkyl, alkenyl, alkynyl, alkoxy, alkylthio, carbocyclyl or heterocyclyl is optionally further substituted with 0 to 4 substituents selected from H, D, halogen, OH, ═O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

$R^2$ is selected from F, Cl, Br, I, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, D, F, Cl, Br, I, OH, cyano or $NH_2$;

each $R^3$ is independently selected from H, F, Cl, Br, I, cyano, methyl, ethyl, propyl, isopropyl, —$CH_2C(═O)OH$, or —$CH_2C(═O)NH_2$, wherein the methyl, ethyl, propyl or isopropyl is optionally further substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

each $R^6$ is independently selected from H, F, Cl, Br, I, OH, $NH_2$, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

R is selected from H, methyl, ethyl, propyl or isopropyl, wherein the methyl, ethyl, propyl or isopropyl is optionally further substituted with 0 to 4 substituents selected from H, F, Cl, Br, I, OH, ═O, cyano, $NH_2$, methyl, ethyl or $CF_3$;

$R^4$ is selected from $C_{5-6}$ monocyclic carbocyclyl, $C_{5-10}$ fused carbocyclyl, $C_{5-11}$ spiro carbocyclyl, $C_{5-12}$ bridged carbocyclyl, 5- to 6-membered monocyclic heterocyclyl, 5- to 10-membered fused heterocyclyl, 5- to 11-membered spiro heterocyclyl, 5- to 12-membered bridged heterocyclyl, $C_{6-10}$ aryl or 5- to 10-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from 0, S or N;

each $R^5$ is independently selected from H, halogen, OH, cyano, —$C(═O)R^{4e}$, —$S(═O)_2R^{4e}$, —$CH_2C(═O)R^{4e}$, —$C(═O)NHS(═O)_2R^{4e}$, —$C(═O)NR^{4e}R^{4f}$, —$S(═O)_2NHC(═O)R^{4e}$, —$S(═O)_2NR^{4e}R^{4f}$, —$P(O)R^{4c}R^{4d}$,

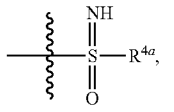
,
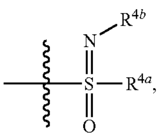
, $C_{1-4}$ alkyl, $C_{1-4}$ alkoxy, $C_{2-4}$ alkenyl, $C_{2-4}$ alkynyl, $C_{3-6}$ cycloalkyl or 4 to 6-membered heterocyclyl, wherein the alkyl, alkoxy, alkenyl, alkynyl, cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl or $C_{3-6}$ cycloalkyl, wherein the heterocyclyl contains 1 to 5 heteroatoms selected from O, S or N;

$R^{4a}$, $R^{4b}$, $R^{4c}$ and $R^{4d}$ are each independently selected from H, OH, $NH_2$, methyl, ethyl, propyl, isopropyl, methoxy, ethoxy, cyclopropyl or cyclobutyl, wherein the methyl, ethyl, propyl, isopropyl, methoxy, ethoxy, cyclopropyl or cyclobutyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

$R^{1a}$ and $R^{1b}$ are each independently selected from H, methyl, ethyl, propyl or isopropyl, wherein the methyl, ethyl, propyl or isopropyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

$R^{4e}$ and $R^{4f}$ are each independently selected from H, OH, $NH_2$, methyl, ethyl, propyl, isopropyl, methoxy, ethoxy, cyclopropyl or cyclobutyl;

each $R^{1d}$ is independently selected from H, methyl, ethyl, propyl, isopropyl, cyclopropyl, cyclobutyl, cyclopentyl, oxacyclobutyl, azacyclobutyl, pyrrolidinyl or phenyl, wherein the methyl, ethyl, propyl, isopropyl, cyclopropyl, cyclobutyl, cyclopentyl, oxacyclobutyl, azacyclobutyl, pyrrolidinyl or phenyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^1$, $R^9$ or $R^{10}$ is independently selected from H, F, Cl, Br, I, OH, cyano, $CF_3$, $NH_2$, methyl, or ethyl;

The definitions of the remaining substituents are consistent with the second embodiment of the present disclosure.

As a fourth embodiment of the present disclosure, the compound represented by the following general formula (Ia), (Ib), (Ic), (Id), (Ie) or (If) or a stereoisomer, a deuterate, a solvate, a prodrug, a metabolite, a pharmaceutically acceptable salt or a co-crystal thereof is provided,

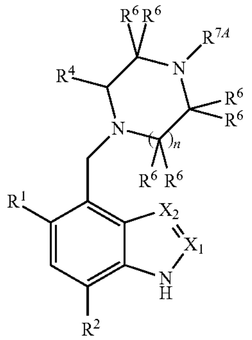

(Ia)

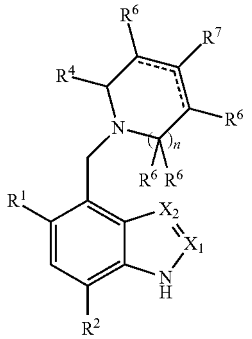

(Ib)

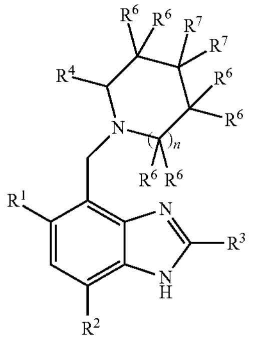

(Ic)

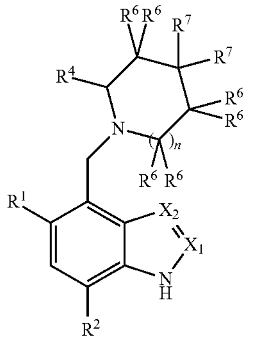

(Id)

-continued (Ie)

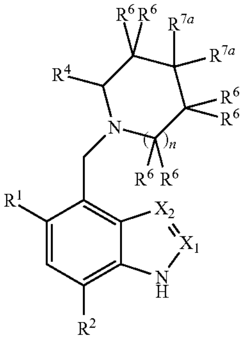

(If)

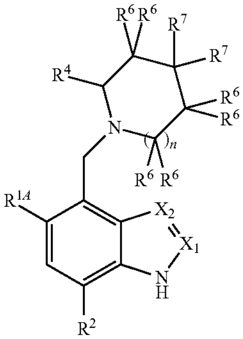

each n is independently selected from 0, 1 or 2;

each $R^3$ is independently selected from H, F, Cl, Br, I, cyano, methyl, ethyl, propyl, isopropyl, —$CH_2C$(═O)OH, or —$CH_2C$(═O)$NH_2$, wherein the methyl, ethyl, propyl or isopropyl is optionally further substituted with 0 to 4 substituents selected from H, F, Cl, Br, I, OH, or cyano;

each $R^6$ is independently selected from H, F, Cl, Br, I, OH, $NH_2$, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, F, Cl, Br, I, OH, ═O, cyano, $NH_2$, methyl, ethyl, methoxy, ethoxy, $CF_3$, —$CH_2F$ or —$CH_2OH$;

each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, —C(═O)$R^{1d}$, —S(═O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

$R^{7A}$ is selected from H, F, Cl, Br, I, methyl, ethyl, propyl, isopropyl, tert-butyl, methoxy, ethoxy, isopropoxy, —C(═O)$R^{1d}$, —S(═O)$_2R^{1d}$, cyclopropyl, cyclobutyl, cyclopentyl, cyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, cyclopropyl, cyclobutyl, cyclopentyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, ═O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^{7a}$ is independently selected from $R^d$, F, Cl, Br, I, vinyl, ethynyl, propynyl, propargyl, —C(═O)$R^{1d}$, —S(═O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, ═O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^d$ is independently selected from methyl, ethyl, propyl, isopropyl, tert-butyl, methoxy, ethoxy, or isopropoxy, the methyl, ethyl, propyl, isopropyl, tert-butyl, methoxy, ethoxy, and isopropoxy is further substituted with 1 to 3 substituents selected from halogen, ethynyl, $C_{2-4}$ alkynyl, $C_{1-4}$ alkoxy, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl;

═ in (Ib) represents a single bond or a double bond, and (Ib) contains only one double bond;

in (Id), alternatively, two $R^7$ together with the carbon atom to which they are attached form oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, halogen, OH, =O, cyano, —C(=O)$R^{1d}$, —S(=O)$_2$$R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

or in (Id), two $R^6$ together with the atom to which they are attached form cyclobutyl, cyclopentyl, cyclohexyl, oxacyclobutyl, oxacyclopentyl, oxacyclohexyl, thiocyclopentyl, azacyclobutyl, pyrrolidinyl, piperidinyl, morpholinyl or piperazinyl;

$R^{1A}$ is selected from ethynyl, propynyl, propargyl, —$CH_2$-cyclopropyl, —$CH_2$— cyclobutyl, —$CH_2$-cyclopentyl, —$CH_2$-oxacyclobutyl, —$CH_2$-azacyclobutyl, —$CH_2$— pyrrolidinyl, —O-cyclopropyl, —O-cyclobutyl, or —O-cyclopentyl, the ethynyl, propynyl, propargyl, —O-cyclopropyl, —O-cyclobutyl, —O-cyclopentyl or —$CH_2$— is optionally further substituted with 0 to 2 substituents selected from H, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^1$ is independently selected from H, F, Cl, Br, I, OH, cyano, $NH_2$, methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl or —W—$R^{1d}$, wherein the methyl, ethyl, propyl, isopropyl, tert-butyl, methoxy, ethoxy, isopropoxy, vinyl, ethynyl, propynyl, propargyl, methylthio, ethylthio, cyclopropyl, or cyclobutyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^4$ is independently selected from cyclopentyl, cyclohexyl, benzocyclohexyl, benzocyclopentyl, phenyl, naphthyl, pyridyl, pyrazolyl, pyrimidinyl or naphthyridinyl, the cyclopentyl, cyclohexyl, benzocyclohexyl, benzocyclopentyl, phenyl, naphthyl, pyridyl, pyrazolyl, pyrimidinyl or naphthyridinyl is optionally further substituted with 0 to 4 $R^5$;

$R^{4a}$, $R^{4b}$, $R^{4c}$ and $R^{4d}$ are each independently selected from H, OH, $NH_2$, methyl, ethyl, propyl, isopropyl, methoxy, ethoxy, cyclopropyl or cyclobutyl, wherein the methyl, ethyl, propyl, isopropyl, methoxy, ethoxy, cyclopropyl or cyclobutyl is optionally further substituted with 0 to 4 substituents selected from H, F, Cl, Br, I, OH, =O, cyano, $NH_2$, methyl, ethyl or $CF_3$;

and each $R^{1d}$ is independently selected from H, methyl, ethyl, propyl, isopropyl, cyclopropyl, cyclobutyl, cyclopentyl, oxacyclobutyl, azacyclobutyl, pyrrolidinyl or phenyl, wherein the methyl, ethyl, propyl, isopropyl, cyclopropyl, cyclobutyl, cyclopentyl, oxacyclobutyl, azacyclobutyl, pyrrolidinyl or phenyl is optionally substituted with 0 to 4 substituents selected from H, F, Cl, Br, I, OH, =O, cyano, $NH_2$, methyl, ethyl, methoxy, ethoxy, $CF_3$, —$CH_2F$, —$CH_2OH$, cyclopropyl, cyclobutyl, azacyclobutyl or pyrrolidinyl;

The definitions of the remaining substituents are consistent with the third embodiment of the present disclosure.

As a fifth embodiment of the present disclosure, the compound represented by the aforementioned general formula (Id) or a stereoisomer, a deuterate, a solvate, a prodrug, a metabolite, a pharmaceutically acceptable salt or a co-crystal thereof is provided, each $R^4$ is independently selected from

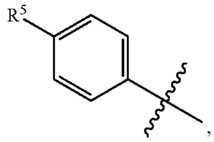,
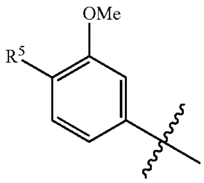,
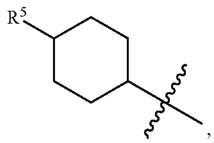,
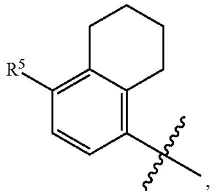,
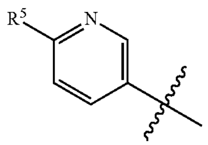 or
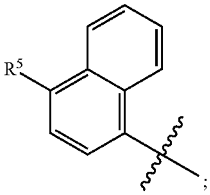;

or each $R^4$ is independently selected from

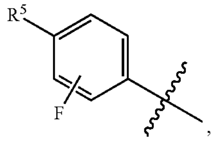,
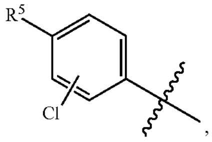, or
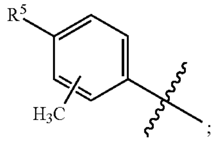;

each $R^5$ is independently selected from H, F, Cl, Br, I, OH, cyano, methyl, ethyl, propyl, isopropyl, methoxy, ethoxy, propoxy, isopropoxy, —COOH, —$CH_2OH$, —S(=O)$_2$$NH_2$, —S(=O)$_2$$NHCH_3$, —S(=O)$_2$OH,

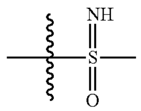,
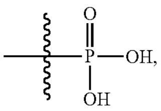,
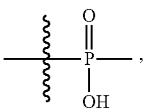,

—C(=O)$NH_2$, —C(=O)NHOH, —S(=O)$_2$NHC(=O)$CH_3$, —C(=O)NHS(=O)$_2$$CH_3$, pyrazolyl, tetrazolyl, wherein the methyl, ethyl, propyl, isopropyl, methoxy, ethoxy, propoxy, isopropoxy, pyrazolyl, or tetrazolyl is optionally further substituted with 0 to 4 substituents selected from H, F, Cl, Br, I, OH, =O, cyano, $NH_2$, methyl, ethyl, methoxy, ethoxy, $CF_3$, —$CH_2F$, —$CH_2OH$, cyclopropyl or cyclobutyl;

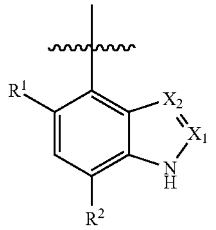

is selected from

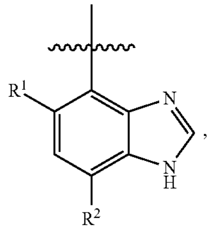
,
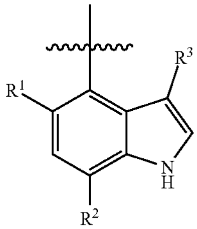
, or
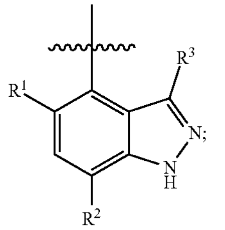

each $R^1$ is independently selected from H, F, Cl, Br, I, OH, cyano, $NH_2$, —$OCD_3$, $CD_3$, methyl, ethyl, propyl, isopropyl, tert-butyl, methoxy, ethoxy, isopropoxy, cyclopropyl, ethynyl, —$CH_2$-cyclopropyl or —O-cyclopropyl;

or each $R^1$ is independently selected from —$OCH_2F$, —$OCHF_2$, —$OCF_3$,

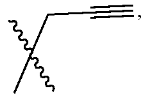
, or
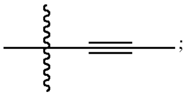

each $R^2$ is independently selected from F, Cl, Br, I, methyl, ethyl, propyl, isopropyl;

or each $R^2$ is independently selected from $CD_3$, $CHD_2$, or $CH_2D$;

each $R^3$ is independently selected from H, methyl or ethyl;

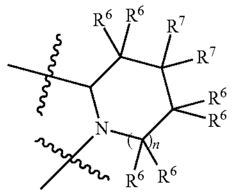

is selected from the fragments in the following table which are connected to $R^4$ at the upper part

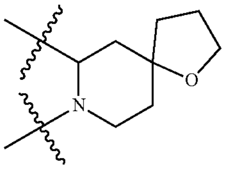

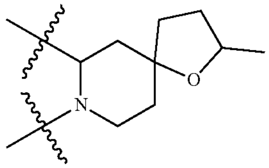

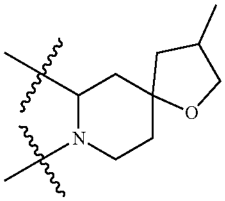

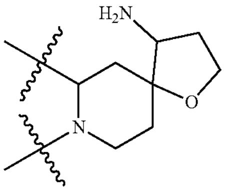

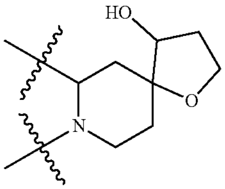

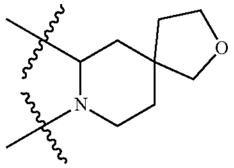

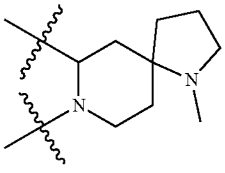

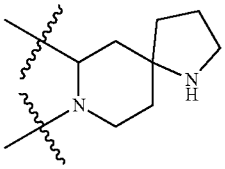

-continued
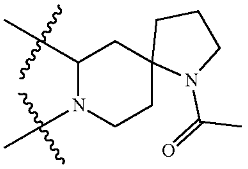
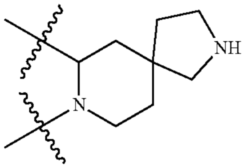
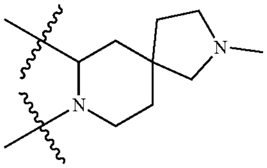
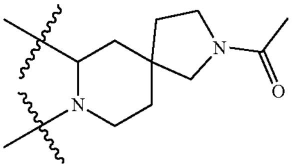
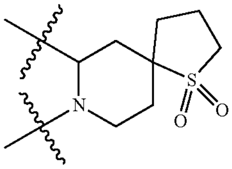
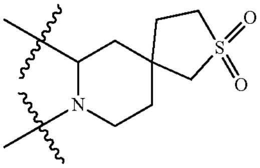
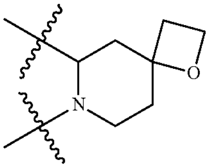
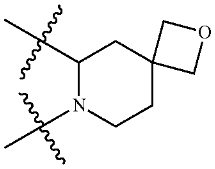
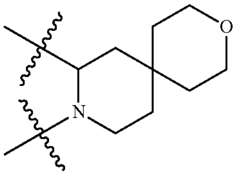
-continued
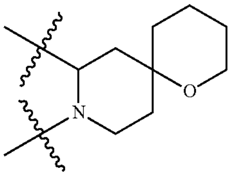
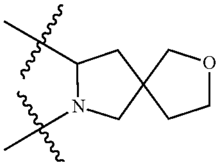 [SMILES: *C1CC2(CCOC2)CN1*]
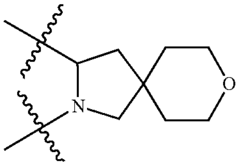 [SMILES: *C1CC2(CCOCC2)CN1*]
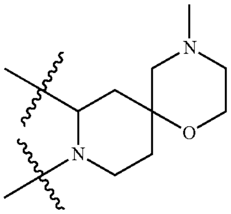 [SMILES: *C1CC2(CCN1*)CN(C)CCO2]
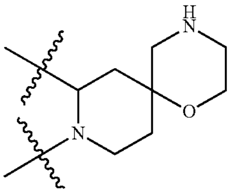 [SMILES: *C1CC2(CCN1*)CNCCO2]
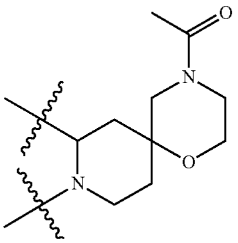 [SMILES: *C1CC2(CCN1*)CN(C(C)=O)CCO2]
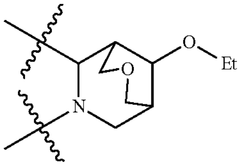 [SMILES: *C1C2COCC(CN1*)C2OCC]
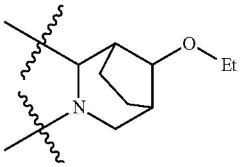 [SMILES: *C1C2CCC(CN1*)C2OCC]

-continued
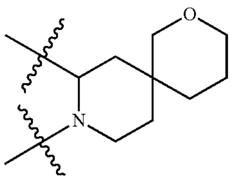 [SMILES: *C1CC2(CCCOC2)CCN1*]
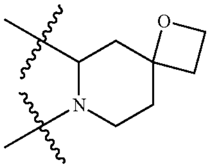
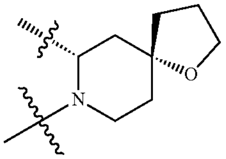
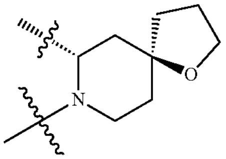
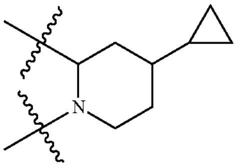 [SMILES: *C1CC(C2CC2)CCN1*]
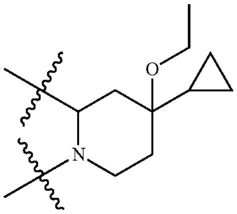 [SMILES: *C1CC(OCC)(C2CC2)CCN1*]
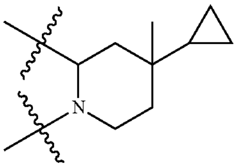 [SMILES: *C1CC(C)(C2CC2)CCN1*]
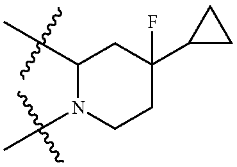
-continued
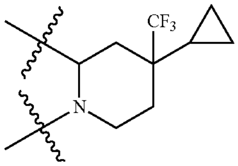
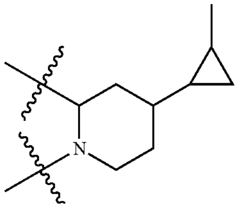 [SMILES: *C1CC(C2CC2C)CCN1*]
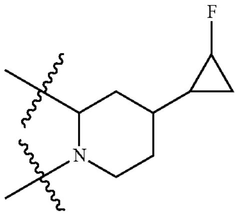 [SMILES: *C1CC(C2CC2F)CCN1*]
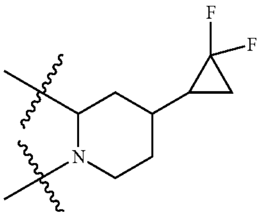 [SMILES: *C1CC(C2CC2(F)F)CCN1*]
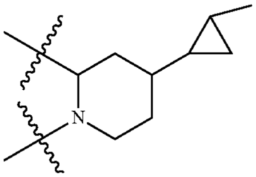 [SMILES: *C1CC(C2CC2C)CCN1*]
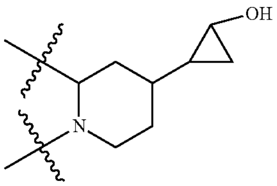 [SMILES: *C1CC(C2CC2O)CCN1*]
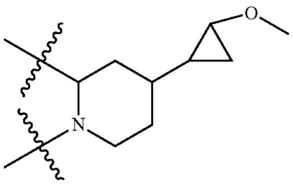 [SMILES: *C1CC(C2CC2OC)CCN1*]
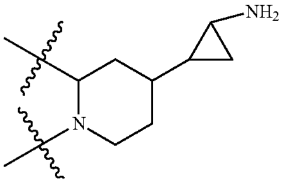 [SMILES: *C1CC(C2CC2N)CCN1*]

-continued

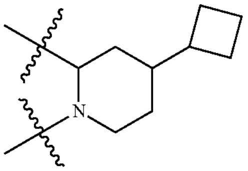 [SMILES: *C1CC(C2CCC2)CCN1*]

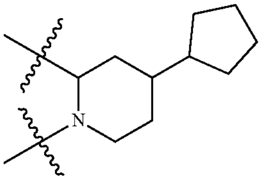 [SMILES: *C1CC(C2CCCC2)CCN1*]

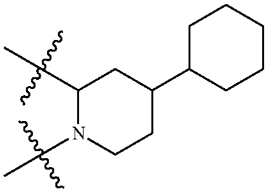 [SMILES: *C1CC(C2CCCCC2)CCN1*]

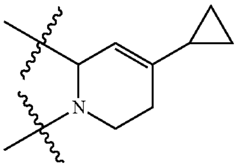 [SMILES: *C1C=C(C2CC2)CCN1*]

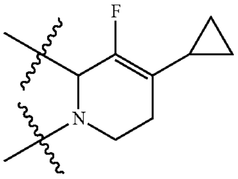 [SMILES: *C1C(F)=C(C2CC2)CCN1*]

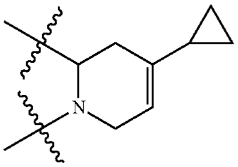 [SMILES: *C1CC(C2CC2)=CCN1*]

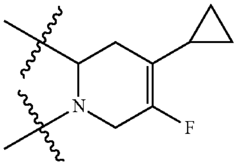 [SMILES: *C1CC(C2CC2)=C(F)CN1*]

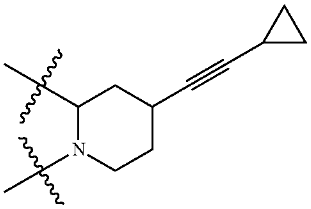 [SMILES: *C1CC(C#CC2CC2)CCN1*]

-continued

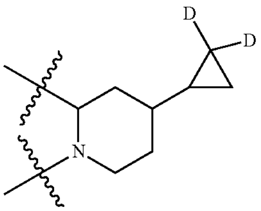 [SMILES: *C1CC(C2CC2([2H])[2H])CCN1*]

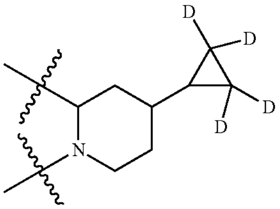 [SMILES: *C1CC(C2C([2H])([2H])C2([2H])[2H])CCN1*]

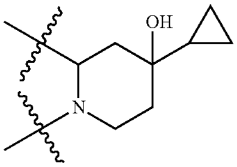 [SMILES: *C1CC(O)(C2CC2)CCN1*]

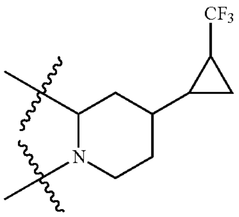

The definitions of the remaining substituents are consistent with the fourth embodiment of the present disclosure.

As a sixth embodiment of the present disclosure, the compound represented by the aforementioned general formula (Ia), (Ib), (Ic), (Ie) or (If) or a stereoisomer, a deuterate, a solvate, a prodrug, a metabolite, a pharmaceutically acceptable salt or a co-crystal thereof is provided,

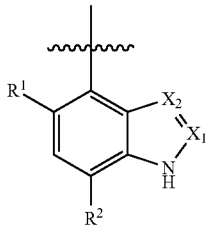

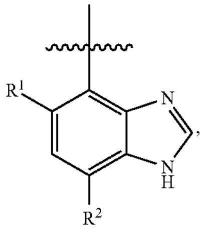, 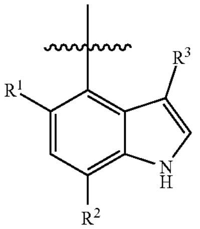 or

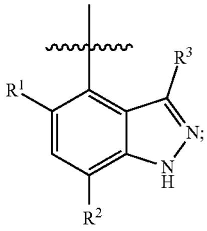; 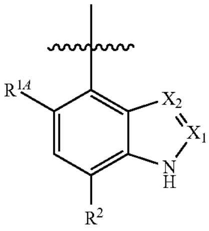

is selected from

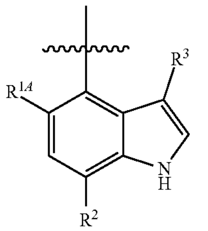 or 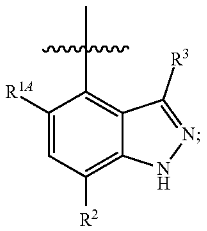;

$R^{1A}$ is selected from ethynyl, propynyl, propargyl, —$CH_2$-cyclopropyl, —$CH_2$— cyclobutyl, —$CH_2$-cyclopentyl, —$CH_2$-oxacyclobutyl, —$CH_2$-azacyclobutyl, —$CH_2$— pyrrolidinyl, —O-cyclopropyl, —O-cyclobutyl, or —O-cyclopentyl, the ethynyl, propynyl, propargyl, —O-cyclopropyl, —O-cyclobutyl, —O-cyclopentyl or —$CH_2$— is optionally further substituted with 0 to 2 substituents selected from H, F, Cl, Br, I, OH, ═O, cyano, $NH_2$, methyl, ethyl, ethynyl, methoxy, ethoxy, $CF_3$, —$CH_2F$, —$CH_2OH$, cyclopropyl, cyclobutyl, azacyclobutyl or pyrrolidinyl;

each $R^1$ is independently selected from H, F, Cl, Br, I, OH, cyano, $NH_2$, —$OCD_3$, $CD_3$, methyl, ethyl, propyl, isopropyl, tert-butyl, methoxy, ethoxy, isopropoxy, cyclopropyl, ethynyl, —$CH_2$-cyclopropyl or —O-cyclopropyl;

or each $R^1$ is independently selected from —$OCH_2F$, —$OCHF_2$, —$OCF_3$,

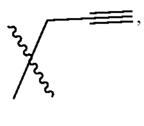, or 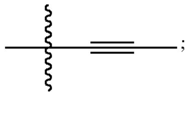;

each $R^2$ is independently selected from F, Cl, Br, I, methyl, ethyl, propyl, isopropyl;

or each $R^2$ is independently selected from $CD_3$, $CHD_2$, or $CH_2D$;

each $R^3$ is independently selected from H, methyl or ethyl;

each $R^4$ is independently selected from

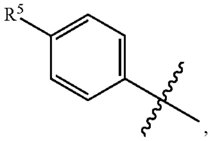, 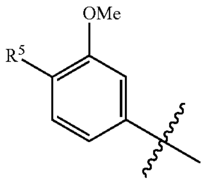,

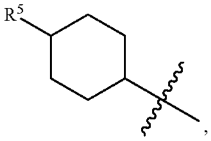, 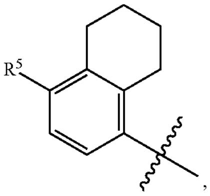,

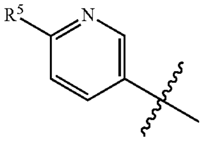 or 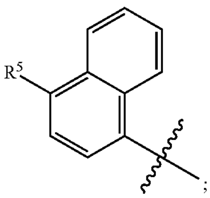;

each $R^5$ is independently selected from H, F, Cl, Br, I, OH, cyano, methyl, ethyl, propyl, isopropyl, methoxy, ethoxy, propoxy, isopropoxy, —COOH, —$CH_2OH$, —$S(═O)_2NH_2$, —$S(═O)_2NHCH_3$, —$S(═O)_2OH$,

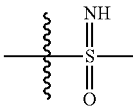, 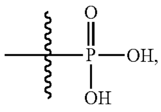, 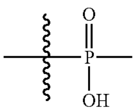,

—$C(═O)NH_2$, —C(═O)NHOH, —$S(═O)_2NHC(═O)CH_3$, —$C(═O)NHS(═O)_2CH_3$, pyrazolyl, tetrazolyl, wherein the methyl, ethyl, propyl, isopropyl, methoxy, ethoxy, propoxy, isopropoxy, pyrazolyl, or tetrazolyl is optionally further substituted with 0 to 4 substituents selected from H, F, Cl, Br, I, OH, ═O, cyano, $NH_2$, methyl, ethyl, methoxy, ethoxy, $CF_3$, —$CH_2F$, —$CH_2OH$, cyclopropyl or cyclobutyl;

in (Ia),

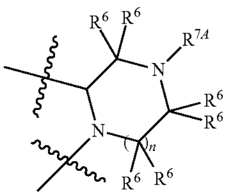

is selected from

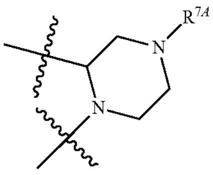

which is connected to $R^4$ at the upper part;

in (Ib),

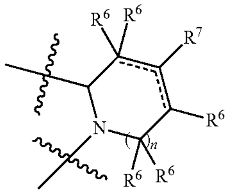

is selected from

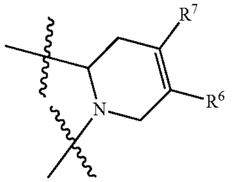

or

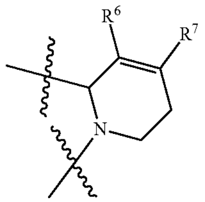

or which is connected to $R^4$ at the upper part;

in (Ic) or (If),

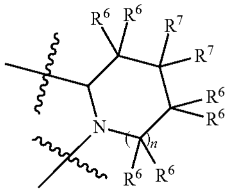

is selected from

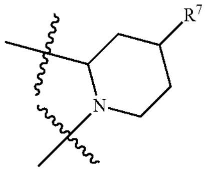

which is connected to $R^4$ at the upper part;

in (Ie),

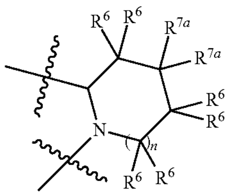

is selected from

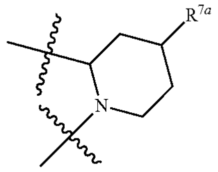

which is connected to $R^4$ at the upper part;

each $R^6$ is independently selected from H, F, Cl, Br, I, OH, $NH_2$, methyl, ethyl, propyl, or isopropyl;

each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, —$CH_2$-propynyl, —$CH_2$-cyclopropyl, —$CH_2$-cyclobutyl, —$CH_2$-azacyclobutyl, —$CH_2OCH_3$, —$OCH_2CH_2OCH_3$, —$CH_2CH_2OCH_3$, —$CH_2CF_3$, —$OCH_2$-cyclopropyl, —C(═O)$CH_3$, —C(═O)-cyclopropyl, —C(═O)-phenyl, —S(═O)$_2$ $CH_3$, —S(═O)$_2CH_2CH_3$, —S(═O)$_2$-cyclopropyl, —S(═O)$_2$—$CH_2$-cyclopropyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl;

$R^{7A}$ is selected from F, Cl, Br, I, methyl, ethyl, propyl, isopropyl, tert-butyl, —$CH_2$— cyclopropyl, —$CH_2$-cyclobutyl, —$CH_2$-azacyclobutyl, —$CH_2OCH_3$, —$CH_2CH_2OCH_3$, —$CH_2CF_3$, —C(═O)$CH_3$, —C(═O)-cyclopropyl, —C(═O)-phenyl, —S(═O)$_2$ $CH_3$, —S(═O)$_2$-cyclopropyl, —S(═O)$_2$—$CH_2$-cyclopropyl, cyclopropyl, cyclobutyl, cyclopentyl or imidazolyl;

$R^{7a}$ is selected from F, Cl, Br, I, $CF_3$, —$CH_2F$, vinyl, ethynyl, propynyl, propargyl, —$CH_2$-propynyl, —$CH_2$-cyclopropyl, —$CH_2$-cyclobutyl, —$CH_2$-azacyclobutyl, —$CH_2OCH_3$, —$OCH_2CH_2OCH_3$, —$CH_2CH_2OCH_3$, —$CH_2CF_3$, —$OCH_2$-cyclopropyl, —C(═O)$CH_3$, —C(═O)-cyclopropyl, —C(═O)-phenyl, —S(═O)$_2CH_3$, —S(═O)$_2CH_2CH_3$, —S(═O)$_2$-cyclopropyl, —S(═O)$_2$—$CH_2$-cyclopropyl, cyclopropyl, cyclobutyl, cyclopentyl, azacyclobutyl, pyrrolidinyl, piperidinyl, morpholinyl, piperazinyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl;

The definitions of the remaining substituents are consistent with the fourth embodiment of the present disclosure.

As a seventh embodiment of the present disclosure, the compound represented by the aforementioned general formula (Id) or a stereoisomer, a deuterate, a solvate, a prodrug, a metabolite, a pharmaceutically acceptable salt or a co-crystal thereof is provided, the compound of general formula (Id) is selected from the compound represented by general formula (Id-1) or general formula (Id-2), (Id-1)

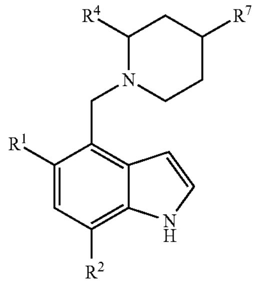

(Id-2)

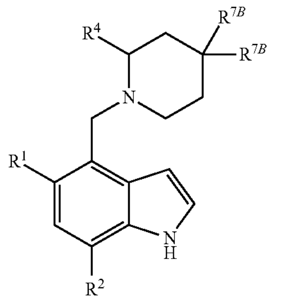

$R^4$ is selected from

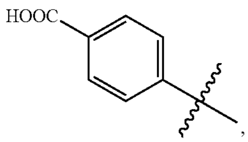

, wherein the $R^4$ is optionally further substituted with 0, 1, 2 or 3 substituents selected from F, Cl, Br, I, OH, cyano, $C_{1-4}$ alkyl, or $C_{1-4}$ alkoxy;

$R^1$ is selected from H, F, Cl, Br, I, —$OCD_3$, $CD_3$, $C_{1-4}$ alkyl, $C_{1-4}$ alkoxy, $C_{3-6}$ cycloalkyl, —$CH_2$—$C_{3-6}$ cycloalkyl or —O—$C_{3-6}$ cycloalkyl, wherein the alkyl, alkoxy, or cycloalkyl is optionally further substituted with 0 to 4 substituents selected from F, ethynyl or propargyl;

$R^2$ is selected from F, Cl, Br, I, or $C_{1-4}$ alkyl;

$R^7$ is selected from methoxymethyl, methoxyethyl, $C_{2-4}$ alkynyl, $C_{3-6}$ cycloalkyl or 4- to 7-membered heterocycle, the alkynyl, cycloalkyl, or heterocyclyl is optionally further substituted with 0 to 4 substituents selected from H, D, halogen, $CF_3$, OH, =O, cyano, $NH_2$, methyl, or methoxy;

two $R^{7B}$ together with the carbon to which they are attached form the following 4- to 7-membered heterocycle, preferably 4- to 6-membered heterocycle, which heterocycle is optionally further substituted with 0 to 2=0.

As a eighth embodiment of the present disclosure, the compound represented by the aforementioned general formula (Id) or a stereoisomer, a deuterate, a solvate, a prodrug, a metabolite, a pharmaceutically acceptable salt or a co-crystal thereof is provided, the compound of general formula (Id) is selected from the compound represented by general formula (Id-1) or general formula (Id-2), (Id-1)

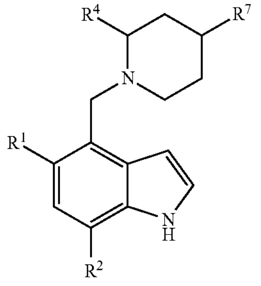

(Id-2)

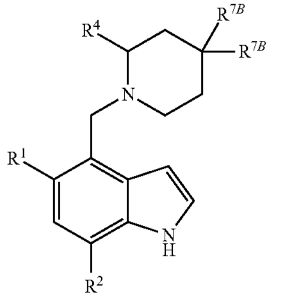

$R^4$ is selected from

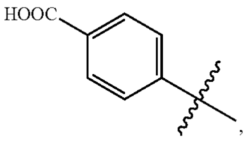 [SMILES: *c1ccc(C(=O)O)cc1]

, or

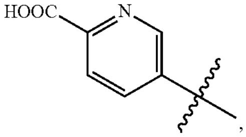

, wherein the $R^4$ is optionally further substituted with 0, 1, 2 or 3 substituents selected from F, Cl, Br, I, OH, cyano, methyl, ethyl, methoxy or ethoxy;

$R^1$ is selected from H, F, Cl, Br, I, —$OCD_3$, $CD_3$, methyl, ethyl, propyl, methoxy, 5 ethoxy, isopropoxy, cyclopropyl, —$CH_2$-cyclopropyl or —O-cyclopropyl;

or each $R^1$ is independently selected from —$OCH_2F$, —$OCHF_2$, —$OCF_3$,

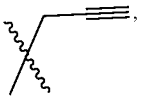

, or

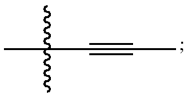

;

$R^2$ is selected from F, Cl, Br, I, methyl, ethyl, propyl, or isopropyl;

or each $R^2$ is independently selected from $CD_3$, $CHD_2$, or $CH_2D$;

$R^7$ is selected from methoxymethyl, methoxyethyl, cyclopropyl, cyclobutyl, cyclopentyl, cyclohexyl, azacyclobutyl, azacyclopentyl, azacyclohexyl, oxacyclobutyl, oxacyclopentyl, oxacyclohexyl, ethynyl, propynyl or propargyl, wherein the cyclopropyl, cyclobutyl, cyclopentyl, cyclohexyl, azacyclobutyl, azacyclopentyl, azacyclohexyl, oxacyclobutyl, oxacyclopentyl, oxacyclohexyl, ethynyl, propynyl or propargyl is optionally further substituted with 0 to 4 substituents selected from H, D, F, Cl, Br, $CF_3$, OH, =O, cyano, $NH_2$, methyl, or methoxy;

two $R^{7B}$ together with the carbon to which they are attached form the following ring:

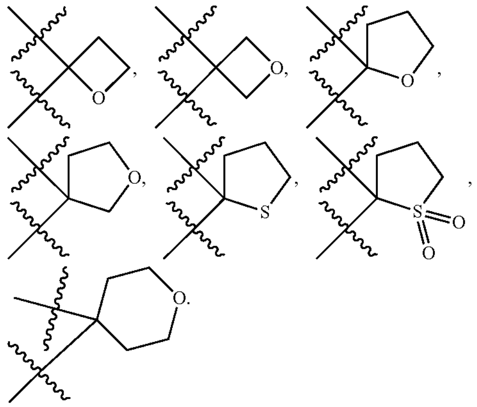

or

As a ninth embodiment of the present disclosure, the compound represented by the aforementioned general formula (I) or a stereoisomer, a deuterate, a solvate, a prodrug, a metabolite, a pharmaceutically acceptable salt or a co-crystal thereof is provided, the compound of general formula (I) is selected from the compound represented by general formula (Id-3) or general formula (Id-4), (Id-3)

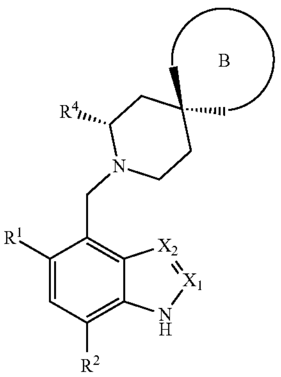

(Id-4)

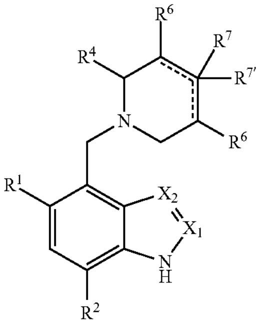

 is selected from a single bond or a double bond, when it is selected from a double bond, $R^{7'}$ does not exist, and at most 1  in the general formula (Id-4) is selected from a double bond;

ring B is selected from 3- to 6-membered heterocyclyl, wherein the heterocyclyl is optionally further substituted with 0 to 4 substituents selected from H, halogen, OH, =O, cyano, $-C(=O)R^{1d}$, $-S(=O)_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^6$ is independently selected from H, halogen, OH, $NH_2$, $C_{1-4}$ alkyl or $C_{1-4}$ alkoxy, wherein the alkyl or alkoxy is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

$R^7$ is selected from $C_{2-4}$ alkynyl, $C_{3-6}$ carbocyclyl, or 3- to 8-membered heterocyclyl, $R^{7'}$ is selected from H, halogen, OH, $-NR^{1a}R^{1b}$, $C_{1-4}$ alkyl, $C_{1-4}$ alkoxy, $C_{2-4}$ alkenyl, $C_{2-4}$ alkynyl, $-C(=O)R^{1d}$, $-S(=O)_2R^{1d}$, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl is contains 1 to 4 heteroatoms selected from O, S or N;

the definitions of other groups are the same as those in the second embodiment of the present disclosure.

As a tenth embodiment of the present disclosure, the compound represented by the aforementioned general formula (Id-3) or general formula (Id-4) or a stereoisomer, a deuterate, a solvate, a prodrug, a metabolite, a pharmaceutically acceptable salt or a co-crystal thereof is provided, $X_1$ is selected from N or CH, $X_2$ is selected from N or CH, wherein the CH is optionally substituted with 1 methyl or ethyl;

ring B is selected from 3- to 6-membered heterocycloalkyl, wherein the heterocycloalkyl is optionally further substituted with 0 to 4 substituents selected from H, halogen, OH, =O, cyano, $NH_2$, $-C(=O)C_{1-4}$ alkyl, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heterocycloalkyl contains 1 to 4 heteroatoms selected from O, S or N;

$R^7$ is selected from $C_{2-4}$ alkynyl, phenyl, $C_{3-6}$ cycloalkyl, 3- to 8-membered heterocycloalkyl or 5- to 6-membered heteroaryl, $R^{7'}$ is selected from H, halogen, OH, $-NH_2$, $C_{1-4}$ alkyl, $C_{1-4}$ alkoxy, $C_{2-4}$ alkenyl, $C_{2-4}$ alkynyl, $-C(=O)C_{1-4}$ alkyl, or $-S(=O)_2C_{1-4}$ alkyl, wherein the alkyl, alkenyl, alkynyl, alkoxy, phenyl, cycloalkyl, heteroaryl, or heterocycloalkyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocycloalkyl, heterocyclyl or heteroaryl contains 1 to 4 heteroatoms selected from O, S or N;

preferably, ring B is selected from oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, halogen, OH, =O, cyano, $NH_2$, —C(=O)$C_{1-4}$ alkyl, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl;

$R^7$ is selected from one of the following substituted or unsubstituted groups: ethynyl, propynyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, $R^{7'}$ is selected from H, F, OH, or $NH_2$, or one of the following substituted or unsubstituted groups: methyl, ethyl, propyl, isopropyl, tert-butyl, methoxy, ethoxy, isopropoxy, vinyl, ethynyl, propynyl or propargyl, $R^7$ or $R^{7'}$, when substituted, is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;

each $R^6$ is independently selected from H, F, Cl, Br, $CF_3$, methyl or ethyl;

the definitions of $R^1$, $R^2$ and $R^4$ are the same as in the fifth embodiment of the present disclosure.

As a eleventh embodiment of the present disclosure, the compound represented by the aforementioned general formula (Id-3) or general formula (Id-4) or a stereoisomer, a deuterate, a solvate, a prodrug, a metabolite, a pharmaceutically acceptable salt or a co-crystal thereof is provided, ring B is selected from oxacyclobutyl, oxacyclopentyl, oxacyclohexyl, thiocyclopentyl, azacyclobutyl, pyrrolidinyl, piperidinyl, morpholinyl, or piperazinyl, wherein the ring B is optionally further substituted with 0 to 4 substituents selected from H, F, Cl, Br, $CF_3$, OH, =O, cyano, $NH_2$, —C(=O)$CH_3$, methyl, ethyl, methoxy or ethoxy;

$R^7$ is selected from one of the following substituted or unsubstituted groups: ethynyl, propynyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, $R^{7'}$ is selected from H, F, OH, or $NH_2$, or one of the following substituted or unsubstituted groups: methyl, ethyl, propyl, isopropyl, tert-butyl, methoxy, ethoxy, isopropoxy, vinyl, ethynyl, propynyl or propargyl, $R^7$ or $R^{7'}$, when substituted, is optionally further substituted with 0 to 4 substituents selected from H, D, F, Cl, Br, $CF_3$, OH, =O, cyano, $NH_2$, methyl, ethyl, methoxy, ethoxy, ethynyl, propynyl, propargyl, cyclopropyl, cyclobutyl, cyclopentyl, azacyclobutyl, pyrrolidinyl, piperidinyl, morpholinyl or piperazinyl;

the definitions of $R^1$, $R^2$ and $R^4$ are the same as in the sixth embodiment of the present disclosure. As a twelfth embodiment of the present disclosure, the compound represented by the aforementioned general formula (Id-3) or general formula (Id-4) or a stereoisomer, a deuterate, a solvate, a prodrug, a metabolite, a pharmaceutically acceptable salt or a co-crystal thereof is provided, $R^4$ is selected from

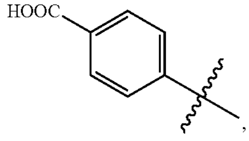

, or

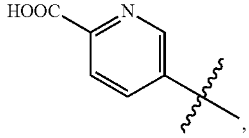

, wherein the $R^4$ is optionally substituted with 1, 2 or 3 substituents selected from F, Cl, Br, I, OH, cyano, methyl, ethyl, methoxy or ethoxy;

the definitions of other groups are the same as those in either the ninth, tenth or eleventh embodiment of the present disclosure.

As a thirteenth embodiment of the present disclosure, the compound represented by the following general formula (Id-5) or a stereoisomer, a deuterate, a solvate, a prodrug, a metabolite, a pharmaceutically acceptable salt or a co-crystal thereof is provided, (Id-5)

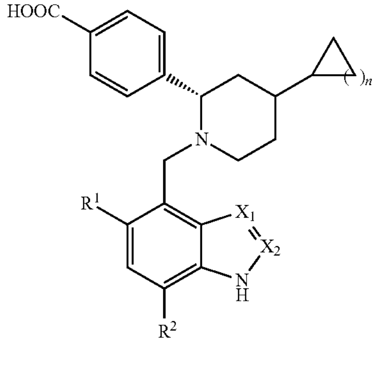

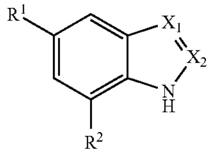

is selected from

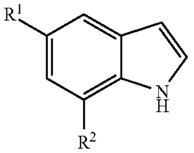
,
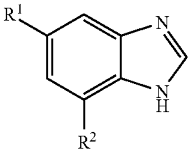
, or
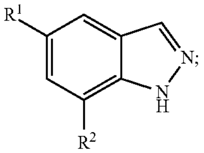
;

$R^1$ is selected from —$OCH_3$ or —$OCD_3$;

$R^2$ is selected from —$CH_3$ or —$CD_3$;

and n is selected from 1, 2 or 3.

As a fourteenth embodiment of the present disclosure, the compound represented by the following general formula (Id-6) or a stereoisomer, a deuterate, a solvate, a prodrug, a metabolite, a pharmaceutically acceptable salt or a co-crystal thereof is provided, (Id-6)

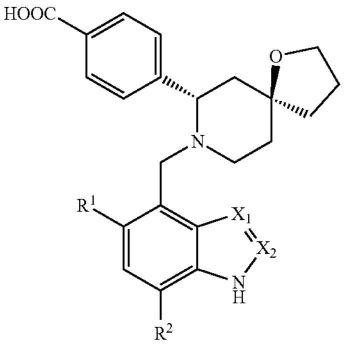

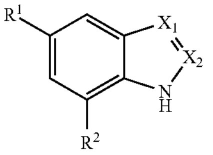

is selected from

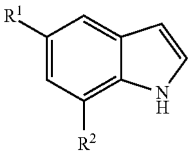
,
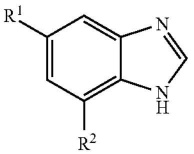
, or
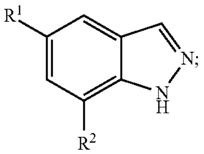
;

$R^1$ is selected from —$OCH_3$ or —$OCD_3$;

and $R^2$ is selected from —$CH_3$ or —$CD_3$.

As a fifteenth embodiment of the present disclosure, the compound represented by the following general formula (Id-7) or general formula (Id-8) or a stereoisomer, a deuterate, a solvate, a prodrug, a metabolite, a pharmaceutically acceptable salt or a co-crystal thereof is provided, (Id-7)

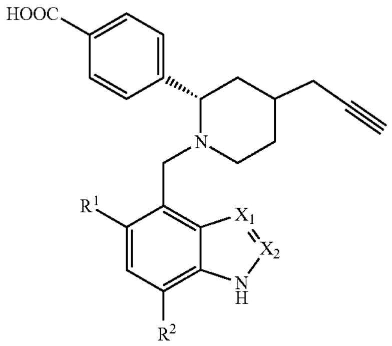

(Id-8)

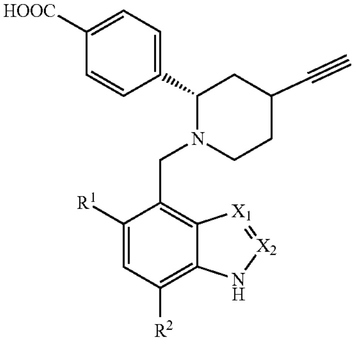

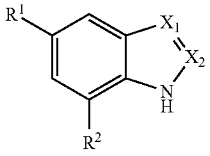

is selected from

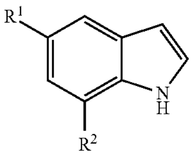
,
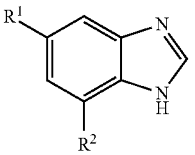
, or
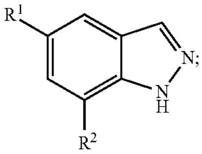
;

$R^1$ is selected from —$OCH_3$ or —$OCD_3$;

and $R^2$ is selected from —$CH_3$ or —$CD_3$.

As a sixteenth embodiment of the present disclosure, the compound of general formula (I) is selected from the compound represented by general formula (Id-3-a), general formula (Id-5-a), general formula (Id-6-a), general formula (Id-7-a) or general formula (Id-8-a), (Id-3-a)

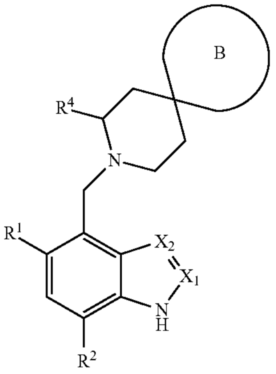

(Id-5-a)

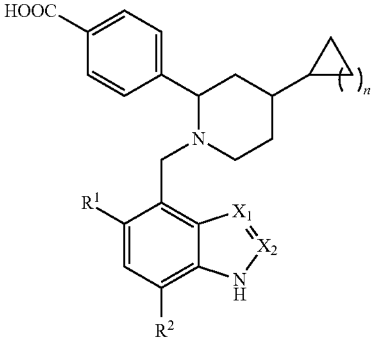

(Id-6-a)

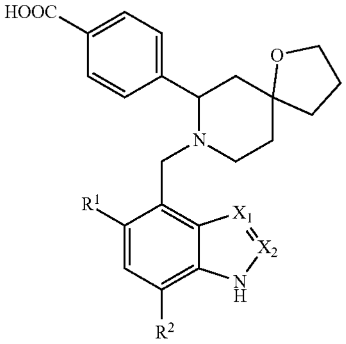

-continued (Id-7-a)

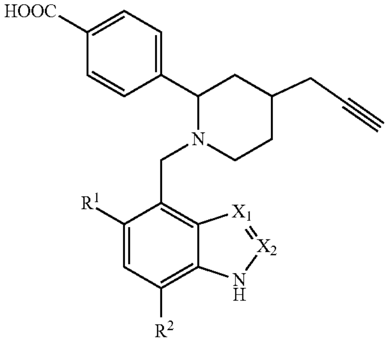

(Id-8-a)

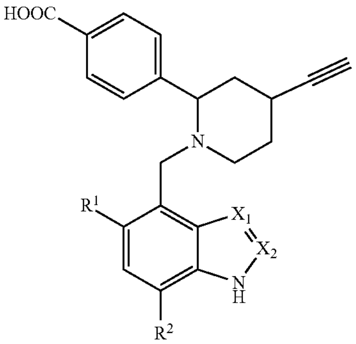

the definition of each group in general formula (Id-3-a) is the same as that in general formula (Id-3);

the definition of each group in general formula (Id-5-a) is the same as that in general formula (Id-5);

the definition of each group in general formula (Id-6-a) is the same as that in general formula (Id-6);

the definition of each group in general formula (Id-7-a) is the same as that in general formula (Id-7);

the definition of each group in general formula (Id-8-a) is the same as that in general formula (Id-7).

The present disclosure relates to a compound as described below or a stereoisomer, deuterate, solvate, prodrug, metabolite, pharmaceutically acceptable salt or co-crystal thereof, wherein the compound is selected from one of the structures in Table E-1.

TABLE E-1

| | | | |
|---|---|---|---|
| 1 | 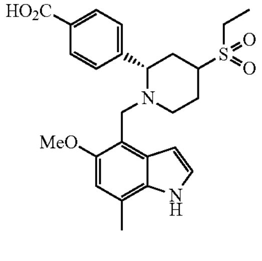 | 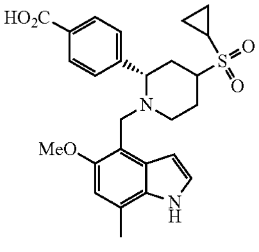 | 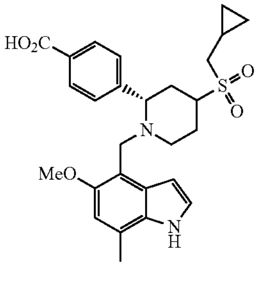 |

TABLE E-1-continued
| | | | |
|---|---|---|---|
| 2 | 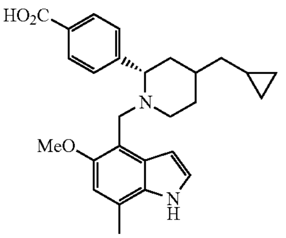 | 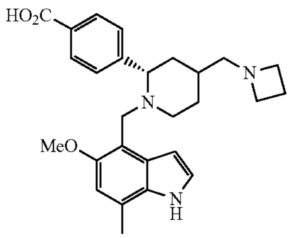 | 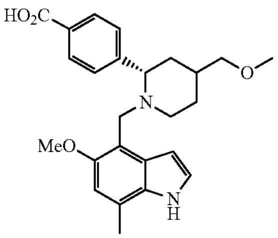 [SMILES: COCC1CCN(Cc2c(OC)cc(C)c3[nH]ccc23)[C@H](c2ccc(C(=O)O)cc2)C1] |
| 3 | 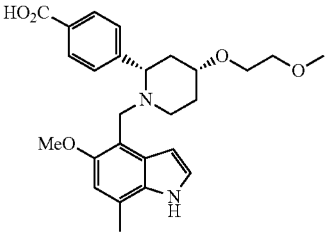 | 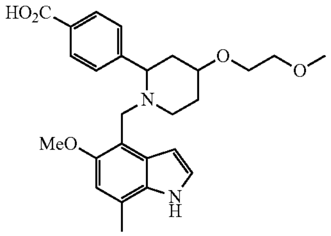 | 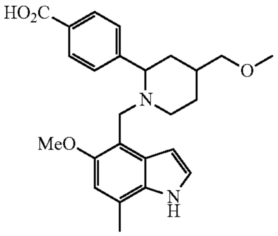 |
| 4 | 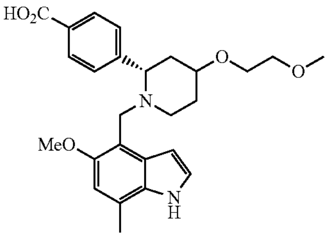 | 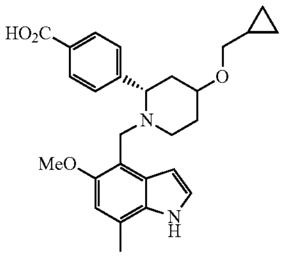 | 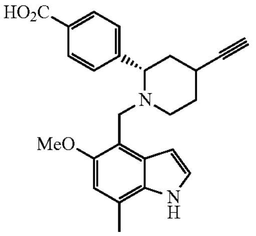 [SMILES: C#CC1CCN(Cc2c(OC)cc(C)c3[nH]ccc23)[C@H](c2ccc(C(=O)O)cc2)C1] |
| 5 | 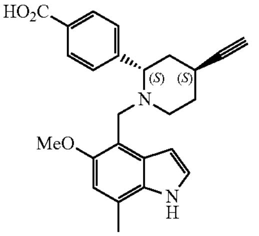 | 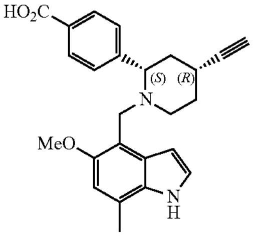 | 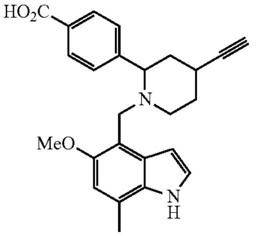 [SMILES: C#CC1CCN(Cc2c(OC)cc(C)c3[nH]ccc23)C(c2ccc(C(=O)O)cc2)C1] |
| 6 | 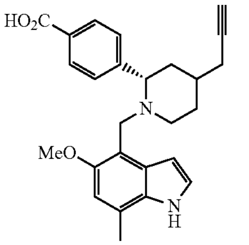 | 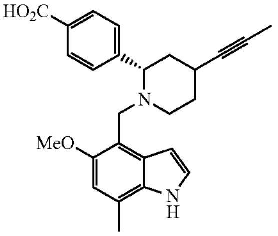 | 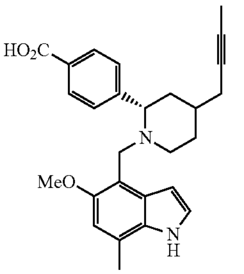 [SMILES: CC#CCC1CCN(Cc2c(OC)cc(C)c3[nH]ccc23)[C@H](c2ccc(C(=O)O)cc2)C1] |
| 7 | 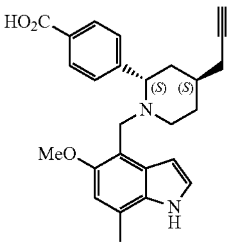 | 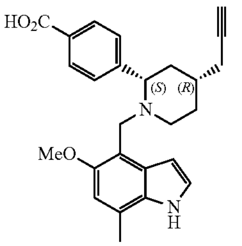 | 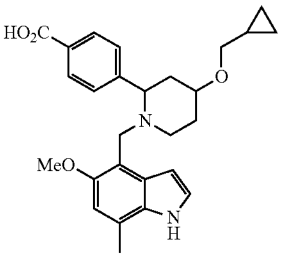 |

TABLE E-1-continued
| | | | |
|---|---|---|---|
| 8 | 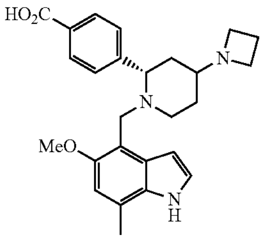 | 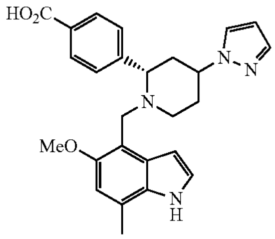 | 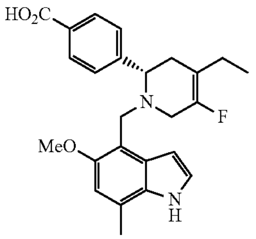 [SMILES: CCC1=C(F)CN(Cc2c(OC)cc(C)c3[nH]ccc23)[C@H](c2ccc(C(=O)O)cc2)C1] |
| 9 | 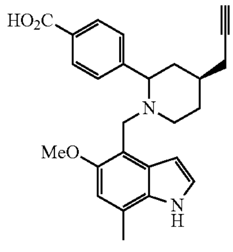 | 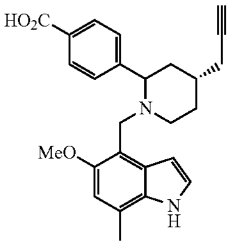 | 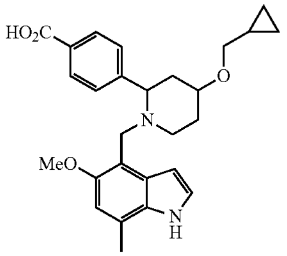 |
| 10 | 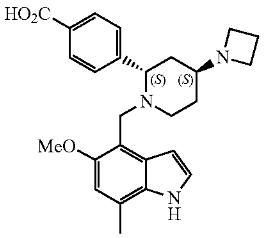 | 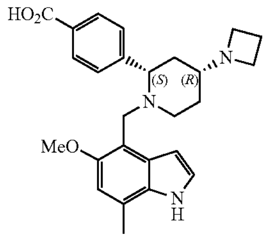 | 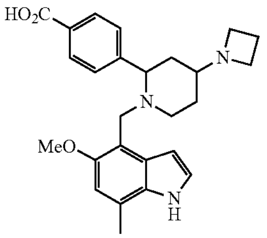 [SMILES: COc1cc(C)c2[nH]ccc2c1CN1CCC(N2CCC2)CC1c1ccc(C(=O)O)cc1] |
| 11 | 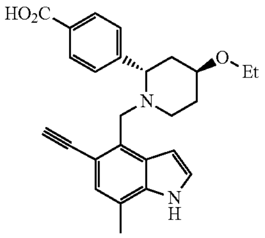 | 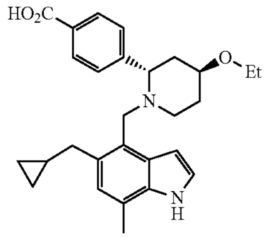 | 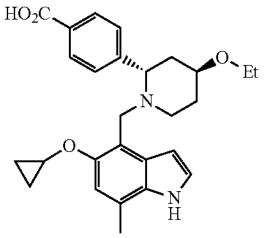 [SMILES: CCO[C@H]1CCN(Cc2c(OC3CC3)cc(C)c3[nH]ccc23)[C@H](c2ccc(C(=O)O)cc2)C1] |
| 12 | 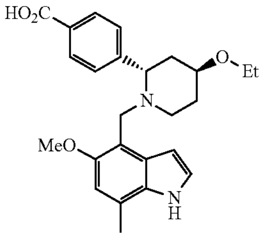 | 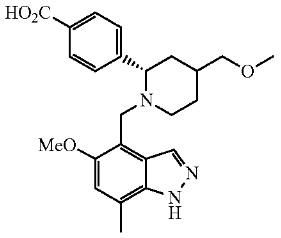 | 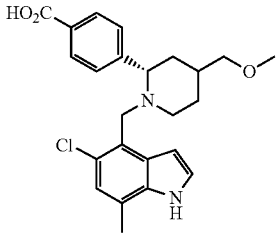 [SMILES: COCC1CCN(Cc2c(Cl)cc(C)c3[nH]ccc23)[C@H](c2ccc(C(=O)O)cc2)C1] |
| 13 | 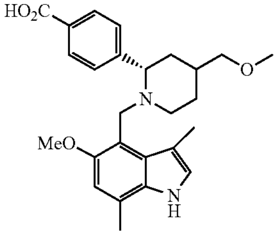 | 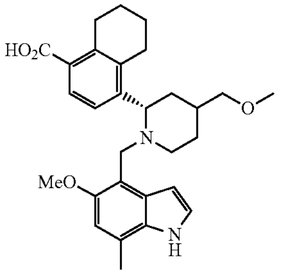 | 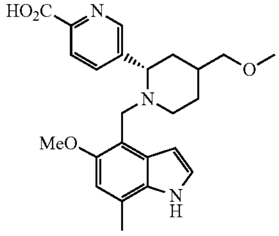 [SMILES: COCC1CCN(Cc2c(OC)cc(C)c3[nH]ccc23)[C@H](c2ccc(C(=O)O)nc2)C1] |

TABLE E-1-continued
14 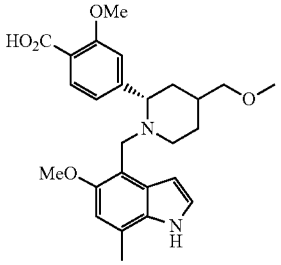 [SMILES: COCC1CCN(Cc2c(OC)cc(C)c3[nH]ccc23)[C@H](c2ccc(C(=O)O)c(OC)c2)C1] 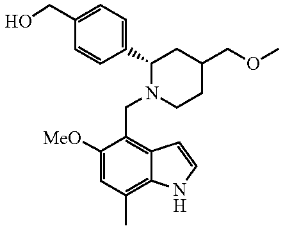 [SMILES: COCC1CCN(Cc2c(OC)cc(C)c3[nH]ccc23)[C@H](c2ccc(CO)cc2)C1] 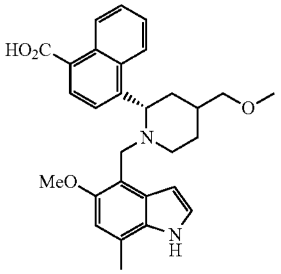 [SMILES: COCC1CCN(Cc2c(OC)cc(C)c3[nH]ccc23)[C@H](c2ccc(C(=O)O)c3ccccc23)C1]
15 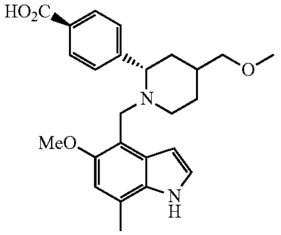 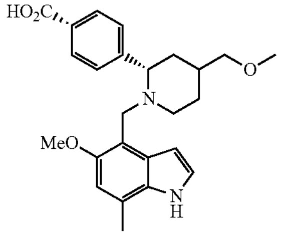 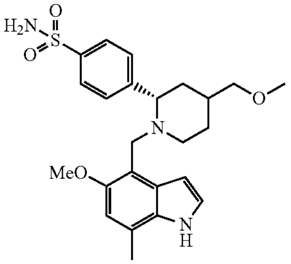 [SMILES: COCC1CCN(Cc2c(OC)cc(C)c3[nH]ccc23)[C@H](c2ccc(S(N)(=O)=O)cc2)C1]
16 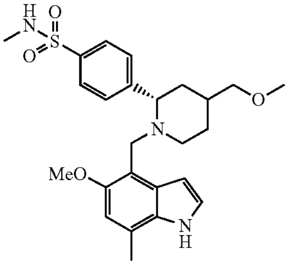 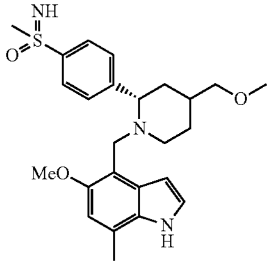 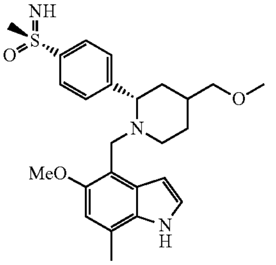
17 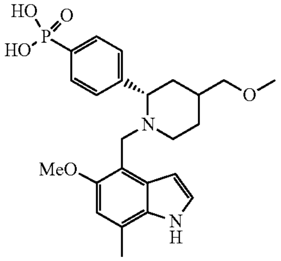 [SMILES: COCC1CCN(Cc2c(OC)cc(C)c3[nH]ccc23)[C@H](c2ccc(P(=O)(O)O)cc2)C1] 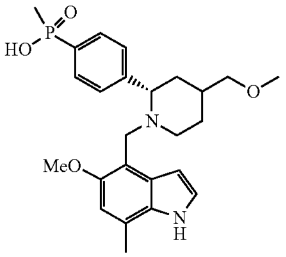 [SMILES: COCC1CCN(Cc2c(OC)cc(C)c3[nH]ccc23)[C@H](c2ccc(P(C)(=O)O)cc2)C1] 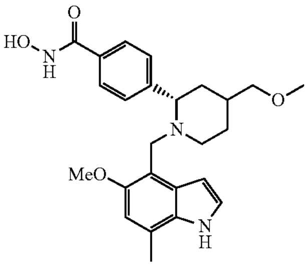 [SMILES: COCC1CCN(Cc2c(OC)cc(C)c3[nH]ccc23)[C@H](c2ccc(C(=O)NO)cc2)C1]
18 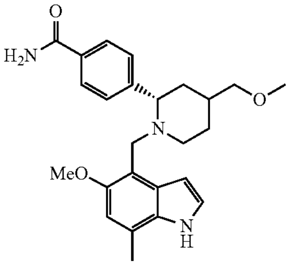 [SMILES: COCC1CCN(Cc2c(OC)cc(C)c3[nH]ccc23)[C@H](c2ccc(C(N)=O)cc2)C1] 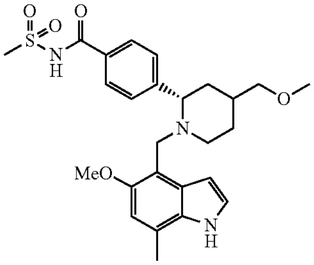 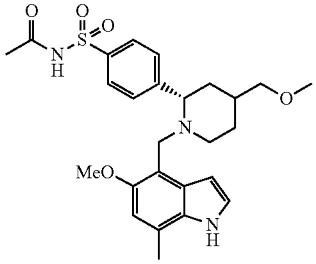 [SMILES: COCC1CCN(Cc2c(OC)cc(C)c3[nH]ccc23)[C@H](c2ccc(S(=O)(=O)NC(C)=O)cc2)C1]
19 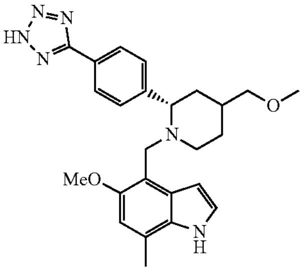 [SMILES: COCC1CCN(Cc2c(OC)cc(C)c3[nH]ccc23)[C@H](c2ccc(-c3nn[nH]n3)cc2)C1] 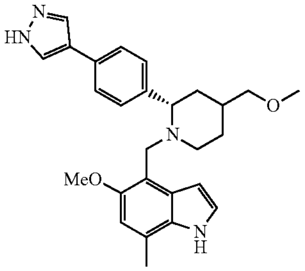 [SMILES: COCC1CCN(Cc2c(OC)cc(C)c3[nH]ccc23)[C@H](c2ccc(-c3cn[nH]c3)cc2)C1] 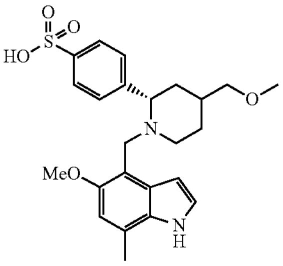 [SMILES: COCC1CCN(Cc2c(OC)cc(C)c3[nH]ccc23)[C@H](c2ccc(S(=O)(=O)O)cc2)C1]

TABLE E-1-continued
| | | | |
|---|---|---|---|
| 20 | 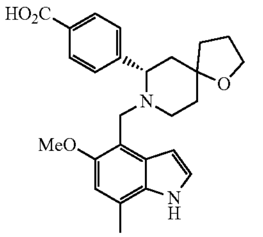 | 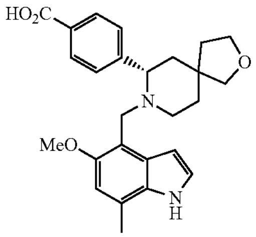 | 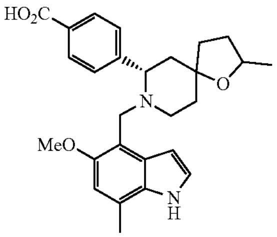 [SMILES: COc1cc(C)c2[nH]ccc2c1CN1CCC2(CCC(C)O2)C[C@H]1c1ccc(C(=O)O)cc1] |
| 21 | 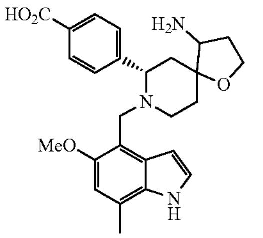 | 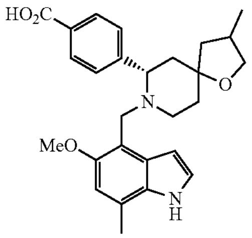 | 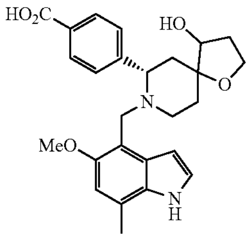 [SMILES: COc1cc(C)c2[nH]ccc2c1CN1CCC2(C[C@H]1c1ccc(C(=O)O)cc1)OCCC2O] |
| 22 | 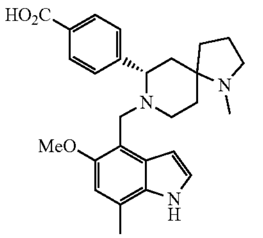 | 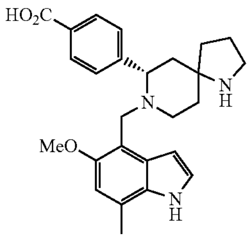 | 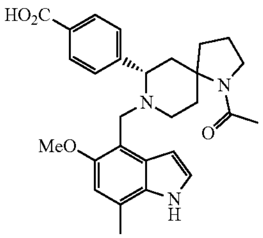 [SMILES: COc1cc(C)c2[nH]ccc2c1CN1CCC2(CCCN2C(C)=O)C[C@H]1c1ccc(C(=O)O)cc1] |
| 23 | | 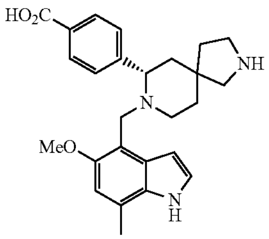 | 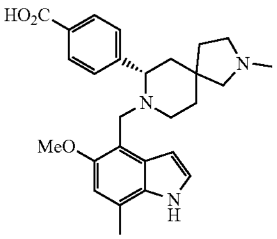 [SMILES: COc1cc(C)c2[nH]ccc2c1CN1CCC2(CCN(C)C2)C[C@H]1c1ccc(C(=O)O)cc1] |
| 24 | 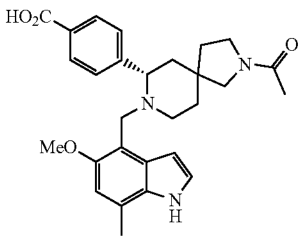 [SMILES: COc1cc(C)c2[nH]ccc2c1CN1CCC2(CCN(C(C)=O)C2)C[C@H]1c1ccc(C(=O)O)cc1] | 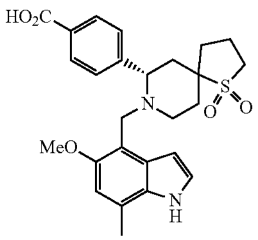 | 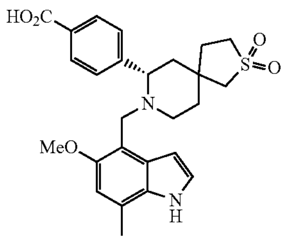 [SMILES: COc1cc(C)c2[nH]ccc2c1CN1CCC2(CCS(=O)(=O)C2)C[C@H]1c1ccc(C(=O)O)cc1] |
| 25 | 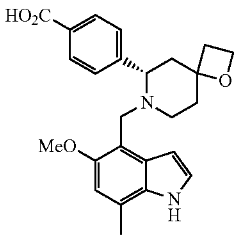 [SMILES: COc1cc(C)c2[nH]ccc2c1CN1CCC2(CCO2)C[C@H]1c1ccc(C(=O)O)cc1] | 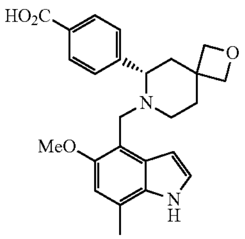 | 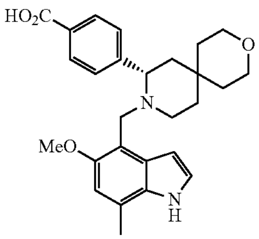 [SMILES: COc1cc(C)c2[nH]ccc2c1CN1CCC2(CCOCC2)C[C@H]1c1ccc(C(=O)O)cc1] |

TABLE E-1-continued
| | | | |
|---|---|---|---|
| 26 | 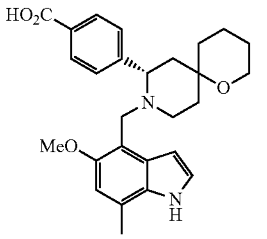 [SMILES: COc1cc(C)c2[nH]ccc2c1CN1CCC2(CCCCO2)C[C@H]1c1ccc(C(=O)O)cc1] | 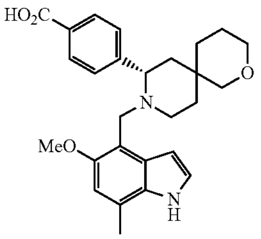 [SMILES: COc1cc(C)c2[nH]ccc2c1CN1CCC2(CCCOC2)C[C@H]1c1ccc(C(=O)O)cc1] | 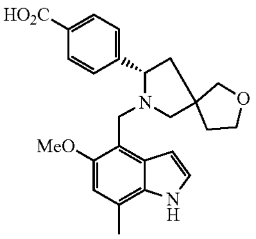 [SMILES: COc1cc(C)c2[nH]ccc2c1CN1CC2(CCOC2)C[C@H]1c1ccc(C(=O)O)cc1] |
| 27 | 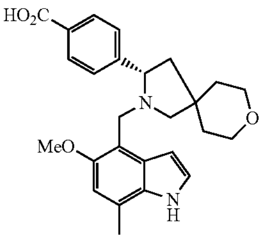 [SMILES: COc1cc(C)c2[nH]ccc2c1CN1CC2(CCOCC2)C[C@H]1c1ccc(C(=O)O)cc1] | 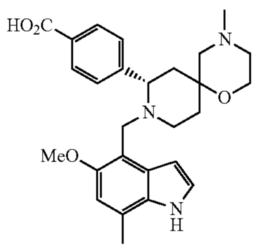 [SMILES: COc1cc(C)c2[nH]ccc2c1CN1CCC2(C[C@H]1c1ccc(C(=O)O)cc1)CN(C)CCO2] | 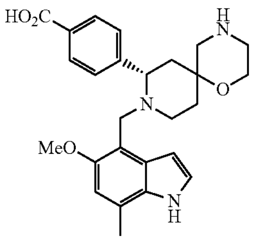 [SMILES: COc1cc(C)c2[nH]ccc2c1CN1CCC2(CNCCO2)C[C@H]1c1ccc(C(=O)O)cc1] |
| 28 | 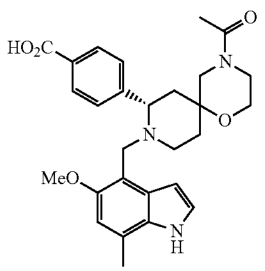 [SMILES: COc1cc(C)c2[nH]ccc2c1CN1CCC2(C[C@H]1c1ccc(C(=O)O)cc1)CN(C(C)=O)CCO2] | 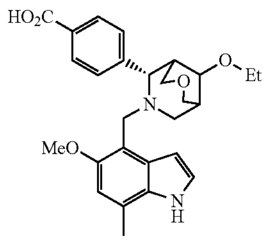 [SMILES: CCOC1C2COCC1[C@@H](c1ccc(C(=O)O)cc1)N(Cc1c(OC)cc(C)c3[nH]ccc13)C2] | 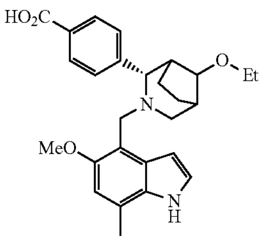 [SMILES: CCOC1C2CCC1[C@@H](c1ccc(C(=O)O)cc1)N(Cc1c(OC)cc(C)c3[nH]ccc13)C2] |
| 29 | 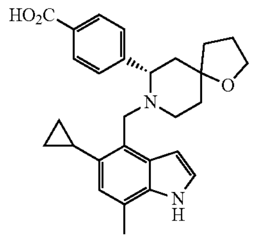 [SMILES: Cc1cc(C2CC2)c(CN2CCC3(CCCO3)C[C@H]2c2ccc(C(=O)O)cc2)c2cc[nH]c12] | 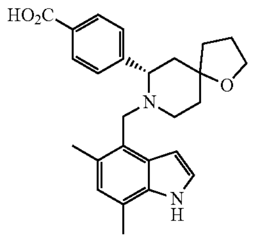 [SMILES: Cc1cc(C)c2[nH]ccc2c1CN1CCC2(CCCO2)C[C@H]1c1ccc(C(=O)O)cc1] | 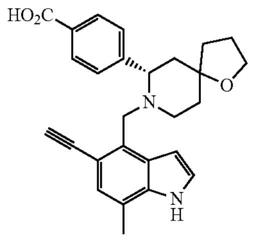 [SMILES: C#Cc1cc(C)c2[nH]ccc2c1CN1CCC2(CCCO2)C[C@H]1c1ccc(C(=O)O)cc1] |
| 30 | 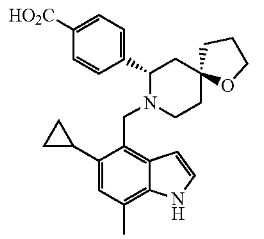 [SMILES: Cc1cc(C2CC2)c(CN2CC[C@@]3(CCCO3)C[C@H]2c2ccc(C(=O)O)cc2)c2cc[nH]c12] | 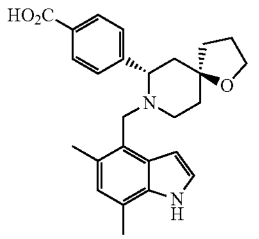 [SMILES: Cc1cc(C)c2[nH]ccc2c1CN1CC[C@@]2(CCCO2)C[C@H]1c1ccc(C(=O)O)cc1] | 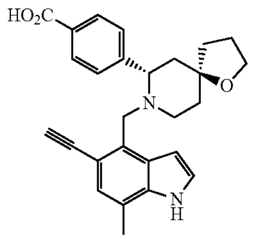 [SMILES: C#Cc1cc(C)c2[nH]ccc2c1CN1CC[C@@]2(CCCO2)C[C@H]1c1ccc(C(=O)O)cc1] |
| 31 | 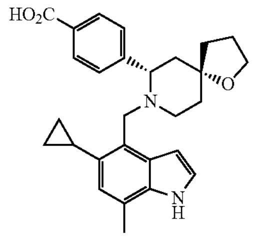 [SMILES: Cc1cc(C2CC2)c(CN2CC[C@]3(CCCO3)C[C@H]2c2ccc(C(=O)O)cc2)c2cc[nH]c12] | 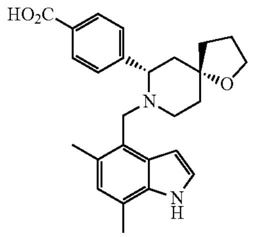 [SMILES: Cc1cc(C)c2[nH]ccc2c1CN1CC[C@]2(CCCO2)C[C@H]1c1ccc(C(=O)O)cc1] | 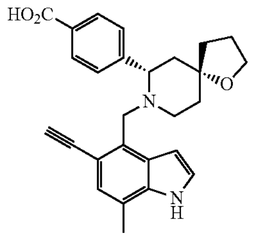 [SMILES: C#Cc1cc(C)c2[nH]ccc2c1CN1CC[C@]2(CCCO2)C[C@H]1c1ccc(C(=O)O)cc1] |

TABLE E-1-continued
| | | | |
|---|---|---|---|
| 32 | 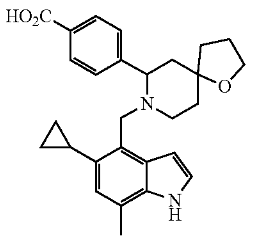 [SMILES: Cc1cc(C2CC2)c(CN2CCC3(CCCO3)CC2c2ccc(C(=O)O)cc2)c2cc[nH]c12] | 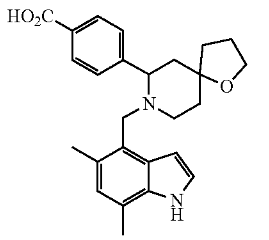 [SMILES: Cc1cc(C)c2[nH]ccc2c1CN1CCC2(CCCO2)CC1c1ccc(C(=O)O)cc1] | 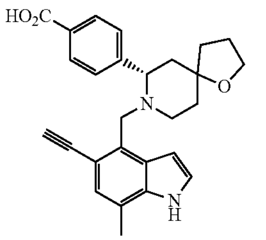 [SMILES: C#Cc1cc(C)c2[nH]ccc2c1CN1CCC2(CCCO2)C[C@H]1c1ccc(C(=O)O)cc1] |
| 33 | 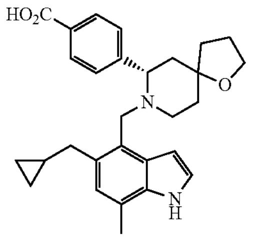 | 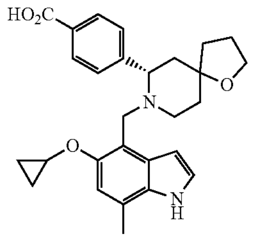 [SMILES: Cc1cc(OC2CC2)c(CN2CCC3(CCCO3)C[C@H]2c2ccc(C(=O)O)cc2)c2cc[nH]c12] | 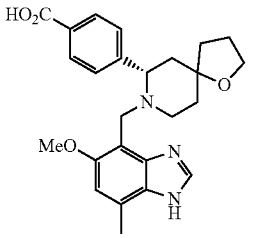 [SMILES: COc1cc(C)c2[nH]cnc2c1CN1CCC2(CCCO2)C[C@H]1c1ccc(C(=O)O)cc1] |
| 34 | 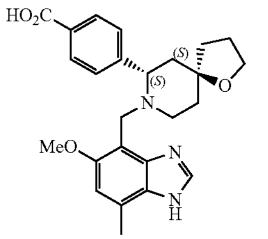 | 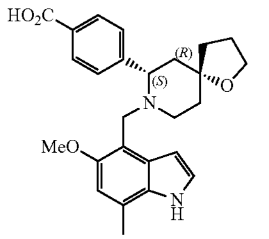 | 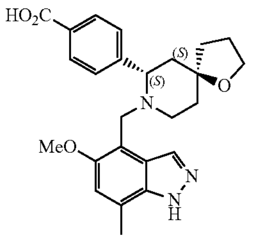 |
| 35 | 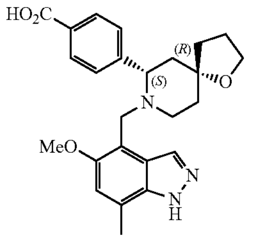 | 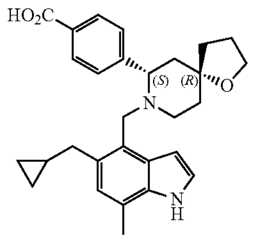 | 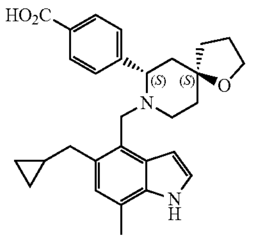 |
| 36 | 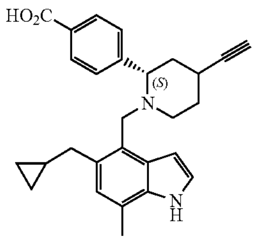 | 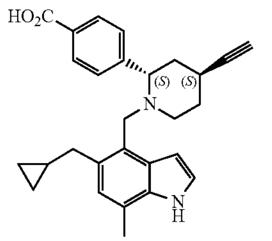 | 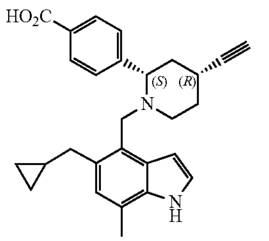 |
| 37 | 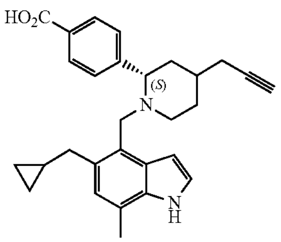 | 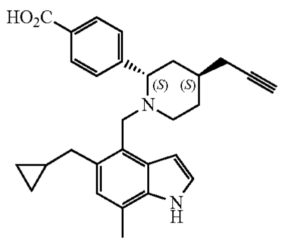 | 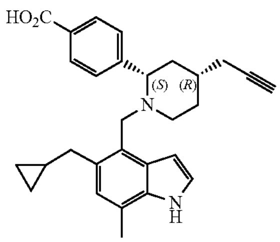 |

TABLE E-1-continued
| | | | |
|---|---|---|---|
| 38 | 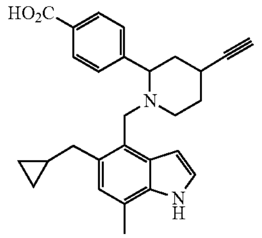 [SMILES: C#CC1CCN(Cc2c(CC3CC3)cc(C)c3[nH]ccc23)C(c2ccc(C(=O)O)cc2)C1] | 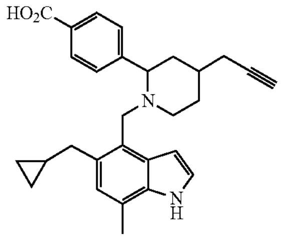 [SMILES: C#CCC1CCN(Cc2c(CC3CC3)cc(C)c3[nH]ccc23)C(c2ccc(C(=O)O)cc2)C1] | 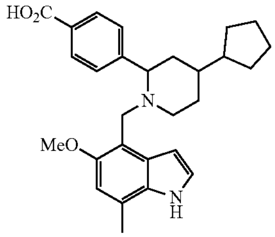 |
| 39 | 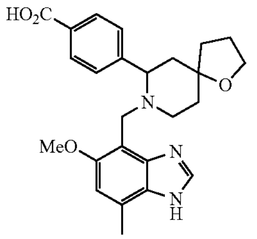 | 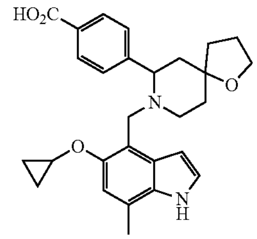 | 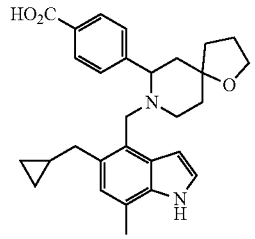 |
| 40 | 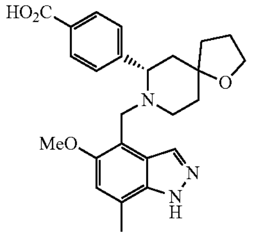 | 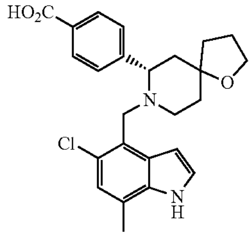 | 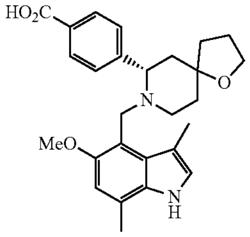 [SMILES: COc1cc(C)c2[nH]cc(C)c2c1CN1CCC2(CCCO2)C[C@H]1c1ccc(C(=O)O)cc1] |
| 41 | 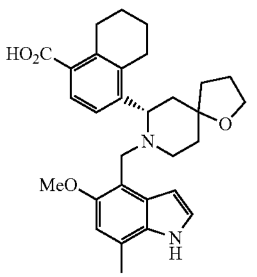 [SMILES: COc1cc(C)c2[nH]ccc2c1CN1CCC2(CCCO2)C[C@H]1c1ccc(C(=O)O)c2c1CCCC2] | 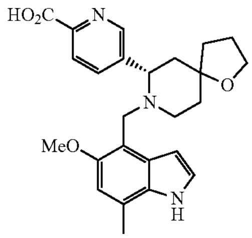 [SMILES: COc1cc(C)c2[nH]ccc2c1CN1CCC2(CCCO2)C[C@H]1c1ccc(C(=O)O)nc1] | 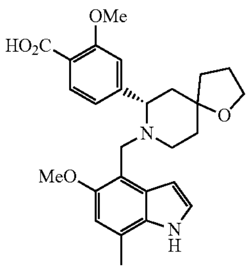 [SMILES: COc1cc([C@@H]2CC3(CCCO3)CCN2Cc2c(OC)cc(C)c3[nH]ccc23)ccc1C(=O)O] |
| 42 | 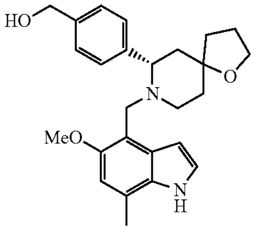 [SMILES: COc1cc(C)c2[nH]ccc2c1CN1CCC2(CCCO2)C[C@H]1c1ccc(CO)cc1] | 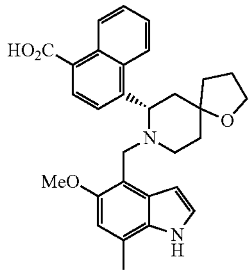 [SMILES: COc1cc(C)c2[nH]ccc2c1CN1CCC2(CCCO2)C[C@H]1c1ccc(C(=O)O)c2ccccc12] | 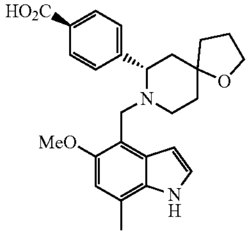 |
| 43 | 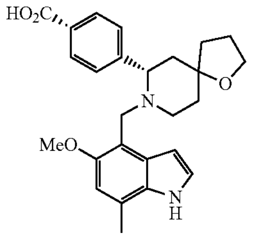 | 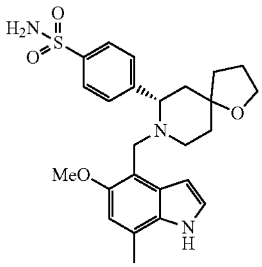 [SMILES: COc1cc(C)c2[nH]ccc2c1CN1CCC2(CCCO2)C[C@H]1c1ccc(S(N)(=O)=O)cc1] | 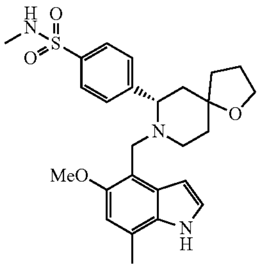 [SMILES: CNS(=O)(=O)c1ccc([C@@H]2CC3(CCCO3)CCN2Cc2c(OC)cc(C)c3[nH]ccc23)cc1] |

TABLE E-1-continued
| | | | |
|---|---|---|---|
| 44 | 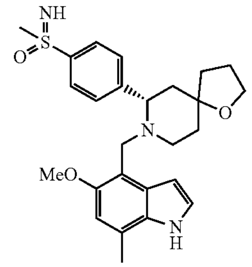 [SMILES: COc1cc(C)c2[nH]ccc2c1CN1CCC2(CCCO2)C[C@H]1c1ccc(S(C)(=N)=O)cc1] | 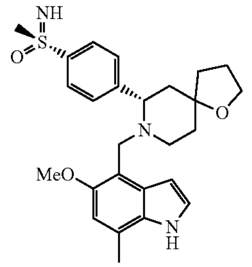 | 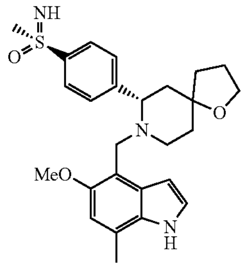 |
| 45 | 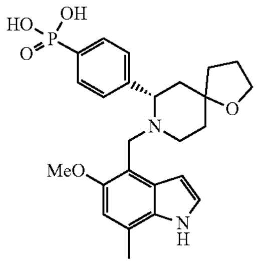 [SMILES: COc1cc(C)c2[nH]ccc2c1CN1CCC2(CCCO2)C[C@H]1c1ccc(P(=O)(O)O)cc1] | 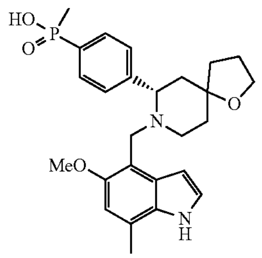 [SMILES: COc1cc(C)c2[nH]ccc2c1CN1CCC2(CCCO2)C[C@H]1c1ccc(P(C)(=O)O)cc1] | 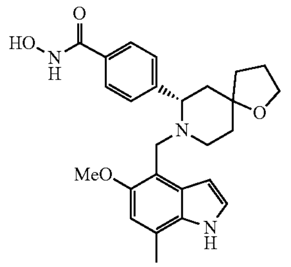 [SMILES: COc1cc(C)c2[nH]ccc2c1CN1CCC2(CCCO2)C[C@H]1c1ccc(C(=O)NO)cc1] |
| 46 | 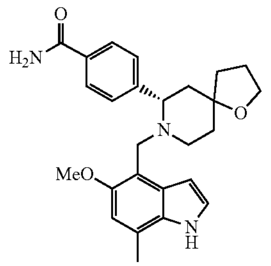 [SMILES: COc1cc(C)c2[nH]ccc2c1CN1CCC2(CCCO2)C[C@H]1c1ccc(C(N)=O)cc1] | 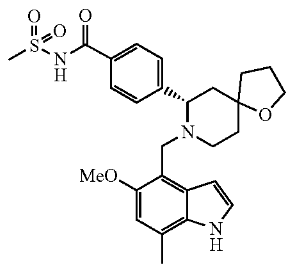 [SMILES: COc1cc(C)c2[nH]ccc2c1CN1CCC2(CCCO2)C[C@H]1c1ccc(C(=O)NS(C)(=O)=O)cc1] | 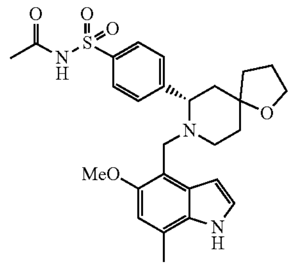 [SMILES: COc1cc(C)c2[nH]ccc2c1CN1CCC2(CCCO2)C[C@H]1c1ccc(S(=O)(=O)NC(C)=O)cc1] |
| 47 | 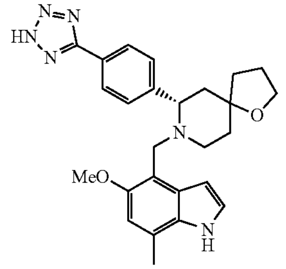 [SMILES: COc1cc(C)c2[nH]ccc2c1CN1CCC2(CCCO2)C[C@H]1c1ccc(-c2nn[nH]n2)cc1] | 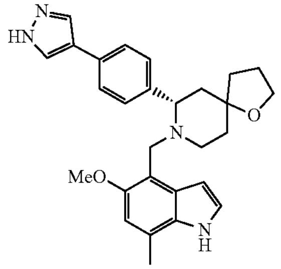 [SMILES: COc1cc(C)c2[nH]ccc2c1CN1CCC2(CCCO2)C[C@H]1c1ccc(-c2cn[nH]c2)cc1] | 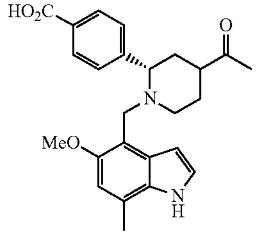 [SMILES: COc1cc(C)c2[nH]ccc2c1CN1CCC(C(C)=O)C[C@H]1c1ccc(C(=O)O)cc1] |
| 48 | 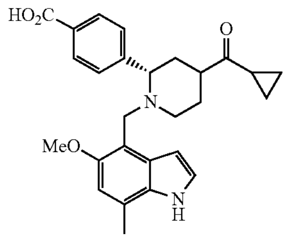 [SMILES: COc1cc(C)c2[nH]ccc2c1CN1CCC(C(=O)C2CC2)C[C@H]1c1ccc(C(=O)O)cc1] | 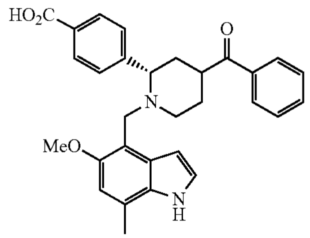 [SMILES: COc1cc(C)c2[nH]ccc2c1CN1CCC(C(=O)c2ccccc2)C[C@H]1c1ccc(C(=O)O)cc1] | 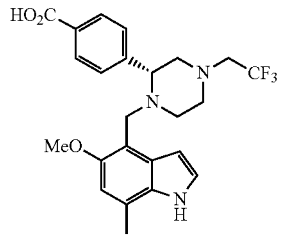 [SMILES: COc1cc(C)c2[nH]ccc2c1CN1CCN(CC(F)(F)F)C[C@H]1c1ccc(C(=O)O)cc1] |
| 49 | 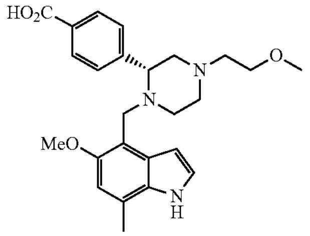 [SMILES: COCCN1CCN(Cc2c(OC)cc(C)c3[nH]ccc23)[C@H](c2ccc(C(=O)O)cc2)C1] | 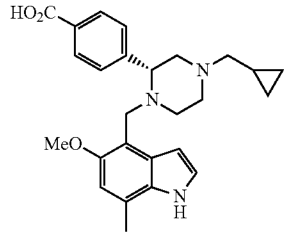 [SMILES: COc1cc(C)c2[nH]ccc2c1CN1CCN(CC2CC2)C[C@H]1c1ccc(C(=O)O)cc1] | 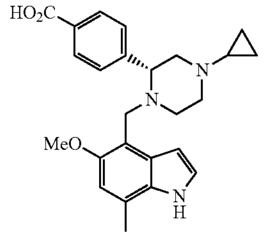 [SMILES: COc1cc(C)c2[nH]ccc2c1CN1CCN(C2CC2)C[C@H]1c1ccc(C(=O)O)cc1] |

TABLE E-1-continued
| | | | |
|---|---|---|---|
| 50 | 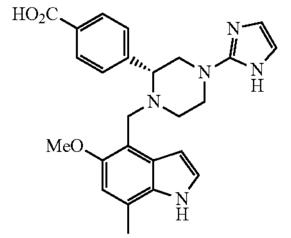 [SMILES: COc1cc(C)c2[nH]ccc2c1CN1CCN(c2ncc[nH]2)C[C@H]1c1ccc(C(=O)O)cc1] | 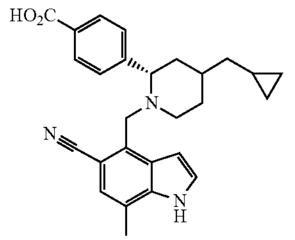 [SMILES: Cc1cc(C#N)c(CN2CCC(CC3CC3)C[C@H]2c2ccc(C(=O)O)cc2)c2cc[nH]c12] | 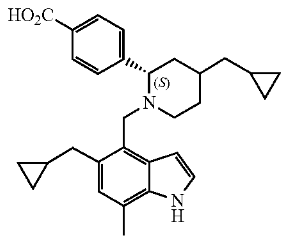 |
| 51 | 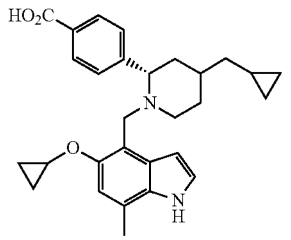 [SMILES: Cc1cc(OC2CC2)c(CN2CCC(CC3CC3)C[C@H]2c2ccc(C(=O)O)cc2)c2cc[nH]c12] | 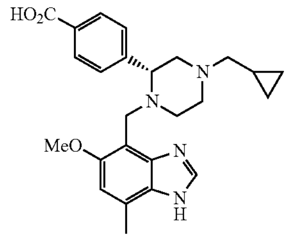 [SMILES: COc1cc(C)c2[nH]cnc2c1CN1CCN(CC2CC2)C[C@H]1c1ccc(C(=O)O)cc1] | 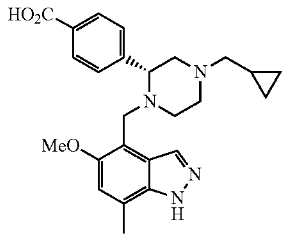 [SMILES: COc1cc(C)c2[nH]ncc2c1CN1CCN(CC2CC2)C[C@H]1c1ccc(C(=O)O)cc1] |
| 52 | 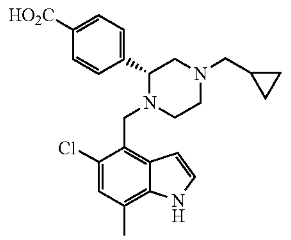 [SMILES: Cc1cc(Cl)c(CN2CCN(CC3CC3)C[C@H]2c2ccc(C(=O)O)cc2)c2cc[nH]c12] | 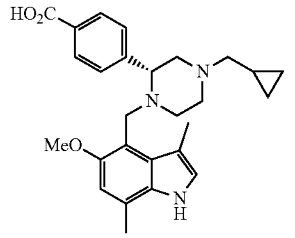 [SMILES: COc1cc(C)c2[nH]cc(C)c2c1CN1CCN(CC2CC2)C[C@H]1c1ccc(C(=O)O)cc1] | 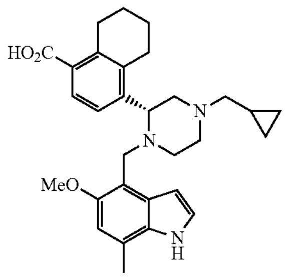 [SMILES: COc1cc(C)c2[nH]ccc2c1CN1CCN(CC2CC2)C[C@H]1c1ccc(C(=O)O)c2c1CCCC2] |
| 53 | 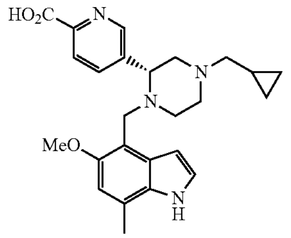 [SMILES: COc1cc(C)c2[nH]ccc2c1CN1CCN(CC2CC2)C[C@H]1c1ccc(C(=O)O)nc1] | 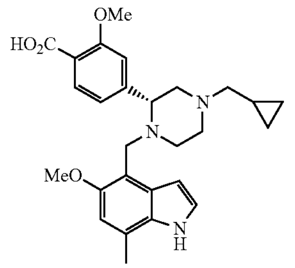 [SMILES: COc1cc([C@@H]2CN(CC3CC3)CCN2Cc2c(OC)cc(C)c3[nH]ccc23)ccc1C(=O)O] | 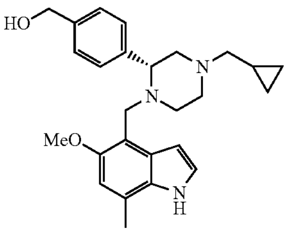 [SMILES: COc1cc(C)c2[nH]ccc2c1CN1CCN(CC2CC2)C[C@H]1c1ccc(CO)cc1] |
| 54 | 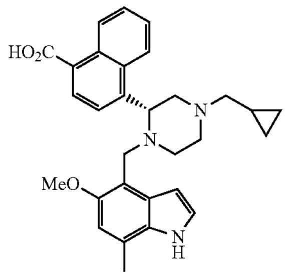 [SMILES: COc1cc(C)c2[nH]ccc2c1CN1CCN(CC2CC2)C[C@H]1c1ccc(C(=O)O)c2ccccc12] | 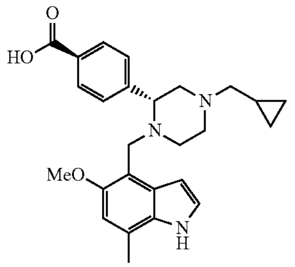 | 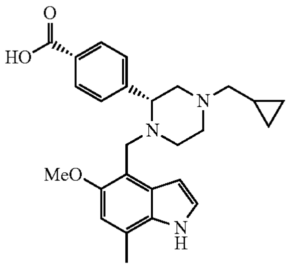 |
| 55 | 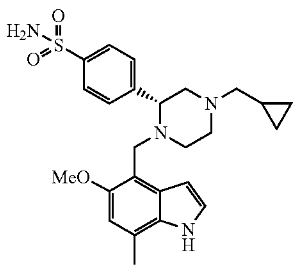 [SMILES: COc1cc(C)c2[nH]ccc2c1CN1CCN(CC2CC2)C[C@H]1c1ccc(S(N)(=O)=O)cc1] | 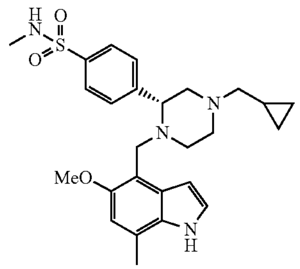 [SMILES: CNS(=O)(=O)c1ccc([C@@H]2CN(CC3CC3)CCN2Cc2c(OC)cc(C)c3[nH]ccc23)cc1] | 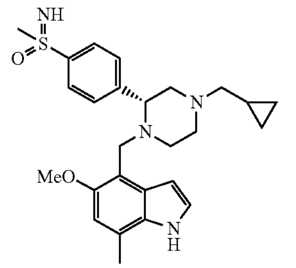 [SMILES: COc1cc(C)c2[nH]ccc2c1CN1CCN(CC2CC2)C[C@H]1c1ccc(S(C)(=N)=O)cc1] |

TABLE E-1-continued
| | | | |
|---|---|---|---|
| 56 | 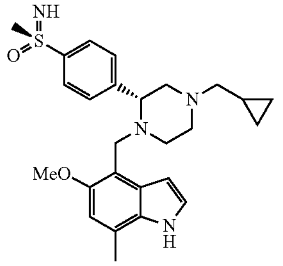 [SMILES: COc1cc(C)c2[nH]ccc2c1CN1CCN(CC2CC2)C[C@H]1c1ccc([S@@](C)(=N)=O)cc1] | 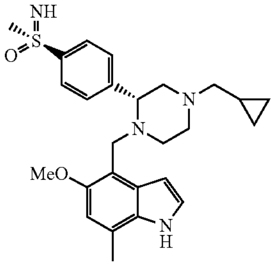 | 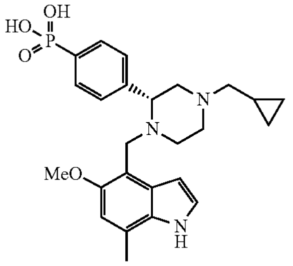 |
| 57 | 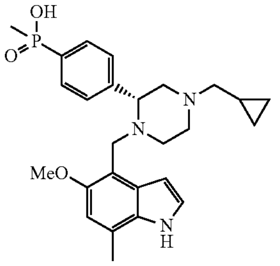 [SMILES: COc1cc(C)c2[nH]ccc2c1CN1CCN(CC2CC2)C[C@H]1c1ccc(P(C)(=O)O)cc1] | 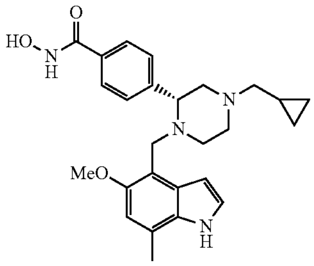 [SMILES: COc1cc(C)c2[nH]ccc2c1CN1CCN(CC2CC2)C[C@H]1c1ccc(C(=O)NO)cc1] | 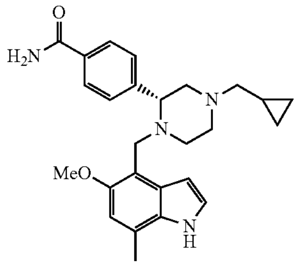 [SMILES: COc1cc(C)c2[nH]ccc2c1CN1CCN(CC2CC2)C[C@H]1c1ccc(C(N)=O)cc1] |
| 58 | 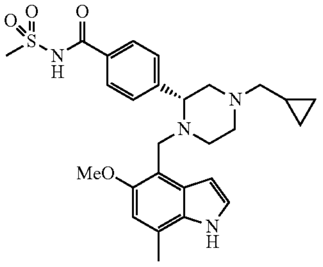 [SMILES: COc1cc(C)c2[nH]ccc2c1CN1CCN(CC2CC2)C[C@H]1c1ccc(C(=O)NS(C)(=O)=O)cc1] | 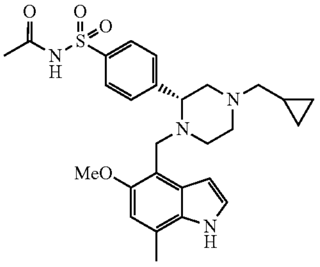 [SMILES: COc1cc(C)c2[nH]ccc2c1CN1CCN(CC2CC2)C[C@H]1c1ccc(S(=O)(=O)NC(C)=O)cc1] | 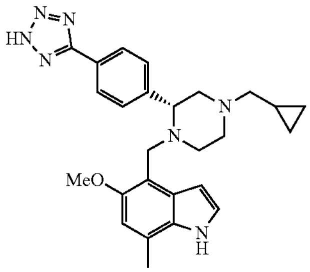 [SMILES: COc1cc(C)c2[nH]ccc2c1CN1CCN(CC2CC2)C[C@H]1c1ccc(-c2nn[nH]n2)cc1] |
| 59 | 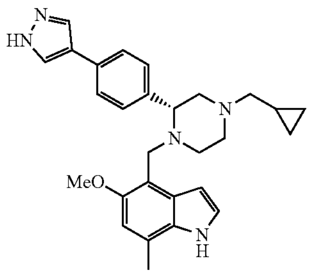 [SMILES: COc1cc(C)c2[nH]ccc2c1CN1CCN(CC2CC2)C[C@H]1c1ccc(-c2cn[nH]c2)cc1] | 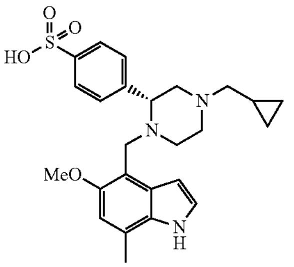 [SMILES: COc1cc(C)c2[nH]ccc2c1CN1CCN(CC2CC2)C[C@H]1c1ccc(S(=O)(=O)O)cc1] | 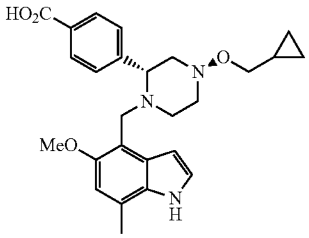 |
| 60 | 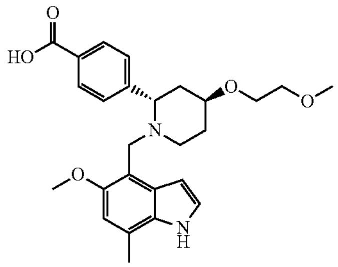 [SMILES: COCCO[C@H]1CCN(Cc2c(OC)cc(C)c3[nH]ccc23)[C@H](c2ccc(C(=O)O)cc2)C1] | 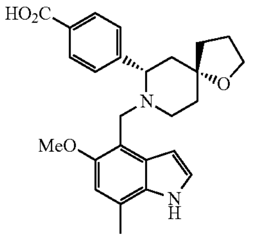 [SMILES: COc1cc(C)c2[nH]ccc2c1CN1CC[C@]2(CCCO2)C[C@H]1c1ccc(C(=O)O)cc1] | 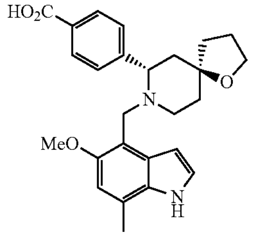 [SMILES: COc1cc(C)c2[nH]ccc2c1CN1CC[C@@]2(CCCO2)C[C@H]1c1ccc(C(=O)O)cc1] |
| 61 | 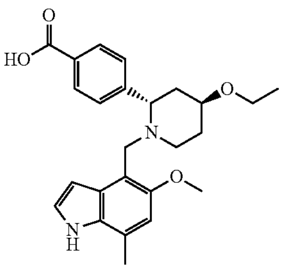 [SMILES: CCO[C@H]1CCN(Cc2c(OC)cc(C)c3[nH]ccc23)[C@H](c2ccc(C(=O)O)cc2)C1] | 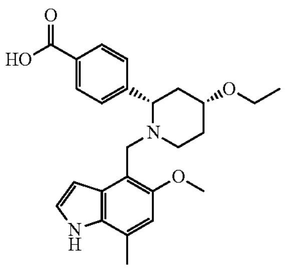 [SMILES: CCO[C@@H]1CCN(Cc2c(OC)cc(C)c3[nH]ccc23)[C@H](c2ccc(C(=O)O)cc2)C1] | 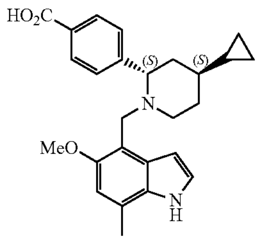 |

TABLE E-1-continued
| | | | |
|---|---|---|---|
| 62 | 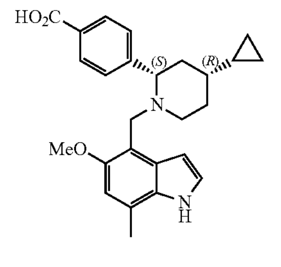 | 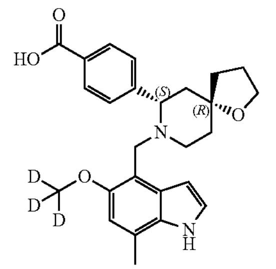 | 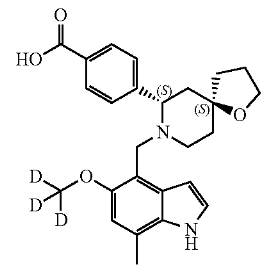 |
| 63 | 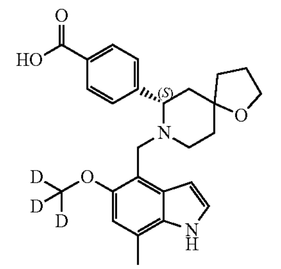 | 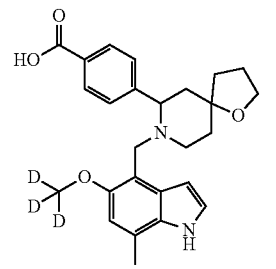 [SMILES: [2H]C([2H])([2H])Oc1cc(C)c2[nH]ccc2c1CN1CCC2(CCCO2)CC1c1ccc(C(=O)O)cc1] | 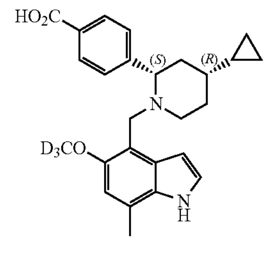 |
| 64 | 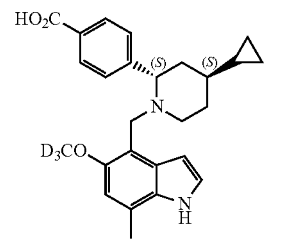 | 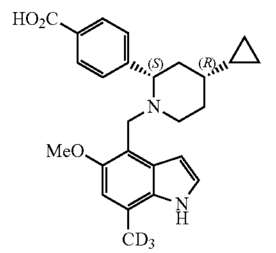 | 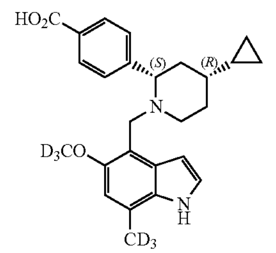 |
| 65 | 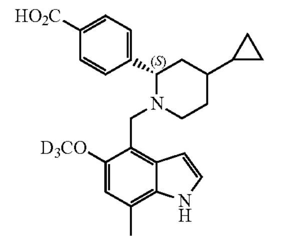 | 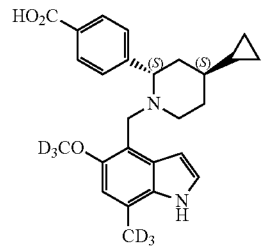 | 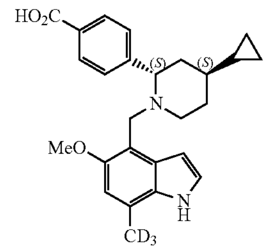 |
| 66 | 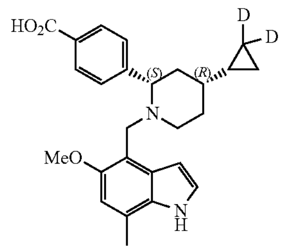 | 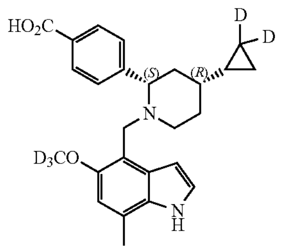 | 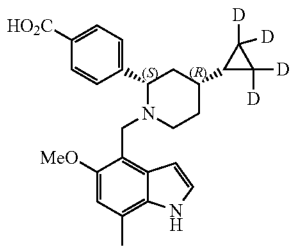 |
| 67 | 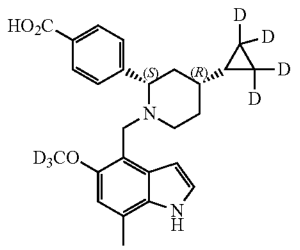 | 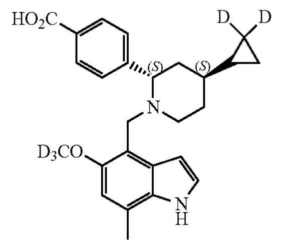 | 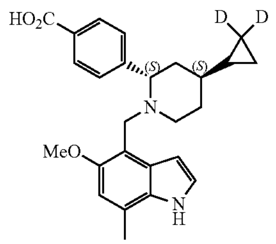 |

TABLE E-1-continued
| | | | |
|---|---|---|---|
| 68 | 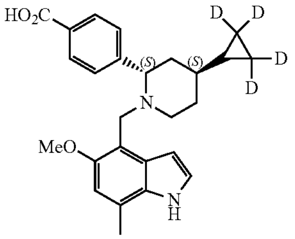 | 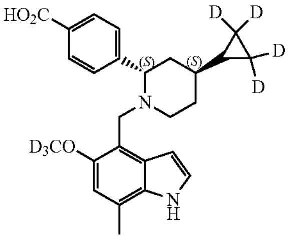 | 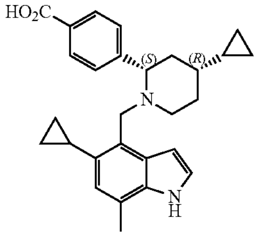 |
| 69 | 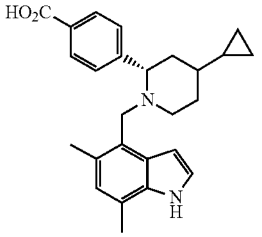 [SMILES: Cc1cc(C)c2[nH]ccc2c1CN1CCC(C2CC2)C[C@H]1c1ccc(C(=O)O)cc1] | 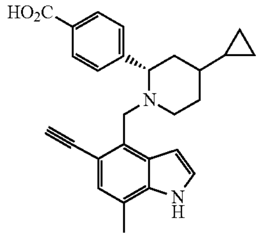 | 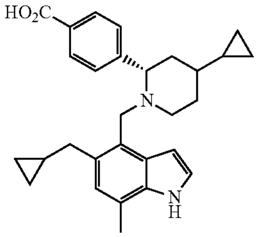 [SMILES: Cc1cc(CC2CC2)c(CN2CCC(C3CC3)C[C@H]2c2ccc(C(=O)O)cc2)c2cc[nH]c12] |
| 70 | 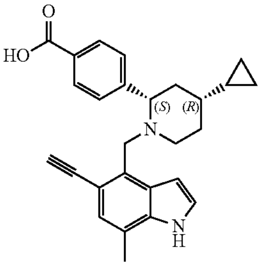 | 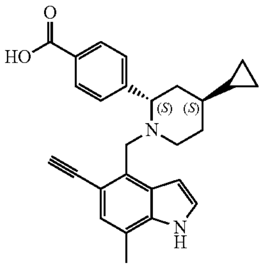 | 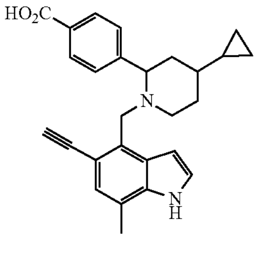 [SMILES: C#Cc1cc(C)c2[nH]ccc2c1CN1CCC(C2CC2)CC1c1ccc(C(=O)O)cc1] |
| 71 | 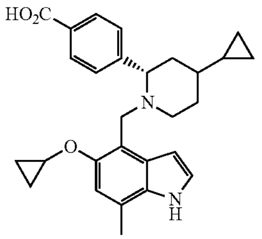 [SMILES: Cc1cc(OC2CC2)c(CN2CCC(C3CC3)C[C@H]2c2ccc(C(=O)O)cc2)c2cc[nH]c12] | 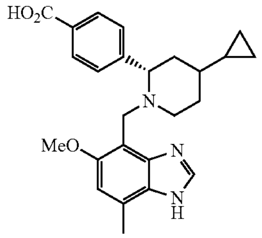 [SMILES: COc1cc(C)c2[nH]cnc2c1CN1CCC(C2CC2)C[C@H]1c1ccc(C(=O)O)cc1] | 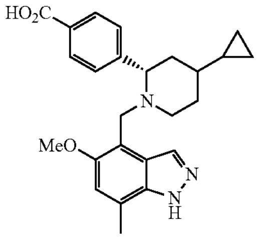 [SMILES: COc1cc(C)c2[nH]ncc2c1CN1CCC(C2CC2)C[C@H]1c1ccc(C(=O)O)cc1] |
| 72 | 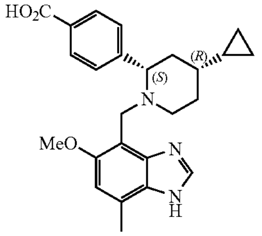 | 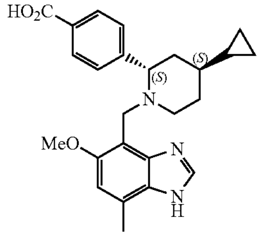 | 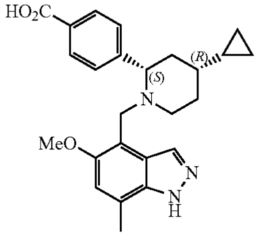 |
| 73 | 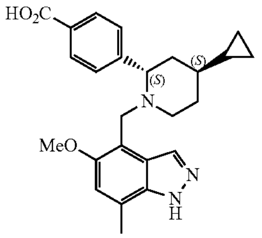 | 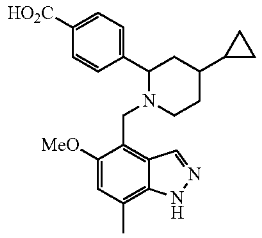 [SMILES: COc1cc(C)c2[nH]ncc2c1CN1CCC(C2CC2)CC1c1ccc(C(=O)O)cc1] | 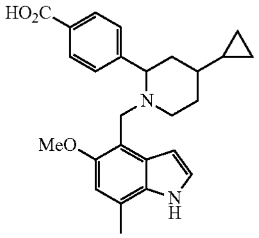 |

TABLE E-1-continued
| | | | |
|---|---|---|---|
| 74 | 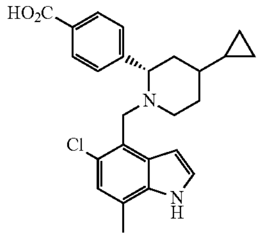 [SMILES: Cc1cc(Cl)c(CN2CCC(C3CC3)C[C@H]2c2ccc(C(=O)O)cc2)c2cc[nH]c12] | 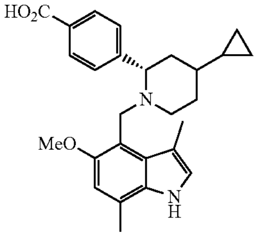 [SMILES: COc1cc(C)c2[nH]cc(C)c2c1CN1CCC(C2CC2)C[C@H]1c1ccc(C(=O)O)cc1] | 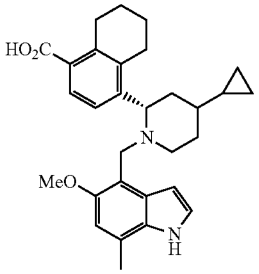 [SMILES: COc1cc(C)c2[nH]ccc2c1CN1CCC(C2CC2)C[C@H]1c1ccc(C(=O)O)c2c1CCCC2] |
| 75 | 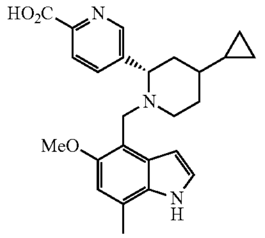 | 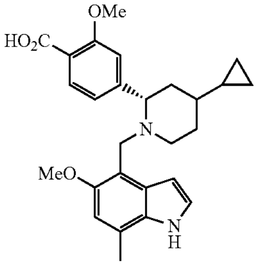 [SMILES: COc1cc([C@@H]2CC(C3CC3)CCN2Cc2c(OC)cc(C)c3[nH]ccc23)ccc1C(=O)O] | 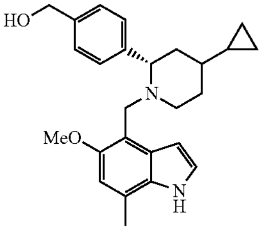 [SMILES: COc1cc(C)c2[nH]ccc2c1CN1CCC(C2CC2)C[C@H]1c1ccc(CO)cc1] |
| 76 | 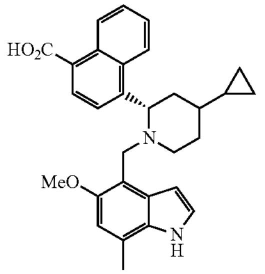 [SMILES: COc1cc(C)c2[nH]ccc2c1CN1CCC(C2CC2)C[C@H]1c1ccc(C(=O)O)c2ccccc12] | 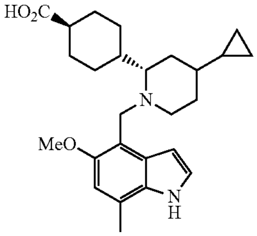 | 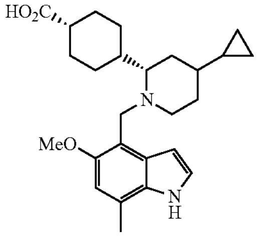 |
| 77 | 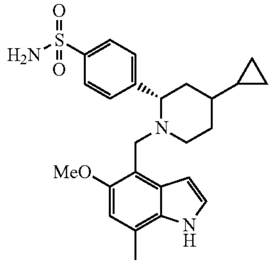 [SMILES: COc1cc(C)c2[nH]ccc2c1CN1CCC(C2CC2)C[C@H]1c1ccc(S(N)(=O)=O)cc1] | 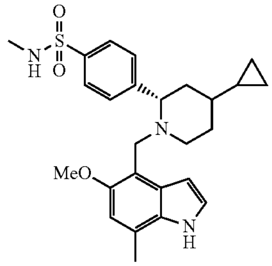 [SMILES: CNS(=O)(=O)c1ccc([C@@H]2CC(C3CC3)CCN2Cc2c(OC)cc(C)c3[nH]ccc23)cc1] | 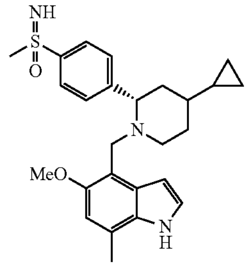 [SMILES: COc1cc(C)c2[nH]ccc2c1CN1CCC(C2CC2)C[C@H]1c1ccc(S(C)(=N)=O)cc1] |
| 78 | 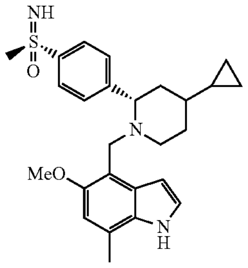 [SMILES: COc1cc(C)c2[nH]ccc2c1CN1CCC(C2CC2)C[C@H]1c1ccc([S@](C)(=N)=O)cc1] | 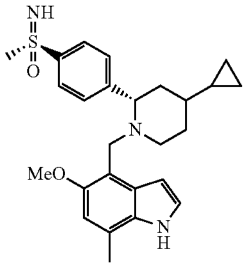 [SMILES: COc1cc(C)c2[nH]ccc2c1CN1CCC(C2CC2)C[C@H]1c1ccc([S@@](C)(=N)=O)cc1] | 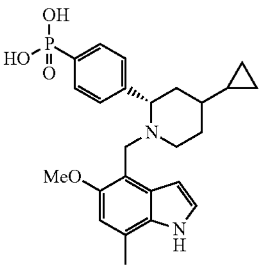 [SMILES: COc1cc(C)c2[nH]ccc2c1CN1CCC(C2CC2)C[C@H]1c1ccc(P(=O)(O)O)cc1] |
| 79 | 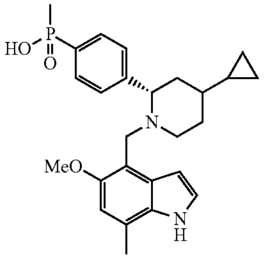 [SMILES: COc1cc(C)c2[nH]ccc2c1CN1CCC(C2CC2)C[C@H]1c1ccc(P(C)(=O)O)cc1] | 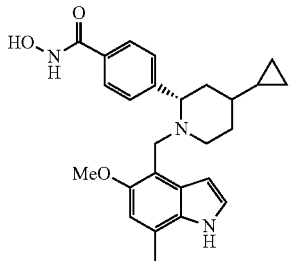 [SMILES: COc1cc(C)c2[nH]ccc2c1CN1CCC(C2CC2)C[C@H]1c1ccc(C(=O)NO)cc1] | 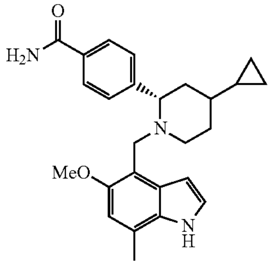 [SMILES: COc1cc(C)c2[nH]ccc2c1CN1CCC(C2CC2)C[C@H]1c1ccc(C(N)=O)cc1] |

TABLE E-1-continued
80 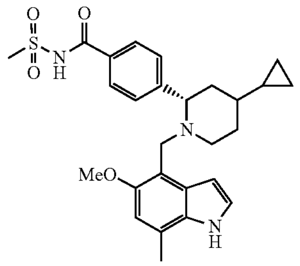 [SMILES: COc1cc(C)c2[nH]ccc2c1CN1CCC(C2CC2)C[C@H]1c1ccc(C(=O)NS(C)(=O)=O)cc1] 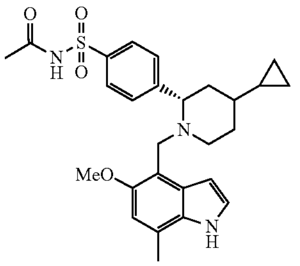 [SMILES: COc1cc(C)c2[nH]ccc2c1CN1CCC(C2CC2)C[C@H]1c1ccc(S(=O)(=O)NC(C)=O)cc1] 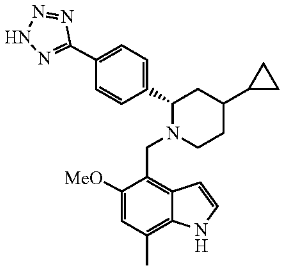 [SMILES: COc1cc(C)c2[nH]ccc2c1CN1CCC(C2CC2)C[C@H]1c1ccc(-c2nn[nH]n2)cc1]
81 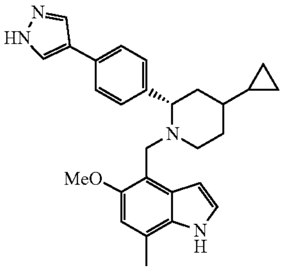 [SMILES: COc1cc(C)c2[nH]ccc2c1CN1CCC(C2CC2)C[C@H]1c1ccc(-c2cn[nH]c2)cc1] 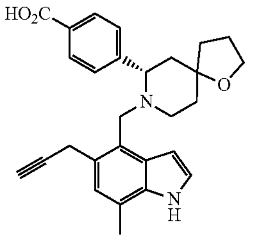 [SMILES: C#CCc1cc(C)c2[nH]ccc2c1CN1CCC2(CCCO2)C[C@H]1c1ccc(C(=O)O)cc1] 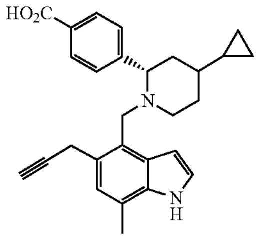 [SMILES: C#CCc1cc(C)c2[nH]ccc2c1CN1CCC(C2CC2)C[C@H]1c1ccc(C(=O)O)cc1]
82 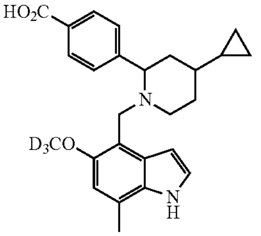 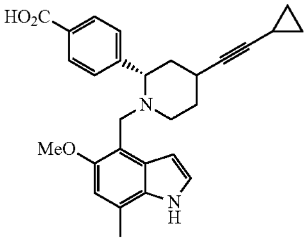 [SMILES: COc1cc(C)c2[nH]ccc2c1CN1CCC(C#CC2CC2)C[C@H]1c1ccc(C(=O)O)cc1] 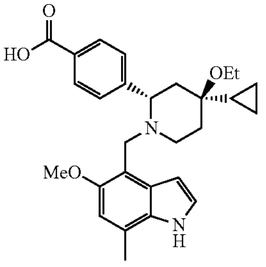
83 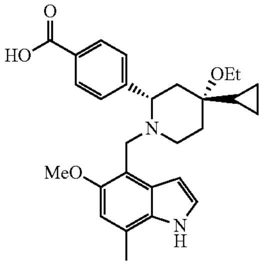 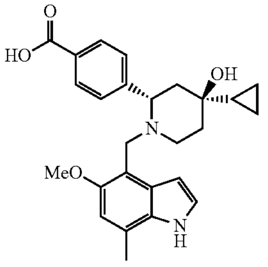 [SMILES: COc1cc(C)c2[nH]ccc2c1CN1CC[C@@](O)(C2CC2)C[C@H]1c1ccc(C(=O)O)cc1] 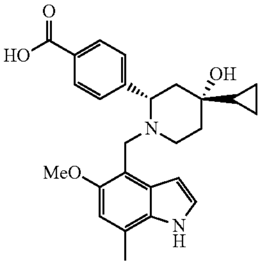 [SMILES: COc1cc(C)c2[nH]ccc2c1CN1CC[C@](O)(C2CC2)C[C@H]1c1ccc(C(=O)O)cc1]
84 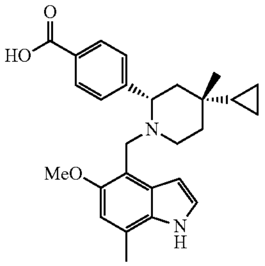 [SMILES: COc1cc(C)c2[nH]ccc2c1CN1CC[C@@](C)(C2CC2)C[C@H]1c1ccc(C(=O)O)cc1] 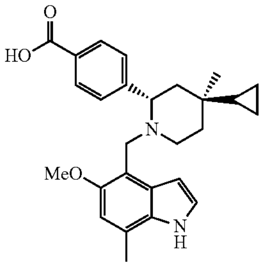 [SMILES: COc1cc(C)c2[nH]ccc2c1CN1CC[C@](C)(C2CC2)C[C@H]1c1ccc(C(=O)O)cc1] 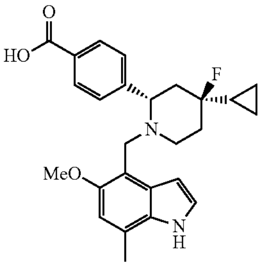 [SMILES: COc1cc(C)c2[nH]ccc2c1CN1CC[C@@](F)(C2CC2)C[C@H]1c1ccc(C(=O)O)cc1]

TABLE E-1-continued
| | | | |
|---|---|---|---|
| 85 | 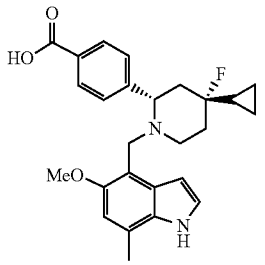 [SMILES: COc1cc(C)c2[nH]ccc2c1CN1CC[C@](F)(C2CC2)C[C@H]1c1ccc(C(=O)O)cc1] | 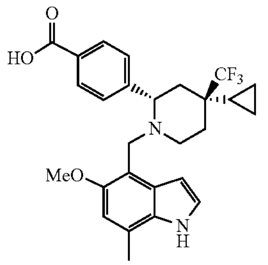 [SMILES: COc1cc(C)c2[nH]ccc2c1CN1CC[C@](C2CC2)(C(F)(F)F)C[C@H]1c1ccc(C(=O)O)cc1] | 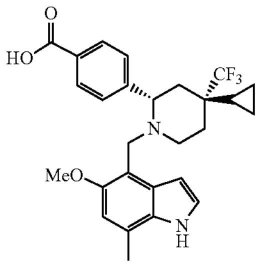 [SMILES: COc1cc(C)c2[nH]ccc2c1CN1CC[C@@](C2CC2)(C(F)(F)F)C[C@H]1c1ccc(C(=O)O)cc1] |
| 86 | 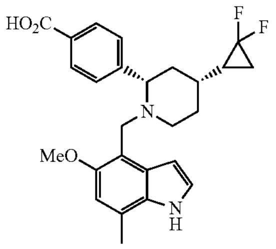 [SMILES: COc1cc(C)c2[nH]ccc2c1CN1CC[C@@H](C2CC2(F)F)C[C@H]1c1ccc(C(=O)O)cc1] | 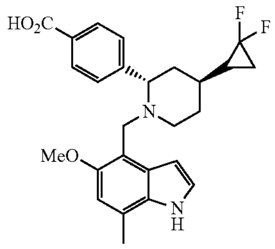 | 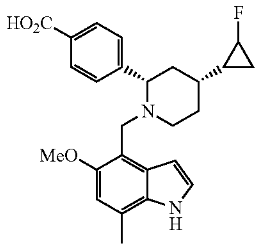 [SMILES: COc1cc(C)c2[nH]ccc2c1CN1CC[C@@H](C2CC2F)C[C@H]1c1ccc(C(=O)O)cc1] |
| 87 | 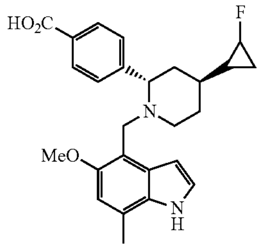 [SMILES: COc1cc(C)c2[nH]ccc2c1CN1CC[C@H](C2CC2F)C[C@H]1c1ccc(C(=O)O)cc1] | 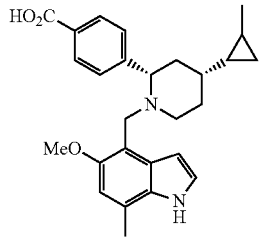 [SMILES: COc1cc(C)c2[nH]ccc2c1CN1CC[C@@H](C2CC2C)C[C@H]1c1ccc(C(=O)O)cc1] | 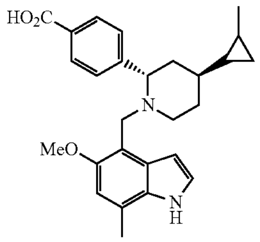 [SMILES: COc1cc(C)c2[nH]ccc2c1CN1CC[C@H](C2CC2C)C[C@H]1c1ccc(C(=O)O)cc1] |
| 88 | 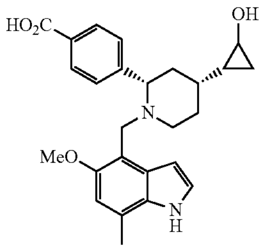 | 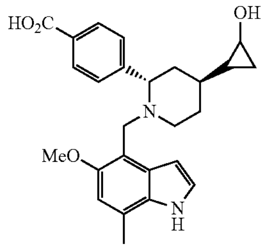 [SMILES: COc1cc(C)c2[nH]ccc2c1CN1CC[C@H](C2CC2O)C[C@H]1c1ccc(C(=O)O)cc1] | 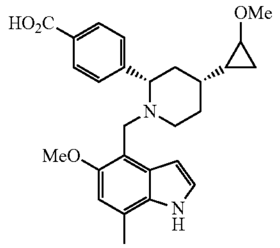 [SMILES: COc1cc(C)c2[nH]ccc2c1CN1CC[C@@H](C2CC2OC)C[C@H]1c1ccc(C(=O)O)cc1] |
| 89 | 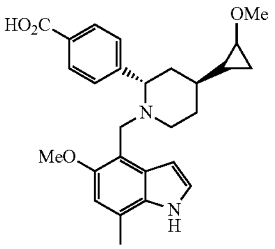 [SMILES: COc1cc(C)c2[nH]ccc2c1CN1CC[C@H](C2CC2OC)C[C@H]1c1ccc(C(=O)O)cc1] | 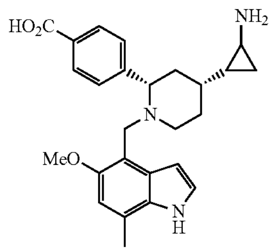 [SMILES: COc1cc(C)c2[nH]ccc2c1CN1CC[C@@H](C2CC2N)C[C@H]1c1ccc(C(=O)O)cc1] | 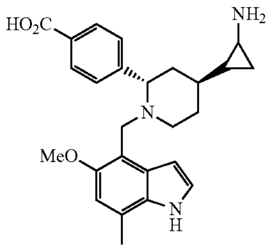 [SMILES: COc1cc(C)c2[nH]ccc2c1CN1CC[C@H](C2CC2N)C[C@H]1c1ccc(C(=O)O)cc1] |
| 90 | 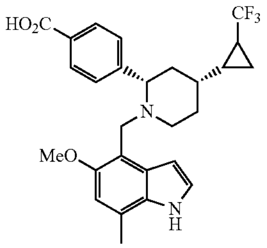 [SMILES: COc1cc(C)c2[nH]ccc2c1CN1CC[C@@H](C2CC2C(F)(F)F)C[C@H]1c1ccc(C(=O)O)cc1] | 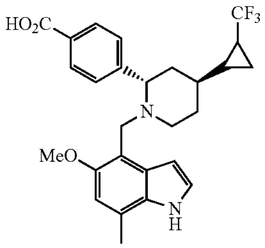 [SMILES: COc1cc(C)c2[nH]ccc2c1CN1CC[C@H](C2CC2C(F)(F)F)C[C@H]1c1ccc(C(=O)O)cc1] | 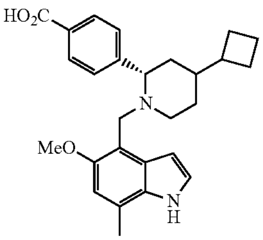 [SMILES: COc1cc(C)c2[nH]ccc2c1CN1CCC(C2CCC2)C[C@H]1c1ccc(C(=O)O)cc1] |

TABLE E-1-continued
| | | | |
|---|---|---|---|
| 91 | 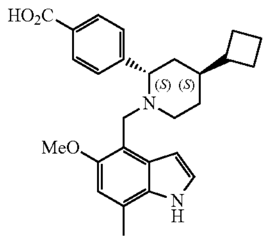 | 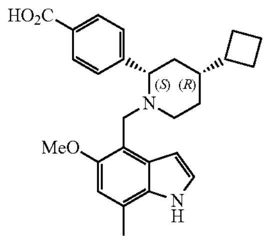 | 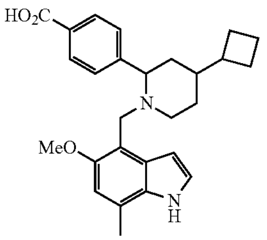 |
| 92 | 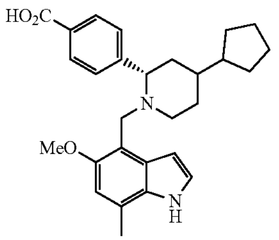 [SMILES: COc1cc(C)c2[nH]ccc2c1CN1CCC(C2CCCC2)C[C@H]1c1ccc(C(=O)O)cc1] | 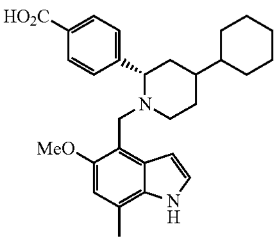 [SMILES: COc1cc(C)c2[nH]ccc2c1CN1CCC(C2CCCCC2)C[C@H]1c1ccc(C(=O)O)cc1] | 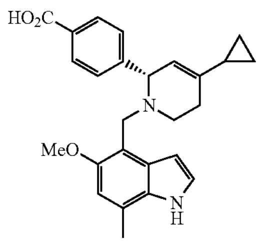 |
| 93 | 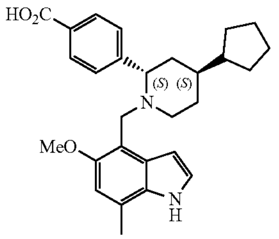 | 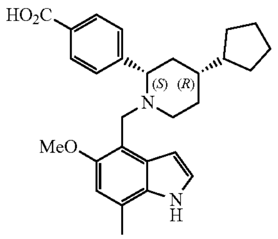 | 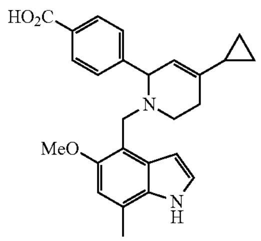 [SMILES: COc1cc(C)c2[nH]ccc2c1CN1CCC(C2CC2)=CC1c1ccc(C(=O)O)cc1] |
| 94 | 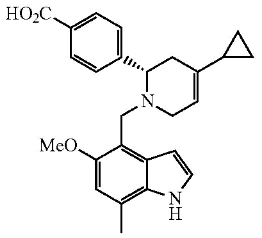 [SMILES: COc1cc(C)c2[nH]ccc2c1CN1CC=C(C2CC2)C[C@H]1c1ccc(C(=O)O)cc1] | 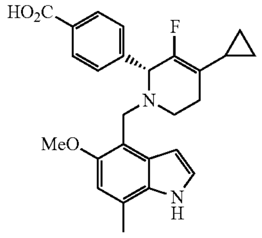 [SMILES: COc1cc(C)c2[nH]ccc2c1CN1CCC(C2CC2)=C(F)[C@H]1c1ccc(C(=O)O)cc1] | 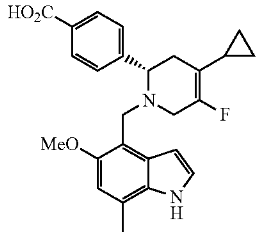 [SMILES: COc1cc(C)c2[nH]ccc2c1CN1CC(F)=C(C2CC2)C[C@H]1c1ccc(C(=O)O)cc1] |
| 95 | 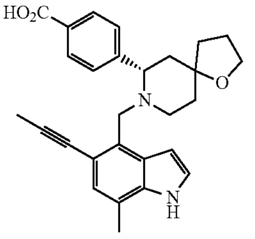 [SMILES: CC#Cc1cc(C)c2[nH]ccc2c1CN1CCC2(CCCO2)C[C@H]1c1ccc(C(=O)O)cc1] | 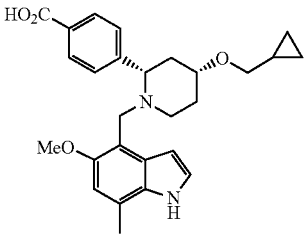 [SMILES: COc1cc(C)c2[nH]ccc2c1CN1CC[C@@H](OCC2CC2)C[C@H]1c1ccc(C(=O)O)cc1] | 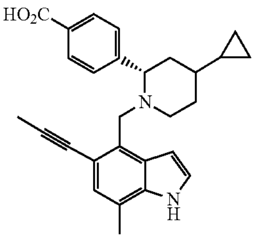 [SMILES: CC#Cc1cc(C)c2[nH]ccc2c1CN1CCC(C2CC2)C[C@H]1c1ccc(C(=O)O)cc1] |
| 96 | 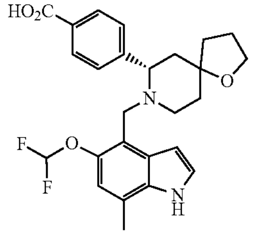 [SMILES: Cc1cc(OC(F)F)c(CN2CCC3(CCCO3)C[C@H]2c2ccc(C(=O)O)cc2)c2cc[nH]c12] | 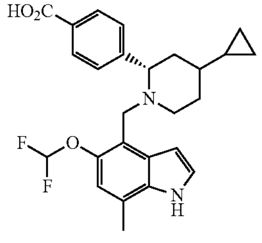 [SMILES: Cc1cc(OC(F)F)c(CN2CCC(C3CC3)C[C@H]2c2ccc(C(=O)O)cc2)c2cc[nH]c12] | 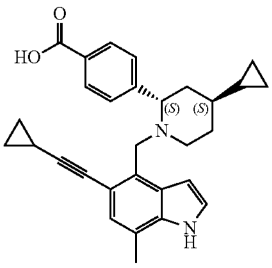 |

TABLE E-1-continued
| | | | |
|---|---|---|---|
| 97 | 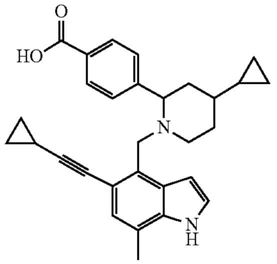 [SMILES: Cc1cc(C#CC2CC2)c(CN2CCC(C3CC3)CC2c2ccc(C(=O)O)cc2)c2cc[nH]c12] | 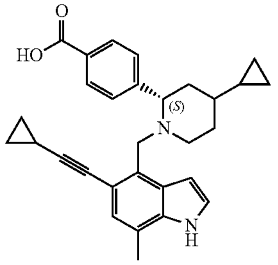 | 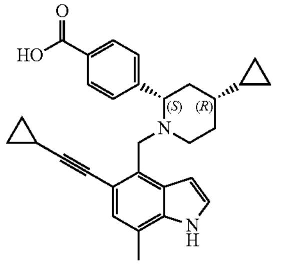 |
| 98 | 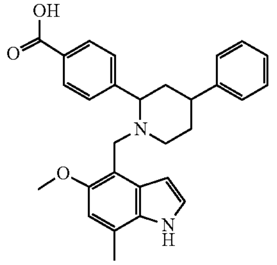 [SMILES: COc1cc(C)c2[nH]ccc2c1CN1CCC(c2ccccc2)CC1c1ccc(C(=O)O)cc1] | 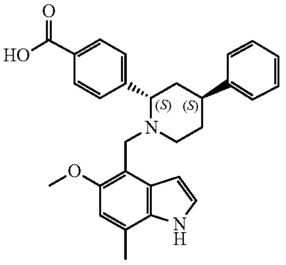 | 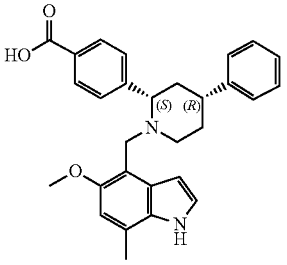 |
| 99 | 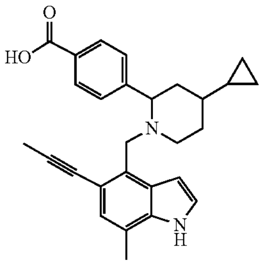 [SMILES: CC#Cc1cc(C)c2[nH]ccc2c1CN1CCC(C2CC2)CC1c1ccc(C(=O)O)cc1] | 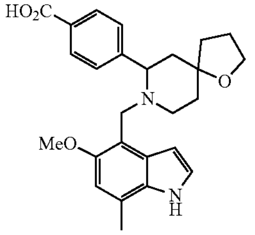 [SMILES: COc1cc(C)c2[nH]ccc2c1CN1CCC2(CCCO2)CC1c1ccc(C(=O)O)cc1] | 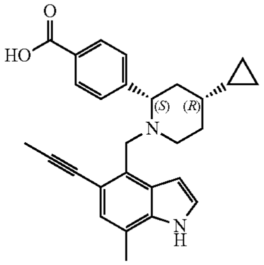 |
| 100 | 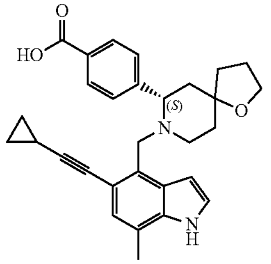 | 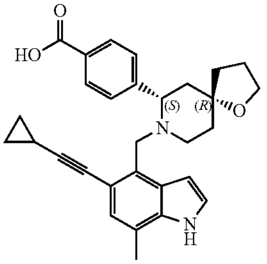 | 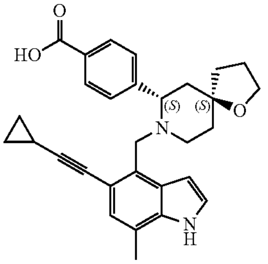 |
| 101 | 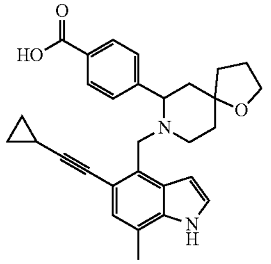 [SMILES: Cc1cc(C#CC2CC2)c(CN2CCC3(CCCO3)CC2c2ccc(C(=O)O)cc2)c2cc[nH]c12] | 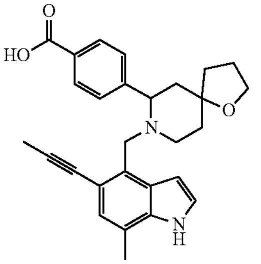 [SMILES: CC#Cc1cc(C)c2[nH]ccc2c1CN1CCC2(CCCO2)CC1c1ccc(C(=O)O)cc1] | 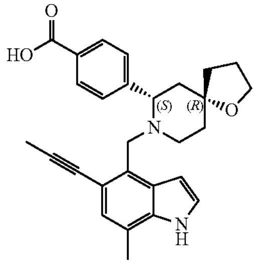 |
| 102 | 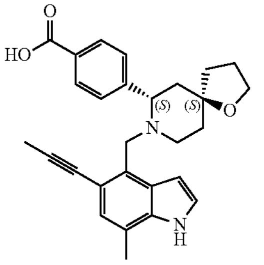 | 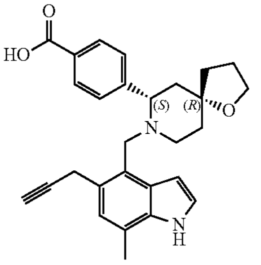 | 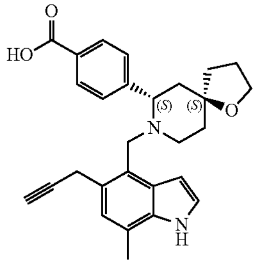 |

TABLE E-1-continued
| | | | |
|---|---|---|---|
| 103 | 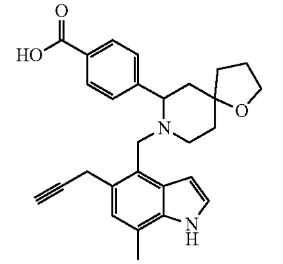 [SMILES: C#CCc1cc(C)c2[nH]ccc2c1CN1CCC2(CCCO2)CC1c1ccc(C(=O)O)cc1] | 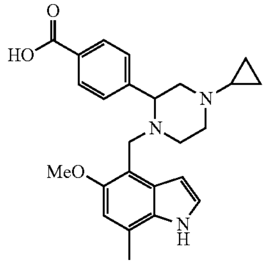 [SMILES: COc1cc(C)c2[nH]ccc2c1CN1CCN(C2CC2)CC1c1ccc(C(=O)O)cc1] | 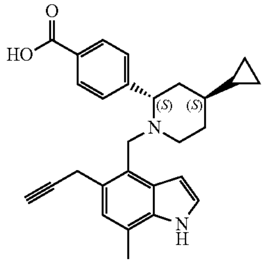 |
| 104 | 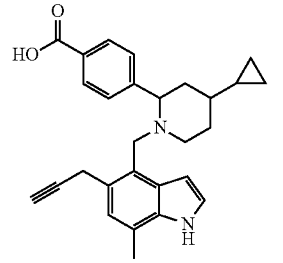 [SMILES: C#CCc1cc(C)c2[nH]ccc2c1CN1CCC(C2CC2)CC1c1ccc(C(=O)O)cc1] | 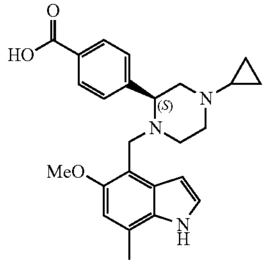 | 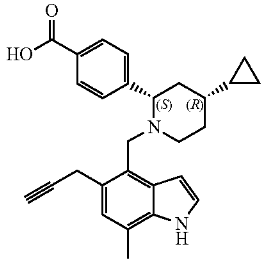 |
| 105 | 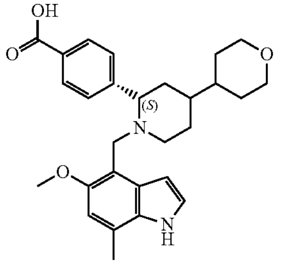 | 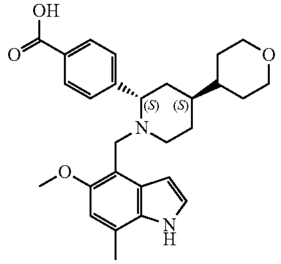 | 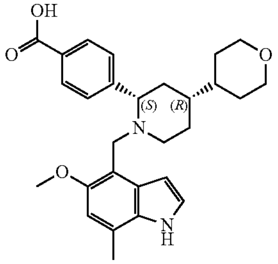 |
| 106 | 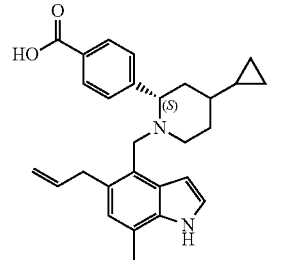 | 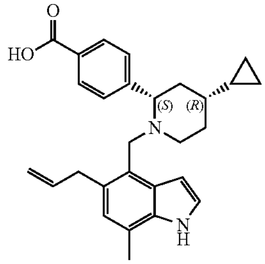 | 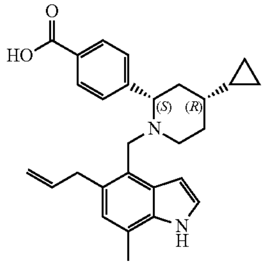 |
| 107 | 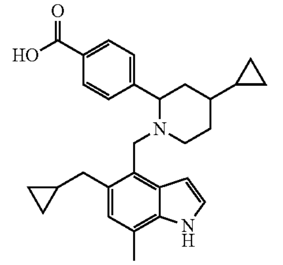 [SMILES: Cc1cc(CC2CC2)c(CN2CCC(C3CC3)CC2c2ccc(C(=O)O)cc2)c2cc[nH]c12] | 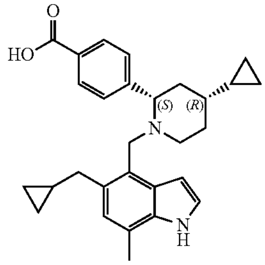 | 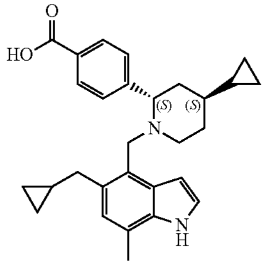 |
| 108 | 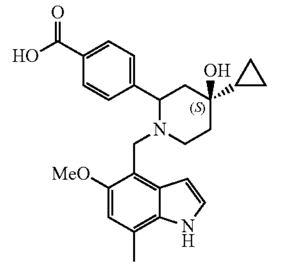 | 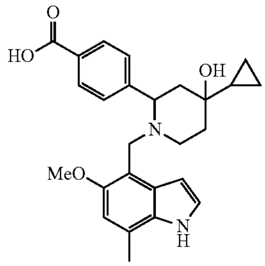 [SMILES: COc1cc(C)c2[nH]ccc2c1CN1CCC(O)(C2CC2)CC1c1ccc(C(=O)O)cc1] | 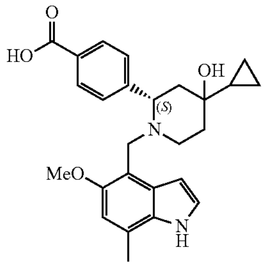 |

TABLE E-1-continued
| | | | |
|---|---|---|---|
| 109 | 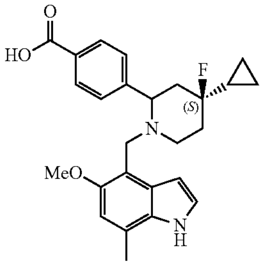 | 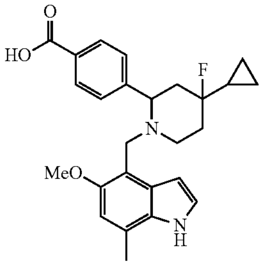 | 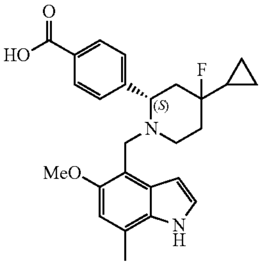 |
| 110 | 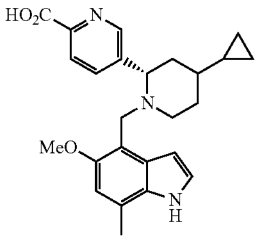 [SMILES: COc1cc(C)c2[nH]ccc2c1CN1CCC(C2CC2)C[C@H]1c1ccc(C(=O)O)nc1] | 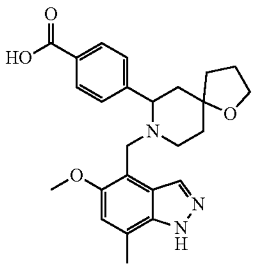 [SMILES: COc1cc(C)c2[nH]ncc2c1CN1CCC2(CCCO2)CC1c1ccc(C(=O)O)cc1] | 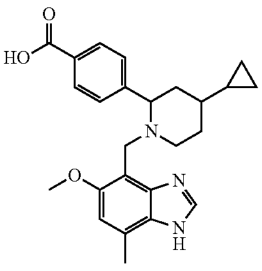 [SMILES: COc1cc(C)c2[nH]cnc2c1CN1CCC(C2CC2)CC1c1ccc(C(=O)O)cc1] |
| 111 | 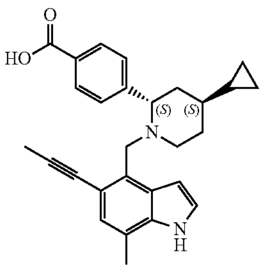 | 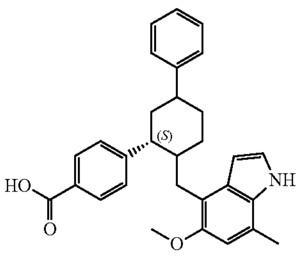 | 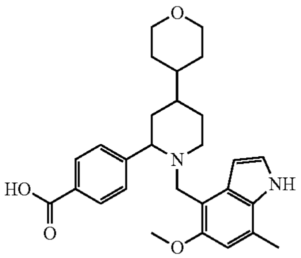 [SMILES: COc1cc(C)c2[nH]ccc2c1CN1CCC(C2CCOCC2)CC1c1ccc(C(=O)O)cc1] |
| 112 | 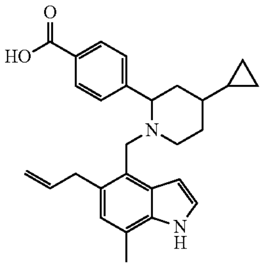 [SMILES: C=CCc1cc(C)c2[nH]ccc2c1CN1CCC(C2CC2)CC1c1ccc(C(=O)O)cc1] | 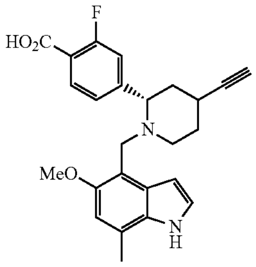 [SMILES: C#CC1CCN(Cc2c(OC)cc(C)c3[nH]ccc23)[C@H](c2ccc(C(=O)O)c(F)c2)C1] | 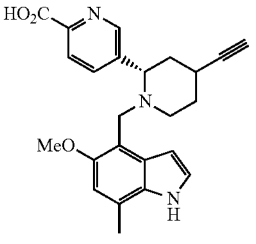 [SMILES: C#CC1CCN(Cc2c(OC)cc(C)c3[nH]ccc23)[C@H](c2ccc(C(=O)O)nc2)C1] |
| 113 | 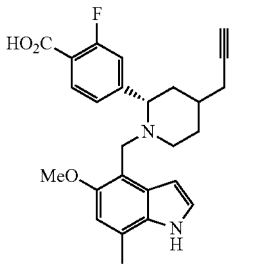 [SMILES: C#CCC1CCN(Cc2c(OC)cc(C)c3[nH]ccc23)[C@H](c2ccc(C(=O)O)c(F)c2)C1] | 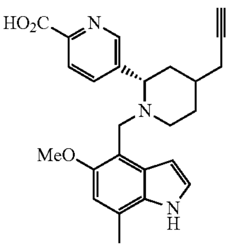 [SMILES: C#CCC1CCN(Cc2c(OC)cc(C)c3[nH]ccc23)[C@H](c2ccc(C(=O)O)nc2)C1] | 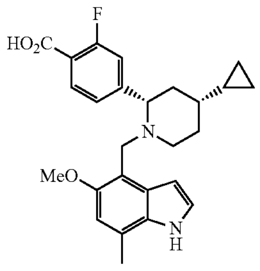 [SMILES: COc1cc(C)c2[nH]ccc2c1CN1CC[C@@H](C2CC2)C[C@H]1c1ccc(C(=O)O)c(F)c1] |

TABLE E-1-continued
| | | | |
|---|---|---|---|
| 114 | 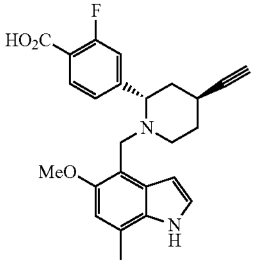 [SMILES: C#C[C@H]1CCN(Cc2c(OC)cc(C)c3[nH]ccc23)[C@H](c2ccc(C(=O)O)c(F)c2)C1] | 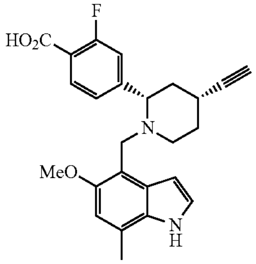 [SMILES: C#C[C@@H]1CCN(Cc2c(OC)cc(C)c3[nH]ccc23)[C@H](c2ccc(C(=O)O)c(F)c2)C1] | 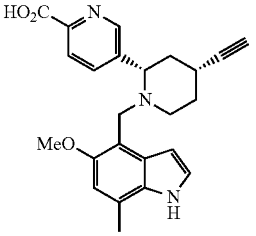 [SMILES: C#C[C@@H]1CCN(Cc2c(OC)cc(C)c3[nH]ccc23)[C@H](c2ccc(C(=O)O)nc2)C1] |
| 115 | 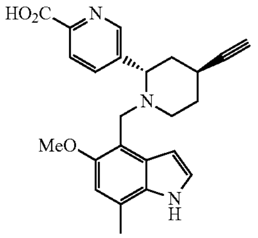 [SMILES: C#C[C@H]1CCN(Cc2c(OC)cc(C)c3[nH]ccc23)[C@H](c2ccc(C(=O)O)nc2)C1] | 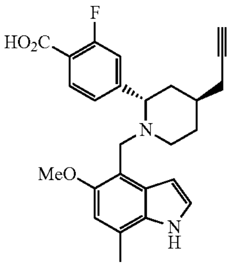 [SMILES: C#CC[C@H]1CCN(Cc2c(OC)cc(C)c3[nH]ccc23)[C@H](c2ccc(C(=O)O)c(F)c2)C1] | 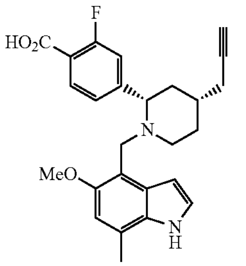 [SMILES: C#CC[C@@H]1CCN(Cc2c(OC)cc(C)c3[nH]ccc23)[C@H](c2ccc(C(=O)O)c(F)c2)C1] |
| 116 | 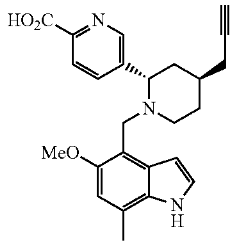 [SMILES: C#CC[C@H]1CCN(Cc2c(OC)cc(C)c3[nH]ccc23)[C@H](c2ccc(C(=O)O)nc2)C1] | 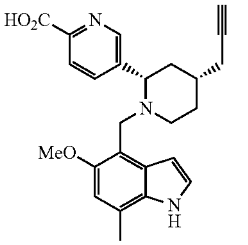 [SMILES: C#CC[C@@H]1CCN(Cc2c(OC)cc(C)c3[nH]ccc23)[C@H](c2ccc(C(=O)O)nc2)C1] | 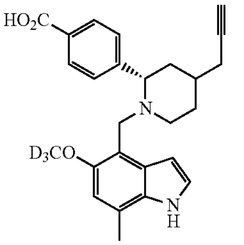 |
| 117 | 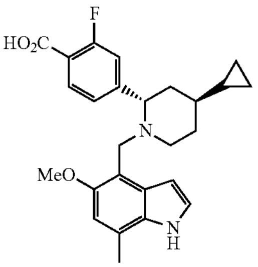 [SMILES: COc1cc(C)c2[nH]ccc2c1CN1CC[C@H](C2CC2)C[C@H]1c1ccc(C(=O)O)c(F)c1] | 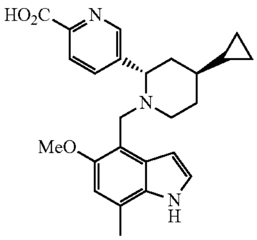 [SMILES: COc1cc(C)c2[nH]ccc2c1CN1CC[C@H](C2CC2)C[C@H]1c1ccc(C(=O)O)nc1] | 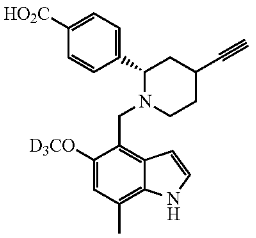 |
| 118 | 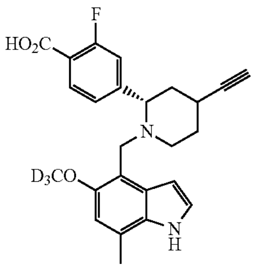 | 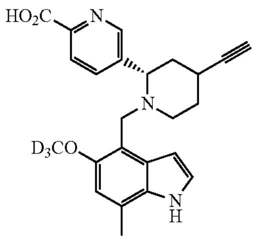 | 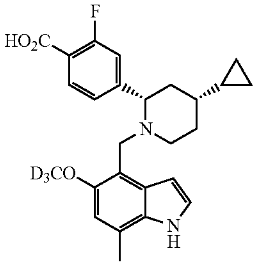 |
| 119 | 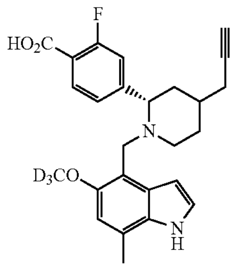 | 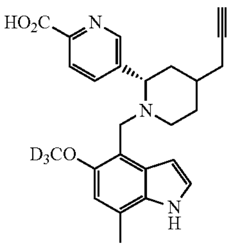 | 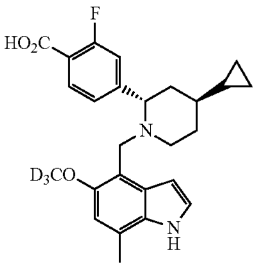 |

TABLE E-1-continued

| | | | |
|---|---|---|---|
| 120 | 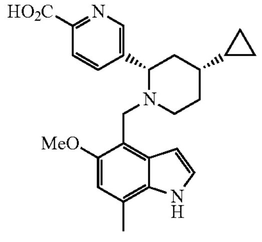 | 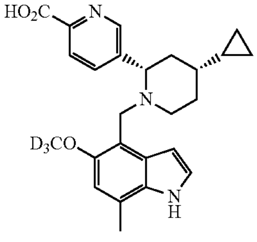 | 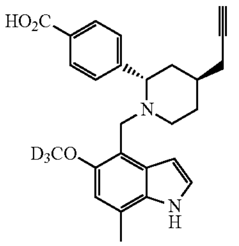 |
| 121 | 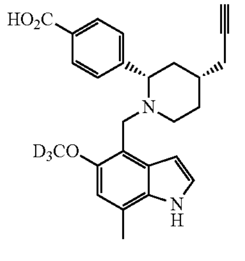 | 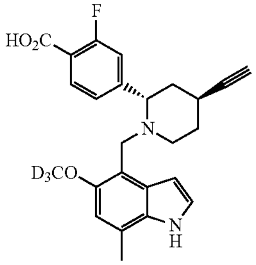 | 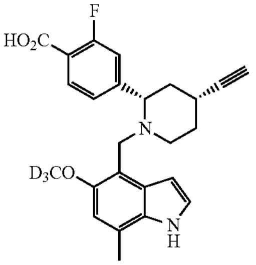 |
| 122 | 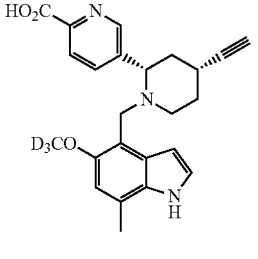 | 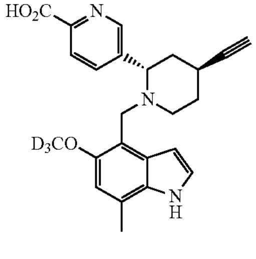 | 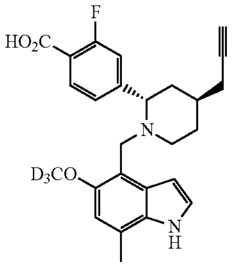 |
| 123 | 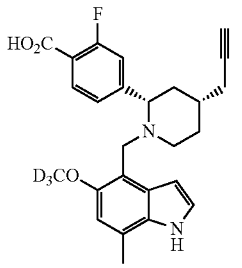 | 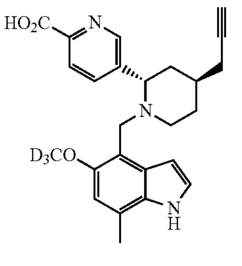 | 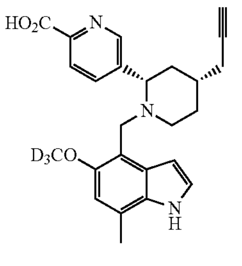 |
| 124 | 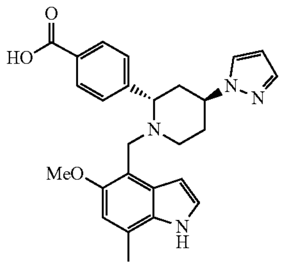 [SMILES: COc1cc(C)c2[nH]ccc2c1CN1CC[C@H](n2cccn2)C[C@H]1c1ccc(C(=O)O)cc1] | 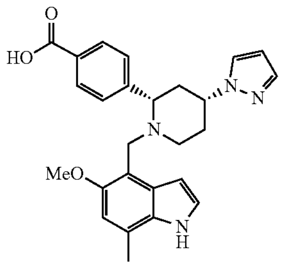 [SMILES: COc1cc(C)c2[nH]ccc2c1CN1CC[C@@H](n2cccn2)C[C@H]1c1ccc(C(=O)O)cc1] | 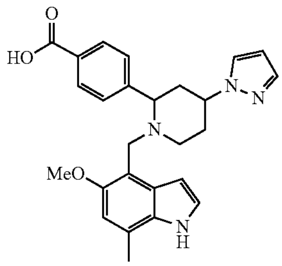 [SMILES: COc1cc(C)c2[nH]ccc2c1CN1CCC(n2cccn2)CC1c1ccc(C(=O)O)cc1] |

In some embodiments of the present disclosure involving general formula (I), (Ia), (Ib), (Ic), (Id), (Id-1), (Id-2), (Id-3), (Id-4) or (Ie), $R^1$ is selected from H, halogen, OH, cyano, $NH_2$, $C_{1-6}$ alkyl, $C_{2-6}$ alkenyl, $C_{2-6}$ alkynyl, $C_{1-6}$ alkoxy, —C(═O)$C_{1-6}$ alkyl, —S(═O)$_p$$C_{1-6}$ alkyl, —W—$R^{1d}$, —$CH_2$NHC(O)$C_{1-4}$ alkyl, —$CH_2$C(═O)$R^{1c}$, —$OCH_2$C(═O)$R^{1c}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-6}$ alkyl, $C_{2-6}$ alkynyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4) or (Ie), $R^1$ is selected from H, halogen, OH, cyano, $NH_2$, $C_{1-4}$ alkyl, $C_{2-4}$ alkenyl, $C_{2-4}$ alkynyl, $C_{1-4}$ alkoxy, —C(═O)$C_{1-4}$ alkyl, —S(═O)$_p$$C_{1-4}$ alkyl, —W—$R^{1d}$, —$CH_2$NHC(O)$C_{1-4}$ alkyl, —$CH_2$C(═O)$R^{1e}$, —$OCH_2$C(═O)$R^{1e}$, $C_{3-6}$ carbocyclyl or 4- to 8-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4) or (Ie), $R^1$ is selected from H, halogen, OH, cyano, $NH_2$, $C_{1-4}$ alkyl, $C_{2-4}$ alkenyl, $C_{2-4}$ alkynyl, $C_{1-4}$ alkoxy, $C_{1-4}$ alkylthio, —W—$R^{1d}$, $C_{3-6}$ carbocyclyl or 4- to 8-membered heterocyclyl, wherein the alkyl, alkenyl, alkynyl, alkoxy, alkylthio, carbocyclyl or heterocyclyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4) or (Ie), $R^1$ is selected from $R^{1A}$ In some embodiments of the present disclosure involving general formula (I), (Ia), (Ib), (Ic), (Id), (Id-1), (Id-2), (Id-3), (Id-4) or (Ie), each $R^1$ is independently selected from H, F, Cl, Br, I, OH, cyano, $NH_2$, methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl or —W—$R^{1d}$, wherein the methyl, ethyl, propyl, isopropyl, tert-butyl, methoxy, ethoxy, isopropoxy, vinyl, ethynyl, propynyl, propargyl, methylthio, ethylthio, cyclopropyl, or cyclobutyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4) or (Ie), each $R^1$ is independently selected from H, F, Cl, Br, I, OH, cyano, $NH_2$, methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl, —O-cyclopropyl, —O-cyclobutyl, or —O-cyclopentyl, wherein the methyl, ethyl, propyl, isopropyl, tert-butyl, methoxy, ethoxy, isopropoxy, vinyl, ethynyl, propynyl, propargyl, methylthio, ethylthio, cyclopropyl, cyclobutyl, —O-cyclopropyl, —O— cyclobutyl, or —O-cyclopentyl is optionally further substituted with 0 to 4 substituents selected from H, D, F, Cl, Br, I, OH, =O, cyano, $NH_2$, methyl, ethyl, ethynyl, methoxy, ethoxy, $CF_3$, —$CH_2$F, —$CH_2$OH, cyclopropyl, cyclobutyl, azacyclobutyl or pyrrolidinyl.

In some embodiments of the present disclosure involving general formula (I), (Ia), (Ib), (Ic), (Id), (Id-1), (Id-2) or (Ie), each $R^1$ is independently selected from H, F, Cl, Br, I, OH, cyano, $NH_2$, —$OCD_3$, $CD_3$, methyl, ethyl, propyl, isopropyl, tert-butyl, methoxy, ethoxy, isopropoxy, cyclopropyl, ethynyl, —$CH_2$-cyclopropyl or —O-cyclopropyl.

In some embodiments of the present disclosure involving general formula (I), (Ia), (Ib), (Ic), (Id), (Id-1), (Id-2) or (Ie), $R^1$ is selected from H, F, Cl, Br, I, —$OCD_3$, $CD_3$, methyl, ethyl, propyl, methoxy, ethoxy, isopropoxy, cyclopropyl, —$CH_2$— cyclopropyl or —O-cyclopropyl.

In some embodiments of the present disclosure involving general formula (I), (Ia), (Ib), (Ic), (Id), (Id-1), (Id-2), (Id-3), (Id-4) or (Ie), each $R^1$ is independently selected from —$OCH_2$F, —$OCHF_2$, —$OCF_3$,

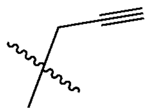,
or
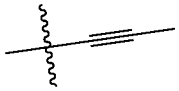.

In some embodiments of present disclosure involving general formula (Id-1), (Id-2), (Id-3) or (Id-4), $R^1$ is selected from H, F, Cl, Br, I, —$OCD_3$, $CD_3$, $C_{1-4}$ alkyl, $C_{1-4}$ alkoxy, $C_{3-6}$ cycloalkyl, —$CH_2$—$C_{3-6}$ cycloalkyl or —O—$C_{3-6}$ cycloalkyl.

In some embodiments of the present disclosure involving general formula (I) or (If), $R^{1A}$ is selected from ethynyl, propynyl, propargyl, —$CH_2$-cyclopropyl, —$CH_2$— cyclobutyl, —$CH_2$-cyclopentyl, —$CH_2$-oxacyclobutyl, —$CH_2$-azacyclobutyl, —$CH_2$— pyrrolidinyl, —O-cyclopropyl, —O-cyclobutyl, —O-cyclopentyl, the ethynyl, propynyl, propargyl, —O-cyclopropyl, —O-cyclobutyl, —O-cyclopentyl or —$CH_2$— is optionally further substituted with 0 to 2 substituents selected from H, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I) or (If), $R^{1A}$ is selected from ethynyl, propynyl, propargyl, —$CH_2$-cyclopropyl, —$CH_2$— cyclobutyl, —$CH_2$-cyclopentyl, —$CH_2$-oxacyclobutyl, —$CH_2$-azacyclobutyl, —$CH_2$— pyrrolidinyl, —O-cyclopropyl, —O-cyclobutyl, —O-cyclopentyl, the ethynyl, propynyl, propargyl, —O-cyclopropyl, —O-cyclobutyl, —O-cyclopentyl or —$CH_2$— is optionally further substituted with 0 to 2 substituents selected from H, F, Cl, Br, I, OH, =O, cyano, $NH_2$, methyl, ethyl, ethynyl, methoxy, ethoxy, $CF_3$, —$CH_2$F, —$CH_2$OH, cyclopropyl, cyclobutyl, azacyclobutyl or pyrrolidinyl.

In some embodiments of the present disclosure involving general formula (I), (Ia), (Ib), (Ic), (Id) or (Ie), W is selected from O or S.

In some embodiments of the present disclosure involving general formula (I), (Ia), (Ib), (Ic), (Id), (Id-1), (Id-2), (Ie) or (If), n is selected from 0, 1 or 2.

In some embodiments of the present disclosure involving general formula (I), (Ia), (Ib), (Ic), (Id), (Id-1), (Id-2), (Ie) or (If), p is selected from 0, 1 or 2.

In some embodiments of the present disclosure involving general formula (I), (Ia), or (Ib), $X_1$ and $X_2$ are each independently selected from N or $CR^3$.

In some embodiments of the present disclosure involving general formula (I), (Ia), or (Ib), $X_1$ is selected from $CR^3$ and $X_2$ is selected from $CR^3$.

In some embodiments of the present disclosure involving general formula (I), (Ia), or (Ib), $X_1$ is selected from N and $X_2$ is selected from $CR^3$.

In some embodiments of the present disclosure involving general formula (I), (Ia), or (Ib), $X_1$ is selected from $CR^3$ and $X_2$ is selected from N.

In some embodiments of the present disclosure involving general formula (I), (Ia), or (Ib), $X_1$ and $X_2$ are each independently selected from N.

In some embodiments of the present disclosure involving general formula (I), Y is selected from $NR^7$ or $C(R^7)_2$.

In some embodiments of the present disclosure involving general formula (I), Y is selected from $NR^{7A}$.

In some embodiments of the present disclosure involving general formula (I), Y is selected from $C(R^{7a})_2$.

In some embodiments of the present disclosure involving general formula (I), Y is selected from $C(R^{7B})_2$. In some embodiments of the present disclosure involving general formula (I),

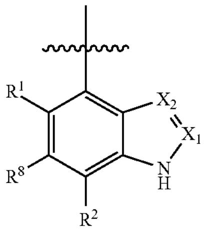

is selected from

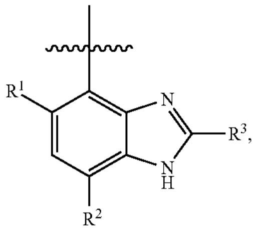

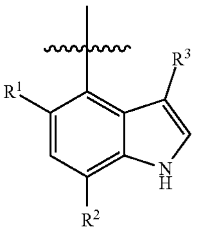

or

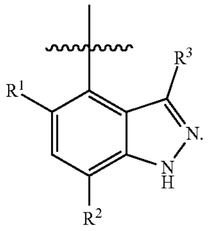

In some embodiments of the present disclosure involving general formula (Ia), (Ib), (Id) or (Ie),

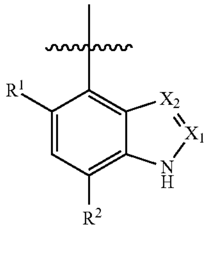

is selected from

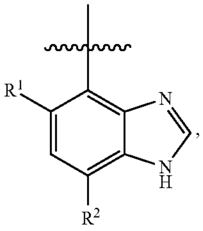

,

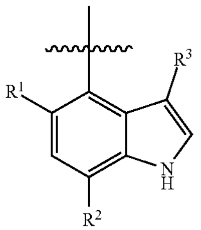

or

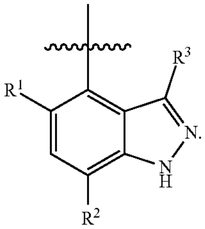

In some embodiments of the present disclosure involving general formula (If),

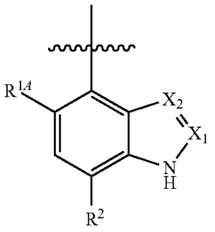

is selected from

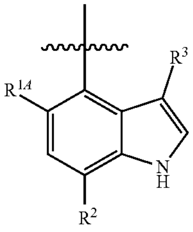

or

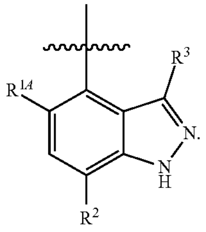

In some embodiments of the present disclosure involving general formula (I), (Ia), (Ib), (Ic), (Id), (Id-1), (Id-2), (Id-3), (Id-4), (Ie) or (If), each $R^3$ is independently selected from H, halogen, cyano, $C_{1-6}$ alkyl, $C_{1-6}$ alkoxy, $C_{2-6}$ alkenyl, $C_{2-6}$ alkynyl, $—CH_2C(=O)R^{1c}$, $—S(=O)_pC_{1-6}$ alkyl, $—CH_2NHC(O)C_{1-4}$ alkyl, $—OCH_2C(=O)R^{1c}$, $C_{3-6}$ carbocyclyl or 5- to 6-membered heteroaryl, wherein the alkyl, $C_{1-6}$ alkoxy, $C_{2-6}$ alkenyl, $C_{2-6}$ alkynyl, carbocyclyl or heteroaryl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^3$ is independently selected from H, halogen, cyano, $C_{1-4}$ alkyl, $C_{1-4}$ alkoxy, $C_{2-4}$ alkenyl, $C_{2-4}$ alkynyl, $—CH_2C(=O)R^{1c}$, $—S(=O)_pC_{1-4}$ alkyl, —$CH_2NHC(O)C_{1-4}$ alkyl, —$OCH_2C(=O)R^{1c}$, $C_{3-6}$ carbocyclyl or 5- to 6-membered heteroaryl, wherein the alkyl, $C_{1-4}$ alkoxy, $C_{2-4}$ alkenyl, $C_{2-4}$ alkynyl, carbocyclyl or heteroaryl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^3$ is independently selected from H, F, Cl, Br, I, cyano, methyl, ethyl, propyl, isopropyl, —$CH_2C(=O)OH$, or —$CH_2C(=O)NH_2$, wherein the methyl, ethyl, propyl or isopropyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I), (Ia), (Ib), (Ic), (Id), (Id-1), (Id-2), (Id-3), (Id-4), (Ie) or (If), each $R^3$ is independently selected from H, F, Cl, Br, I, cyano, methyl, ethyl, propyl, isopropyl, —$CH_2C(=O)OH$, or —$CH_2C(=O)NH_2$, wherein the methyl, ethyl, propyl or isopropyl is optionally further substituted with 0 to 4 substituents selected from H, F, Cl, Br, I, OH, or cyano.

In some embodiments of the present disclosure involving general formula (I), (Ia), (Ib), (Ic), (Id), (Id-1), (Id-2), (Id-3), (Id-4), (Ie) or (If), each $R^3$ is independently selected from H, methyl or ethyl.

In some embodiments of the present disclosure involving general formula (I), (Ia), (Ib), (Ic), (Id), (Id-1), (Id-2), (Id-3), (Id-4), (Ie) or (If), $R^2$ is selected from halogen, $C_{1-6}$ alkyl or $C_{1-6}$ alkoxy, wherein the alkyl or alkoxy is optionally further substituted with 0 to 4 substituents selected from H, D, halogen, OH, cyano or $NH_2$.

In some embodiments of the present disclosure involving general formula (I), (Ia), (Ib), (Ic), (Id), (Id-1), (Id-2), (Id-3), (Id-4), (Ie) or (If), $R^2$ is selected from halogen, $C_{1-4}$ alkyl or $C_{1-4}$ alkoxy, wherein the alkyl or alkoxy is optionally further substituted with 0 to 4 substituents selected from H, D, halogen, OH, cyano or $NH_2$.

In some embodiments of the present disclosure involving general formula (I), (Ia), (Ib), (Ic), (Id), (Id-1), (Id-2), (Id-3), (Id-4), (Ie) or (If), $R^2$ is selected from F, Cl, Br, I, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, D, F, Cl, Br, I, OH, cyano or $NH_2$.

In some embodiments of the present disclosure involving general formula (I), (Ia), (Ib), (Ic), (Id), (Id-1), (Id-2), (Id-3), (Id-4), (Ie) or (If), $R^2$ is selected from F, Cl, Br, I, methyl, ethyl, propyl, isopropyl, tert-butyl, methoxy, ethoxy or isopropoxy.

In some embodiments of the present disclosure involving general formula (I), (Ia), (Ib), (Ic), (Id), (Id-1), (Id-2), (Id-3), (Id-4), (Ie) or (If), each $R^2$ is independently selected from F, Cl, Br, I, methyl, ethyl, propyl, or isopropyl.

In some embodiments of the present disclosure involving general formula (I), (Ia), (Ib), (Ic), (Id), (Id-1), (Id-2), (Id-3), (Id-4), (Ie) or (If), $R^2$ is selected from F, Cl, Br, I, methyl, ethyl, propyl, or isopropyl.

In some embodiments of the present disclosure involving general formula (I), (Ia), (Ib), (Ic), (Id), (Id-1), (Id-2), (Id-3), (Id-4), (Id-5), (Ie) or (If), each $R^2$ is independently selected from $CD_3$, $CHD_2$, or $CH_2D$.

In some embodiments of the present disclosure involving general formula (Id-1), or (Id-2), $R^2$ is selected from F, Cl, Br, I, or $C_{1-4}$ alkyl.

In some embodiments of the present disclosure involving general formula (I), (Ia), (Ib), (Ic), (Id), (Id-1), (Id-2), (Id-3), (Id-4), (Ie) or (If), each $R^6$ is independently selected from H, halogen, OH, —$NR^{1a}R^{1b}$, $C_{1-6}$ alkyl or $C_{1-6}$ alkoxy, wherein the alkyl, and alkoxy are optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^6$ is independently selected from H, halogen, OH, —$NR^{1a}R^{1b}$, $C_{1-4}$ alkyl or $C_{1-4}$ alkoxy, wherein the alkyl, and alkoxy are optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^6$ is independently selected from H, F, Cl, Br, I, OH, $NH_2$, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I), (Ia), (Ib), (Ic), (Id), (Id-1), (Id-2), (Id-3), (Id-4), (Ie) or (If), each $R^6$ is independently selected from H, F, Cl, Br, I, OH, $NH_2$, methyl, ethyl, propyl, isopropyl, tert-butyl, methoxy, ethoxy or isopropoxy, wherein the methyl, ethyl, propyl, isopropyl, tert-butyl, methoxy, ethoxy or isopropoxy is optionally further substituted with 0 to 4 substituents selected from H, F, Cl, Br, I, OH, =O, cyano, $NH_2$, methyl, ethyl, methoxy, ethoxy, $CF_3$, —$CH_2F$ or —$CH_2OH$.

In some embodiments of the present disclosure involving general formula (I), (Ia), (Ib), (Ic), (Id), (Id-1), (Id-2), (Id-3), (Id-4), (Ie) or (If), each $R^6$ is independently selected from H, F, Cl, Br, I, OH, $NH_2$, methyl, ethyl, propyl, isopropyl, tert-butyl, methoxy, ethoxy or isopropoxy.

In some embodiments of the present disclosure involving general formula (I), (Ia), (Ib), (Ic), (Id), (Id-1), (Id-2), (Id-3), (Id-4), (Ie) or (If), each $R^6$ is independently selected from H, F, Cl, Br, I, OH, $NH_2$, methyl, ethyl, propyl, or isopropyl.

In some embodiments of the present disclosure involving general formula (I), R is selected from H, or $C_{1-6}$ alkyl, wherein the alkyl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl.

In some embodiments of the present disclosure involving general formula (I), R is selected from H, or $C_{1-4}$ alkyl, wherein the alkyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I), R is selected from H, methyl, ethyl, propyl or isopropyl, wherein the methyl, ethyl, propyl or isopropyl is optionally further substituted with 0 to 4 substituents selected from H, F, Cl, Br, I, OH, =O, cyano, $NH_2$, methyl, ethyl or $CF_3$.

In some embodiments of the present disclosure involving general formula (I), R is selected from H.

In some embodiments of the present disclosure involving general formula (I), (Ib), (Ic), (Id), (Id-1), (Id-3), (Id-4) or (If), each $R^7$ is independently selected from H, halogen, OH, $—NR^{1a}R^{1b}$, $C_{1-6}$ alkyl, $C_{1-6}$ alkoxy, $C_{2-6}$ alkenyl, $C_{2-6}$ alkynyl, $—C(=O)R^{1d}$, $—S(=O)_2R^{1d}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-6}$ alkyl, $C_{1-6}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ib), (Ic), (Id), (Id-1), (Id-3), (Id-4) or (If), each $R^7$ is independently selected from H, halogen, OH, $—NR^{1a}R^{1b}$, $C_{1-4}$ alkyl, $C_{1-4}$ alkoxy, $C_{2-4}$ alkenyl, $C_{2-4}$ alkynyl, $—C(=O)R^{1d}$, $—S(=O)_2R^{1d}$, $C_{3-6}$ carbocyclyl or 3- to 8-membered heterocyclyl, wherein the alkyl, alkenyl, alkynyl, alkoxy, carbocyclyl or heterocyclyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ib), (Ic), (Id), (Id-1), (Id-3), (Id-4) or (If), each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, $—C(=O)R^{1d}$, $—S(=O)_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, =O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ib), (Ic), (Id), (Id-1), (Id-3), (Id-4) or (If), each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, $—C(=O)R^{1d}$, $—S(=O)_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, ethynyl, propynyl, methoxy, ethoxy, $CF_3$, $—CH_2F$, $—CH_2OH$, cyclopropyl, cyclobutyl, azacyclobutyl or pyrrolidinyl.

In some embodiments of the present disclosure involving general formula (I), (Ib), (Ic) or (If), each $R^7$ is independently selected from H, F, Cl, Br, I, OH, $NH_2$, methyl, ethyl, propyl, isopropyl, tert-butyl, methoxy, ethoxy, isopropoxy, vinyl, ethynyl, propynyl, propargyl, $—CH_2$-propynyl, $—CH_2$-cyclopropyl, $—CH_2$-cyclobutyl, $—CH_2—$ azacyclobutyl, $—CH_2OCH_3$, $—OCH_2CH_2OCH_3$, $—CH_2CH_2OCH_3$, $—CH_2CF_3$, $—OCH_2—$ cyclopropyl, $—C(=O)CH_3$, $—C(=O)$-cyclopropyl, $—C(=O)$-phenyl, $—S(=O)_2CH_3$, $—S(=O)_2CH_2CH_3$, $—S(=O)_2$-cyclopropyl, $—S(=O)_2—CH_2$-cyclopropyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, ethynyl, propynyl, methoxy, ethoxy, $CF_3$, $—CH_2F$, $—CH_2OH$, cyclopropyl, cyclobutyl, azacyclobutyl or pyrrolidinyl;

In some embodiments of the present disclosure involving general formula (I), $R^7$ is selected from $R^{7A}$, $R^{7B}$ or $R^{7a}$.

In some embodiments of the present disclosure involving general formula (I), $R^7$ is selected from $R^{7'}$.

In some embodiments of the present disclosure involving general formula (Id-1), $R^7$ is selected from H, methoxymethyl, methoxyethyl, cyclopropyl, cyclobutyl, cyclopentyl, cyclohexyl, azacyclobutyl, azacyclopentyl, azacyclohexyl, oxacyclobutyl, oxacyclopentyl, or oxacyclohexyl.

In some embodiments of the present disclosure involving general formula (Id-1), $R^7$ is selected from methoxymethyl, methoxyethyl, cyclopropyl, cyclobutyl, cyclopentyl, cyclohexyl, azacyclobutyl, azacyclopentyl, azacyclohexyl, oxacyclobutyl, oxacyclopentyl, oxacyclohexyl, ethynyl, propynyl or propargyl, wherein the cyclopropyl, cyclobutyl, cyclopentyl, cyclohexyl, azacyclobutyl, azacyclopentyl, azacyclohexyl, oxacyclobutyl, oxacyclopentyl, oxacyclohexyl, ethynyl, propynyl or propargyl is optionally further substituted with 0 to 4 substituents selected from H, D, F, Cl, Br, $CF_3$, OH, =O, cyano, $NH_2$, methyl, or methoxy.

In some embodiments of the present disclosure involving general formula (Id-2), two $R^{7B}$ together with the carbon to which they are attached form the following ring:

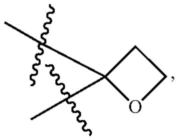
,
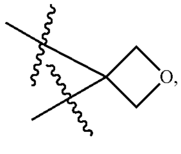
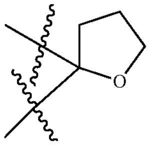
,
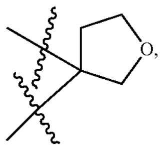
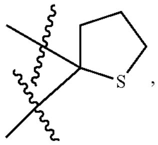
,
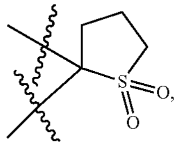
or
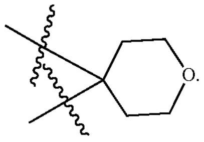

In some embodiments of the present disclosure involving general formula (Id-1), $R^7$ is selected from methoxymethyl, methoxyethyl, $C_{2-4}$ alkynyl, $C_{3-6}$ cycloalkyl or 4- to 7-membered heterocycle.

In some embodiments of the present disclosure involving general formula (Id-2), two $R^{7B}$ together with the carbon to which they are attached form the following 4- to 7-membered heterocycle (preferably 4- to 6-membered heterocycle).

In some embodiments of the present disclosure involving general formula (Ia), $R^{7A}$ is selected from H, F, Cl, Br, I, methyl, ethyl, propyl, isopropyl, tert-butyl, methoxy, ethoxy, isopropoxy, —C(=O)$R^{1d}$, —S(=O)$_2R^{1d}$, cyclopropyl, cyclobutyl, cyclopentyl, cyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, cyclopropyl, cyclobutyl, cyclopentyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, =O, cyano, $NH_2$, $C_{1-4}$ alkyl, C24 alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (Ia), $R^{7A}$ is selected from H, F, Cl, Br, I, methyl, ethyl, propyl, isopropyl, tert-butyl, methoxy, ethoxy, isopropoxy, —C(=O)$R^{1d}$, —S(=O)$_2R^{1d}$, cyclopropyl, cyclobutyl, cyclopentyl, cyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the methyl, ethyl, propyl, isopropyl, tert-butyl, methoxy, ethoxy, isopropoxy, cyclopropyl, cyclobutyl, cyclopentyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, methoxy, ethoxy, $CF_3$, —$CH_2F$, —$CH_2OH$, cyclopropyl or cyclobutyl.

In some embodiments of the present disclosure involving general formula (Ia), $R^{7A}$ is selected from F, Cl, Br, I, methyl, ethyl, propyl, isopropyl, tert-butyl, —$CH_2$— cyclopropyl, —$CH_2$-cyclobutyl, —$CH_2$-azacyclobutyl, —$CH_2OCH_3$, —$CH_2CH_2OCH_3$, —$CH_2CF_3$, —C(=O)$CH_3$, —C(=O)-cyclopropyl, —C(=O)-phenyl, —S(=O)$_2CH_3$, —S(=O)$_2$-cyclopropyl, —S(=O)$_2$—$CH_2$-cyclopropyl, cyclopropyl, cyclobutyl, cyclopentyl or imidazolyl.

In some embodiments of the present disclosure involving general formula (Ie), each $R^{7a}$ is independently selected from $R^d$, F, Cl, Br, I, vinyl, ethynyl, propynyl, propargyl, —C(=O)$R^{1d}$, —S(=O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (Ie), each $R^{7a}$ is independently selected from $R^d$, F, Cl, Br, I, vinyl, ethynyl, propynyl, propargyl, —C(=O)$R^{1d}$, —S(=O)$_2R^{1d}$, cyclopropyl, cyclobutyl, cyclopentyl, cyclohexyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, wherein the vinyl, ethynyl, propynyl, propargyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl is optionally further substituted with 0 to 4 substituents selected from H, D, F, Cl, Br, I, OH, =O, cyano, $NH_2$, methyl, ethyl, ethynyl, methoxy, ethoxy, $CF_3$, —$CH_2F$, —$CH_2OH$, cyclopropyl, cyclobutyl, azacyclobutyl or pyrrolidinyl.

In some embodiments of the present disclosure involving general formula (Ie), $R^{7a}$ is selected from F, Cl, Br, I, $CF_3$, —$CH_2F$, vinyl, ethynyl, propynyl, propargyl, —$CH_2$-propynyl, —$CH_2$-cyclopropyl, —$CH_2$-cyclobutyl, —$CH_2$-azacyclobutyl, —$CH_2OCH_3$, —$OCH_2CH_2OCH_3$, —$CH_2CH_2OCH_3$, —$CH_2CF_3$, —$OCH_2$-cyclopropyl, —C(=O)$CH_3$, —C(=O)-cyclopropyl, —C(=O)-phenyl, —S(=O)$_2CH_3$, —S(=O)$_2CH_2CH_3$, —S(=O)$_2$-cyclopropyl, —S(=O)$_2$—$CH_2$-cyclopropyl, cyclopropyl, cyclobutyl, cyclopentyl, azacyclobutyl, pyrrolidinyl, piperidinyl, morpholinyl, piperazinyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl.

In some embodiments of the present disclosure involving general formula (Ie), each $R^d$ is independently selected from methyl, ethyl, propyl, isopropyl, tert-butyl, methoxy, ethoxy, or isopropoxy, the methyl, ethyl, propyl, isopropyl, tert-butyl, methoxy, ethoxy, and isopropoxy is further substituted with 1 to 3 substituents selected from halogen, ethynyl, $C_{2-4}$ alkynyl, $C_{1-4}$ alkoxy, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl.

In some embodiments of the present disclosure involving general formula (Ie), each $R^d$ is independently selected from methyl, ethyl, propyl, isopropyl, tert-butyl, methoxy, ethoxy, or isopropoxy, the methyl, ethyl, propyl, isopropyl, tert-butyl, methoxy, ethoxy, and isopropoxy is further substituted with 1 to 3 substituents selected from F, Cl, Br, I, ethynyl, methoxy, ethoxy, $CF_3$, $—CH_2F$, cyclopropyl, cyclobutyl, azacyclobutyl or pyrrolidinyl.

In some embodiments of the present disclosure involving general formula (I), (Id), (Id-1), or (Id-2), two $R^7$ together with the carbon atom to which they are attached form a 3- to 6-membered heterocyclyl, wherein the heterocyclyl is optionally further substituted with 0 to 4 substituents selected from H, halogen, OH, =O, cyano, $—C(=O)R^{1d}$, $—S(=O)_2R^{1d}$, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Id), (Id-1), (Id-2), two $R^7$ together with the carbon atom to which they are attached form a 3- to 6-membered heterocyclyl, wherein the heterocyclyl is optionally further substituted with 0 to 4 substituents selected from H, halogen, OH, =O, cyano, $—C(=O)R^{1d}$, $—S(=O)_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Id), (Id-1), or (Id-2), two $R^7$ together with the carbon atom to which they are attached form oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, halogen, OH, =O, cyano, $—C(=O)R^{1d}$, $—S(=O)_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I) or (Ib), $R^6$ and $R^7$ at adjacent positions can form a double bond.

In some embodiments of the present disclosure involving general formula (I), (Id), (Id-1), or (Id-2), two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl, wherein the heterocyclyl contains 1 to 4 heteroatoms selected from O, S or N.

In some embodiments of the present disclosure involving general formula (I), (Id), (Id-1), or (Id-2), two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heterocyclyl contains 1 to 4 heteroatoms selected from O, S or N.

In some embodiments of the present disclosure involving general formula (I) or (Id), two $R^6$ together with the atom to which they are attached form cyclobutyl, cyclopentyl, cyclohexyl, oxacyclobutyl, oxacyclopentyl, oxacyclohexyl, thiocyclopentyl, azacyclobutyl, pyrrolidinyl, piperidinyl, morpholinyl or piperazinyl.

In some embodiments of the present disclosure involving general formula (I),

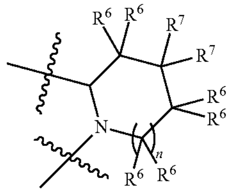

is selected from

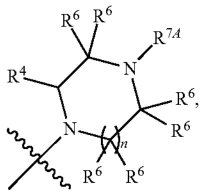

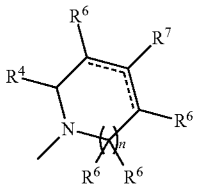

or

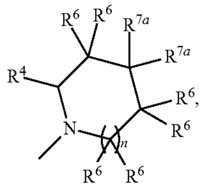

═ represents a single bond or a double bond, and wherein only one double bond is contained.

In some embodiments of the present disclosure involving general formula (I),

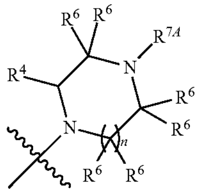

is selected from
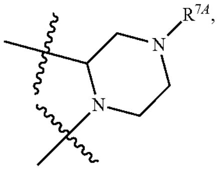
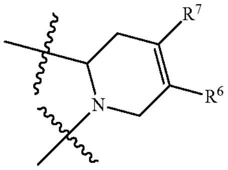
,
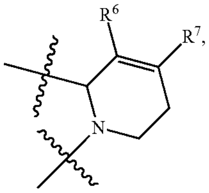
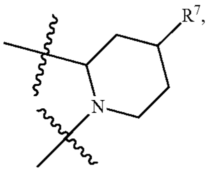
or
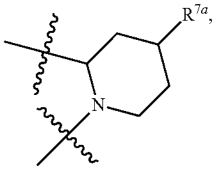
which is connected to $R^4$ at the upper part.
In some embodiments of the present disclosure involving general formula (I), (Ic), (Id), (Id-1), (Id-2), or (If),
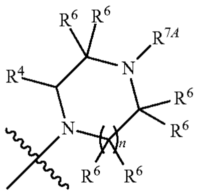
is selected from the fragments in the following table which are connected to $R^4$ at the upper part
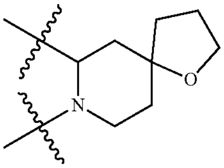
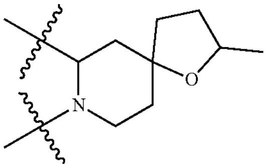
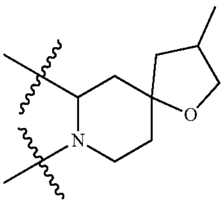
-continued
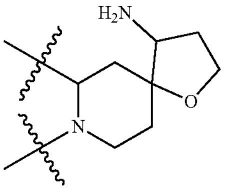
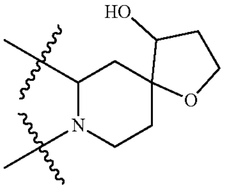
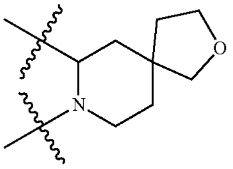
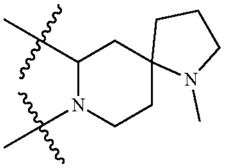
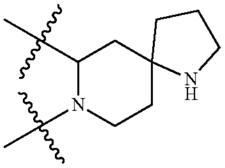
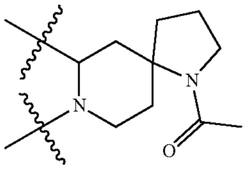
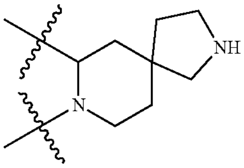
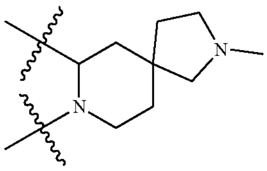

-continued
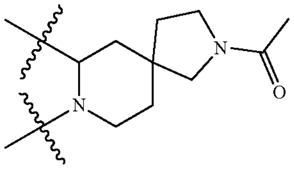
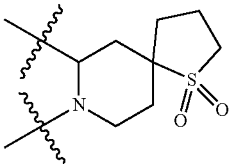
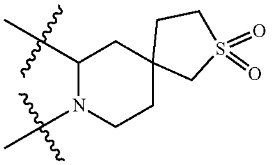
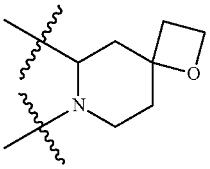
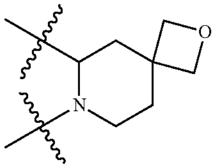
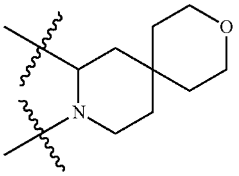
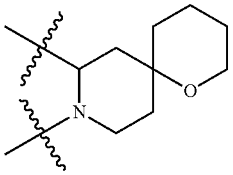
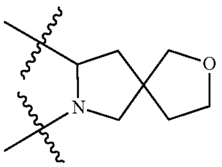 [SMILES: *C1CC2(CCOC2)CN1*]
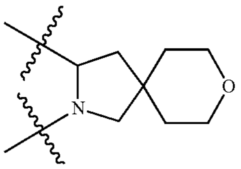 [SMILES: *C1CC2(CCOCC2)CN1*]
-continued
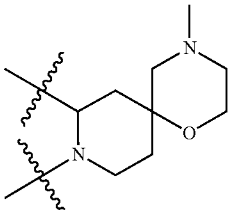 [SMILES: *C1CC2(CCN1*)CN(C)CCO2]
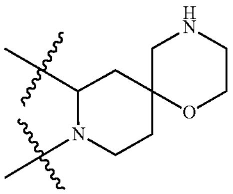 [SMILES: *C1CC2(CCN1*)CNCCO2]
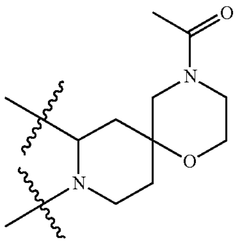 [SMILES: *C1CC2(CCN1*)CN(C(C)=O)CCO2]
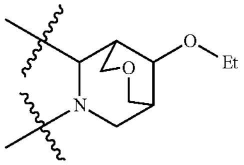 [SMILES: *C1C2COCC(CN1*)C2OCC]
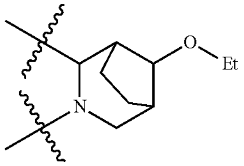 [SMILES: *C1C2CCC(CN1*)C2OCC]
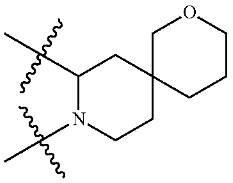
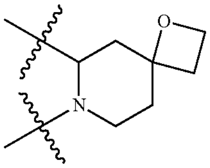
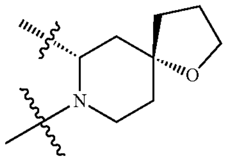

-continued
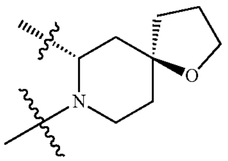
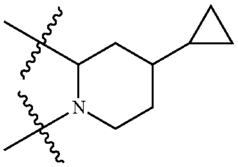 [SMILES: *C1CC(C2CC2)CCN1*]
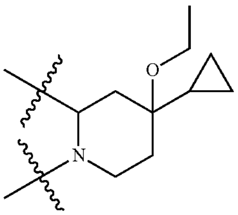 [SMILES: *C1CC(OCC)(C2CC2)CCN1*]
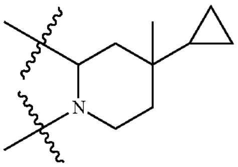
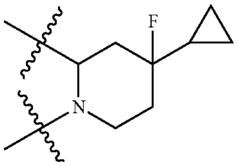
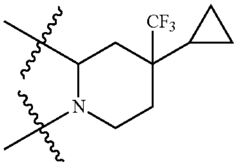
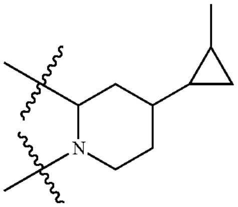 [SMILES: *C1CC(C2CC2C)CCN1*]
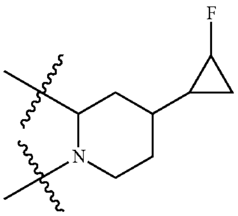 [SMILES: *C1CC(C2CC2F)CCN1*]
-continued
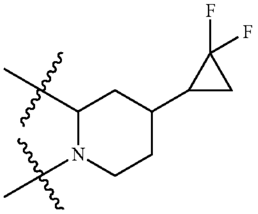 [SMILES: *C1CC(C2CC2(F)F)CCN1*]
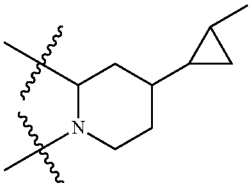 [SMILES: *C1CC(C2CC2C)CCN1*]
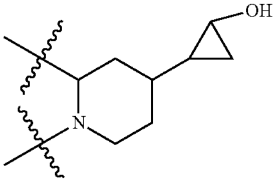 [SMILES: *C1CC(C2CC2O)CCN1*]
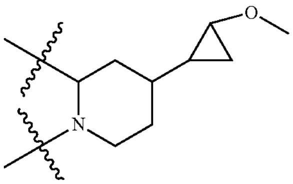 [SMILES: *C1CC(C2CC2OC)CCN1*]
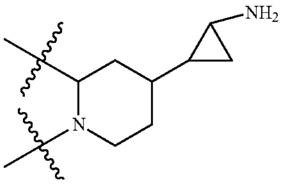 [SMILES: *C1CC(C2CC2N)CCN1*]
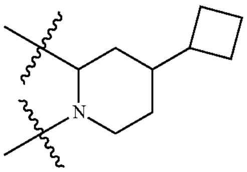 [SMILES: *C1CC(C2CCC2)CCN1*]
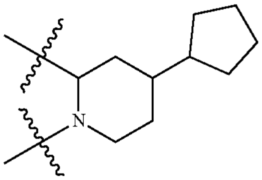 [SMILES: *C1CC(C2CCCC2)CCN1*]
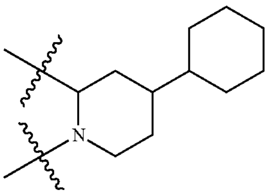 [SMILES: *C1CC(C2CCCCC2)CCN1*]

-continued

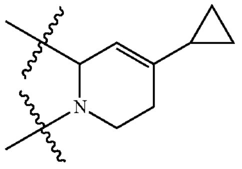 [SMILES: *C1C=C(C2CC2)CCN1*]

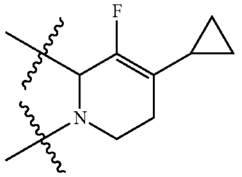 [SMILES: *C1C(F)=C(C2CC2)CCN1*]

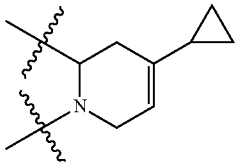 [SMILES: *C1CC(C2CC2)=CCN1*]

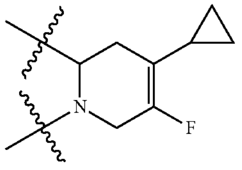 [SMILES: *C1CC(C2CC2)=C(F)CN1*]

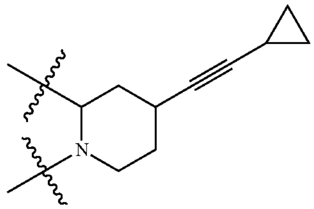 [SMILES: *C1CC(C#CC2CC2)CCN1*]

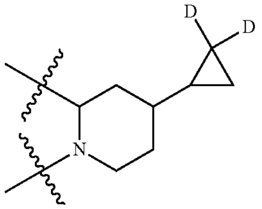 [SMILES: *C1CC(C2CC2([2H])[2H])CCN1*]

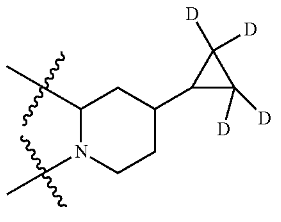 [SMILES: *C1CC(C2C([2H])([2H])C2([2H])[2H])CCN1*]

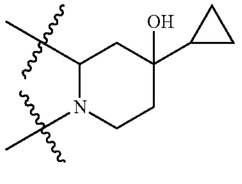

-continued

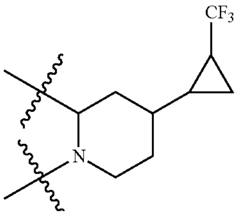 [SMILES: *C1CC(C2CC2C(F)(F)F)CCN1*]

In some embodiments of the present disclosure involving general formula (Id-3), or (Id-4), ring B is selected from 3- to 6-membered heterocyclyl, wherein the heterocyclyl is optionally further substituted with 0 to 4 substituents selected from H, halogen, OH, =O, cyano, —C(=O)$R^{1d}$, —$S(=O)_2R^{1d}$, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (Id-3) or (Id-4), ring B is selected from 3- to 6-membered heterocycloalkyl, wherein the heterocycloalkyl is optionally further substituted with 0 to 4 substituents selected from H, halogen, OH, =O, cyano, $NH_2$, —C(=O)$C_{1-4}$ alkyl, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heterocycloalkyl contains 1 to 4 heteroatoms selected from O, S or N.

In some embodiments of the present disclosure involving general formula (Id-3) or (Id-4), ring B is selected from oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, halogen, OH, =O, cyano, $NH_2$, —C(=O)$C_{1-4}$ alkyl, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (Id-3), ring B is selected from oxacyclobutyl, oxacyclopentyl, oxacyclohexyl, thiocyclopentyl, azacyclobutyl, pyrrolidinyl, piperidinyl, morpholinyl or piperazinyl, wherein the oxacyclobutyl, oxacyclopentyl, oxacyclohexyl, thiocyclopentyl, azacyclobutyl, pyrrolidinyl, piperidinyl, morpholinyl or piperazinyl is optionally further substituted with 0 to 4 substituents selected from H, F, Cl, Br, $CF_3$, OH, =O, cyano, $NH_2$, —C(=O)$CH_3$, methyl, ethyl, methoxy or ethoxy.

In some embodiments of the present disclosure involving general formula (Id-4), each $R^6$ is independently selected from H, halogen, OH, $NH_2$, $C_{1-4}$ alkyl or $C_{1-4}$ alkoxy, wherein the alkyl or alkoxy is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (Id-4), each $R^6$ is independently selected from H, F, Cl, Br, $CF_3$, methyl, or ethyl.

In some embodiments of the present disclosure involving general formula (Id-4), $R^7$ is selected from $C_{2-4}$ alkynyl, $C_{3-6}$ carbocyclyl, or 3- to 8-membered heterocyclyl, $R^{7'}$ is selected from H, halogen, OH, —$NR^{1a}R^{1b}$, $C_{1-4}$ alkyl, $C_{1-4}$ alkoxy, $C_2$-4 alkenyl, $C_{2-4}$ alkynyl, —C(═O)$R^{1d}$, —S(═O)$_2R^{1d}$, wherein the alkyl, alkenyl, alkynyl, alkoxy, carbocyclyl or heterocyclyl is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl is contains 1 to 4 heteroatoms selected from O, S or N.

In some embodiments of the present disclosure involving general formula (Id-4), $R^7$ is selected from $C_{2-4}$ alkynyl, phenyl, $C_{3-6}$ cycloalkyl, 3- to 8-membered heterocycloalkyl or 5- to 6-membered heteroaryl, $R^{7'}$ is selected from H, halogen, OH, —$NH_2$, $C_{1-4}$ alkyl, $C_{1-4}$ alkoxy, $C_{2-4}$ alkenyl, $C_{2-4}$ alkynyl, —C(═O)$C_{1-4}$ alkyl, —S(═O)$_2C_{1-4}$ alkyl, wherein the alkyl, alkenyl, alkynyl, alkoxy, phenyl, cycloalkyl, heteroaryl, or heterocycloalkyl is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocycloalkyl, heterocyclyl or heteroaryl contains 1 to 4 heteroatoms selected from O, S or N.

In some embodiments of the present disclosure involving general formula (Id-4), $R^7$ is selected from one of the following substituted or unsubstituted groups: ethynyl, propynyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, $R^{7'}$ is selected from H, F, OH, or $NH_2$, or one of the following substituted or unsubstituted groups: methyl, ethyl, propyl, isopropyl, tert-butyl, methoxy, ethoxy, isopropoxy, vinyl, ethynyl, propynyl or propargyl, $R^7$ or $R^{7'}$, when substituted, is optionally further substituted with 0 to 4 substituents selected from H, D, halogen, OH, ═O, cyano, $NH_2$, $C_{1-4}$ alkyl, $C_{1-4}$ alkoxy, $C_{2-4}$ alkenyl, $C_{2-4}$ alkynyl, $C_{1-4}$ alkyl substituted $C_{2-4}$ alkenyl, $C_{1-4}$ alkyl substituted $C_{2-4}$ alkynyl, $C_{1-4}$ alkyloxy substituted $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (Id-4), $R^7$ is selected from one of the following substituted or unsubstituted groups: ethynyl, propynyl, cyclopropyl, cyclobutyl, cyclopentyl, azacyclobutyl, pyrrolidinyl, piperidinyl, morpholinyl, piperazinyl, oxacyclobutyl, oxacyclopentyl, oxacyclohexyl, pyrazolyl, pyrrolyl, imidazolyl, furanyl, thienyl, thiazolyl, oxazolyl, isoxazolyl, triazolyl, 1,2,4-oxadiazolyl, pyridyl, pyridazinyl, pyrazinyl or pyrimidinyl, $R^{7'}$ is selected from H, F, OH, or $NH_2$, or one of the following substituted or unsubstituted groups: methyl, ethyl, propyl, isopropyl, tert-butyl, methoxy, ethoxy, isopropoxy, vinyl, ethynyl, propynyl or propargyl, $R^7$ or $R^{7'}$, when substituted, is optionally further substituted with 0 to 4 substituents selected from H, D, F, Cl, Br, $CF_3$, OH, ═O, cyano, $NH_2$, methyl, ethyl, methoxy, ethoxy, ethynyl, propynyl, propargyl, cyclopropyl, cyclobutyl, cyclopentyl, azacyclobutyl, pyrrolidinyl, piperidinyl, morpholinyl or piperazinyl.

In some embodiments of the present disclosure involving general formula (Id-4), $R^7$ is selected from ethynyl, propynyl, propargyl, cyclopropyl, cyclobutyl, cyclopentyl, wherein the propynyl, propargyl, cyclopropyl, cyclobutyl, or cyclopentyl is optionally further substituted with 0 to 4 substituents selected from H, D, F, Cl, Br, $CF_3$, OH, methyl, ethyl, methoxy, ethoxy, or cyclopropyl, $R^{7'}$ is selected from H, F, OH, $NH_2$, methyl, ethyl, methoxy, or ethoxy, wherein the methyl, ethyl, methoxy, and ethoxy are optionally further substituted with 0 to 4 substituents selected from H, D, F, Cl, Br, $CF_3$, OH, methyl, ethyl, methoxy or ethoxy.

In some embodiments of the present disclosure involving general formula (Id-3) or (Id-4), $X_1$ is selected from N or CH, $X_2$ is selected from N or CH, wherein the CH is optionally substituted with 1 methyl or ethyl.

In some embodiments of the present disclosure involving general formula (Id-3), or (Id-4), $X_1$ is selected from CH, and $X_2$ is selected from CH.

In some embodiments of the present disclosure involving general formula (Id-4),

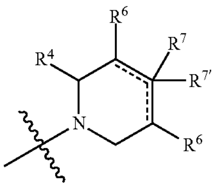

is selected from one of the following structures:

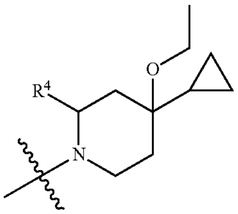

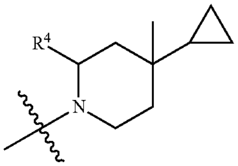

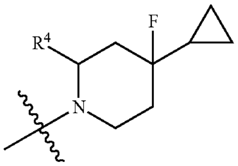

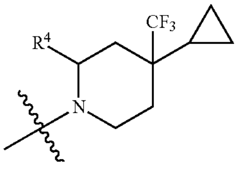

-continued
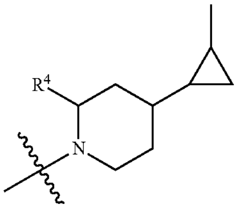
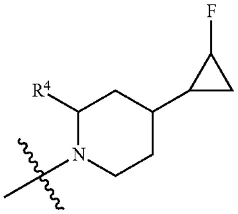
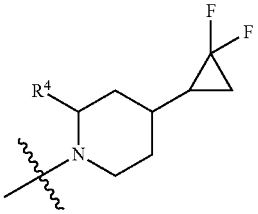
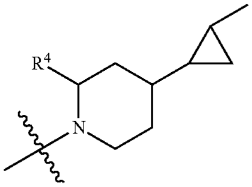
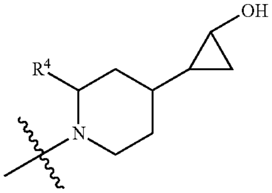
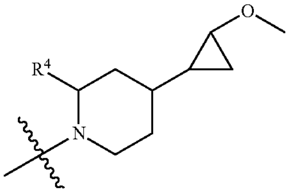
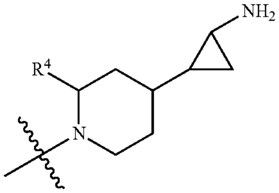
-continued
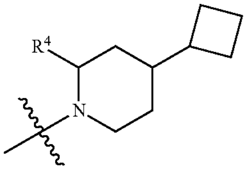
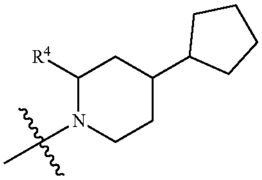
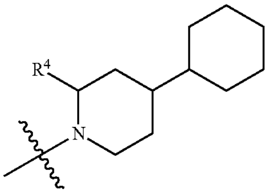
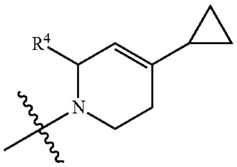
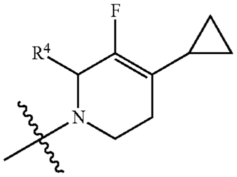
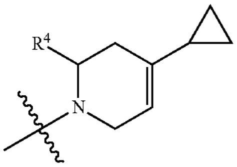
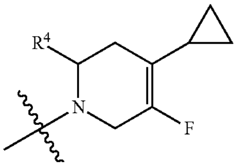
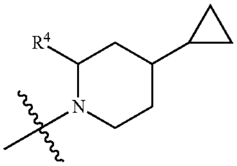

-continued
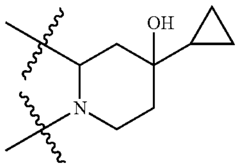
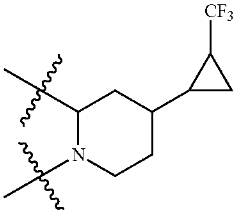 [SMILES: *C1CC(C2CC2C(F)(F)F)CCN1*]
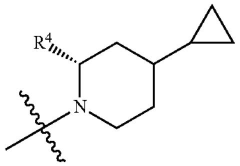
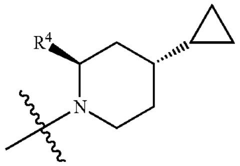
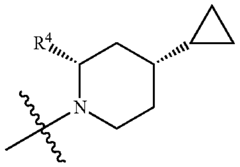
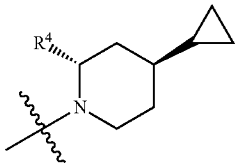
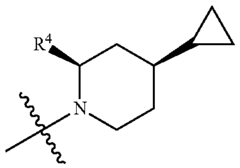
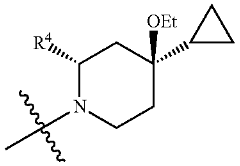
-continued
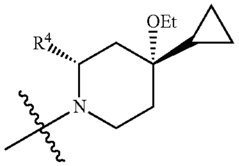
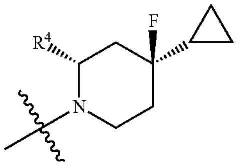
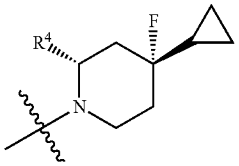
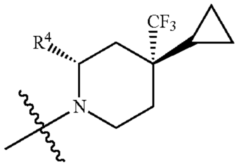
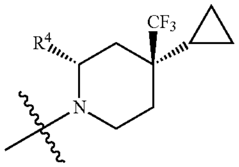
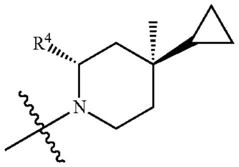
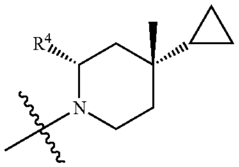
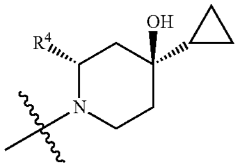
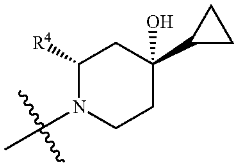

-continued
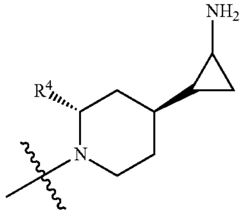
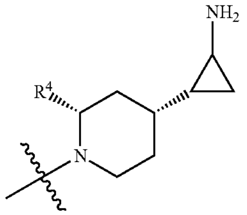
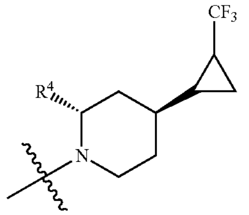
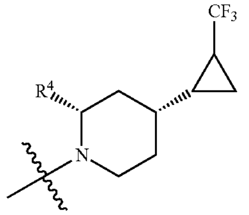
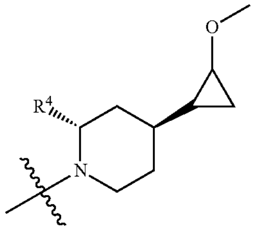
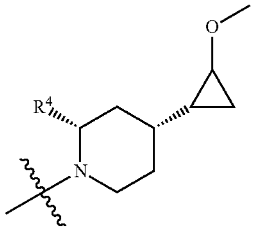
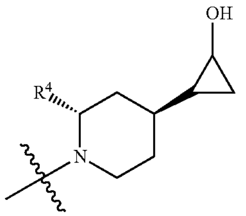
-continued
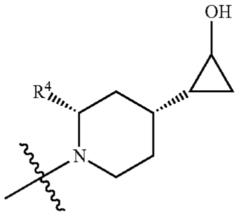
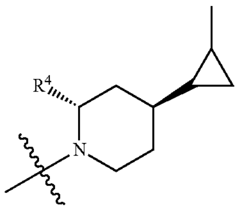
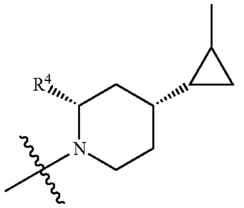
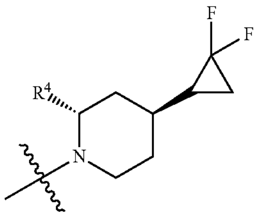
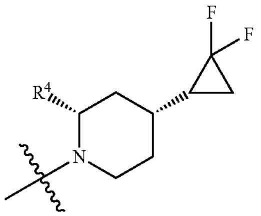
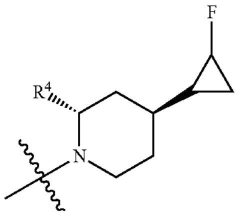
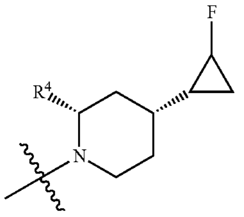

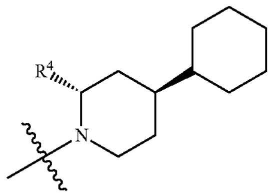
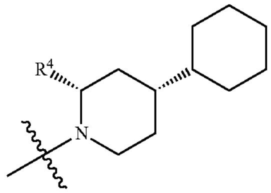
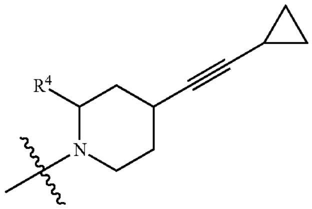
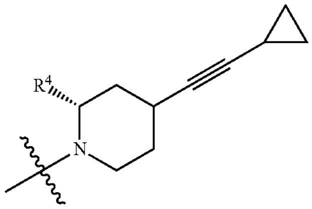
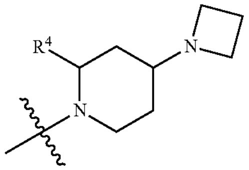
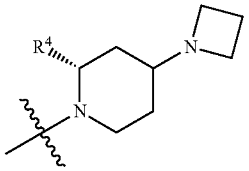
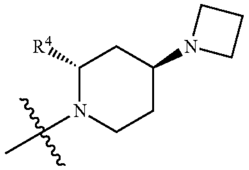
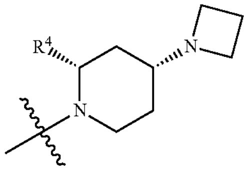
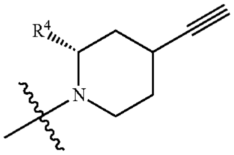
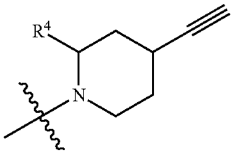
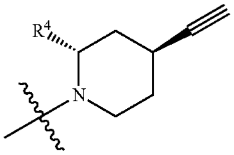
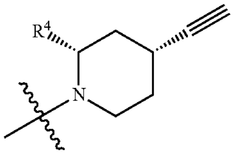
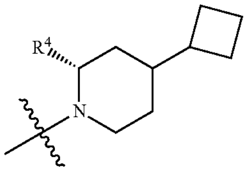
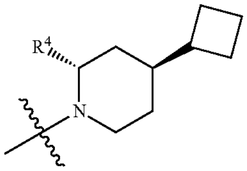
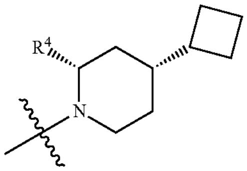
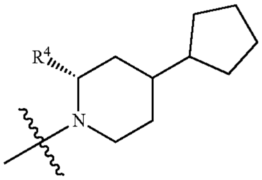
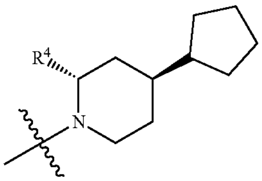

-continued
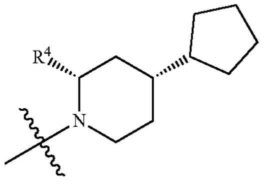
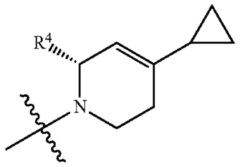
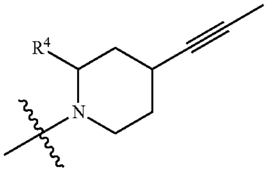
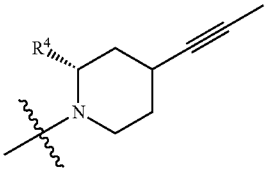
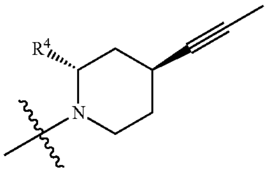
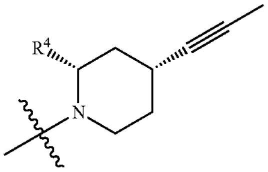
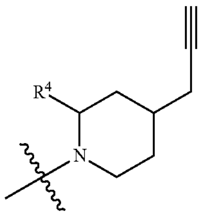
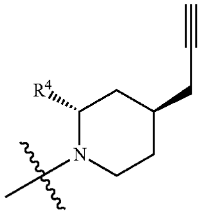
-continued
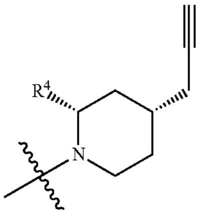
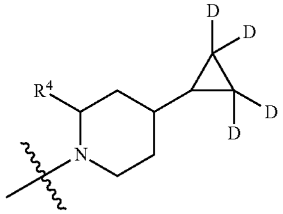
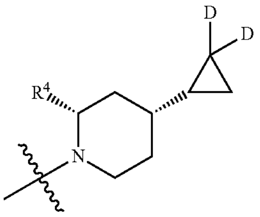
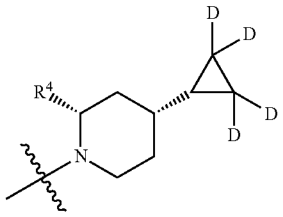
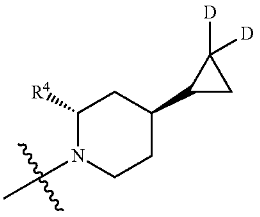
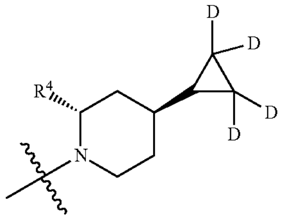
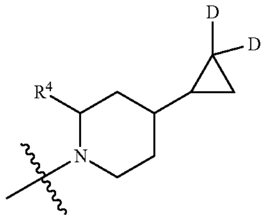
In some embodiments of the present disclosure involving general formula (I), (Ia), (Ib), (Ic), (Id), (Id-1), (Id-2), (Id-3), (Id-4), (Ie) or (If), $R^4$ is selected from $C_{5-12}$ carbocyclyl, 5- to 12-membered heterocyclyl, $C_{6-12}$ aryl or 5- to 12-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^4$ is selected from $C_{5-7}$ monocyclic carbocyclyl, $C_{5-12}$ fused carbocyclyl, $C_{5-12}$ spiro carbocyclyl, $C_{5-12}$ bridged carbocyclyl, 5- to 7-membered monocyclic heterocyclyl, 5- to 12-membered fused heterocyclyl, 5- to 12-membered spiro heterocyclyl or 5- to 12-membered bridged heterocyclyl, $C_{6-10}$ aryl or 5- to 10-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^4$ is selected from $C_{5-7}$ monocyclic carbocyclyl, $C_{5-10}$ fused carbocyclyl, $C_{5-11}$ spiro carbocyclyl, $C_{5-12}$ bridged carbocyclyl, 5- to 6-membered monocyclic heterocyclyl, 5- to 10-membered fused heterocyclyl, 5- to 11-membered spiro heterocyclyl, 5- to 12-membered bridged heterocyclyl, $C_{6-10}$ aryl or 5- to 10-membered heteroaryl, wherein the carbocyclyl, heterocyclyl, aryl or heteroaryl is optionally further substituted with 0 to 4 $R^5$, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^4$ is independently selected from cyclopentyl, cyclohexyl, benzocyclohexyl, benzocyclopentyl, phenyl, naphthyl, pyridyl, pyrazolyl, pyrimidinyl or naphthyridinyl, the cyclopentyl, cyclohexyl, benzocyclohexyl, benzocyclopentyl, phenyl, naphthyl, pyridyl, pyrazolyl, pyrimidinyl or naphthyridinyl is optionally further substituted with 0 to 4 $R^5$.

In some embodiments of the present disclosure involving general formula (I), (Ia), (Ib), (Ic), (Id), (Id-1), (Id-2), (Id-3), (Id-4), (Ie) or (If), each $R^4$ is independently selected from

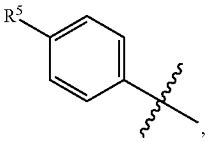,
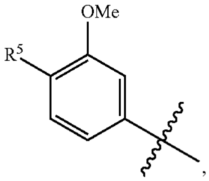,
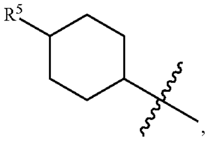,
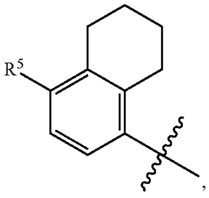,
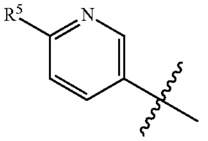 or
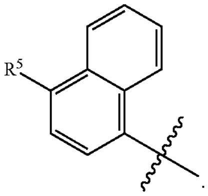.

In some embodiments of the present disclosure involving general formula (I), (Ia), (Ib), (Ic), (Id), (Id-1), (Id-2), (Id-3), (Id-4), (Ie) or (If), each $R^4$ is independently selected from

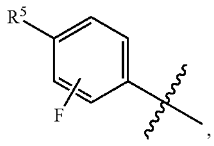,
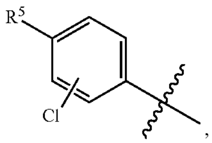, or
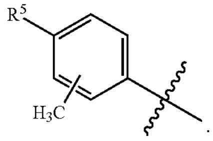.

In some embodiments of the present disclosure involving general formula (I), (Ia), (Ib), (Ic), (Id), (Id-1), (Id-2), (Id-3), (Id-4), (Ie) or (If), $R^4$ is selected from

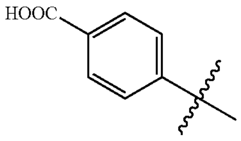 or
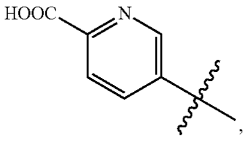, wherein the $R^4$ is optionally further substituted with 0, 1, 2 or 3 substituents selected from F, Cl, Br, I, OH, cyano, methyl, ethyl, methoxy or ethoxy.

In some embodiments of the present disclosure involving general formula (Id-1), (Id-2), (Id-3), or (Id-4), $R^4$ is selected from

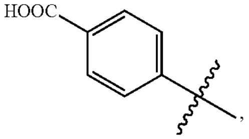, wherein the $R^4$ is optionally further substituted with 0, 1, 2 or 3 substituents selected from F, Cl, Br, I, OH, cyano, $C_{1-4}$ alkyl, or $C_{1-4}$ alkoxy.

In some embodiments of the present disclosure involving general formula (I), (Ia), (Ib), (Ic), (Id), (Id-1), (Id-2), (Id-3), (Id-4), (Ie) or (If), each $R^5$ is independently selected from H, halogen, OH, cyano, $-C(=O)R^{4e}$, $-S(=O)_2R^{4e}$, $-CH_2C(=O)R^{4e}$, $-C(=O)NHS(=O)_2R^{4e}$, $-C(=O)NR^{4e}R^{4f}$, $-S(=O)_2NHC(=O)R^{4e}$, $-S(=O)_2NR^{4e}R^{4f}$, $-P(O)R^{4c}R^{4d}$,

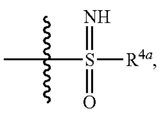,
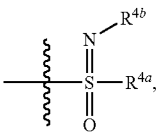, $C_{1-6}$ alkyl, $C_{1-6}$ alkoxy, $C_{2-6}$ alkenyl, $C_{2-6}$ alkynyl, $C_{3-10}$ cycloalkyl or 4- to 12-membered heterocyclyl, wherein the alkyl, alkoxy, alkenyl, alkynyl, cycloalkyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl or $C_{3-6}$ cycloalkyl, wherein the heterocyclyl contains 1 to 5 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^5$ is independently selected from H, halogen, OH, cyano, —C(═O)$R^{4e}$, —S(═O)$_2R^{4e}$, —$CH_2$C(═O)$R^{4e}$, —C(═O)NHS(═O)$_2R^{4e}$, —C(═O)N$R^{4e}R^{4f}$, —S(═O)$_2$NHC(═O)$R^{4e}$, —S(═O)$_2$N$R^{4e}R^{4f}$, —P(O)$R^{4c}R^{4d}$,

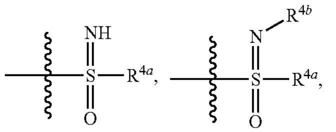

$C_{1-4}$ alkyl, $C_{1-4}$ alkoxy, $C_{2-4}$ alkenyl, $C_{2-4}$ alkynyl, $C_{3-8}$ cycloalkyl or 4 to 10-membered heterocyclyl, wherein the alkyl, alkoxy, alkenyl, alkynyl, cycloalkyl or heterocyclyl is optionally further substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl or $C_{3-6}$ cycloalkyl, wherein the heterocyclyl contains 1 to 5 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^5$ is independently selected from H, halogen, OH, cyano, —C(═O)$R^{4e}$, —S(═O)$_2R^{4e}$, —$CH_2$C(═O)$R^{4e}$, —C(═O)NHS(═O)$_2R^{4e}$, —C(═O)N$R^{4e}R^{4f}$, —S(═O)$_2$NHC(═O)$R^{4e}$, —S(═O)$_2$N$R^{4e}R^{4f}$, —P(O)$R^{4c}R^{4d}$,

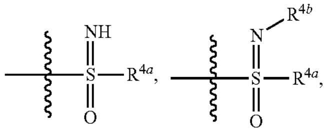

$C_{1-4}$ alkyl, $C_{1-4}$ alkoxy, $C_{2-4}$ alkenyl, $C_{2-4}$ alkynyl, $C_{3-6}$ cycloalkyl or 4 to 6-membered heterocyclyl, wherein the alkyl, alkoxy, alkenyl, alkynyl, cycloalkyl or heterocyclyl is optionally further substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl or $C_{3-6}$ cycloalkyl, wherein the heterocyclyl contains 1 to 5 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^5$ is independently selected from H, F, Cl, Br, I, OH, cyano, methyl, ethyl, propyl, isopropyl, methoxy, ethoxy, propoxy, isopropoxy, —COOH, —$CH_2$OH, —S(═O)$_2NH_2$, —S(═O)$_2NHCH_3$, —S(═O)$_2$OH,

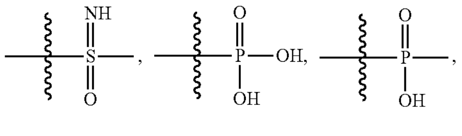

—C(═O)$NH_2$, —C(═O)NHOH, —S(═O)$_2$NHC(═O)$CH_3$, —C(═O)NHS(═O)$_2CH_3$, pyrazolyl, tetrazolyl, wherein the methyl, ethyl, propyl, isopropyl, methoxy, ethoxy, propoxy, isopropoxy, pyrazolyl, or tetrazolyl is optionally further substituted with 0 to 4 substituents selected from H, F, Cl, Br, I, OH, ═O, cyano, $NH_2$, methyl, ethyl, methoxy, ethoxy, $CF_3$, —$CH_2$F, —$CH_2$OH, cyclopropyl or cyclobutyl.

In some embodiments of the present disclosure involving general formula (I), (Ia), (Ib), (Ic), (Id), (Id-1), (Id-2), (Id-3), (Id-4), (Ie) or (If), $R^{1c}$ is selected from OH, $NH_2$, $C_{1-6}$ alkoxy, NH$C_{1-4}$ alkyl or N($C_{1-4}$ alkyl)$_2$.

In some embodiments of the present disclosure involving general formula (I), (Ia), (Ib), (Ic), (Id), (Id-1), (Id-2), (Id-3), (Id-4), (Ie) or (If), $R^{1c}$ is selected from OH, $NH_2$, $C_{1-4}$ alkoxy, NH$C_{1-4}$ alkyl or N($C_{1-4}$ alkyl)$_2$.

In some embodiments of the present disclosure involving general formula (I), (Ia), (Ib), (Ic), (Id), (Id-1), (Id-2), (Id-3), (Id-4), (Ie) or (If), $R^{1c}$ is selected from OH, $NH_2$, methoxy, ethoxy, $NHCH_3$, or N($CH_3$)$_2$.

In some embodiments of the present disclosure involving general formula (I), (Ia), (Ib), (Ic), (Id), (Id-1), (Id-2), (Id-3), (Id-4), (Ie) or (If), $R^{4a}$ and $R^{4b}$ are each independently selected from H, OH, cyano, —N$R^{1a}R^{1b}$, $C_{1-6}$ alkyl, $C_{1-6}$ alkoxy, $C_{3-8}$ carbocyclyl, 4- to 10-membered heterocyclyl, $C_{6-10}$ aryl or 5 to 10 membered heteroaryl, wherein the alkyl, carbocyclyl, heterocyclyl, aryl or heteroaryl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4a}$ and $R^{4b}$ are each independently selected from H, OH, cyano, $NH_2$, $C_{1-4}$ alkyl, $C_{1-4}$ alkoxy, $C_{3-6}$ carbocyclyl, 4- to 8-membered heterocyclyl, $C_{6-10}$ aryl or 5 to 6 membered heteroaryl, wherein the alkyl, carbocyclyl, heterocyclyl, aryl or heteroaryl is optionally substituted with 0 to 4 substituents selected from H, halogen, OH, ═O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4c}$ and $R^{4d}$ are each independently selected from H, OH, $C_{1-6}$ alkyl, $C_{1-6}$ alkoxy, —N$R^{1a}R^{1b}$, —O$R^{1d}$, —$C_{3-8}$ carbocyclyl, 4- to 10-membered heterocyclyl, $C_{6-10}$ aryl or 5 to 10 membered heteroaryl, wherein the alkyl, alkoxy, carbocyclyl, heterocyclyl, aryl or heteroaryl is optionally substituted with 0 to 4 substituents selected from H, halogen, OH, ═O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4c}$ and $R^{4d}$ are each independently selected from H, OH, $C_{1-4}$ alkyl, $C_{1-4}$ alkoxy, —N$R^{1a}R^{1b}$, —O$R^{1d}$, $C_{3-6}$ carbocyclyl, 4- to 8-membered heterocyclyl, $C_{6-10}$ aryl or 5 to 10 membered heteroaryl, wherein the alkyl, alkoxy, carbocyclyl, heterocyclyl, aryl or heteroaryl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl or heteroaryl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4e}$ and $R^{4f}$ are each independently selected from H, OH, —$NR^{1a}R^{1b}$, $C_{1-6}$ alkyl, $C_{1-6}$ alkoxy, $C_{3-8}$ cycloalkyl, or 5- to 12-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4e}$ and $R^{4f}$ are each independently selected from H, OH, —$NR^{1a}R^{1b}$, $C_{1-4}$ alkyl, $C_{1-4}$ alkoxy, $C_{3-6}$ cycloalkyl, or 5- to 10-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4a}$, $R^{4b}$, $R^{4c}$ and $R^{4d}$ are each independently selected from H, OH, $NH_2$, methyl, ethyl, propyl, isopropyl, methoxy, ethoxy, cyclopropyl or cyclobutyl, wherein the methyl, ethyl, propyl, isopropyl, methoxy, ethoxy, cyclopropyl or cyclobutyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{4a}$, $R^{4b}$, $R^{4c}$ and $R^{4d}$ are each independently selected from H, OH, $NH_2$, methyl, ethyl, propyl, isopropyl, methoxy, ethoxy, cyclopropyl or cyclobutyl, wherein the methyl, ethyl, propyl, isopropyl, methoxy, ethoxy, cyclopropyl or cyclobutyl is optionally further substituted with 0 to 4 substituents selected from H, F, Cl, Br, I, OH, =O, cyano, $NH_2$, methyl, ethyl or $CF_3$.

In some embodiments of the present disclosure involving general formula (I), (Ia), (Ib), (Ic), (Id), (Id-1), (Id-2), (Id-3), (Id-4), (Ie) or (If), $R^{4e}$ and $R^{4f}$ are each independently selected from H, OH, $NH_2$, methyl, ethyl, propyl, isopropyl, methoxy, ethoxy, cyclopropyl or cyclobutyl.

In some embodiments of the present disclosure involving general formula (I), (Ia), (Ib), (Ic), (Id), (Id-1), (Id-2), (Id-3), (Id-4), (Ie) or (If), each $R^{1d}$ is independently selected from H, $C_{1-6}$ alkyl, $C_{3-8}$ carbocyclyl or 4- to 10-membered heterocyclyl, wherein the alkyl, carbocyclyl or heterocyclyl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^{1d}$ is independently selected from H, $C_{1-4}$ alkyl, $C_{3-6}$ carbocyclyl or 4- to 8-membered heterocyclyl, wherein the alkyl, carbocyclyl or heterocyclyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^{1d}$ is independently selected from H, methyl, ethyl, propyl, isopropyl, cyclopropyl, cyclobutyl, cyclopentyl, oxacyclobutyl, azacyclobutyl, pyrrolidinyl or phenyl, wherein the methyl, ethyl, propyl, isopropyl, cyclopropyl, cyclobutyl, cyclopentyl, oxacyclobutyl, azacyclobutyl, pyrrolidinyl or phenyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), each $R^{1d}$ is independently selected from H, methyl, ethyl, propyl, isopropyl, cyclopropyl, cyclobutyl, cyclopentyl, oxacyclobutyl, azacyclobutyl, pyrrolidinyl or phenyl, wherein the methyl, ethyl, propyl, isopropyl, cyclopropyl, cyclobutyl, cyclopentyl, oxacyclobutyl, azacyclobutyl, pyrrolidinyl or phenyl is optionally substituted with 0 to 4 substituents selected from H, F, Cl, Br, I, OH, =O, cyano, $NH_2$, methyl, ethyl, methoxy, ethoxy, $CF_3$, —$CH_2F$, —$CH_2OH$, cyclopropyl, cyclobutyl, azacyclobutyl or pyrrolidinyl.

In some embodiments of the present disclosure involving general formula (I), (Ia), (Ib), (Ic), (Id), (Id-1), (Id-2), (Id-3), (Id-4), (Ie) or (If), each $R^{1d}$ is independently selected from methyl, ethyl, propyl, isopropyl, cyclopropyl, cyclobutyl, cyclopentyl, oxacyclobutyl, azacyclobutyl, pyrrolidinyl, phenyl, —$CH_2$-cyclopropyl or —$CH_2$— cyclobutyl.

In some embodiments of the present disclosure involving general formula (I), $R^8$ is selected from H, halogen, OH, cyano, $NH_2$, $C_{1-6}$ alkyl, $C_{2-6}$ alkenyl, $C_{2-6}$ alkynyl, $C_{1-6}$ alkoxy, —$S(=O)_pC_{1-6}$ alkyl, —$CH_2NHC(O)C_{1-4}$ alkyl, —$OCH_2C(=O)R^{1c}$, $C_{3-8}$ carbocyclyl or 3- to 10-membered heterocyclyl, wherein the alkyl, alkenyl, alkynyl, alkoxy, carbocyclyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), each $R^9$ or $R^{10}$ is independently selected from H, halogen, OH, cyano, $NH_2$, $C_{1-6}$ alkyl, $C_{2-6}$ alkenyl, $C_{2-6}$ alkynyl, $C_{1-6}$ alkoxy, $C_{1-6}$ alkylthio, $C_{3-8}$ carbocyclyl or 3- to 10-membered heterocyclyl, wherein the alkyl, alkenyl, alkynyl, alkoxy, alkylthio, carbocyclyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), each $R^8$, $R^9$ or $R^{10}$ is independently selected from H, halogen, OH, cyano, $NH_2$, $C_{1-4}$ alkyl, C24 alkenyl, C24 alkynyl, $C_{1-4}$ alkoxy, or $C_{1-4}$ alkylthio, wherein the alkyl, alkenyl, alkynyl, alkoxy, and alkylthio are optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I), each $R^8$, $R^9$ or $R^{10}$ is independently selected from H, F, Cl, Br, I, OH, cyano, $CF_3$, $NH_2$, methyl, or ethyl.

In some embodiments of the present disclosure involving general formula (I), (Ia), (Ib), (Ic), (Id), (Id-1), (Id-2), (Id-3), (Id-4), (Ie) or (If), $R^{1a}$ and $R^{1b}$ are each independently selected from H, or $C_{1-6}$ alkyl, wherein the alkyl is optionally substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N.

In some embodiments of the present disclosure involving general formula (I), (Ia), (Ib), (Ic), (Id), (Id-1), (Id-2), (Id-3), (Id-4), (Ie) or (If), $R^{1a}$ and $R^{1b}$ are each independently selected from H, or $C_{1-4}$ alkyl, wherein the alkyl is optionally substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I), (Ia), (Ib), (Ic), (Id), (Id-1), (Id-2), (Id-3), (Id-4), (Ie) or (If), $R^{1a}$ and $R^{1b}$ are each independently selected from H, methyl, ethyl, propyl or isopropyl, wherein the methyl, ethyl, propyl or isopropyl is optionally further substituted with 0 to 4 substituents selected from H, halogen, OH, =O, cyano, $NH_2$, $C_{1-4}$ alkyl, Cia alkoxy, halogen-substituted $C_{1-4}$ alkyl, hydroxy-substituted $C_{1-4}$ alkyl, or cyano-substituted $C_{1-4}$ alkyl.

In some embodiments of the present disclosure involving general formula (I), (Ia), (Ib), (Ic), (Id), (Id-1), (Id-2), (Id-3), (Id-4), (Ie) or (If), $R^{1a}$ and $R^{1b}$ are each independently selected from H, methyl, ethyl, propyl or isopropyl, wherein the methyl, ethyl, propyl or isopropyl is optionally further substituted with 0 to 4 substituents selected from H, F, Cl, Br, I, OH, =O, cyano, $NH_2$, methyl, ethyl, methoxy, ethoxy, $CF_3$, $-CH_2F$, or $-CH_2OH$.

In some embodiments of the present disclosure involving general formula (I), when Y is selected from $C(R^7)_2$, $R^7$ is selected from H, OH, $-NR^{1a}R^{1b}$, unsubstituted $C_{1-6}$ alkyl, hydroxy $C_{1-6}$ alkyl, cyano $C_{1-6}$ alkyl or unsubstituted $C_{1-6}$ alkoxy, and the two $R^7$ and the carbon atom to which they are attached do not form 3- to 6-membered heterocyclyl together, one of the following conditions must be met:

1) $R^1$ is selected from $C_{2-6}$ alkynyl, $C_{3-6}$ cycloalkyl substituted $C_{1-6}$ alkyl, 3 to 8 membered heterocyclyl substituted $C_{1-6}$ alkyl, $-W-C_{3-8}$ carbocyclyl or —W-4- to 10-membered heterocyclyl, wherein the alkynyl, alkyl, carbocyclyl, or heterocyclyl is optionally further substituted with 0 to 4 substituents selected from H, D, halogen, OH, =O, cyano, $NH_2$, $C_{1-6}$ alkyl, $C_{2-6}$ alkynyl, $C_{1-6}$ alkoxy, halogen-substituted $C_{1-6}$ alkyl, hydroxy-substituted $C_{1-6}$ alkyl, cyano-substituted $C_{1-6}$ alkyl, $C_{3-6}$ cycloalkyl or 3- to 8-membered heterocyclyl, wherein the heterocyclyl contains 1 to 4 heteroatoms selected from O, S or N;
2) $R^6$ and $R^7$ at adjacent positions form a double bond;
3) two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-6}$ alkyl, $C_{1-6}$ alkoxy, halogen-substituted $C_{1-6}$ alkyl, hydroxy-substituted $C_{1-6}$ alkyl, or cyano-substituted $C_{1-6}$ alkyl, wherein the heterocyclyl contains 1 to 4 heteroatoms selected from O, S or N;
4) $X_2$ is selected from N.

In some embodiments of the present disclosure involving general formula (I), when Y is selected from $C(R^7)_2$, $R^7$ is selected from H, OH, $-NR^{1a}R^{1b}$, unsubstituted $C_{1-4}$ alkyl, hydroxy $C_{1-4}$ alkyl, cyano $C_{1-4}$ alkyl or unsubstituted $C_{1-4}$ alkoxy, and the two $R^7$ and the carbon atom to which they are attached do not form 3- to 6-membered heterocyclyl together, one of the following conditions must be met:

1) $R^1$ is selected from $C_{2-4}$ alkynyl, $C_{3-6}$ cycloalkyl substituted $C_{1-4}$ alkyl, 3 to 8 membered heterocyclyl substituted $C_{1-4}$ alkyl, $-W-C_{3-6}$ carbocyclyl or —W-4- to 8-membered heterocyclyl, wherein the alkynyl, alkyl, carbocyclyl, or heterocyclyl is optionally further substituted with 0 to 4 substituents selected from H, D, halogen, OH, =O, cyano, $NH_2$, $C_{1-4}$ alkyl, $C_{2-4}$ alkynyl, $C_{1-4}$ alkoxy, halogen-substituted $C_{1-4}$ alkyl, hydroxy-substituted $C_{1-4}$ alkyl, cyano-substituted $C_{1-4}$ alkyl, $C_{3-6}$ cycloalkyl or 3- to 8-membered heterocyclyl, wherein the heterocyclyl contains 1 to 4 heteroatoms selected from O, S or N;
2) $R^6$ and $R^7$ at adjacent positions form a double bond;
3) two $R^6$ together with the atom to which they are attached form $C_{3-6}$ cycloalkyl or 3- to 6-membered heterocyclyl, wherein the cycloalkyl or heterocyclyl is optionally further substituted with 0 to 4 substituents selected from H, halogen, OH, =O, cyano, $NH_2$, $C_{1-4}$ alkyl, $C_{1-4}$ alkoxy, halogen-substituted $C_{1-4}$ alkyl, hydroxy-substituted $C_{1-4}$ alkyl, or cyano-substituted $C_{1-4}$ alkyl, wherein the heterocyclyl contains 1 to 4 heteroatoms selected from O, S or N;
4) $X_2$ is selected from N.

The present disclosure relates to a pharmaceutical composition, comprising the compound or the stereoisomer, deuterate, solvate, prodrug, metabolite, pharmaceutically acceptable salt or co-crystal thereof according to the present disclosure, and a pharmaceutically acceptable carrier.

The present disclosure relates to a compound or a stereoisomer, deuterate, solvate, prodrug, metabolite, pharmaceutically acceptable salt or co-crystal thereof according to the present disclosure, or use of the pharmaceutical composition and pharmaceutical preparation according to the present disclosure in the preparation of a drug for treating a disease associated with the activity or expression quantity of complement factor B, preferably in the preparation of a drug for a kidney disease.

The present disclosure relates to a pharmaceutical composition or pharmaceutical preparation, wherein the pharmaceutical composition or pharmaceutical preparation contains a therapeutically effective amount of the compound or the stereoisomer, deuterate, solvate, prodrug, metabolite, pharmaceutically acceptable salt or co-crystal thereof according to the present disclosure, and a pharmaceutically acceptable excipient. The pharmaceutical composition can be in a unit preparation form (the amount of the active drug in the unit preparation is also referred to as the "preparation specification").

The present disclosure further provides a method for treating a disease in a mammal, the method comprises administering to the mammal a therapeutically effective amount of the compound or the stereoisomer, deuterate, solvate, prodrug, metabolite, pharmaceutically acceptable salt or co-crystal thereof or the pharmaceutical composition according to the present disclosure. In some embodiments, the mammal according to the present disclosure comprises humans.

The term “effective amount” or “therapeutically effective amount” according to the present application refers to a sufficient amount of the compound disclosed in the present application that is administered to ameliorate, to some extent, one or more symptoms of a disease or condition being treated (e.g., a kidney disease). In some embodiments, the outcome is the reduction and/or remission of signs, symptoms or causes of the disease, or any other desired change in the biological system. For example, an “effective amount” in terms of the therapeutic use is an amount of the composition comprising the compound disclosed in the present application that is required to provide clinically significant reduction of the symptoms of the disease. Examples of the therapeutically effective amount include, but are not limited to, 1-600 mg, 2-600 mg, 3-600 mg, 4-600 mg, 5-600 mg, 6-600 mg, 10-600 mg, 20-600 mg, 25-600 mg, 30-600 mg, 40-600 mg, 50-600 mg, 60-600 mg, 70-600 mg, 75-600 mg, 80-600 mg, 90-600 mg, 100-600 mg, 200-600 mg, 1-500 mg, 2-500 mg, 3-500 mg, 4-500 mg, 5-500 mg, 6-500 mg, 10-500 mg, 20-500 mg, 25-500 mg, 30-500 mg, 40-500 mg, 50-500 mg, 60-500 mg, 70-500 mg, 75-500 mg, 80-500 mg, 90-500 mg, 100-500 mg, 125-500 mg, 150-500 mg, 200-500 mg, 250-500 mg, 300-500 mg, 400-500 mg, 5-400 mg, 10-400 mg, 20-400 mg, 25-400 mg, 30-400 mg, 40-400 mg, 50-400 mg, 60-400 mg, 70-400 mg, 75-400 mg, 80-400 mg, 90-400 mg, 100-400 mg, 125-400 mg, 150-400 mg, 200-400 mg, 250-400 mg, 300-400 mg, 1-300 mg, 2-300 mg, 5-300 mg, 10-300 mg, 20-300 mg, 25-300 mg, 30-300 mg, 40-300 mg, 50-300 mg, 60-300 mg, 70-300 mg, 75-300 mg, 80-300 mg, 90-300 mg, 100-300 mg, 125-300 mg, 150-300 mg, 200-300 mg, 250-300 mg, 1-200 mg, 2-200 mg, 5-200 mg, 10-200 mg, 20-200 mg, 25-200 mg, 30-200 mg, 40-200 mg, 50-200 mg, 60-200 mg, 70-200 mg, 75-200 mg, 80-200 mg, 90-200 mg, 100-200 mg, 125-200 mg, and 150-200 mg.

In some embodiments, the pharmaceutical composition comprises the compound or the stereoisomer, deuterate, solvate, prodrug, metabolite, pharmaceutically acceptable salt or co-crystal thereof according to the present disclosure in an amount including but not limited to 1-600 mg, 20-400 mg, 25-200 mg, 1 mg, 5 mg, 10 mg, 15 mg, 20 mg, 25 mg, 30 mg, 35 mg, 40 mg, 45 mg, 50 mg, 55 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 180 mg, 190 mg, 200 mg, 210 mg, 220 mg, 230 mg, 240 mg, 250 mg, and 300 mg.

In some embodiments, the pharmaceutical composition may be formulated for specific routes of administration, such as oral administration, parenteral administration, and rectal administration. In addition, the pharmaceutical composition of the present disclosure can be formulated into a solid form (including but not limited to capsules, tablets, pills, granules, powders or suppositories) or a liquid form (including but not limited to solutions, suspensions or emulsions).

A method for treating a disease in a mammal, the method comprises administering to a subject a therapeutically effective amount of the compound or the stereoisomer, deuterate, solvate, prodrug, metabolite, pharmaceutically acceptable salt or co-crystal thereof according to the present disclosure, the therapeutically effective amount is preferably 1-600 mg, and the disease is preferably a kidney disease.

A method for treating a disease in a mammal, the method comprises administrating a drug, that is, the compound or the stereoisomer, deuterate, solvate, prodrug, metabolite, pharmaceutically acceptable salt or co-crystal thereof according to the present disclosure to a subject at a daily dose of 1-800 mg/day, the daily dose can be a single dose or a divided dose. In some embodiments, the daily dose includes but is not limited to 10-800 mg/day, 25-800 mg/day, 50-800 mg/day, 100-800 mg/day, 200-800 mg/day, 25-400 mg/day, 50-400 mg/day, 100-400 mg/day and 200-400 mg/day. In some embodiments, the daily dose includes but is not limited to 10 mg/day, 20 mg/day, 25 mg/day, 50 mg/day, 100 mg/day, 125 mg/day, 150 mg/day, 200 mg/day, 400 mg/day, 600 mg/day and 800 mg/day.

The present disclosure relates to a kit, wherein the kit can comprise a composition in the form of a single dose or multiple doses and comprises the compound, or the stereoisomer, deuterate, solvate, prodrug, metabolite, pharmaceutically acceptable salt or co-crystal thereof according to the present disclosure, and the amount of the compound, or the stereoisomer, deuterate, solvate, prodrug, metabolite, pharmaceutically acceptable salt or co-crystal thereof according to the present disclosure is identical to the amount of same in the above-mentioned pharmaceutical composition.

In the present disclosure, the amount of the compound, or the stereoisomer, deuterate, solvate, prodrug, metabolite, pharmaceutically acceptable salt or co-crystal thereof according to the present disclosure is calculated in the form of a free base in each case.

Unless stated to the contrary, the terms used in the description and claims have the following meanings.

The carbon, hydrogen, oxygen, sulfur, nitrogen or F, Cl, Br, I involved in the groups and compounds of the present disclosure all comprise their isotopes, and the carbon, hydrogen, oxygen, sulfur or nitrogen involved in the groups and compounds of the present disclosure is optionally further substituted with one or more of their corresponding isotopes, wherein the isotopes of carbon comprise $^{12}C$, $^{13}C$ and $^{14}C$, the isotopes of hydrogen comprise protium (H), deuterium (D, also known as heavy hydrogen), tritium (T, also known as superheavy hydrogen), the isotopes of oxygen comprise $^{16}O$, $^{17}O$ and $^{18}O$, the isotopes of sulfur comprise $^{32}S$, $^{33}S$, $^{34}S$ and $^{36}S$, the isotopes of nitrogen comprise $^{14}N$ and 15N, the isotopes of fluorine comprise $^{17}F$ and $^{19}F$, the isotopes of chlorine comprise $^{35}Cl$ and $^{37}Cl$, and the isotopes of bromine comprise $^{79}Br$ and $^{81}Br$.

“Halogen” refers to F, Cl, Br or I.

“Halogen-substituted” refers to F, Cl, Br or I substitution, including but not limited to a substitution with 1 to 10 substituents selected from F, Cl, Br or I, a substitution with 1 to 6 substituents selected from F, Cl, Br or I, or a substitution with 1 to 4 substituents selected from F, Cl, Br or I. “Halogen-substituted” is referred to simply as “halo”.

“Alkyl” refers to a substituted or unsubstituted linear or branched saturated aliphatic hydrocarbyl group, including but not limited to an alkyl group of 1 to 20 carbon atoms, an alkyl group of 1 to 8 carbon atoms, an alkyl group of 1 to 6 carbon atoms, or an alkyl group of 1 to 4 carbon atoms. Non-limiting examples of alkyl include methyl, ethyl, n-propyl, isopropyl, n-butyl, sec-butyl, neobutyl, tert-butyl, n-pentyl, isoamyl, neopentyl, n-hexyl and various branched isomers thereof. The definition of the “alkyl” herein is consistent with this definition. Alkyl can be monovalent, divalent, trivalent or tetravalent.

“Heteroalkyl” refers to a substituted or unsubstituted alkyl group in which one or more (including but not limited to 2, 3, 4, 5 or 6) carbon atoms are replaced by heteroatoms (including but not limited to N, O or S). Non-limiting examples include $—X(CH_2)v-X(CH_2)v-X(CH_2)v-H$ (v is an integer from 1 to 5; each X is independently selected from a bond or a heteroatom, which includes but is not limited to N, O or S; at least one X is selected from a heteroatom; and N or S in the heteroatom can be oxidized to various oxidation states). Heteroalkyl can be monovalent, divalent, trivalent or tetravalent.

“Alkylene” refers to a substituted or unsubstituted linear or branched divalent saturated hydrocarbyl group, including $—(CH_2)_v—$ (v is an integer from 1 to 10), and examples of alkylene include, but are not limited to, methylene, ethylene, propylene, butylene, etc.

“Heteroalkylene” refers to a substituted or unsubstituted alkylene group in which one or more (including but not limited to 2, 3, 4, 5 or 6) carbon atoms are replaced by heteroatoms (including but not limited to N, O or S). Non-limiting examples include $—X(CH_2)v\text{-}X(CH_2)v\text{-}X(CH_2)v\text{-}$, wherein v is an integer from 1 to 5, each X is independently selected from a bond, N, O or S, and at least one X is selected from N, O or S.

“Cycloalkyl” refers to a substituted or unsubstituted saturated carbocyclic hydrocarbyl group, usually having from 3 to 10 carbon atoms, and non-limiting examples include cyclopropyl, cyclobutyl, cyclopentyl, cyclohexyl, cycloheptyl, etc. The “cycloalkyl” herein is as defined above. Cycloalkyl can be monovalent, divalent, trivalent or tetravalent.

“Heterocycloalkyl” refers to a substituted or unsubstituted saturated heteroatom-containing cyclic hydrocarbyl group, including but not limited to 3 to 10 atoms, 3 to 8 atoms, or 1 to 3 heteroatoms selected from N, O or S. N and S selectively substituted in the heterocycloalkyl ring can be oxidized to various oxidation states. Heterocycloalkyl can be connected to a heteroatom or a carbon atom; heterocycloalkyl can be connected to an aromatic ring or a non-aromatic ring; and heterocycloalkyl can be connected to a bridged ring or a spiro ring. Non-limiting examples include oxiranyl, azacyclopropyl, oxacyclobutyl, azacyclobutyl, tetrahydrofuranyl, tetrahydro-2H-pyranyl, dioxolanyl, dioxanyl, pyrrolidinyl, piperidinyl, imidazolidinyl, oxazolidinyl, oxazinanyl, morpholinyl, hexahydropyrimidinyl or piperazinyl. Heterocycloalkyl can be monovalent, divalent, trivalent or tetravalent.

“Alkenyl” refers to a substituted or unsubstituted linear or branched unsaturated hydrocarbyl group, having at least 1, usually 1, 2 or 3 carbon-carbon double bonds, with a main chain including but not limited to 2 to 10, 2 to 6, or 2 to 4 carbon atoms. Examples of alkenyl include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 3-octenyl, 1-nonenyl, 3-nonenyl, 1-decenyl, 4-decenyl, 1,3-butadiene, 1,3-pentadiene, 1,4-pentadiene, 1,4-hexadiene, etc. The definition of the “alkenyl” herein is consistent with this definition. Alkenyl can be monovalent, divalent, trivalent or tetravalent.

“Alkynyl” refers to a substituted or unsubstituted linear or branched monovalent unsaturated hydrocarbyl group, having at least 1, usually 1, 2 or 3 carbon-carbon triple bonds, with a main chain including 2 to 10 carbon atoms, including but not limited to a main chain including 2 to 6 carbon atoms, or a main chain including 2 to 4 carbon atoms. Examples of alkynyl include, but are not limited to, ethynyl, propargyl, 1-propynyl, 2-propynyl, 1-butynyl, 2-butynyl, 3-butynyl, 1-pentynyl, 2-pentynyl, 3-pentynyl, 4-pentynyl, 1-methyl-1-butynyl, 2-methyl-1-butynyl, 2-methyl-3-butynyl, 1-hexynyl, 2-hexynyl, 3-hexynyl, 4-hexynyl, 5-hexynyl, 1-methyl-1-pentynyl, 2-methyl-1-pentynyl, 1-heptynyl, 2-heptynyl, 3-heptynyl, 4-heptynyl, 1-octynyl, 3-octynyl, 1-nonynyl, 3-nonynyl, 1-decynyl, 4-decynyl, etc. Alkynyl can be monovalent, divalent, trivalent or tetravalent.

“Alkoxy” refers to a substituted or unsubstituted —O-alkyl group. Non-limiting examples include methoxy, ethoxy, n-propoxy, isopropoxy, n-butoxy, sec-butoxy, tert-butoxy, n-pentoxy, n-hexyloxy, cyclopropoxy and cyclobutoxy.

“Carbocyclyl” or “carbocycle” refers to a substituted or unsubstituted aromatic ring or a substituted or unsubstituted saturated or unsaturated non-aromatic ring, wherein the aromatic ring or non-aromatic ring can be a 3- to 8-membered monocyclic ring, a 4- to 12-membered bicyclic ring or a 10- to 15-membered tricyclic ring system. Carbocyclyl can be connected to an aromatic ring or a non-aromatic ring, wherein the aromatic ring or non-aromatic ring is optionally a monocyclic ring, a bridged ring or a spiro ring. Non-limiting examples include cyclopropane, cyclobutane, cyclopentane, cyclohexane, cycloheptane, 1-cyclopentyl-1-enyl, 1-cyclopentyl-2-enyl, 1-cyclopentyl-3-enyl, cyclohexyl, 1-cyclohexyl-2-enyl, 1-cyclohexyl-3-enyl, cyclohexenyl, a benzene ring, a naphthalene ring,

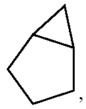,
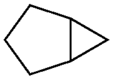,
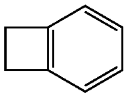,
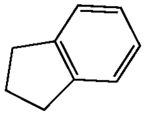 or
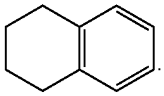.

“Carbocyclyl” or “carbocycle” can be monovalent, divalent, trivalent or tetravalent.

“Heterocyclyl” or “heterocycle” refers to a substituted or unsubstituted aromatic ring or a substituted or unsubstituted saturated or unsaturated non-aromatic ring, wherein the aromatic ring or non-aromatic ring can be 3- to 8-membered monocyclic ring, 4- to 12-membered bicyclic ring or 10- to 15-membered tricyclic ring system, and contains one or more (including but not limited to 2, 3, 4 or 5) heteroatoms selected from N, O or S, and the selectively substituted N and S in the heterocyclyl ring can be oxidized to various oxidation states. Heterocyclyl can be connected to a heteroatom or a carbon atom; heterocyclyl can be connected to an aromatic ring or a non-aromatic ring; and heterocyclyl can be connected to a bridged ring or a spiro ring. Non-limiting examples include oxiranyl, azacyclopropyl, oxacyclobutyl, azacyclobutyl, 1,3-dioxolanyl, 1,4-dioxolanyl, 1,3-dioxanyl, azacycloheptyl, pyridyl, furanyl, thienyl, pyranyl, N-alkylpyrrolyl, pyrimidinyl, pyrazinyl, pyridazinyl, imidazolyl, piperidinyl, morpholinyl, thiomorpholinyl, 1,3-dithianyl, dihydrofuranyl, dihydropyranyl, dithiolanyl, tetrahydrofuranyl, tetrahydropyrrolyl, tetrahydroimidazolyl, tetrahydrothiazolyl, tetrahydropyranyl, benzoimidazolyl, benzopyridinyl, pyrrolopyridinyl, benzodihydrofuranyl, pyrrolyl, pyrazolyl, thiazolyl, oxazolyl, pyrazinyl, indazolyl, benzothienyl, benzofuranyl, benzopyrrolyl, benzoimidazolyl, benzothiazolyl, benzoxazolyl, benzopyridyl, benzopyrimidinyl, benzopyrazinyl, piperazinyl, azabicyclo[3.2.1]octanyl, azabicyclo[5.2.0]nonanyl, oxatricyclo[5.3.1.1]dodecyl, azaadamantyl, oxaspiro[3.3]heptanyl,

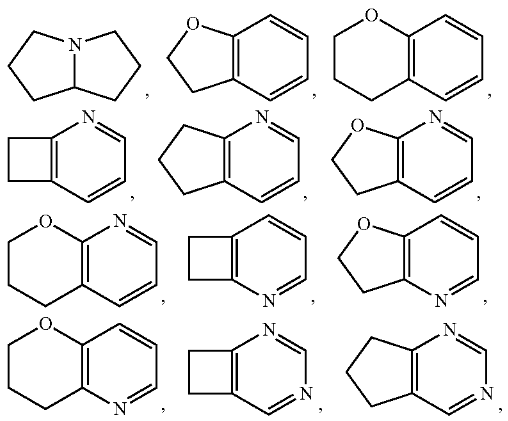

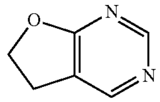

or

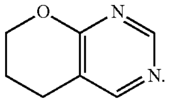

"Heterocyclyl" or "heterocycle" can be monovalent, divalent, trivalent or tetravalent.

"Spiro ring" or "spiro ring group" refers to a polycyclic group that shares one atom (called a spiro atom) between substituted or unsubstituted monocyclic rings. The number of ring atoms in the spiro ring system includes but is not limited to 5 to 20, 6 to 14, 6 to 12, or 6 to 10, wherein one or more rings may contain 0 or more (including but not limited to 1, 2, 3 or 4) double bonds, and can optionally contain 0 to 5 heteroatoms selected from N, O or S(=O)$_n$.

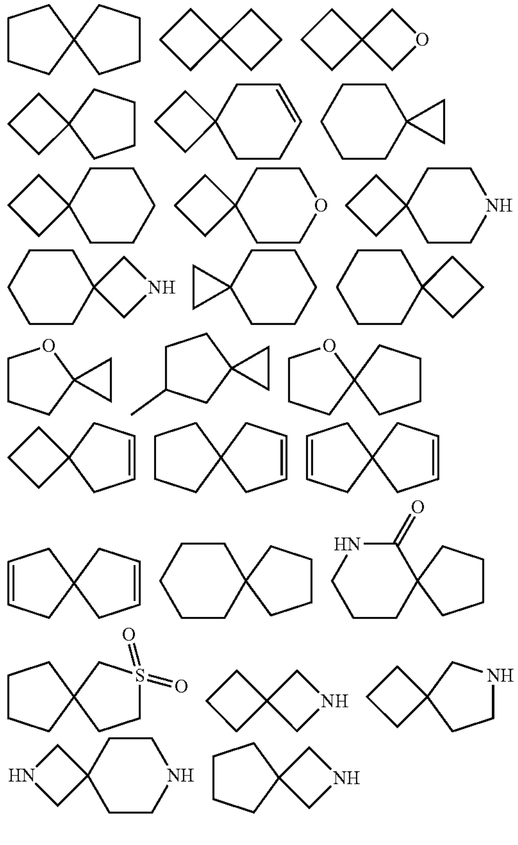

-continued

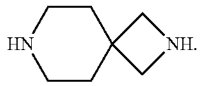

"Spiro ring" or "spiro ring group" can be monovalent, divalent, trivalent or tetravalent.

"Fused ring" or "fused ring group" refers to a polycyclic group in which each ring in the system shares an adjacent pair of atoms with other rings in the system, wherein one or more rings may contain 0 or more (including but not limited to 1, 2, 3 or 4) double bonds, and may be substituted or unsubstituted, and each ring in the fused ring system may contain 0 to 5 heteroatoms or groups containing heteroatoms (including but not limited to N, S(=O)$_n$ or O, wherein n is 0, 1 or 2). The number of ring atoms in the fused ring system includes but is not limited to 5 to 20, 5 to 14, 5 to 12, or 5 to 10. Non-limiting examples include:

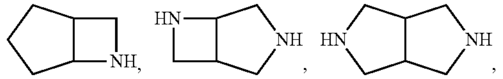

or

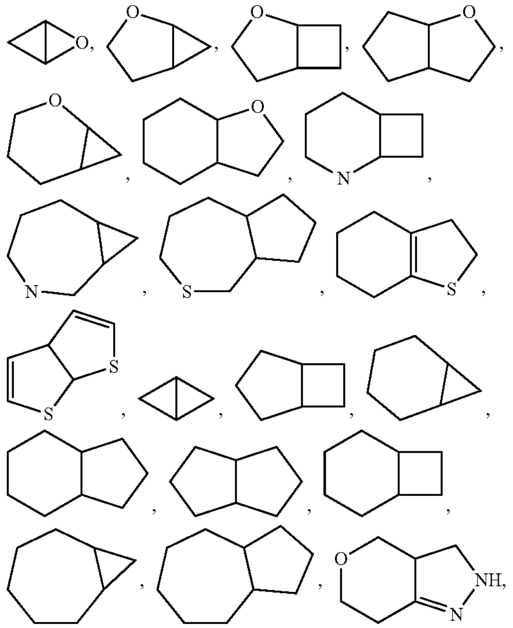

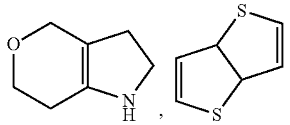

or

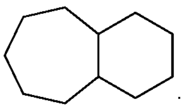

"Fused ring" or "fused ring group" can be monovalent, divalent, trivalent or tetravalent.

"Bridged ring" or "bridged ring group" refers to a substituted or unsubstituted polycyclic group containing any two atoms that are not directly connected, and may contain 0 or more double bonds. Any ring in the fused ring system may contain 0 to 5 groups selected from heteroatoms or groups containing heteroatoms (including but not limited to N, S(=O)n or O, wherein n is 0, 1 or 2). The number of ring atoms includes but is not limited to 5 to 20, 5 to 14, 5 to 12 or 5 to 10. Non-limiting examples include

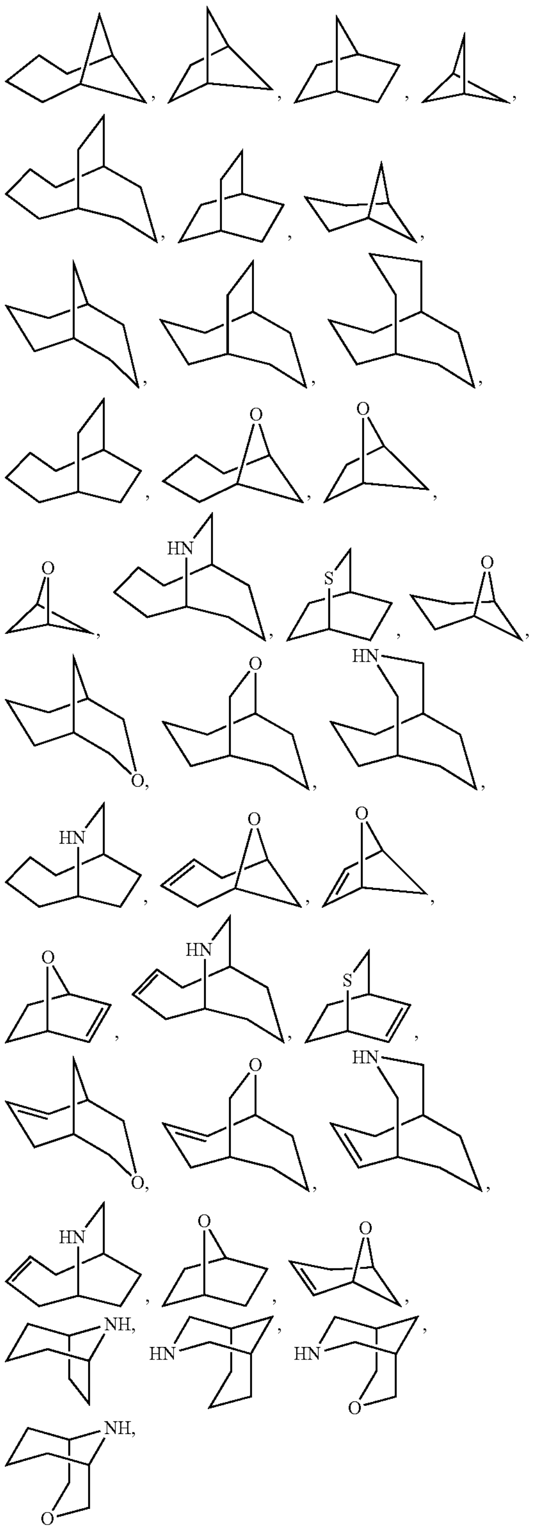

cubane or adamantane. “Bridged ring” or “bridged ring group” can be monovalent, divalent, trivalent or tetravalent.

“Carbospiro ring”, “spiro ring carbocyclyl”, “spirocarbocyclyl” or “carbospiro ring group” refers to a “spiro ring” with a ring system consisting only of carbon atoms. The definition of the “carbospiro ring”, “spiro ring carbocyclyl”, “spirocarbocyclyl” or “carbospiro ring group” herein is consistent with that of a spiro ring.

“Carbo-fused ring”, “fused ring carbocyclyl”, “fused carbocyclyl” or “carbo-fused ring group” refers to a “fused ring” with a ring system consisting only of carbon atoms. The definition of the “carbo-fused ring”, “fused ring carbocyclyl”, “fused carbocyclyl” or “carbo-fused ring group” herein is consistent with that of a fused ring.

“Carbo-bridged ring”, “bridged ring carbocyclyl”, “bridged carbocyclyl” or “carbo-bridged ring group” refers to a “bridged ring” with a ring system consisting only of carbon atoms. The definition of the “carbo-bridged ring”, “bridged ring carbocyclyl”, “bridged carbocyclyl” or “carbo-bridged ring group” herein is consistent with that of a bridged ring.

“Mono-heterocyclic ring”, “monocyclic heterocyclyl” or “mono-heterocyclic ring group” refers to “heterocyclyl” or “heterocycle” with a monocyclic system. The definition of the “heterocyclyl”, “monocyclic heterocyclyl” or “mono-heterocyclic ring group” herein is consistent with that of heterocycle.

“Fused heterocyclic ring”, “fused heterocyclic ring group”, “fused ring heterocyclyl” or “fused heterocyclic ring group” refers to a “fused ring” containing a heteroatom. The definition of the “fused heterocyclic ring”, “fused heterocyclic ring group”, “fused ring heterocyclyl” or “fused heterocyclic ring group” herein is consistent with that of a fused ring.

“Spiro-heterocyclic ring”, “spiro-heterocyclic ring group”, “spiro ring heterocyclyl” or “spiro-heterocyclic ring group” refers to a “spiro ring” containing a heteroatom. The definition of the “spiro-heterocyclic ring”, “spiro-heterocyclic ring group”, “spiro ring heterocyclyl” or “spiro-heterocyclic ring group” herein is consistent with that of a spiro ring.

“Bridged-heterocyclic ring”, “bridged-heterocyclic ring group”, “bridged ring heterocyclyl” or “bridged-heterocyclic ring group” refers to a “bridged ring” containing a heteroatom. The definition of the “bridged-heterocyclic ring”, “bridged-heterocyclic ring group”, “bridged ring heterocyclyl” or “bridged-heterocyclic ring group” herein is consistent with that of a bridged ring.

“Aryl” or “aromatic ring” refers to a substituted or unsubstituted aromatic hydrocarbyl group with a monocyclic ring or a fused ring, wherein the number of ring atoms in the aromatic ring includes but is not limited to 6 to 18, 6 to 12 or 6 to 10 carbon atoms. The aryl ring can be fused to a saturated or unsaturated carbocycle or heterocycle, wherein the ring connected to the parent structure is an aryl ring. Non-limiting examples include a benzene ring, a naphthalene ring, or

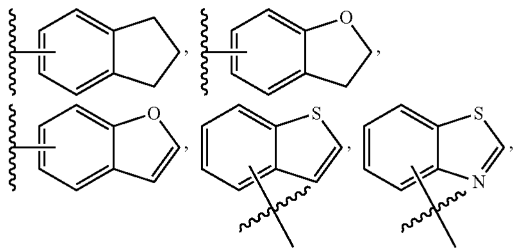

“Aryl or aromatic ring” can be monovalent, divalent, trivalent or tetravalent. When divalent, trivalent or tetravalent, the point of connection is on the aryl ring.

"Heteroaryl" or "heteroaromatic ring" refers to a substituted or unsubstituted aromatic hydrocarbyl group containing 1 to 5 heteroatoms or groups containing heteroatoms (including but not limited to N, O or S(=O)n, wherein n is 0, 1 or 2), wherein the number of ring atoms in the heteroaromatic ring includes but is not limited to 5-15, 5-10 or 5-6. Non-limiting examples of heteroaryl include, but are not limited to pyridyl, furanyl, thienyl, pyridyl, pyranyl, N-alkylpyrrolyl, pyrimidinyl, pyrazinyl, pyridazinyl, imidazolyl, benzopyrazole, benzimidazole, benzopyridine, pyrrolopyridine, etc. The heteroaryl ring may be fused to a saturated or unsaturated carbocycle or heterocycle, wherein the ring connected to the parent structure is an heteroaryl ring. Non-limiting examples include

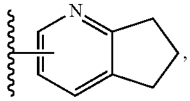,
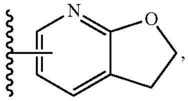,
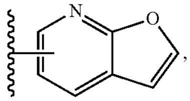,
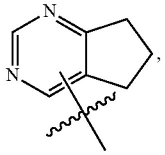,
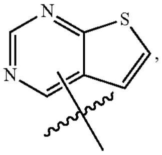,
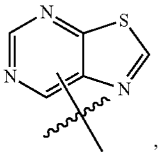,
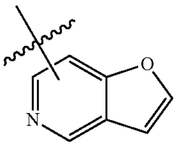 and
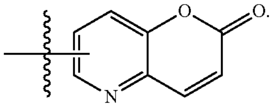

The definition of the "heteroaryl" herein is consistent with this definition. Heteroaryl can be monovalent, divalent, trivalent or tetravalent. When divalent, trivalent or tetravalent, the point of connection is on the heteroaryl ring.

"5-membered ring fused 5-membered heteroaromatic ring" refers to a 5 fused 5-membered fused heteroaromatic ring, wherein at least one of the two fused rings contains at least one heteroatom (including but not limited to O, S or N), and the entire group is aromatic. Non-limiting examples include a pyrrolopyrrole ring, a pyrazolopyrrole ring, a pyrazolopyrazole ring, a pyrrolofuran ring, a pyrazolofuran ring, a pyrrolothiophene ring and a pyrazolothiophene ring.

"5 fused 6-membered heteroaromatic ring" refers to a 5 fused 6-membered fused heteroaromatic ring, wherein at least one of the two fused rings contains at least one heteroatom (including but not limited to O, S or N), and the entire group is aromatic. Non-limiting examples include a benzo 5-membered heteroaryl and 6-membered heteroaromatic ring fused 5-membered heteroaromatic ring.

"Substitution" or "substituted" refers to a substitution with 1 or more (including but not limited to 2, 3, 4 or 5) substituents including but not limited to H, F, Cl, Br, I, alkyl, cycloalkyl, alkoxy, haloalkyl, mercaptan, hydroxyl, nitro, mercapto, amino, cyano, isocyano, aryl, heteroaryl, heterocyclyl, bridged ring group, spiro ring group, fused ring group, hydroxyalkyl, =O, carbonyl, aldehyde, carboxylic acid, carboxylate, $-(CH_2)_m-C(=O)-R^a$, $-O-(CH_2)_m-C(=O)-R^a$, $-(CH_2)_m-C(=O)-NR^bR^c$, $-(CH_2)_mS(=O)_nR^a$, $-(CH_2)_m$-alkenyl-$R^a$, $OR^d$ or $-(CH_2)_m$-alkynyl-$R^a$ (wherein m and n are 0, 1 or 2), arylthio, thiocarbonyl, silyl, $-NR^bR^c$, etc., wherein $R^b$ and $R^c$ are independently selected from H, hydroxyl, amino, carbonyl, alkyl, alkoxy, cycloalkyl, heterocyclyl, aryl, heteroaryl, sulfonyl, or trifluoromethylsulfonyl. Alternatively, $R^b$ and $R^c$ may form a five- or six-membered cycloalkyl or heterocyclyl.

"Containing 1 to 5 heteroatoms selected from O, S or N" means containing 1, 2, 3, 4 or 5 heteroatoms selected from O, S or N.

"Substituted with 0 to X substituents" refers to substituted with 0, 1, 2, 3 . . . X substituents, wherein X is selected from any integer between 1 and 10. For example, "substituted with 0 to 4 substituents" refers to substituted with 0, 1, 2, 3 or 4 substituents. For example, "substituted with 0 to 5 substituents" refers to substituted with 0, 1, 2, 3, 4 or 5 substituents. For example, "bridged-heterocyclic ring is optionally further substituted with 0 to 4 substituents selected from H or F" means that the bridged-heterocyclic ring is optionally further substituted with 0, 1, 2, 3 or 4 substituents selected from H or F.

An X- to Y-membered ring (X is selected from an integer less than Y and greater than 3, and Y is selected from any integer between 4 and 12) includes X+1-, X+2-, X+3-, X+4-, . . . , Y-membered rings. Rings include heterocycle, carbocycle, an aromatic ring, aryl, heteroaryl, cycloalkyl, a mono-heterocyclic ring, a fused heterocyclic ring, a spiro-heterocyclic ring or a bridged-heterocyclic ring. For example, a "4- to 7-membered mono-heterocyclic ring" refers to a 4-, 5-, 6- or 7-membered mono-heterocyclic ring, and a "5- to 10-membered fused heterocyclic ring" refers to a 5-, 6-, 7-, 8-, 9- or 10-membered fused heterocyclic ring.

The term "optional" or "optionally" refers to that the events or circumstances subsequently described may but not necessarily occur, and the description includes the occasions where the events or circumstances occur or do not occur. For example, "alkyl optionally substituted with F" means that the alkyl may but not necessarily be substituted by F, and the description includes the case where the alkyl is substituted with F and the case where the alkyl is not substituted with F.

"Pharmaceutically acceptable salt" or "pharmaceutically acceptable salt thereof" refers to a salt of the compound of the present disclosure, which salt maintains the biological effectiveness and characteristics of a free acid or a free base, and is obtained by reacting the free acid with a non-toxic inorganic base or organic base, or reacting the free base with a non-toxic inorganic acid or organic acid.

"Pharmaceutical composition" refers to a mixture of one or more compounds, or stereoisomers, tautomers, deuterates, solvates, prodrugs, metabolites, pharmaceutically acceptable salts or co-crystals thereof according to the present disclosure and other chemical components, wherein "other chemical components" refer to pharmaceutically acceptable carriers, excipients and/or one or more other therapeutic agents.

"Carrier" refers to a material that does not cause significant irritation to an organism and does not eliminate the biological activity and characteristics of a compound administered.

"Excipient" refers to an inert substance added to a pharmaceutical composition to facilitate the administration of a compound. Non-limiting examples include calcium carbonate, calcium phosphate, sugar, starch, cellulose derivatives (including microcrystalline cellulose), gelatin, vegetable oils, polyethylene glycols, diluents, granulating agents, lubricants, adhesives and disintegrants.

The term “preparation specification” refers to the weight of the active drug contained in each vial, tablet or other unit preparation.

“Prodrug” refers to a compound that can be converted into the compound of the present disclosure with the biological activity by metabolism in vivo. The prodrug of the present disclosure is prepared by modifying an amino or carboxyl group in the compound of the present disclosure, and the modification can be removed by conventional operations or in vivo to obtain a parent compound. When the prodrug of the present disclosure is administered to a mammalian individual, the prodrug is split to form a free amino or carboxyl group.

The term “co-crystal” refers to a crystal formed by the combination of active pharmaceutical ingredient (API) and co-crystal former (CCF) under the action of hydrogen bonds or other non-covalent bonds. The pure state of API and CCF are both solid at room temperature, and there is a fixed stoichiometric ratio between various components. The co-crystal is a multi-component crystal, which includes both a binary co-crystal formed between two neutral solids and a multi-element co-crystal formed between a neutral solid and a salt or solvate.

“Animal” is meant to include mammals, such as humans, companion animals, zoo animals, and domestic animals, preferably humans, horses, or dogs.

The term “stereoisomer” refers to an isomer produced as a result of different spatial arrangement of atoms in molecules, including cis-trans isomers, enantiomers and conformational isomers.

“Tautomer” refers to a functional group isomer produced by the rapid movement of an atom in two positions in a molecule, such as keto-enol isomerization and amide-imino alcohol isomerization.

“$IC_{50}$” refers to the concentration of a medicament or inhibitor required to inhibit half of a given biological process (or a component of the process such as an enzyme, a receptor and a cell).

DETAILED DESCRIPTION OF EMBODIMENTS

The technical solutions of the present disclosure will be described in detail by the following examples, but the scope of protection of the present disclosure includes but is not limited thereto.

The structures of the compounds are determined by nuclear magnetic resonance (NMR) or (and) mass spectrometry (MS). The NMR shift (δ) is given in the unit of 10-6 (ppm). NMR is determined with Bruker Avance III 400 and Bruker Avance 300; the solvent for determination is deuterated dimethyl sulfoxide (DMSO-d6), deuterated chloroform (CDCl3) and deuterated methanol (CD3OD); and the internal standard is tetramethylsilane (TMS);

MS is determined with Agilent 6120B (ESI) and Agilent 6120B (APCI));

HPLC is determined with Agilent 1260DAD high pressure liquid chromatograph (Zorbax SB-C18 100×4.6 mm, 3.5 μM);

Yantai Huanghai HSGF254 or Qingdao GF254 silica gel plate is used as a thin layer chromatography silica plate, and the silica gel plate for the thin layer chromatography (TLC) is of the specification of 0.15 mm-0.20 mm, and the specification when separating and purifying a product by thin layer chromatography is 0.4 mm-0.5 mm.

and for the column chromatography, Yantai Huanghai silica gel of 200-300 mesh silica gel is generally used as a carrier.

The known starting materials of the present disclosure can be synthesized by or according to methods known in the art, or can be purchased from Titan Technology Co., Ltd., Energy Chemical Co., Ltd., Shanghai Demo Co., Ltd., Chengdu Kelong Chemical Co., Ltd., Accela ChemBio Co., Ltd., J&K Scientific Co., Ltd. and other companies.

Tf: trifluoromethylsulfonyl. Boc: tert-butoxycarbonyl. Ts: P-toluenesulfonyl. Cbz: benzyloxycarbonyl.

TMS: trimethylsilane.

Chemical bond wavy lines represent the stereoisomerism of the connected atoms as R or S.

DMA: dimethylacetamide; Solutol: polyethylene glycol-15-hydroxystearate; Saline: physiological saline; MC: Methyl cellulose solution

Example 1

4-((2S,4S)-1-((5-methoxy-7-methyl-1H-indol-4-yl)methyl)-4-(methoxymethyl)piperidin-2-yl)benzoic acid (compound 1-A) trifluoroacetate 4-((2S,4R)-1-((5-methoxy-7-methyl-1H-indol-4-yl)methyl)-4-(methoxymethyl)piperidin-2-yl)benzoic acid (compound 1-B) trifluoroacetate

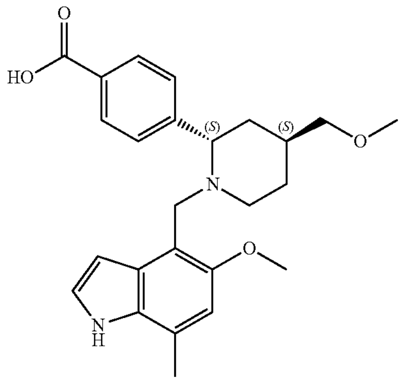

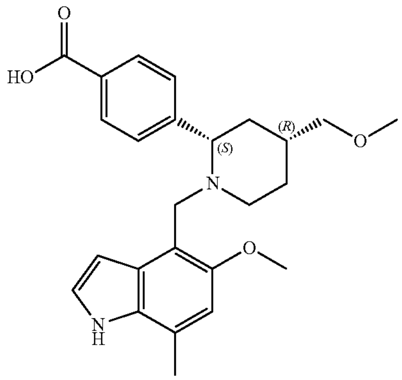

-continued

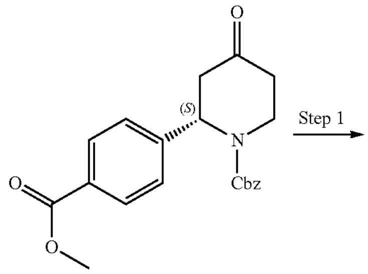

1a

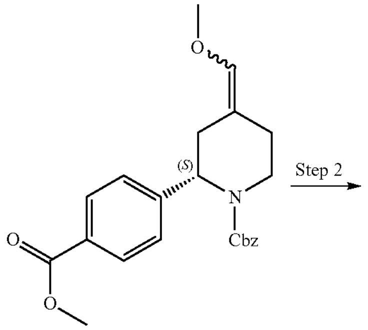

1b

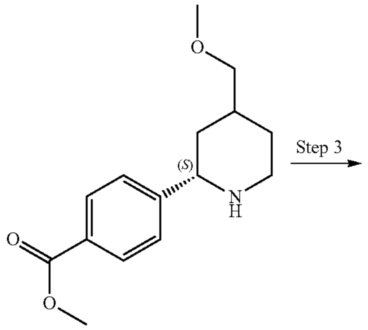

1c

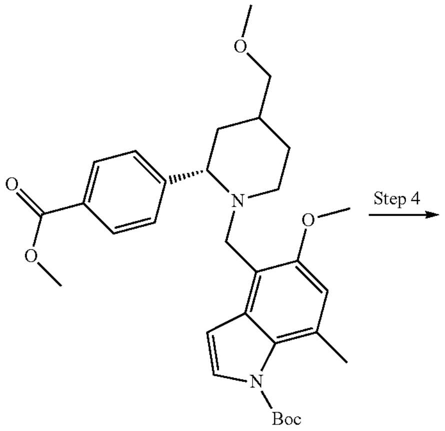

1d

-continued

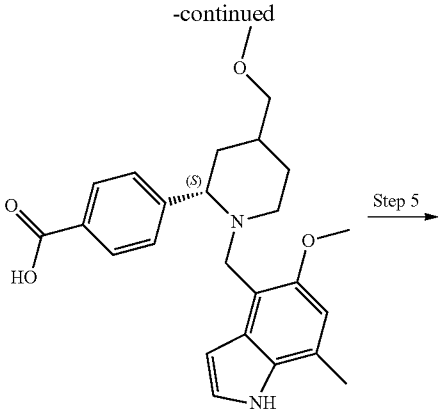

Compound 1

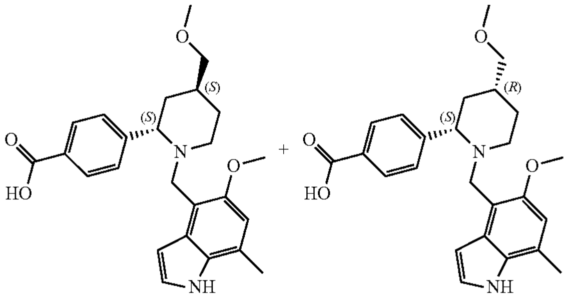

Compound 1-A Compound 1-B

Compound 1-a and Compound 1-b

Step 1: benzyl (S)-2-(4-(methoxycarbonyl)phenyl)-4-(methoxymethylene) piperidine-1-carboxylate (1b)

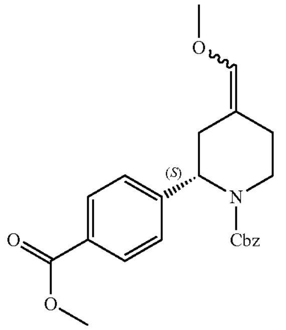

Methoxymethyltriphenylphosphine chloride (970 mg, 2.83 mmol) was added to 40 mL of ultra-dry THF, cooled with an ice-water bath, and 1 mol/L of potassium tert-butoxide in tetrahydrofuran (3.3 mL) was slowly added dropwise under nitrogen atmosphere, and the mixture was continuously stirred at 0° C. for 30 min. A solution of benzyl (S)-2-(4-(methoxycarbonyl)phenyl)-4-oxopiperidine-1-carboxylate (0.8 g, 2.18 mmol) (1a) (for the synthetic method, see WO 2020016749) in tetrahydrofuran (5 mL) was added and reacted at room temperature for 16 h. 50 mL of ethyl acetate was added into the reaction system, washed with 50 mL of saturated ammonium chloride aqueous solution, dried over anhydrous sodium sulfate, and concentrated under reduced pressure. The obtained crude product was separated and purified with silica gel column chromatography (petroleum ether/ethyl acetate (v/v)=5:1) to afford benzyl (S)-2-(4-(methoxycarbonyl)phenyl)-4-(methoxymethylene)piperidine-1-carboxylate (1b) (550 mg, yield: 64%).

LCMS m/z=396.1 $[M+1]^+$

Step 2: methyl 4-((2S)-4-(methoxymethyl)piperidin-2-yl)benzoate (1c) maleate

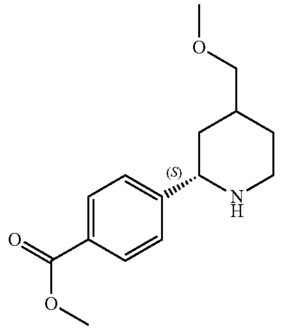

Benzyl (S)-2-(4-(methoxycarbonyl)phenyl)-4-(methoxymethylene) piperidine-1-carboxylate (1b) (550 mg, 1.39 mmol) was dissolved in 10 mL of methanol, 0.2 g of 10% palladium carbon was added, and the mixture was stirred at room temperature for 16 h under hydrogen atmosphere. The reaction system was suction-filtered under reduced pressure, and the filtrate was concentrated under reduced pressure to afford a crude product (350 mg). The above-mentioned crude product (350 mg) was dissolved in 20 mL of isopropyl acetate, and maleic acid (77 mg, 0.66 mmol) was added, and stirred at room temperature for 16 h. The reaction system was concentrated under reduced pressure to afford crude methyl 4-((2S)-4-(methoxymethyl)piperidin-2-yl)benzoate (1c) maleate (430 mg).

Step 3: tert-butyl 5-methoxy-4-(((2S)-2-(4-(methoxycarbonyl)phenyl)-4-(methoxymethyl)piperidin-1-yl)methyl)-7-methyl-1H-indole-1-carboxylate (1d)

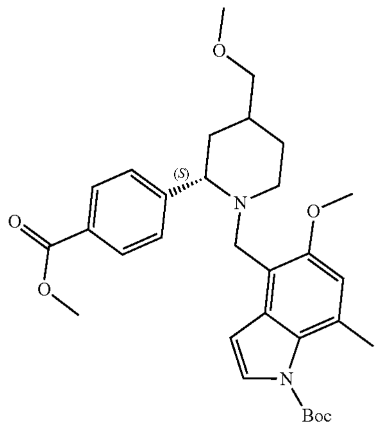

The above-mentioned crude methyl 4-((2S)-4-(methoxymethyl)piperidin-2-yl)benzoate (1c) maleate (430 mg) was dissolved in 10 mL of ethanol, tert-butyl 4-formyl-5-methoxy-7-methyl-1H-indole-1-carboxylate (385 mg, 1.33 mmol) (see WO 2015009616 for the synthesis method) was added and 10 mg of $Ir(CO)_2acac$ (CAS: 14023-80-4) was added. The mixture was heated to 75° C., and reacted for 48 h under the atmosphere of hydrogen balloon. The reaction liquid was cooled to room temperature, concentrated under reduced pressure, and the crude product was separated and purified with silica gel column chromatography (petroleum ether/ethyl acetate (v/v)=10:1) to afford tert-butyl 5-methoxy-4-(((2S)-2-(4-(methoxycarbonyl)phenyl)-4-(methoxymethyl)piperidin-1-yl)methyl)-7-methyl-1H-indole-1-carboxylate (1d) (340 mg, two-step yield from compound 1b: 46%).

LCMS m/z=537.5 $[M+1]^+$

Step 4: 4-((2S)-1-((5-methoxy-7-methyl-1H-indol-4-yl)methyl)-4-(methoxymethyl) piperidin-2-yl)benzoic acid (compound 1) trifluoroacetate

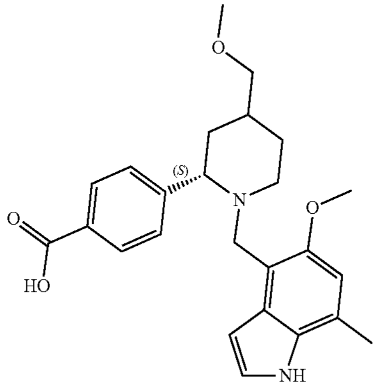

Tert-butyl 5-methoxy-4-(((2S)-2-(4-(methoxycarbonyl) phenyl)-4-(methoxymethyl)piperidin-1-yl)methyl)-7-methyl-1H-indole-1-carboxylate (1d) (340 mg, 0.63 mmol) was dissolved in 10 mL of methanol, solid potassium carbonate (410 mg, 2.97 mmol) was added, and the mixture was heated to 85° C. and reacted for 3 hours at reflux. The reaction liquid was cooled to room temperature and concentrated under reduced pressure to afford a crude product (750 mg). The above-mentioned crude product (750 mg) was dissolved in a mixed solvent of 10 mL of THF, 5 mL of methanol and 2 mL of water, lithium hydroxide monohydrate (250 mg, 5.95 mmol) was added, and the mixture was stirred at room temperature for 16 h. The reaction system was concentrated under reduced pressure, and the crude product was subjected to Pre-HPLC (instrument and preparative column: using Glison GX-281 preparative liquid phase chromatographic instrument, preparative column model: Sunfire C18, 5 μm, inner diameter×length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((2S)-1-((5-methoxy-7-methyl-1H-indol-4-yl)methyl)-4-(methoxymethyl) piperidin-2-yl) benzoic acid (compound 1) trifluoroacetate (180 mg).

LCMS m/z=423.2 $[M+1]^+$

Step 5: 4-((2S,4S)-1-((5-methoxy-7-methyl-1H-indol-4-yl)methyl)-4-(methoxymethyl)piperidin-2-yl)benzoic acid (compound 1-A) trifluoroacetate 4-((2S,4R)-1-((5-methoxy-7-methyl-1H-indol-4-yl)methyl)-4-(methoxymethyl)piperidin-2-yl)benzoic acid (compound 1-B) trifluoroacetate Compound 1-A

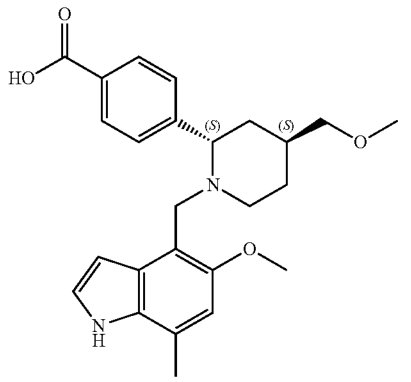

Compound 1-B

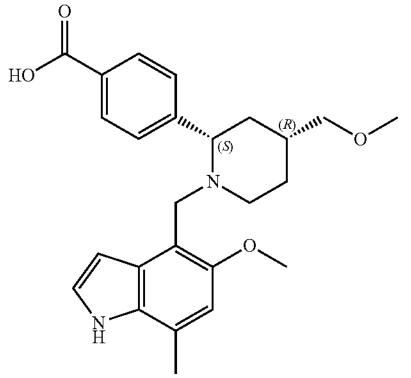

The trifluoroacetate of compound 1 was separated by high performance liquid chromatography to prepare and obtain the trifluoroacetate of compounds 1-a and 1-b. The preparation conditions were as follows: instrument and preparative column: Waters 350 preparative liquid phase chromatographic instrument was used, and the preparative column model was DAICEL CHIRALCEL AD. Mobile phase system: $sCO_2$ (supercritical $CO_2$)/ethanol, isocratic elution: $sCO_2$/ethanol=60/40, flow rate: 100 mL/min Analysis methods for compounds 1-a and 1-b: instrument: SHIMADZU LC-30AD sfc chromatographic column: Chiralpak AD-3 50×4.6 mm, I.D., 3 μm, mobile phase A: $sCO_2$ (supercritical $CO_2$), mobile phase B: isopropanol (containing 0.05% diethylamine), column temperature: 35° C., flow rate: 3 mL/min, wavelength: 220 nm, elution program: mobile phase A:B: 95:5-60:40.

Retention time of compound 1-a: 2.009 min;

Nuclear Magnetic Resonances Spectrum of Trifluoroacetate of Compound 1-a:

$^1H$ NMR (400 MHz, $CD_3OD$) δ 8.20-8.05 (m, 2H), 7.70-7.54 (m, 2H), 7.34-7.26 (m, 1H), 6.80-6.70 (m, 1H), 6.40-6.20 (m, 1H), 4.65-4.43 (m, 1H), 4.40-4.22 (m, 1H), 4.15-3.95 (m, 1H), 3.79-3.64 (m, 5H), 3.44 (s, 3H), 3.37-3.31 (m, 2H), 2.53-2.47 (m, 3H), 2.40-1.77 (m, 5H).

LCMS m/z=423.2 $[M+1]^+$

Retention time of compound 1-b: 2.339 min.

Nuclear Magnetic Resonances Spectrum of Trifluoroacetate of Compound 1-b:

$^1H$ NMR (400 MHz, $CD_3OD$) δ 8.28-8.16 (m, 2H), 7.79-7.64 (m, 2H), 7.37-7.29 (m, 1H), 6.76 (s, 1H), 6.33 (s, 1H), 4.65-4.47 (m, 1H), 4.45-4.27 (m, 1H), 4.23-4.05 (m, 1H), 3.75 (s, 3H), 3.65-3.50 (m, 1H), 3.45-3.28 (m, 6H), 2.51 (s, 3H), 2.25-2.05 (m, 2H), 2.00-1.75 (m, 2H), 1.74-1.50 (m, 1H).

LCMS m/z=423.2 $[M+1]^+$

Compound 1-a or compound 1-b is one of the isomers of compound 1-A or compound 1-B respectively.

Example 2

4-[(5R,7S)-8-[(5-methoxy-7-methyl-1H-indol-4-yl)methyl]-1-oxa-8-azaspiro[4.5]decan-7-yl]benzoic acid (compound 2-A) trifluoroacetate 4-((5S,7S)-8-((5-methoxy-7-methyl-1H-indol-4-yl)methyl)-1-oxa-8-azaspiro[4.5]decan-7-yl)benzoic acid (compound 2-B) trifluoroacetate

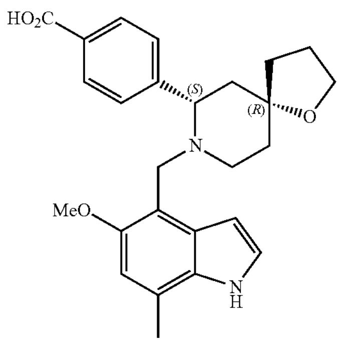

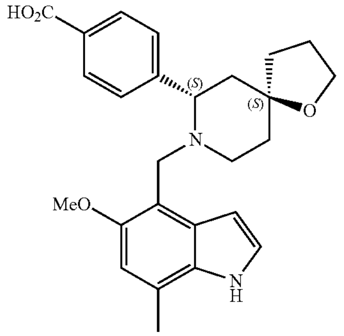

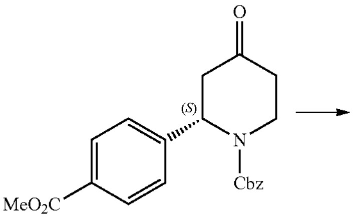

1a

-continued

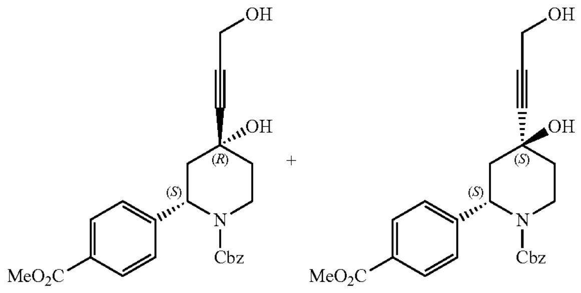

2b-a (diastereomer 1) and 2b-b (diastereomer 2)

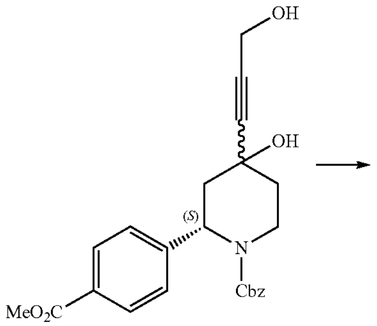

2b-a (diastereomer 1) or
2b-b (diastereomer 2)

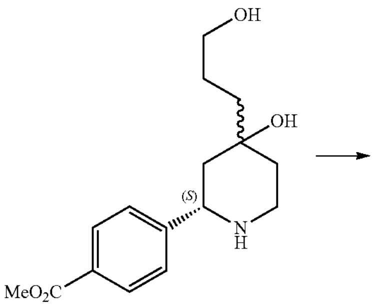

2c-a (diastereomer 1) or
2c-b (diastereomer 2)

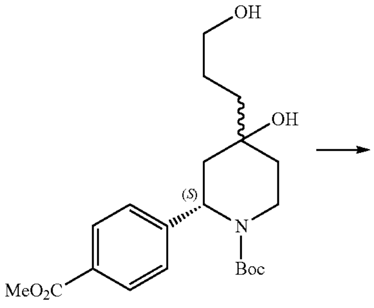

2d-a (diastereomer 1) or
2d-b (diastereomer 2)

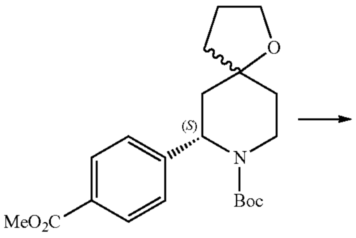

2e-a (diastereomer 1) or
2e-b (diastereomer 2)

-continued

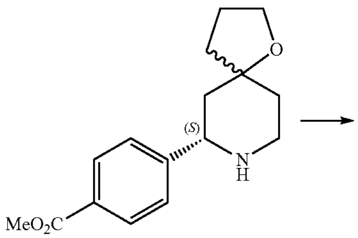

2f-a (diastereomer 1) or
2f-b (diastereomer 2)

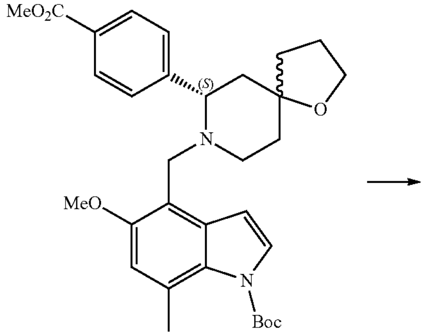

2g-a (diastereomer 1) or
2g-b (diastereomer 2)

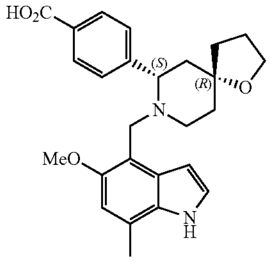

Compound 2-A or

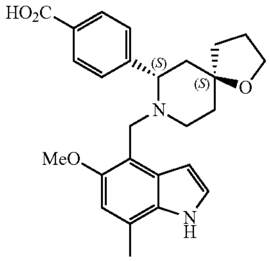

Compound 2-B

Compound 2-a (diastereomer 1) or
compound 2-b (diastereomer 2)

1. Synthesis of Intermediates 2b-a (Diastereomer 1) and 2b-b (Diastereomer 2)

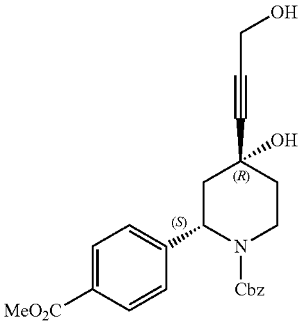

-continued

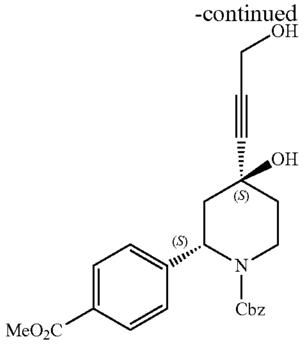

Under a nitrogen atmosphere, propynyloxytrimethylsilane (0.90 mL, 5.86 mmol) and anhydrous tetrahydrofuran (6 mL) were added to the reaction flask respectively, and then the system was cooled to 0° C. At this temperature, a solution of ethyl magnesium bromide solution in tetrahydrofuran (6 mL, 1.0 mol/L) was slowly added dropwise into the reaction bottle. After the dropwise addition was completed, stirring was continued at 0° C. for 30 min, then the mixture was raised to room temperature and stirred for 90 min. The reaction system was cooled to 0° C., and then a solution of benzyl (S)-2-(4-(methoxycarbonyl)phenyl)-4-oxopiperidine-1-carboxylate (1.1 g, 3.0 mmol) (1a) (see WO 2020016749 for the synthesis method) in tetrahydrofuran solution (6 mL) was slowly added dropwise, the reaction was continued at 0° C. for 3 h, then the reaction system was slowly returned to room temperature, and the reaction was continued at room temperature for 96 h. The reaction liquid was cooled to 0° C., and saturated ammonium chloride solution (20 mL) was slowly added dropwise to quench the reaction. After the dropwise addition was completed, the system was returned to room temperature and stirred for 2 h, and then extracted with ethyl acetate (30 mL×3). The organic phase was washed with 20 mL of saturated sodium chloride solution, dried over anhydrous sodium sulfate, and concentrated under reduced pressure. The crude product was separated and purified with silica gel column chromatography (ethyl acetate/petroleum ether (v/v)=1:1) to afford the intermediate. 2b-a (diastereomer 1) (0.47 g, yield: 37%, Rf=0.25) and 2b-b (diastereomer 2) (0.24 g, yield: 19%, Rf=0.20).

2. Synthesis of Compound 2-a (Diastereomer 1)

Step 1: methyl 4-((2S)-4-hydroxy-4-(3-hydroxypropyl)piperidin-2-yl)benzoate [2c-a (diastereomer 1)]

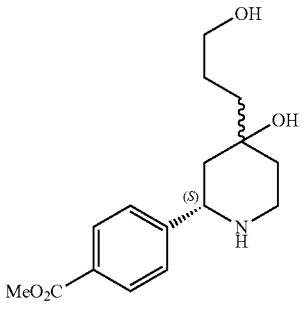

The intermediate 2b-a (diastereomer 1) (1.50 g, 3.54 mmol) was dissolved in 10 mL of methanol, 10% palladium on carbon (750 mg) was added, and the mixture was reacted under the atmosphere of hydrogen balloon for 5 h. The reaction system was suction-filtered, and the filtrate was concentrated under reduced pressure to afford crude methyl 4-((2S)-4-hydroxy-4-(3-hydroxypropyl)piperidin-2-yl)benzoate [2c-a (diastereomer 1)] (1.0 g).

LCMS m/z=294.1 $[M+1]^+$

Step 2: tert-butyl (2S)-4-hydroxy-4-(3-hydroxypropyl)-2-(4-(methoxycarbonyl) phenyl)piperidine-1-carboxylate [2d-a (diastereomer 1)]

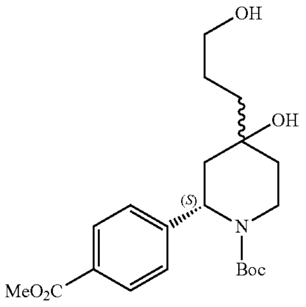

The above-mentioned crude methyl 4-((2S)-4-hydroxy-4-(3-hydroxypropyl)piperidin-2-yl)benzoate [2c-a (diastereomer 1)] (1.0 g) was dissolved in 10 mL of dichloromethane, 1 mL of anhydrous methanol and triethylamine (1.03 g, 10.2 mmol) were added in sequence, then $Boc_2O$ (1.48 g, 6.78 mmol) was added, and the mixture was reacted at room temperature for 4 h after addition. 20 mL of water and 20 mL of dichloromethane were added to the reaction liquid, the liquid separation was conducted, and the organic layer was washed with 10 mL of saturated sodium chloride solution, dried over anhydrous sodium sulfate and concentrated under reduced pressure. The residue was separated and purified with silica gel column chromatography (petroleum ether/ethyl acetate (v/v)=2:3) to afford tert-butyl (2S)-4-hydroxy-4-(3-hydroxypropyl)-2-(4-(methoxycarbonyl)phenyl)piperidine-1-carboxylate [2d-a (diastereomer 1)] (0.800 g, the two-step yield from intermediate 2b-a (diastereomer 1): 57%).

Step 3: tert-butyl (7S)-7-(4-(methoxycarbonyl)phenyl)-1-oxa-8-azaspiro decane-8-carboxylate [2e-a (diastereomer 1)]

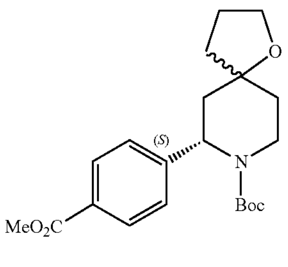

Tert-butyl (2S)-4-hydroxy-4-(3-hydroxypropyl)-2-(4-(methoxycarbonyl) phenyl)piperidine-1-carboxylate [2d-a (diastereomeric 1)] (0.650 g, 1.65 mmol) was dissolved in 10 mL of dichloromethane, and triethylamine (0.501 g, 4.95 mmol) and DMAP (0.020 g, 0.164 mmol) were added in sequence, then p-toluenesulfonyl chloride (0.629 g, 3.30 mmol) was added, and the mixture was reacted at room temperature for 16 h after addition. 20 mL of water and 50 mL of ethyl acetate were added to the reaction liquid, the liquid separation was conducted, and the organic layer was washed with 20 mL of saturated sodium chloride solution, dried over anhydrous sodium sulfate and concentrated under reduced pressure. The obtained crude product was separated and purified with silica gel column chromatography (petroleum ether/ethyl acetate (v/v)=9:1) to afford tert-butyl (7S)-7-(4-(methoxycarbonyl)phenyl)-1-oxa-8-azaspiro[4.5]decane-8-carboxylate [2e-a (diastereomer 1)] (0.360 g, yield: 58%).

$^1$H NMR (400 MHz, $CDCl_3$) δ 7.97 (d, 2H), 7.28 (d, 2H), 5.38-5.30 (m, 1H), 4.14-4.04 (m, 1H), 3.90 (s, 3H), 3.63-3.54 (m, 1H), 3.54-3.45 (m, 1H), 3.30-3.19 (m, 1H), 2.37-2.29 (m, 1H), 1.99-1.78 (m, 3H), 1.78-1.55 (m, 4H), 1.41 (s, 9H).

LCMS m/z=398.2 $[M+23]^+$

Step 4: methyl 4-((7S)-1-oxa-8-azaspiro[4.5]decan-7-yl)benzoate [2f-a (diastereomer 1)]hydrochloride

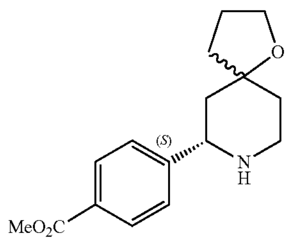

Tert-butyl (7S)-7-(4-(methoxycarbonyl)phenyl)-1-oxa-8-azaspiro[4.5]decane-8-carboxylate [2e-a (diastereomer 1)] (0.350 g, 0.93 mmol) was dissolved in 5 mL of dichloromethane, 5 mL of 4 mol/L hydrochloric acid in 1,4-dioxane was added, and stirred at room temperature for 4 h. The reaction liquid was concentrated under reduced pressure to afford crude methyl 4-((7S)-1-oxa-8-azaspiro[4.5]decan-7-yl)benzoate [2f-a (diastereomer 1)]hydrochloride (0.290 g).

LCMS m/z=276.2 $[M+1]^+$

Step 5: tert-butyl 5-methoxy-4-(((7S)-7-(4-(methoxycarbonyl)phenyl)-1-oxa-8-azaspiro[4.5]decan-8-yl)methyl)-7-methyl-1H-indole-1-carboxylate [2g-a (diastereomer 1)]

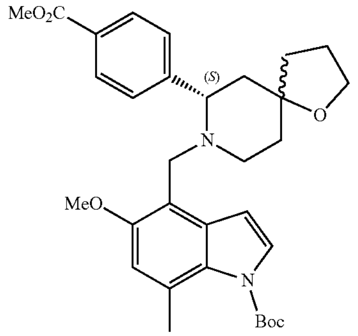

The above-mentioned crude methyl 4-((7S)-1-oxa-8-azaspiro[4.5]decan-7-yl)benzoate [2f-a (diastereomer 1)]hydrochloride (0.290 g) was dissolved in 10 mL of absolute ethanol, and tert-butyl 4-formyl-5-methoxy-7-methyl-1H-indole-1-carboxylate (270 mg, 0.93 mmol) was added (see WO 2015009616 for the synthesis method), nitrogen replacement was performed three times, 10 mg of $Ir(CO)_2$acac was added, then nitrogen replacement was performed three times, the mixture was heated to 75° C., and reacted under the atmosphere of hydrogen balloon for 24 hours. The reaction liquid was cooled to room temperature and concentrated under reduced pressure, and the residue was separated and purified with silica gel column chromatography (petroleum ether/ethyl acetate (v/v)=85:15) to afford tert-butyl 5-methoxy-4-(((7S)-7-(4-(methoxycarbonyl)phenyl)-1-oxa-8-azaspiro[4.5]decan-8-yl)methyl)-7-methyl-1H-indole-1-carboxylate [2g-a (diastereomer 1)] (0.170 g, two-step yield from compound 2e-a (diastereomer 1): 33%).

$^1$H NMR (400 MHz, $CDCl_3$) δ 8.04 (d, 2H), 7.60 (d, 2H), 7.47 (d, 1H), 6.68-6.62 (m, 2H), 3.91 (s, 3H), 3.83-3.71 (m, 5H), 3.59 (d, 1H), 3.25 (d, 1H), 3.21 (dd, 1H), 2.92-2.83 (m, 1H), 2.58 (s, 3H), 2.10-2.00 (m, 1H), 1.99-1.65 (m, 7H), 1.61 (s, 9H), 1.53-1.43 (m, 1H).

LCMS m/z=549.3 $[M+1]^+$

Step 6: 4-((7S)-8-((5-methoxy-7-methyl-1H-indol-4-yl)methyl)-1-oxa-8-azaspiro[4.5]decan-7-yl)benzoic acid [compound 2-a (diastereomer 1)]trifluoroacetate Compound 2-A

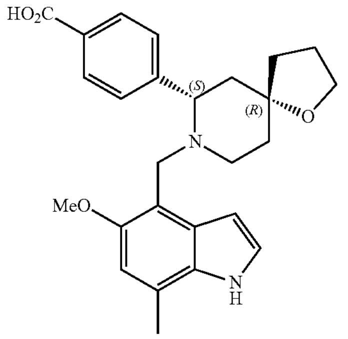

or

Compound 2-B

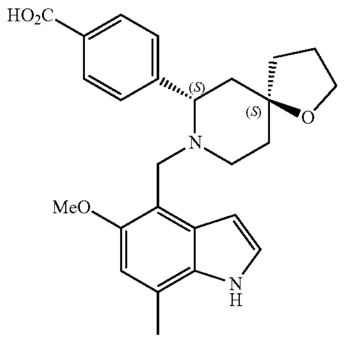

Tert-butyl 5-methoxy-4-(((7S)-7-(4-(methoxycarbonyl)phenyl)-1-oxa-8-azaspiro[4.5]decan-8-yl)methyl)-7-methyl-1H-indole-1-carboxylate [2g-a (diastereomer 1)] (0.160 g, 0.29 mmol) was dissolved in 10 mL of anhydrous methanol, solid potassium carbonate was added (0.200 g, 1.45 mmol), and the mixture was heated to 75° C. and reacted for 3 hours at reflux after the addition. The reaction liquid was cooled to room temperature, 10 mL of tetrahydrofuran, 2 mL of water and 2 mL of methanol were added in sequence, then lithium hydroxide monohydrate (0.120 g, 2.9 mmol) was added and reacted at room temperature for 16 h. The reaction liquid was concentrated under reduced pressure, 10 mL of water was added to the residue, 0.1 mol/L of citric acid aqueous solution was added dropwise to adjust the pH to 8, and the solution was subjected to Pre-HPLC (instrument and preparative column: using Glison GX-281 preparative liquid phase chromatographic instrument, preparative column model: Sunfire C18, 5 μm, inner diameter×length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((7S)-8-((5-methoxy-7-methyl-1H-indol-4-yl)methyl)-1-oxa-8-azaspiro[4.5]decan-7-yl)benzoic acid [compound 2-a (diastereomer 1)]trifluoroacetate (0.100 g).

$^1$H NMR (400 MHz, $CD_3OD$) δ 8.23 (d, 2H), 7.74 (d, 2H), 7.33 (d, 1H), 6.77 (s, 1H), 6.34 (d, 1H), 4.62 (d, 1H), 4.34 (d, 1H), 4.20 (d, 1H), 3.90-3.79 (m, 2H), 3.76 (s, 3H), 3.65-3.55 (m, 1H), 3.43-3.34 (m, 1H), 2.51 (s, 3H), 2.34-2.23 (m, 1H), 2.23-1.98 (m, 6H), 1.92-1.82 (m, 1H).

LCMS m/z=435.3 $[M+1]^+$

Compound 2-a (diastereomer 1) is one of the isomers of compound 2-A or compound 2-B.

3. Synthesis of Compound 2-b (Diastereomer 2)

Step 1: methyl 4-((2S)-4-hydroxy-4-(3-hydroxypropyl)piperidin-2-yl)benzoate [2c-b (diastereomer 2)]

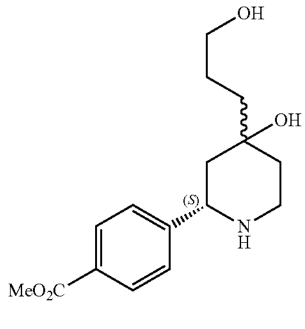

The intermediate 2b-b (diastereomer 2) (0.700 g, 1.65 mmol) was dissolved in 10 mL of methanol, 10% palladium on carbon (350 mg) was added, and the mixture was reacted under the atmosphere of hydrogen balloon for 5 h. The reaction system was suction-filtered, and the filtrate was concentrated under reduced pressure to afford crude methyl 4-((2S)-4-hydroxy-4-(3-hydroxypropyl)piperidin-2-yl)benzoate [2c-b (diastereomer 2)] (0.480 g).

LCMS m/z=294.1 $[M+1]^+$

Step 2: tert-butyl (2S)-4-hydroxy-4-(3-hydroxypropyl)-2-(4-(methoxycarbonyl) phenyl)piperidine-1-carboxylate [2d-b (diastereomer 2)]

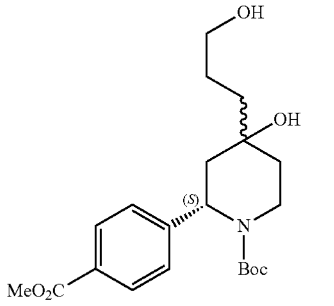

The above-mentioned crude methyl 4-((2S)-4-hydroxy-4-(3-hydroxypropyl)piperidin-2-yl)benzoate [2c-b (diastereomer 2)] (0.480 g) was dissolved in 10 mL of dichloromethane, 1 mL of anhydrous methanol and triethylamine (0.500 g, 4.94 mmol) were added in sequence, then $Boc_2O$ (0.720 g, 3.30 mmol) was added, and the mixture was reacted at room temperature for 4 h after addition. 20 mL of water and 20 mL of dichloromethane were added to the reaction liquid, the liquid separation was conducted, and the organic layer was washed with 10 mL of saturated sodium chloride solution, dried over anhydrous sodium sulfate and concentrated under reduced pressure. The residue was separated and purified with silica gel column chromatography (petroleum ether/ethyl acetate (v/v)=2:3) to afford tert-butyl (2S)-4-hydroxy-4-(3-hydroxypropyl)-2-(4-(methoxycarbonyl)phenyl)piperidine-1-carboxylate [2d-b (diastereomer 2)] (0.320 g, the two-step yield from intermediate 2b-b (diastereomer 2): 49%).

Step 3: tert-butyl (7S)-7-(4-(methoxycarbonyl)phenyl)-1-oxa-8-azaspiro[4.5]decane-8-carboxylate [2e-b (diastereomer 2)]

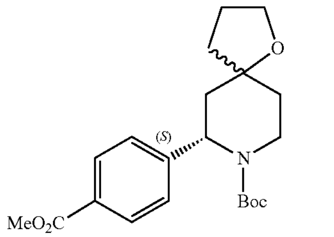

Tert-butyl (2S)-4-hydroxy-4-(3-hydroxypropyl)-2-(4-(methoxycarbonyl) phenyl)piperidine-1-carboxylate [2d-b (diastereomeric 2)] (0.320 g, 0.81 mmol) was dissolved in 10 mL of dichloromethane, and triethylamine (0.250 g, 2.47 mmol) and DMAP (0.010 g, 0.0820 mmol) were added in sequence, then p-toluenesulfonyl chloride (0.310 g, 1.63 mmol) was added, and the mixture was reacted at room temperature for 16 h after addition. 20 mL of water and 50 mL of ethyl acetate were added to the reaction liquid, the liquid separation was conducted, and the organic layer was washed with 20 mL of saturated sodium chloride solution, dried over anhydrous sodium sulfate and concentrated under reduced pressure. The obtained crude product was separated and purified with silica gel column chromatography (petroleum ether/ethyl acetate (v/v)=9:1) to afford tert-butyl (7S)-7-(4-(methoxycarbonyl)phenyl)-1-oxa-8-azaspiro[4.5]decane-8-carboxylate [2e-b (diastereomer 2)] (0.160 g, yield: 53%).

$^1$H NMR (400 MHz, $CDCl_3$) δ 7.99 (d, 2H), 7.28-7.23 (m, 2H), 5.37 (t, 1H), 4.25-4.15 (m, 1H), 3.91 (s, 3H), 3.79 (t, 2H), 3.18-3.08 (m, 1H), 2.17-2.12 (m, 2H), 1.85-1.72 (m, 3H), 1.66-1.56 (m, 1H), 1.44-1.31 (m, 10H), 1.30-1.17 (m, 1H).

Step 4: methyl 4-((7S)-1-oxa-8-azaspiro[4.5]decan-7-yl)benzoate [2f-b (diastereomer 2)]hydrochloride

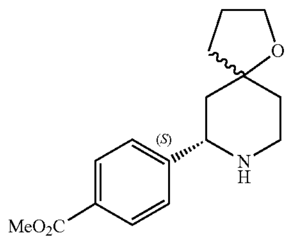

Tert-butyl (7S)-7-(4-(methoxycarbonyl)phenyl)-1-oxa-8-azaspiro[4.5]decane-8-carboxylate [2e-b (diastereomer 2)] (0.160 g, 0.426 mmol) was dissolved in 5 mL of dichloromethane, 5 mL of 4 mol/L hydrochloric acid in 1,4-dioxane was added, and stirred at room temperature for 4 h. The reaction liquid was concentrated under reduced pressure to afford crude methyl 4-((7S)-1-oxa-8-azaspiro[4.5]decan-7-yl)benzoate [2f-b (diastereomer 2)]hydrochloride (0.130 g).

LCMS m/z=276.2 $[M+1]^+$

Step 5: tert-butyl 5-methoxy-4-(((7S)-7-(4-(methoxycarbonyl)phenyl)-1-oxa-8-azaspiro[4.5]decan-8-yl)methyl)-7-methyl-1H-indole-1-carboxylate [2g-b (diastereomer 2)]

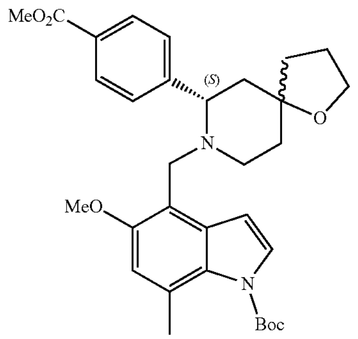

The above-mentioned crude methyl 4-((7S)-1-oxa-8-azaspiro[4.5]decan-7-yl)benzoate [2f-b (diastereomer 2)]hydrochloride (0.130 g) was dissolved in 10 mL of absolute ethanol, and tert-butyl 4-formyl-5-methoxy-7-methyl-1H-indole-1-carboxylate (144 mg, 0.50 mmol) was added (see WO 2015009616 for the synthesis method), nitrogen replacement was performed three times, 10 mg of $Ir(CO)_2acac$ was added, then nitrogen replacement was performed three times, the mixture was heated to 75° C., and reacted under the atmosphere of hydrogen balloon for 24 hours. The reaction liquid was cooled to room temperature and concentrated under reduced pressure, and the residue was separated and purified with silica gel column chromatography (petroleum ether/ethyl acetate (v/v)=85:15) to afford tert-butyl 5-methoxy-4-(((7S)-7-(4-(methoxycarbonyl)phenyl)-1-oxa-8-azaspiro[4.5]decan-8-yl)methyl)-7-methyl-1H-indole-1-carboxylate [2g-b (diastereomer 2)] (0.09 g, two-step yield from compound 2e-b (diastereomer 2): 39%).

LCMS m/z=549.3 $[M+1]^+$

Step 6: 4-((7S)-8-((5-methoxy-7-methyl-1H-indol-4-yl)methyl)-1-oxa-8-azaspiro[4.5]decan-7-yl)benzoic acid [compound 2-b (diastereomer 2)]trifluoroacetate Compound 2-A

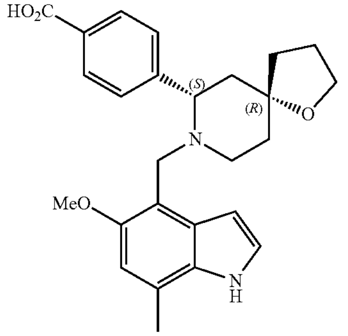

or

Compound 2-B

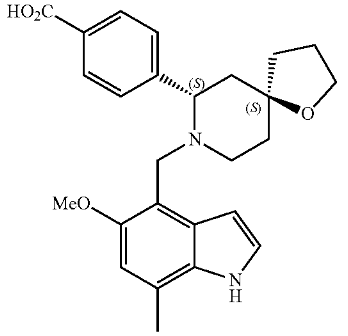

Tert-butyl 5-methoxy-4-(((7S)-7-(4-(methoxycarbonyl)phenyl)-1-oxa-8-azaspiro [4.5]decan-8-yl)methyl)-7-methyl-1H-indole-1-carboxylate [2g-b (diastereomer 2)] (0.090 g, 0.16 mmol) was dissolved in 10 mL of anhydrous methanol, solid potassium carbonate was added (0.11 g, 0.80 mmol), and the mixture was heated to 75° C. and reacted for 3 hours at reflux after the addition. The reaction liquid was cooled to room temperature, 10 mL of tetrahydrofuran, 2 mL of water and 2 mL of methanol were added in sequence, then lithium hydroxide monohydrate (0.067 g, 1.6 mmol) was added and reacted at room temperature for 16 h. The reaction liquid was concentrated under reduced pressure, 10 mL of water was added to the residue, 0.1 mol/L of citric acid aqueous solution was added dropwise to adjust the pH to 8, and the solution was subjected to Pre-HPLC (instrument and preparative column: using Glison GX-281 preparative liquid phase chromatographic instrument, preparative column model: Sunfire C18, 5 μm, inner diameter×length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((7S)-8-((5-methoxy-7-methyl-1H-indol-4-yl)methyl)-1-oxa-8-azaspiro[4.5]decan-7-yl) benzoic acid [compound 2-b (diastereomer 2)]trifluoroacetate (0.045 g).

$^1$H NMR (400 MHz, $CD_3OD$) δ 8.22 (d, 2H), 7.74 (d, 2H), 7.33 (d, 1H), 6.77 (s, 1H), 6.36 (d, 1H), 4.83-4.70 (m, 1H), 4.34 (d, 1H), 4.22 (d, 1H), 4.00-3.86 (m, 2H), 3.76 (s, 3H), 3.63-3.52 (m, 1H), 3.50-3.40 (m, 1H), 2.51 (s, 3H), 2.31-2.20 (m, 1H), 2.10-1.92 (m, 4H), 1.90-1.77 (m, 3H).

LCMS m/z=435.3 $[M+1]^+$

Compound 2-b (diastereomer 2) is one of the isomers of compound 2-A or compound 2-B.

Example 3

4-[(2S,4S)-1-[(5-methoxy-7-methyl-1H-indol-4-yl) methyl]-4-(2-methoxyethoxy) piperidin-2-yl]benzoic acid (compound 3) trifluoroacetate

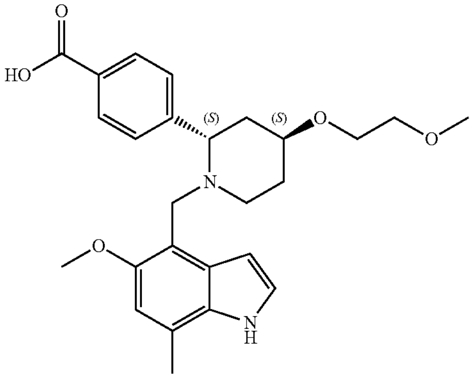

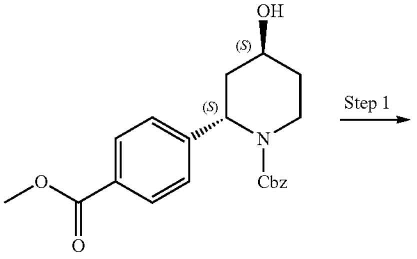

3a

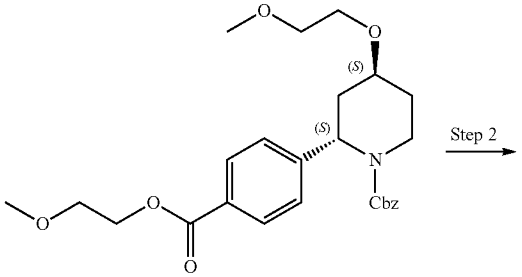

3b

-continued

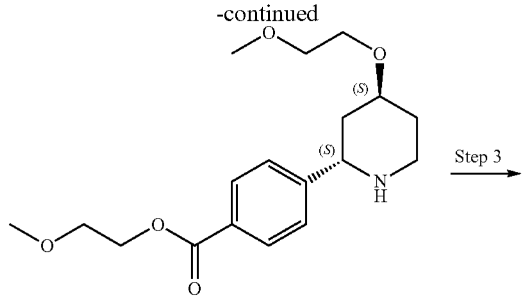

3c

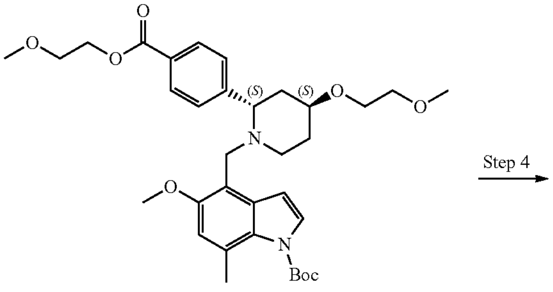

3d

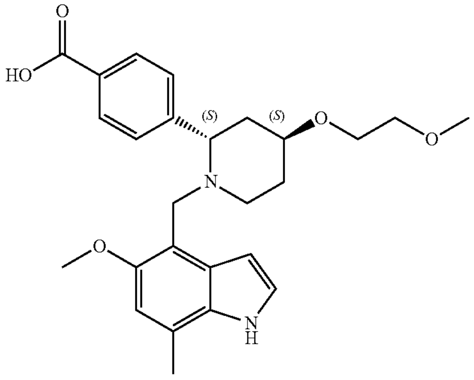

Compound 3

Step 1: benzyl (2S,4S)-4-(2-methoxyethoxy)-2-(4-((2-methoxyethoxy) carbonyl)phenyl)piperidine-1-carboxylate (3b)

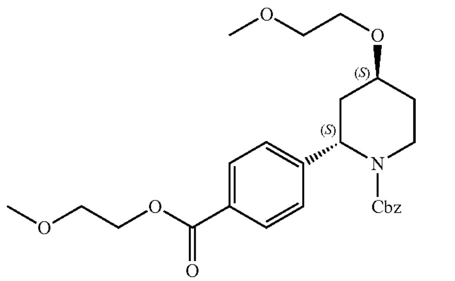

Benzyl (2S,4S)-4-Hydroxy-2-(4-(methoxycarbonyl)phenyl)piperidine-1-carboxylate (3a) (0.300 g, 0.81 mmol) (see WO 2020016749 for the synthesis method) and 1-bromo-2-methoxyethane (0.370 g, 2.66 mmol) were dissolved in 3 mL of DMF, 60% sodium hydride (0.072 g) was added at room temperature, and the mixture was reacted at room temperature for 16 hours after addition. 2 mL of water was slowly added to the reaction liquid at room temperature to quench the reaction, 10 mL of ethyl acetate was added for extraction, the liquid separation was conducted, and the organic phase was washed with 5 mL of saturated sodium chloride aqueous solution, dried over anhydrous sodium sulfate, and concentrated under reduced pressure. The residue was separated and purified with silica gel column chromatography (petroleum ether/ethyl acetate (v/v)=85:15) to afford benzyl (2S,4S)-4-(2-methoxyethoxy)-2-(4-((2-methoxyethoxy)carbonyl)phenyl)piperidine-1-carboxylate (3b)(0.180 g, yield: 47%).

Step 2: 2-methoxyethyl 4-[(2S,4S)-4-(2-methoxyethoxy)piperidin-2-yl]benzoate (3c) maleate

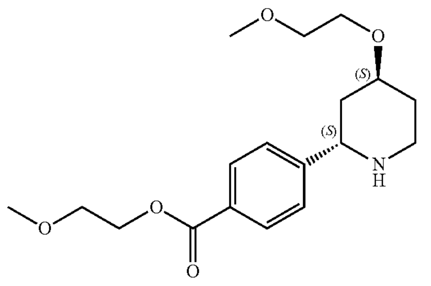

Benzyl (2S,4S)-4-(2-methoxyethoxy)-2-(4-((2-methoxyethoxy)carbonyl) phenyl)piperidine-1-carboxylate (3b) (0.180 g, 0.382 mmol) was dissolved in 5 mL of methanol, 30 mg of 10% palladium on carbon was added, and the mixture was reacted at room temperature under the atmosphere of hydrogen balloon for 2 h. The reaction system was filtered, and the filter cake was washed with 5 mL of methanol. The filtrate was combined and concentrated under reduced pressure to afford crude 2-methoxyethyl 4-[(2S,4S)-4-(2-methoxyethoxy)piperidin-2-yl]benzoate (3c) (0.128 g). The above-mentioned crude 2-methoxyethyl 4-[(2S,4S)-4-(2-methoxyethoxy)piperidin-2-yl]benzoate (3c) (0.128 g) was dissolved in 5 ml of isopropyl acetate, 1 mL of anhydrous methanol was added, maleic acid (0.044 g, 0.38 mmol) was added and stirred at room temperature for 16 h. The reaction liquid was concentrated under reduced pressure to afford crude 2-methoxyethyl 4-[(2S,4S)-4-(2-methoxyethoxy)piperidin-2-yl]benzoate (3c) maleate (0.173 g).

Step 3: tert-butyl 5-methoxy-4-{[(2S,4S)-4-(2-methoxyethoxy)-2-(4-[(2-methoxyethoxy)carbonyl] phenyl)piperidin-1-yl]methyl}-7-methyl-1H-indole-1-carboxylate (3d)

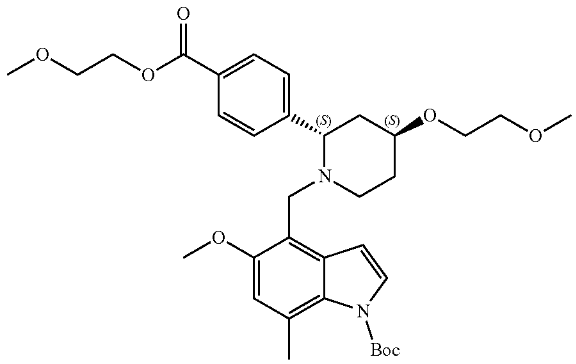

The above-mentioned crude 2-methoxyethyl 4-[(2S,4S)-4-(2-methoxyethoxy)piperidin-2-yl]benzoate (3c) maleate (0.173 g) was dissolved in 10 mL of absolute ethanol, tert-butyl 4-formyl-5-methoxy-7-methyl-1H-indole-1-carboxylate (0.140 g, 0.484 mmol) (see WO 2015009616 for the synthesis method) was added, nitrogen replacement was performed three times, 5 mg $Ir(CO)_2$acac was added, nitrogen replacement was performed three times, the mixture was heated to 75° C., and reacted under the atmosphere of hydrogen balloon for 24 h. The reaction liquid was cooled to room temperature and concentrated under reduced pressure, and the residue was separated and purified with silica gel column chromatography (petroleum ether/ethyl acetate (v/v)=85:15) to afford tert-butyl 5-methoxy-4-{[(2S,4S)-4-(2-methoxyethoxy)-2-(4-[(2-methoxyethoxy)carbonyl]phenyl) piperidin-1-yl]methyl}-7-methyl-1H-indole-1-carboxylate (3d) (0.130 g, two-step yield from compound 3b: 56%).

LCMS m/z=611.3 $[M+1]^+$

Step 4: 4-[(2S,4S)-1-[(5-methoxy-7-methyl-1H-indol-4-yl)methyl]-4-(2-methoxyethoxy)piperidin-2-yl]benzoic acid (compound 3) trifluoroacetate

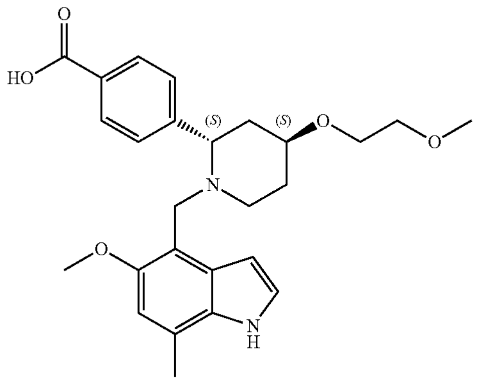

Tert-butyl 5-methoxy-4-{[(2S,4S)-4-(2-methoxyethoxy)-2-(4-[(2-methoxyethoxy) carbonyl]phenyl)piperidin-1-yl] methyl}-7-methyl-1H-indole-1-carboxylate (3d) (0.130 g, 0.213 mmol) was dissolved in 10 mL of anhydrous methanol, and solid potassium carbonate (0.147 g, 1.06 mmol) was added and the mixture was heated to 75° C. for 3 h after addition. The reaction liquid was cooled to room temperature and concentrated under reduced pressure, 10 mL of water was added to the residue, 0.1 mol/L of citric acid aqueous solution was added dropwise to adjust the pH to 8, and the solution was subjected to Pre-HPLC (instrument and preparative column: using Glison GX-281 preparative liquid phase chromatographic instrument, preparative column model: Sunfire C18, 5 μm, inner diameter×length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-[(2S,4S)-1-[(5-methoxy-7-methyl-1H-indol-4-yl)methyl]-4-(2-methoxyethoxy)piperidin-2-yl]benzoic acid (compound 3) trifluoroacetate (0.022 g).

$^1$H NMR (400 MHz, $CD_3OD$) δ 8.23 (d, 2H), 7.74 (d, 2H), 7.34 (d, 1H), 6.77 (s, 1H), 6.37 (d, 1H), 4.89-4.81 (m, 1H), 4.33 (d, 1H), 4.23 (d, 1H), 3.92-3.82 (m, 1H), 3.76 (s, 3H), 3.73-3.54 (m, 5H), 3.46 (s, 3H), 3.43-3.30 (m, 1H), 2.51 (s, 3H), 2.34-2.18 (m, 2H), 2.16-2.05 (m, 1H), 2.05-1.91 (m, 1H).

LCMS m/z=453.3 $[M+1]^+$

Example 4

4-((2S,4S)-4-(cyclopropylmethoxy)-1-((5-methoxy-7-methyl-1H-indol-4-yl)methyl)piperidin-2-yl)benzoic acid (compound 4)

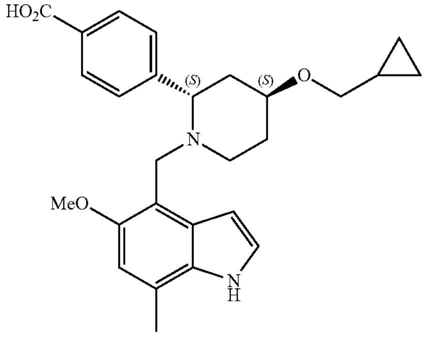

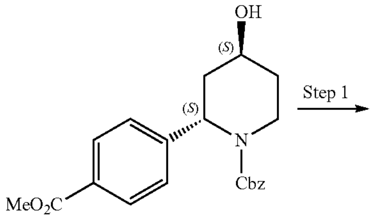

3a

-continued

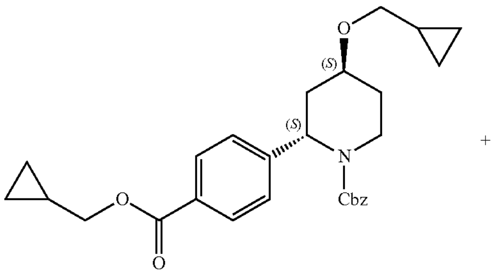

4a-1

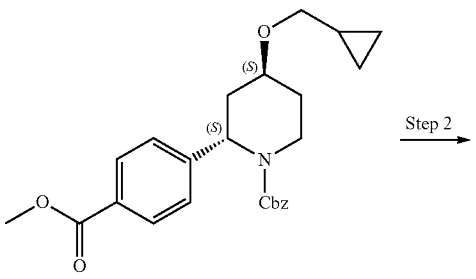

4a-2

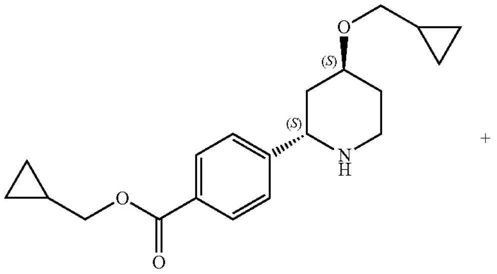

4b-1

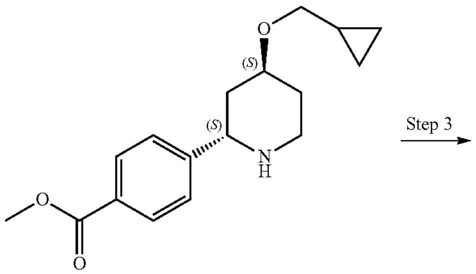

4b-2

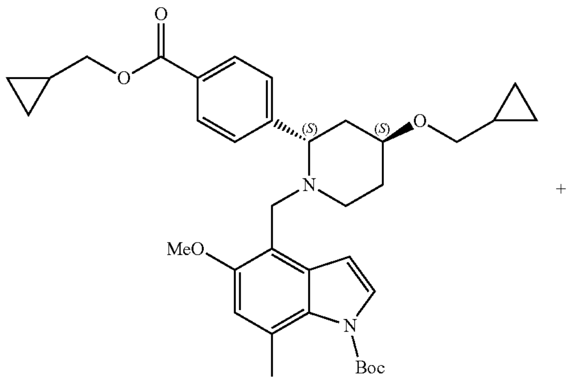

4c-1

-continued

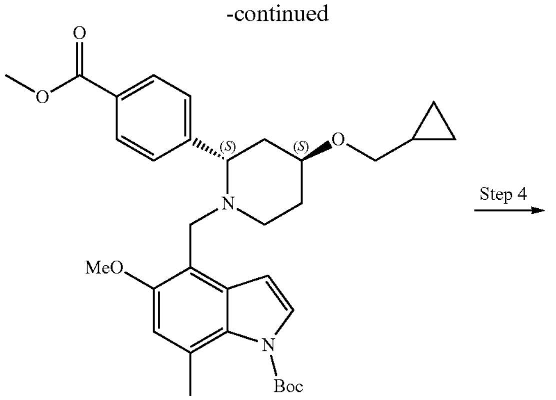

4c-2

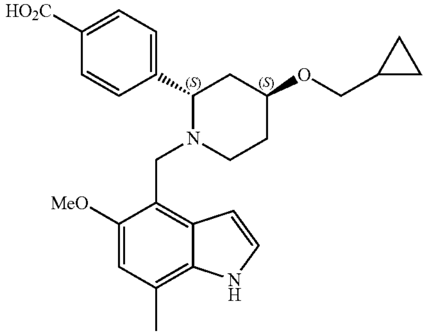

Compound 4

Step 1: benzyl (2S,4S)-4-(cyclopropylmethoxy)-2-(4-((cyclopropylmethoxy) carbonyl)phenyl)piperidine-1-carboxylate (4a-1) benzyl (2S,4S)-4-(cyclopropylmethoxy)-2-(4-(methoxycarbonyl)phenyl) piperidine-1-carboxylate (4a-2)

4a-1

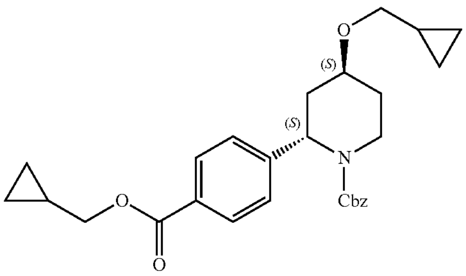

4a-2

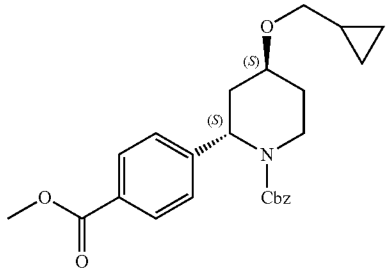

Benzyl (2S,4S)-4-hydroxy-2-(4-(methoxycarbonyl)phenyl)piperidine-1-carboxylate (3a) (400 mg, 1.08 mmol) (see WO 2020016749 for the synthesis method) was added to 10 mL of DMF, the mixture was cooled to 0° C., 60% sodium hydride (95 mg) was added, stirring was continued for 1 h, (bromomethyl)cyclopropane (321 mg, 2.38 mmol) was added, and the mixture was warmed room temperature and reacted for 16 h. 20 mL of water was slowly added to the reaction liquid at room temperature to quench the reaction, 50 mL of ethyl acetate was added for extraction, the liquid separation was conducted, and the organic phase was washed with 50 mL of saturated sodium chloride aqueous solution, dried over anhydrous sodium sulfate, and concentrated under reduced pressure. The crude product was separated and purified with silica gel column chromatography (petroleum ether/ethyl acetate (v/v)=5:1) to afford a mixture (450 mg) of benzyl (2S,4S)-4-(cyclopropylmethoxy)-2-(4-((cyclopropylmethoxy) carbonyl)phenyl)piperidine-1-carboxylate (4a-1) and benzyl (2S,4S)-4-(cyclopropylmethoxy)-2-(4-(methoxycarbonyl)phenyl)piperidine-1-carboxylate (4a-2).

LCMS m/z=464.2 $[M+1]^+$ of compound (4a-1)

LCMS m/z=424.2 $[M+1]^+$ of compound (4a-2)

Step 2: cyclopropylmethyl 4-((2S,4S)-4-(cyclopropylmethoxy)piperidin-2-yl)benzoate (4b-1) maleate methyl 4-((2S,4S)-4-(cyclopropylmethoxy)piperidin-2-yl)benzoate (4b-2) maleate 4b-1

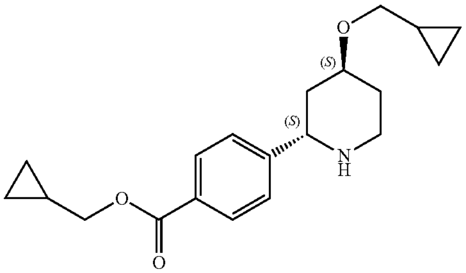

4b-2

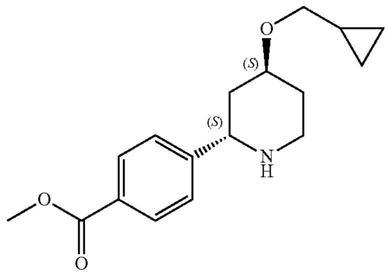

The above-mentioned mixture (450 mg) of benzyl (2S,4S)-4-(cyclopropylmethoxy)-2-(4-((cyclopropylmethoxy) carbonyl)phenyl)piperidine-1-carboxylate (4a-1) and benzyl (2S,4S)-4-(cyclopropylmethoxy)-2-(4-(methoxycarbonyl) phenyl)piperidine-1-carboxylate (4a-2) was dissolved in 10 mL of methanol, 90 mg of 10% palladium on carbon was added and stirred at room temperature under a hydrogen atmosphere for 5 h. The reaction system was suction-filtered under reduced pressure, and the filtrate was concentrated under reduced pressure to afford a crude product (320 mg). The above-mentioned crude product (320 mg) was dissolved in 10 mL of isopropyl acetate, and maleic acid (77 mg, 0.66 mmol) was added, and stirred at room temperature for 16 h. The reaction system was concentrated under reduced pressure to afford crude mixture (420 mg) of cyclopropylmethyl 4-((2S,4S)-4-(cyclopropylmethoxy)piperidin-2-yl)benzoate (4b-1) maleate and methyl 4-((2S,4S)-4-(cyclopropylmethoxy)piperidin-2-yl)benzoate (4b-2) maleate.

Step 3: tert-butyl 4-(((2S,4S)-4-(cyclopropylmethoxy)-2-(4-((cyclopropylmethoxy)carbonyl)phenyl)piperidin-1-yl)methyl)-5-methoxy-7-methyl-1H-indole-1-carboxylate (4c-1)

tert-butyl 4-(((2S,4S)-4-(cyclopropylmethoxy)-2-(4-(methoxycarbonyl)phenyl) piperidin-1-yl)methyl)-5-methoxy-7-methyl-1H-indole-1-carboxylate (4c-2)

4c-1

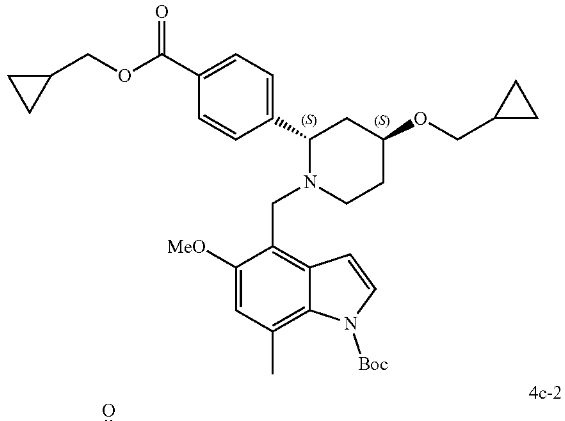

4c-2

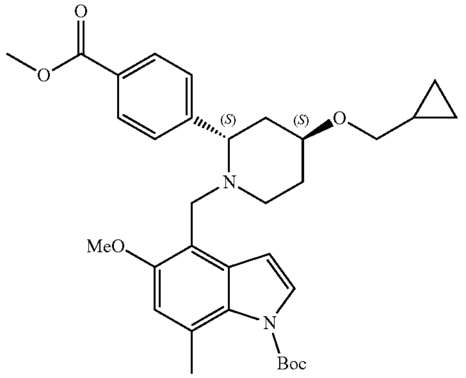

The above-mentioned crude mixture (420 mg) of cyclopropylmethyl 4-((2S,4S)-4-(cyclopropylmethoxy)piperidin-2-yl)benzoate (4b-1) maleate and methyl 4-((2S,4S)-4-(cyclopropylmethoxy)piperidin-2-yl)benzoate (4b-2) maleate was dissolved in 10 mL of ethanol, tert-butyl 4-formyl-5-methoxy-7-methyl-1H-indole-1-carboxylate (350 mg, 1.2 mmol) (see WO 2015009616 for the synthesis method) was added and 35 mg of $Ir(CO)_2acac$ was added. The mixture was heated to 75° C., and reacted for 16 h under the atmosphere of hydrogen balloon. The reaction liquid was cooled to room temperature and concentrated under reduced pressure, and the crude product was separated and purified with silica gel column chromatography (petroleum ether/ethyl acetate (v/v)=10:1) to afford a mixture (130 mg) of tert-butyl 4-(((2S,4S)-4-(cyclopropylmethoxy)-2-(4-((cyclopropylmethoxy)carbonyl)phenyl)piperidin-1-yl)methyl)-5-methoxy-7-methyl-1H-indole-1-carboxylate (4c-1) and tert-butyl 4-(((2S,4S)-4-(cyclopropylmethoxy)-2-(4-(methoxycarbonyl)phenyl)piperidin-1-yl)methyl)-5-methoxy-7-methyl-1H-indole-1-carboxylate (4c-2).

LCMS m/z=603.3 $[M+1]^+$ of compound (4c-1)

LCMS m/z=563.3 $[M+1]^+$ of compound (4c-2)

Step 4: 4-((2S,4S)-4-(cyclopropylmethoxy)-1-((5-methoxy-7-methyl-1H-indol-4-yl)methyl)piperidin-2-yl)benzoic acid (compound 4)

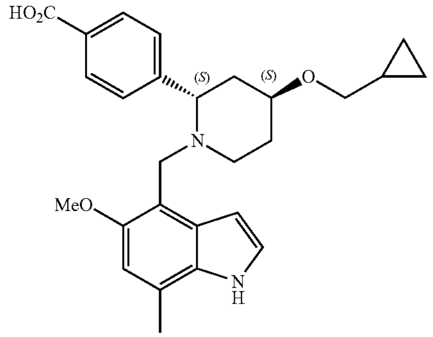

The above-mentioned mixture (130 mg) of tert-butyl 4-(((2S,4S)-4-(cyclopropylmethoxy)-2-(4-((cyclopropylmethoxy)carbonyl)phenyl)piperidin-1-yl)methyl)-5-methoxy-7-methyl-1H-indole-1-carboxylate (4c-1) and tert-butyl 4-(((2S,4S)-4-(cyclopropylmethoxy)-2-(4-(methoxycarbonyl)phenyl)piperidin-1-yl)methyl)-5-methoxy-7-methyl-1H-indole-1-carboxylate (4c-2) was dissolved in 10 mL of methanol, solid potassium carbonate (149 mg, 1.08 mmol) was added, and the mixture was heated to 85° C. and reacted for 3 hours at reflux. The reaction solution was cooled to room temperature and concentrated under reduced pressure to afford a crude product. The above-mentioned crude product was dissolved in a mixed solvent of 10 mL of THF, 5 mL of methanol and 2 mL of water, lithium hydroxide monohydrate (181 mg, 4.3 mmol) was added and stirred at room temperature for 16 h. The reaction system was concentrated under reduced pressure, and the crude product was subjected to Pre-HPLC (instrument and preparative column: using Glison GX-281 preparative liquid phase chromatographic instrument, preparative column model: Sunfire C18, 5 μm, inner diameter×length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 5 mmol/L ammonium acetate). Gradient elution method: gradient elution of 5% to 60% acetonitrile (elution time 15 min), and lyophilization was performed to afford 4-((2S,4S)-4-(cyclopropylmethoxy)-1-((5-methoxy-7-methyl-1H-indol-4-yl)methyl)piperidin-2-yl)benzoic acid (compound 4) (5 mg).

$^1H$ NMR (400 MHz, $CD_3OD$) δ 8.10 (d, 2H), 7.60 (d, 2H), 7.28 (d, 1H), 6.73 (s, 1H), 6.32 (s, 1H), 4.70-4.40 (m, 1H), 4.32-4.14 (m, 1H), 4.09-3.90 (m, 1H), 3.88-3.79 (m, 1H), 3.75 (s, 3H), 3.42-3.34 (m, 2H), 3.30-3.14 (m, 2H), 2.49 (s, 3H), 2.26-2.10 (m, 2H), 2.06-1.90 (m, 2H), 1.19-1.04 (m, 1H), 0.64-0.50 (m, 2H), 0.31-0.22 (m, 2H).

LCMS m/z=449.2 $[M+1]^+$

Example 5
4-((2S)-4-cyclopropyl-1-((5-methoxy-7-methyl-1H-indol-4-yl)methyl)piperidin-2-yl)benzoic acid [compound 5 (diastereomer 1)]trifluoroacetate
5-A
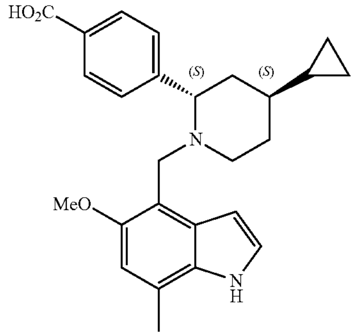
or
5-B
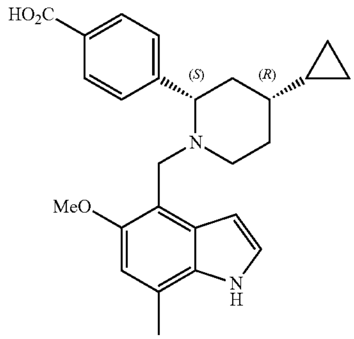
Compound 5 (diastereomer 1)
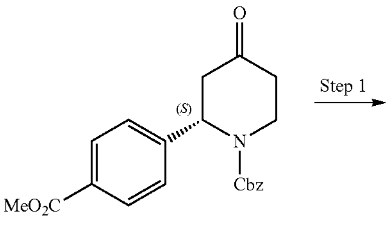
1a
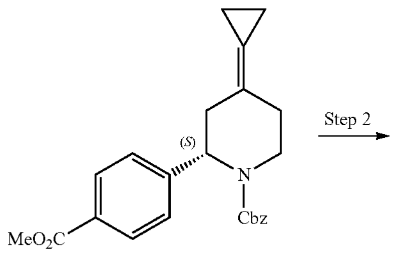
5a
-continued
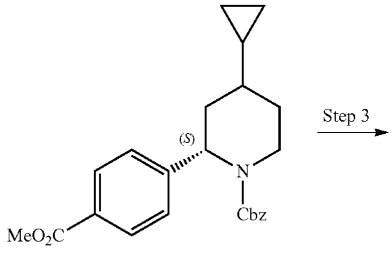
5b
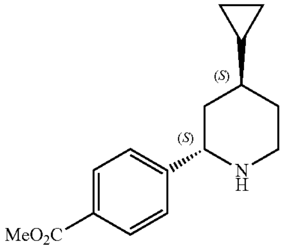
or
5c-A
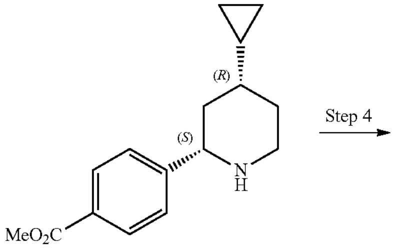
5c-B
5c (diastereomer1)
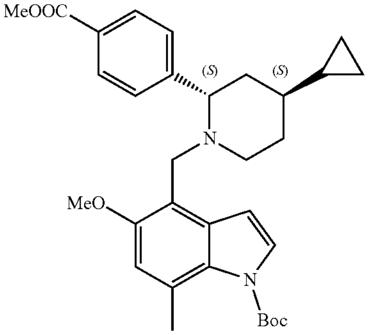
or
5d-A
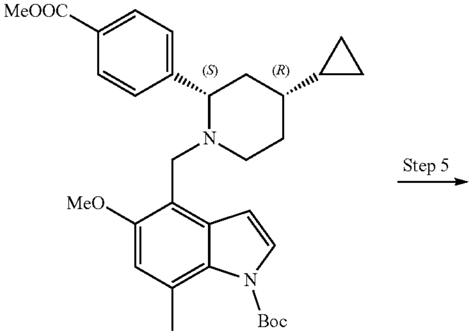
5d-B
5d (diastereomer 1)

-continued

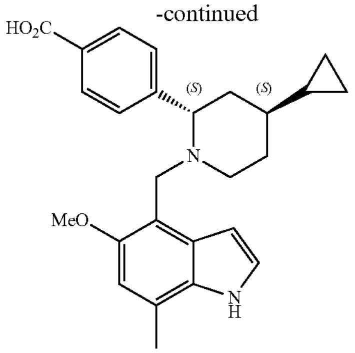

or

5-A

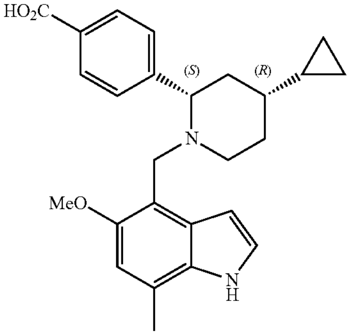

5-B
Compound 5 (diastereomer 1)

Step 1: benzyl (S)-4-cyclopropylidene-2-(4-(methoxycarbonyl)phenyl) piperidine-1-carboxylate (5a)

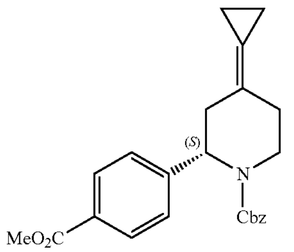

(3-bromopropyl)triphenylphosphine bromide (12.2 g, 26.3 mmol) was added to 100 mL of ultra-dry THF, the mixture was cooled with an ice-water bath, and solid potassium tert-butoxide (5.9 g, 52.6 mmol) was slowly added under nitrogen atmosphere, and stirring was continued at 0° C. for 45 mi. A solution of benzyl (S)-2-(4-(methoxycarbonyl)phenyl)-4-oxopiperidine-1-carboxylate (8.0 g, 21.8 mmol) (1a) (for the synthetic method, see WO 2020016749) in tetrahydrofuran (20 mL) was added and reacted at room temperature for 16 h. 100 mL of ethyl acetate was added into the reaction system, washed with 100 mL of saturated ammonium chloride aqueous solution, dried over anhydrous sodium sulfate, and concentrated under reduced pressure. The obtained crude product was separated and purified with silica gel column chromatography (petroleum ether/ethyl acetate (v/v)=5:1) to afford benzyl (S)-4-cyclopropylidene-2-(4-(methoxycarbonyl)phenyl)piperidine-1-carboxylate (5a) (5.5 g, yield: 64%).

LCMS m/z=392.2 $[M+1]^+$

Step 2: benzyl (2S)-4-cyclopropyl-2-(4-(methoxycarbonyl)phenyl)piperidine-1-carboxylate (5b)

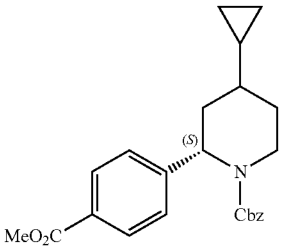

Benzyl (S)-4-cyclopropylidene-2-(4-(methoxycarbonyl)phenyl)piperidine-1-carboxylate (5a) (3.7 g, 9.45 mmol) was added to 50 mL of ultra-dry DMF, solid benzenesulfonyl hydrazide (8.2 g, 47.6 mmol) was added under nitrogen atmosphere, and the mixture was heated to 100° C. and reacted for 16 h. The reaction liquid was cooled to room temperature, 100 mL of ethyl acetate was added, the organic phase was washed three times with 100 mL of saturated sodium chloride aqueous solution, dried over anhydrous sodium sulfate, and concentrated under reduced pressure. The obtained crude product was separated and purified with silica gel column chromatography (petroleum ether/ethyl acetate (v/v)=5:1) to afford benzyl (2S)-4-cyclopropyl-2-(4-(methoxycarbonyl)phenyl)piperidine-1-carboxylate (5b) (2.0 g, yield: 54%). Rf value of compound 5b: 0.27 (developing agent: ethyl acetate/petroleum ether (v/v)=1:10)

Nuclear Magnetic Resonances of Compound 5b:

$^1H$ NMR (400 MHz, $CDCl_3$) δ 8.01-7.91 (m, 2H), 7.36-7.21 (m, 5H), 7.20-7.10 (m, 2H), 5.12-5.00 (m, 3H), 4.18-4.02 (m, 1H), 3.91 (s, 3H), 3.42-3.28 (m, 1H), 2.20-2.08 (m, 1H), 2.04-1.83 (m, 2H), 1.56-1.44 (m, 1H), 0.98-0.84 (m, 1H), 0.46-0.21 (m, 3H), 0.10-0.01 (m, 2H).

5b-A

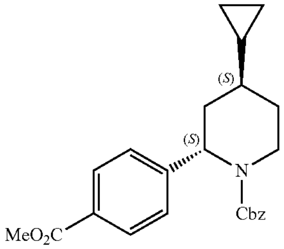

or

5b-B

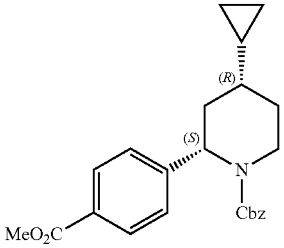

LCMS m/z=394.2 $[M+1]^+$

According to the $^1H$-$^1H$ NOESY verification of the C1 and C3 hydrogens of the final product compound 5, compound 5b has structure 5b-B.

Step 3: methyl 4-((2S)-4-cyclopropylpiperidin-2-yl) benzoate [5c (diastereomer 1)] maleate 5c (diastereomer 1)

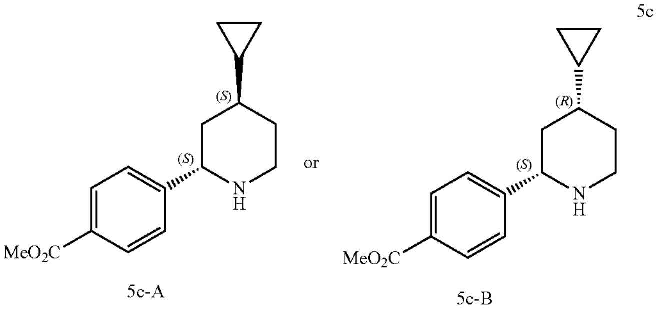

5c-A or 5c-B

Benzyl (2S)-4-cyclopropyl-2-(4-(methoxycarbonyl)phenyl)piperidine-1-carboxylate (5b) (2.0 g, 5.08 mmol) was dissolved in 50 mL of acetonitrile. Trimethylsilyl iodide (5.1 g, 25.5 mmol) was slowly added dropwise and stirred at room temperature for 30 min. 100 mL of water was added to the reaction system, the pH of the system was adjusted to 3-4 with 1 mol/L dilute hydrochloric acid, the organic phase was extracted with 50 mL of ethyl acetate, and the pH of the aqueous phase was adjusted to 10 with 1 mol/L sodium hydroxide solution. The mixture was extracted three times by adding 100 mL dichloromethane, dried over anhydrous sodium sulfate, and concentrated under reduced pressure to afford compound 5c (diastereomer 1) (1.0 g). Compound 5c (diastereomer 1) (1.0 g, 3.86 mmol) was dissolved in 20 mL of isopropyl acetate, maleic acid (267 mg, 2.3 mmol) was added, and the mixture was reacted at room temperature for 16 h. The reaction system was concentrated under reduced pressure to afford crude methyl 4-((2S)-4-cyclopropylpiperidin-2-yl)benzoate [5c (diastereomer 1)] maleate (1.2 g).

LCMS m/z=260.2 $[M+1]^+$

Nuclear Magnetic Resonances of Compound 5c (Diastereomer 1):

$^1H$ NMR (400 MHz, $CDCl_3$) δ 8.03-7.94 (m, 2H), 7.50-7.41 (m, 2H), 3.91 (s, 3H), 3.62 (dd, 1H), 3.28-3.19 (m, 1H), 2.79-2.66 (m, 1H), 2.39 (br.s, 1H), 1.99-1.75 (m, 2H), 1.50-1.22 (m, 2H), 0.86-0.70 (m, 1H), 0.64-0.50 (m, 1H), 0.46-0.32 (m, 2H), 0.15-0.04 (m, 2H).

According to the $^1H$-$^1H$ NOESY verification of the C1 and C3 hydrogens of the final product compound 5, compound 5c (diastereomer 1) has structure 5c-B.

Step 4: tert-butyl 4-(((2S)-4-cyclopropyl-2-(4-(methoxycarbonyl)phenyl) piperidin-1-yl)methyl)-5-methoxy-7-methyl-1H-indole-1-carboxylate [5d (diastereomer 1)]

5d (diastereomer 1)

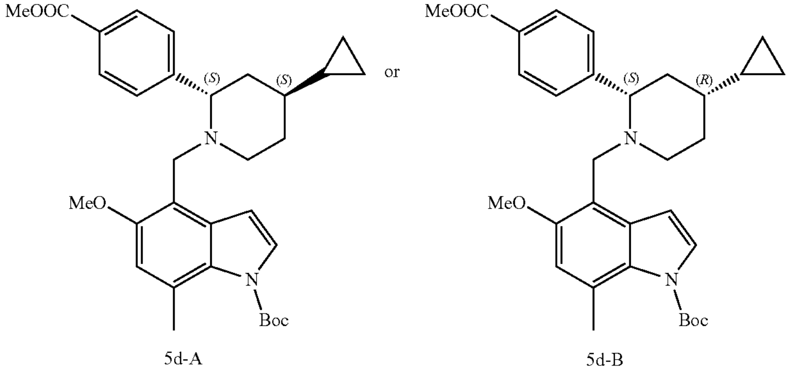

5d-A or 5d-B

The above-mentioned crude methyl 4-((2S)-4-cyclopropylpiperidin-2-yl)benzoate [5c (diastereomer 1)] maleate (1.2 g) was dissolved in 50 mL of ethanol, tert-butyl 4-formyl-5-methoxy-7-methyl-1H-indole-1-carboxylate (1.23 g, 4.25 mmol) (see WO 2015009616 for the synthesis method) was added and 135 mg of $Ir(CO)_2acac$ was added. The mixture was heated to 75° C., and reacted for 16 h under the atmosphere of hydrogen balloon. The reaction liquid was cooled to room temperature and concentrated under reduced pressure, and the crude product was separated and purified with silica gel column chromatography (petroleum ether/ethyl acetate (v/v)=10:1) to afford tert-butyl 4-(((2S)-4-cyclopropyl-2-(4-(methoxycarbonyl)phenyl)piperidin-1-yl)methyl)-5-methoxy-7-methyl-1H-indole-1-carboxylate [5d (diastereomer 1)] (800 mg, yield: 35%).

LCMS m/z=533.3 $[M+1]^+$

According to the $^1H$-$^1H$ NOESY verification of the C1 and C3 hydrogens of the final product compound 5, compound 5d (diastereomer 1) has structure 5d-B.

Step 5: 4-((2S)-4-cyclopropyl-1-((5-methoxy-7-methyl-1H-indol-4-yl)methyl) piperidin-2-yl)benzoic acid [compound 5 (diastereomer 1)]trifluoroacetate Compound 5 (diastereomer 1)

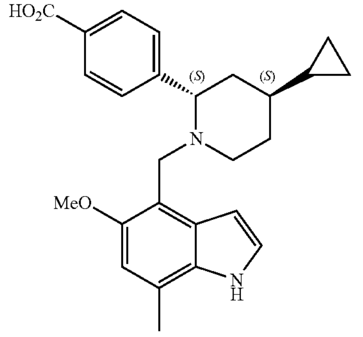

5-A or

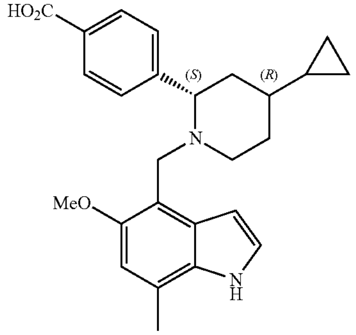

5-B tert-butyl 4-(((2S)-4-cyclopropyl-2-(4-(methoxycarbonyl)phenyl)piperidin-1-yl)methyl)-5-methoxy-7-methyl-1H-indole-1-carboxylate [5d (diastereomer 1)] (740 mg, 1.39 mmol) was dissolved in 10 mL of methanol, solid potassium carbonate (960 mg, 6.95 mmol) was added, and the mixture was heated to 80° C. and reacted for 3 hours at reflux. The reaction solution was cooled to room temperature and concentrated under reduced pressure to afford a crude product. The above-mentioned crude product was dissolved in a mixed solvent of 10 mL of THF and 2 mL of water, lithium hydroxide monohydrate (588 mg, 14.01 mmol) was added and stirred at room temperature for 16 h. The reaction system was concentrated under reduced pressure, and the crude product was subjected to Pre-HPLC (instrument and preparative column: using Glison GX-281 preparative liquid phase chromatographic instrument, preparative column model: Sunfire C18, 5 μm, inner diameter× length=30 mmx 150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((2S)-4-cyclopropyl-1-((5-methoxy-7-methyl-1H-indol-4-yl)methyl)piperidin-2-yl)benzoic acid [compound 5 (diastereomer 1)]trifluoroacetate (480 mg).

$^1H$ NMR (400 MHz, $CD_3OD$) δ 8.23 (d, 2H), 7.73 (d, 2H), 7.33 (d, 1H), 6.77 (s, 1H), 6.33 (d, 1H), 4.48 (dd, 1H), 4.38-4.31 (m, 1H), 4.17-4.09 (m, 1H), 3.76 (s, 3H), 3.62-3.53 (m, 1H), 3.30-3.21 (m, 1H), 2.51 (s, 3H), 2.25-2.11 (m, 1H), 2.05-1.88 (m, 2H), 1.78-1.60 (m, 1H), 1.21-1.05 (m, 1H), 0.65-0.53 (m, 1H), 0.51-0.39 (m, 2H), 0.24-0.14 (m, 2H).

LCMS m/z=419.2 $[M+1]^+$

The trifluoroacetate of compound 5 (diastereomer 1) had obvious $^1H$-$^1H$ NOESY signals on C1 and C3 hydrogens of piperidine ring, which proved that the configuration of compound 5 (diastereomer 1) was as shown in the following formula:

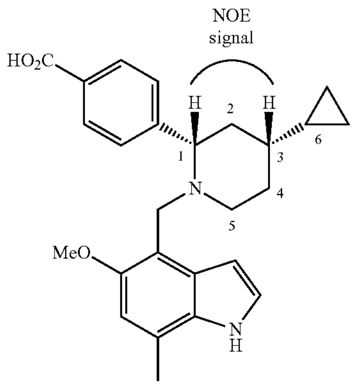 [SMILES: COc1cc(C)c2[nH]ccc2c1CN1CC[C@@H](C2CC2)C[C@H]1c1ccc(C(=O)O)cc1]

According to the nuclear magnetic resonances analysis of trifluoroacetate of compound 5 (diastereomer 1), compound 5 (diastereomer 1) has structure 5-B.

Example 5-1
4-((2S)-4-cyclopropyl-1-((5-methoxy-7-methyl-1H-indol-4-yl)methyl)piperidin-2-yl)benzoic acid [compound 5-1 (diastereomer 2)]trifluoroacetate
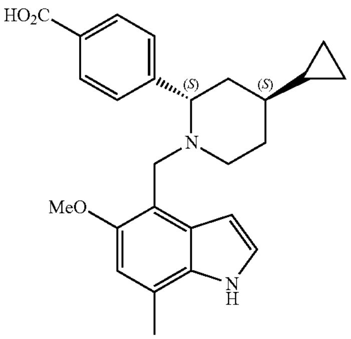
or
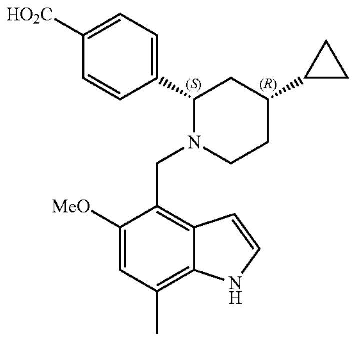
5-A 5-B
Compound 5-1 (diastereomer 2)
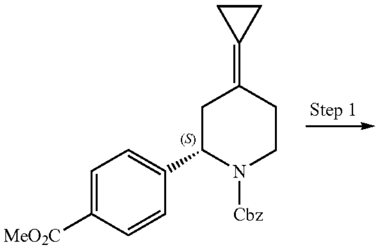
5a
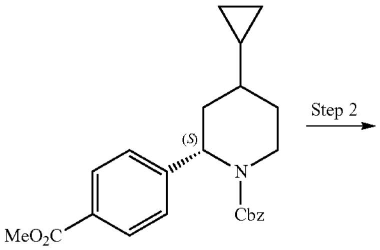
5b-1
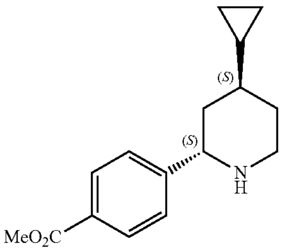
or
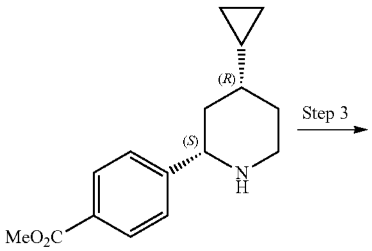
5c-A 5c-B
5c-1 (diastereomer 2)
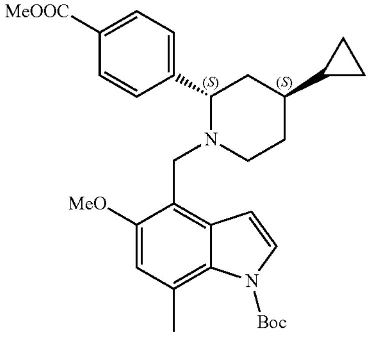
or
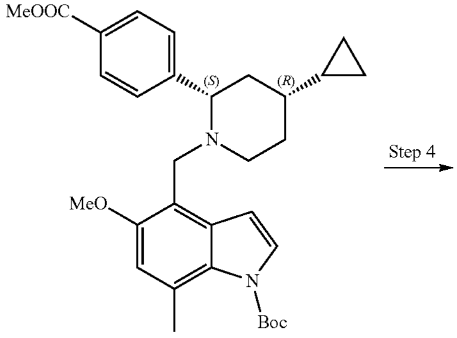
5d-A 5d-B
5d-1 (diastereomer 2)

-continued

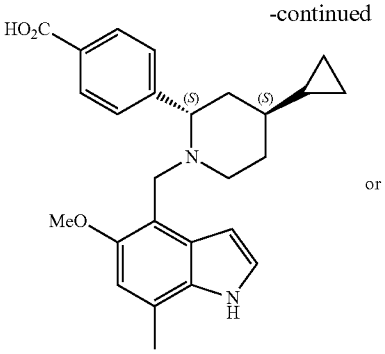

5-A or

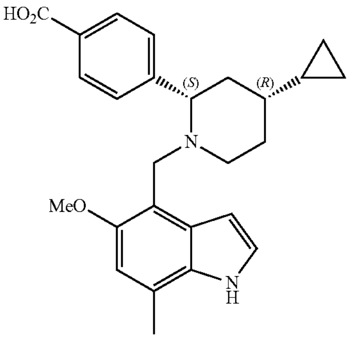

5-B

Compound 5-1 (diastereomer 2)

Step 1: benzyl (2S)-4-cyclopropyl-2-(4-(methoxycarbonyl)phenyl)piperidine-1-carboxylate (5b-1)

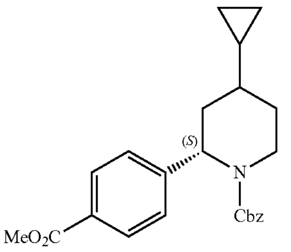

Benzyl (S)-4-cyclopropylidene-2-(4-(methoxycarbonyl)phenyl)piperidine-1-carboxylate (5a) (3.7 g, 9.45 mmol) was added to 50 mL of ultra-dry DMF, solid benzenesulfonyl hydrazide (8.2 g, 47.6 mmol) was added under nitrogen atmosphere, and the mixture was heated to 100° C. and reacted for 16 h. The reaction liquid was cooled to room temperature, 100 mL of ethyl acetate was added, the organic phase was washed three times with 100 mL of saturated sodium chloride aqueous solution, dried over anhydrous sodium sulfate, and concentrated under reduced pressure. The obtained crude product was separated and purified with silica gel column chromatography (petroleum ether/ethyl acetate (v/v)=15:1) to afford benzyl (2S)-4-cyclopropyl-2-(4-(methoxycarbonyl)phenyl)piperidine-1-carboxylate (5b-1) (0.7 g, yield: 19%). Rf value of compound 5b-1:0.36 (developing agent: ethyl acetate/petroleum ether (v/v)=1:10)

Nuclear Magnetic Resonances of Compound 5b-1:

$^1H$ NMR (400 MHz, $CDCl_3$) δ 8.04-7.90 (m, 2H), 7.50-7.10 (m, 7H), 5.75-5.45 (m, 1H), 5.19 (s, 2H), 4.40-4.05 (m, 1H), 3.85 (s, 3H), 2.84-2.66 (m, 1H), 2.54-2.33 (m, 1H), 1.84-1.55 (m, 2H), 1.45-1.18 (m, 1H), 0.72-0.27 (m, 4H), 0.09--0.06 (m, 2H).

According to the $^1H$-$^1H$ NOESY verification of the C1 hydrogen of the piperidine ring and the C6 hydrogen of the cyclopropyl of the final product compound 5-1, compound 5b-1 has structure 5b-A.

5b-1

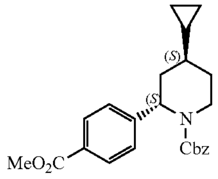

5b-A or

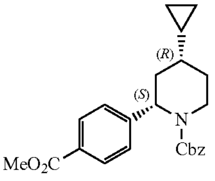

5b-B

LCMS m/z=394.2 $[M+1]^+$

Step 2: methyl 4-((2S)-4-cyclopropylpiperidin-2-yl)benzoate [5c-1 (diastereomer 2)] maleate 5c-1 (diastereomer 2)

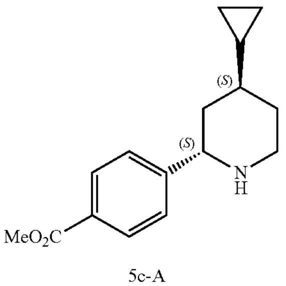

5c-A or

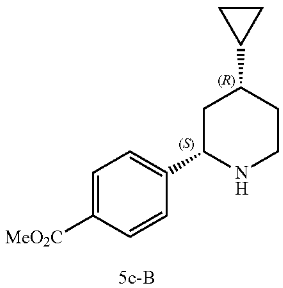

5c-B

Benzyl (2S)-4-cyclopropyl-2-(4-(methoxycarbonyl)phenyl)piperidine-1-carboxylate (5b-1) (1.0 g, 2.54 mmol) was dissolved in 10 mL of acetonitrile. Trimethylsilyl iodide (2.54 g, 12.7 mmol) was slowly added dropwise and stirred at room temperature for 30 min. 10 mL of methanol was added to the reaction system, the pH of the system was adjusted to 2-3 with 2 mol/L dilute hydrochloric acid, the organic phase was extracted with 20 mL of ethyl acetate, and the pH of the aqueous phase was adjusted to 10 with 2 mol/L sodium hydroxide solution. The mixture was extracted three times by adding 100 mL dichloromethane, dried over anhydrous sodium sulfate, and concentrated under reduced pressure to afford compound 5c-1 (diastereomer 2) (0.6 g). Compound 5c-1 (diastereomer 2) (0.6 g, 2.31 mmol) was dissolved in 10 mL of isopropyl acetate, maleic acid (270 mg, 2.33 mmol) was added, and the mixture was reacted at room temperature for 16 h. The reaction system was concentrated under reduced pressure to afford crude methyl 4-((2S)-4-cyclopropylpiperidin-2-yl)benzoate [5c-1 (diastereomer 2)] maleate (0.85 g).

According to the $^1H$-$^1H$ NOESY verification of the C1 hydrogen of the piperidine ring and the C6 hydrogen of the cyclopropyl of the final product compound 5-1, compound 5c-1 (diastereomer 2) has structure 5c-A.

Step 3: tert-butyl 4-(((2S)-4-cyclopropyl-2-(4-(methoxycarbonyl)phenyl) piperidin-1-yl)methyl)-5-methoxy-7-methyl-1H-indole-1-carboxylate [5d-1 (diastereomer 2)]

5d-1 (diastereomer 2)

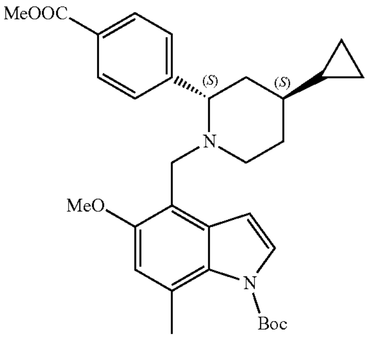

5d-A or

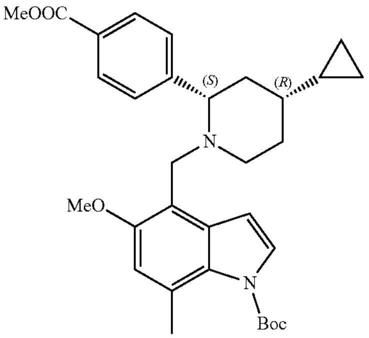

5d-B

The methyl 4-((2S)-4-cyclopropylpiperidin-2-yl)benzoate [5c-1 (diastereomer 2)] maleate (0.85 g) was dissolved in 10 mL of ethanol, tert-butyl 4-formyl-5-methoxy-7-methyl-1H-indole-1-carboxylate (0.67 g, 2.32 mmol) (see WO 2015009616 for the synthesis method) was added and 80 mg of $Ir(CO)_2acac$ was added. The mixture was heated to 80° C., and reacted for 16 h under the atmosphere of hydrogen balloon. The reaction liquid was cooled to room temperature and concentrated under reduced pressure, and the crude product was separated and purified with silica gel column chromatography (petroleum ether/ethyl acetate (v/v)=15:1) to afford tert-butyl 4-(((2S)-4-cyclopropyl-2-(4-(methoxycarbonyl) phenyl)piperidin-1-yl)methyl)-5-methoxy-7-methyl-1H-indole-1-carboxylate [5d-1 (diastereomer 2)] (850 mg, yield: 69%).

Nuclear Magnetic Resonances of Compound 5d-1 (Diastereomer 2):

$^1H$ NMR (400 MHz, $CDCl_3$) δ 8.08-7.96 (m, 2H), 7.67-7.56 (m, 2H), 7.48 (d, 1H), 6.71 (d, 1H), 6.67 (s, 1H), 3.91 (s, 3H), 3.80 (s, 3H), 3.74-3.64 (m, 1H), 3.60-3.50 (m, 1H), 3.44-3.33 (m, 1H), 2.76-2.65 (m, 1H), 2.59 (s, 3H), 2.45-2.32 (m, 1H), 1.96-1.50 (m, 13H), 1.23-1.10 (m, 1H), 0.90-0.75 (m, 1H), 0.57-0.41 (m, 2H), 0.10-0.01 (m, 2H).

LCMS m/z=533.3 $[M+1]^+$

According to the $^1H$-$^1H$ NOESY verification of the C1 hydrogen of the piperidine ring and the C6 hydrogen of the cyclopropyl of the final product compound 5-1, compound 5d-1 (diastereomer 2) has structure 5d-A.

Step 4: 4-((2S)-4-cyclopropyl-1-((5-methoxy-7-methyl-1H-indol-4-yl)methyl) piperidin-2-yl)benzoic acid [compound 5-1 (diastereomer 2)]trifluoroacetate

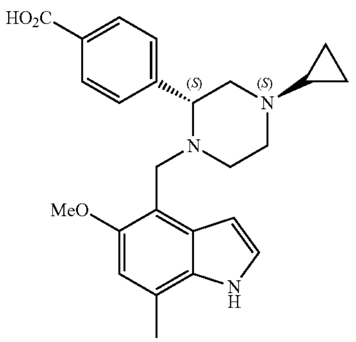

5-A or

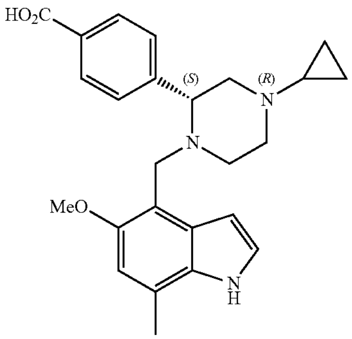

5-B

Compound 5-1 (diastereomer 2)

Tert-butyl 4-(((2S)-4-cyclopropyl-2-(4-(methoxycarbonyl)phenyl) piperidin-1-yl)methyl)-5-methoxy-7-methyl-1H-indole-1-carboxylate [5d-1 (diastereomer 2)] (850 mg, 1.596 mmol) was dissolved in 10 mL of methanol, solid potassium carbonate (1.1 g, 7.96 mmol) was added, and the mixture was heated to 80° C. and reacted for 3 hours at reflux. The reaction solution was cooled to room temperature and concentrated under reduced pressure to afford a crude product. The above-mentioned crude product was dissolved in a mixed solvent of 10 mL of THF and 2 mL of water, lithium hydroxide monohydrate (670 mg, 15.97 mmol) was added and stirred at room temperature for 16 h. The reaction system was concentrated under reduced pressure, and the crude product was subjected to Pre-HPLC (instrument and preparative column: using Glison GX-281 preparative liquid phase chromatographic instrument, preparative column model: Sunfire C18, 5 μm, inner diameter× length=30 mm× 150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((2S)-4-cyclopropyl-1-((5-methoxy-7-methyl-1H-indol-4-yl)methyl)piperidin-2-yl)benzoic acid [compound 5-1 (diastereomer 2)]trifluoroacetate (400 mg).

$^1$H NMR (400 MHz, $CD_3OD$) δ 8.29-8.18 (m, 2H), 7.79-7.72 (m, 2H), 7.37-7.32 (m, 1H), 6.78 (s, 1H), 6.38 (d, 1H), 4.83-4.78 (m, 1H), 4.41-4.32 (m, 1H), 4.30-4.20 (m, 1H), 3.77 (s, 3H), 3.65-3.42 (m, 2H), 2.51 (s, 3H), 2.40-2.25 (m, 1H), 2.18-2.02 (m, 2H), 1.98-1.82 (m, 1H), 1.52-1.38 (m, 1H), 1.18-1.04 (m, 1H), 0.72-0.60 (m, 2H), 0.25-0.17 (m, 2H).

LCMS m/z=419.2 $[M+1]^+$

The trifluoroacetate of compound 5-1 (diastereomer 2) had obvious $^1$H-$^1$H NOESY signals on C1 hydrogen of the piperidine ring and the C6 hydrogen of the cyclopropyl, which proved that the configuration of compound 5-1 (diastereomer 2) was as shown in the following formula:

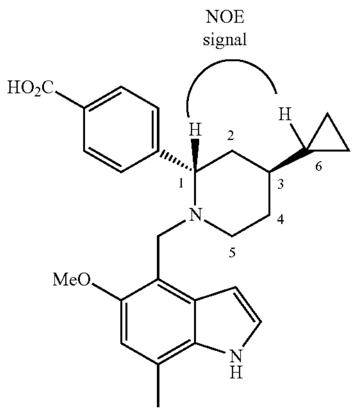 [SMILES: COc1cc(C)c2[nH]ccc2c1CN1CC[C@H](C2CC2)C[C@H]1c1ccc(C(=O)O)cc1]

According to the nuclear magnetic resonances analysis of trifluoroacetate of compound 5-1 (diastereomer 2), compound 5-1 (diastereomer 2) has structure 5-A.

Example 6

4-((7S)-8-((5-(methoxy-d3)-7-methyl-1H-indol-4-yl) methyl)-1-oxa-8-azaspiro[4.5]decan-7-yl)benzoic acid (compound 6) trifluoroacetate

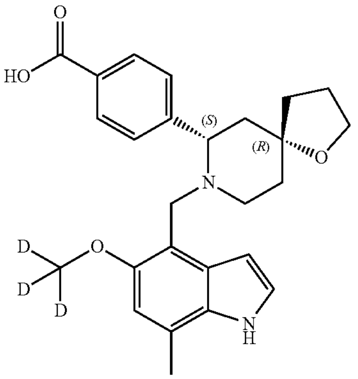

6-A or

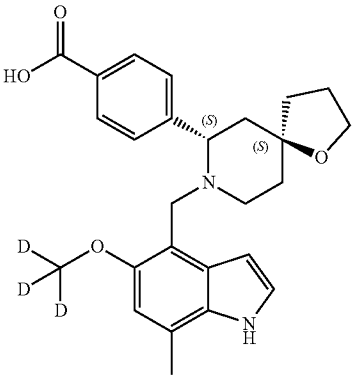

6-B

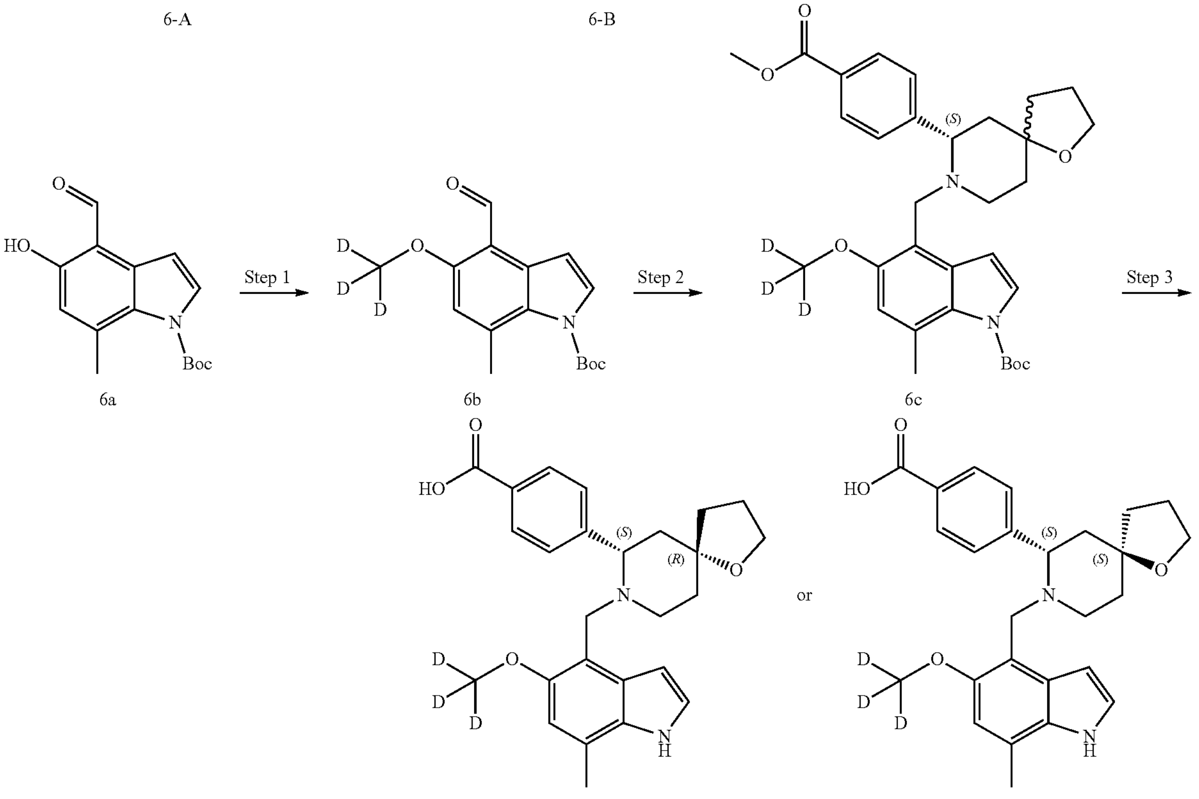

6a 6b 6c

6-A or 6-B

Compound 6

Step 1: tert-butyl 4-formyl-5-trideuterio methoxy-7-methyl-1H-indole-1-carboxylate (6b)

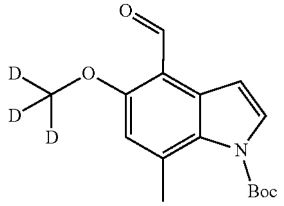 [SMILES: [2H]C([2H])([2H])Oc1cc(C)c2c(ccn2C(=O)OC(C)(C)C)c1C=O]

Tert-butyl 4-formyl-5-hydroxy-7-methyl-1H-indole-1-carboxylate (6a) (see WO 2020016749 for synthesis method) (0.3 g, 1.09 mmol) was dissolved in 5 mL of DMF, solid potassium carbonate (0.2 g, 1.45 mmol) was added, and then deuterated methyl iodide (0.32 g, 2.21 mmol) was added and after addition, the mixture was react at room temperature for 3 h. 10 mL of water and 20 mL of ethyl acetate were added to the reaction liquid, the liquid separation was conducted, and the organic layer was washed with 10 mL of saturated sodium chloride solution, dried over anhydrous sodium sulfate and concentrated under reduced pressure. The crude product was separated and purified with silica gel chromatography column (ethyl acetate/petroleum ether (v/v)=1:9) to afford tert-butyl 4-formyl-5-trideuterio methoxy-7-methyl-1H-indole-1-carboxylate (6b) (0.3 g, yield: 94%).

$^1$H NMR (400 MHz, $CDCl_3$) δ 10.63 (s, 1H), 7.62 (d, 1H), 7.47 (d, 1H), 6.73 (s, 1H), 2.68 (s, 3H), 1.63 (s, 9H).

LCMS m/z=293.1 $[M+1]^+$

Step 2: tert-butyl 5-(methoxy-d3)-4-(((7S)-7-(4-(methoxycarbonyl)phenyl)-1-oxa-8-azaspiro[4.5]decan-8-yl)methyl)-7-methyl-1H-indole-1-carboxylate (6c)

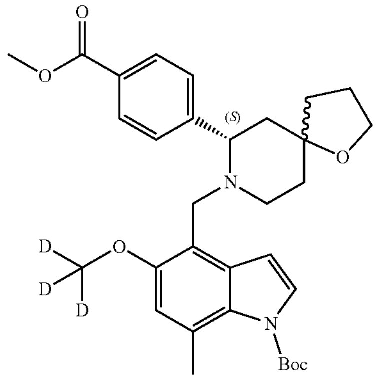

To the above-mentioned crude methyl 4-((7S)-1-oxa-8-azaspiro[4.5]decan-7-yl)benzoate [2f-b (diastereomer 2)]hydrochloride (200 mg) was added 50 mL of dichloromethane, the pH was adjusted to 9 with saturated sodium bicarbonate solution, the organic phase was separated, concentrated under reduced pressure, the residue was dissolved in 4 mL of tetrahydrofuran, 1 mL of anhydrous methanol was added, and maleic acid (0.034 g, 0.292 mmol) was added, the mixture was heated to 50° C. and stirred for 1 h. The reaction liquid was cooled to room temperature and concentrated under reduced pressure to afford a crude product (0.194 g). The crude product (0.194 g) was dissolved in 10 mL of absolute ethanol, and tert-butyl 4-formyl-5-trideuterio methoxy-7-methyl-1H-indole-1-carboxylate (6b) (0.17 g, 0.58 mmol) was added, nitrogen replacement was performed three times, 6 mg $Ir(CO)_2acac$ was added, nitrogen replacement was performed three times, the mixture was heated to 75° C., and reacted under the atmosphere of hydrogen balloon for 24 h. The reaction liquid was cooled to room temperature and concentrated under reduced pressure, and the residue was separated and purified with silica gel column chromatography (petroleum ether/ethyl acetate (v/v)=1:0-85:15) to afford tert-butyl 5-(methoxy-d3)-4-(((7S)-7-(4-(methoxycarbonyl)phenyl)-1-oxa-8-azaspiro[4.5]decan-8-yl)methyl)-7-methyl-1H-indole-1-carboxylate (6c) (0.17 g, yield: 53%).

LCMS m/z=552.3 $[M+1]^+$

Step 3: 4-((7S)-8-((5-(methoxy-d3)-7-methyl-1H-indol-4-yl)methyl)-1-oxa-8-azaspiro[4.5]decan-7-yl) benzoic acid (compound 6) trifluoroacetate

6-A

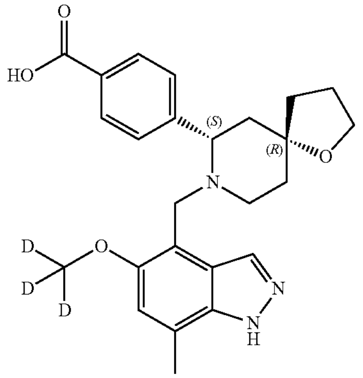

or

6-B

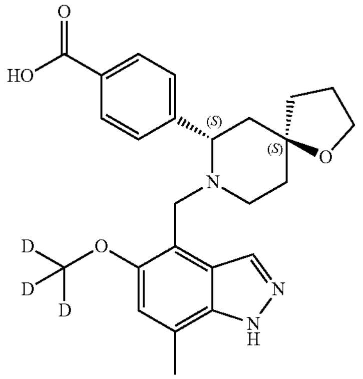

Tert-butyl 5-(methoxy-d3)-4-(((7S)-7-(4-(methoxycarbonyl)phenyl)-1-oxa-8-azaspiro[4.5]decan-8-yl)methyl)-7-methyl-1H-indole-1-carboxylate (6c) (0.14 g, 0.25 mmol) was dissolved in 10 mL of anhydrous methanol, solid potassium carbonate was added (0.17 g, 1.23 mmol), and the mixture was heated to 75° C. and reacted for 3 hours at reflux after the addition. The reaction liquid was cooled to room temperature, concentrated under reduced pressure, and 10 mL of tetrahydrofuran, 2 mL of water, and 2 mL of methanol were added to the residue in sequence, then lithium hydroxide monohydrate (0.1 g, 2.38 mmol) was added and reacted at room temperature for 16 h. The reaction liquid was concentrated under reduced pressure, 10 mL of water was added to the residue, 0.1 mol/L of citric acid aqueous solution was added dropwise to adjust the pH to 8, and the solution was subjected to Pre-HPLC (instrument and preparative column: using Glison GX-281 preparative liquid phase chromatographic instrument, preparative column model: Sunfire C18, 5 μm, inner diameter×length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((7S)-8-((5-(methoxy-d3)-7-methyl-1H-indol-4-yl)methyl)-1-oxa-8-azaspiro[4.5]decan-7-yl)benzoic acid (compound 6) trifluoroacetate (0.085 g).

$^1$H NMR (400 MHz, $CD_3OD$) δ 8.22 (d, 2H), 7.75 (d, 2H), 7.33 (d, 1H), 6.76 (s, 1H), 6.36 (d, 1H), 4.83-4.70 (m,

1H), 4.34 (d, 1H), 4.22 (d, 1H), 4.00-3.86 (m, 2H), 3.63-3.40 (m, 2H), 2.51 (s, 3H), 2.31-2.20 (m, 1H), 2.10-1.92 (m, 4H), 1.90-1.77 (m, 3H).
LCMS m/z=438.2 $[M+1]^+$
Compound 6 is one of the isomers of structure 6-A or 6-B.
Example 7
4-((2S)-4-cyclopropyl-1-((5-(methoxy-d3)-7-methyl-1H-indol-4-yl)methyl) piperidin-2-yl)benzoic acid [compound 7 (diastereomer 1)]trifluoroacetate
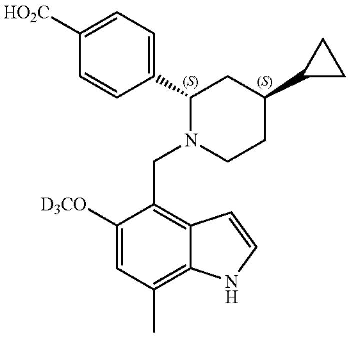
7-A
or
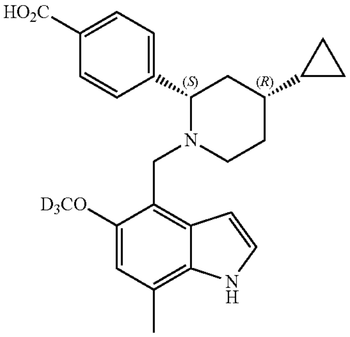
7-B
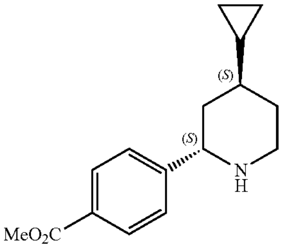
5c-A
or
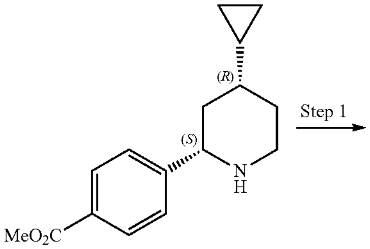
5c-B
5c (diastereomer 1)
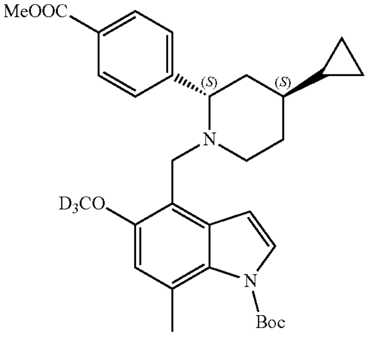
7a-A
or
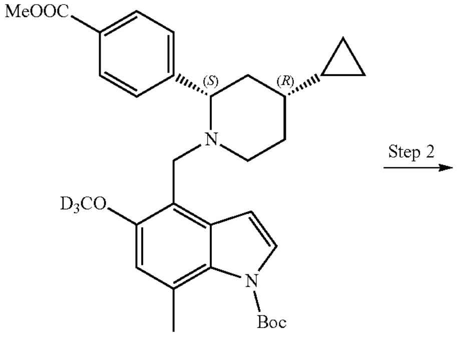
7a-B
7a (diastereomer 1)
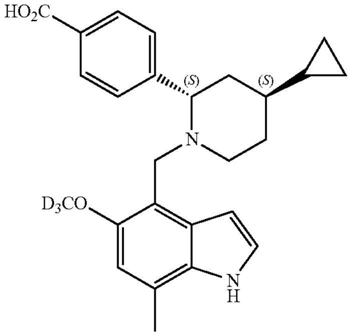
7-A
or
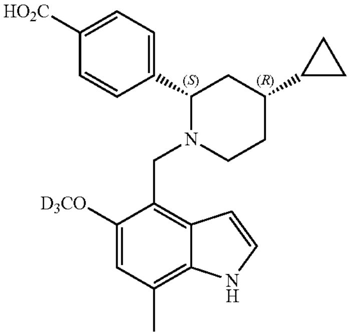
7-B
Compound 7 (diastereomer 1)

Step 1: tert-butyl 4-(((2S)-4-cyclopropyl-2-(4-(methoxycarbonyl)phenyl) piperidin-1-yl)methyl)-5-(methoxy-d3)-7-methyl-1H-indole-1-carboxylate [7a (diastereomer 1)]

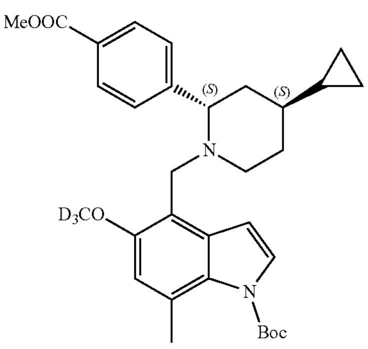

7a-A or

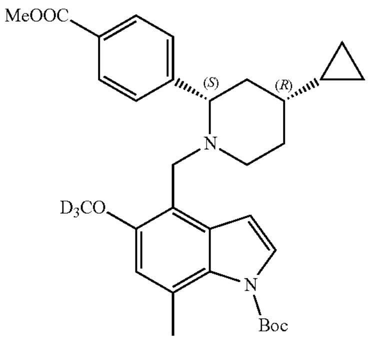

7a-B 7a (diastereomer 1)

Compound 5c (diastereomer 1) (162 mg, 0.625 mmol) was dissolved in 5 mL of isopropyl acetate, maleic acid (73 mg, 0.628 mmol) was added, and the mixture was reacted at room temperature for 1 h. The reaction system was concentrated under reduced pressure to afford crude methyl 4-((2S)-4-cyclopropylpiperidin-2-yl)benzoate [5c (diastereomer 1)] maleate (235 mg). The above-mentioned crude methyl 4-((2S)-4-cyclopropylpiperidin-2-yl)benzoate [5c (diastereomer 1)] maleate (235 mg) was dissolved in 10 mL of ethanol, tert-butyl 4-formyl-5-trideuterio methoxy-7-methyl-1H-indole-1-carboxylate (6b) (165 mg, 0.564 mmol) was added, 20 mg $Ir(CO)_2acac$ was added, hydrogen replacement was performed three times. The mixture was heated to 80° C., and reacted for 16 h under the atmosphere of hydrogen balloon. The reaction liquid was cooled to room temperature and concentrated under reduced pressure, and the crude product was separated and purified with silica gel column chromatography (petroleum ether/ethyl acetate (v/v)= 10:1) to afford tert-butyl 4-(((2S)-4-cyclopropyl-2-(4-(methoxycarbonyl)phenyl) piperidin-1-yl)methyl)-5-(methoxy-d3)-7-methyl-1H-indole-1-carboxylate [7a (diastereomer 1)] (200 mg, yield: 60%).

LCMS m/z=536.3 $[M+1]^+$

According to the $^1H$-$^1H$ NOESY verification of the C1 and C3 hydrogens of the final product compound 5, compound 7a (diastereomer 1) has structure 7a-B.

Step 2: 4-((2S)-4-cyclopropyl-1-((5-(methoxy-d3)-7-methyl-1H-indol-4-yl)methyl)piperidin-2-yl)benzoic acid [compound 7 (diastereomer 1)]trifluoroacetate

7-A

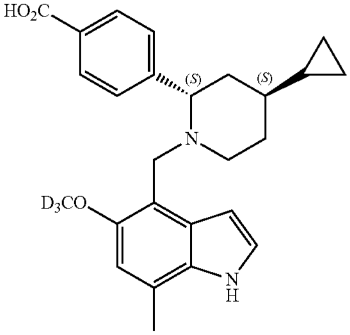

or

-continued

7-B

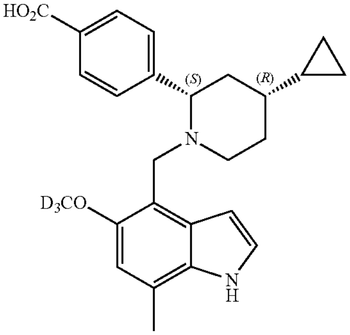

Tert-butyl 4-(((2S)-4-cyclopropyl-2-(4-(methoxycarbonyl)phenyl) piperidin-1-yl)methyl)-5-(methoxy-d3)-7-methyl-1H-indole-1-carboxylate [7a (diastereomer 1)] (200 mg, 0.37 mmol) was dissolved in 5 mL of methanol, solid potassium carbonate (257 mg, 1.86 mmol) was added, and the mixture was heated to 80° C. and reacted for 3 hours at reflux. The reaction solution was cooled to room temperature and concentrated under reduced pressure to afford a crude product. The above-mentioned crude product was dissolved in a mixed solvent of 5 mL of THF and 1 mL of water, lithium hydroxide monohydrate (155 mg, 3.7 mmol) was added and stirred at room temperature for 16 h. The reaction system was concentrated under reduced pressure, and the crude product was subjected to Pre-HPLC (instrument and preparative column: using Glison GX-281 preparative liquid phase chromatographic instrument, preparative column model: Sunfire C18, 5 μm, inner diameter× length=30 mm×150 mm). Preparation method: the crude product was dissolved with methanol and dimethyl sulfoxide, and filtered with a 0.45 μm filter membrane, to prepare into a sample liquid. Mobile phase system: acetonitrile/water (containing 0.1% TFA). Gradient elution method: gradient elution of 5% to 60% acetonitrile (elution time 15 min), and lyophilization was performed to afford 4-((2S)-4-cyclopropyl-1-((5-(methoxy-d3)-7-methyl-1H-indol-4-yl) methyl)piperidin-2-yl)benzoic acid [Compound 7 (diastereomer 1)]trifluoroacetate (125 mg).

$^1$H NMR (400 MHz, $CD_3OD$) δ 8.28-8.18 (m, 2H), 7.77-7.68 (m, 2H), 7.36-7.30 (m, 1H), 6.77 (s, 1H), 6.32 (d, 1H), 4.48 (dd, 1H), 4.40-4.29 (m, 1H), 4.18-4.08 (m, 1H), 3.62-3.52 (m, 1H), 3.30-3.21 (m, 1H), 2.51 (s, 3H), 2.25-2.12 (m, 1H), 2.09-1.85 (m, 2H), 1.79-1.60 (m, 1H), 1.20-1.03 (m, 1H), 0.67-0.53 (m, 1H), 0.52-0.40 (m, 2H), 0.26-0.12 (m, 2H).

LCMS m/z=422.2 $[M+1]^+$

According to the $^1$H-$^1$H NOESY verification of the C1 and C3 hydrogens of the final product compound 5, compound 7 (diastereomer 1) has structure 7-B.

Example 8

4-((2S)-4-cyclobutyl-1-((5-methoxy-7-methyl-1H-indol-4-yl)methyl)piperidin-2-yl)benzoic acid [compound 8 (diastereomer 1)] formate

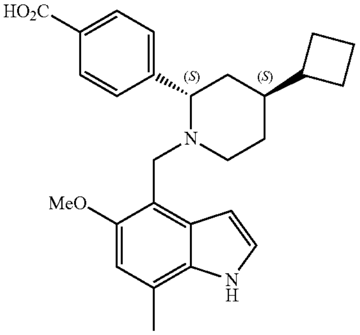

8-A or

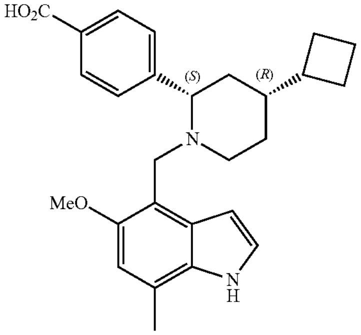

8-B

Compound 8 (diastereomer 1)

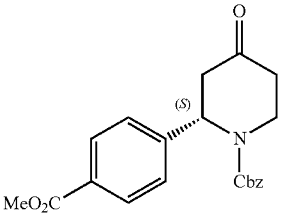

8a

Step 1

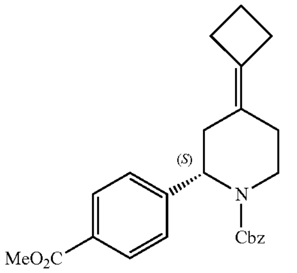

8b

Step 2

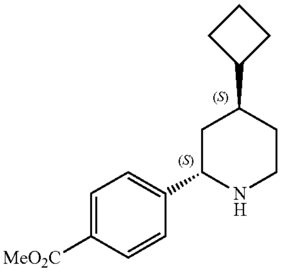

8c-A or

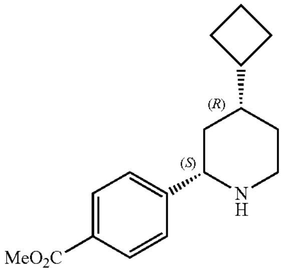

8c-B

Step 3

8c (diastereomer 1)

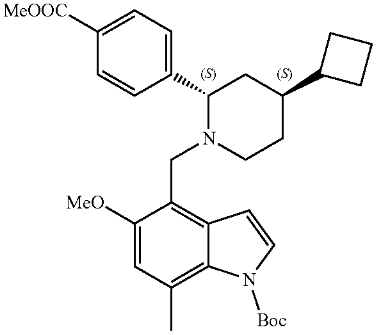

8d-A or

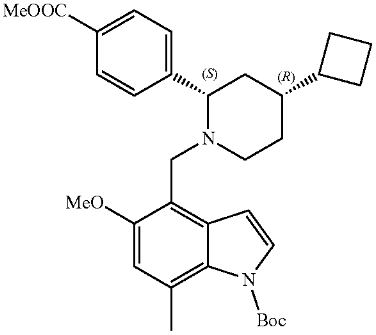

8d-B

Step 4

8d (diastereomer 1)

-continued

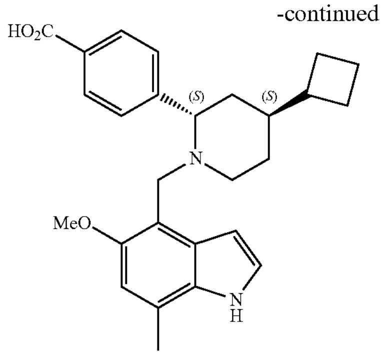

or

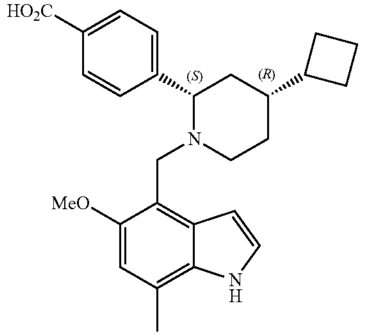

8-A

8-B

Compound 8 (diastereomer 1)

Step 1: benzyl (S)-4-cyclobutylidene-2-(4-(methoxycarbonyl)phenyl) piperidine-1-carboxylate (8b)

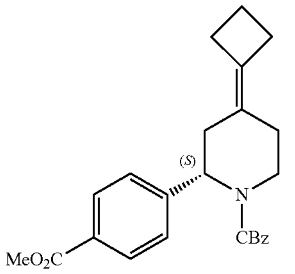

(4-bromobutyl)triphenylphosphine bromide (7.8 g, 16.31 mmol) was added to 60 mL of ultra-dry THF, the mixture was cooled to 0° C., and solid potassium tert-butoxide (3.7 g, 32.97 mmol) was slowly added under nitrogen atmosphere, and stirring was continued at 0° C. for 45 min, then a solution of benzyl (S)-2-(4-(methoxycarbonyl)phenyl)-4-oxopiperidine-1-carboxylate (5.0 g, 13.6 mmol) (1a) (for the synthetic method, see WO 2020016749) in tetrahydrofuran (20 mL) was added and the mixture was heated to 35° C. and reacted at room temperature for 16 h. 100 mL of saturated aqueous ammonium chloride solution was added to the reaction system, the mixture was extracted twice with 100 mL of ethyl acetate, dried over anhydrous sodium sulfate, concentrated under reduced pressure, and then the crude product was separated and purified with silica gel column chromatography (petroleum ether/ethyl acetate (v/v)=10:1) to afford benzyl (S)-4-cyclobutylidene-2-(4-(methoxycarbonyl)phenyl) piperidine-1-carboxylate (8b) (2.8 g, yield: 51%).

LCMS m/z=406.2 $[M+1]^+$

Step 2: methyl 4-((2S)-4-cyclobutylpiperidin-2-yl) benzoate [8c (diastereomer 1)] maleate

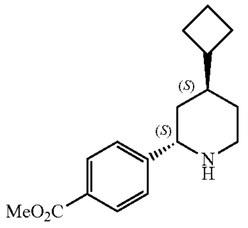

or

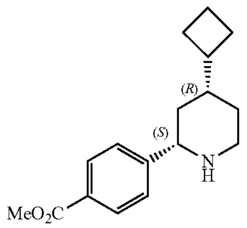

8c-A

8c-B 8c (diastereomer 1)

Benzyl (S)-4-cyclobutylidene-2-(4-(methoxycarbonyl) phenyl)piperidine-1-carboxylate (8b) (1.4 g, 3.45 mmol) was dissolved in 20 mL tetrahydrofuran, 430 mg of 10% palladium on carbon was added and reacted at 35° C. for 16 h under hydrogen atmosphere. The reaction system was suction-filtered under reduced pressure, and the filtrate was concentrated under reduced pressure to afford compound 8c (diastereomer 1) (640 mg). Compound 8c (diastereomer 1) (560 mg) was dissolved in 20 mL of isopropyl acetate, maleic acid (237 mg, 2.04 mmol) was added, and the mixture was stirred at room temperature for 16 h. The reaction system was concentrated under reduced pressure to afford crude methyl 4-((2S)-4-cyclobutylpiperidin-2-yl)benzoate [8c (diastereomer 1)] maleate (700 mg).

Nuclear Magnetic Resonances of Compound 8c (Diastereomer 1):

$^1$H NMR (400 MHz, $CDCl_3$) δ 8.02-7.94 (m, 2H), 7.47-7.39 (m, 2H), 3.90 (s, 3H), 3.63 (dd, 1H), 3.28-3.19 (m, 1H), 2.83-2.70 (m, 1H), 2.15-1.56 (m, 10H), 1.49-1.35 (m, 1H), 1.14-0.92 (m, 2H). Compound 8c (diastereomer 1) is one of the isomers of structure 8c-A or 8c-B.

Step 3: tert-butyl 4-(((2S)-4-cyclobutyl-2-(4-(methoxycarbonyl)phenyl)piperidin-1-yl)methyl)-5-methoxy-7-methyl-1H-indole-1-carboxylate [8d (diastereomer 1)]

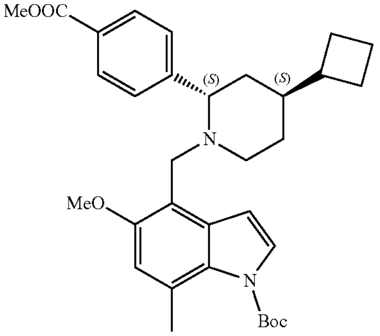

8d-A or

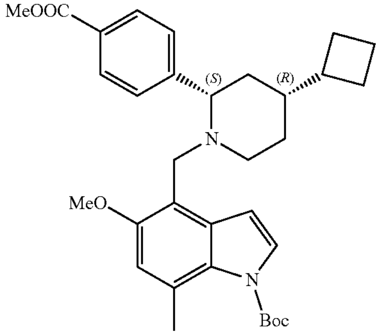

8d-B 8d (diastereomer 1)

The above-mentioned crude methyl 4-((2S)-4-cyclobutylpiperidin-2-yl)benzoate [8c (diastereomer 1)] maleate (700 mg) was dissolved in 15 mL of ethanol, tert-butyl 4-formyl-5-methoxy-7-methyl-1H-indole-1-carboxylate (650 mg, 2.25 mmol) (see WO 2015009616 for the synthesis method) was added and 70.8 mg of $Ir(CO)_2acac$ was added. The mixture was heated to 75° C., and reacted for 16 h under the atmosphere of hydrogen balloon. The reaction liquid was cooled to room temperature and concentrated under reduced pressure, and the crude product was separated and purified with silica gel column chromatography (petroleum ether/ethyl acetate (v/v)=10:1) to afford tert-butyl 4-(((2S)-4-cyclobutyl-2-(4-(methoxycarbonyl)phenyl)piperidin-1-yl)methyl)-5-methoxy-7-methyl-1H-indole-1-carboxylate [8d (diastereomer 1)] (750 mg, yield: 61%).

Compound 8d (diastereomer 1) is one of the isomers of structure 8d-A or 8d-B.

Step 4: 4-((2S)-4-cyclobutyl-1-((5-methoxy-7-methyl-1H-indol-4-yl)methyl) piperidin-2-yl)benzoic acid [compound 8 (diastereomer 1)] formate

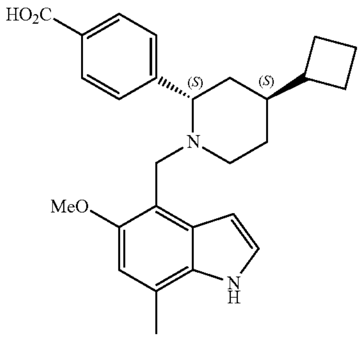

8-A or

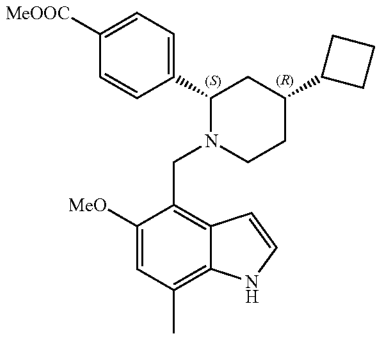

8-B

Compound 8 (diastereomer 1)

Tert-butyl 4-(((2S)-4-cyclobutyl-2-(4-(methoxycarbonyl)phenyl)piperidin-1-yl)methyl)-5-methoxy-7-methyl-1H-indole-1-carboxylate [8d (diastereomer 1)] (600 mg, 1.097 mmol) was dissolved in 10 mL of methanol, solid potassium carbonate (760 mg, 5.5 mmol) was added, and the mixture was heated to 80° C. and reacted for 3 hours at reflux. The reaction solution was cooled to room temperature and concentrated under reduced pressure to afford a crude product. The above-mentioned crude product was dissolved in a mixed solvent of 10 mL of THF and 2 mL of water, lithium hydroxide monohydrate (470 mg, 11.20 mmol) was added and stirred at room temperature for 16 h. The reaction system was concentrated under reduced pressure, and the crude product was subjected to Pre-HPLC (instrument and preparative column: using SHIMADZU LC-20AP & SHIMADZU SPD-20A preparative liquid phase chromatographic instrument, preparative column model: YMC Triart C18, 7 μm, inner diameter×length=50 mm×250 mm). Preparation method: the crude product was dissolved with methanol and dimethyl sulfoxide, and filtered with a 0.45 μm filter membrane, to prepare into a sample liquid. Mobile phase system: acetonitrile/water (containing 0.225% formic acid). Gradient elution method: gradient elution of 23% to 53% acetonitrile (elution time 18 min), and lyophilization was performed to afford 4-((2S)-4-cyclobutyl-1-((5-methoxy-7-methyl-1H-indol-4-yl)methyl)piperidin-2-yl)benzoic acid [compound 8 (diastereomer 1)] formate (500 mg).

$^1H$ NMR (400 MHz, $CD_3OD$) δ 8.35 (s, 1H), 8.21-8.13 (m, 2H), 7.72-7.60 (m, 2H), 7.35-7.28 (m, 1H), 6.75 (s, 1H), 6.37-6.24 (m, 1H), 4.62-4.27 (m, 2H), 4.19-4.05 (m, 1H), 3.80-3.68 (m, 3H), 3.62-3.42 (m, 1H), 3.39-3.21 (m, 1H), 2.50 (s, 3H), 2.30-1.20 (m, 12H).
LCMS m/z=433.3 $[M+1]^+$
Compound 8 (diastereomer 1) is one of the isomers of structure 8-A or 8-B.
Example 9
4-((2S)-4-(azetidin-1-yl)-1-((5-methoxy-7-methyl-1H-indol-4-yl)methyl) piperidin-2-yl)benzoic acid [compound 9 (diastereomer 1)]
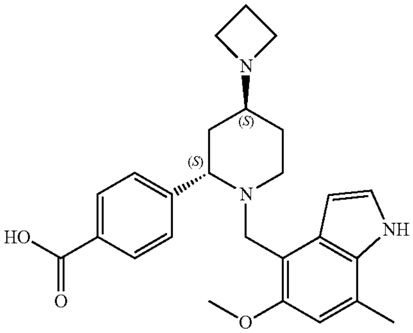
9-A
or
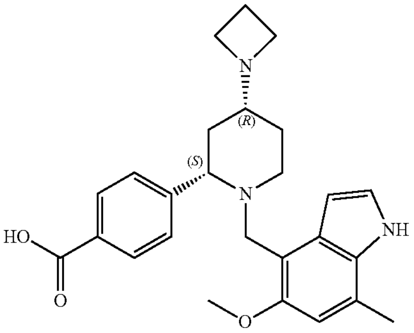
9-B
Compound 9 (diastereomer 1)
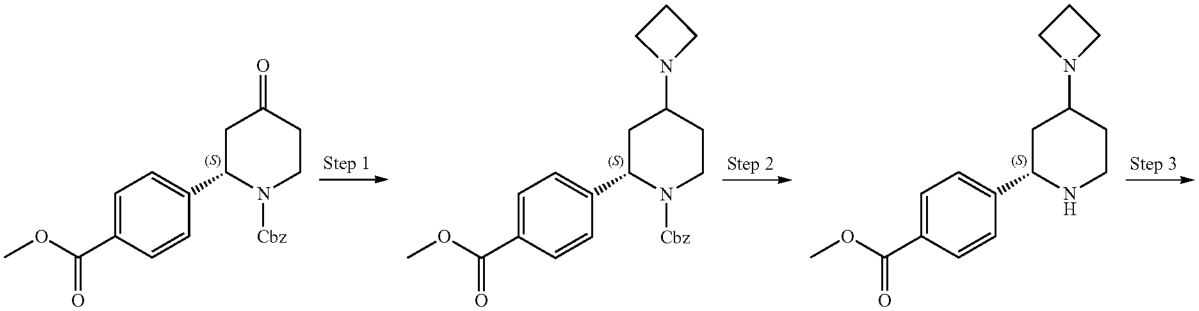
1a
9a
9b
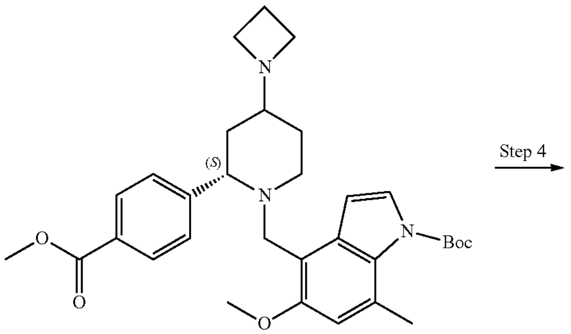
9c
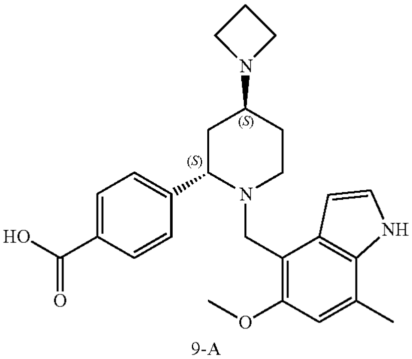
9-A
or
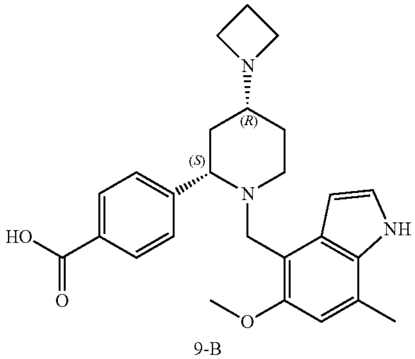
9-B
Compound 9 (diastereomer 1)

Step 1: benzyl (2S)-4-(azetidin-1-yl)-2-(4-(methoxycarbonyl)phenyl) piperidine-1-carboxylate (9a)

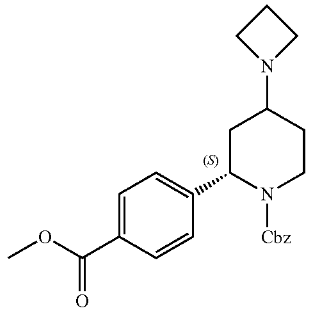

Benzyl (S)-2-(4-(methoxycarbonyl)phenyl)-4-oxopiperidine-1-carboxylate (1.5 g, 4.08 mmol) (1a) (see WO 2020016749 for the synthesis method) was dissolved in 30 mL of THF, azetidine (0.47 g, 8.23 mmol) and acetic acid (0.74 g, 12.33 mmol) were added, the mixture was stirred at room temperature for 1.5 h, then sodium triacetoxyborohydride (1.73 g, 8.16 mmol) was added, and the mixture was reacted at room temperature for 16 h. 120 mL of saturated aqueous sodium bicarbonate solution was added to the reaction system, the mixture was extracted with 100 mL of DCM, the organic phase was washed with 50 mL of water, dried over anhydrous sodium sulfate, and concentrated under reduced pressure. The crude product was separated and purified with silica gel chromatography column (DCM/MeOH (v/v)=15:1) to afford benzyl (2S)-4-(azetidin-1-yl)-2-(4-(methoxycarbonyl)phenyl)piperidine-1-carboxylate (9a) (1.5 g, yield: 91%).

LCMS m/z=409.2 $[M+1]^+$

Step 2: methyl 4-((2S)-4-(azetidin-1-yl)piperidin-2-yl)benzoate (9b) maleate

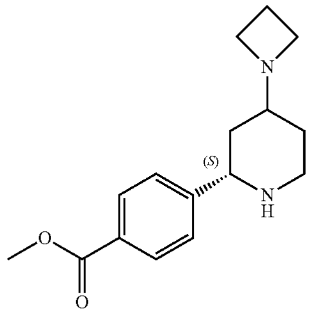

Benzyl (2S)-4-(azetidin-1-yl)-2-(4-(methoxycarbonyl)phenyl)piperidine-1-carboxylate (9a) (1.5 g, 3.67 mmol) was dissolved in 30 mL of methanol, 0.2 g of 10% palladium on carbon was added, hydrogen replacement was performed three times, and the mixture was reacted at room temperature for 16 h under the atmosphere of hydrogen balloon. The reaction system was filtered, and the filtrate was concentrated under reduced pressure to afford a crude product (1.0 g). The above-mentioned crude product (1.0 g) was dissolved in 25 mL of isopropyl acetate, add maleic acid (0.46 g, 3.96 mmol) was added, and stirred at room temperature for 3 h. The reaction system was directly rotated to dryness to afford crude methyl 4-((2S)-4-(azetidin-1-yl)piperidin-2-yl)benzoate (9b) maleate (1.5 g).

Step 3: tert-butyl 4-(((2S)-4-(azetidin-1-yl)-2-(4-(methoxycarbonyl)phenyl) piperidin-1-yl)methyl)-5-methoxy-7-methyl-1H-indole-1-carboxylate (9c)

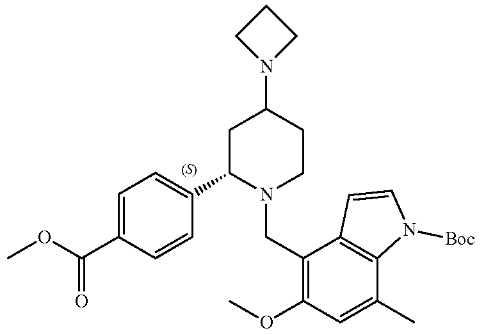

The above-mentioned crude methyl 4-((2S)-4-(azetidin-1-yl)piperidin-2-yl)benzoate (9b) maleate (1.5 g) was dissolved in 60 mL of ethanol, tert-butyl 4-formyl-5-methoxy-7-methyl-1H-indole-1-carboxylate (see WO 2015009616 for synthesis method) (1.18 g, 4.08 mmol) was added, 46 mg of $Ir(CO)_2acac$ was added, the mixture was heated to 75° C., and reacted under the atmosphere of hydrogen balloon for 48 h. The reaction liquid was cooled to room temperature and concentrated under reduced pressure, 30 mL of water was added to the residue, the pH was adjusted to 8 with 1 mol/L aqueous sodium hydroxide solution, the mixture was extracted with 100 mL of ethyl acetate, and the organic phase was washed with 50 mL of water, dried over anhydrous sodium sulfate and concentrated under reduced pressure. The crude product was separated and purified with silica gel chromatography column (petroleum ether/ethyl acetate (v/v)=1:1) to afford tert-butyl 4-(((2S)-4-(azetidin-1-yl)-2-(4-(methoxycarbonyl)phenyl)piperidin-1-yl)methyl)-5-methoxy-7-methyl-1H-indole-1-carboxylate (9c) (1.5 g, yield: 67%).

LCMS m/z=548.3 $[M+1]^+$

Step 4: 4-((2S)-4-(azetidin-1-yl)-1-((5-methoxy-7-methyl-1H-indol-4-yl)methyl)piperidin-2-yl)benzoic acid [compound 9 (diastereomer 1)]

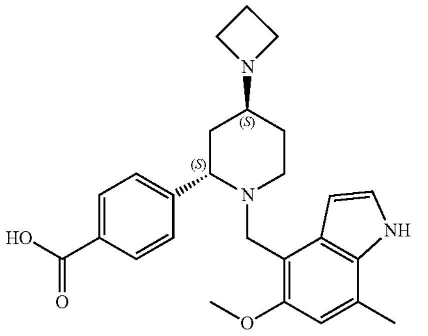

9-A or

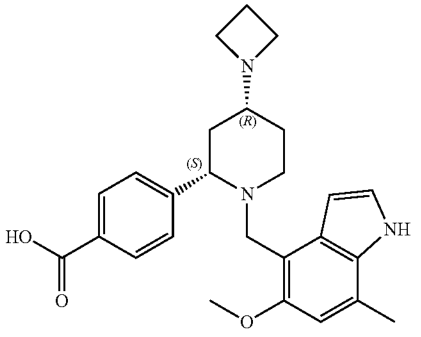

9-B

Compound 9 (diastereomer 1)

Tert-butyl 4-(((2S)-4-(azetidin-1-yl)-2-(4-(methoxycarbonyl)phenyl) piperidin-1-yl)methyl)-5-methoxy-7-methyl-1H-indole-1-carboxylate (9c) (0.6 g, 1.10 mmol) was dissolved in 10 mL of methanol, solid potassium carbonate (0.76 g, 5.50 mmol) was added, and the mixture was reacted at reflux for 3 h. The reaction system was cooled to room temperature and concentrated under reduced pressure to afford a crude product (1.3 g). The above-mentioned crude product (1.3 g) was dissolved in a mixed solvent of 10 mL of THF, 2 mL of methanol and 2 mL of water, lithium hydroxide monohydrate (0.45 g, 10.7 mmol) was added, and the mixture was heated to 60° C. and reacted for 2.5 h. The reaction liquid was cooled to room temperature, the pH was adjusted to 7 with 5 mol/L aqueous hydrochloric acid solution, the mixture was concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water. Gradient elution method: gradient elution of 10% to 40% acetonitrile (elution time 15 min), and lyophilization was performed to afford 4-((2S)-4-(azetidin-1-yl)-1-((5-methoxy-7-methyl-1H-indol-4-yl)methyl) piperidin-2-yl)benzoic acid [Compound 9 (diastereomer 1)] (220 mg, yield: 46%).

$^1$H NMR (400 MHz, DMSO-$d_6$) δ 10.80 (s, 1H), 8.01-7.90 (m, 2H), 7.66-7.54 (m, 2H), 7.29-7.19 (m, 1H), 6.64 (s, 1H), 6.46-6.38 (m, 1H), 3.69 (s, 3H), 3.59-3.47 (m, 1H), 3.26-3.08 (m, 6H), 2.84-2.71 (m, 1H), 2.41 (s, 3H), 2.30-2.16 (m, 1H), 2.05-1.85 (m, 3H), 1.79-1.66 (m, 1H), 1.65-1.50 (m, 1H), 1.32-1.14 (m, 1H), 1.13-0.91 (m, 1H).

LCMS m/z=434.3 $[M+1]^+$

Compound 9 (diastereomer 1) is one of the isomers of structure 9-A or 9-B.

Example 10

4-((2S)-4-ethynyl-1-((5-methoxy-7-methyl-1H-indol-4-yl)methyl)piperidin-2-yl)benzoic acid [compound 10 (diastereomer 1)]

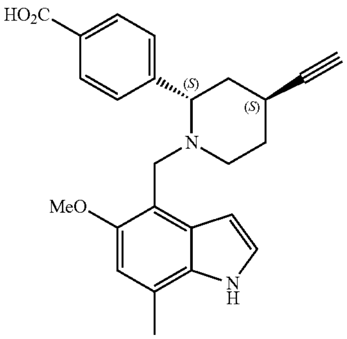

10-A or

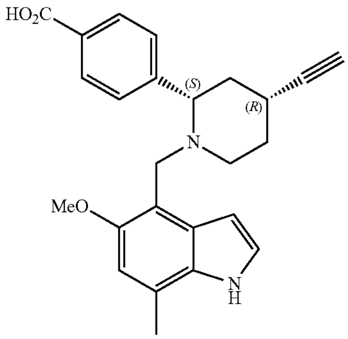

10-B

Compound 10 (diastereomer 1)

-continued
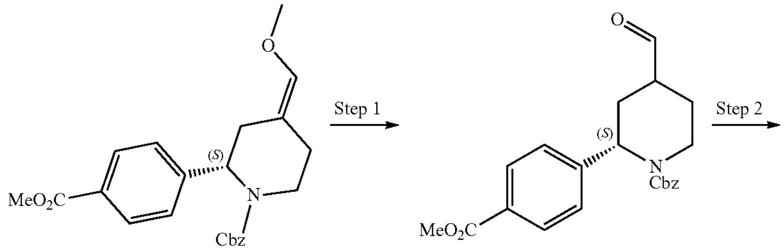
1b 10a
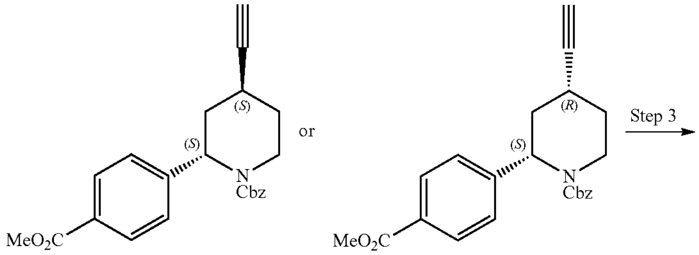
or
10b-A 10b-B
10b (diastereomer 1)
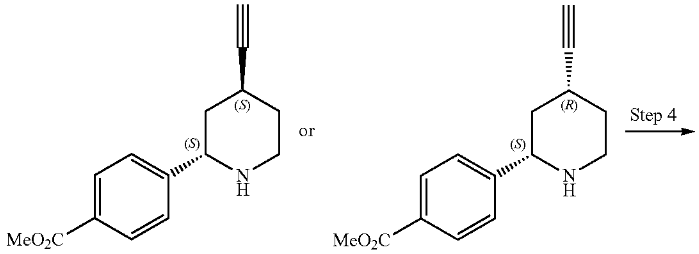
or
10c-A 10c-B
10c (diastereomer 1)
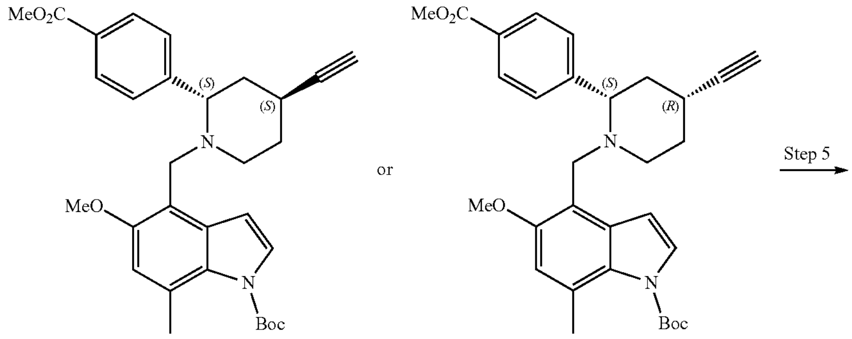
or
10d-A 10d-B
10d (diastereomer 1)

-continued

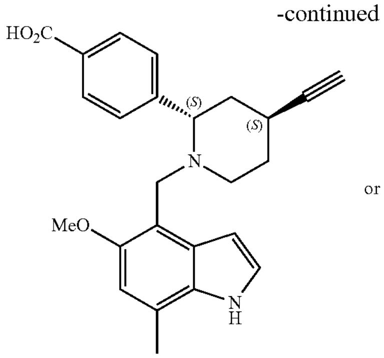

10-A or

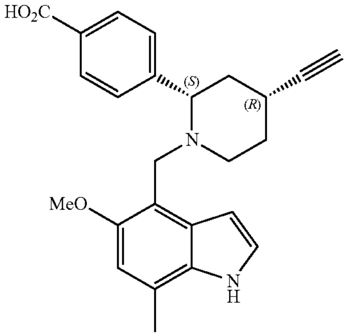

10-B

Compound 10 (diastereomer 1)

Step 1: benzyl (2S)-4-formyl-2-(4-(methoxycarbonyl)phenyl)piperidine-1-carboxylate (10a)

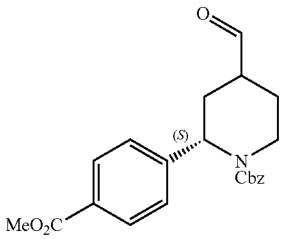

Benzyl (S)-2-(4-(methoxycarbonyl)phenyl)-4-(methoxymethylene) piperidine-1-carboxylate (1b) (3.8 g, 9.61 mmol) was added to 40 mL of methanol, 40 mL of 2 mol/L aqueous hydrochloric acid solution was added, and the mixture was reacted at reflux for 5 h. The reaction liquid was cooled to room temperature and concentrated under reduced pressure, the pH was adjusted to 12 with 5 mol/L sodium hydroxide solution, 200 mL of dichloromethane was added for extraction, the organic phase was separated, dried over anhydrous sodium sulfate, and concentrated under reduced pressure to afford crude benzyl (2S)-4-formyl-2-(4-(methoxycarbonyl)phenyl)piperidine-1-carboxylate (10a) (3.5 g).

Step 2: Benzyl (2S)-4-ethynyl-2-(4-(methoxycarbonyl)phenyl)piperidine-1-carboxylate [10b (diastereomer 1)]

10b (diastereomer 1)

10b-A

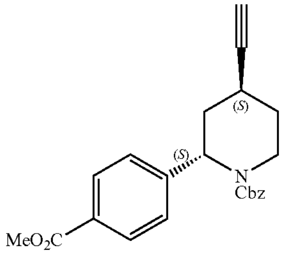

or

-continued

10b-B

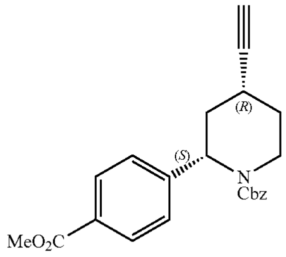

The above-mentioned crude benzyl (2S)-4-formyl-2-(4-(methoxycarbonyl)phenyl)piperidine-1-carboxylate (10a) (3.5 g) was dissolved in 60 mL of methanol, and solid potassium carbonate (2.6 g, 18.8 mmol) was added, the reaction liquid was cooled to 0° C., dimethyl (1-diazo-2-oxopropyl)phosphonate (2.1 g, 10.93 mmol) was slowly added dropwise, and the mixture was reacted at room temperature for 16 h under nitrogen atmosphere. The reaction system was concentrated under reduced pressure, 100 mL of ethyl acetate was added, the organic phase was washed with 100 mL of purified water, the organic phase was separated, dried over anhydrous sodium sulfate, concentrated under reduced pressure, and the crude product was separated and purified with silica gel chromatography column (petroleum ether/ethyl acetate (v/v)=4:1) to afford benzyl (2S)-4-ethynyl-2-(4-(methoxycarbonyl)phenyl)piperidine-1-carboxylate [10b (diastereomer 1)] (1.1 g, two-step yield from compound 1b: 30%).

$^1$H NMR (400 MHz, $CDCl_3$) δ 8.04-7.95 (m, 2H), 7.40-7.21 (m, 7H), 5.66-5.55 (m, 1H), 5.19 (s, 2H), 4.26-4.14 (m, 1H), 3.91 (s, 3H), 2.86-2.74 (m, 1H), 2.66-2.55 (m, 1H), 2.48-2.34 (m, 1H), 2.11-1.96 (m, 2H), 1.92-1.81 (m, 1H), 1.71-1.55 (m, 1H).

LCMS m/z=378.1 $[M+1]^+$

Compound 10b (diastereomer 1) is one of the isomers of structure 10b-A or 10b-B. According to NMR$^1$H-$^1$H NOESY analysis, compound 10b (diastereomer 1) was confirmed to have structure 10b-A.

Step 3: methyl 4-((2S)-4-ethynylpiperidin-2-yl)benzoate [10c (diastereomer 1)]

10c (diastereomer 1)

10c-A

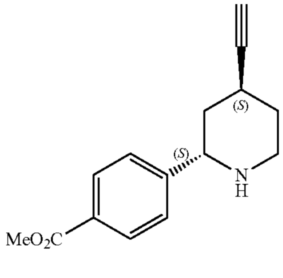

or

10c-B

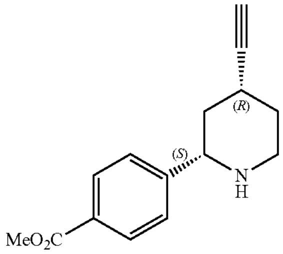

Benzyl (2S)-4-ethynyl-2-(4-(methoxycarbonyl)phenyl) piperidine-1-carboxylate [10b (diastereomer 1)] (0.76 g, 2.0 mmol) was dissolved in 20 mL of dichloromethane, the mixture was cooled to 0° C., iodotrimethylsilane (2.0 g, 10.0 mmol) was slowly added dropwise, and the mixture was reacted at room temperature for 3 h. 2 mL of methanol was added to the reaction liquid to quench the reaction, the reaction liquid was concentrated under reduced pressure, 10 mL of mixed solvent of petroleum ether/ethyl acetate (v/v)=10:1 was added to make a slurry, and a white solid was precipitated and suction-filtered to afford crude methyl 4-((2S)-4-ethynylpiperidin-2-yl)benzoate [10c (diastereomer 1)] (0.42 g).

LCMS m/z=244.1 $[M+1]^+$

Compound 10c (diastereomer 1) is one of the isomers of structure 10c-A or 10c-B. According to the NMR analysis of compound 10b (diastereomer 1), compound 10c (diastereomer 1) was confirmed to have structure 10c-A.

Step 4: tert-butyl 4-(((2S)-4-ethynyl-2-(4-(methoxycarbonyl)phenyl)piperidin-1-yl)methyl)-5-methoxy-7-methyl-1H-indole-1-carboxylate [10d (diastereomer 1)]

10d (diastereomer 1)

10d-A

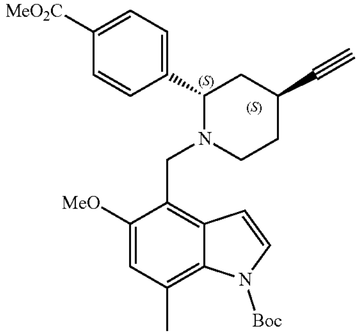

or

-continued

10d-B

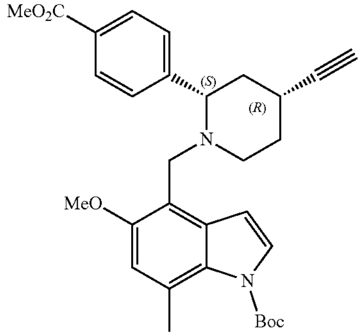

The above-mentioned crude methyl 4-((2S)-4-ethynylpiperidin-2-yl)benzoate [10c (diastereomer 1)] (0.42 g) was added to 10 mL of DMA, and tert-butyl 4-formyl-5-methoxy-7-methyl-1H-indole-1-carboxylate (0.5 g, 1.73 mmol) (see WO 2015009616 for synthesis method) and sodium triacetoxyborohydride (0.42 g, 2.0 mmol) were added in sequence, and the mixture was reacted at room temperature for 16 h. 50 mL of ethyl acetate was added to the reaction liquid, the organic phase was washed with 100 mL of purified water, dried over anhydrous sodium sulfate, and concentrated under reduced pressure. The crude product was separated and purified with silica gel chromatography column (petroleum ether/ethyl acetate (v/v)=4:1) to afford tert-butyl 4-(((2S)-4-ethynyl-2-(4-(methoxycarbonyl)phenyl) piperidin-1-yl)methyl)-5-methoxy-7-methyl-1H-indole-1-carboxylate [10d (diastereomer 1)] (0.39 g, yield: 44%).

Compound 10d (diastereomer 1) is one of the isomers of structure 10d-A or 10d-B. According to the NMR analysis of compound 10b (diastereomer 1), compound 10d (diastereomer 1) was confirmed to have structure 10d-A.

Step 5: 4-((2S)-4-ethynyl-1-((5-methoxy-7-methyl-1H-indol-4-yl)methyl) piperidin-2-yl)benzoic acid [compound 10 (diastereomer 1)]

Compound 10 (diastereomer 1)

10-A

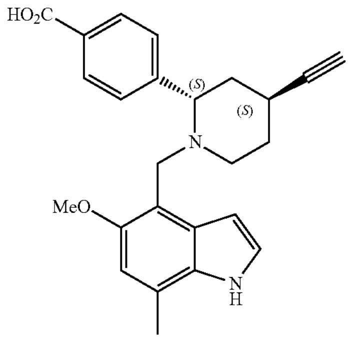

or

-continued

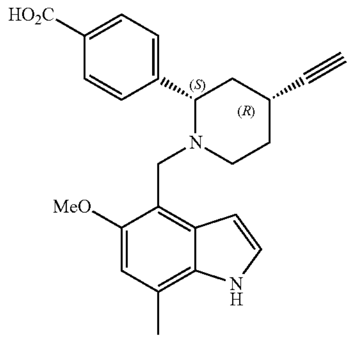

10-B

Tert-butyl 4-(((2S)-4-ethynyl-2-(4-(methoxycarbonyl)phenyl)piperidin-1-yl)methyl)-5-methoxy-7-methyl-1H-indole-1-carboxylate [10d (diastereomer 1)] (0.39 g, 0.755 mmol) was dissolved in 20 mL of methanol, solid potassium carbonate (0.3 g, 2.17 mmol) was added, and the mixture was reacted for 3 h at reflux. The reaction solution was cooled to room temperature and concentrated under reduced pressure to afford a crude product. The above-mentioned crude product was dissolved in a mixed solvent of 10 mL of THF, 5 mL of methanol and 2 mL of water, lithium hydroxide monohydrate (181 mg, 4.3 mmol) was added, and the mixture was heated to 60° C. and reacted for 1 h. The reaction liquid was cooled to room temperature and concentrated under reduced pressure, and the crude product was subjected to Pre-HPLC (instrument and preparative column: using SHIMADZU LC-20AP & SHIMADZU SPD-20A preparative liquid phase chromatographic instrument, preparative column model: C18 packing material, 7 μm, inner diameter×length=50 mm×250 mm). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 15% to 45% acetonitrile (elution time 15 min), and lyophilization was performed to afford 4-((2S)-4-ethynyl-1-((5-methoxy-7-methyl-1H-indol-4-yl)methyl)piperidin-2-yl)benzoic acid [Compound 10 (diastereomer 1)] (0.24 g, yield: 79%).

$^1H$ NMR (400 MHz, DMSO-$d_6$) δ 10.80 (s, 1H), 8.02-7.86 (m, 2H), 7.68-7.53 (m, 2H), 7.28-7.20 (m, 1H), 6.65 (s, 1H), 6.48-6.36 (m, 1H), 3.71 (s, 3H), 3.58-3.47 (m, 2H), 3.29-3.19 (m, 1H), 3.08-3.02 (m, 1H), 2.93-2.80 (m, 1H), 2.68-2.56 (m, 1H), 2.46-2.30 (m, 4H), 1.89-1.45 (m, 4H).

LCMS m/z=403.2 $[M+1]^+$

Compound 10 (diastereomer 1) is one of the isomers of structure 10-A or 10-B. According to NMR$^1H$-$^1H$ NOESY analysis, compound 10 (diastereomer 1) was confirmed to have structure 10-A.

Example 11

4-((2S)-4-cyclopentyl-1-((5-methoxy-7-methyl-1H-indol-4-yl)methyl) piperidin-2-yl)benzoic acid [compound 11 (diastereomer 1)]ammonium

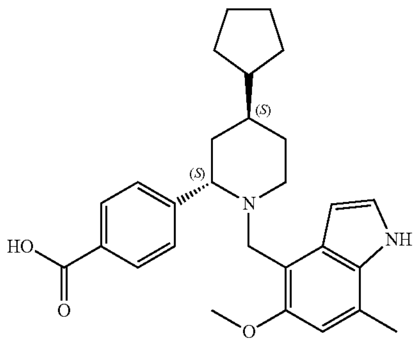

11-A or

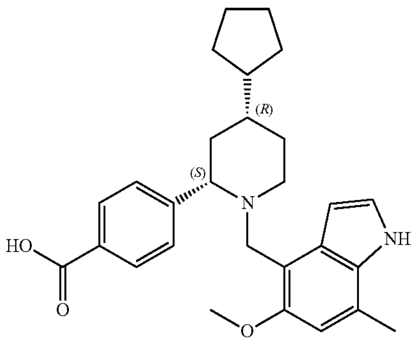

11-B

Compound 11 (diastereomer 1)

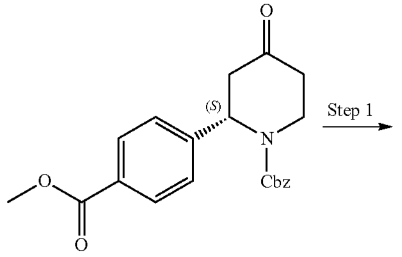

1a

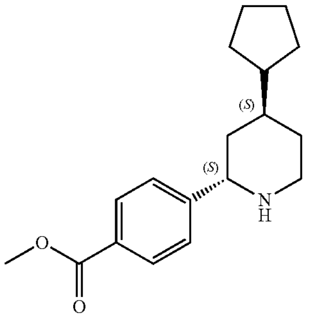

11a-A or

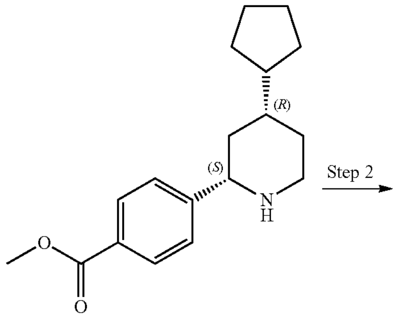

11a-B 11a (diastereomer 1)

-continued

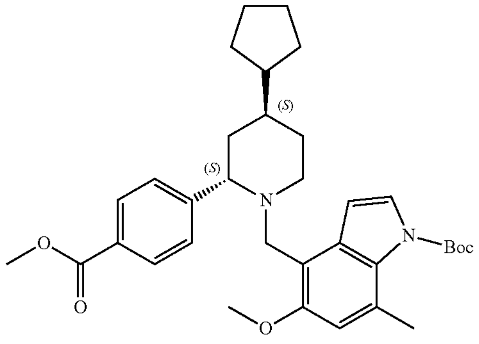

or

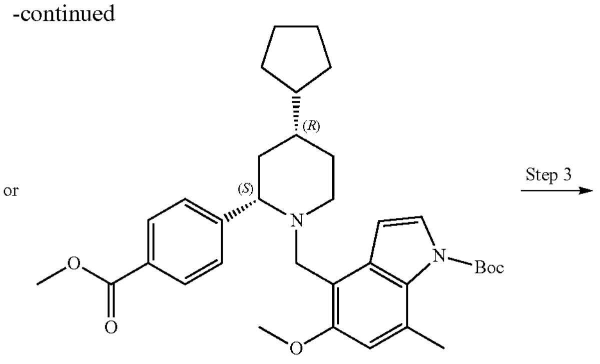

11b-A

11b-B 11b (diastereomer 1)

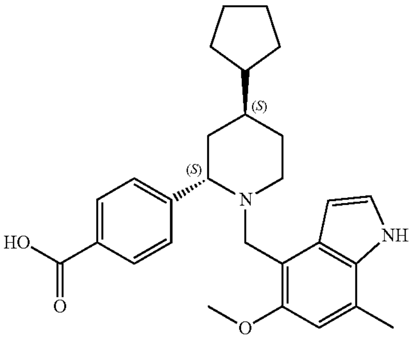

or

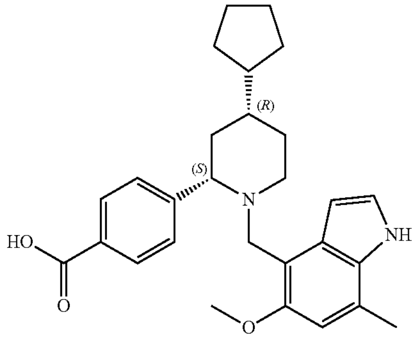

11-A

11-B

Compound 11 (diastereomer 1)

Step 1: methyl 4-((2S)-4-cyclopentylpiperidin-2-yl) benzoate [11a(diastereomer 1)] maleate 11a (diastereomer 1)

11a-A

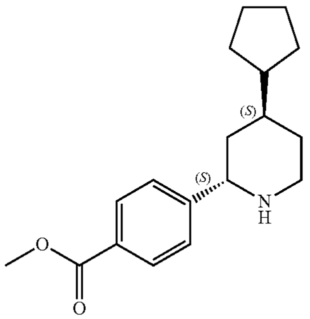

or

11a-B

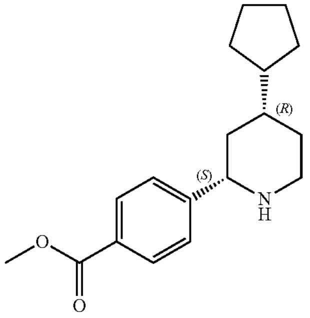

Benzyl (S)-2-(4-(methoxycarbonyl)phenyl)-4-oxopiperidine-1-carboxylate (2.0 g, 5.44 mmol) (1a) (see WO 2020016749 for the synthesis method) was added into 50 mL of ultra-dry THF, the mixture was cooled to −70° C. under nitrogen protection, a solution of 2 mol/L lithium diisopropylamide in tetrahydrofuran (3.5 mL, 2.0 mol/L) was slowly added dropwise and stirred further at −70° C. for 60 min, and N-phenylbis(trifluoromethanesulfonyl)imide (2.33 g, 6.53 mmol) was added and stirred further at −70° C. for 1 h, then the mixture was slowly warmed to room temperature and stirred for 2 h. 50 mL of ethyl acetate was added to the reaction system, the mixture was washed with 30 mL of saturated aqueous ammonium chloride solution, dried over anhydrous sodium sulfate, and concentrated under reduced pressure. The crude product was separated and purified with silica gel chromatography column (petroleum ether/ethyl acetate (v/v)=10:1) to afford a crude product 1 (2.1 g). The crude product 1 (1.0 g) was dissolved in 10 mL of DME and 10 mL of water, then 1-(cyclopenteneboronic acid pinacol ester (0.47 g, 2.42 mmol), solid sodium carbonate (0.64 g, 6.04 mmol) and tetrakis triphenylphosphine palladium (0.23 g, 0.20 mmol) were added in sequence, nitrogen replacement was performed three times, and the mixture was heated to 80° C. and reacted for 6 h. The reaction liquid was cooled to room temperature, 20 mL of water was added, the mixture was extracted with 50 mL of ethyl acetate, dried over anhydrous sodium sulfate, and concentrated under reduced pressure. The crude product was separated and purified with silica gel chromatography column (petroleum ether/ethyl acetate (v/v)=10:1) to afford a crude product 2 (0.6 g). The crude product 2 (600 mg) was dissolved in 10 mL of methanol, 0.2 g of 10% palladium on carbon was added, hydrogen replacement was performed three times, the mixture was reacted at room temperature under hydrogen atmosphere for 16 h. The reaction system was filtered, and the filtrate was concentrated under reduced pressure to afford methyl 4-((2S)-4-cyclopentylpiperidin-2-yl)benzoate [11a (diastereomer 1)] (0.36 g). Methyl 4-((2S)-4-cyclopentylpiperidin-2-yl)benzoate [11a (diastereomer 1)] (360 mg, 1.253 mmol) was dissolved in 10 mL of isopropyl acetate, maleic acid (150 mg, 1.29 mmol) was added, stirred at room temperature for 3 h, and then the reaction system was concentrated under reduced pressure to afford crude methyl 4-((2S)-4-cyclopentylpiperidin-2-yl)benzoate [11a (diastereomer 1)] maleate (500 mg).

Nuclear Magnetic Resonances of Compound 11a (Diastereomer 1):

$^{1}$H NMR (400 MHz, $CDCl_3$) δ 8.03-7.95 (m, 2H), 7.53-7.44 (m, 2H), 3.90 (s, 3H), 3.76-3.62 (m, 1H), 3.28-3.16 (m, 1H), 2.83-2.72 (m, 1H), 1.99-0.96 (m, 14H).

Compound 11a (diastereomer 1) is one of the isomers of structure 11a-A or 11a-B.

Step 2: tert-butyl 4-(((2S)-4-cyclopentyl-2-(4-(methoxycarbonyl)phenyl) piperidin-1-yl)methyl)-5-methoxy-7-methyl-1H-indole-1-carboxylate [11b (diastereomer 1)]

11b (diastereomer 1)

11b-A

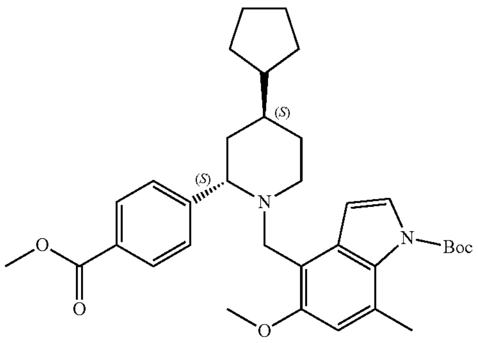

or

11b-B

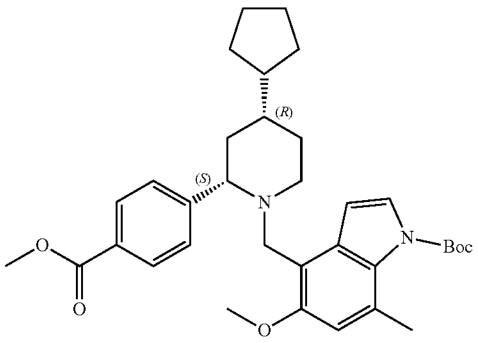

The above-mentioned crude methyl 4-((2S)-4-cyclopentylpiperidin-2-yl)benzoate [11a (diastereomer 1)] maleate (500 mg) was dissolved in 10 mL of ethanol, tert-butyl 4-formyl-5-methoxy-7-methyl-1H-indole-1-carboxylate (0.36 g, 1.24 mmol) (see WO 2015009616 for the synthesis method) was added and 22 mg of $Ir(CO)_2$acac was added, hydrogen replacement was performed three times, the mixture was heated to 75° C., and reacted for 48 h under the atmosphere of hydrogen balloon. The reaction liquid was concentrated under reduced pressure, 20 mL of water was added to the residue, the pH was adjusted to 8 with 1 mol/L sodium hydroxide solution, the mixture was extracted with 50 mL of ethyl acetate, and the organic phase was washed with 20 mL of water, dried over anhydrous sodium sulfate and concentrated under reduced pressure. The crude product was separated and purified with silica gel chromatography column (petroleum ether/ethyl acetate (v/v)=10:1) to afford tert-butyl 4-(((2S)-4-cyclopentyl-2-(4-(methoxycarbonyl)phenyl) piperidin-1-yl)methyl)-5-methoxy-7-methyl-1H-indole-1-carboxylate [11b (diastereomer 1)] (400 mg, two-step yield from compound 1a: 28%).

LCMS m/z=561.3 $[M+1]^+$

Compound 11b (diastereomer 1) is one of the isomers of structure 11b-A or 11b-B.

Step 3: 4-((2S)-4-cyclopentyl-1-((5-methoxy-7-methyl-1H-indol-4-yl)methyl) piperidin-2-yl)benzoic acid [compound 11 (diastereomer 1)]ammonium Compound 11 (diastereomer 1)

11-A

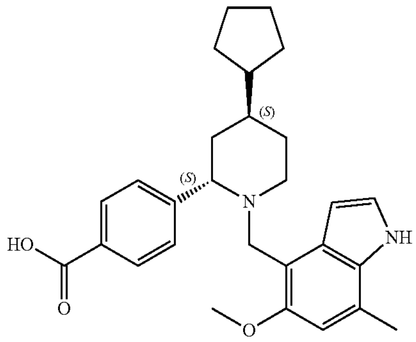

or

11-B

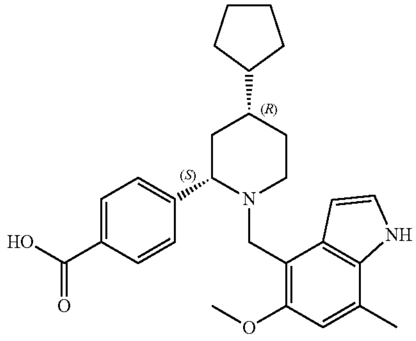

Tert-butyl 4-(((2S)-4-cyclopentyl-2-(4-(methoxycarbonyl)phenyl) piperidin-1-yl)methyl)-5-methoxy-7-methyl-1H-indole-1-carboxylate [11b (diastereomer 1)] (0.4 g, 0.713 mmol) was dissolved in 10 mL of methanol, solid potassium carbonate (490 mg, 3.55 mmol) was added, and the mixture was reacted for 3 h at reflux. The reaction liquid was cooled to room temperature and concentrated under reduced pressure to afford a crude product (0.8 mg). The above-mentioned crude product (0.8 g) was dissolved in 10 mL of THF, 2 mL of methanol and 2 mL of water, lithium hydroxide monohydrate (290 mg, 6.91 mmol) was added, and the mixture was heated to 60° C. and reacted for 2.5 h. The reaction liquid was cooled to room temperature, the pH of the reaction system was adjusted to 8 with 5 mol/L aqueous hydrochloric acid solution, the mixture was concentrated under reduced pressure, and the crude product was subjected to Pre-HPLC (instrument and preparative column: using SHIMADZU LC-20AP+Gilson 281 preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 10% to 40% acetonitrile (elution time 10 min). After lyophilization, the sample was subjected to chiral separation (instrument and preparative column: using Waters 150 SFC preparative liquid phase chromatographic instrument, preparative column model: Chiralpak Column). Preparation method: the crude product was dissolved with methanol and dimethyl sulfoxide, and filtered with a 0.45 μm filter membrane, to prepare into a sample liquid. Mobile phase system: a mixed solvent of supercritical carbon dioxide/methanol and acetonitrile (containing 0.1% ammonia). Gradient elution method: isocratic elution of 40% mixed solvent of methanol and acetonitrile (containing 0.1% ammonia water) and lyophilization was performed to afford 4-((2S)-4-cyclopentyl-1-((5-methoxy-7-methyl-1H-indol-4-yl)methyl)piperidin-2-yl)benzoic acid [compound 11 (diastereomer 1)]ammonium (148.3 mg).

Analysis Method of Ammonium of Compound 11 instrument: SHIMADZU LC-30AD sf, chromatographic column: Chiralcel IG-3, specifications: 50 mm×4.6 mm, 3 μm mobile phase A: supercritical $CO_2$, mobile phase B: mixed solution of methanol and acetonitrile containing 0.05% diethylamine, column temperature: 35° C., flow rate: 3 mL/min, wavelength: 220 nm, elution program: mobile phase A:B=60:40.

retention time of ammonium of compound 11 (diastereomer 1): 1.208 min $^1$H NMR (400 MHz, DMSO-$d_6$) δ 12.81 (br.s, 1H), 10.79 (s, 1H), 8.00-7.91 (m, 2H), 7.73-7.59 (m, 2H), 7.28-7.20 (m, 1H), 6.64 (s, 1H), 6.50-6.40 (m, 1H), 3.69 (s, 3H), 3.58-3.48 (m, 1H), 3.24-3.08 (m, 2H), 2.86-2.74 (m, 1H), 2.41 (s, 3H), 2.04-1.89 (m, 1H), 1.82-0.94 (m, 14H).

LCMS m/z=447.3 $[M+1]^+$

Compound 11 (diastereomer 1) is one of the isomers of structure 11-A or 11-B.

Example 12

(S)-4-(4-cyclopropyl-1-((5-methoxy-7-methyl-1H-indol-4-yl)methyl)-1,2,5,6-tetrahydropyridin-2-yl) benzoic acid (compound 12) ammonium

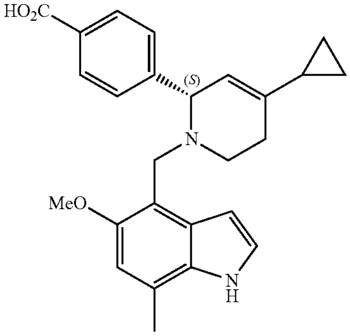

-continued

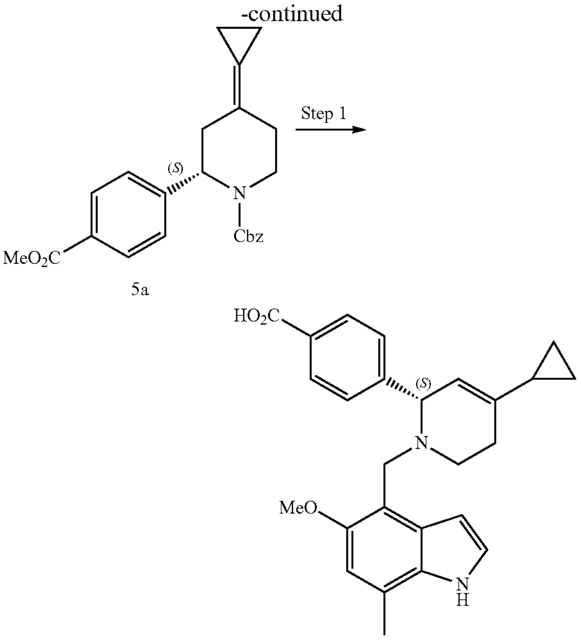

5a

Compound 12

Benzyl (S)-4-cyclopropylene-2-(4-(methoxycarbonyl)phenyl)piperidine-1-carboxylate (5a) (700 mg, 1.79 mmol) was dissolved in 15 mL of acetonitrile. Trimethylsilyl iodide (1.79 g, 8.91 mmol) was slowly added dropwise and reacted at room temperature for 30 min. 10 mL of methanol was added to the reaction system, the pH was adjusted to 2 with 2 mol/L aqueous hydrochloric acid solution, the organic phase was extracted with 50 mL of ethyl acetate, the organic phase was washed twice with 20 mL of 1 mol/L aqueous hydrochloric acid solution, and the water phases were combined, the pH of the aqueous phase was adjusted to 10 with 2 mol/L aqueous sodium hydroxide solution, the aqueous phase was extracted three times by adding 50 mL of dichloromethane, dried over anhydrous sodium sulfate, and concentrated under reduced pressure to afford crude product 1 (0.68 g). The above-mentioned crude product 1 (680 mg) was dissolved in 15 mL of N,N-dimethylacetamide, and tert-butyl 4-formyl-5-methoxy-7-methyl-1H-indole-1-carboxylate (840 mg, 2.90 mmol) (see WO 2015009616 for the synthesis method) was added, the mixture was stirred at room temperature for 45 min, then sodium triacetoxyborohydride (1.67 g, 7.88 mmol) was added and the mixture was warmed to 35° C. and reacted for 16 h. 100 mL of saturated aqueous sodium bicarbonate solution was added to the reaction system, the mixture was extracted twice with 100 mL of ethyl acetate, dried over anhydrous sodium sulfate, concentrated under reduced pressure, and the crude product was separated and purified with silica gel column chromatography (petroleum ether/ethyl acetate (v/v)=10:1) to afford crude product 2 (500 mg). The above-mentioned crude product 2 (500 mg) was dissolved in 15 mL of methanol, solid potassium carbonate (650 mg, 4.70 mmol) was added, and the mixture was heated to 80° C. and reacted at reflux for 5 h. The reaction liquid was cooled to room temperature and concentrated under reduced pressure to afford a crude product. The crude product was dissolved in a mixed solvent of 15 mL of THF and 3 mL of water, lithium hydroxide monohydrate (390 mg, 9.29 mmol) was added and reacted at room temperature for 16 h. The reaction system was concentrated under reduced pressure, and the crude product was subjected to Pre-HPLC (instrument and preparative column: using FRC-10A preparative liquid phase chromatographic instrument, preparative column model: C18 material, 7 μm, inner diameter×length=50 mm×250 mm). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 29% to 54% acetonitrile. After lyophilization, the sample was subjected to chiral separation (instrument and preparative column: using Waters 150 SFC preparative liquid phase chromatographic instrument, preparative column model: Chiralpak Column). Preparation method: the crude product was dissolved with methanol and dimethyl sulfoxide, and filtered with a 0.45 μm filter membrane, to prepare into a sample liquid. Mobile phase system: a mixed solvent of supercritical carbon dioxide/methanol and acetonitrile (containing 0.1% ammonia). Gradient elution method: isocratic elution of 40% mixed solvent of methanol and acetonitrile (containing 0.1% ammonia water) and lyophilization was performed to afford (S)-4-(4-cyclopropyl-1-((5-methoxy-7-methyl-1H-indol-4-yl)methyl)-1,2,5,6-tetrahydropyridin-2-yl)benzoic acid (compound 12) ammonium (50 mg).

Analysis Method of Ammonium of Compound 12 instrument: CAS-CD-ANA-SFC—B (SHIMADZU LC-30ADsf), chromatographic column: Chiralcel OD-3, specifications: 50 mm×4.6 mm, 3 μm, mobile phase A: supercritical CO, mobile phase B: methanol containing 0.05% diethylamine, column temperature: 35° C., flow rate: 3 mL/min, wavelength: 220 nm, elution program: mobile phase A:B=95:5-60:40. Retention time of ammonium of compound 12: 2.037 min Nuclear Magnetic Resonances Spectrum of Ammonium of Compound 12:

$^1H$ NMR (400 MHz, $CD_3OD$) δ 8.09-8.01 (m, 2H), 7.49-7.38 (m, 2H), 7.30-7.22 (m, 1H), 6.75 (s, 1H), 6.18 (d, 1H), 5.39 (s, 1H), 4.93-4.81 (m, 1H), 4.56-4.13 (m, 2H), 3.71 (s, 3H), 3.55-3.40 (m, 1H), 3.30-3.10 (m, 1H), 2.55-2.15 (m, 5H), 1.57-1.45 (m, 1H), 0.78-0.66 (m, 2H), 0.62-0.52 (m, 2H).

LCMS m/z=417.2 $[M+1]^+$

Example 13

4-((2S)-1-((5-methoxy-7-methyl-1H-indol-4-yl)methyl)-4-(prop-2-yn-1-yl)piperidin-2-yl)benzoic acid (compound 13)

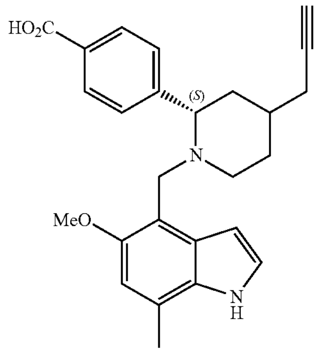

-continued

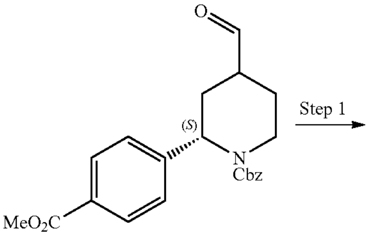

10a

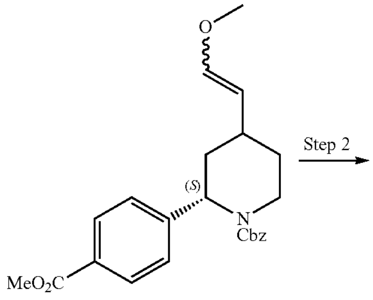

13a

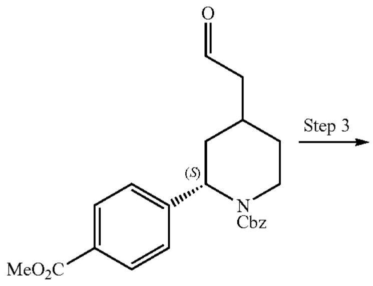

13b

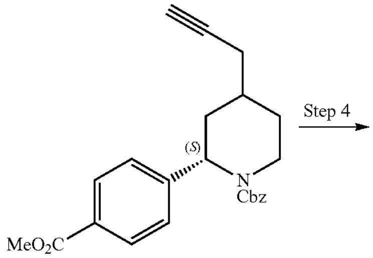

13c

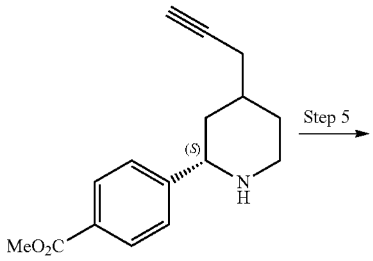

13d

-continued

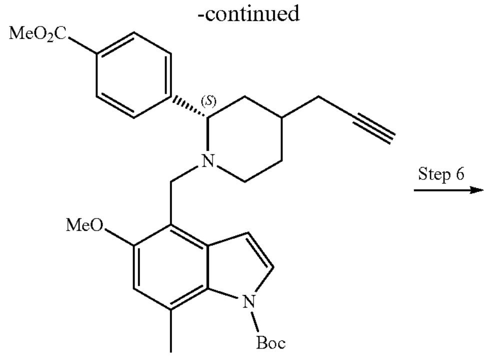

13a

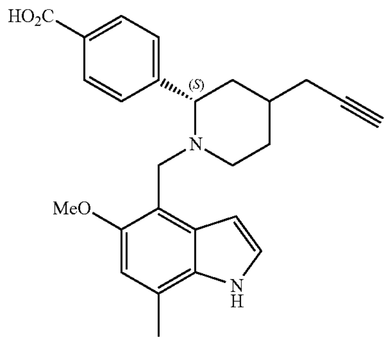

Compound 13

Step 1: benzyl (2S)-2-(4-(methoxycarbonyl)phenyl)-4-(2-methoxyvinyl) piperidine-1-carboxylate (13a)

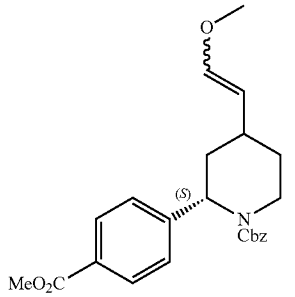

(methoxymethyl)triphenylphosphine chloride (3.4 g, 9.92 mmol) was added to 80 mL of anhydrous tetrahydrofuran, the mixture was cooled to 0° C., and solid potassium tert-butoxide (1.1 g, 9.80 mmol) was added and reacted at room temperature 1 h. Benzyl (2S)-4-formyl-2-(4-(methoxycarbonyl)phenyl)piperidine-1-carboxylate (10a) (2.9 g, 7.6 mmol) was added and reacted at room temperature 16 h. 100 mL saturated ammonium chloride solution was added to the reaction liquid, the mixture was extracted with 100 mL of ethyl acetate, and the organic phase was dried over anhydrous sodium sulfate and concentrated under reduced pressure. The crude product was separated and purified with silica gel chromatographic column (petroleum ether/ethyl acetate (v/v)=4:1) to afford benzyl (2S)-2-(4-(methoxycarbonyl)phenyl)-4-(2-methoxyvinyl)piperidine-1-carboxylate (13a) (1.6 g, yield: 51%).

LCMS m/z=410.1 $[M+1]^+$

Step 2: benzyl (2S)-2-(4-(methoxycarbonyl)phenyl)-4-(2-oxoethyl)piperidine-1-carboxylate (13b)

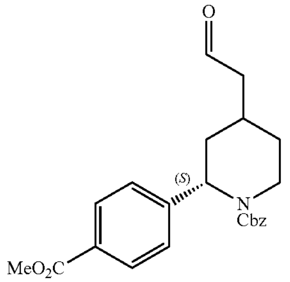

Benzyl (2S)-2-(4-(methoxycarbonyl)phenyl)-4-(2-methoxyvinyl) piperidine-1-carboxylate (13a) (1.6 g, 3.91 mmol) was added to 40 mL of methanol, 40 mL of 2 mol/L aqueous hydrochloric acid solution was added, and the mixture was reacted at reflux for 5 h. The reaction liquid was cooled to room temperature and concentrated under reduced pressure, the pH was adjusted to 12 with 5 mol/L aqueous sodium hydroxide solution, 100 mL of dichloromethane was added for extraction, the organic phase was separated, dried over anhydrous sodium sulfate, and concentrated under reduced pressure to afford crude benzyl (2S)-2-(4-(methoxycarbonyl)phenyl)-4-(2-oxoethyl)piperidine-1-carboxylate (13b) (1.2 g).

$^1$H NMR (400 MHz, $CDCl_3$) δ 9.77-9.72 (m, 1H), 8.07-7.96 (m, 2H), 7.50-7.20 (m, 7H), 5.75-5.45 (m, 1H), 5.27-5.05 (m, 2H), 4.30-4.05 (m, 1H), 3.91 (s, 3H), 2.92-2.75 (m, 1H), 2.54-2.32 (m, 3H), 2.20-2.00 (m, 1H), 1.70-1.52 (m, 2H), 1.40-1.15 (m, 1H).

Through NMR$^1$H-$^1$H NOESY analysis, compound 13b was confirmed to have structure 13b-A.

13b-A

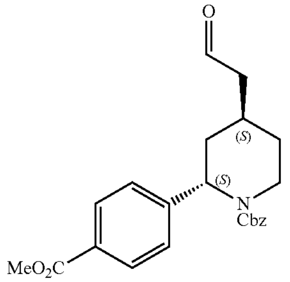

Step 3: Benzyl (2S)-2-(4-(methoxycarbonyl)phenyl)-4-(prop-2-yn-1-yl)piperidine-1-carboxylate (13c)

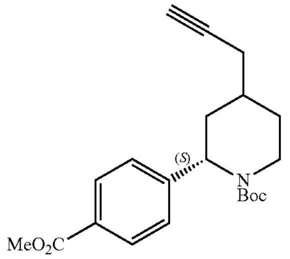

The above-mentioned crude benzyl (2S)-2-(4-(methoxycarbonyl)phenyl)-4-(2-oxoethyl)piperidine-1-carboxylate (13b) (1.2 g) was dissolved in 30 mL of methanol, and solid potassium carbonate (0.83 g, 6 mmol) was added, the mixture was cooled to 0° C., dimethyl (1-diazo-2-oxopropyl)phosphonate (0.77 g, 4 mmol) was slowly added dropwise, and the mixture was stirred at room temperature for 16 h under nitrogen atmosphere. The reaction system was concentrated under reduced pressure, 100 mL of ethyl acetate was added, the organic phase was washed with 100 mL of purified water, the organic phase was separated, dried over anhydrous sodium sulfate, concentrated under reduced pressure, and the crude product was separated and purified with silica gel chromatography column (petroleum ether/ethyl acetate (v/v)=4:1) to afford benzyl (2S)-2-(4-(methoxycarbonyl)phenyl)-4-(prop-2-yn-1-yl)piperidine-1-carboxylate (13c) (0.33 g, two-step yield from compound 13a: 22%).

$^1$H NMR (400 MHz, $CDCl_3$) δ 8.05-7.95 (m, 2H), 7.53-7.15 (m, 7H), 5.80-5.45 (m, 1H), 5.20 (s, 2H), 4.37-4.10 (m, 1H), 3.90 (s, 3H), 2.90-2.75 (m, 1H), 2.58-2.42 (m, 1H), 2.18-2.07 (m, 2H), 2.03-1.97 (m, 1H), 1.78-1.60 (m, 3H), 1.40-1.20 (m, 1H).

Through NMR$^1$H-$^1$H NOESY analysis, compound 13c was confirmed to have structure 13c-A.

13c-A

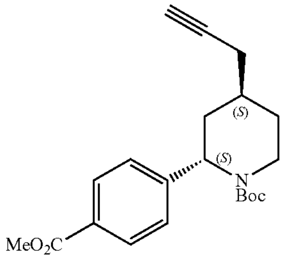

Step 4: methyl 4-((2S)-4-(prop-2-yn-1-yl)piperidin-2-yl)benzoate (13d)

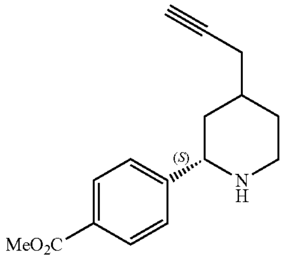

Benzyl (2S)-2-(4-(methoxycarbonyl)phenyl)-4-(prop-2-yn-1-yl)piperidine-1-carboxylate (13c) (0.33 g, 0.843 mmol) was dissolved in 20 mL of dichloromethane, the mixture was cooled to 0° C., iodotrimethylsilane (0.8 g, 4.0 mmol) was slowly added dropwise, and the mixture was reacted at room temperature for 3 h. 2 mL of methanol was added to the reaction liquid to quench the reaction, the reaction liquid was concentrated under reduced pressure, 10 mL of mixed solvent of petroleum ether/ethyl acetate (v/v)=10:1 was added to make a slurry, and a white solid was precipitated and suction-filtered to afford crude methyl 4-((2S)-4-(prop-2-yn-1-yl)piperidin-2-yl)benzoate (13d) (0.17 g).

According to the NMR structure analysis of compound 13c, compound 13d was confirmed to have structure 13d-A.

13d-A

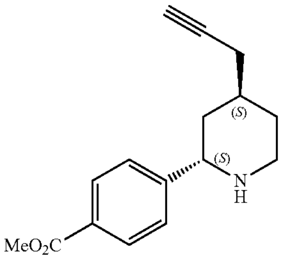

Step 5: tert-butyl 5-methoxy-4-(((2S)-2-(4-(methoxycarbonyl)phenyl)-4-(prop-2-yn-1-yl)piperidin-1-yl)methyl)-7-methyl-1H-indole-1-carboxylate (13e)

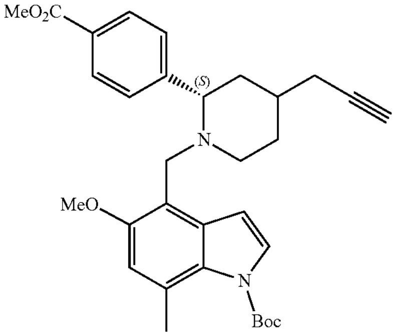

The above-mentioned crude methyl 4-((2S)-4-(prop-2-yn-1-yl)piperidin-2-yl)benzoate (13d) (0.17 g) was added to 10 mL of DMA, and tert-butyl 4-formyl-5-methoxy-7-methyl-1H-indole-1-carboxylate (0.19 g, 0.66 mmol) (see WO 2015009616 for synthesis method) and sodium triacetoxyborohydride (0.21 g, 0.99 mmol) were added in sequence, and the mixture was reacted at room temperature for 16 h. 50 mL of ethyl acetate was added to the reaction liquid, the organic phase was washed with 100 mL of purified water, dried over anhydrous sodium sulfate, and concentrated under reduced pressure. The crude product was separated and purified with silica gel chromatography column (petroleum ether/ethyl acetate (v/v)=4:1) to afford crude tert-butyl 5-methoxy-4-(((2S)-2-(4-(methoxycarbonyl) phenyl)-4-(prop-2-yn-1-yl)piperidin-1-yl)methyl)-7-methyl-1H-indole-1-carboxylate (13e) (0.27 g).

According to the NMR structure analysis of compound 13c, compound 13e was confirmed to have structure 13e-A.

13e-A

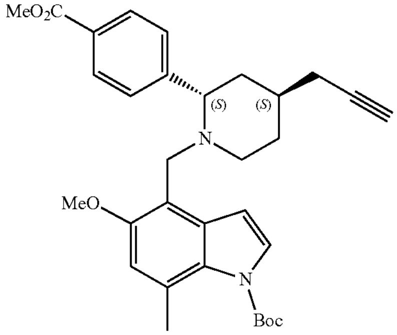

Step 6: 4-((2S)-1-((5-methoxy-7-methyl-1H-indol-4-yl)methyl)-4-(prop-2-yn-1-yl)piperidin-2-yl)benzoic acid (compound 13)

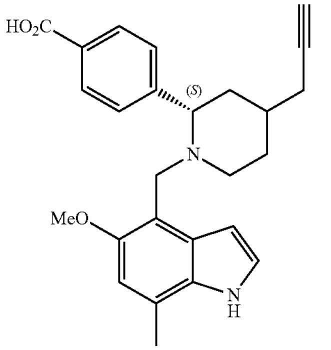

The above-mentioned crude tert-butyl 5-methoxy-4-(((2S)-2-(4-(methoxycarbonyl)phenyl)-4-(prop-2-yn-1-yl) piperidin-1-yl)methyl)-7-methyl-1H-indole-1-carboxylate (13e) (0.27 g) was dissolved in 20 mL of methanol, solid potassium carbonate (0.3 g, 2.17 mmol) was added, and the mixture was reacted for 3 h at reflux. The reaction solution was cooled to room temperature and concentrated under reduced pressure to afford a crude product. The above-mentioned crude product was dissolved in a mixed solvent of 10 mL of THF, 5 mL of methanol and 2 mL of water, lithium hydroxide monohydrate (181 mg, 4.3 mmol) was added, and the mixture was heated to 60° C. and reacted for 1 h. The reaction liquid was cooled to room temperature and concentrated under reduced pressure, and the crude product was subjected to Pre-HPLC (instrument and preparative column: using SHIMADZU LC-20AP+Gilson 281 preparative liquid phase chromatographic instrument, preparative column model: Phenomenex C18 (10 um particle size)). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 25% to 55% acetonitrile (elution time 15 min), and lyophilization was performed to afford 4-((2S)-1-((5-methoxy-7-methyl-1H-indol-4-yl)methyl)-4-(prop-2-yn-1-yl)piperidin-2-yl)benzoic acid (compound 13) (20 mg, three-step yield from compound 13c: 6%).

$^1$H NMR (400 MHz, DMSO-$d_6$) δ 10.81 (s, 1H), 8.01-7.91 (m, 2H), 7.70-7.58 (m, 2H), 7.26 (t, 1H), 6.66 (s, 1H), 6.54-6.43 (m, 1H), 3.72 (s, 3H), 3.68-3.58 (m, 1H), 3.55-3.44 (m, 1H), 3.42-3.31 (m, 1H), 2.82-2.76 (m, 1H), 2.62-2.52 (m, 1H), 2.47-2.33 (m, 5H), 2.32-2.19 (m, 1H), 1.99-1.48 (m, 5H).

LCMS m/z=417.2 $[M+1]^+$

13-A

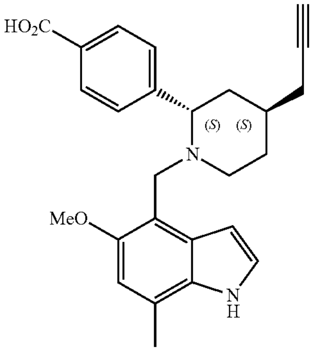

or

13-B

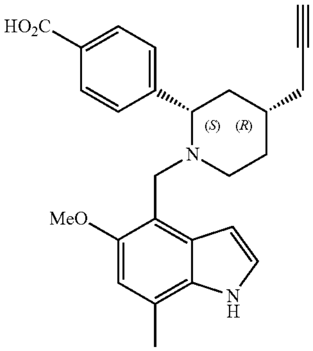

Compound 13 is one of the isomers of structure 13-A or 13-B. According to NMR$^1$H-$^1$H NOESY analysis, compound 13 was confirmed to have structure 13-A.

Example 14
4-((7S)-8-((5-methoxy-7-methyl-1H-indazol-4-yl)methyl)-1-oxa-8-azaspiro[4.5]decan-7-yl)benzoic acid (compound 14)
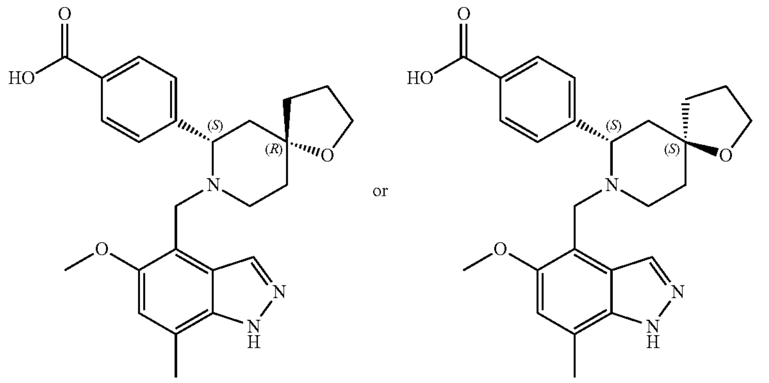
14-A or 14-B
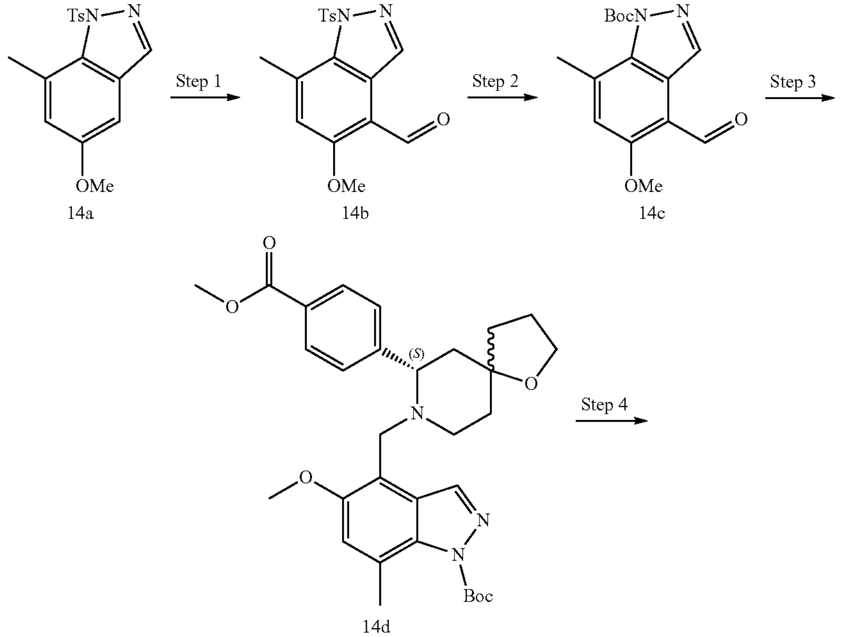
14a 14b 14c 14d
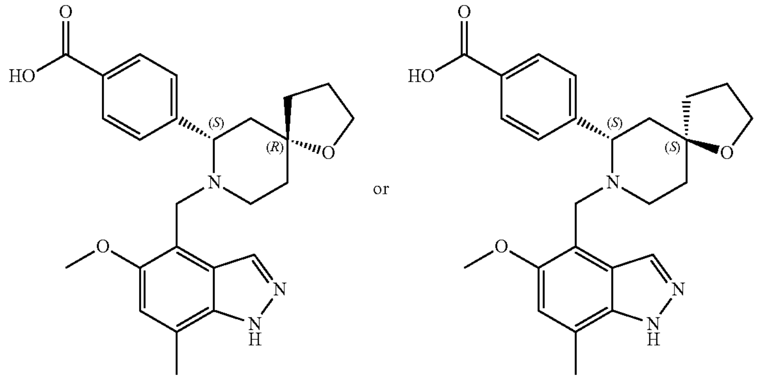
14-A or 14-B
Compound 14

Step 1: 5-methoxy-7-methyl-1H-indazole-4-carbaldehyde (14b)

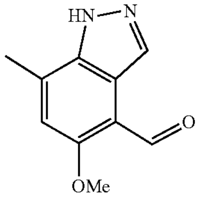

5-methoxy-7-methyl-1-methylsulfonyl-1H-indazole (14a) (see CN 114057692 for synthesis method) (4.0 g, 12.64 mmol) was dissolved in 30 mL of dichloromethane, and the reaction system was cooled to −78° C., titanium tetrachloride (9.0 g, 47.45 mmol) was slowly added dropwise, the reaction was continued at this temperature for 5 min, 1,1-dichloromethyl methyl ether (6.0 g, 52.19 mml) was added, and the reaction system was slowly warmed to 0° C. for 6 h. The reaction system was cooled to −40° C., 50 mL of water was slowly added to quench the reaction, 100 mL of ethyl acetate was added, the organic phase was separated and extracted with ethyl acetate (50 mL×5), the organic phases were combined, and washed with 100 mL of saturated sodium bicarbonate solution, dried over anhydrous sodium sulfate, and concentrated under reduced pressure. The crude product was separated and purified with silica gel chromatography column (first eluted with ethyl acetate/petroleum ether (v/v)=1:1, and then eluted with dichloromethane/methanol (v/v)=5:1) to afford 5-methoxy-7-methyl-1H-indazole-4-carbaldehyde (14b) (1.26 g, yield: 52%).

Step 2: tert-butyl 4-formyl-5-methoxy-7-methyl-1H-indazole-1-carboxylate (14c)

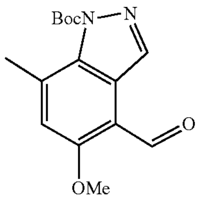 [SMILES: COc1cc(C)c2c(cnn2C(=O)OC(C)(C)C)c1C=O]

5-methoxy-7-methyl-1H-indazole-4-carbaldehyde (14b) (1.10 g, 5.78 mmol) was dissolved in 20 mL of acetonitrile, and di-tert-butyl dicarbonate ($Boc_2O$) (1.26 g, 5.78 mmol) and 4-dimethylaminopyridine (0.15 g, 1.23 mmol) were added and stirred at room temperature for 30 min. The reaction liquid was concentrated under reduced pressure, and 50 mL of ethyl acetate was added. The organic phase was washed with 50 mL of 0.5 mol/L aqueous hydrochloric acid solution, dried over anhydrous sodium sulfate, and concentrated under reduced pressure. The crude product was separated and purified with silica gel chromatography column (ethyl acetate/petroleum (v/v)=3:1) to afford tert-butyl 4-formyl-5-methoxy-7-methyl-1H-indazole-1-carboxylate (14c) (1.23 g, yield: 73%).

Step 3: tert-butyl 5-methoxy-4-(((7S)-7-(4-(methoxycarbonyl)phenyl)-1-oxa-8-azaspiro[4.5]decan-8-yl)methyl)-7-methyl-1H-indazole-1-carboxylate (14d)

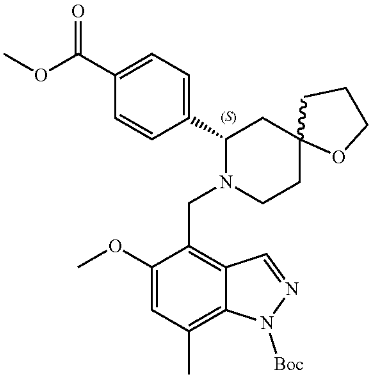

Tert-butyl 4-formyl-5-methoxy-7-methyl-1H-indazole-1-carboxylate (14c) (0.40 g, 1.38 mmol), the above-mentioned crude methyl 4-((7S)-1-oxa-8-azaspiro[4.5]decan-7-yl)benzoate [2f-b (diastereomer 2)]hydrochloride (0.65 g) and 4 molecular sieve (100 mg) were added to a reaction flask, glacial acetic acid (0.5 mL) and dichloroethane (10 mL) were added, and the mixture was heated to 60° C. and reacted for 16 h. The reaction system was cooled to room temperature, and sodium triacetoxyborohydride (0.88 g, 4.15 mmol) was added. The resulting mixture was reacted at room temperature for 6 h. 20 mL of saturated aqueous sodium bicarbonate solution was added dropwise into the reaction system, the insoluble matter was filtered through diatomaceous earth, the filtrate was collected, extracted with dichloromethane (20 mL×3), dried over anhydrous sodium sulfate, concentrated under reduced pressure, and the crude product was separated and purified with silica gel chromatography column (ethyl acetate/petroleum ether (v/v)=10:1-1:0) to afford crude tert-butyl 5-methoxy-4-(((7S)-7-(4-(methoxycarbonyl) phenyl)-1-oxa-8-azaspiro[4.5]decan-8-yl)methyl)-7-methyl-1H-indazole-1-carboxylate (14d) (90 mg).

LCMS m/z=550.2 $[M+1]^+$

Step 4: 4-((7S)-8-((5-methoxy-7-methyl-1H-indazol-4-yl)methyl)-1-oxa-8-azaspiro[4.5]decan-7-yl) benzoic acid (compound 14)

14-A

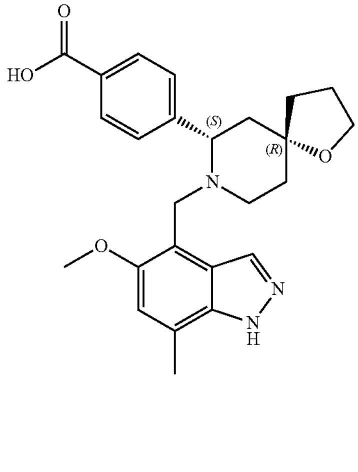

or

-continued

14-B

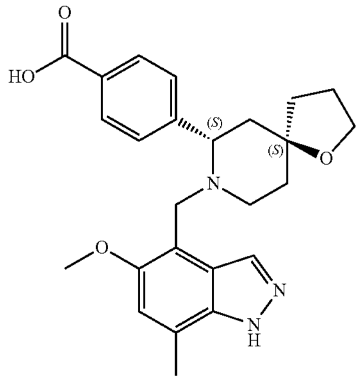

To the above-mentioned crude tert-butyl 5-methoxy-4-(((7S)-7-(4-(methoxycarbonyl)phenyl)-1-oxa-8-azaspiro[4.5]decan-8-yl)methyl)-7-methyl-1H-indazole-1-carboxylate (14d) (90 mg) was added solid potassium carbonate (0.11 g, 0.796 mmol), 10 mL of methanol was added, and the mixture was heated to 80° C. and reacted at reflux for 3 h. The reaction solution was cooled to room temperature and concentrated under reduced pressure to afford a crude product. The above-mentioned crude product was dissolved in a mixed solvent of 5 mL of THF and 1 mL of water, lithium hydroxide monohydrate (67 mg, 1.6 mmol) was added and the mixture was heated to 60° C. and stirred for 2 h. The reaction system was cooled to room temperature and concentrated under reduced pressure, and the crude product was subjected to Pre-HPLC (instrument and preparative column: using SHIMADZU LC-20AP+Gilson 281 preparative liquid phase chromatographic instrument, preparative column model: Phenomenex C18 (particle size: 10 um)). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 13% to 43% acetonitrile (elution time 13 min), and lyophilization was performed to afford 4-((7S)-8-((5-methoxy-7-methyl-1H-indazol-4-yl)methyl)-1-oxa-8-azaspiro[4.5]decan-7-yl)benzoic acid (compound 14) (10 mg, two-step yield from compound 14c: 3%).

$^1$H NMR (400 MHz, $CD_3OD$) δ 8.17-8.01 (m, 3H), 7.67-7.57 (m, 2H), 7.07 (s, 1H), 4.43-4.05 (m, 2H), 4.02-3.85 (m, 3H), 3.81 (s, 3H), 3.25-3.03 (m, 2H), 2.57 (s, 3H), 2.24-1.70 (m, 8H).

LCMS m/z=436.2 $[M+1]^+$

Compound 14 is one of the isomers of structure 14-A or 14-B.

Example 15

4-((2S)-4-cyclopropyl-1-((5-methoxy-7-methyl-1H-indazol-4-yl)methyl)piperidin-2-yl)benzoic acid [compound 15 (diastereomer 1)]

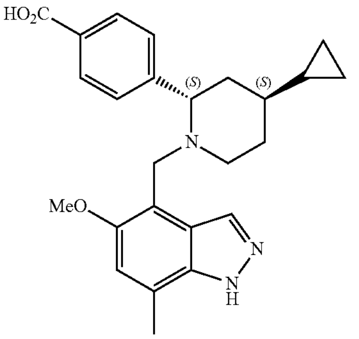

15-A or

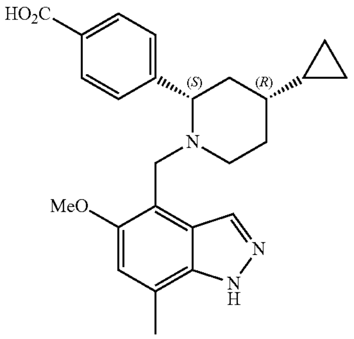

15-B

Compound 15 (diastereomer 1)

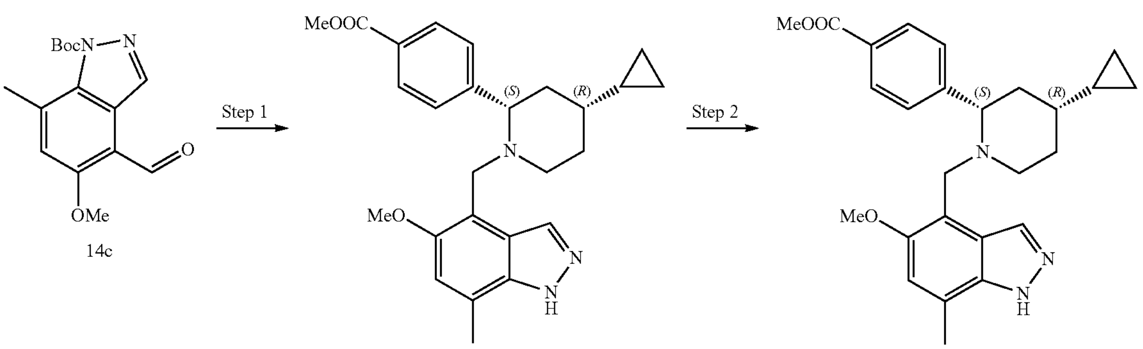

14c

15a-B
15a (diastereomer 1)

15-B
Compound 15 (diastereomer 1)

Step 1: methyl 4-((2S)-4-cyclopropyl-1-((5-methoxy-7-methyl-1H-indazol-4-yl)methyl)piperidin-2-yl)benzoate [15a (diastereomer 1)]

15a-B

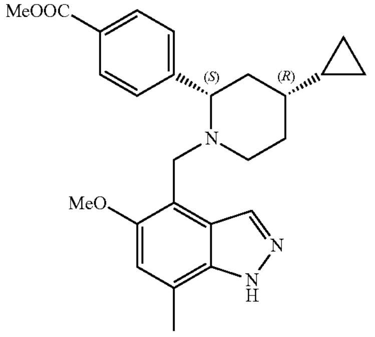

15a (diastereomer 1)

Tert-butyl 4-formyl-5-methoxy-7-methyl-1H-indazole-1-carboxylate (14c) (0.40 g, 1.38 mmol), the above-mentioned crude methyl 4-((2S)-4-cyclopropylpiperidin-2-yl)benzoate [5c (diastereomer 1)] maleate (0.62 g) and 4 Å molecular sieve (100 mg) were added to a reaction flask, glacial acetic acid (0.5 mL) and dichloroethane (10 mL) were added, and the mixture was heated to 60° C. and reacted for 16 h. The reaction system was cooled to room temperature, and sodium triacetoxyborohydride (0.88 g, 4.15 mmol) was added. The resulting mixture was reacted at room temperature for 6 h. 20 mL of saturated aqueous sodium bicarbonate solution was added dropwise into the reaction system, the insoluble matter was filtered through diatomaceous earth, the filtrate was collected, extracted with dichloromethane (20 mL×3), dried over anhydrous sodium sulfate, and concentrated under reduced pressure, and the crude product was separated and purified with silica gel chromatography column (ethyl acetate/petroleum ether (v/v)=10:1-1:0) to afford crude methyl 4-((2S)-4-cyclopropyl-1-((5-methoxy-7-methyl-1H-indazol-4-yl)methyl)piperidin-2-yl)benzoate [15a (diastereomer 1)] (102 mg).

LCMS m/z=434.3 $[M+1]^+$

According to the $^1H$-$^1H$ NOESY verification of the C1 and C3 hydrogens of the final product compound 5, compound 15a (diastereomer 1) has structure 15a-B.

Step 2: 4-((2S)-4-cyclopropyl-1-((5-methoxy-7-methyl-1H-indazol-4-yl)methyl)piperidin-2-yl)benzoic acid [compound 15 (diastereomer 1)]

15-B

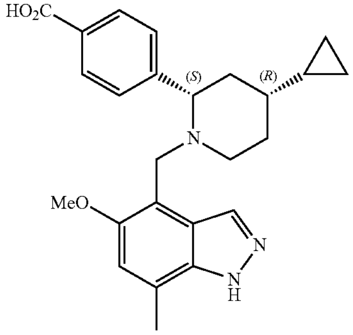

Compound 15 (diastereomer 1)

To the above-mentioned crude methyl 4-((2S)-4-cyclopropyl-1-((5-methoxy-7-methyl-1H-indazol-4-yl)methyl)piperidin-2-yl)benzoate [15a (diastereomer 1)] (102 mg) was added solid sodium hydroxide (100 mg, 2.50 mmol), 5 mL of methanol and 5 mL of water were added, and the mixture was heated to 75° C. and reacted at reflux for 0.5 h. The reaction liquid was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 15% to 45% acetonitrile (elution time 10 min), and lyophilization was performed to afford 4-((2S)-4-cyclopropyl-1-((5-methoxy-7-methyl-1H-indazol-4-yl)methyl)piperidin-2-yl)benzoic acid [compound 15 (diastereomer 1)] (9 mg, two-step yield from compound 14c: 2%).

$^1H$ NMR (400 MHz, $CD_3OD$) δ 8.16-8.06 (m, 2H), 7.98 (s, 1H), 7.65-7.56 (m, 2H), 7.06 (s, 1H), 4.30-3.83 (m, 3H), 3.79 (s, 3H), 3.40-3.32 (m, 1H), 2.56 (s, 3H), 2.17-2.03 (m, 1H), 1.99-1.76 (m, 2H), 1.74-1.52 (m, 1H), 1.09-0.93 (m, 1H), 0.67-0.52 (m, 1H), 0.50-0.36 (m, 2H), 0.23-0.10 (m, 2H).

LCMS m/z=420.2 $[M+1]^+$

According to the $^1H$-$^1H$ NOESY verification of the C1 and C3 hydrogens of the final product compound 5 (diastereomer 1), compound 15 (diastereomer 1) has structure 15-B.

Example 16

4-((2S,4R)-4-cyclopropyl-1-((5-methoxy-7-methyl-1H-benzo[d]imidazol-4-yl)methyl)piperidin-2-yl)benzoic acid (compound 16)

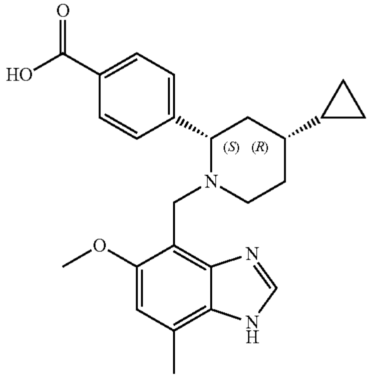

Compound 16

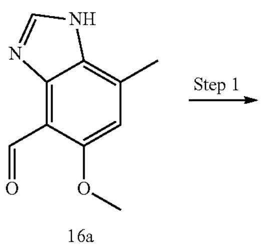

16a

-continued

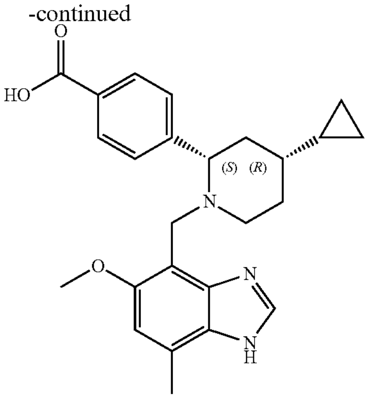

5-methoxy-7-methyl-1H-benzo[d]imidazole-4-carbaldehyde (16a) (see WO 2022028507 for synthesis method) (165 mg, 0.868 mmol) was dissolved in 10 mL of dichloromethane, triethylamine (260.78 mg, 2.6 mmol), $(Boc)_2O$ (227.0 mg, 1.04 mmol) and 4-dimethylaminopyridine (5.3 mg, 0.043 mmol) were added in sequence, and the mixture was reacted at room temperature for 1 h. 50 mL of dichloromethane was added to the reaction liquid, and the organic phase was washed with 0.5 mol/L aqueous hydrochloric acid solution (30 mL×2), water (30 mL×2), and saturated sodium chloride solution (30 mL×2), dried over anhydrous sodium sulfate, and concentrated under reduced pressure, and the crude product was separated and purified with silica gel chromatography column (petroleum ether/ethyl acetate (v/v)= 3:1) to afford crude product 1 (0.22 g). The above-mentioned crude product 1 (70 mg) was dissolved in 10 mL of 1,2-dichloroethane, and methyl 4-((2S)-4-cyclopropylpiperidin-2-yl)benzoate [5c (diastereomer 1)] maleate (91 mg), solid sodium bicarbonate (61 mg, 0.726 mmol) and 0.02 mL acetic acid were added in sequence, the mixture was stirred at room temperature for 0.5 h, then heated to 70° C. and reacted for 16 h. The reaction liquid was cooled to room temperature, and sodium triacetoxyborohydride (102 mg, 0.48 mmol) was added. The resulting mixture was reacted at room temperature for 16 h. 50 mL of saturated aqueous sodium bicarbonate solution was added to the reaction liquid, the mixture was extracted with ethyl acetate (50 mL×2), the organic phase was washed with saturated sodium chloride solution (30 mL×2), dried over anhydrous sodium sulfate, and concentrated under reduced pressure, the crude product was separated and purified with silica gel chromatography column (petroleum ether/ethyl acetate (v/v)= 1:3) to afford a crude product (40 mg), which was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution with acetonitrile from 35% to 65% (elution time: 10 min), affording crude product 2 (8 mg). The above-mentioned crude product 2 (8 mg) was dissolved in a mixed solvent of 2 mL of methanol and 2 mL of water, then solid sodium hydroxide (4 mg, 0.1 mmol) was added, and the mixture was heated to 75° C. and reacted for 2 h. The reaction liquid was cooled to room temperature, the pH was adjusted to 8 with 1 mol/L aqueous hydrochloric acid solution, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 35% to 65% acetonitrile (elution time 10 min), affording 4-((2S,4R)-4-cyclopropyl-1-((5-methoxy-7-methyl-1H-benzo[d]imidazol-4-yl)methyl)piperidin-2-yl)benzoic acid (compound 16) (4 mg, yield: 3%).

$^1H$ NMR (400 MHz, $CD_3OD$) δ 8.00 (s, 1H), 7.94-7.84 (m, 2H), 7.48-7.36 (m, 2H), 6.68 (s, 1H), 4.20-3.70 (m, 3H), 3.59 (s, 3H), 3.23-3.09 (m, 1H), 2.90-2.66 (m, 1H), 2.38 (s, 3H), 2.00-1.87 (m, 1H), 1.81-1.66 (m, 2H), 1.60-1.40 (m, 1H), 0.96-0.78 (m, 1H), 0.50-0.35 (m, 1H), 0.34-0.20 (m, 2H), 0.07--0.05 (m, 2H).

LCMS m/z=420.3 $[M+1]^+$

Example 17

4-((7S)-8-((5-methoxy-7-methyl-1H-benzo[d]imidazol-4-yl)methyl)-1-oxa-8-azaspiro[4.5]decan-7-yl)benzoic acid (compound 17)

17-A

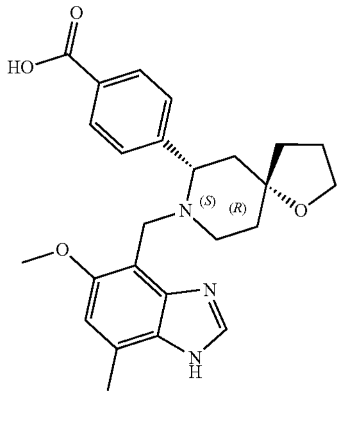

or

-continued

17-B

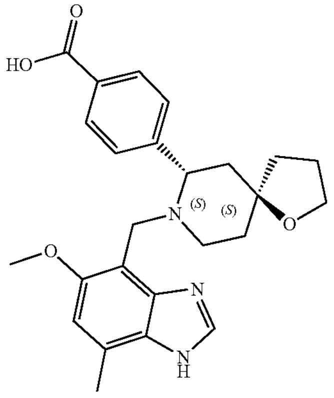

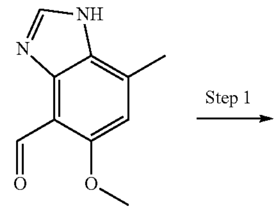

16a

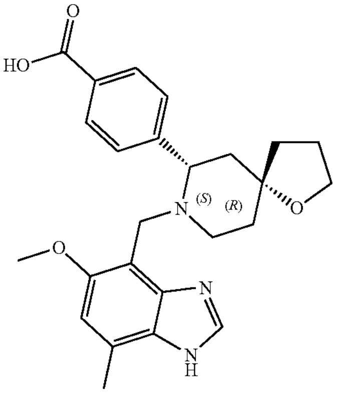

or

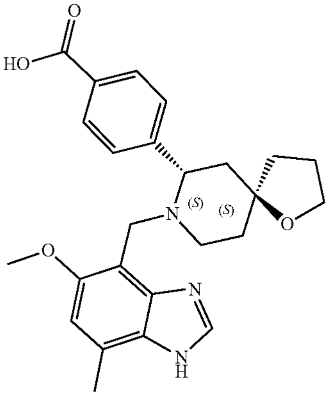

17-A

17-B

Compound 17

5-methoxy-7-methyl-1H-benzo[d]imidazole-4-carbaldehyde (16a) (0.1 g, 0.526 mmol) was dissolved in 10 mL of 1,2-dichloroethane, and the above-mentioned crude methyl 4-((7S)-1-oxa-8-azaspiro[4.5]decan-7-yl)benzoate [2f-b (diastereomer 2)]hydrochloride (0.206 g) and solid sodium bicarbonate (132.5 mg, 1.577 mmol) were added in sequence and stirred at room temperature for 0.5 h, 0.02 mL acetic acid was added, and the mixture was heated to 70° C. and reacted for 6 h. The reaction liquid was cooled to room temperature, and sodium triacetoxyborohydride (222 mg, 1.048 mmol) was added. The resulting mixture was reacted at room temperature for 16 h. 50 mL of saturated aqueous sodium bicarbonate solution was add to the reaction liquid, the mixture was extracted with ethyl acetate (60 mL×3), the organic phases were combined, the organic phase was washed with saturated aqueous sodium chloride solution (40 mL×2), dried over anhydrous sodium sulfate, and concentrated under reduced pressure, the crude product was separated and purified with silica gel chromatography column (dichloromethane:methanol (v/v)=87:13) to afford a crude product (40 mg), which was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution with acetonitrile from 50% to 80% (elution time: 10 min), affording crude product 2 (11 mg). The above-mentioned crude product 2 (11 mg) was dissolved in a mixed solvent of 3 mL of methanol and 3 mL of water, then solid sodium hydroxide (5 mg, 0.125 mmol) was added, and the mixture was heated to 75° C. and reacted for 2 h. The reaction liquid was cooled to room temperature, the pH was adjusted to 8 with 1 mol/L aqueous hydrochloric acid solution, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 20% to 50% acetonitrile (elution time 10 min), affording 4-((7S)-8-((5-methoxy-7-methyl-1H-benzo[d]imidazol-4-yl)methyl)-1-oxa-8-azaspiro[4.5]decan-7-yl)benzoic acid (compound 17) (6 mg, yield: 3%).

$^1$H NMR (400 MHz, $CD_3OD$) δ 8.21 (s, 1H), 8.16-8.09 (m, 2H), 7.70-7.60 (m, 2H), 6.89 (s, 1H), 4.70-4.50 (m, 1H), 4.45-4.26 (m, 1H), 4.25-4.10 (m, 1H), 4.04-3.85 (m, 2H), 3.79 (s, 3H), 3.55-3.40 (m, 1H), 3.35-3.21 (m, 1H), 2.58 (s, 3H), 2.38-2.17 (m, 1H), 2.10-1.93 (m, 4H), 1.90-1.77 (m, 3H).

LCMS m/z=436.3 $[M+1]^+$

Compound 17 is one of the isomers of structure 17-A or 17-B.

Example 18

4-((2S,4R)-4-cyclopropyl-1-((7-methyl-5-(prop-2-yn-1-yl)-1H-indol-4-yl)methyl)piperidin-2-yl)benzoic acid (compound 18)

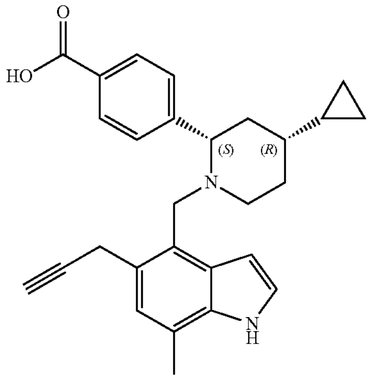

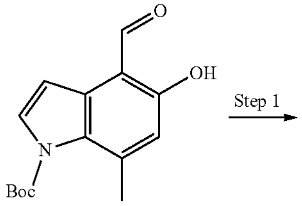

18a

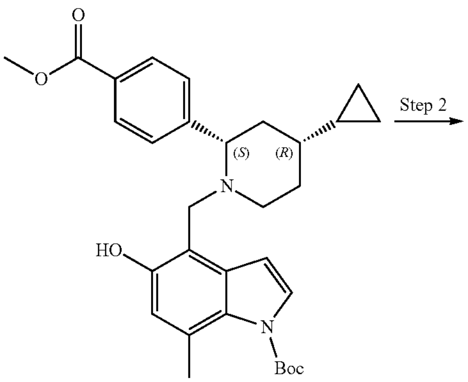

18b

-continued

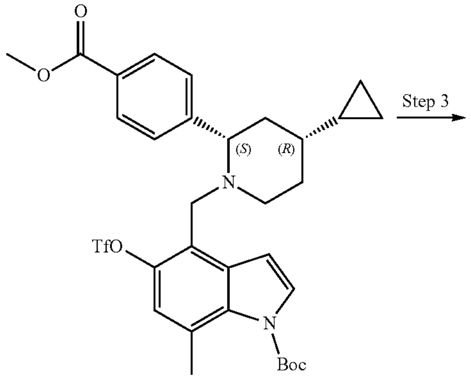

18c

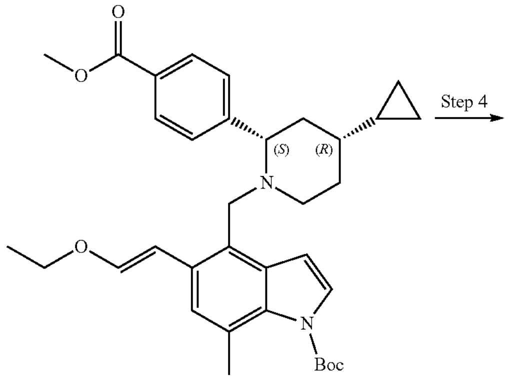

18d

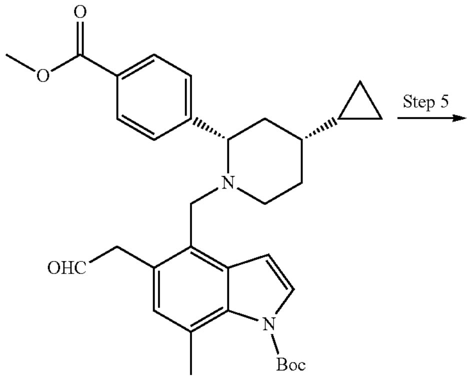

18e

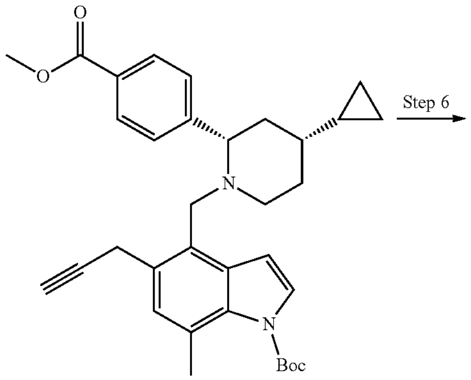

18f

-continued

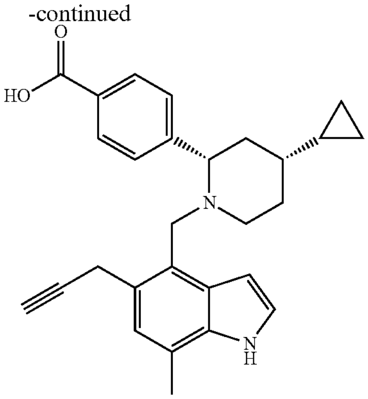

Compound 18

Step 1: tert-butyl 4-(((2S,4R)-4-cyclopropyl-2-(4-(methoxycarbonyl)phenyl) piperidin-1-yl)methyl)-5-hydroxy-7-methyl-1H-indole-1-carboxylate (18b)

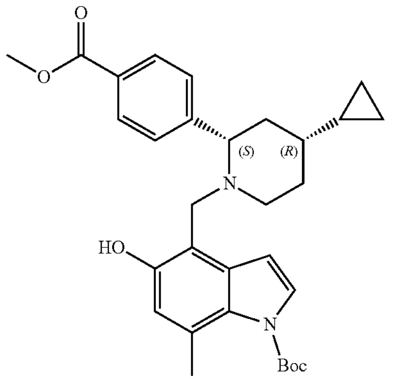

The above-mentioned crude methyl 4-((2S)-4-cyclopropylpiperidin-2-yl)benzoate [5c (diastereomer 1)] maleate (1.37 g) was dissolved in 50 mL of ethanol, tert-butyl 4-formyl-5-hydroxy-7-methyl-1H-indole-1-carboxylate (18a) (see WO 2020016749 for synthesis method) (1.0 g, 3.63 mmol) was added, 64 mg of $Ir(CO)_2acac$ was added, hydrogen replacement was performed three times. The mixture was heated to 80° C., and reacted for 16 h under the atmosphere of hydrogen balloon. The reaction liquid was cooled to room temperature and concentrated under reduced pressure, 100 mL of dichloromethane and 100 mL of saturated aqueous sodium bicarbonate solution were added, the aqueous phase was extracted twice with 100 mL of dichloromethane, the organic phases were combined, and the organic phase was dried over anhydrous sodium sulfate and concentrated under reduced pressure, then the crude product was separated and purified with silica gel column chromatography (petroleum ether/ethyl acetate (v/v)=20:1) to afford tert-butyl 4-(((2S,4R)-4-cyclopropyl-2-(4-(methoxycarbonyl)phenyl)piperidin-1-yl)methyl)-5-hydroxy-7-methyl-1H-indole-1-carboxylate (18b) (0.54 g, yield: 29%).

Step 2: tert-butyl 4-(((2S,4R)-4-cyclopropyl-2-(4-(methoxycarbonyl)phenyl) piperidin-1-yl)methyl)-7-methyl-5-(((trifluoromethyl)sulfonyl)oxy)-1H-indole-1-carboxylate (18c)

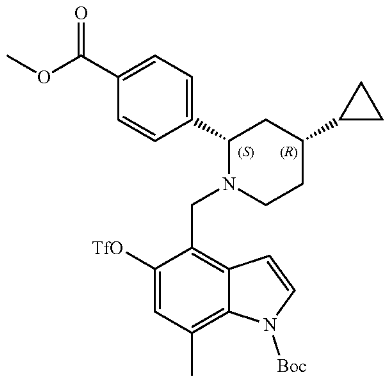

Tert-butyl 4-(((2S,4R)-4-cyclopropyl-2-(4-(methoxycarbonyl)phenyl) piperidin-1-yl)methyl)-5-hydroxy-7-methyl-1H-indole-1-carboxylate (18b) (0.54 g, 1.04 mmol) was dissolved in 20 mL of ultra-dry dichloromethane, and N-phenylbis(trifluoromethanesulfonyl)imide (1.11 g, 3.11 mmol) and triethylamine (0.31 g, 3.06 mmol) were added in sequence, and the mixture was heated to 40° C. and reacted for 16 h. The reaction liquid was cooled to room temperature and concentrated under reduced pressure, and the crude product was separated and purified with silica gel column chromatography (petroleum ether/ethyl acetate (v/v)=15:1) to afford tert-butyl 4-(((2S,4R)-4-cyclopropyl-2-(4-(methoxycarbonyl) phenyl)piperidin-1-yl)methyl)-7-methyl-5-(((trifluoromethyl)sulfonyl)oxy)-1H-indole-1-carboxylate (18c) (0.65 g, yield: 96%).

Step 3: tert-butyl 4-(((2S,4R)-4-cyclopropyl-2-(4-(methoxycarbonyl)phenyl) piperidin-1-yl)methyl)-5-((E)-2-ethoxyvinyl)-7-methyl-1H-indole-1-carboxylate (18d)

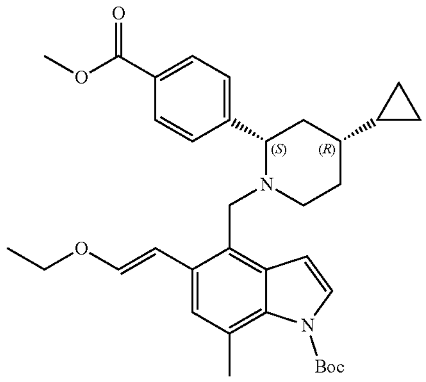

Tert-butyl 4-(((2S,4R)-4-cyclopropyl-2-(4-(methoxycarbonyl)phenyl) piperidin-1-yl)methyl)-7-methyl-5-(((trifluoromethyl)sulfonyl)oxy)-1H-indole-1-carboxylate (18c) (650 mg, 1.0 mmol) was dissolved in 10 mL of 1,4-dioxane, 2 mL of water, solid potassium carbonate (690 mg, 4.99 mmol) and (E)-1-ethoxyvinyl-2-boronic acid pinacol ester (400 mg, 2.02 mmol) were added in sequence, nitrogen replacement was performed three times, and [1,1'-bis(diphenylphosphine)ferrocene]palladium dichloride dichloromethane complex (CAS: 95464-05-4) (82 mg, 0.101 mmol) was added under nitrogen atmosphere, nitrogen replacement was performed three times, and the mixture was heated to 80° C. and reacted for 16 h under the atmosphere of nitrogen balloon. The reaction liquid was cooled to room temperature, the insoluble matter was filter out with a filter membrane, 50 mL of ethyl acetate was added to the filtrate, the liquid separation was conducted, the organic phase was washed twice with 50 mL of water, dried over anhydrous sodium sulfate, and concentrated under reduced pressure, and the crude product was separated and purified with silica gel column chromatography (petroleum ether/ethyl acetate (v/v)=15:1) to afford tert-butyl 4-(((2S,4R)-4-cyclopropyl-2-(4-(methoxycarbonyl)phenyl)piperidin-1-yl)methyl)-5-((E)-2-ethoxyvinyl)-7-methyl-1H-indole-1-carboxylate (18d) (400 mg, yield: 70%).

Step 4: tert-butyl 4-(((2S,4R)-4-cyclopropyl-2-(4-(methoxycarbonyl)phenyl) piperidin-1-yl)methyl)-7-methyl-5-(2-oxoethyl)-1H-indole-1-carboxylate (18e)

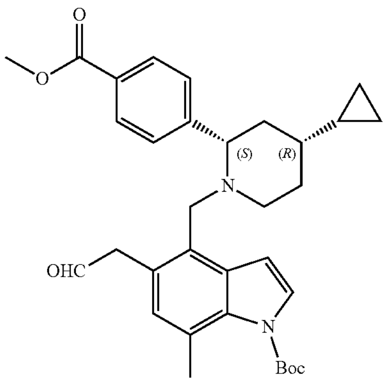

Tert-butyl 4-(((2S,4R)-4-cyclopropyl-2-(4-(methoxycarbonyl)phenyl) piperidin-1-yl)methyl)-5-((E)-2-ethoxyvinyl)-7-methyl-1H-indole-1-carboxylate (18d) (270 mg, 0.47 mmol) was dissolved in 10 mL of tetrahydrofuran and 1 mL of water, and cooled to 0° C. in an ice bath, 2.0 mL of 37% concentrated hydrochloric acid was slowly added dropwise, and the mixture was warmed to room temperature and reacted for 2 h. The reaction liquid was cooled to 0° C. in an ice bath, saturated aqueous sodium bicarbonate solution was added dropwise to adjust the pH of the system to 8, 50 mL of ethyl acetate and 50 mL of water were added, the liquid separation was conducted, the organic phase was dried over anhydrous sodium sulfate, and concentrated under reduced pressure, then the crude product was separated and purified with silica gel column chromatography (petroleum ether/ethyl acetate (v/v)=10:1) to afford crude tert-butyl 4-(((2S,4R)-4-cyclopropyl-2-(4-(methoxycarbonyl)phenyl)piperidin-1-yl)methyl)-7-methyl-5-(2-oxoethyl)-1H-indole-1-carboxylate (18e) (150 mg).

Step 5: tert-butyl 4-(((2S,4R)-4-cyclopropyl-2-(4-(methoxycarbonyl)phenyl) piperidin-1-yl)methyl)-7-methyl-5-(prop-2-yn-1-yl)-1H-indole-1-carboxylate (18f)

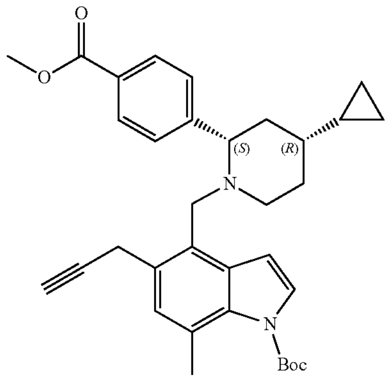

The above-mentioned crude tert-butyl 4-(((2S,4R)-4-cyclopropyl-2-(4-(methoxycarbonyl)phenyl)piperidin-1-yl) methyl)-7-methyl-5-(2-oxoethyl)-1H-indole-1-carboxylate (18e) (150 mg) was dissolved in 5 mL of methanol, and solid potassium carbonate (77 mg, 0.56 mmol) and 200 mg of 4 Å molecular sieve were added, nitrogen replacement was performed three times, the mixture was cooled to 0° C. in ice bath, dimethyl (1-diazo-2-oxopropyl)phosphonate (81 mg, 0.42 mmol) was added dropwise, nitrogen replacement was performed three times, and the mixture was reacted at room temperature for 16 h. The reaction liquid was cooled to room temperature, 30 mL of dichloromethane and 20 mL of water were added, the aqueous phase was extracted twice with 50 mL of dichloromethane, the organic phases were combined, the organic phase was dried over anhydrous sodium sulfate and concentrated under reduced pressure, then the crude product was separated and purified with silica gel column chromatography (petroleum ether/ethyl acetate (v/v)=20:1) to afford crude tert-butyl 4-(((2S,4R)-4-cyclopropyl-2-(4-(methoxycarbonyl) phenyl)piperidin-1-yl)methyl)-7-methyl-5-(prop-2-yn-1-yl)-1H-indole-1-carboxylate (18f) (140 mg).

Step 6: 4-((2S,4R)-4-cyclopropyl-1-((7-methyl-5-(prop-2-yn-1-yl)-1H-indol-4-yl)methyl)piperidin-2-yl)benzoic acid (compound 18)

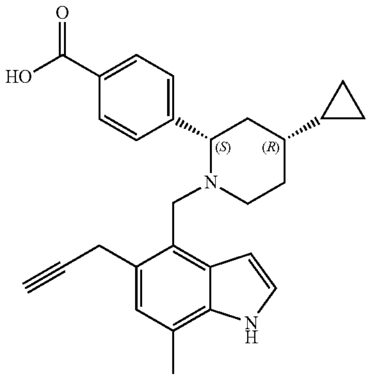

The above-mentioned crude tert-butyl 4-(((2S,4R)-4-cyclopropyl-2-(4-(methoxycarbonyl)phenyl)piperidin-1-yl)methyl)-7-methyl-5-(prop-2-yn-1-yl)-1H-indole-1-carboxylate (18f) (140 mg) was dissolved in 8 mL of methanol, solid potassium carbonate (180 mg, 1.3 mmol) was added, and the mixture was heated to 80° C. and reacted for 5 h. The reaction solution was cooled to room temperature and concentrated under reduced pressure to afford a crude product. The above-mentioned crude product was dissolved in a mixed solvent of 8 mL of THF and 2 mL of water, lithium hydroxide monohydrate (63 mg, 1.5 mmol) was added and the mixture was heated to 60° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 0.05% ammonium bicarbonate). Gradient elution method: gradient elution of 22% to 52% acetonitrile (elution time 15 min), and lyophilization was performed to afford 4-((2S,4R)-4-cyclopropyl-1-((7-methyl-5-(prop-2-yn-1-yl)-1H-indol-4-yl)methyl)piperidin-2-yl)benzoic acid (compound 18) (15 mg, three-step yield from compound 18d: 7%).

$^1$H NMR (400 MHz, $CD_3OD$) δ 8.04-7.91 (m, 2H), 7.56-7.40 (m, 2H), 7.20-7.07 (m, 1H), 6.88 (s, 1H), 6.38-6.22 (m, 1H), 4.15-3.25 (m, 5H), 3.11-2.95 (m, 1H), 2.70-2.40 (m, 1H), 2.33 (s, 3H), 2.17-2.10 (m, 1H), 1.99-1.83 (m, 1H), 1.80-1.60 (m, 2H), 1.47-1.29 (m, 1H), 0.90-0.67 (m, 1H), 0.53-0.35 (m, 1H), 0.34-0.16 (m, 2H), 0.10--0.10 (m, 2H).

LCMS m/z=427.3 $[M+1]^+$

Example 19

4-((7S)-8-((7-methyl-5-(prop-2-yn-1-yl)-1H-indol-4-yl)methyl)-1-oxa-8-azaspiro[4.5]decan-7-yl)benzoic acid (compound 19)

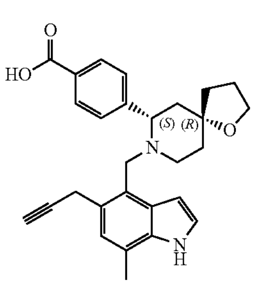

19-A or

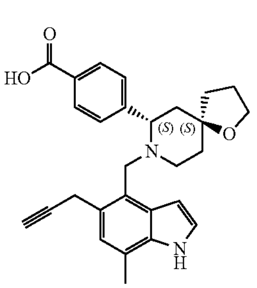

19-B

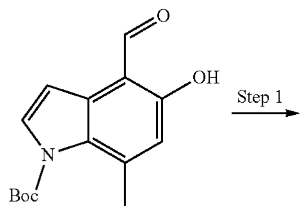

18a

-continued

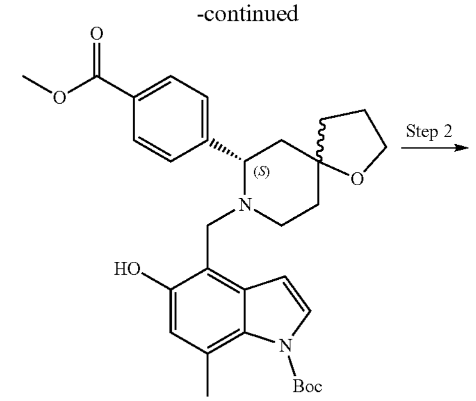

19a

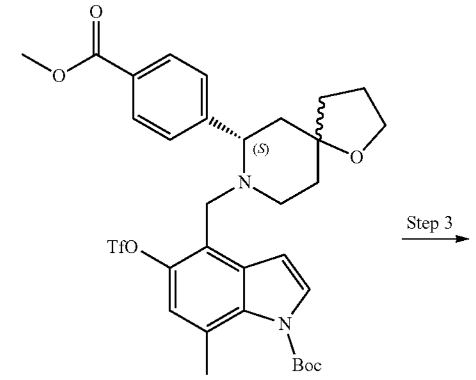

19b

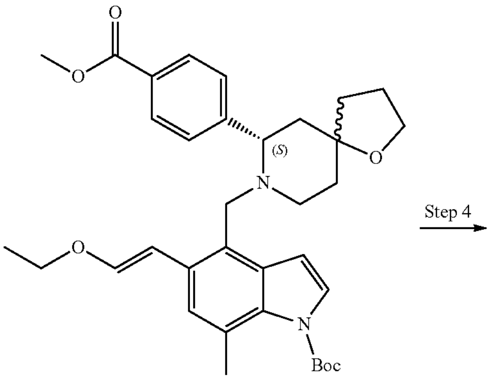

19c

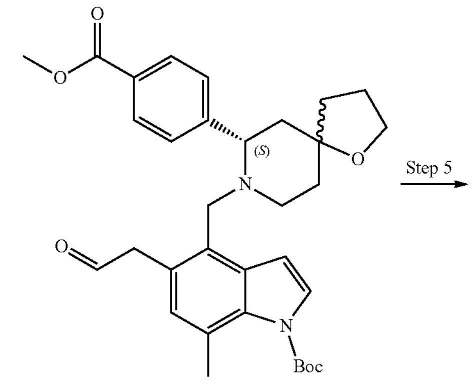

19d

-continued

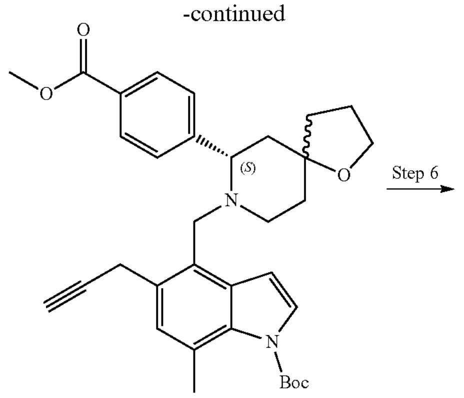

19e

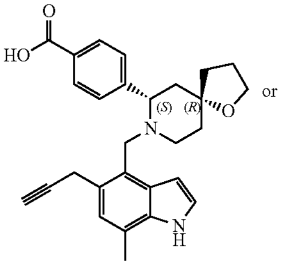

or

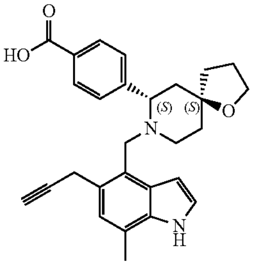

19-A

19-B

Compound 19

Step 1: tert-butyl 5-hydroxy-4-(((7S)-7-(4-(methoxycarbonyl)phenyl)-1-oxa-8-azaspiro[4.5]decan-8-yl)methyl)-7-methyl-1H-indole-1-carboxylate (19a)

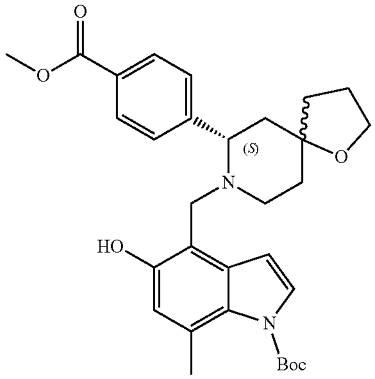

The above-mentioned crude methyl 4-((7S)-1-oxa-8-azaspiro[4.5]decan-7-yl)benzoate [2f-b (diastereomer 2)]hydrochloride (1.425 g) was dissolved in 50 mL of ethanol, tert-butyl 4-formyl-5-hydroxy-7-methyl-1H-indole-1-carboxylate (18a) (see WO 2020016749 for synthesis method) (1.0 g, 3.63 mmol) was added, 63 mg of $Ir(CO)_2acac$ was added, hydrogen replacement was performed three times. The mixture was heated to 80° C., and reacted for 16 h under the atmosphere of hydrogen balloon. The reaction liquid was cooled to room temperature and concentrated under reduced pressure, 100 mL of dichloromethane and 100 mL of saturated aqueous sodium bicarbonate solution were added, the aqueous phase was further extracted twice with 100 mL of dichloromethane, the organic phases were combined, and the organic phase was dried over anhydrous sodium sulfate and concentrated under reduced pressure, then the crude product was separated and purified with silica gel column chromatography (petroleum ether/ethyl acetate (v/v)=10:1) to afford tert-butyl 5-hydroxy-4-(((7S)-7-(4-(methoxycarbonyl)phenyl)-1-oxa-8-azaspiro[4.5]decan-8-yl)methyl)-7-methyl-1H-indole-1-carboxylate (19a) (1.2 g, yield: 62%).

Step 2: tert-butyl 4-(((7S)-7-(4-(methoxycarbonyl)phenyl)-1-oxa-8-azaspiro[4.5]decan-8-yl)methyl)-7-methyl-5-(((trifluoromethyl)sulfonyl)oxy)-1H-indole-1-carboxylate (19b)

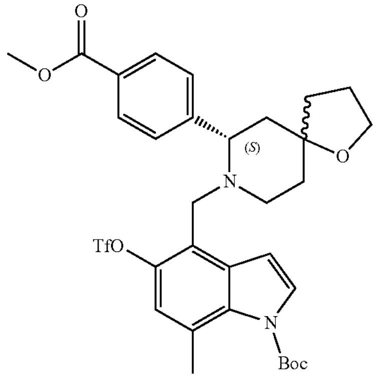

Tert-butyl 5-hydroxy-4-(((7S)-7-(4-(methoxycarbonyl)phenyl)-1-oxa-8-azaspiro [4.5]decan-8-yl)methyl)-7-methyl-1H-indole-1-carboxylate (19a) (1.2 g, 2.24 mmol) was dissolved in 50 mL of ultra-dry dichloromethane, and N-phenylbis(trifluoromethanesulfonyl)imide (2.4 g, 6.72 mmol) and triethylamine (0.68 g, 6.72 mmol) were added in sequence, and the mixture was heated to 40° C. and reacted for 16 h. The reaction liquid was cooled to room temperature and concentrated under reduced pressure, and the crude product was separated and purified with silica gel column chromatography (petroleum ether/ethyl acetate (v/v)=10:1) to afford tert-butyl 4-(((7S)-7-(4-(methoxycarbonyl)phenyl)-1-oxa-8-azaspiro[4.5]decan-8-yl)methyl)-7-methyl-5-(((trifluoromethyl)sulfonyl)oxy)-1H-indole-1-carboxylate (19b) (1.3 g, yield: 87%).

Step 3: tert-butyl 5-(2-ethoxyvinyl)-4-(((7S)-7-(4-(methoxycarbonyl)phenyl)-1-oxa-8-azaspiro[4.5]decan-8-yl)methyl)-7-methyl-1H-indole-1-carboxylate (19c)

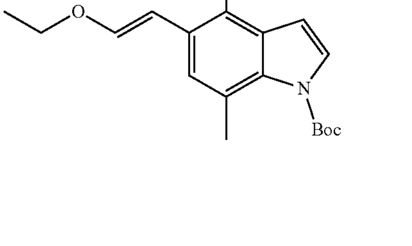

Tert-butyl 4-(((7S)-7-(4-(methoxycarbonyl)phenyl)-1-oxa-8-azaspiro[4.5]decan-8-yl)methyl)-7-methyl-5-(((trifluoromethyl)sulfonyl)oxy)-1H-indole-1-carboxylate (19b) (920 mg, 1.38 mmol) was dissolved in 15 mL of 1,4-dioxane, 3 mL of water, solid potassium carbonate (950 mg, 6.87 mmol) and (E)-1-ethoxyvinyl-2-boronic acid pinacol ester (550 mg, 2.78 mmol) were added in sequence, nitrogen replacement was performed three times, and [1,1'-bis(diphenylphosphine)ferrocene]palladium dichloride dichloromethane complex (CAS: 95464-05-4) (110 mg, 0.135 mmol) was added under nitrogen atmosphere, nitrogen replacement was performed three times, and the mixture was heated to 80° C. and reacted for 16 h under the atmosphere of nitrogen balloon. The reaction liquid was cooled to room temperature, the insoluble matter was filter out with a filter membrane, 60 mL of ethyl acetate was added to the filtrate, the liquid separation was conducted, the organic phase was washed twice with 60 mL of water, dried over anhydrous sodium sulfate, and concentrated under reduced pressure, and the crude product was separated and purified with silica gel column chromatography (petroleum ether/ethyl acetate (v/v)=9:1) to afford tert-butyl 5-(2-ethoxyvinyl)-4-(((7S)-7-(4-(methoxycarbonyl)phenyl)-1-oxa-8-azaspiro[4.5]decan-8-yl)methyl)-7-methyl-1H-indole-1-carboxylate (19c) (370 mg, yield: 46%).

Step 4: tert-butyl 4-(((7S)-7-(4-(methoxycarbonyl)phenyl)-1-oxa-8-azaspiro[4.5]decan-8-yl)methyl)-7-methyl-5-(2-oxoethyl)-1H-indole-1-carboxylate (19d)

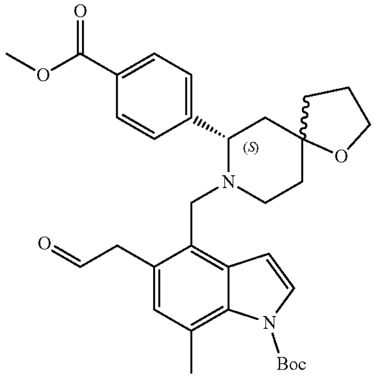

Tert-butyl 5-(2-ethoxyvinyl)-4-(((7S)-7-(4-(methoxycarbonyl)phenyl)-1-oxa-8-azaspiro[4.5]decan-8-yl)methyl)-7-methyl-1H-indole-1-carboxylate (19c) (0.37 g, 0.63 mmol) was dissolved in 16 mL of tetrahydrofuran and 2 mL of water, and cooled to 0° C. in an ice bath, 3.5 mL of 37% concentrated hydrochloric acid was slowly added dropwise, and the mixture was warmed to room temperature and reacted for 2 h. The reaction liquid was cooled to 0° C. in an ice bath, saturated aqueous sodium bicarbonate solution was added dropwise to adjust the pH of the system to 8, 50 mL of ethyl acetate and 50 mL of water were added, the liquid separation was conducted, the organic phase was dried over anhydrous sodium sulfate, and concentrated under reduced pressure, then the crude product was separated and purified with silica gel column chromatography (petroleum ether/ethyl acetate (v/v)=8:1) to afford crude tert-butyl 4-(((7S)-7-(4-(methoxycarbonyl) phenyl)-1-oxa-8-azaspiro[4.5]decan-8-yl)methyl)-7-methyl-5-(2-oxoethyl)-1H-indole-1-carboxylate (19d) (350 mg).

Step 5: tert-butyl 4-(((7S)-7-(4-(methoxycarbonyl)phenyl)-1-oxa-8-azaspiro[4.5]decan-8-yl)methyl)-7-methyl-5-(prop-2-yn-1-yl)-1H-indole-1-carboxylate (19e)

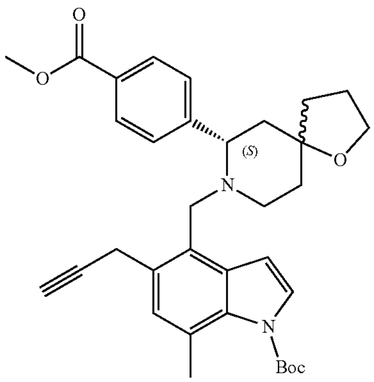

The above-mentioned crude tert-butyl 4-(((7S)-7-(4-(methoxycarbonyl)phenyl)-1-oxa-8-azaspiro[4.5]decan-8-yl)methyl)-7-methyl-5-(2-oxoethyl)-1H-indole-1-carboxylate (19d) (150 mg) was dissolved in 5 mL of methanol, and solid potassium carbonate (75 mg, 0.54 mmol) and 200 mg of 4 Å molecular sieve were added, nitrogen replacement was performed three times, the mixture was cooled to 0° C. in ice bath, dimethyl (1-diazo-2-oxopropyl)phosphonate (78 mg, 0.40 mmol) was added dropwise, nitrogen replacement was performed three times, and the mixture was reacted at room temperature for 16 h. The reaction liquid was cooled to room temperature, 30 mL of dichloromethane and 20 mL of water were added, the aqueous phase was extracted twice with 50 mL of dichloromethane, the organic phases were combined, the organic phase was dried over anhydrous sodium sulfate and concentrated under reduced pressure, then the crude product was separated and purified with silica gel column chromatography (petroleum ether/ethyl acetate (v/v)=20:1) to afford crude tert-butyl 4-(((7S)-7-(4-(methoxycarbonyl)phenyl)-1-oxa-8-azaspiro[4.5]decan-8-yl)methyl)-7-methyl-5-(prop-2-yn-1-yl)-1H-indole-1-carboxylate (19e) (120 mg).

Step 6: 4-((7S)-8-((7-methyl-5-(prop-2-yn-1-yl)-1H-indol-4-yl)methyl)-1-oxa-8-azaspiro[4.5]decan-7-yl) benzoic acid (compound 19)

19-A

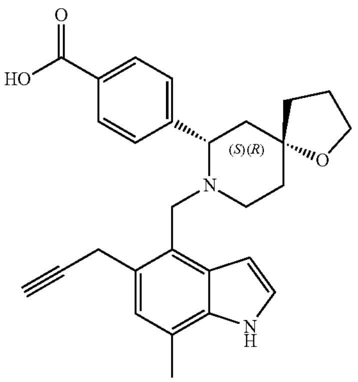

-continued

19-B

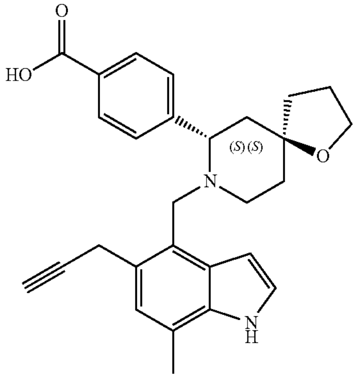

The above-mentioned crude tert-butyl 4-(((7S)-7-(4-(methoxycarbonyl)phenyl)-1-oxa-8-azaspiro[4.5]decan-8-yl)methyl)-7-methyl-5-(prop-2-yn-1-yl)-1H-indole-1-carboxylate (19e) (120 mg) was dissolved in 8 mL of methanol, solid potassium carbonate (150 mg, 1.09 mmol) was added, and the mixture was heated to 80° C. and reacted for 5 h. The reaction solution was cooled to room temperature and concentrated under reduced pressure to afford a crude product. The above-mentioned crude product was dissolved in a mixed solvent of 8 mL of THF and 2 mL of water, lithium hydroxide monohydrate (53 mg, 1.26 mmol) was added and the mixture was heated to 60° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 0.05% ammonium bicarbonate). Gradient elution method: gradient elution of 25% to 55% acetonitrile (elution time 15 min), and lyophilization was performed to afford 4-((7S)-8-((7-methyl-5-(prop-2-yn-1-yl)-1H-indol-4-yl)methyl)-1-oxa-8-azaspiro[4.5]decan-7-yl)benzoic acid (compound 19) (10 mg, three-step yield from compound 19c: 8%).

$^1$H NMR (400 MHz, $CD_3OD$) δ 8.15-8.06 (m, 2H), 7.69-7.59 (m, 2H), 7.30-7.24 (m, 1H), 7.08-6.99 (m, 1H), 6.55-6.45 (m, 1H), 4.20-3.45 (m, 7H), 3.04-2.81 (m, 2H), 2.52-2.44 (m, 3H), 2.30-2.26 (m, 1H), 2.20-1.59 (m, 8H).

LCMS m/z=443.3 $[M+1]^+$

Compound 19 is one of the isomers of structure 19-A or 19-B.

Example 20

4-((7S)-8-((5-ethynyl-7-methyl-1H-indol-4-yl)methyl)-1-oxa-8-azaspiro[4.5]decan-7-yl)benzoic acid (compound 20)

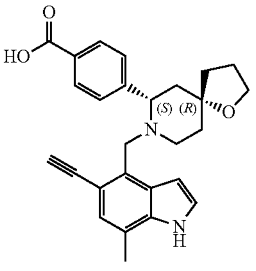

20-A or

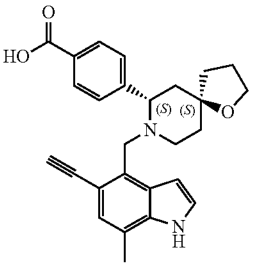

20-B

-continued

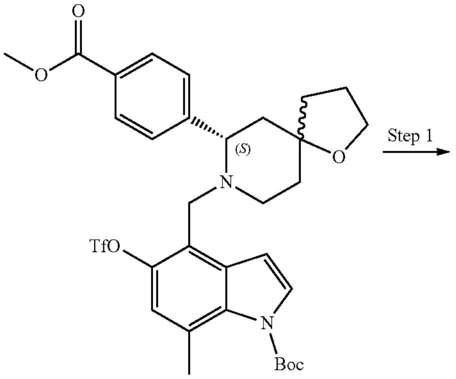

19b

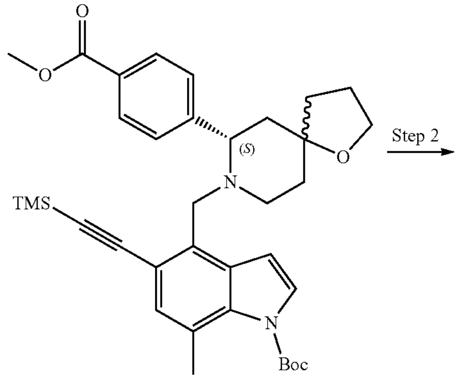

20a

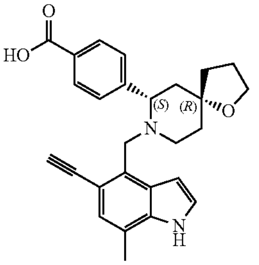

20-A or

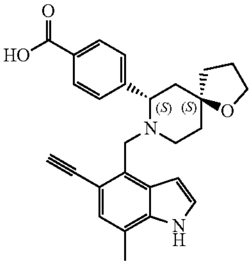

20-B

Compound 20

Step 1: tert-butyl 4-(((7S)-7-(4-(methoxycarbonyl)phenyl)-1-oxa-8-azaspiro[4.5]decan-8-yl)methyl)-7-methyl-5-((trimethylsilyl)ethynyl)-1H-indole-1-carboxylate (20a)

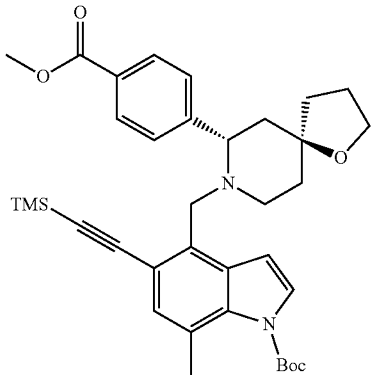 [SMILES: COC(=O)c1ccc([C@@H]2C[C@]3(CCCO3)CCN2Cc2c(C#C[Si](C)(C)C)cc(C)c3c2ccn3C(=O)OC(C)(C)C)cc1]

Tert-butyl 4-(((7S)-7-(4-(methoxycarbonyl)phenyl)-1-oxa-8-azaspiro[4.5]decan-8-yl)methyl)-7-methyl-5-(((trifluoromethyl)sulfonyl)oxy)-1H-indole-1-carboxylate (19b) (280 mg, 0.42 mmol) and 6 mL of ultra-dry DMF were added to the sealed tube, and [1,1-bis(diphenylphosphine) ferrocene]palladium dichloride dichloromethane complex (CAS: 95464-05-4) (34 mg, 0.042 mmol), CuI (16 mg, 0.084 mmol), $Cs_2CO_3$ (410 mg, 1.26 mmol) and trimethylethynyl silicon (120 mg, 1.22 mmol) were added, nitrogen replacement was performed three times, and the mixture was heated to 80° C. and reacted under nitrogen atmosphere for 8 h. The reaction liquid was cooled to room temperature, 80 mL of ethyl acetate and 100 mL of saturated aqueous sodium chloride solution were added, the liquid separation was conducted, the aqueous phase was extracted twice with 50 mL of ethyl acetate, the organic phases were combined, and the organic phase was dried over anhydrous sodium sulfate and concentrated under reduced pressure, then the crude product was separated and purified with silica gel column chromatography (petroleum ether/ethyl acetate (v/v)=15:1) to afford tert-butyl 4-(((7S)-7-(4-(methoxycarbonyl)phenyl)-1-oxa-8-azaspiro[4.5]decan-8-yl)methyl)-7-methyl-5-((trimethylsilyl)ethynyl)-1H-indole-1-carboxylate (20a) (90 mg, yield: 35%).

LCMS m/z=615.3 $[M+1]^+$

Step 2: 4-((7S)-8-((5-ethynyl-7-methyl-1H-indol-4-yl)methyl)-1-oxa-8-azaspiro decan-7-yl)benzoic acid (compound 20)

20-A

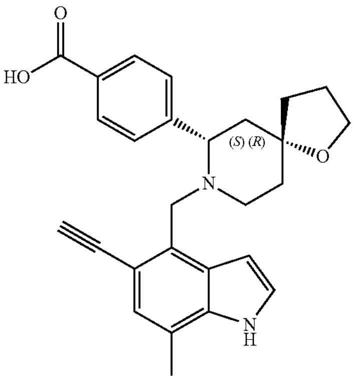

or

-continued

20-B

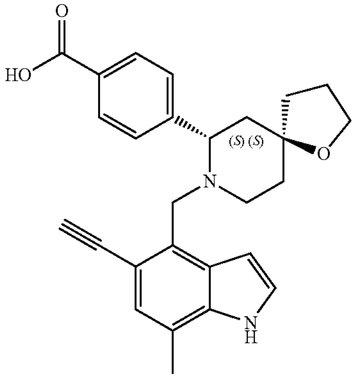

Tert-butyl 4-(((7S)-7-(4-(methoxycarbonyl)phenyl)-1-oxa-8-azaspiro[4.5]decan-8-yl)methyl)-7-methyl-5-((trimethylsilyl)ethynyl)-1H-indole-1-carboxylate (20a) (90 mg, 0.15 mmol) was dissolved in 6 mL of methanol, solid potassium carbonate (100 mg, 0.72 mmol) was added, and the mixture was heated to 80° C. and reacted for 2 h. The reaction liquid was cooled to room temperature, 2 mL of water and lithium hydroxide monohydrate (63 mg, 1.50 mmol) were added to the reaction liquid, and the mixture was heated to 80° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 25% to 55% acetonitrile (elution time 10 min), and lyophilization was performed to afford 4-((7S)-8-((5-ethynyl-7-methyl-1H-indol-4-yl)methyl)-1-oxa-8-azaspiro[4.5]decan-7-yl)benzoic acid (compound 20) (20 mg, yield: 31%).

$^1H$ NMR (400 MHz, $CD_3OD$) δ 7.55-7.46 (m, 2H), 7.38-7.30 (m, 2H), 7.23-7.17 (m, 1H), 6.77 (s, 1H), 6.45-6.35 (m, 1H), 5.90-5.82 (m, 1H), 5.76-5.60 (m, 2H), 5.15-4.96 (m, 2H), 4.40-4.24 (m, 1H), 4.00-3.80 (m, 2H), 3.68-3.55 (m, 1H), 3.10-2.95 (m, 1H), 2.48-2.32 (m, 1H), 2.25 (s, 3H), 2.10-1.86 (m, 6H).

LCMS m/z=429.2 $[M+1]^+$

Compound 20 is one of the isomers of structure 20-A or 20-B.

Example 21

4-((7S)-8-((7-methyl-5-(prop-1-yn-1-yl)-1H-indol-4-yl)methyl)-1-oxa-8-azaspiro[4.5]decan-7-yl)benzoic acid (compound 21)

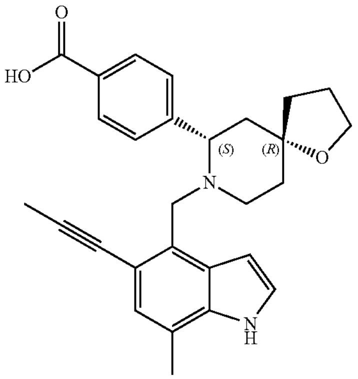

or

21-A

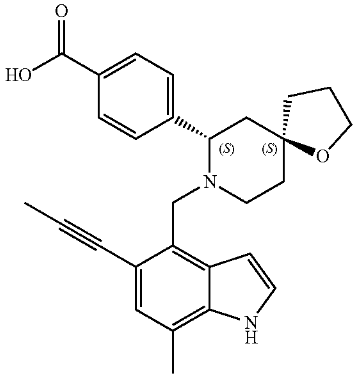

21-B

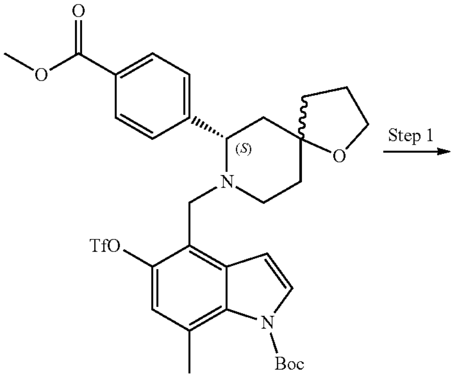

19b

-continued

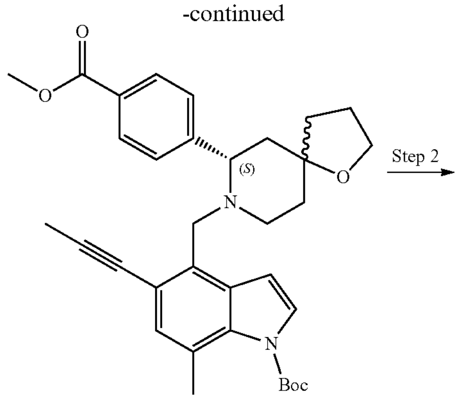

21a

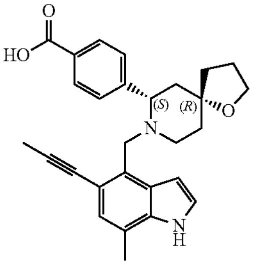

or

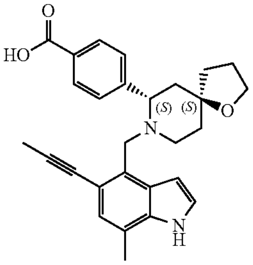

21-A 21-B

Compound 21

Step 1: tert-butyl 4-(((7S)-7-(4-(methoxycarbonyl)phenyl)-1-oxa-8-azaspiro[4.5]decan-8-yl)methyl)-7-methyl-5-(prop-1-yn-1-yl)-1H-indole-1-carboxylate (21a)

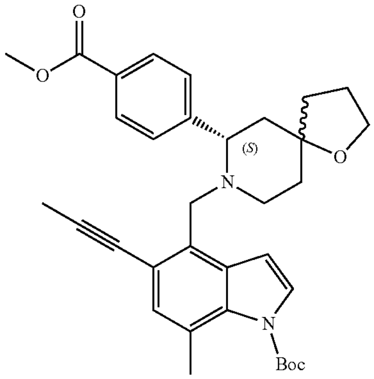

Tert-butyl 4-(((7S)-7-(4-(methoxycarbonyl)phenyl)-1-oxa-8-azaspiro[4.5]decan-8-yl)methyl)-7-methyl-5-(((trifluoromethyl)sulfonyl)oxy)-1H-indole-1-carboxylate (19b) (100 mg, 0.15 mmol) and 5 mL of ultra-dry DMF were added to the sealed tube, and [1,1-bis(diphenylphosphine) ferrocene]palladium dichloride dichloromethane complex (CAS: 95464-05-4) (12 mg, 0.015 mmol), CuI (6 mg, 0.032 mmol), solid cesium carbonate (150 mg, 0.46 mmol) and 1-(trimethylsilyl)propyne (50 mg, 0.45 mmol) were added, nitrogen replacement was performed three times, and the mixture was heated to 80° C. and reacted under nitrogen atmosphere for 7 h. The reaction liquid was cooled to room temperature, 80 mL of ethyl acetate and 100 mL of saturated aqueous sodium chloride solution were added, the liquid separation was conducted, the aqueous phase was extracted twice with 50 mL of ethyl acetate, the organic phases were combined, and the organic phase was dried over anhydrous sodium sulfate and concentrated under reduced pressure, then the crude product was separated and purified with silica gel column chromatography (petroleum ether/ethyl acetate (v/v)=15:1) to afford tert-butyl 4-(((7S)-7-(4-(methoxycarbonyl)phenyl)-1-oxa-8-azaspiro[4.5]decan-8-yl)methyl)-7-methyl-5-(prop-1-yn-1-yl)-1H-indole-1-carboxylate (21a) (80 mg, yield: 96%).

LCMS m/z=557.3 $[M+1]^+$

Step 2: 4-((7S)-8-((7-methyl-5-(prop-1-yn-1-yl)-1H-indol-4-yl)methyl)-1-oxa-8-azaspiro[4.5]decan-7-yl) benzoic acid (compound 21)

21-A

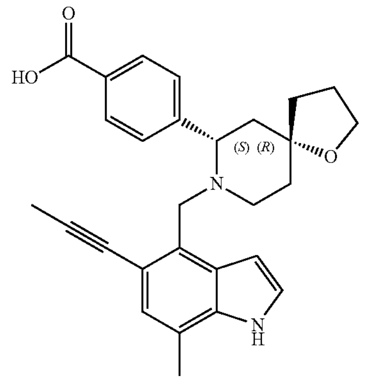

or

21-B

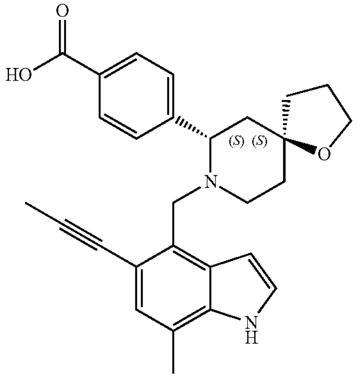

The above-mentioned tert-butyl 4-(((7S)-7-(4-(methoxycarbonyl)phenyl)-1-oxa-8-azaspiro[4.5]decan-8-yl)methyl)-7-methyl-5-(prop-1-yn-1-yl)-1H-indole-1-carboxylate (21a) (80 mg, 0.14 mmol) was dissolved in 6 mL of methanol, solid potassium carbonate (97 mg, 0.7 mmol) was added, and the mixture was heated to 80° C. and reacted for 4 h. The reaction liquid was cooled to room temperature, 2 mL of water and lithium hydroxide monohydrate (59 mg, 1.4 mmol) were added to the reaction liquid, and the mixture was heated to 80° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 15% to 45% acetonitrile (elution time 10 min), and lyophilization was performed to afford 4-((7S)-8-((7-methyl-5-(prop-1-yn-1-yl)-1H-indol-4-yl)methyl)-1-oxa-8-azaspiro[4.5]decan-7-yl)benzoic acid (compound 21) (40 mg).

$^1H$ NMR (400 MHz, $CD_3OD$) δ 8.20-8.07 (m, 2H), 7.71-7.60 (m, 2H), 7.34-7.24 (m, 1H), 7.00 (s, 1H), 6.29 (br.s, 1H), 4.67-4.10 (m, 3H), 4.00-3.80 (m, 2H), 3.40-3.27 (m, 1H), 3.26-3.15 (m, 1H), 2.44 (s, 3H), 2.35-2.12 (m, 1H), 2.05 (s, 3H), 2.03-1.87 (m, 4H), 1.87-1.70 (m, 3H).

LCMS m/z=443.3 $[M+1]^+$

Compound 21 is one of the isomers of structure 21-A or 21-B.

Example 22

4-((7S)-8-((5-(cyclopropylethynyl)-7-methyl-1H-indol-4-yl)methyl)-1-oxa-8-azaspiro[4.5]decan-7-yl)benzoic acid (compound 22)

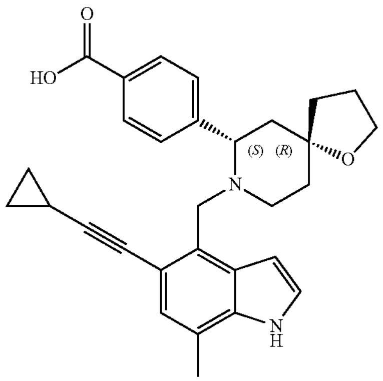

or

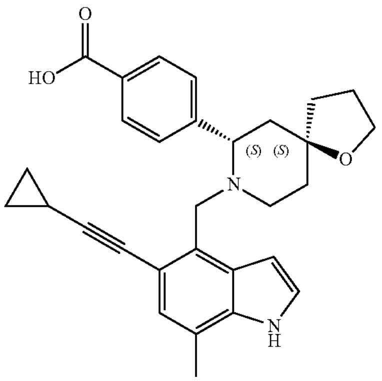

22-A 22-B

-continued

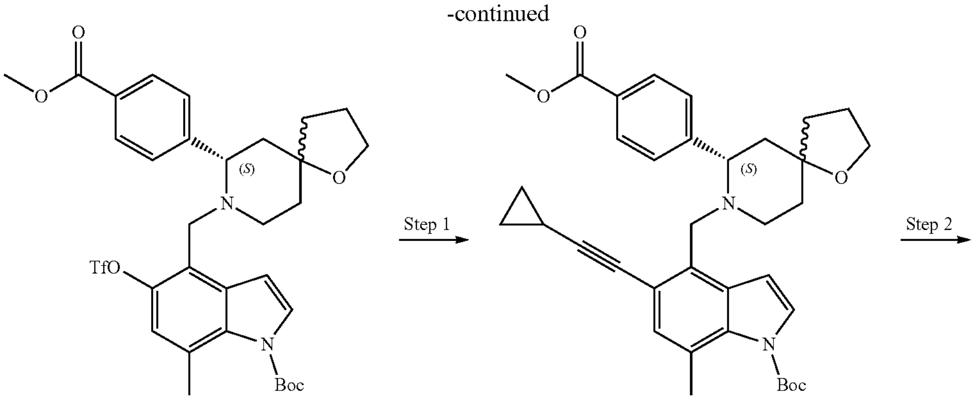

19b 22a

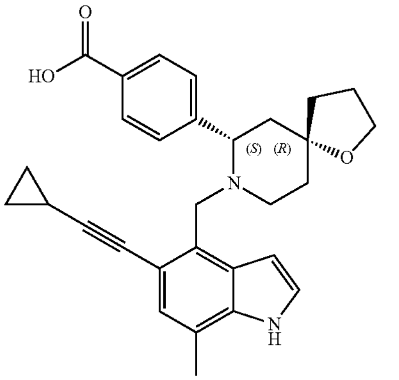

or

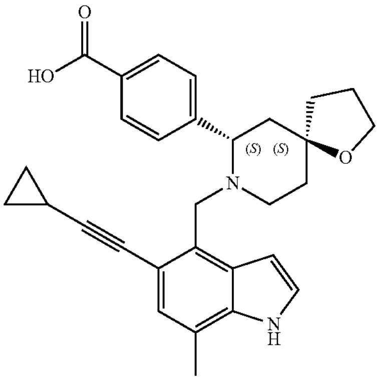

22-A 22-B

Compound 22

Step 1: tert-butyl 5-(cyclopropylethynyl)-4-(((7S)-7-(4-(methoxycarbonyl) phenyl)-1-oxa-8-azaspiro[4.5] decan-8-yl)methyl)-7-methyl-1H-indole-1-carboxylate (22a)

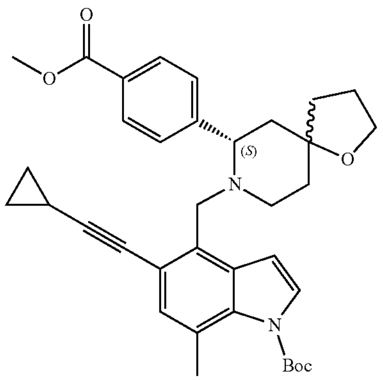

Tert-butyl 4-(((7S)-7-(4-(methoxycarbonyl)phenyl)-1-oxa-8-azaspiro[4.5]decan-8-yl)methyl)-7-methyl-5-(((trifluoromethyl)sulfonyl)oxy)-1H-indole-1-carboxylate (19b) (150 mg, 0.225 mmol) and 5 mL of ultra-dry DMF were added to the sealed tube, and [1,1'-bis(diphenylphosphine) ferrocene]palladium dichloride dichloromethane complex (CAS: 95464-05-4) (18 mg, 0.0225 mmol), CuI (8.4 mg, 0.044 mmol), solid cesium carbonate (220 mg, 0.68 mmol) and ethynylcyclopropane (44 mg, 0.67 mmol) were added, nitrogen replacement was performed three times, and the mixture was heated to 80° C. and reacted under nitrogen atmosphere for 7 h. The reaction liquid was cooled to room temperature, 80 mL of ethyl acetate and 100 mL of saturated aqueous sodium chloride solution were added, the liquid separation was conducted, the aqueous phase was extracted twice with 50 mL of ethyl acetate, the organic phases were combined, and the organic phase was dried over anhydrous sodium sulfate and concentrated under reduced pressure, then the crude product was separated and purified with silica gel column chromatography (petroleum ether/ethyl acetate (v/v)=15:1) to afford tert-butyl 5-(cyclopropylethynyl)-4-(((7S)-7-(4-(methoxycarbonyl)phenyl)-1-oxa-8-azaspiro [4.5]decan-8-yl)methyl)-7-methyl-1H-indole-1-carboxylate (22a) (120 mg, yield: 92%).

LCMS m/z=583.3 $[M+1]^+$

Step 2: 4-((7S)-8-((5-(cyclopropylethynyl)-7-methyl-1H-indol-4-yl)methyl)-1-oxa-8-azaspiro[4.5]decan-7-yl)benzoic acid (compound 22)

22-A

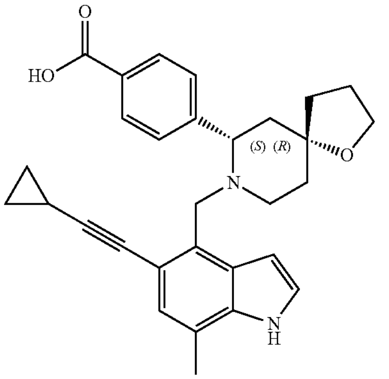

or

22-B

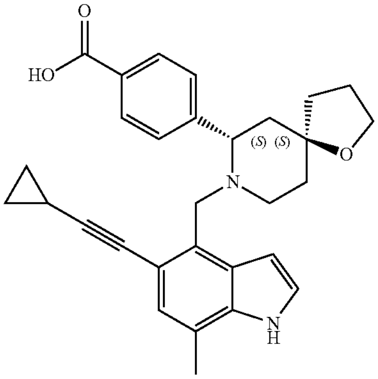

The tert-butyl 5-(cyclopropylethynyl)-4-(((7S)-7-(4-(methoxycarbonyl)phenyl)-1-oxa-8-azaspiro[4.5]decan-8-yl)methyl)-7-methyl-1H-indole-1-carboxylate (22a) (120 mg, 0.21 mmol) was dissolved in 6 mL of methanol, solid potassium carbonate (150 mg, 1.09 mmol) was added, and the mixture was heated to 80° C. and reacted for 5 h. The reaction liquid was cooled to room temperature, additional 2 mL of water and lithium hydroxide monohydrate (88 mg, 2.1 mmol) were added to the reaction liquid, and the mixture was heated to 80° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 25% to 55% acetonitrile (elution time 10 min), and lyophilization was performed to afford 4-((7S)-8-((5-(cyclopropylethynyl)-7-methyl-1H-indol-4-yl)methyl)-1-oxa-8-azaspiro[4.5]decan-7-yl)benzoic acid (compound 22) (40 mg, yield: 41%).

$^1$H NMR (400 MHz, $CD_3OD$) δ 8.24-8.06 (m, 2H), 7.80-7.60 (m, 2H), 7.35-7.25 (m, 1H), 6.99 (s, 1H), 6.22 (s, 1H), 4.60-4.43 (m, 1H), 4.40-4.25 (m, 1H), 4.23-4.10 (m, 1H), 4.03-3.85 (m, 2H), 3.40-3.12 (m, 2H), 2.45 (s, 3H), 2.35-2.15 (m, 1H), 2.08-1.90 (m, 4H), 1.87-1.72 (m, 3H), 1.60-1.45 (m, 1H), 1.05-0.90 (m, 2H), 0.87-0.70 (m, 2H).

LCMS m/z=469.3 $[M+1]^+$

Example 23

4-((2S,4R)-4-cyclopropyl-1-((7-methyl-5-(prop-1-yn-1-yl)-1H-indol-4-yl)methyl)piperidin-2-yl)benzoic acid (compound 23)

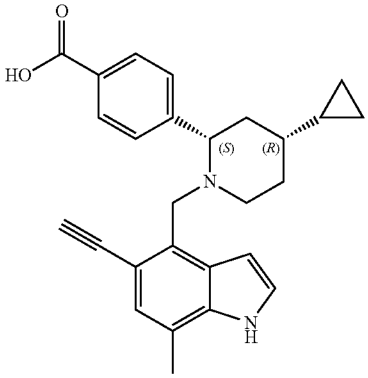

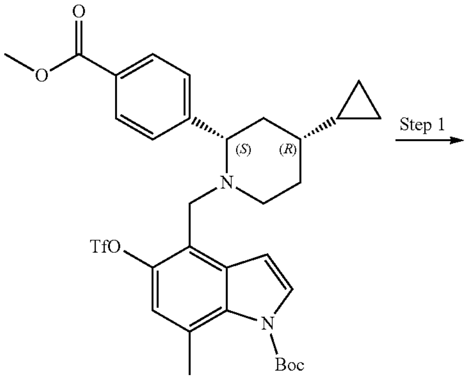

18c

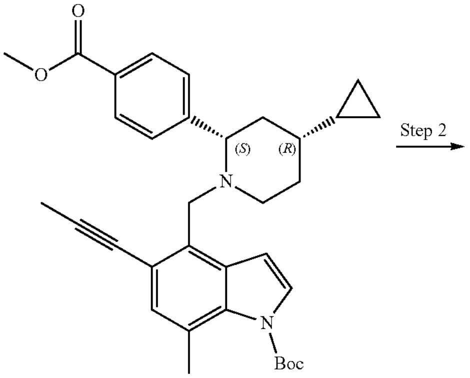

23a

-continued

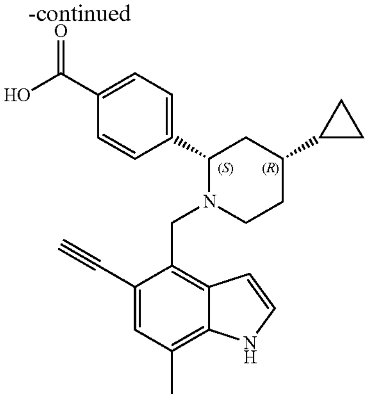

Compound 23

Step 1: tert-butyl 4-(((2S,4R)-4-cyclopropyl-2-(4-(methoxycarbonyl)phenyl) piperidin-1-yl)methyl)-7-methyl-5-(prop-1-yn-1-yl)-1H-indole-1-carboxylate (23a)

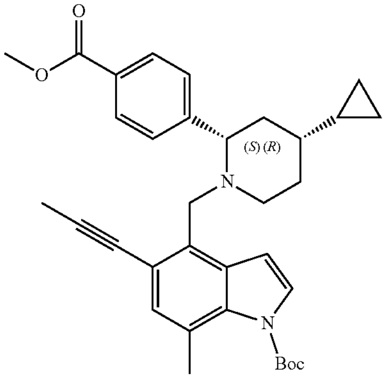

Tert-butyl 4-(((2S,4R)-4-cyclopropyl-2-(4-(methoxycarbonyl)phenyl) piperidin-1-yl)methyl)-7-methyl-5-(((trifluoromethyl)sulfonyl)oxy)-1H-indole-1-carboxylate (18c) (150 mg, 0.23 mmol) and 5 mL of ultra-dry DMF were added to the sealed tube, and [1,1-bis(diphenylphosphine)ferrocene] palladium dichloride dichloromethane complex (CAS: 95464-05-4) (19 mg, 0.024 mmol), CuI (9 mg, 0.047 mmol), solid cesium carbonate (220 mg, 0.68 mmol) and 1-(trimethylsilyl)propyne (77 mg, 0.69 mmol) were added, nitrogen replacement was performed three times, and the mixture was heated to 80° C. and reacted under nitrogen atmosphere for 6 h. The reaction liquid was cooled to room temperature, 80 mL of dichloromethane and 100 mL of saturated aqueous sodium chloride solution were added, the liquid separation was conducted, the aqueous phase was extracted twice with 50 mL of dichloromethane, the organic phases were combined, the organic phase was dried over anhydrous sodium sulfate and concentrated under reduced pressure, then the crude product was separated and purified with silica gel column chromatography (petroleum ether/ethyl acetate (v/v)= 15:1) to afford tert-butyl 4-(((2S,4R)-4-cyclopropyl-2-(4-(methoxycarbonyl)phenyl)piperidin-1-yl)methyl)-7-methyl-5-(prop-1-yn-1-yl)-1H-indole-1-carboxylate (23a) (100 mg, yield: 80%).

LCMS m/z=541.4 $[M+1]^+$

Step 2: 4-((2S,4R)-4-cyclopropyl-1-((7-methyl-5-(prop-1-yn-1-yl)-1H-indol-4-yl)methyl)piperidin-2-yl)benzoic acid (compound 23)

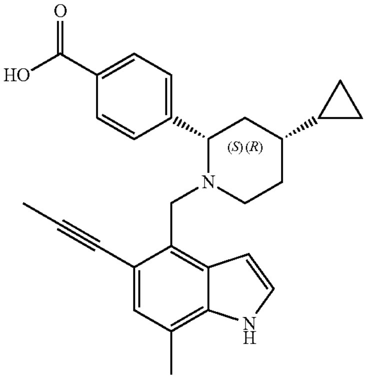

Tert-butyl 4-(((2S,4R)-4-cyclopropyl-2-(4-(methoxycarbonyl)phenyl)piperidin-1-yl)methyl)-7-methyl-5-(prop-1-yn-1-yl)-1H-indole-1-carboxylate (23a) (100 mg, 0.185 mmol) was dissolved in 6 mL of methanol, solid potassium carbonate (120 mg, 0.87 mmol) was added, and the mixture was heated to 80° C. and reacted at reflux for 4 h. The reaction liquid was cooled to room temperature, 2 mL of water and lithium hydroxide monohydrate (76 mg, 1.81 mmol) were added to the reaction liquid, and the mixture was heated to 80° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 25% to 55% acetonitrile (elution time 10 min), and lyophilization was performed to afford 4-((2S,4R)-4-cyclopropyl-1-((7-methyl-5-(prop-1-yn-1-yl)-1H-indol-4-yl)methyl)piperidin-2-yl)benzoic acid (compound 23) (35 mg, yield: 44%).

$^1$H NMR (400 MHz, $CD_3OD$) δ 8.20-8.07 (m, 2H), 7.70-7.57 (m, 2H), 7.34-7.25 (m, 1H), 7.00 (s, 1H), 6.27 (br.s, 1H), 4.45-4.03 (m, 3H), 3.45-3.31 (m, 1H), 3.14-2.90 (m, 1H), 2.45 (s, 3H), 2.17-1.80 (m, 6H), 1.77-1.50 (m, 1H), 1.15-0.95 (m, 1H), 0.70-0.52 (m, 1H), 0.52-0.35 (m, 2H), 0.25-0.06 (m, 2H).

LCMS m/z=427.3 $[M+1]^+$

Example 24

4-((2S,4R)-4-cyclopropyl-1-((5-ethynyl-7-methyl-1H-indol-4-yl)methyl)piperidin-2-yl)benzoic acid (compound 24) trifluoroacetate

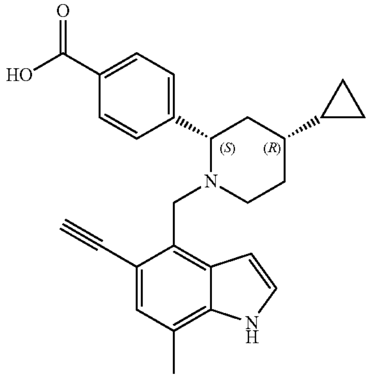

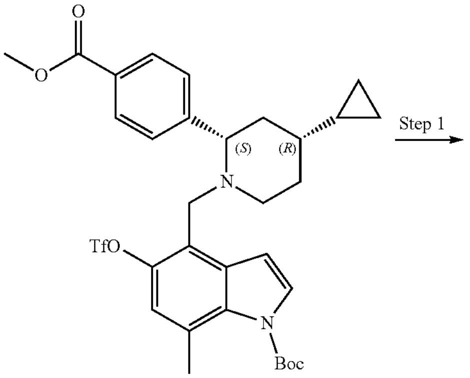

18c

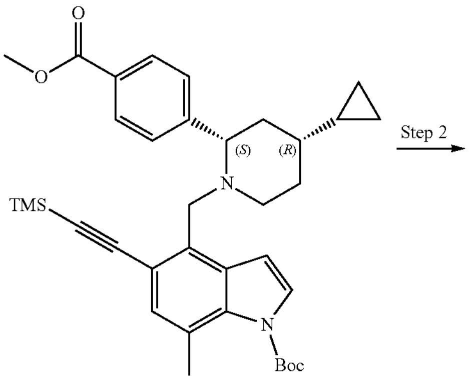

24a

-continued

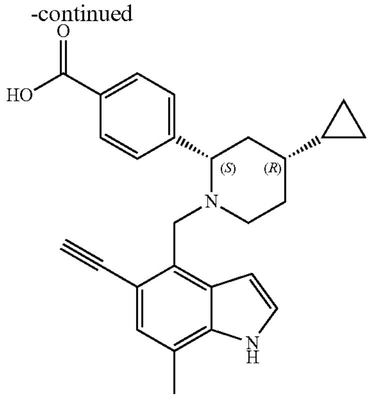

Compound 24

Step 1: tert-butyl 4-(((2S,4R)-4-cyclopropyl-2-(4-(methoxycarbonyl)phenyl) piperidin-1-yl)methyl)-7-methyl-5-((trimethylsilyl)ethynyl)-1H-indole-1-carboxylate (24a)

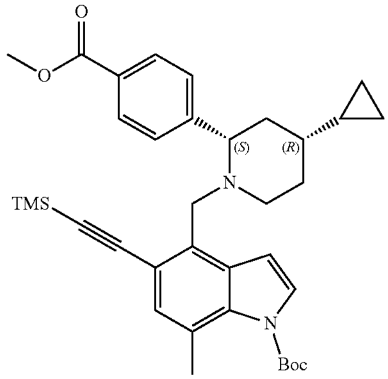

Tert-butyl 4-(((2S,4R)-4-cyclopropyl-2-(4-(methoxycarbonyl)phenyl) piperidin-1-yl)methyl)-7-methyl-5-(((trifluoromethyl)sulfonyl)oxy)-1H-indole-1-carboxylate (18c) (150 mg, 0.23 mmol) and 5 mL of ultra-dry DMF were added to the sealed tube, and [1,1'-bis(diphenylphosphine)ferrocene] palladium dichloride dichloromethane complex (CAS: 95464-05-4) (19 mg, 0.024 mmol), CuI (9 mg, 0.047 mmol), solid cesium carbonate (220 mg, 0.68 mmol) and trimethylethynyl silicon (68 mg, 0.69 mmol) were added, nitrogen replacement was performed three times, and the mixture was heated to 80° C. and reacted under nitrogen atmosphere for 6 h. The reaction liquid was cooled to room temperature, 80 mL of dichloromethane and 100 mL of saturated aqueous sodium chloride solution were added, the liquid separation was conducted, the aqueous phase was extracted twice with 50 mL of dichloromethane, the organic phases were combined, the organic phase was dried over anhydrous sodium sulfate and concentrated under reduced pressure, then the crude product was separated and purified with silica gel column chromatography (petroleum ether/ethyl acetate (v/v)= 15:1) to afford tert-butyl 4-(((2S,4R)-4-cyclopropyl-2-(4-(methoxycarbonyl)phenyl) piperidin-1-yl)methyl)-7-methyl-5-((trimethylsilyl)ethynyl)-1H-indole-1-carboxylate (24a) (70 mg, yield: 51%).

LCMS m/z=599.5 $[M+1]^+$

Step 2: 4-((2S,4R)-4-cyclopropyl-1-((5-ethynyl-7-methyl-1H-indol-4-yl)methyl) piperidin-2-yl)benzoic acid (compound 24) trifluoroacetate

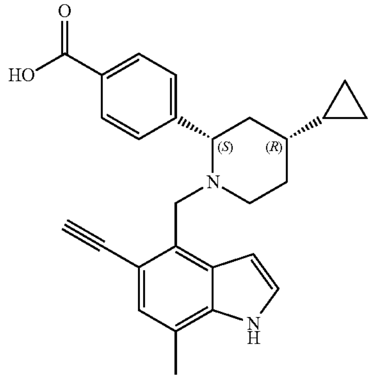

Tert-butyl 4-(((2S,4R)-4-cyclopropyl-2-(4-(methoxycarbonyl)phenyl) piperidin-1-yl)methyl)-7-methyl-5-((trimethylsilyl)ethynyl)-1H-indole-1-carboxylate (24a) (70 mg, 0.117 mmol) was dissolved in 6 mL of methanol, solid potassium carbonate (83 mg, 0.6 mmol) was added, and the mixture was heated to 80° C. and reacted for 2 h. The reaction liquid was cooled to room temperature, additional 2 mL of water and lithium hydroxide monohydrate (50 mg, 1.19 mmol) were added to the reaction liquid, and the mixture was heated to 80° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 0.1% trifluoroacetic acid). Gradient elution method: gradient elution of 10% to 40% acetonitrile (elution time 10 min), and lyophilization was performed to afford 4-((2S,4R)-4-cyclopropyl-1-((5-ethynyl-7-methyl-1H-indol-4-yl)methyl) piperidin-2-yl)benzoic acid (compound 24) trifluoroacetate (46 mg).

$^1$H NMR (400 MHz, $CD_3OD$) δ 7.64-7.56 (m, 2H), 7.48-7.40 (m, 2H), 7.32-7.26 (m, 1H), 6.87-6.83 (m, 1H), 6.55-6.50 (m, 1H), 5.97-5.87 (m, 1H), 5.85-5.68 (m, 2H), 5.15-5.04 (m, 1H), 5.02-4.92 (m, 1H), 4.24-4.05 (m, 1H), 3.85-3.72 (m, 1H), 2.90-2.70 (m, 1H), 2.40-2.10 (m, 6H), 1.44-1.26 (m, 1H), 0.95-0.78 (m, 1H), 0.67-0.50 (m, 2H), 0.40-0.20 (m, 2H).

LCMS m/z=413.3 [M+1]$^+$

Example 25

4-((2S,4R)-4-cyclopropyl-1-((5-(cyclopropylethynyl)-7-methyl-1H-indol-4-yl)methyl)piperidin-2-yl) benzoic acid (compound 25)

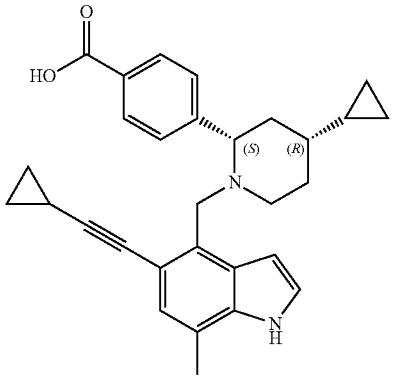

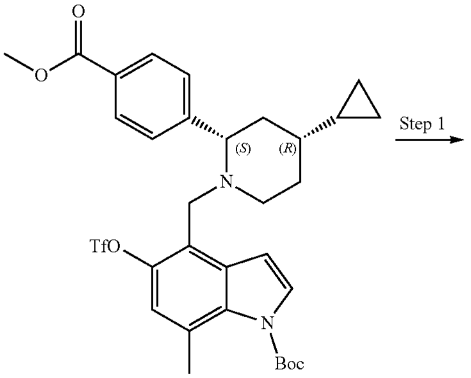

18c

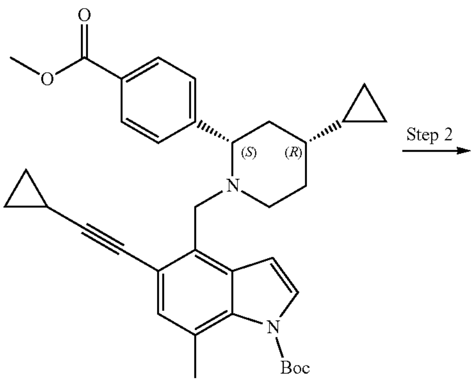

25a

-continued

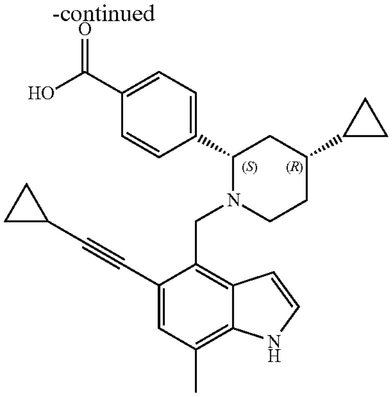

Compound 25

Step 1: tert-butyl 4-(((2S,4R)-4-cyclopropyl-2-(4-(methoxycarbonyl)phenyl) piperidin-1-yl)methyl)-5-(cyclopropylethynyl)-7-methyl-1H-indole-1-carboxylate (25a)

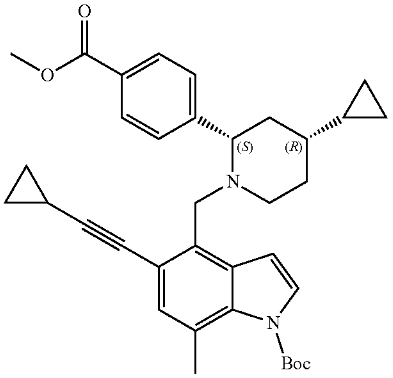

Tert-butyl 4-(((2S,4R)-4-cyclopropyl-2-(4-(methoxycarbonyl)phenyl) piperidin-1-yl)methyl)-7-methyl-5-(((trifluoromethyl)sulfonyl)oxy)-1H-indole-1-carboxylate (18c) (150 mg, 0.23 mmol) and 5 mL of ultra-dry DMF were added to the sealed tube, and [1,1-bis(diphenylphosphine)ferrocene] palladium dichloride dichloromethane complex (CAS: 95464-05-4) (19 mg, 0.024 mmol), CuI (9 mg, 0.047 mmol), solid cesium carbonate (220 mg, 0.68 mmol) and ethynylcyclopropane (45 mg, 0.69 mmol) were added, nitrogen replacement was performed three times, and the mixture was heated to 80° C. and reacted under nitrogen atmosphere for 6 h. The reaction liquid was cooled to room temperature, 80 mL of dichloromethane and 100 mL of saturated aqueous sodium chloride solution were added, the liquid separation was conducted, the aqueous phase was extracted twice with 50 mL of dichloromethane, the organic phases were combined, the organic phase was dried over anhydrous sodium sulfate and concentrated under reduced pressure, then the crude product was separated and purified with silica gel column chromatography (petroleum ether/ethyl acetate (v/v) =15:1) to afford tert-butyl 4-(((2S,4R)-4-cyclopropyl-2-(4-(methoxycarbonyl)phenyl)piperidin-1-yl)methyl)-5-(cyclopropylethynyl)-7-methyl-1H-indole-1-carboxylate (25a) (100 mg, yield: 77%).

LCMS m/z=567.5 [M+1]$^+$

Step 2: 4-((2S,4R)-4-cyclopropyl-1-((5-(cyclopropylethynyl)-7-methyl-1H-indol-4-yl)methyl)piperidin-2-yl)benzoic acid (compound 25)

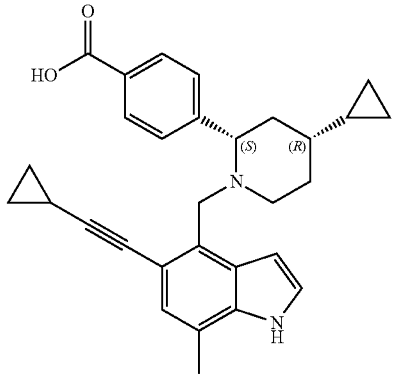

Tert-butyl 4-(((2S,4R)-4-cyclopropyl-2-(4-(methoxycarbonyl)phenyl) piperidin-1-yl)methyl)-5-(cyclopropylethynyl)-7-methyl-1H-indole-1-carboxylate (25a) (100 mg, 0.177 mmol) was dissolved in 6 mL of methanol, solid potassium carbonate (120 mg, 0.868 mmol) was added, and the mixture was heated to 80° C. and reacted for 5 h. The reaction liquid was cooled to room temperature, additional 2 mL of water and lithium hydroxide monohydrate (76 mg, 1.81 mmol) were added to the reaction liquid, and the mixture was heated to 80° C. and reacted for 1 h. The reaction system was cooled to room temperature and concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 25% to 55% acetonitrile (elution time 10 min), and lyophilization was performed to afford 4-((2S,4R)-4-cyclopropyl-1-((5-(cyclopropylethynyl)-7-methyl-1H-indol-4-yl)methyl)piperidin-2-yl)benzoic acid (compound 25) (61 mg, yield: 76%).

$^1$H NMR (400 MHz, $CD_3OD$) δ 8.20-8.09 (m, 2H), 7.73-7.60 (m, 2H), 7.34-7.24 (m, 1H), 6.97 (s, 1H), 6.19 (br.s, 1H), 4.45-4.00 (m, 3H), 3.47-3.32 (m, 1H), 3.10-2.87 (m, 1H), 2.43 (s, 3H), 2.17-1.82 (m, 3H), 1.79-1.42 (m, 2H), 1.13-0.85 (m, 3H), 0.84-0.53 (m, 3H), 0.50-0.36 (m, 2H), 0.24-0.10 (m, 2H).

LCMS m/z=453.3 [M+1]$^+$

Example 26
4-((2S)-1-((5-methoxy-7-methyl-1H-indol-4-yl)methyl)-4-phenylpiperidin-2-yl)benzoic acid [compound 26 (diastereomer 1)]
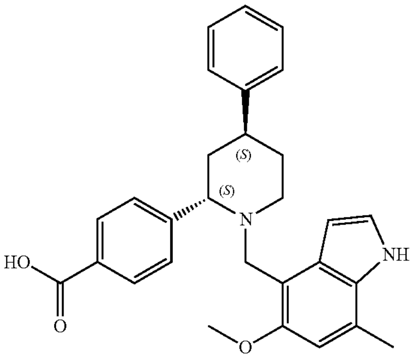
or
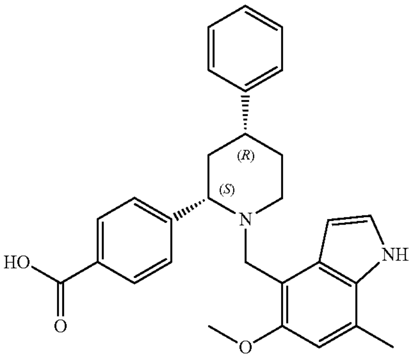
26-A 26-B
Compound 26 (diastereomer 1)
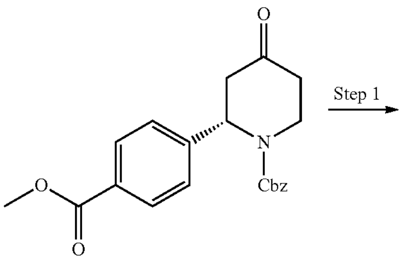
1a
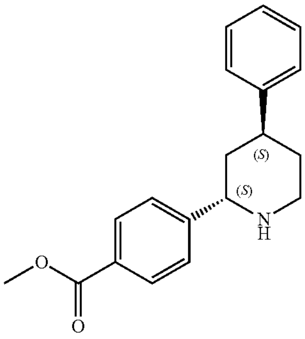
or
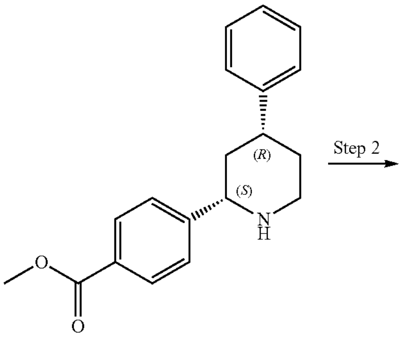
26a-A 26a-B
26a (diastereomer 1)
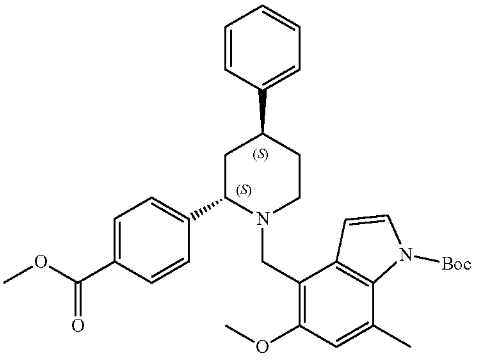
or
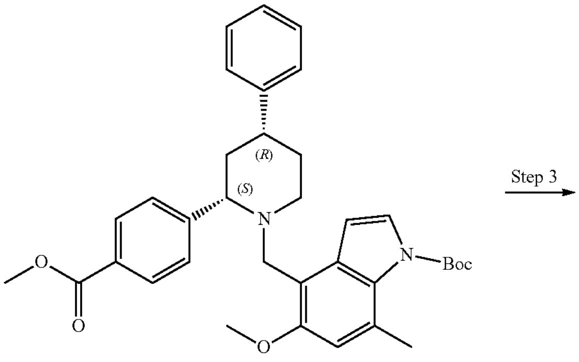
26-A 26-B
26b (diastereomer 1)

-continued

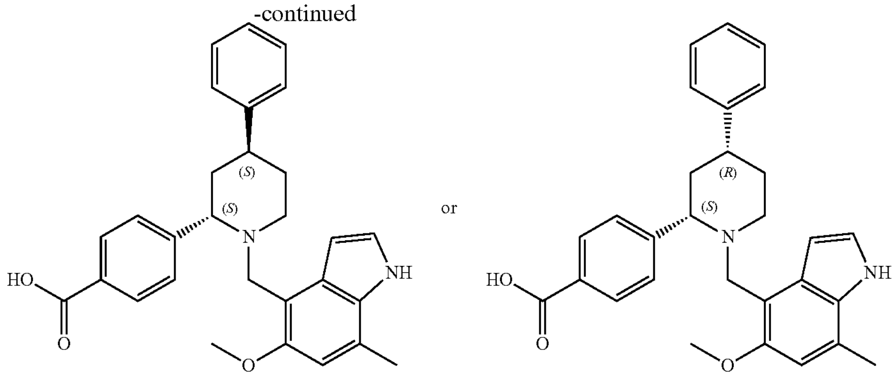

26-A or 26-B

Compound 26 (diastereomer 1)

Step 1: methyl 4-((2S)-4-phenylpiperidin-2-yl)benzoate [26a (diastereomer 1)] maleate 26a (diastereomer 1)

26a-A

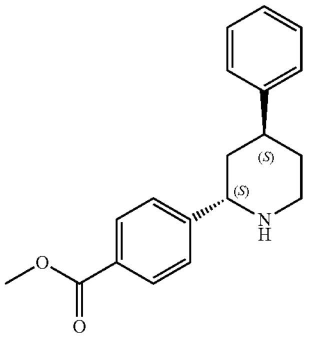

or

26a-B

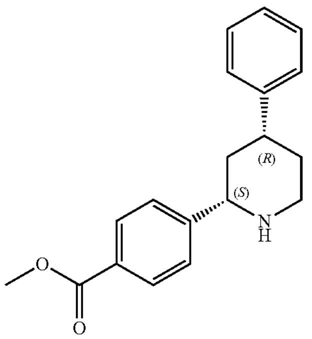

Benzyl (S)-2-(4-(methoxycarbonyl)phenyl)-4-oxopiperidine-1-carboxylate (2.0 g, 5.44 mmol) (1a) (see WO 2020016749 for the synthesis method) was added into 50 mL of ultra-dry THF, the mixture was cooled to −70° C. under nitrogen protection, a solution of 2 mol/L lithium diisopropylamide in tetrahydrofuran (3.5 mL, 2.0 mol/L) was slowly added dropwise and stirred further at −70° C. for 60 min, and N-phenylbis(trifluoromethanesulfonyl)imide (2.33 g, 6.53 mmol) was added and stirred further at −70° C. for 1 h, then the mixture was slowly warmed to room temperature and stirred for 2 h. 50 mL of ethyl acetate was added to the reaction system, the mixture was washed with 30 mL of saturated aqueous ammonium chloride solution, dried over anhydrous sodium sulfate, and concentrated under reduced pressure. The crude product was separated and purified with silica gel chromatography column (petroleum ether/ethyl acetate (v/v)=10:1) to afford a crude product 1 (2.1 g). The crude product 1 (1.2 g) was dissolved in 10 mL of DME and 10 mL of water, then phenylboronic acid (0.50 g, 4.1 mmol), solid sodium carbonate (0.64 g, 6.04 mmol) and tetrakis triphenylphosphine palladium (0.35 g, 0.30 mmol) were added in sequence, nitrogen replacement was performed three times, and the mixture was heated to 80° C. and reacted for 6 h. The reaction liquid was cooled to room temperature, 20 mL of water was added, the mixture was extracted with 50 mL of ethyl acetate, dried over anhydrous sodium sulfate, and concentrated under reduced pressure. The crude product was separated and purified with silica gel chromatography column (petroleum ether/ethyl acetate (v/v)=10:1) to afford a crude product 2 (0.35 g). The crude product 2 (350 mg) was dissolved in 5 mL of methanol, 0.1 g of 10% palladium on carbon was added, hydrogen replacement was performed three times, the mixture was reacted at room temperature under hydrogen atmosphere for 16 h. The reaction system was filtered, and the filtrate was concentrated under reduced pressure to afford methyl 4-((2S)-4-phenylpiperidin-2-yl)benzoate [26a (diastereomer 1)] (0.133 g). Methyl 4-((2S)-4-phenylpiperidin-2-yl)benzoate [26a (diastereomer 1)] (133 mg, 0.45 mmol) was dissolved in 5 mL of isopropyl acetate, maleic acid (52 mg, 0.45 mmol) was added, stirred at room temperature for 1 h, and then the reaction system was concentrated under reduced pressure to afford crude methyl 4-((2S)-4-phenylpiperidin-2-yl)benzoate [26a (diastereomer 1)] maleate (208 mg). Compound 26a (diastereomer 1) is one of the isomers of structure 26a-A or 26a-B.

Step 2: tert-butyl 5-methoxy-4-(((2S)-2-(4-(methoxycarbonyl)phenyl)-4-phenylpiperidin-1-yl)methyl)-7-methyl-1H-indole-1-carboxylate [26b (diastereomer 1)]

26b (diastereomer 1)

26b-A

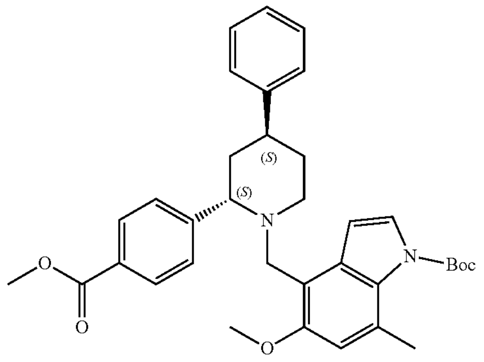

or

26b-B

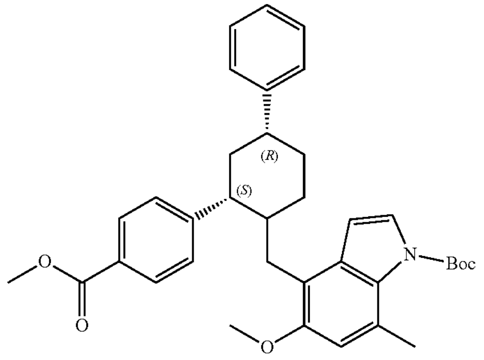

The above-mentioned crude methyl 4-((2S)-4-phenylpiperidin-2-yl)benzoate [26a (diastereomer 1)] maleate (208 mg) was dissolved in 10 mL of ethanol, tert-butyl 4-formyl-5-methoxy-7-methyl-1H-indole-1-carboxylate (0.16 g, 0.55 mmol) (see WO 2015009616 for the synthesis method) was added and 16 mg of $Ir(CO)_2acac$ was added, hydrogen replacement was performed three times, the mixture was heated to 80° C., and reacted for 19 h under the atmosphere of hydrogen balloon. The reaction liquid was concentrated under reduced pressure, 20 mL of water was added to the residue, the pH was adjusted to 8 with saturated sodium bicarbonate aqueous solution, extraction was performed with 50 mL of ethyl acetate, the organic phase was washed with 20 mL of water, dried over anhydrous sodium sulfate, and concentrated under reduced pressure. The crude product was separated and purified with silica gel chromatography column (petroleum ether/ethyl acetate (v/v)=10:1) to afford tert-butyl 5-methoxy-4-(((2S)-2-(4-(methoxycarbonyl) phenyl)-4-phenylpiperidin-1-yl)methyl)-7-methyl-1H-indole-1-carboxylate [26b (diastereomer 1)] (141 mg, yield: 45%).

LCMS m/z=569.2 $[M+1]^+$

Compound 26b (diastereomer 1) is one of the isomers of structure 26b-A or 26b-B.

Step 3: 4-((2S)-1-((5-methoxy-7-methyl-1H-indol-4-yl)methyl)-4-phenylpiperidin-2-yl)benzoic acid [compound 26 (diastereomer 1)]

Compound 26 (diastereomer 1)

26-A

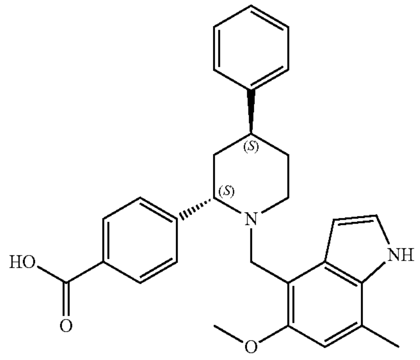

or

26-B

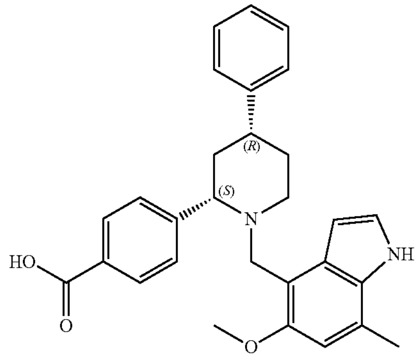

Tert-butyl 5-methoxy-4-(((2S)-2-(4-(methoxycarbonyl) phenyl)-4-phenylpiperidin-1-yl)methyl)-7-methyl-1H-indole-1-carboxylate [26b (diastereomer 1)](0.141 g, 0.248 mmol) was dissolved in 8 mL of methanol, lithium hydroxide monohydrate (100 mg, 2.38 mmol) was added, and the mixture was heated to 80° C. and reacted for 4 h. The reaction system was cooled to room temperature, 2 mL of water was added, and the mixture was heated to 80° C. and reacted for 2 h. The reaction liquid was cooled to room temperature, the pH was adjusted to 7 with 2 mol/L aqueous hydrochloric acid solution, the mixture was concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 8% to 38% acetonitrile (elution time 15 min), and lyophilization was performed to afford 4-((2S)-1-((5-methoxy-7-methyl-1H-indol-4-yl)methyl)-4-phenylpiperidin-2-yl)benzoic acid [compound 26 (diastereomer 1)] (46 mg, yield: 41%).

$^1H$ NMR (400 MHz, $CD_3OD$) δ 8.25-8.09 (m, 2H), 7.78-7.60 (m, 2H), 7.40-7.11 (m, 6H), 6.77 (s, 1H), 6.35 (s, 1H), 4.65-4.30 (m, 2H), 4.19-4.00 (m, 1H), 3.78 (s, 3H), 3.68-3.52 (m, 1H), 3.45-3.32 (m, 1H), 3.22-3.04 (m, 1H), 2.52 (s, 3H), 2.44-1.95 (m, 4H).
LCMS m/z=455.2 [M+1]$^+$
Compound 26 (diastereomer 1) is one of the isomers of structure 26-A or 26-B.
Example 27
(R)-4-(4-cyclopropyl-1-((5-methoxy-7-methyl-1H-indol-4-yl)methyl)piperazin-2-yl)benzoic acid (compound 27-A)
(S)-4-(4-cyclopropyl-1-((5-methoxy-7-methyl-1H-indol-4-yl)methyl)piperazin-2-yl)benzoic acid (compound 27-B)
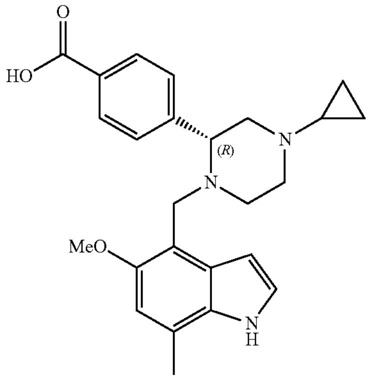
Compound 27-A
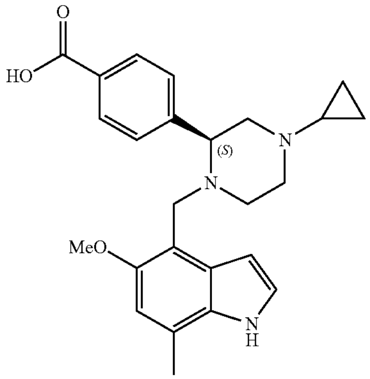
Compound 27-B
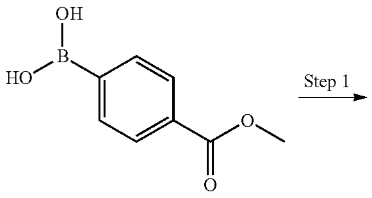
27a
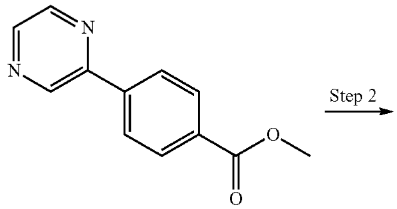
27b
-continued
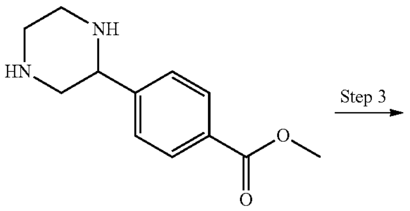
27c
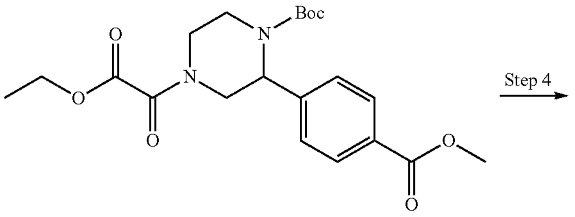
27d
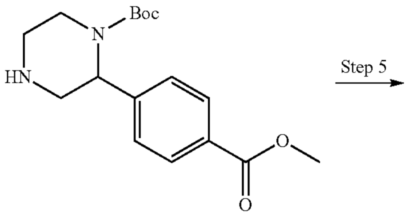
27e
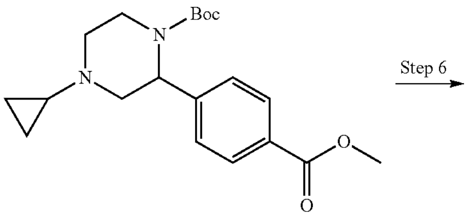
27f
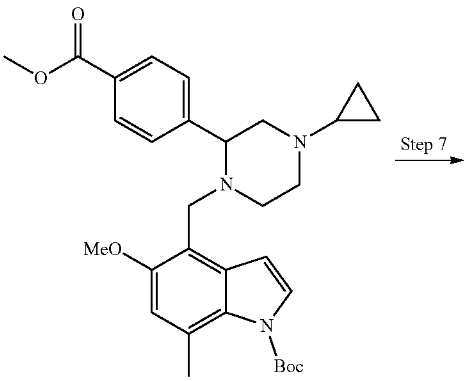
27g -continued

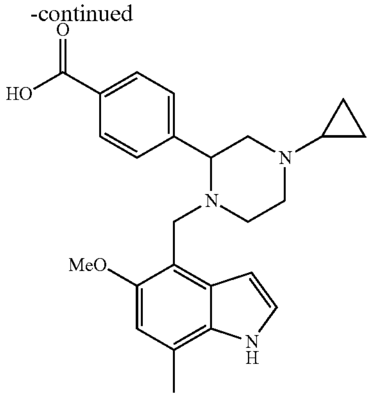

Compound 27

Step 1: methyl 4-(pyrazin-2-yl)benzoate (27b)

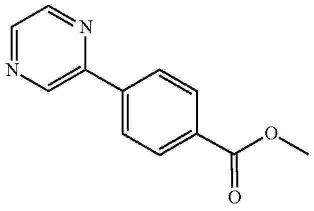 [SMILES: COC(=O)c1ccc(-c2cnccn2)cc1]

2-chloropyrazine (10.0 g, 87.3 mmol) was dissolved in 50 mL of 1,4-dioxane and 10 ml of water, and (4-(methoxycarbonyl)phenyl)boronic acid (27a) (17.28 g, 96.02 mmol), anhydrous potassium phosphate (24.13 g, 113.68 mmol) and [1,1'-bis(diphenylphosphine)ferrocene]palladium dichloride dichloromethane complex (CAS: 95464-05-4) (7.13 g, 8.80 mmol) were added in sequence, nitrogen replacement was performed three times, and the mixture was heated to 100° C. and reacted for 12 h under nitrogen atmosphere. The reaction liquid was cooled to room temperature, 20 mL of water was added, and the mixture was extracted with 100 mL of ethyl acetate. The organic phase was dried over anhydrous sodium sulfate and concentrated under reduced pressure. The crude product was separated and purified with silica gel chromatography column (petroleum ether/ethyl acetate (v/v)=3:1) to afford methyl 4-(pyrazin-2-yl)benzoate (27b) (5.1 g, yield: 27%).

LCMS m/z=215.1 $[M+1]^+$

Step 2: methyl 4-(piperazin-2-yl)benzoate (27c)

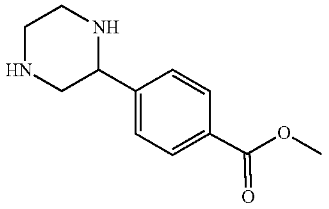 [SMILES: COC(=O)c1ccc(C2CNCCN2)cc1]

Methyl 4-(pyrazin-2-yl)benzoate (27b) (2.0 g, 9.34 mmol) was dissolved in 20 mL of acetic acid, palladium acetate (0.42 g, 1.87 mmol) was added, hydrogen replacement was performed three times, and the mixture was reacted at room temperature for 16 h under the atmosphere of hydrogen balloon. The reaction system was filtered, and the filtrate was concentrated under reduced pressure to afford crude methyl 4-(piperazin-2-yl)benzoate (27c) (2.4 g).

Step 3: tert-butyl 4-(2-ethoxy-2-oxoacetyl)-2-(4-(methoxycarbonyl)phenyl) piperazine-1-carboxylate (27d)

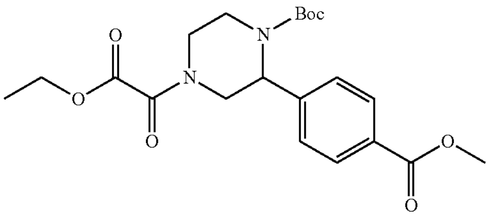 [SMILES: CCOC(=O)C(=O)N1CCN(C(=O)OC(C)(C)C)C(c2ccc(C(=O)OC)cc2)C1]

The above-mentioned crude methyl 4-(piperazin-2-yl) benzoate (27c) (2.4 g) was dissolved in 10 mL of tetrahydrofuran, solid sodium bicarbonate (2.24 g, 26.7 mmol) was added and stirred at room temperature for 1 h. Diethyl oxalate (1.96 g, 13.41 mmol) was added and reacted at room temperature for 19 h. Then Boc anhydride (2.53 g, 11.59 mmol) was added and reacted at room temperature for 19 h. 30 mL of water was added to the reaction liquid, the mixture was extracted with 100 mL of ethyl acetate, the liquid separation was conducted, the organic phase was washed with 50 mL of water, dried over anhydrous sodium sulfate, and concentrated under reduced pressure to afford crude tert-butyl 4-(2-ethoxy-2-oxoacetyl)-2-(4-(methoxycarbonyl)phenyl)piperazine-1-carboxylate (27d) (350 mg).

Step 4: tert-butyl 2-(4-(methoxycarbonyl)phenyl) piperazine-1-carboxylate (27e)

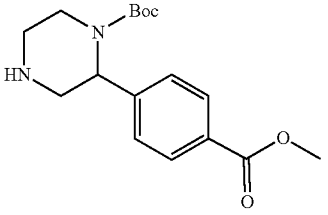 [SMILES: COC(=O)c1ccc(C2CNCCN2C(=O)OC(C)(C)C)cc1]

The above-mentioned crude tert-butyl 4-(2-ethoxy-2-oxoacetyl)-2-(4-(methoxycarbonyl)phenyl)piperazine-1-carboxylate (27d) (350 mg) was dissolved in 15 mL of methanol, 5 mL of water was added, solid sodium hydroxide (0.33 g, 8.25 mmol) was added, and the mixture was heated to 70° C. and reacted for 19 h. The reaction liquid was cooled to room temperature, the pH was adjusted to 5 with 1 mol/L aqueous hydrochloric acid solution, the reaction liquid was concentrated under reduced pressure, mL of methanol and 5 mL of dichloromethane were added, and trimethylsilyldiazomethane (0.47 g, 4.12 mmol) was slowly added, and the mixture was reacted at room temperature for 3 h. The reaction liquid was concentrated under reduced pressure, and the crude product was separated and purified with silica gel chromatography column (petroleum ether/ ethyl acetate (v/v)=1:1) to afford tert-butyl 2-(4-(methoxycarbonyl)phenyl)piperazine-1-carboxylate (27e) (0.25 g, three-step yield from compound 27b: 8%).

LCMS m/z=321.1 $[M+1]^+$

Step 5: tert-butyl 4-cyclopropyl-2-(4-(methoxycarbonyl)phenyl)piperazine-1-carboxylate (27f)

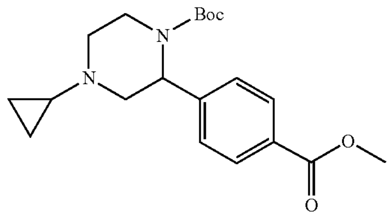 [SMILES: COC(=O)c1ccc(C2CN(C3CC3)CCN2C(=O)OC(C)(C)C)cc1]

Tert-butyl 2-(4-(methoxycarbonyl)phenyl)piperazine-1-carboxylate (27e) (130 mg, 0.41 mmol) was dissolved in 5 mL of methanol, and acetic acid (0.24 g, 4.0 mmol), (1-ethoxycyclopropoxy)trimethylsilane (86 mg, 0.49 mmol) and sodium cyanoborohydride (39 mg, 0.62 mmol) were added in sequence, nitrogen replacement was performed three times, and the mixture was heated to 70° C. and reacted for 4 h under nitrogen atmosphere. The reaction system was cooled to room temperature, the pH was adjusted to 9 with saturated aqueous sodium bicarbonate solution, 30 mL of water was added, the mixture was extracted with 40 mL of ethyl acetate, the organic phase was washed with 30 mL of water, dried over anhydrous sodium sulfate and concentrated under reduced pressure, and the crude product was separated and purified with silica gel chromatography column (petroleum ether/ethyl acetate (v/v)=3:1) to afford tert-butyl 4-cyclopropyl-2-(4-(methoxycarbonyl) phenyl)piperazine-1-carboxylate (27f) (0.15 g, yield: >99%).

LCMS m/z=361.1 $[M+1]^+$

Step 6: tert-butyl 4-((4-cyclopropyl-2-(4-(methoxycarbonyl)phenyl)piperazin-1-yl)methyl)-5-methoxy-7-methyl-1H-indole-1-carboxylate (27g)

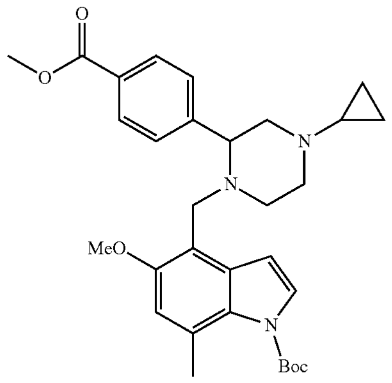 [SMILES: COC(=O)c1ccc(C2CN(C3CC3)CCN2Cc2c(OC)cc(C)c3c2ccn3C(=O)OC(C)(C)C)cc1]

Tert-butyl 4-cyclopropyl-2-(4-(methoxycarbonyl)phenyl) piperazine-1-carboxylate (27f) (150 mg, 0.42 mmol) was dissolved in 5 mL of ethyl acetate, and a solution of 2 mol/L hydrochloric acid in ethyl acetate (4 mL) was added, and the mixture was reacted at room temperature for 2 h. The pH of the reaction system was adjusted to 8 with saturated aqueous sodium bicarbonate solution, 10 mL of water was added, the mixture was extracted with 20 mL of ethyl acetate, the organic phase was dried over anhydrous sodium sulfate and concentrated under reduced pressure, and the residue was dissolved in 5 mL of DCE. Tert-butyl 4-formyl-5-methoxy-7-methyl-1H-indole-1-carboxylate (0.12 g, 0.42 mmol) (see WO 2015009616 for the synthesis method) and acetic acid (0.13 g, 2.17 mmol) were added, the mixture was reacted at room temperature for 2 h, then sodium triacetoxyborohydride (260 mg, 1.23 mmol) was added, and the mixture was reacted at room temperature for 19 h. The pH of the reaction liquid was adjusted to 8 with saturated aqueous sodium bicarbonate solution, 30 mL of water was added, the mixture was extracted with 40 mL of ethyl acetate, the organic phase was washed with 30 mL of water, dried over anhydrous sodium sulfate and concentrated under reduced pressure. The crude product was separated and purified with silica gel chromatography column (petroleum ether/ethyl acetate (v/v)=5:1) to afford tert-butyl 4-((4-cyclopropyl-2-(4-(methoxycarbonyl)phenyl) piperazin-1-yl)methyl)-5-methoxy-7-methyl-1H-indole-1-carboxylate (27g) (0.075 g, yield: 33%).

LCMS m/z=534.3 $[M+1]^+$

Step 7: (R)-4-(4-cyclopropyl-1-((5-methoxy-7-methyl-1H-indol-4-yl)methyl) piperazin-2-yl)benzoic acid (compound 27-A)

(S)-4-(4-cyclopropyl-1-((5-methoxy-7-methyl-1H-indol-4-yl)methyl)piperazin-2-yl)benzoic acid (compound 27-B)

Compound 27-A

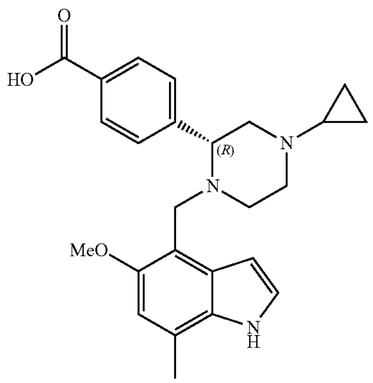

Compound 27-B

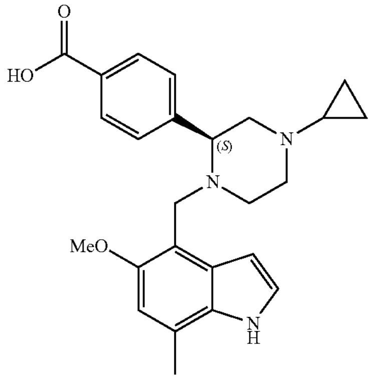

Tert-butyl 4-((4-cyclopropyl-2-(4-(methoxycarbonyl)phenyl)piperazin-1-yl)methyl)-5-methoxy-7-methyl-1H-indole-1-carboxylate (27g) (0.075 g, 0.14 mmol) was dissolved in 4 mL of methanol, lithium hydroxide monohydrate (59 mg, 1.41 mmol) was added, and the mixture was heated to 80° C. and reacted for 4 h. The reaction liquid was cooled to room temperature, 1 mL of water was added, and the mixture was heated to 80° C. and reacted for 2 h. The reaction system was cooled to room temperature, the pH was adjusted to 8 with 2 mol/L aqueous hydrochloric acid solution and concentrated under reduced pressure. The crude product was subjected to chiral resolution (instrument and preparative column: using Waters 150 SFC preparative liquid phase chromatographic instrument, preparative column model: Chiralpak Column). Preparation method: the crude product was dissolved with methanol and dimethyl sulfoxide, and filtered with a 0.45 μm filter membrane, to prepare into a sample liquid. Mobile phase system: a mixed solvent of supercritical carbon dioxide/methanol and acetonitrile (containing 0.1% ammonia). Gradient elution method: isocratic elution of 40% mixed solvent of methanol and acetonitrile (containing 0.1% ammonia water). After lyophilization, the sample was subjected to Pre-HPLC (instrument and preparative column: using SHIMADZU LC-20AP preparative liquid phase chromatographic instrument, preparative column model: C18 packing material). Preparation method: the crude product was dissolved with methanol and dimethyl sulfoxide, and filtered with a 0.45 μm filter membrane, to prepare into a sample liquid. Mobile phase system: acetonitrile/water (containing 10 mmol/L ammonium bicarbonate). Gradient elution method: gradient elution of 8% to 38% acetonitrile (elution time 15 min), and lyophilization was performed to afford chiral isomer 1 (compound 27-1) (16 mg, yield: 27%) of and chiral isomer 2 (compound 27-2) (18 mg, yield: 31%) of 4-(4-cyclopropyl-1-((5-methoxy-7-methyl-1H-indol-4-yl)methyl)piperazin-2-yl)benzoic acid, respectively.

Analysis Method for Chiral Isomers of Compound 27:

instrument: SHIMADZU LC-30AD sf, chromatographic column: Chiralcel AD-3, specifications: 50 mm×4.6 mm, 3 μm, mobile phase A: supercritical $CO_2$, mobile phase B: methanol containing 0.05% diethylamine, column temperature: 35° C., flow rate: 3 mL/min, wavelength: 220 nm, elution program: mobile phase A:B=95:5-60:40.

Retention time of compound 27-1: 2.149 min;

retention time of compound 27-2: 2.556 min.

Nuclear Magnetic Resonances Spectrum of Compound 27-1:

$^1H$ NMR (400 MHz, $CD_3OD$) δ 8.06-7.96 (m, 2H), 7.62-7.48 (m, 2H), 7.20-7.12 (m, 1H), 6.63 (s, 1H), 6.29-6.22 (m, 1H), 4.10-3.85 (m, 2H), 3.78-3.60 (m, 4H), 3.15-2.73 (m, 4H), 2.72-2.45 (m, 2H), 2.38 (s, 3H), 1.74-1.63 (m, 1H), 0.48-0.30 (m, 4H).

LCMS m/z=420.2 $[M+1]^+$

Nuclear Magnetic Resonances Spectrum of Compound 27-2:

$^1H$ NMR (400 MHz, $CD_3OD$) δ 8.06-7.96 (m, 2H), 7.62-7.48 (m, 2H), 7.20-7.13 (m, 1H), 6.63 (s, 1H), 6.29-6.22 (m, 1H), 4.13-3.87 (m, 2H), 3.80-3.60 (m, 4H), 3.15-2.74 (m, 4H), 2.72-2.45 (m, 2H), 2.38 (s, 3H), 1.74-1.63 (m, 1H), 0.48-0.30 (m, 4H).

LCMS m/z=420.2 $[M+1]^+$

Compound 27-1 and compound 27-2 are one of the chiral isomers of compound 27-A and compound 27-B, respectively.

Example 28

4-((2S)-1-((5-methoxy-7-methyl-1H-indol-4-yl)methyl)-4-(tetrahydro-2H-pyran-4-yl)piperidin-2-yl)benzoic acid [compound 28 (diastereomer 1)]trifluoroacetate

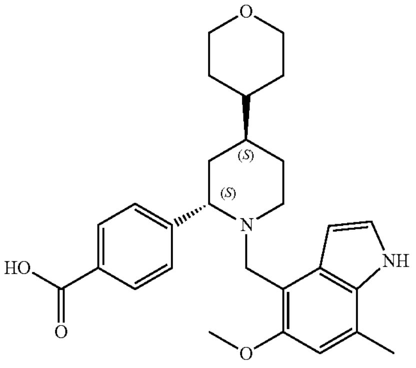

28-A or

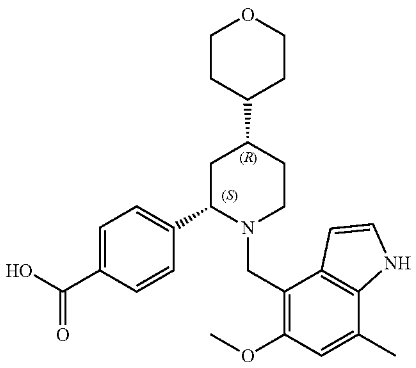

28-B

Compound 28 (diastereomer 1)

-continued
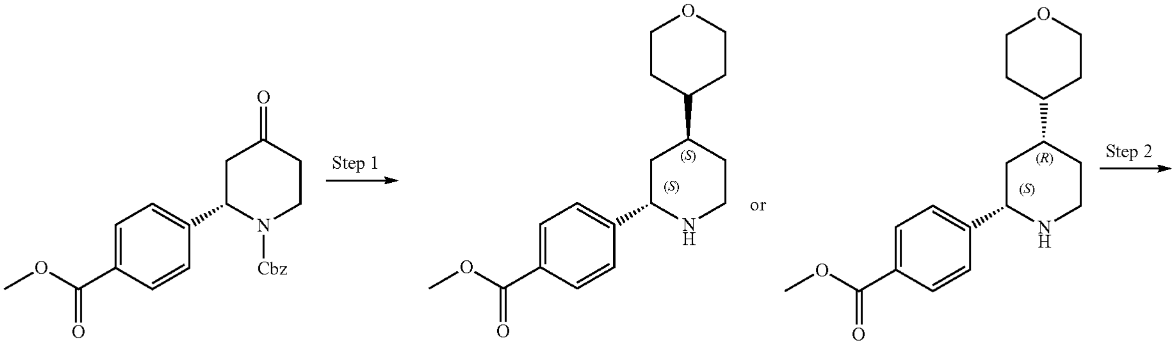
1a 28a-A 28a-B
28a (diastereomer 1)
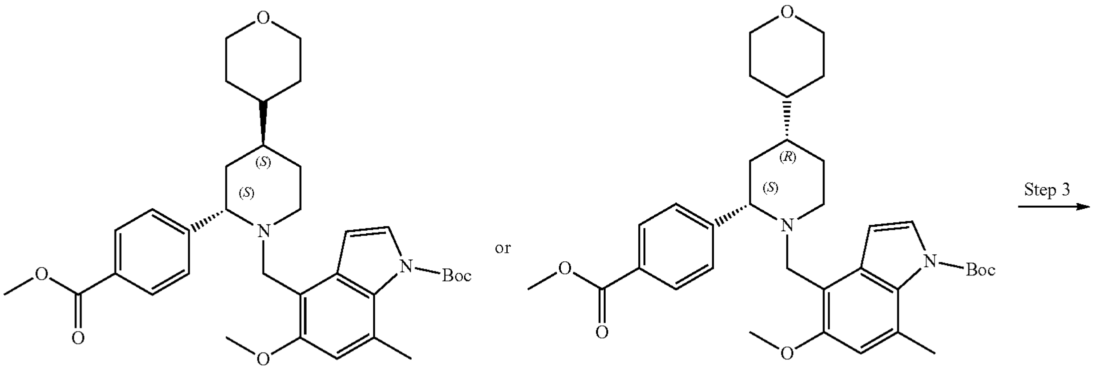
28b-A 28b-B
28b (diastereomer 1)
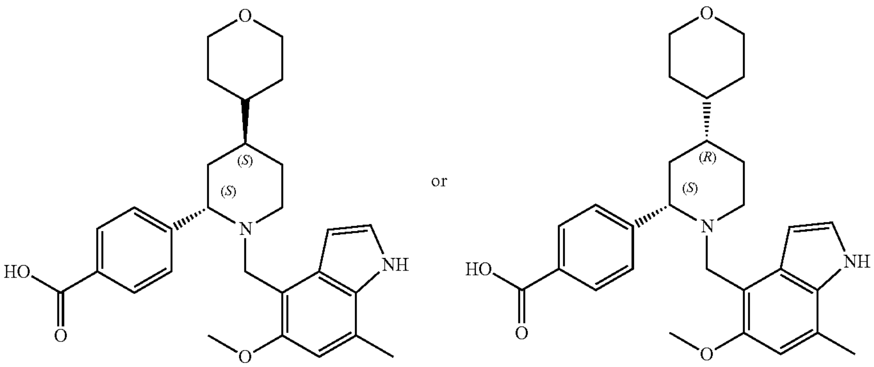
28-A 28-B
Compound 28 (diastereomer 1)

Step 1: methyl 4-((2S)-4-(tetrahydro-2H-pyran-4-yl)piperidin-2-yl)benzoate [28a (diastereomer 1)] maleate 28a (diastereomer 1)

28a-A

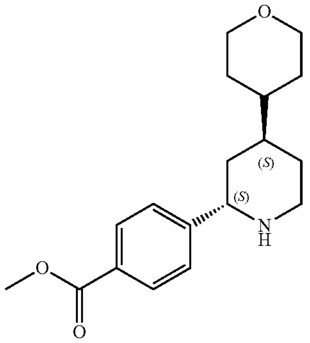

or

28a-B

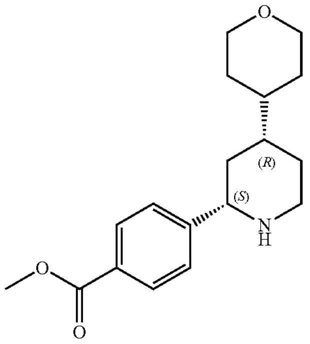

Benzyl (S)-2-(4-(methoxycarbonyl)phenyl)-4-oxopiperidine-1-carboxylate (2.0 g, 5.44 mmol) (1a) (see WO 2020016749 for the synthesis method) was added into 50 mL of ultra-dry THF, the mixture was cooled to −70° C. under nitrogen protection, a solution of 2 mol/L lithium diisopropylamide in tetrahydrofuran (3.5 mL, 2.0 mol/L) was slowly added dropwise and stirred further at −70° C. for 60 min, and N-phenylbis(trifluoromethanesulfonyl)imide (2.33 g, 6.53 mmol) was added and stirred further at −70° C. for 1 h, then the mixture was slowly warmed to room temperature and stirred for 2 h. 50 mL of ethyl acetate was added to the reaction system, the mixture was washed with 30 mL of saturated aqueous ammonium chloride solution, dried over anhydrous sodium sulfate, and concentrated under reduced pressure. The crude product was separated and purified with silica gel chromatography column (petroleum ether/ethyl acetate (v/v)=10:1) to afford a crude product 1 (2.1 g). The crude product 1 (1.0 g) was dissolved in 8 mL of DME and 8 mL of water, then 2-(3,6-dihydro-2H-pyran-4-yl)-4,4,5,5-tetramethyl-1,3,2-dioxaborane (0.50 g, 2.38 mmol), solid sodium carbonate (0.64 g, 6.04 mmol) and tetrakis triphenylphosphine palladium (0.23 g, 0.20 mmol) were added in sequence, nitrogen replacement was performed three times, and the mixture was heated to 80° C. and reacted for 6 h. The reaction liquid was cooled to room temperature, 30 mL of water was added, the mixture was extracted with 50 mL of ethyl acetate, dried over anhydrous sodium sulfate, and concentrated under reduced pressure. The crude product was separated and purified with silica gel chromatography column (petroleum ether/ethyl acetate (v/v)=10:1) to afford a crude product 2 (0.81 g). The crude product 2 (810 mg) was dissolved in 15 mL of methanol, 0.3 g of 10% palladium on carbon was added, hydrogen replacement was performed three times, the mixture was reacted at room temperature under hydrogen atmosphere for 16 h. The reaction system was filtered, and the filtrate was concentrated under reduced pressure to afford methyl 4-((2S)-4-(tetrahydro-2H-pyran-4-yl)piperidin-2-yl)benzoate [28a (diastereomer 1)] (0.51 g). Methyl 4-((2S)-4-(tetrahydro-2H-pyran-4-yl)piperidin-2-yl)benzoate [28a (diastereomer 1)] (150 mg, 0.49 mmol) was dissolved in 3 mL of isopropyl acetate, maleic acid (57 mg, 0.49 mmol) was added, stirred at room temperature for 1 h, and then the reaction system was concentrated under reduced pressure to afford crude methyl 4-((2S)-4-(tetrahydro-2H-pyran-4-yl)piperidin-2-yl)benzoate [28a (diastereomer 1)] maleate (220 mg). Compound 28a (diastereomer 1) is one of the isomers of structure 28a-A or 28a-B.

Step 2: tert-butyl 5-methoxy-4-(((2S)-2-(4-(methoxycarbonyl)phenyl)-4-(tetrahydro-2H-pyran-4-yl)piperidin-1-yl)methyl)-7-methyl-1H-indole-1-carboxylate [28b (diastereomer 1)]

28b (diastereomer 1)

28b-A

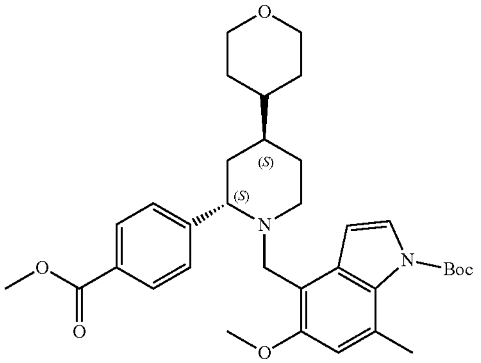

or

28b-B

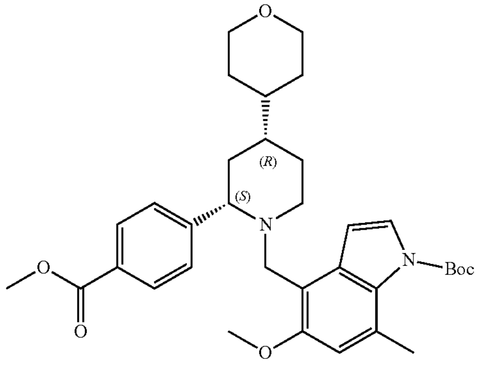

The above-mentioned crude methyl 4-((2S)-4-(tetrahydro-2H-pyran-4-yl)piperidin-2-yl)benzoate [28a (diastereomer 1)] maleate (220 mg) was dissolved in 5 mL of ethanol, tert-butyl 4-formyl-5-methoxy-7-methyl-1H-indole-1-carboxylate (0.11 g, 0.38 mmol) (see WO 2015009616 for the synthesis method) was added and 85 mg of $Ir(CO)_2acac$ was added, hydrogen replacement was performed three times, the mixture was heated to 80° C., and reacted for 19 h under the atmosphere of hydrogen balloon. The reaction liquid was concentrated under reduced pressure, 20 mL of water was added to the residue, the pH was adjusted to 8 with saturated sodium bicarbonate aqueous solution, extraction was performed with 50 mL of ethyl acetate, the organic phase was washed with 20 mL of water, dried over anhydrous sodium sulfate, and concentrated under reduced pressure. The crude product was separated and purified with silica gel chromatography column (petroleum ether/ethyl acetate (v/v)=10:1) to afford tert-butyl 5-methoxy-4-(((2S)-2-(4-(methoxycarbonyl)phenyl)-4-(tetrahydro-2H-pyran-4-yl)piperidin-1-yl)methyl)-7-methyl-1H-indole-1-carboxylate [28b (diastereomer 1)](110 mg, yield: 50%).

LCMS m/z=577.3 $[M+1]^+$

Compound 28b (diastereomer 1) is one of the isomers of structure 28b-A or 28b-B.

Step 3: 4-((2S)-1-((5-methoxy-7-methyl-1H-indol-4-yl)methyl)-4-(tetrahydro-2H-pyran-4-yl)piperidin-2-yl)benzoic acid [compound 28 (diastereomer 1)]trifluoroacetate Compound 28 (diastereomer 1)

28-A

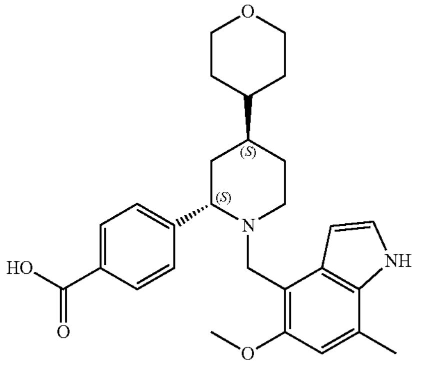

or

28-B

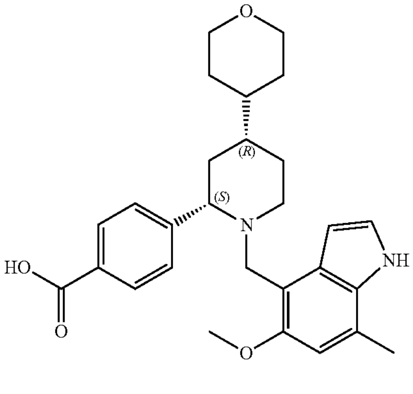

Tert-butyl 5-methoxy-4-(((2S)-2-(4-(methoxycarbonyl)phenyl)-4-(tetrahydro-2H-pyran-4-yl)piperidin-1-yl)methyl)-7-methyl-1H-indole-1-carboxylate [28b (diastereomer 1)] (0.11 g, 0.19 mmol) was dissolved in 5 mL of methanol, lithium hydroxide monohydrate (80 mg, 1.91 mmol) was added, and the mixture was heated to 80° C. and reacted for 4 h. The reaction liquid was cooled to room temperature, 5 mL of water was added, and the mixture was heated to 80° C. and reacted for 2 h. The reaction system was cooled to room temperature, the pH was adjusted to 7 with 2 mol/L aqueous hydrochloric acid solution, the mixture was concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved with methanol and dimethyl sulfoxide, and filtered with a 0.45 μm filter membrane, to prepare into a sample liquid. Mobile phase system: acetonitrile/water (containing 0.1% trifluoroacetic acid). Gradient elution method: gradient elution of 10% to 40% acetonitrile (elution time 10 min), and lyophilization was performed to afford 4-((2S)-1-((5-methoxy-7-methyl-1H-indol-4-yl)methyl)-4-(tetrahydro-2H-pyran-4-yl)piperidin-2-yl)benzoic acid [compound 28 (diastereomer 1)]trifluoroacetate (36 mg).

$^1H$ NMR (400 MHz, $CD_3OD$) δ 8.30-8.15 (m, 2H), 7.80-7.65 (m, 2H), 7.37-7.27 (m, 1H), 6.80-6.70 (m, 1H), 6.38-6.30 (m, 1H), 4.60-4.47 (m, 1H), 4.40-4.30 (m, 1H), 4.22-4.10 (m, 1H), 4.00-3.86 (m, 2H), 3.76 (s, 3H), 3.68-3.54 (m, 1H), 3.42-3.26 (m, 3H), 2.51 (s, 3H), 2.24-2.12 (m, 1H), 2.07-1.92 (m, 1H), 1.91-1.20 (m, 8H).

LCMS m/z=463.2 $[M+1]^+$

Compound 28 (diastereomer 1) is one of the isomers of structure 28-A or 28-B.

Example 29

4-((2S,4S)-1-((5-methoxy-7-methyl-1H-indol-4-yl)methyl)-4-(1H-pyrazol-1-yl)piperidin-2-yl)benzoic acid (compound 29) trifluoroacetate

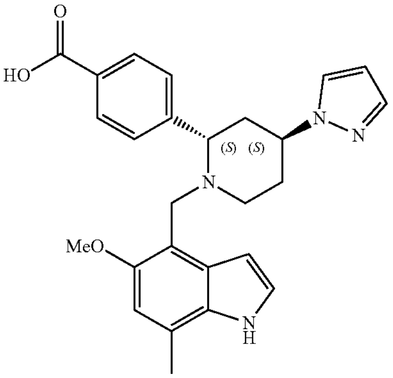

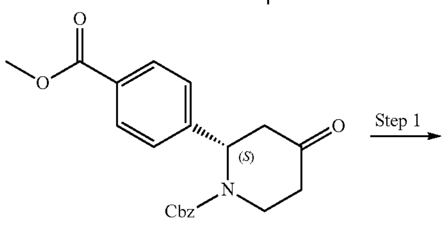

1a

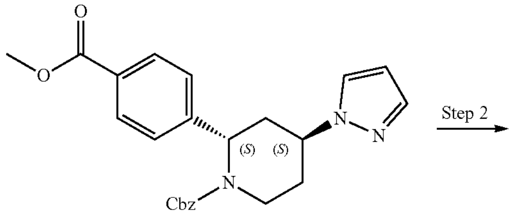

29a

-continued

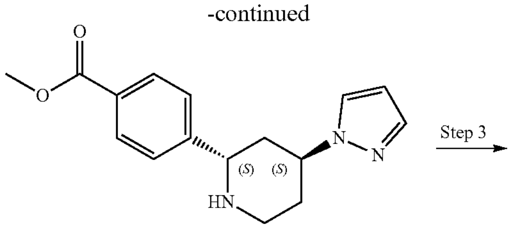

29b

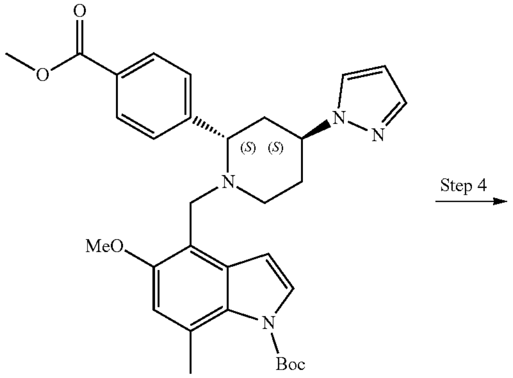

29c

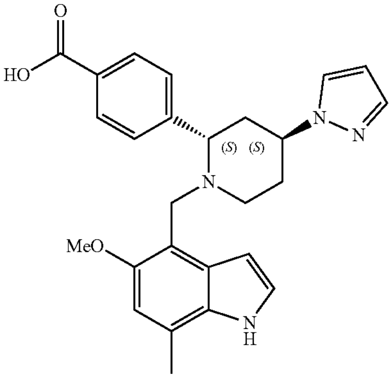

Compound 29

Step 1: benzyl (2S,4S)-2-(4-(methoxycarbonyl)phenyl)-4-(1H-pyrazol-1-yl)piperidine-1-carboxylate (29a)

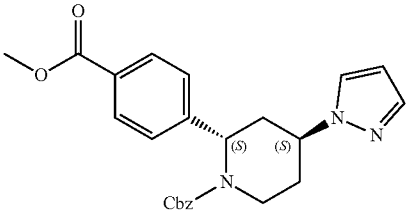

Benzyl (S)-2-(4-(methoxycarbonyl)phenyl)-4-oxopiperidine-1-carboxylate (1a) (3.03 g, 8.25 mmol) (see WO 2020016749 for the synthesis method) was dissolved in 30 mL of methanol, the mixture was cooled to 0° C., sodium borohydride (0.60 g, 15.86 mmol) was added at this temperature, and the mixture was returned to room temperature and reacted for 2 h. 60 mL of water was added to the reaction system, the mixture was extracted with 150 mL of ethyl acetate, the organic phase was dried over anhydrous sodium sulfate, and concentrated under reduced pressure. The residue was dissolved in 30 mL of dichloromethane, the mixture was cooled to 0° C., and triethylamine (2.49 g, 24.61 mmol) and methylsulfonyl chloride (1.23 g, 10.74 mmol) were added in sequence, and the mixture was reacted at room temperature for 12 h. 60 mL of water was added to the reaction liquid, the mixture was extracted with 150 mL of dichloromethane, dried over anhydrous sodium sulfate, and concentrated under reduced pressure. The crude product was separated and purified with silica gel chromatography column (petroleum ether/ethyl acetate (v/v)=10:1) to afford a crude product (2.76 g). The above-mentioned crude product (2.4 g) was dissolved in 5 mL of acetonitrile, solid cesium carbonate (5.24 g, 16.08 mmol) and pyrazole (0.73 g, 10.72 mmol) were added, and the mixture was heated to 80° C. and reacted for 16 h. The reaction liquid was cooled to room temperature and filtered, and the filtrate was concentrated under reduced pressure. The crude product was separated and purified with silica gel chromatography column (petroleum ether/ethyl acetate (v/v)=10:1) to afford benzyl (2S,4S)-2-(4-(methoxycarbonyl)phenyl)-4-(1H-pyrazol-1-yl)piperidine-1-carboxylate (29a) (1.9 g, yield: 42%).

LCMS m/z=420.1 $[M+1]^+$

Step 2: methyl 4-((2S,4S)-4-(1H-pyrazol-1-yl)piperidin-2-yl)benzoate (29b)

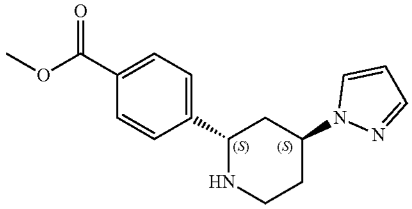

Benzyl (2S,4S)-2-(4-(methoxycarbonyl)phenyl)-4-(1H-pyrazol-1-yl)piperidine-1-carboxylate (29a) (1.9 g, 4.53 mmol) was dissolved in 20 mL of methanol, 0.1 g of 10% palladium on carbon was added, hydrogen replacement was performed three times, and the mixture was reacted at room temperature for 16 h under the atmosphere of hydrogen balloon. The reaction system was filtered, and the filtrate was concentrated under reduced pressure to afford crude methyl 4-((2S,4S)-4-(1H-pyrazol-1-yl)piperidin-2-yl)benzoate (29b) (0.7 g).

Step 3: tert-butyl 5-methoxy-4-(((2S,4S)-2-(4-(methoxycarbonyl)phenyl)-4-(1H-pyrazol-1-yl)piperidin-1-yl)methyl)-7-methyl-1H-indole-1-carboxylate (29c)

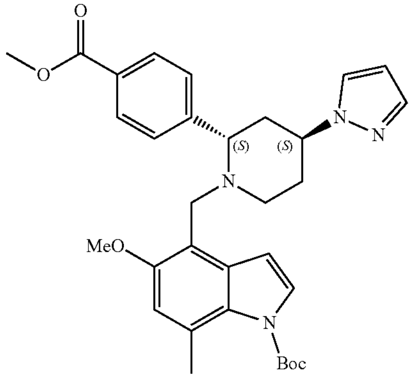

The above-mentioned crude methyl 4-((2S,4S)-4-(1H-pyrazol-1-yl)piperidin-2-yl)benzoate (29b) (0.7 g) was dissolved in 20 mL of N,N-dimethylacetamide, and tert-butyl 4-formyl-5-methoxy-7-methyl-1H-indole-1-carboxylate (1.06 g, 3.66 mmol) (see WO 2015009616 for the synthesis method) was added, the mixture was stirred at room temperature for 2 h, then sodium triacetoxyborohydride (1.56 g, 7.36 mmol) was added and the mixture was stirred at room temperature for 19 h. 5 mL of water was added to the reaction liquid, the pH was adjusted to 9 with saturated aqueous sodium bicarbonate solution, extraction was performed with 10 mL of ethyl acetate, the organic phase was washed with 5 mL of water, dried over anhydrous sodium sulfate, and concentrated under reduced pressure. The crude product was separated and purified with silica gel chromatography column (petroleum ether/ethyl acetate (v/v)=10:1) to afford tert-butyl 5-methoxy-4-(((2S,4S)-2-(4-(methoxycarbonyl)phenyl)-4-(1H-pyrazol-1-yl)piperidin-1-yl)methyl)-7-methyl-1H-indole-1-carboxylate (29c) (0.45 g, two-step yield from compound 29a: 18%).

LCMS m/z=559.2 $[M+1]^+$

Step 4: 4-((2S,4S)-1-((5-methoxy-7-methyl-1H-indol-4-yl)methyl)-4-(1H-pyrazol-1-yl)piperidin-2-yl)benzoic acid (compound 29) trifluoroacetate

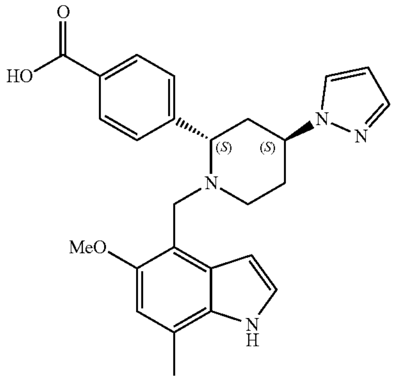

Tert-butyl 5-methoxy-4-(((2S,4S)-2-(4-(methoxycarbonyl)phenyl)-4-(1H-pyrazol-1-yl)piperidin-1-yl)methyl)-7-methyl-1H-indole-1-carboxylate (29c) (0.45 g, 0.81 mmol) was dissolved in 8 mL of methanol, lithium hydroxide monohydrate (0.34 g, 8.1 mmol) was added, and the mixture was heated to 80° C. and reacted for 4 h. The reaction system was cooled to room temperature, 3 mL of water was added, and the mixture was heated to 80° C. and reacted for 2 h. The reaction system was cooled to room temperature, the pH was adjusted to 7 with 2 mol/L aqueous hydrochloric acid solution, the mixture was concentrated under reduced pressure, and the crude product was subjected to Pre-HPLC (instrument and preparative column: using SHIMADZU LC-20AP preparative liquid phase chromatographic instrument, preparative column model: Phenomenex C18). Preparation method: the crude product was dissolved in acetonitrile and water, and filtered with a 0.45 μm filter membrane to prepare into a sample liquid. Mobile phase system: acetonitrile/water (containing 0.1% trifluoroacetic acid). Gradient elution method: gradient elution of 18% to 48% acetonitrile (elution time 10 min), and lyophilization was performed to afford 4-((2S,4S)-1-((5-methoxy-7-methyl-1H-indol-4-yl)methyl)-4-(1H-pyrazol-1-yl)piperidin-2-yl)benzoic acid (compound 29) trifluoroacetate (0.25 g).

$^1H$ NMR (400 MHz, $CD_3OD$) δ 8.28-8.18 (m, 2H), 7.85-7.64 (m, 4H), 7.37-7.28 (m, 1H), 6.78 (s, 1H), 6.48-6.40 (m, 1H), 6.37-6.25 (m, 1H), 5.20-5.07 (m, 1H), 4.80-4.70 (m, 1H), 4.44-4.22 (m, 2H), 3.90-3.66 (m, 4H), 3.62-3.45 (m, 1H), 2.75-2.62 (m, 2H), 2.57-2.37 (m, 5H).

LCMS m/z=445.3 $[M+1]^+$

Example 30

4-[(2S)-4-cyclopropyl-4-hydroxy-1-[(5-methoxy-7-methyl-1H-indol-4-yl)methyl]piperidin-2-yl]benzoic acid [compound 30 (diastereomer 1)]

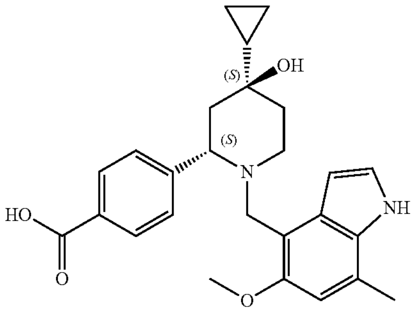

30-A or

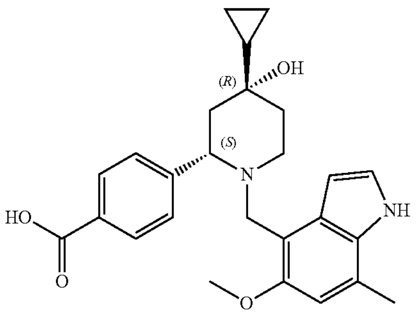

30-B

Compound 30 (diastereomer 1)

-continued
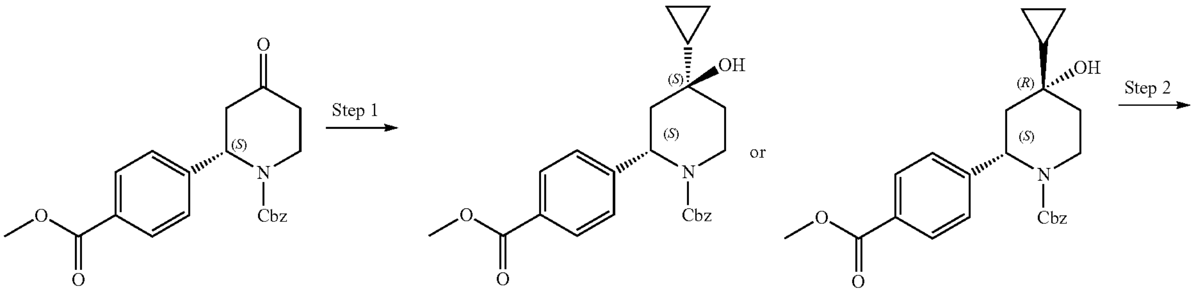
1a 30a-A 30a-B
30a (diastereomer 1)
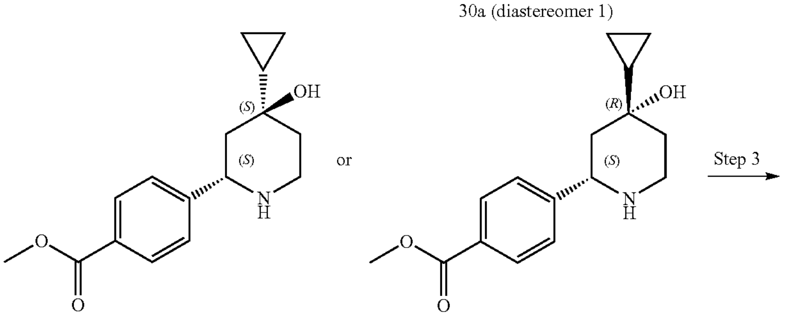
30b-A 30b-B
30b (diastereomer 1)
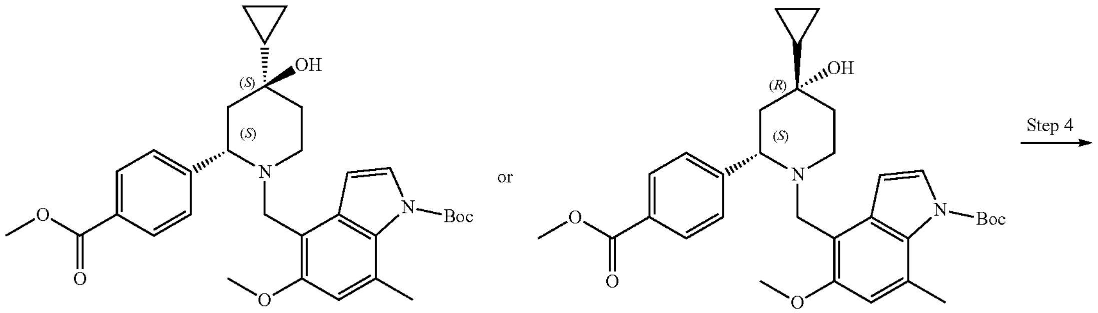
30c-A 30c-B
30c (diastereomer 1)
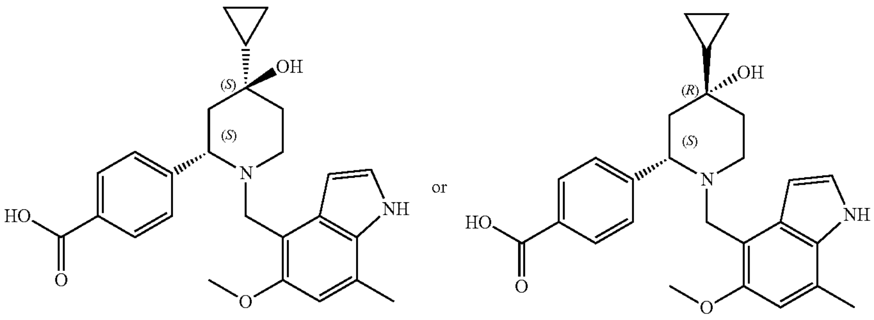
30-A 30-B
Compound 30 (diastereomer 1)

Step 1: benzyl (2S)-4-cyclopropyl-4-hydroxy-2-(4-(methoxycarbonyl)phenyl) piperidine-1-carboxylate [30a (diastereomer 1)]

30a (diastereomer 1)

30a-A

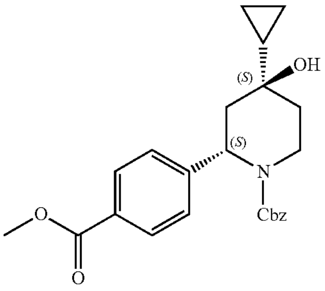

or

30a-B

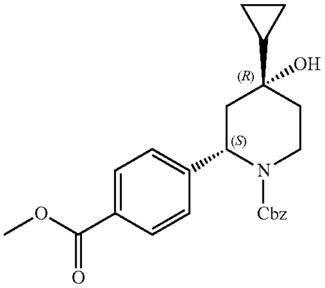

A solution of 1 mol/L cyclopropylmagnesium bromide in tetrahydrofuran (81.6 mL, 81.6 mmol) was added to a 250 mL three-necked flask, the mixture was cooled to 0° C. under nitrogen protection, and benzyl (S)-2-(4-(methoxycarbonyl)phenyl)-4-oxopiperidine-1-carboxylate (15.0 g, 40.8 mmol) (1a) (see WO 2020016749 for the synthesis method) was dissolved in 100 mL of dry tetrahydrofuran, and slowly added dropwise into the above solution of cyclopropylmagnesium bromide in tetrahydrofuran, stirring was continued at 0° C. for 30 min, and then the mixture was warmed to room temperature and reacted for 4 h. The reaction system was cooled to 0° C., 50 mL of saturated aqueous ammonium chloride solution was slowly added dropwise, 200 mL of ethyl acetate was added, the liquid separation was conducted, and the organic layer was washed with saturated aqueous sodium chloride solution (30 mL×2), dried over anhydrous sodium sulfate and concentrated under reduced pressure. The crude product was separated and purified with silica gel column chromatography (ethyl acetate/petroleum ether (v/v)=5:95-40:60) to afford benzyl (2S)-4-cyclopropyl-4-hydroxy-2-(4-(methoxycarbonyl)phenyl)piperidine-1-carboxylate [30a (diastereomer 1)] (1.15 g, yield: 7%) and its diastereomer benzyl (2S)-4-cyclopropyl-4-hydroxy-2-(4-(methoxycarbonyl)phenyl)piperidine-1-carboxylate [30a (diastereomer 2)] (2.45 g, yield: 15%).

Nuclear Magnetic Resonances Spectrum of 30a (Diastereomer 1):

$^1$H NMR (400 MHz, $CDCl_3$) δ 8.05-7.90 (m, 2H), 7.42-7.06 (m, 7H), 5.40-5.28 (m, 1H), 5.16-5.00 (m, 2H), 4.30-4.15 (m, 1H), 3.91 (s, 3H), 3.40-3.22 (m, 1H), 2.20-1.98 (m, 2H), 1.80-1.62 (m, 2H), 0.75-0.56 (m, 1H), 0.45-0.10 (m, 4H).

Nuclear Magnetic Resonances Spectrum of the Diastereomer [30a (Diastereomer 2)] of 30a (Diastereomer 1):

$^1$H NMR (400 MHz, $CDCl_3$) δ 8.03-7.90 (m, 2H), 7.42-7.15 (m, 7H), 5.60-5.45 (m, 1H), 5.14 (s, 2H), 4.30-4.11 (m, 1H), 3.88 (s, 3H), 3.42-3.26 (m, 1H), 2.38-2.26 (m, 1H), 2.15-2.00 (m, 1H), 1.68-1.42 (m, 2H), 0.95-0.75 (m, 1H), 0.43-0.23 (m, 4H).

Compound 30a (diastereomer 1) is one of the isomers of structure 30a-A or 30a-B.

Step 2: methyl 4-[(2S)-4-cyclopropyl-4-hydroxypiperidin-2-yl]benzoate [30b (diastereomer 1)]

30b (diastereomer 1)

30b-A

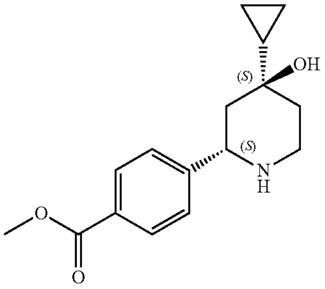

or

30b-B

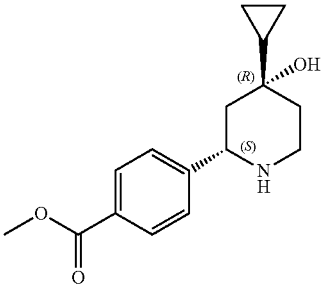

Benzyl (2S)-4-cyclopropyl-4-hydroxy-2-(4-(methoxycarbonyl)phenyl) piperidine-1-carboxylate [30a (diastereomer 1)] (0.370 g, 0.903 mmol) was dissolved in 5 mL of methanol, 100 mg of 10% palladium on carbon was added, hydrogen replacement was performed three times, and the mixture was reacted under the atmosphere of hydrogen balloon for 10 min. The reaction liquid was filtered through diatomaceous earth pad, and the filtrate was concentrated under reduced pressure to afford crude methyl 4-[(2S)-4-cyclopropyl-4-hydroxypiperidin-2-yl]benzoate [30b (diastereomer 1)] (0.24 g).

LCMS m/z=276.1 $[M+1]^+$

Compound 30b (diastereomer 1) is one of the isomers of structure 30b-A or 30b-B.

Step 3: tert-butyl 4-{[(2S)-4-cyclopropyl-4-hydroxy-2-(4-(methoxycarbonyl) phenyl)piperidin-1-yl]methyl}-5-methoxy-7-methyl-1H-indole-1-carboxylate [30c (diastereomer 1)]

30c (diastereomer 1)

30c-A

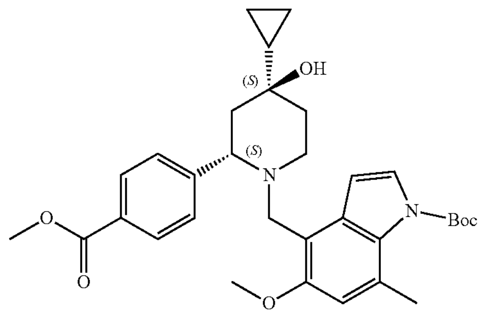

or

30c-B

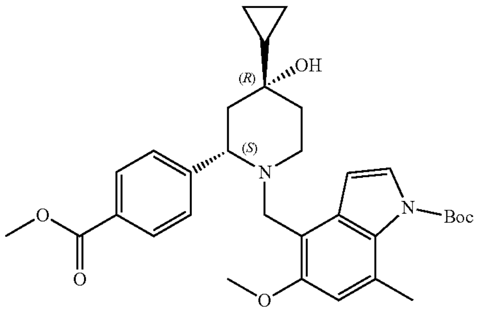

The above-mentioned crude methyl 4-[(2S)-4-cyclopropyl-4-hydroxypiperidin-2-yl]benzoate [30b (diastereomer 1)] (0.26 g) was dissolved in 2 mL of isopropyl acetate, maleic acid (0.11 g, 0.95 mmol) was added, and stirred at room temperature for 1 h. The reaction liquid was concentrated under reduced pressure, and tert-butyl 4-formyl-5-methoxy-7-methyl-1H-indole-1-carboxylate (see WO 2015009616 for the synthesis method) (0.290 g, 1.00 mmol) was added to the residue, 33 mg of $Ir(CO)_2acac$ was added, hydrogen replacement was performed three times, and the mixture was heated to 80° C. and reacted for 16 h under the atmosphere of hydrogen balloon. The reaction liquid was cooled to room temperature and concentrated under reduced pressure. The residue was dissolved in 20 mL of dichloromethane and washed with 10 mL of saturated aqueous sodium bicarbonate solution, and the liquid separation was conducted. The organic phase was dried over anhydrous sodium sulfate, concentrated under reduced pressure, and the crude product was separated and purified with silica gel column chromatography (petroleum ether/ethyl acetate (v/v) =1:0-7:3) to afford tert-butyl 4-{[(2S)-4-cyclopropyl-4-hydroxy-2-(4-(methoxycarbonyl)phenyl)piperidin-1-yl] methyl}-5-methoxy-7-methyl-1H-indole-1-carboxylate [30c (diastereomer 1)] (0.09 g, yield: 16%).

LCMS m/z=549.3 $[M+1]^+$

Compound 30c (diastereomer 1) is one of the isomers of structure 30c-A or 30c-B.

Step 4: 4-[(2S)-4-cyclopropyl-4-hydroxy-1-[(5-methoxy-7-methyl-1H-indol-4-yl)methyl]piperidin-2-yl]benzoic acid [compound 30 (diastereomer 1)]

Compound 30 (diastereomer 1)

30-A

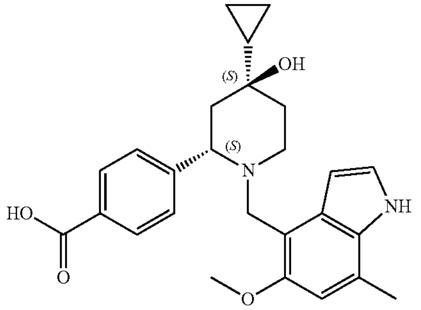

or

30-B

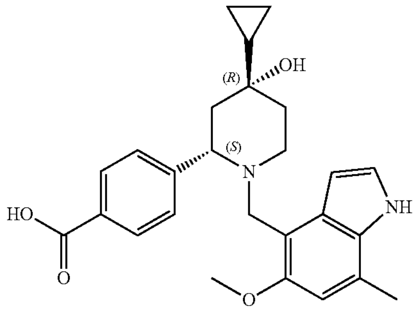

Tert-butyl 4-{[(2S)-4-cyclopropyl-4-hydroxy-2-(4-(methoxycarbonyl) phenyl)piperidin-1-yl]methyl}-5-methoxy-7-methyl-1H-indole-1-carboxylate [30c (diastereomer 1)] (82 mg, 0.15 mmol) was dissolved in 5 mL of methanol, solid potassium carbonate (100 mg, 0.724 mmol) was added, and the mixture was heated to 80° C. and reacted for 3 hours. The reaction liquid was cooled to 60° C., 3 mL of water and lithium hydroxide monohydrate (63 mg, 1.5 mmol) were added, and the reaction was continued at 60° C. for 1 h. The reaction system was cooled to room temperature and filtered, the filter residue was washed with 10 ml of methanol, the filtrate was combined and cooled to 0° C., the pH of the filtrate was adjusted to 8 with 5 mol/L aqueous hydrochloric acid solution, and the resulting solution was subjected to Pre-HPLC (instrument and preparative column: using SHIMADZU LC-20AP preparative liquid phase chromatographic instrument, preparative column model: Phenomenex C18). Preparation method: the crude product was dissolved in acetonitrile and water, and filtered with a 0.45 μm filter membrane to prepare into a sample liquid. Mobile phase system: acetonitrile/water (containing 10 mmol/L ammonium bicarbonate). Gradient elution method: gradient elution of 5% to 35% acetonitrile (elution time 10 min), affording 4-[(2S)-4-cyclopropyl-4-hydroxy-1-[(5-methoxy-7-methyl-1H-indol-4-yl)methyl]piperidin-2-yl]benzoic acid [compound 30 (diastereomer 1)] (30 mg, yield: 46%).

$^1H$ NMR (400 MHz, DMSO-$d_6$) δ 10.79 (s, 1H), 8.00-7.91 (m, 2H), 7.70-7.55 (m, 2H), 7.28-7.20 (m, 1H), 6.65 (s, 1H), 6.50-6.42 (m, 1H), 3.90-3.76 (m, 1H), 3.70 (s, 3H), 3.62-3.46 (m, 2H), 3.28-3.14 (m, 1H), 2.56-2.30 (m, 5H), 1.65-1.17 (m, 4H), 0.79-0.65 (m, 1H), 0.35-0.21 (m, 2H), 0.18-0.05 (m, 2H).

LCMS m/z=435.3 $[M+1]^+$

Compound 30 (diastereomer 1) is one of the isomers of structure 30-A or 30-B.

Example 31
4-[(2S)-4-cyclopropyl-4-hydroxy-1-[(5-methoxy-7-methyl-1H-indol-4-yl)methyl]piperidin-2-yl]benzoic acid [compound 31 (diastereomer 2)]
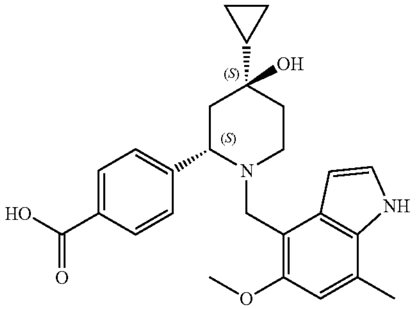
or
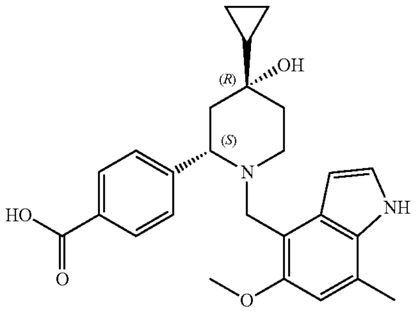
30-A
30-B
Compound 31 (diastereomer 2)
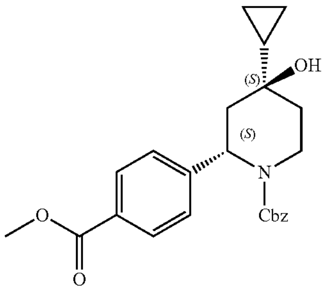
or
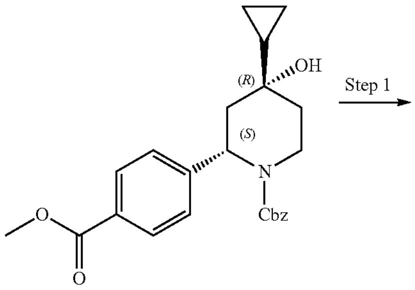
30a-A
30a-B
30a (diastereomer 2)
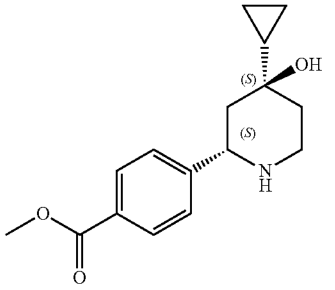
or
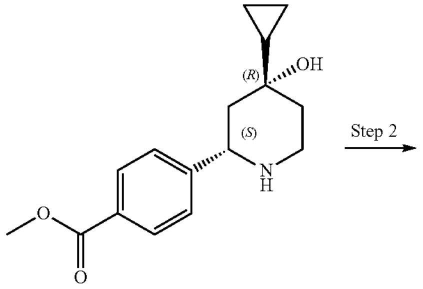
30b-A
30b-B
31a (diastereomer 2)
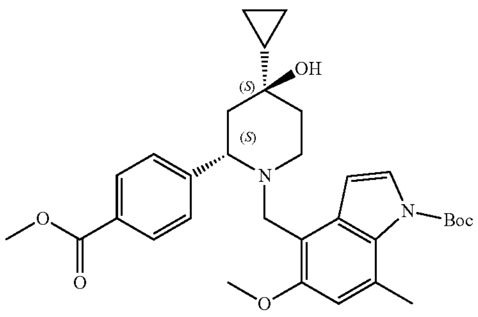
or
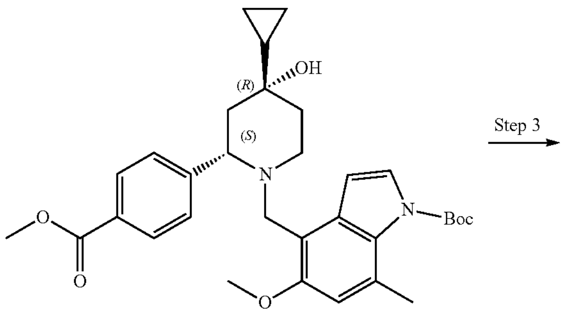
30c-A
30c-B
31b (diastereomer 2)

-continued

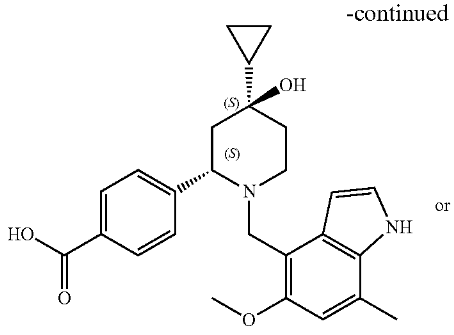

30-A or

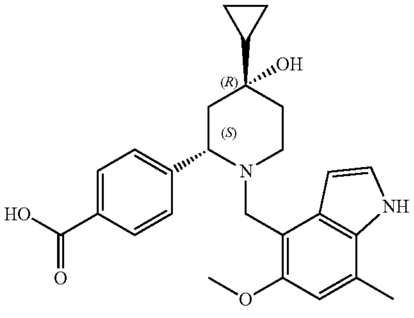

30-B

Compound 31 (diastereomer 2)

Step 1: methyl 4-[(2S)-4-cyclopropyl-4-hydroxypiperidin-2-yl]benzoate [31a (diastereomer 2)]

31a (diastereomer 2)

30b-A

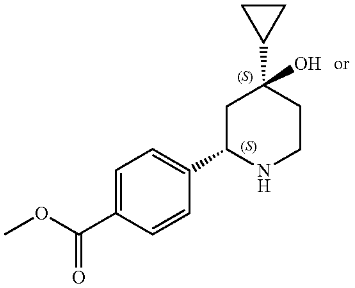

or

30b-B

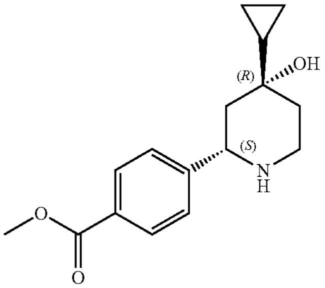

Benzyl (2S)-4-cyclopropyl-4-hydroxy-2-(4-(methoxycarbonyl)phenyl) piperidine-1-carboxylate [30a (diastereomer 2)] (1.40 g, 3.42 mmol) was dissolved in 15 mL of methanol, 400 mg of 10% palladium on carbon was added, hydrogen replacement was performed three times, and the mixture was reacted under the atmosphere of hydrogen balloon for 20 min. The reaction system was filtered through diatomaceous earth pad, and the filtrate was concentrated under reduced pressure to afford crude methyl 4-[(2S)-4-cyclopropyl-4-hydroxypiperidin-2-yl]benzoate [31a (diastereomer 2)] (0.94 g).

LCMS m/z=276.1 $[M+1]^+$

Compound 31a (diastereomer 2) is one of the isomers of structure 30b-A or 30b-B.

Step 2: tert-butyl 4-{[(2S)-4-cyclopropyl-4-hydroxy-2-(4-(methoxycarbonyl) phenyl)piperidin-1-yl]methyl}-5-methoxy-7-methyl-1H-indole-1-carboxylate [31b (diastereomer 2)]

31b (diastereomer 2)

30c-A

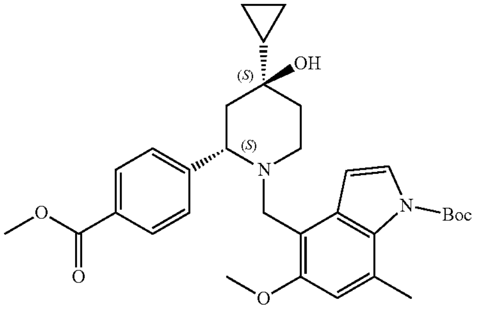

or

30c-B

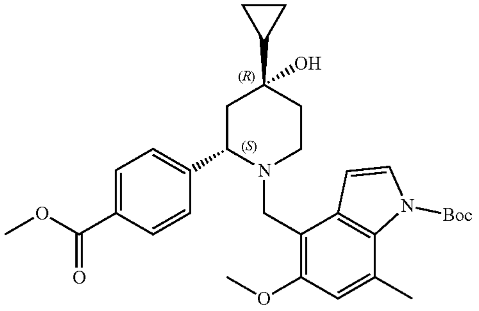

The above-mentioned crude methyl 4-[(2S)-4-cyclopropyl-4-hydroxypiperidin-2-yl]benzoate [31a (diastereomer 2)] (0.22 g) was dissolved in 2 mL of isopropyl acetate, maleic acid (0.093 g, 0.80 mmol) was added, and stirred at room temperature for 1 h. The reaction liquid was concentrated under reduced pressure, and tert-butyl 4-formyl-5-methoxy-7-methyl-1H-indole-1-carboxylate (see WO 2015009616 for the synthesis method) (0.240 g, 0.83 mmol) was added to the residue, 28 mg of $Ir(CO)_2acac$ was added, hydrogen replacement was performed three times, and the mixture was heated to 80° C. and reacted for 16 h under the atmosphere of hydrogen balloon. The reaction liquid was cooled to room temperature and concentrated under reduced pressure. The residue was dissolved in 20 mL of dichloromethane and washed with 10 mL of saturated aqueous sodium bicarbonate solution, and the liquid separation was conducted. The organic phase was dried over anhydrous sodium sulfate, concentrated under reduced pressure, and the crude product was separated and purified with silica gel column chromatography (petroleum ether/ethyl acetate (v/v) =1:0-7:3) to afford tert-butyl 4-{[(2S)-4-cyclopropyl-4-hydroxy-2-(4-(methoxycarbonyl) phenyl)piperidin-1-yl] methyl}-5-methoxy-7-methyl-1H-indole-1-carboxylate [31b (diastereomer 2)] (0.37 g, yield: 81%).

LCMS m/z=549.6 $[M+1]^+$

Compound 31b (diastereomer 2) is one of the isomers of structure 30c-A or 30c-B.

Step 3: 4-[(2S)-4-cyclopropyl-4-hydroxy-1-[(5-methoxy-7-methyl-1H-indol-4-yl)methyl]piperidin-2-yl]benzoic acid [compound 31 (diastereomer 2)]

Compound 31 (diastereomer 2)

30-A

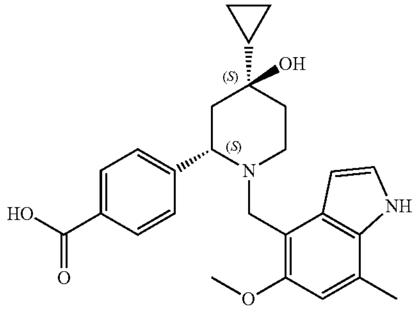

or

30-B

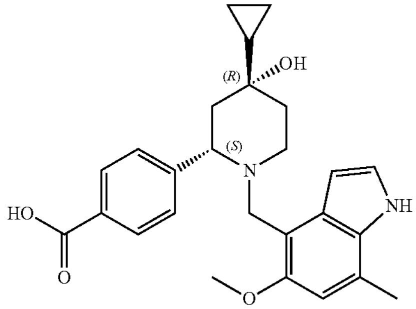

Tert-butyl 4-{[(2S)-4-cyclopropyl-4-hydroxy-2-(4-(methoxycarbonyl) phenyl)piperidin-1-yl]methyl}-5-methoxy-7-methyl-1H-indole-1-carboxylate [31b (diastereomer 2)] (200 mg, 0.36 mmol) was dissolved in 10 mL of methanol, solid potassium carbonate (250 mg, 1.81 mmol) was added, and the mixture was heated to 80° C. and reacted for 3 hours. The reaction liquid was cooled to 60° C., 5 mL of water and lithium hydroxide monohydrate (150 mg, 3.57 mmol) were added, and the reaction was continued at 60° C. for 1 h. The reaction system was cooled to room temperature and filtered, the filter residue was washed with 10 mL of methanol, the filtrate was combined and cooled to 0° C., the pH of the filtrate was adjusted to 8 with 5 mol/L aqueous hydrochloric acid solution, and the resulting solution was subjected to Pre-HPLC (instrument and preparative column: using SHIMADZU LC-20AP preparative liquid phase chromatographic instrument, preparative column model: Phenomenex C18). Preparation method: the crude product was dissolved in acetonitrile and water, and filtered with a 0.45 μm filter membrane to prepare into a sample liquid. Mobile phase system: acetonitrile/water (containing 10 mmol/L ammonium bicarbonate). Gradient elution method: gradient elution of 5% to 35% acetonitrile (elution time 10 min), affording 4-[(2S)-4-cyclopropyl-4-hydroxy-1-[(5-methoxy-7-methyl-1H-indol-4-yl)methyl]piperidin-2-yl]benzoic acid [compound 31 (diastereomer 2)] (84 mg, yield: 54%).

$^1H$ NMR (400 MHz, DMSO-$d_6$) δ 10.83 (s, 1H), 7.95-7.86 (m, 2H), 7.56-7.44 (m, 2H), 7.28-7.20 (m, 1H), 6.64 (s, 1H), 6.52-6.44 (m, 1H), 3.71 (s, 3H), 3.63-3.52 (m, 1H), 3.47-3.37 (m, 1H), 3.27-3.16 (m, 1H), 2.74-2.61 (m, 1H), 2.42 (s, 3H), 2.34-2.20 (m, 1H), 1.80-1.32 (m, 5H), 0.48-0.16 (m, 4H).

LCMS m/z=435.3 $[M+1]^+$

Example 32

4-[(2S,4R)-4-cyclopropyl-1-[(5-methoxy-7-methyl-1H-indol-4-yl)methyl]piperidin-2-yl]-2-fluorobenzoic acid (compound 32)

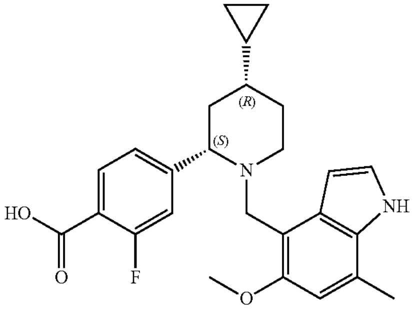

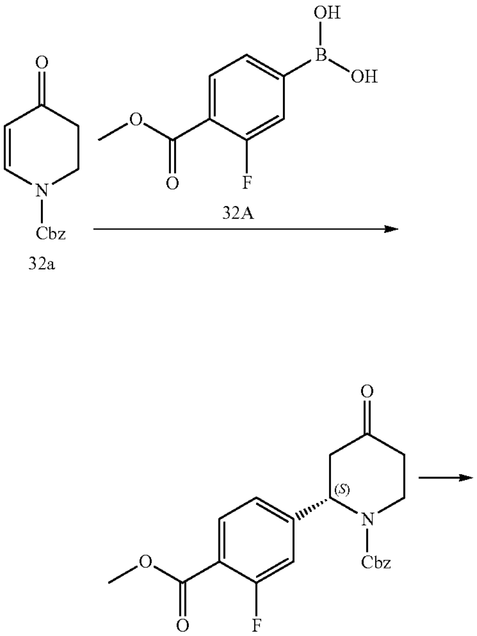

32a

32A

32b

-continued

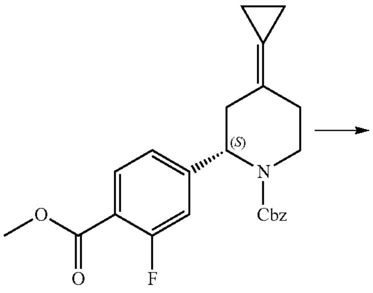

32c

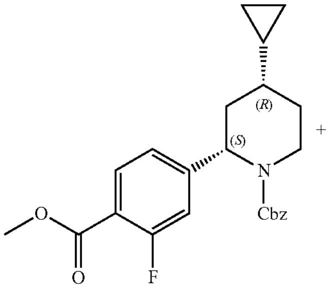

32d-1

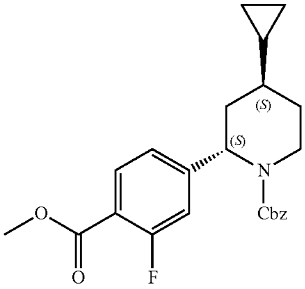

32d-2

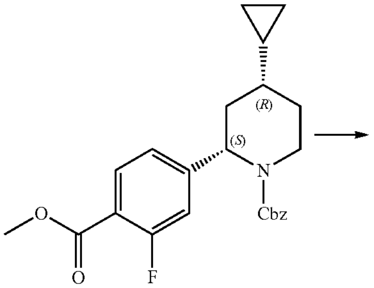

32d-1

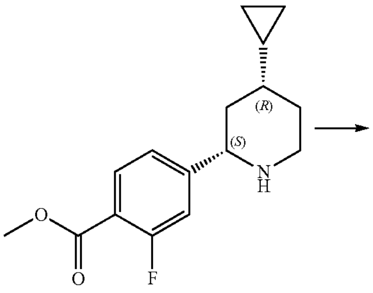

32e

-continued

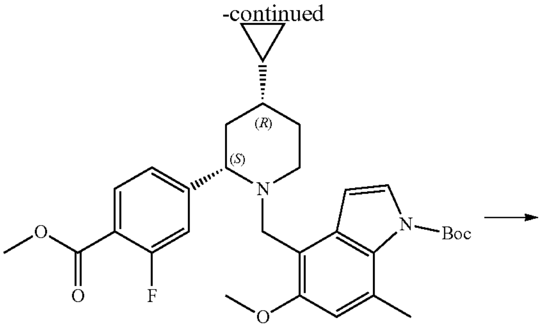

32f

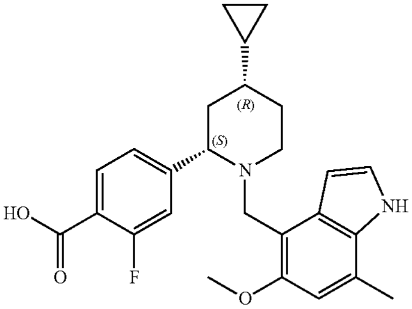

Compound 32

Step 1: benzyl (2S)-2-(3-fluoro-4-(methoxycarbonyl)phenyl)-4-oxopiperidine-1-carboxylate (32b)

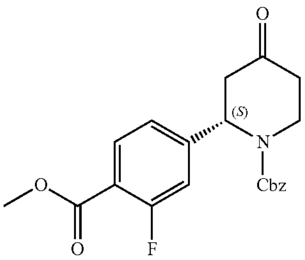

32a (12.0 g, 51.89 mmol) was dissolved in 80 mL of 2-methylbutanol, and 10 mL of water, 32A (30.8 g, 155.6 mmol), TEA (15.8 g, 156.1 mmol) and (S)-binaphthyl(3,5-xylyl)phosphine (CAS: 135139-00-3) (2.67 g, 3.63 mmol) were added in sequence, nitrogen replacement was performed three times, and bis(ethylene)rhodium acetylacetonate (CAS: 12082-47-2) (0.54 g, 2.09 mmol) was added, nitrogen replacement was performed three times, and the mixture was reacted at 100° C. for 16 h. The reaction system was cooled to room temperature and filtered through diatomaceous earth pad, the filter cake was washed with 100 mL of ethyl acetate, the filtrate was concentrated under reduced pressure, the crude product was dissolved in 200 mL of ethyl acetate, the mixture was washed with saturated aqueous sodium bicarbonate solution (50 mL×3) and then washed with 50 mL of saturated aqueous sodium chloride solution, dried over anhydrous sodium sulfate and concentrated under reduced pressure, and the crude product was separated and purified with silica gel column chromatography (ethyl acetate:petroleum ether (v/v)=1:9-1:3) to afford 32b (5.0 g, yield: 25%).

$^1$H NMR (400 MHz, $CDCl_3$) δ 7.89 (t, 1H), 7.46-7.22 (m, 5H), 7.12-6.96 (m, 2H), 5.92-5.60 (m, 1H), 5.28-5.12 (m, 2H), 4.40-4.24 (m, 1H), 3.92 (s, 3H), 3.35-3.19 (m, 1H), 2.99-2.84 (m, 2H), 2.64-2.48 (m, 1H), 2.46-2.32 (m, 1H).

LCMS m/z=386.4 [M+1]$^+$

Step 2: benzyl (2S)-4-[cyclopropylidene]-2-(3-fluoro-4-(methoxycarbonyl) phenyl)piperidine-1-carboxylate (32c)

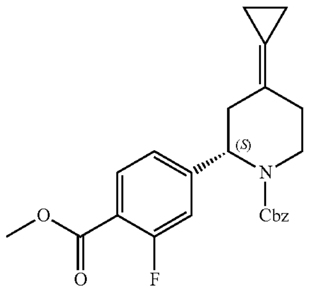

(3-bromopropyl)triphenylphosphonium bromide (3.90 g, 8.40 mmol) was suspended in 30 mL of tetrahydrofuran, the mixture was cooled to 0° C. under nitrogen protection, and potassium tert-butoxide (1.89 g, 16.84 mmol) was slowly added, stirring was continued at 0° C. for 1 h, 32b (2.70 g, 7.01 mmol) was slowly added, and the mixture was reacted at room temperature for 16 h. The reaction system was cooled to 0° C., 10 mL of saturated aqueous ammonium chloride solution was slowly added dropwise, 100 mL of ethyl acetate and 100 mL of water were added, the liquid separation was conducted, the organic phase was washed with 100 mL of saturated aqueous sodium chloride solution, dried over anhydrous sodium sulfate and concentrated under reduced pressure, and the crude product was separated and purified with silica gel column chromatography (petroleum ether:ethyl acetate (v/v)=1:0-9:1) to afford 32c (0.7 g, yield: 24%).

$^1$H NMR (400 MHz, $CDCl_3$) δ 7.83 (t, 1H), 7.41-7.28 (m, 5H), 7.13-7.00 (m, 2H), 5.68-5.51 (m, 1H), 5.34-5.14 (m, 2H), 4.27-4.10 (m, 1H), 3.91 (s, 3H), 3.08-2.95 (m, 1H), 2.87-2.65 (m, 2H), 2.46-2.29 (m, 2H), 1.14-0.96 (m, 4H).

LCMS m/z=410.1 [M+1]$^+$

Step 3: benzyl (2S,4R)-4-cyclopropyl-2-(3-fluoro-4-(methoxycarbonyl) phenyl)piperidine-1-carboxylate (32d-1) and benzyl (2S,4S)-4-cyclopropyl-2-(3-fluoro-4-(methoxycarbonyl)phenyl)piperidine-1-carboxylate (32d-2)

32d-1

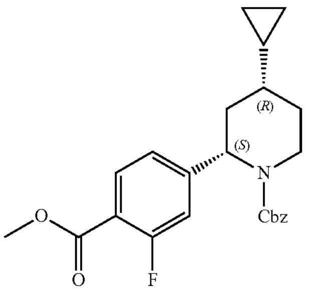

-continued 32d-2

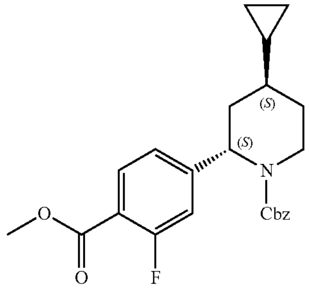

32c (0.7 g, 1.71 mmol) was dissolved in 10 mL of DMF, benzenesulfonyl hydrazide (1.47 g, 8.54 mmol) was added, nitrogen replacement was performed three times, and the mixture was reacted at 100° C. for 16 h. The reaction system was cooled to room temperature, 80 mL of water was added, the mixture was extracted with n-hexane (50 mL×3), the organic phases were combined, the organic phase was washed with saturated aqueous sodium chloride solution (50 mL×2), dried over anhydrous sodium sulfate and concentrated under reduced pressure, and the crude product was separated and purified with silica gel column chromatography (petroleum ether:ethyl acetate (v/v)=1:0-9:1) to afford 32d-1 (0.33 g, yield: 47%) and 32d-2 (0.17 g, yield: 24%). Rf value of 32d-1:0.3 (developing agent: ethyl acetate/petroleum ether (v/v)=1:9)

$^1$H NMR (400 MHz, $CDCl_3$) δ 7.82 (t, 1H), 7.30-7.08 (m, 5H), 7.07-6.90 (m, 2H), 5.10-4.94 (m, 3H), 4.06-3.96 (m, 1H), 3.88 (s, 3H), 3.35-3.22 (m, 1H), 2.14-2.03 (m, 1H), 1.98-1.76 (m, 2H), 1.52-1.41 (m, 1H), 0.93-0.79 (m, 1H), 0.42-0.19 (m, 3H), 0.07--0.05 (m, 2H).

LCMS m/z=412.5 [M+1]$^+$

Rf value of 32d-2: 0.4 (developing agent: ethyl acetate/petroleum ether (v/v)=1:9)

$^1$H NMR (400 MHz, $CDCl_3$) δ 7.88 (t, 1H), 7.49-7.21 (m, 5H), 7.05-6.87 (m, 2H), 5.70-5.40 (m, 1H), 5.19 (s, 2H), 4.35-4.10 (m, 1H), 3.92 (s, 3H), 2.83-2.65 (m, 1H), 2.50-2.30 (m, 1H), 1.85-1.55 (m, 2H), 1.45-1.22 (m, 1H), 0.70-0.33 (m, 4H), 0.12--0.06 (m, 2H).

LCMS m/z=412.5 [M+1]$^+$

Step 4: methyl 4-[(2S,4R)-4-cyclopropylpiperidin-2-yl]-2-fluorobenzoate (32e)

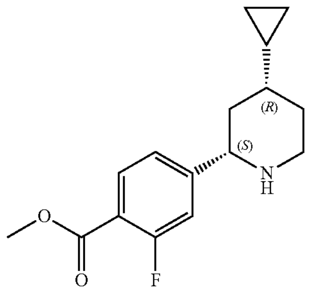

32d-1 (0.33 g, 0.8 mmol) was dissolved in 5 mL of acetonitrile, the mixture was cooled to 0° C. under nitrogen protection, TMSI (0.48 g, 2.39 mmol) was slowly added dropwise, and the reaction was continued at 0° C. for 10 min. 1 mL of anhydrous methanol was slowly added dropwise into the reaction system, saturated aqueous sodium bicarbonate solution was slowly added dropwise to adjust the pH to 8, the mixture was extracted with dichloromethane (20 mL×2), the organic phases were combined, and the organic phase was washed with 10 mL of saturated aqueous sodium chloride solution, dried over anhydrous sodium sulfate and concentrated under reduced pressure. The crude product was separated and purified with silica gel column chromatography (first eluted with petroleum ether:ethyl acetate (v/v)=9:1, and then eluted with methanol dichloromethane (v/v)=1:20) to afford 32e (0.14 g, yield: 63%).

LCMS m/z=278.4 [M+1]$^+$

Step 5: tert-butyl 4-{[(2S,4R)-4-cyclopropyl-2-(3-fluoro-4-(methoxycarbonyl) phenyl)piperidin-1-yl] methyl}-5-methoxy-7-methyl-1H-indole-1-carboxylate (32f)

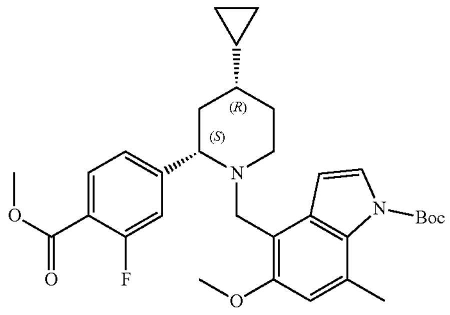

32e (0.14 g, 0.5 mmol) was dissolved in 2 mL of isopropyl acetate, maleic acid (0.058 g, 0.5 mmol) was added and stirred at room temperature for 1 h, then the reaction liquid was concentrated under reduced pressure, and 10 mL of absolute ethanol, tert-butyl 4-formyl-5-methoxy-7-methyl-1H-indole-1-carboxylate (see WO 2015009616 for synthesis method) (0.15 g, 0.52 mmol) and 0.035 g Ir(CO)$_2$acac were added to the residue, hydrogen replacement was performed three times, and the mixture was reacted at 80° C. for 16 h under the atmosphere of hydrogen balloon. The reaction liquid was cooled to room temperature and concentrated under reduced pressure. The residue was dissolved in 30 mL of ethyl acetate. The pH was adjusted to 8 with saturated aqueous sodium bicarbonate solution, the liquid separation was conducted, the organic phase was washed with 10 mL of saturated aqueous sodium chloride solution, dried over anhydrous sodium sulfate and concentrated under reduced pressure. The crude product was separated and purified with silica gel column chromatography (petroleum ether:ethyl acetate (v/v)=1:0-17:3) to afford 32f (0.14 g, yield: 51%).

LCMS m/z=551.3 [M+1]$^+$

Step 6: 4-[(2S,4R)-4-cyclopropyl-1-[(5-methoxy-7-methyl-1H-indol-4-yl)methyl]piperidin-2-yl]-2-fluorobenzoic acid (compound 32)

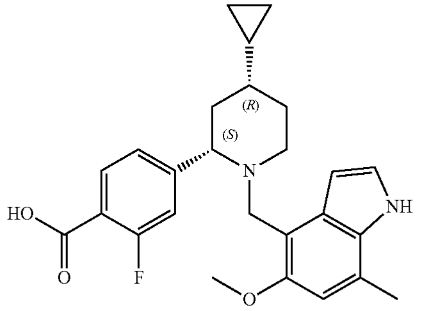

32f (0.14 g, 0.25 mmol) was dissolved in 5 mL of methanol, potassium carbonate (0.17 g, 1.23 mmol) was added, and the mixture was reacted under reflux at 80° C. for 3 h. The reaction system was cooled to room temperature, 1 mL of water and lithium hydroxide monohydrate (0.1 g, 2.38 mmol) were added, and the mixture was reacted at 80° C. for 1 h. The reaction system was cooled to room temperature and filtered, the filter residue was washed with 10 mL of methanol, the filtrate was collected, and the pH was adjusted to 8 with 5 mol/L hydrochloric acid at 0° C. The resulting solution was purified to afford compound 32 (0.07 g, yield: 64%).

$^1$H NMR (400 MHz, $CD_3OD$) δ 7.82 (t, 1H), 7.45-7.27 (m, 3H), 6.75 (s, 1H), 6.34 (s, 1H), 4.45-4.24 (m, 2H), 4.12-3.96 (m, 1H), 3.78 (s, 3H), 3.58-3.43 (m, 1H), 3.26-3.10 (m, 1H), 2.50 (s, 3H), 2.22-2.07 (m, 1H), 2.02-1.52 (m, 3H), 1.16-0.98 (m, 1H), 0.70-0.35 (m, 3H), 0.30-0.10 (m, 2H).

LCMS m/z=437.2 [M+1]$^+$

Example 33

4-[(2S,4S)-4-cyclopropyl-1-[(5-methoxy-7-methyl-1H-indol-4-yl)methyl]piperidin-2-yl]-2-fluorobenzoic acid (compound 33)

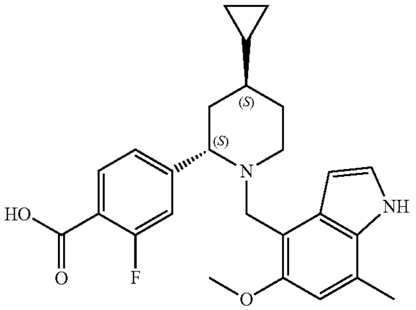

-continued

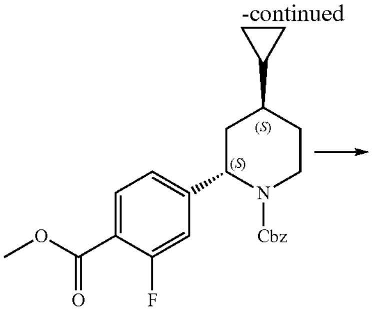

32d-2

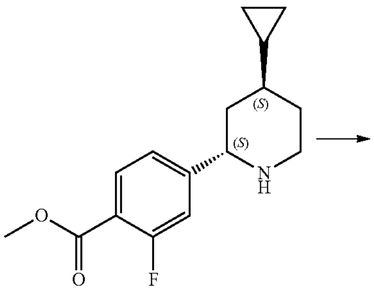

33a

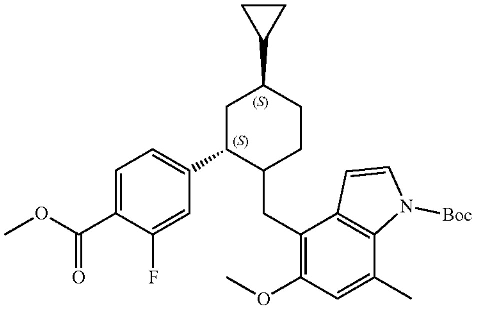

33b

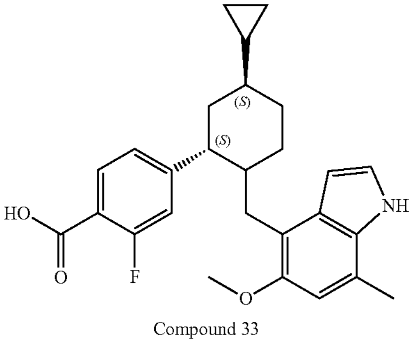

Compound 33

Step 1: methyl 4-[(2S,4S)-4-cyclopropylpiperidin-2-yl]-2-fluorobenzoate (33a)

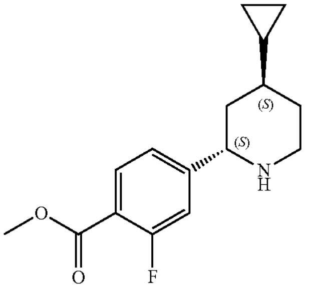

32d-2 (0.17 g, 0.41 mmol) was dissolved in 5 mL of acetonitrile, the mixture was cooled to 0° C. under nitrogen protection, TMSI (0.24 g, 1.2 mmol) was slowly added dropwise, and the reaction was continued at 0° C. for 10 min. 1 mL of anhydrous methanol was slowly added dropwise into the reaction system, saturated aqueous sodium bicarbonate solution was slowly added dropwise to adjust the pH to 8, the mixture was extracted with dichloromethane (20 mL×2), the organic phases were combined, and the organic phase was washed with 10 mL of saturated aqueous sodium chloride solution, dried over anhydrous sodium sulfate and concentrated under reduced pressure. The crude product was separated and purified with silica gel column chromatography (first eluted with petroleum ether:ethyl acetate (v/v)=9:1, and then eluted with methanol dichloromethane (v/v)=1:20) to afford 33a (0.05 g, yield: 44%).

LCMS m/z=278.4 $[M+1]^+$

Step 2: tert-butyl 4-{[(2S,4S)-4-cyclopropyl-2-(3-fluoro-4-(methoxycarbonyl) phenyl)piperidin-1-yl] methyl}-5-methoxy-7-methyl-1H-indole-1-carboxylate (33b)

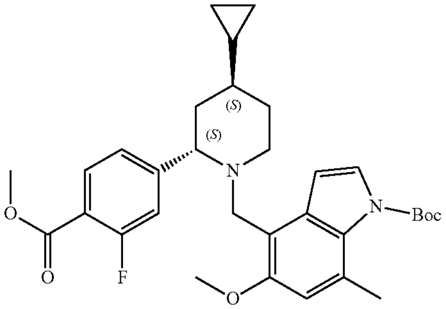

33a (0.05 g, 0.18 mmol) was dissolved in 2 mL of isopropyl acetate, maleic acid (0.021 g, 0.18 mmol) was added and stirred at room temperature for 1 h, then the reaction liquid was concentrated under reduced pressure, and 10 mL of absolute ethanol, tert-butyl 4-formyl-5-methoxy-7-methyl-1H-indole-1-carboxylate (see WO 2015009616 for synthesis method) (0.055 g, 0.19 mmol) and 0.013 g $Ir(CO)_2acac$ were added to the residue, hydrogen replacement was performed three times, and the mixture was reacted at 80° C. for 16 h under the atmosphere of hydrogen balloon. The reaction liquid was cooled to room temperature and concentrated under reduced pressure. The residue was dissolved in 30 mL of ethyl acetate. The pH was adjusted to 8 with saturated aqueous sodium bicarbonate solution, the liquid separation was conducted, the organic layer was washed with 10 mL of saturated aqueous sodium chloride solution, dried over anhydrous sodium sulfate and concentrated under reduced pressure. The crude product was separated and purified with silica gel column chromatography (petroleum ether:ethyl acetate (v/v)=1:0-17:3) to afford 33b (0.05 g, yield: 50%).

LCMS m/z=551.3 $[M+1]^+$

Step 3: 4-[(2S,4S)-4-cyclopropyl-1-[(5-methoxy-7-methyl-1H-indol-4-yl)methyl]piperidin-2-yl]-2-fluorobenzoic acid (compound 33)

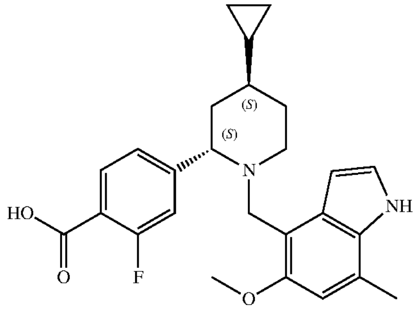

33b (0.05 g, 0.091 mmol) was dissolved in 5 mL of methanol, potassium carbonate (0.063 g, 0.456 mmol) was added, and the mixture was reacted under reflux at 80° C. for 3 h. The reaction system was cooled to room temperature, 1 mL of water and lithium hydroxide monohydrate (0.038 g, 0.91 mmol) were added, and the mixture was reacted at 80° C. for 1 h. The reaction system was cooled to room temperature and filtered, the filter residue was washed with 10 mL of methanol, the filtrate was collected, and the pH was adjusted to 8 with 5 mol/L hydrochloric acid at 0° C. The resulting solution was purified to afford compound 33 (0.038 g, yield: 96%).

$^1H$ NMR (400 MHz, $CD_3OD$) δ 7.82 (t, 1H), 7.45-7.29 (m, 3H), 6.77 (s, 1H), 6.39 (s, 1H), 4.79-4.62 (m, 1H), 4.47-4.32 (m, 1H), 4.24-4.10 (m, 1H), 3.79 (s, 3H), 3.58-3.35 (m, 2H), 2.51 (s, 3H), 2.38-1.77 (m, 4H), 1.50-1.26 (m, 1H), 1.16-1.01 (m, 1H), 0.73-0.57 (m, 2H), 0.27-0.12 (m, 2H).

LCMS m/z=437.2 $[M+1]^+$

Biological Test Example 1

CVF (1 μM), FB (1 μM) and FD (300 nM) were incubated in Assay buffer (pH=7.4, 10 mM $MgCl_2$, 0.05% (m/v), CHAPS) for 3 h at room temperature, so that all FB was cleaved into Baby FD and CVF:Bb complex was generated. SDS-PAGE analysis confirmed that FB was completely hydrolyzed, that is, the concentration of the generated CVF:Bb complex was 300 nM. The CVF:Bb complex was diluted to a concentration of 3 nM using Assay buffer and preincubated with different concentrations of the compounds in assay buffer for 1 h at room temperature. C3 was added to a final concentration of 1 μM to start the enzymatic reaction. After reacting at room temperature for 1 h, protease inhibitor mixture (Roche Complete Inhibitor Tablets) was added to stop the enzyme reaction. Enzyme-linked immunosorbent assay was used to quantify the formation of C3a, and the operation was as follows. 3 μL of the reaction sample after the above-mentioned reaction was terminated was transferred to a 384-well high-capacity protein binding plate (NUNC Maxisorp™), and 97 μL/well of 100 mM sodium carbonate buffer (pH 9.0, 1 M NaCl) was added in advance. After overnight incubation at 4° C., the assay plate was washed with washing buffer (PBS, pH 7.4, containing 0.05% (v/v) Tween 20). Starting Block T20 (PIERCE, #37539) was added and let stand at room temperature for 5 min for blocking. The ELISA plate was washed again with washing buffer. Anti-C3a neoepitope antibody was added to a final concentration of 0.2 μg/well, the mixture was incubated at room temperature for 60 min, and the well plate was washed with washing buffer. HRP-labeled secondary antibody was added at a concentration of 0.2 μg/well and the mixture was incubated at room temperature for 60 min. The well plate was washed with washing buffer. 100 mL of Quantablu fluorogenic peroxidase substrate (#15169, PIERCE) was added and the mixture was incubated at room temperature for 20 min. A microplate reader was used to set the excitation light to 325 nm and the emission light to 420 nm to read the fluorescence value. Nonlinear regression analysis software was used to calculate the $IC_{50}$ value from the plot of FB activity inhibition rate versus inhibitor concentration.

Conclusion: the compounds of the present disclosure had good inhibitory effect on complement factor B.

Biological Test Example 2

The inhibitory effect of the compounds on the complement alternative pathway was detected using the IBL alternative pathway kit (COMPL AP330 RUO). Serum from healthy volunteers was collected and 1 portion was diluted with a buffer of 20 mM EDTA in gelatin (0.15 mM $CaCl_2$, 141 mM NaCl, 4.5 mM $MgCl_2$, 4.2 mM HEPES, and 0.1% gelatin at pH 7.4) to 50% (v/v), and 1 portion was diluted to 50% (v/v) with a buffer of 20 mM EGTA in gelatin. The compounds were prepared in DMSO to a working solution 100 times the final concentration. Before use, 50% of the above serum was diluted 1/18 with the AP diluent in the kit. 1 part of the compound working solution (v/v) or DMSO (positive control PC) was added to 99 parts of the diluted serum containing EGTA for pretreatment for 30 min, and 1 part of DMSO (v/v) was added to 99 parts of the diluted serum containing EDTA, as negative control (NC). The serum pretreated with the above compounds (or DMSO) was added at 100 mL/well to the LPS-coated 96-well plate, incubated at 37° C. for 1 h, and the plate was washed 3 times with washing solution in the kit; the conjugated chromogenic substrate was added according to the instruction in the kit, and the absorbance was read at 405 nm with a microplate reader. The inhibitory activity of the compounds on alternative pathway was calculated using the following formula.

$$\text{Inhibition rate } \% = 100\% \times \frac{OD^{CPD} - OD^{NC}}{OD^{PC} - OD^{NC}}$$

$OD^{CPD}$ was the OD value when the inhibitor was added, $OD^{NC}$ was the OD value of the negative control, and $OD^{PC}$ was the OD value of the positive control.

Graphpad was used to perform nonlinear regression on the final concentrations and inhibition rates of the compounds to obtain the $IC_{50}$ of the compounds for inhibiting the alternative pathway.

The $IC_{50}$ value results inhibiting the alternative pathway are shown in Table 1.

TABLE 1

| $IC_{50}$ values of the compounds of the present disclosure for inhibiting alternative pathway | | |
|---|---|---|
| Serial No. | Compound No. | $IC_{50}$ (nM) |
| 1 | Trifluoroacetate of compound 1-a | A |
| 2 | Trifluoroacetate of compound 2-a (diastereomer 1) | A |
| 3 | Trifluoroacetate of compound 2-b (diastereomer 2) | A |
| 4 | Trifluoroacetate of compound 3 | A |
| 5 | Compound 4 | A |
| 6 | Trifluoroacetate of compound 5 (diastereomer 1) | A |
| 7 | Trifluoroacetate of compound 5-1 (diastereomer 2) | A |
| 8 | Trifluoroacetate of compound 6 | A |
| 9 | Trifluoroacetate of [compound 7 (diastereomer 1)] | A |
| 10 | Formate of [compound 8 (diastereomer 1)] | A |
| 11 | Compound 10 (diastereomer 1) | A |
| 12 | Ammonium of compound 11 (diastereomer 1) | A |
| 13 | Ammonium salt of compound 12 | A |
| 14 | Compound 13 | A |
| 15 | Compound 27-1 | A |

A: <200 nM;
B: 200-1000 nM;
C: >1000 nM.

Conclusion: the compounds of the present disclosure had significant inhibitory effect on the complement alternative pathway.

Biological Test Example 3

CVF (1 μM), FB (1 μM) and FD (300 nM) were incubated in Assay buffer (pH=7.4, 10 mM $MgCl_2$, 0.05% (m/v), CHAPS) for 3 h at room temperature, so that all FB was cleaved into Baby FD and CVF:Bb complex was generated. SDS-PAGE analysis confirmed that FB was completely hydrolyzed, that is, the concentration of the generated CVF:Bb complex was 300 nM. The CVF:Bb complex was diluted to a concentration of 5 nM using Assay buffer and preincubated with different concentrations of the compounds in assay buffer for 1 h at room temperature. C3 was added to a final concentration of 1 μM to start the enzymatic reaction. After reacting at room temperature for 1 h, protease inhibitor mixture (Roche Complete Inhibitor Tablets) was added to stop the enzyme reaction. Human C3a ELISA kit (Hycult HK354-01) was used to determine the generation of C3a according to the instruction in the kit. The FB activity inhibition rate was plotted against the inhibitor concentration, and graphpad nonlinear regression was used to calculate the $IC_{50}$ value.

The $IC_{50}$ value results for inhibiting the FB activity are shown in Table 2.

TABLE 2

| $IC_{50}$ values of the compounds of the present disclosure for inhibiting FB activity | | |
|---|---|---|
| Serial No. | Compound No. | $IC_{50}$ (nM) |
| 1 | Trifluoroacetate of compound 1-a | A |
| 2 | Trifluoroacetate of compound 2-b (diastereomer 2) | A |
| 3 | Compound 4 | A |
| 4 | Trifluoroacetate of compound 5 (diastereomer 1) | A |
| 5 | Trifluoroacetate of compound 6 | A |

A: <500 nM;
B: 500-1000 nM;
C: >1000 nM.

Conclusion: the compounds of the present disclosure had significant inhibitory effect on the FB activity.

Biological Test Example 4

Mice were intravenously given 0.5 mg/ml LPS solution at 100 L/mouse to create a model, and the naive group was given physiological saline. Mice were given the compounds 3.5 h after injection of physiological saline/LPS solution, and the naive group and model group were given vehicle (0.5% MC+0.5% Tween 80). 7.5 h after the mice in each group were injected with physiological saline/LPS, blood was collected from the orbit and the plasma was separated. The plasma C3a level was detected using mouse C3a ELISA kit (NOVUS/NBP2-70037), and the inhibition rate of C3a was calculated. The formula is as follows:

$$\text{Inhibition rate } \% = \left(1 - \frac{Ct - Cnaive}{Cmodel - Cnaive}\right) * 100\%$$

Among them: Ct, C3a level after administration; Cnaive, C3a level of naive group; Cmodel, C3a level of model group.

| Administration and blood collection time schedule | | | |
|---|---|---|---|
| Time point | 0 h | 3.5 h | 7.5 h |
| Treatment | LPS | CPDs | Plasma collection |

The results of the inhibition rates of C3a levels in mice by the compounds of the present disclosure are shown in Table 3.

TABLE 3

| Inhibition rates of C3a levels in mice by the compounds of the present disclosure | | | |
|---|---|---|---|
| Serial No. | Compound No. | Dosage | Inhibition rate |
| 1 | Trifluoroacetate of control compound (LNP023) | 60 mg/kg | 37.36% |
| 2 | Trifluoroacetate of compound 2-b (diastereomer 2) | 60 mg/kg | 73.12% |
| 3 | Trifluoroacetate of compound 2-b (diastereomer 2) | 30 mg/kg | 35.04% |

Conclusion: the compounds of the present disclosure had obvious inhibition on the C3a levels in mice, and the inhibition is better than the control compound.

Structure of control compound (LNP023):

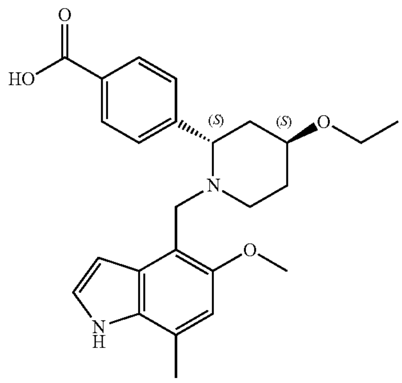

5. Pharmacokinetic Test in Rats

Test objective: In this experiment, a single dose of each test compound was administered to SD rats intravenously and intragastrically, and the concentrations of the test compounds in plasma of rats were measured to evaluate the pharmacokinetic characteristics of the test compounds in rats.

Experimental animals: male SD rats, 200-250 g, 6-8 weeks old, 6 rats/compound, purchased from Chengdu Ddossy Experimental Animals Co., Ltd.

Experimental method: on the day of the test, 6 SD rats were randomly grouped according to their body weight. The animals were fasted with water available for 12 to 14 hours one day before the administration of a test compound, and were fed 4 hours after the administration.

TABLE 4

| | | | Administration information | | | | | |
|---|---|---|---|---|---|---|---|---|
| Group | Quantity Male | Test compound | Adminis-tration dosage* (mg/kg) | Adminis-tration concentration (mg/mL) | Adminis-tration volume (mL/kg) | Collected samples | Mode of Mode | Vehicle |
| G1 | 3 | Compound of the present disclosure | 10 | 1 | 10 | Plasma | Oral (intragastrically) | 0.5% MC |
| G2 | 3 | Compound of the present disclosure | 1 | 0.2 | 5 | Plasma | Intravenous injection | 5% DMA+ 5% Solutol+ 90% Saline |

*Dosage is calculated based on free base.

Sampling: Before and after the administration, 0.15 mL of blood sample was drawn from the orbit under isoflurane anesthesia, and placed in an EDTAK2 centrifuge tube. Centrifugation was carried out at 5000 rpm at 4° C. for 10 min, and the plasma was collected.

Time points for plasma collection in JV&PO group: 0, 5 min, 15 min, 30 min, 2 h, 4 h, 6 h, 8 h, and 24 h.

Before analysis and detection, all samples were stored at −60° C. The samples were analyzed quantitatively by LC-MS/MS.

TABLE 5

| Pharmacokinetic parameters of the compounds of the present disclosure in plasma of rats Test compounds | Mode of administration* | Cmax (ng · mL-1) | $T_{1/2}$ (h) | Tmax (h) | $AUC_{0-24\ h}$ (ng/mL · h) | F % |
|---|---|---|---|---|---|---|
| Trifluoroacetate of compound 7 (diastereomer 1) | i.g. (10 mg/kg) | 1128 | 3.20 | — | 9164 | 72.1 |
| Compound 13 | i.g. (10 mg/kg) | 1602 | 3.41 | 0.583 | 6034 | 65.5 |
| Compound 10 (diastereomer 1) | i.g. (10 mg/kg) | 2244 | 4.15 | 0.333 | 7925 | 57.8 |
| LNP023 | i.g. (10 mg/kg) | 867 | 3.39 | 3.5 | 9867 | 49 |

*Note:
i.g. (intragastrically) administration of the compounds

Conclusion: the compounds of the present disclosure had good oral absorption in rats. Compared with LNPO23, the trifluoroacetate of compound 7 (diastereomer 1), the compound 13 and the compound 10 (diastereomer 1) have higher maximum plasma concentration and oral bioavailability in rats, and the compound 13 and the compound 10 (diastereomer 1) have shorter time to peak.

6. Pharmacokinetic Test in Mice

Test objective: In this experiment, a single dose of test compounds was administered to C57 mice intravenously and intragastrically, the concentrations of the test compounds in plasma of mice were measured, and the pharmacokinetic characteristics of the test compounds in mice were evaluated.

Experimental animals: Male C57 mice, 20-25 g, 6-8 weeks old, 18 mice/compound. purchased from Chengdu Ddossy Experimental Animals Co., Ltd.

Experimental method: On the day of the experiment, 18 C57 mice were randomly grouped according to their body weight. The animals were fasted with water available for 12 to 14 hours one day before the administration of a test compound, and were fed 4 hours after the administration.

TABLE 6

| | | Administration information | | | | | | |
|---|---|---|---|---|---|---|---|---|
| Group | Quantity Male | Test compound | Administration dosage* (mg/kg) | Administration concentration (mg/mL) | Administration volume (mL/kg) | Collected samples | Mode of Mode | Vehicle |
| G1 | 9 | Compound of the present disclosure | 10 | 1 | 10 | Plasma | Oral (intragastrically) | 0.5% MC (containing 0.5% Tween 80) |
| G2 | 9 | Compound of the present disclosure | 1 | 0.2 | 5 | Plasma | Intravenous injection | 5% DMA + 5% Solutol + 90% Saline |

*Dosage is calculated based on free base.

Sampling: Before and after the administration, 0.08 mL of blood sample was drawn from the orbit under isoflurane anesthesia, and placed in an EDTAK2 centrifuge tube. Centrifugation was carried out at 5000 rpm at 4° C. for 10 min, and the plasma was collected.

Time points for plasma collection in IV&PO group: 0, 5 min, 15 min, 30 min, 1 h, 2 h, 4 h, 6 h, 8 h, and 24 h.

Before analysis and detection, all samples were stored at −60° C. The samples were analyzed quantitatively by LC-MS/MS.

TABLE 7

| Pharmacokinetic parameters of the compounds of the present disclosure in plasma of mice | | | |
|---|---|---|---|
| Test compounds | Mode of administration* | $AUC_{0-t}$ (ng/mL· h) | F % |
| Trifluoroacetate of compound 5 (diastereomer 1) | i.g. (10 mg/kg) | 15884 | 81.5 |

*Note:
i.g. (intragastrically) administration of the compounds

Conclusion: the compounds of the present disclosure had good oral absorption in mice.

7. Pharmacokinetic Test of Dogs

Test objective: In this experiment, a single dose of test compounds was administered to beagle dogs intravenously and intragastrically, and the concentrations of the test compounds in plasma of the beagle dogs were measured to evaluate pharmacokinetic characteristics of the test compounds in the beagle dogs.

Experimental animals: Male beagle dogs, 8-11 kg, 1-3 years old, 6 dogs/compound. purchased from Beijing Marshall Biotechnology Co. Ltd.

Experimental method: on the day of the test, 6 beagle dogs were randomly grouped according to their body weights. The animals were fasted with water available for 14 to 18 hours one day before the administration of a test compound, and were fed 4 hours after the administration.

TABLE 8

| | | Administration information | | | | | | |
|---|---|---|---|---|---|---|---|---|
| Group | Quantity Male | Test compound | Adminis-tration dosage* (mg/kg) | Adminis-tration concentration (mg/mL) | Adminis-tration volume (mL/kg) | Collected samples | Mode of Mode | Vehicle |
| G1 | 3 | Compound of the present disclosure | 5 | 1 | 5 | Plasma | Oral (intragastrically) | 0.5% MC (containing 0.5% Tween 80) |
| G2 | 3 | Compound of the present disclosure | 1 | 0.5 | 2 | Plasma | Intravenous injection | 5% DMA + 5% Solutol + 90% Saline |

*Dosage is calculated based on free base.

Sampling: Before and after the administration, 1.0 mL of blood was taken from the jugular veins or limb veins, and placed in an EDTAK2 centrifuge tube. Centrifugation was carried out at 5000 rpm at 4° C. for 10 min, and the plasma was collected.

Time points for plasma collection in IV&PO group: 0, 5 min, 15 min, 30 min, 1 h, 2 h, 4 h, 6 h, 8 h, 10 h, 12 h, and 24 h.

Before analysis and detection, all samples were stored at −60° C. The samples were analyzed quantitatively by LC-MS/MS.

TABLE 9

| Pharmacokinetic parameters of the compounds of the present disclosure in plasma of dogs | | | | |
|---|---|---|---|---|
| Test compounds | Mode of administration* | $AUC_{0-t}$ (ng/mL· h) | $T_{1/2}$ (h) | F % |
| Trifluoroacetate of compound 5 (diastereomer 1) | i.g. (5 mg/kg) | 49274 | 20.9 | 62.6 |
| Trifluoroacetate of compound 7 (diastereomer 1) | i.g. (5 mg/kg) | 45447 | 15.1 | 75.5 |

TABLE 9-continued

| Pharmacokinetic parameters of the compounds of the present disclosure in plasma of dogs | | | | |
|---|---|---|---|---|
| Test compounds | Mode of administration* | $AUC_{0-t}$ (ng/mL· h) | $T_{1/2}$ (h) | F % |
| Compound 13 | i.g. (5 mg/kg) | 36058 | 7.26 | >60 |
| Compound 10 (diastereomer 1) | i.g. (5 mg/kg) | 25318 | 8.89 | 56.2 |
| Trifluoroacetate of LNP023 | i.g. (4 mg/kg) | 19129 | 7.06 | 45.9 |

*Note:
i.g. (intragastrically) administration of the compounds

Conclusion: the compounds of the present disclosure had good oral absorption in beagle dogs.

8. Pharmacokinetic Experiment in Monkeys

Test objective: In this experiment, a single dose of test compounds was administered to cynomolgus monkeys intravenously and intragastrically, and the concentrations of the test compounds in plasma of the monkeys were measured to evaluate pharmacokinetic characteristics of the test compounds in the monkeys.

Experimental animals: Male cynomolgus monkeys, 3-5 kg, 3-6 years old, 6 monkeys/compound. Purchased from Suzhou Xishan Biotechnology Inc.

Experimental method: on the day of the test, 6 monkeys were randomly grouped according to their body weights. The animals were fasted with water available for 14 to 18 hours one day before the administration of a test compound, and were fed 4 hours after the administration.

TABLE 10

| | | Administration information | | | | | | |
|---|---|---|---|---|---|---|---|---|
| Group | Quantity Male | Test compound | Adminis-tration dosage* (mg/kg) | Adminis-tration concentration (mg/mL) | Adminis-tration volume (mL/kg) | Collected samples | Mode of Mode | Vehicle |
| G1 | 3 | Compound of the present disclosure | 5 | 1 | 5 | Plasma | Oral (intragastrically) | 0.5% MC (containing 0.5% Tween 80) |
| G2 | 3 | Compound of the present disclosure | 1 | 0.5 | 2 | Plasma | Intravenous injection | 5% DMA + 5% Solutol + 90% Saline |

*Dosage is calculated based on free base.

Sampling: before and after the administration, 1.0 mL of blood was taken from the limb veins, and placed in an EDTAK2 centrifuge tube. Centrifugation was carried out at 5000 rpm at 4° C. for 10 min, and the plasma was collected.

Time points for plasma collection in IV&PO group: 0, 5 min, 15 min, 30 min, 1 h, 2 h, 4 h, 6 h, 8 h, 10 h, 12 h, and 24 h.

Before analysis and detection, all samples were stored at −60° C. The samples were analyzed quantitatively by LC-MS/MS.

TABLE 11

Pharmacokinetic parameters of the compounds of the present disclosure in plasma of monkeys

| Test compounds | Mode of administration* | $AUC_{0-t}$ (ng/mL· h) | F % |
|---|---|---|---|
| Trifluoroacetate of compound 5 (diastereomer 1) | i.g. (5 mg/kg) | 38759 ± 1429 | 54.1 ± 2.0 |
| Trifluoroacetate of compound 7 (diastereomer 1) | i.g. (5 mg/kg) | 48279 ± 3664 | 98.3 ± 7.5 |
| Compound 13 | i.g. (5 mg/kg) | 16603 ± 1071 | 70.5 ± 4.5 |
| Trifluoroacetate of LNP023 | i.g. (5 mg/kg) | 13188 ± 1472 | 35.2 ± 3.9 |

*Note:
i.g. (intragastrically) administration of the compounds

Conclusion: the compounds of the present disclosure had good oral absorption in monkeys. Compared with the trifluoroacetate of LNP023, the trifluoroacetate of compound 5 (diastereomer 1) and the trifluoroacetate of compound 7 (diastereomer 1) and the compound 13 had higher oral exposure and bioavailability in monkeys.

9. Caco2 Permeability Test

The experiment used a monolayer of Caco-2 cells incubated in triplicate in a 96-well Transwell plate. A transport buffer solution (HBSS, 10 mM HEPES, pH 7.4±0.05) containing the compound of the present disclosure (2 μM) or the control compounds of digoxin (10 μM), nadolol (2 M) and metoprolol (2 μM) was added to the administration end hole on the apical side or the basal side. DMSO-containing transport buffer solution was added to the corresponding receiving end hole. After incubation for 2 h at 37±1° C., the cell plate was removed and a appropriate amount of samples were taken from the apical side and basal side and transferred to a new 96-well plate. Acetonitrile containing internal standard was then added to precipitate the protein. Samples were analyzed using LC MS/MS and the concentrations of the compounds of the present disclosure and the control compounds were determined. Concentration data were used to calculate apparent permeability coefficients for transport from the apical side to the basal side, and from the basal side to the apical side of the cell monolayer, and thus to calculate the efflux ratio. The integrity of the cell monolayer after 2 h of incubation was assessed by leakage of Lucifer Yellow.

TABLE 12

Caco2 test results of the compounds of the present disclosure

| Test compounds | Mean $P_{app}$ ($10^{-6}$ cm/s) A to B | Mean $P_{app}$ ($10^{-6}$ cm/s) B to A | Efflux Ratio |
|---|---|---|---|
| Trifluoroacetate of compound 5 (diastereomer 1) | 2.17 | 23.9 | 11.0 |
| Trifluoroacetate of compound 7 (diastereomer 1) | 1.77 | 19.4 | 11.0 |
| Compound 10 (diastereomer 1) | 2.62 | 12.1 | 4.62 |
| Compound 13 | 2.55 | 20.9 | 8.18 |
| Trifluoroacetate of LNP023 | 0.570 | 14.4 | 25.3 |

Conclusion: the compounds of the present disclosure had good Caco2 permeability. Compared with the trifluoroacetate of LNP023, the trifluoroacetate of compound 5 (diastereomer 1), the trifluoroacetate of compound 7 (diastereomer 1), the compound 10 (diastereomer 1), and the compound 13 had better permeability and lower efflux ratio.

Test Example 8: Stability of Test Compounds in Liver Microsome

The total volume of the incubation system was 100 μL, the medium was 100 mM phosphate buffer (PBS, pH 7.4), including liver microsomal protein with a final concentration of 0.50 mg/mL, 1.00 μM test substance and 1.00 mM NADPH, 37° C. water bath was used for incubation, and 300 μL of ice-cold acetonitrile containing internal standard was added to terminate the reaction after 0, 5, 10, 20, 30, and 60 min of reaction, respectively. The negative control was incubated with heat-inactivated liver microsomes of the corresponding species, and the incubation time points were 0 and 60 min respectively. The LC/MS/MS method was used to detect the concentration of the test substance in the sample and the remaining rate of the compound was calculated.

The results of stability of the compounds of the present disclosure in liver microsome are shown in Table 13 below.

TABLE 13

Stability of test compounds in liver microsome

| | | Remaining % (T = 60 min) | | | | |
|---|---|---|---|---|---|---|
| Serial No. | Compound | HLM0.5 | CLM0.5 | DLM0.5 | RLM0.5 | MouLM0.5 |
| 1 | Trifluoroacetate of compound 5 (diastereomer 1) | >90 | >90 | >90 | >90 | >90 |

Conclusion: the compounds of the present disclosure had good stability in liver microsome.

What is claimed is:

1. A compound or a stereoisomer, deuterate, solvate, prodrug, metabolite, pharmaceutically acceptable salt or co-crystal thereof, wherein the compound is selected from a compound of general formula (Id), (Id)

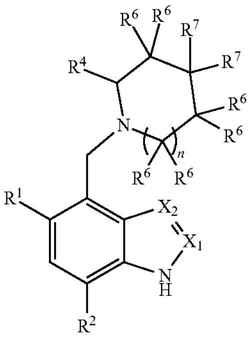

n is 1; $X_1$ and $X_2$ are $CR^3$;

$R^3$ is H; each $R^6$ is H;

one $R^7$ is H, another $R^7$ is selected from cyclopropyl, cyclobutyl, cyclopentyl, wherein the cyclopropyl, cyclobutyl, cyclopentyl is optionally further substituted with 0 to 4 substituents selected from H, D, halogen, $C_{1-4}$ alkyl;

$R^1$ is selected from methoxy, ethoxy, isopropoxy, wherein the methoxy, ethoxy, isopropoxy is substituted with 1 to 4 substituents selected from D, halogen;

$R^2$ is selected from methyl, ethyl, wherein the methyl, ethyl is optionally further substituted with 0 to 4 substituents selected from H, D, F, Cl, Br, I;

$R^4$ is phenyl, the phenyl is optionally further substituted with 0 to 4 $R^5$;

$R^5$ is independently selected from halogen, OH, cyano, $—C(=O)R^{4e}$, $C_{1-4}$ alkyl, $C_{1-4}$ alkoxy;

$R^{4e}$ is OH.

2. The compound or the stereoisomer, deuterate, solvate, prodrug, metabolite, pharmaceutically acceptable salt or co-crystal thereof according to claim 1, wherein each $R^4$ is independently selected from

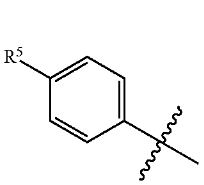
,
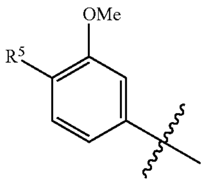
,
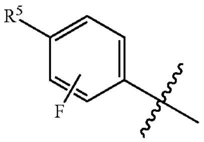
,
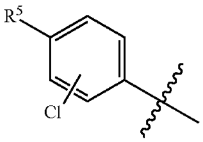
,

-continued

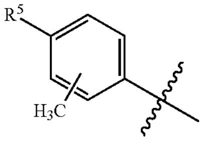
;

each $R^5$ is —COOH;

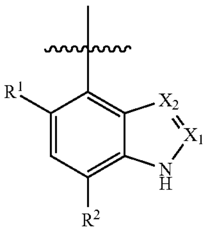

is selected from

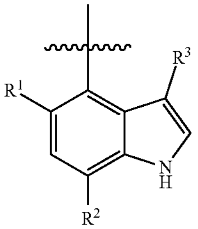
;

$R^1$ is independently selected from $—OCD_3$, $—OCH_2F$, $—OCHF_2$, $—OCF_3$; each $R^2$ is methyl, ethyl, $CD_3$, $CHD_2$, or $CH_2D$;

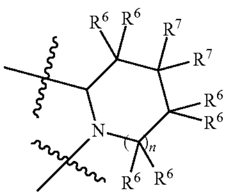

is selected from

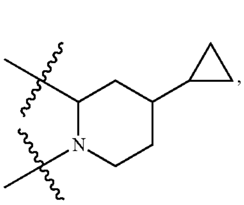
,
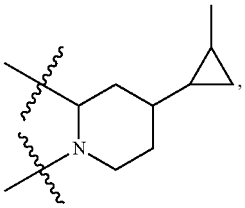
,

-continued

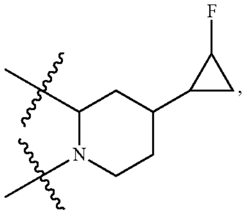

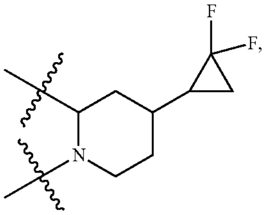

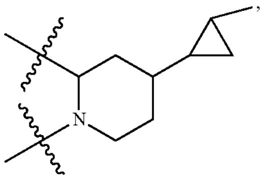

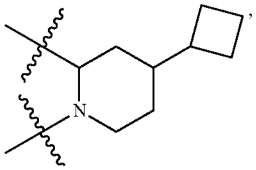

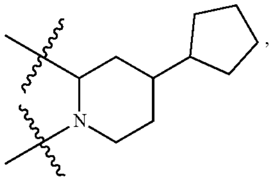

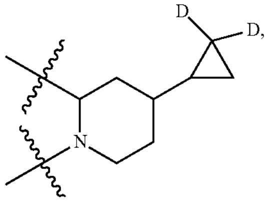

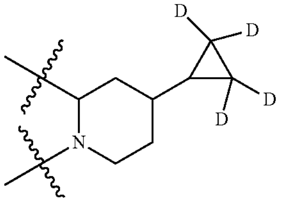

or

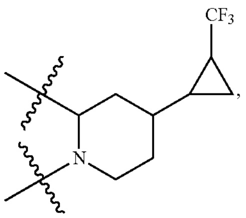

the fragments which are connected to $R^4$ at the upper part.

3. The compound or the stereoisomer, deuterate, solvate, prodrug, metabolite, pharmaceutically acceptable salt or co-crystal thereof according to claim 1, wherein the compound is selected from the compound of general formula (Id-5), (Id-5)

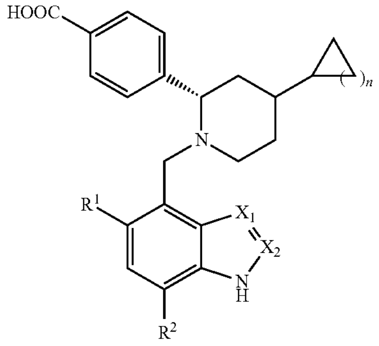

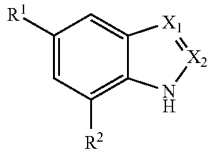

is selected from

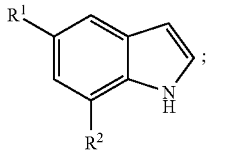

$R^1$ is selected from —$OCD_3$;

$R^2$ is selected from —$CH_3$ or —$CD_3$;

and n is selected from 1, 2 or 3.

4. The compound or the stereoisomer, deuterate, solvate, prodrug, metabolite, pharmaceutically acceptable salt or co-crystal thereof according to claim 1, wherein the compound is selected from one of the structures shown in following Table

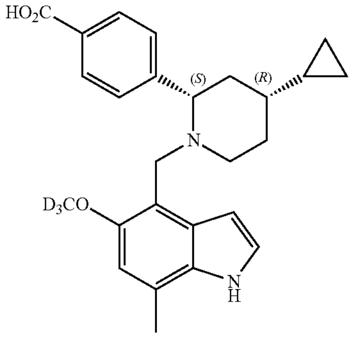

-continued
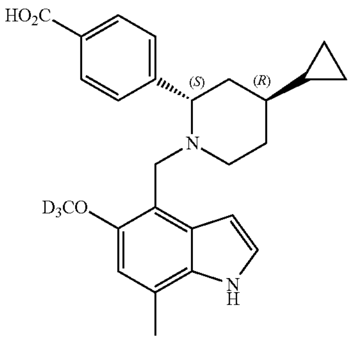
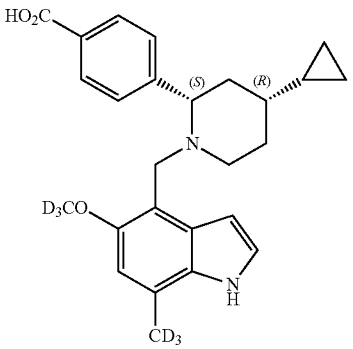
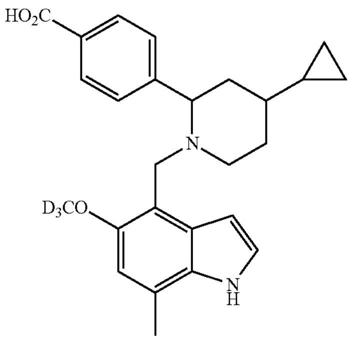
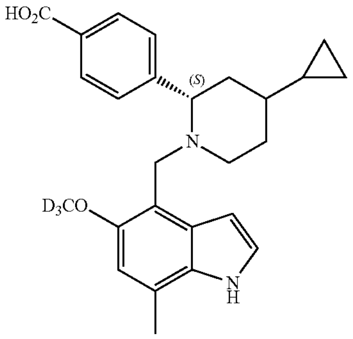
-continued
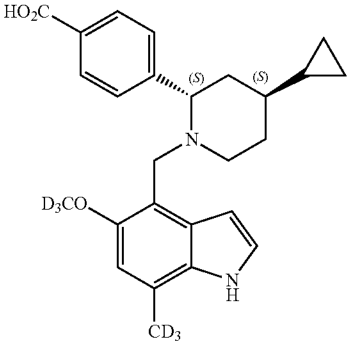
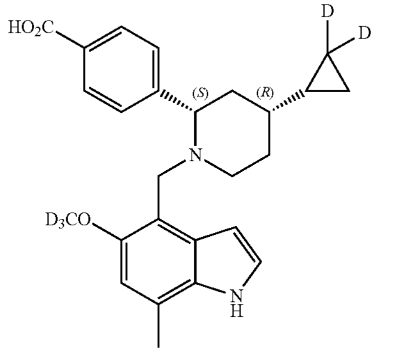
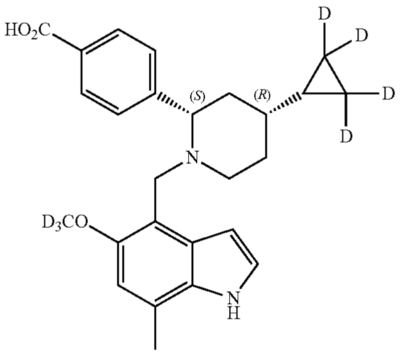
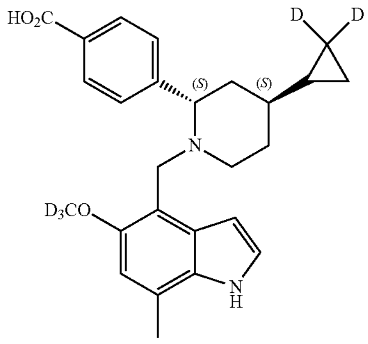

-continued

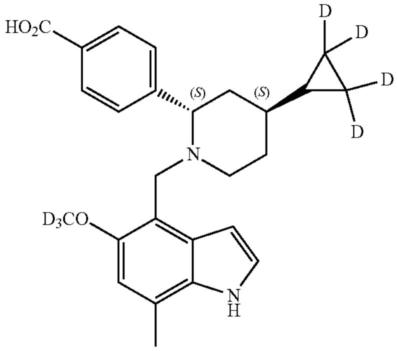

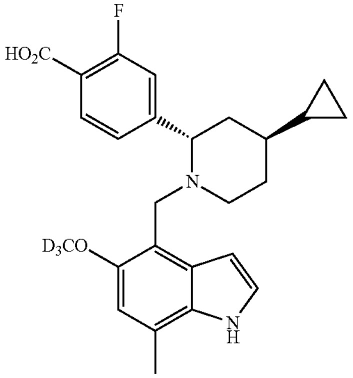

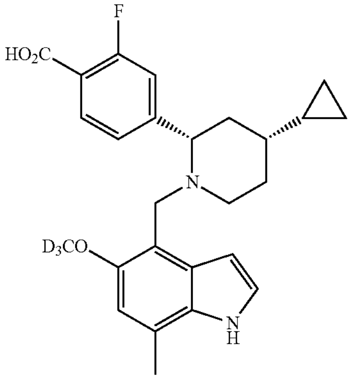

-continued

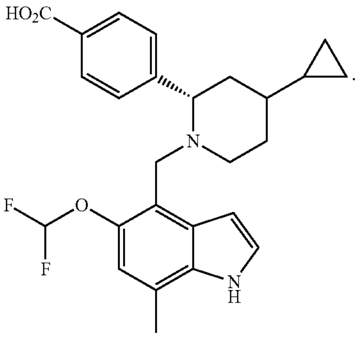 [SMILES: Cc1cc(OC(F)F)c(CN2CCC(C3CC3)C[C@H]2c2ccc(C(=O)O)cc2)c2cc[nH]c12]

5. A pharmaceutical composition, comprising the compound or the stereoisomer, deuterate, solvate, prodrug, metabolite, pharmaceutically acceptable salt or co-crystal thereof according to claim 1, and a pharmaceutically acceptable carrier.

6. The pharmaceutical composition according to claim 5, wherein the pharmaceutical composition comprises 1-600 mg of the compound or the stereoisomer, deuterate, solvate, prodrug, metabolite, pharmaceutically acceptable salt or co-crystal thereof, and a pharmaceutically acceptable excipient.

7. A method for inhibiting Factor B (FB) activity, comprising administering to the mammal a therapeutically effective amount of the compound or the stereoisomer, deuterate, solvate, prodrug, metabolite, pharmaceutically acceptable salt or co-crystal thereof according to claim 1.

8. The method of claim 7, wherein the therapeutically effective amount is 1-600 mg.

* * * * *